(12) United States Patent
Bruenker et al.

(10) Patent No.: US 11,214,622 B2
(45) Date of Patent: Jan. 4, 2022

(54) ANTIBODIES SPECIFIC FOR DR5 AND METHODS OF USE

(71) Applicant: Roche Glycart AG, Schlieren (CH)

(72) Inventors: Peter Bruenker, Hittnau (CH); Sherif Daouti, Totowa, NJ (US); Ningping Feng, Richmond Hill (CA); Claudia Ferrara Koller, Zug (CH); Guy Georges, Habach (DE); Sandra Grau-Richards, Birmensdorf (CH); Ralf Hosse, Cham (CH); Christian Klein, Bonstetten (CH); Maximiliane Koenig, Pullach (DE); Joerg Moelleken, Munich (DE); Ekkehard Moessner, Kreuzlingen (CH); Huifeng Niu, Scotch Plains, NJ (US); Kathryn E. Packman, Newton, MA (US); Valeria Runza, Penzberg (DE); Stefan Seeber, Sindelsdorf (DE); Pablo Umana, Wollerau (CH); Inja Waldhauer, Urdorf (CH); Huisheng Wang, Edison, NJ (US); Barbara Weiser, Sindelsdorf (DE)

(73) Assignee: ROCHE GLYCART AG, Schlieren (CH)

( * ) Notice: Subject to any disclaimer, the term of this patent is extended or adjusted under 35 U.S.C. 154(b) by 448 days.

(21) Appl. No.: 15/913,713

(22) Filed: Mar. 6, 2018

(65) Prior Publication Data
US 2019/0062453 A1     Feb. 28, 2019

Related U.S. Application Data

(63) Continuation of application No. 14/231,933, filed on Apr. 1, 2014, now Pat. No. 9,926,379.
(Continued)

(51) Int. Cl.
*A61K 39/395*      (2006.01)
*C07K 16/28*       (2006.01)
(Continued)

(52) U.S. Cl.
CPC .... *C07K 16/2878* (2013.01); *A61K 39/39558* (2013.01); *C07K 16/30* (2013.01);
(Continued)

(58) Field of Classification Search
None
See application file for complete search history.

(56) References Cited

U.S. PATENT DOCUMENTS

| 5,580,774 A | 3/1996 | Beavers et al. |
| 5,965,710 A | 12/1999 | Bodmer et al. |

(Continued)

FOREIGN PATENT DOCUMENTS

| EP | 1 870 459 A1 | 12/2007 |
| WO | 1999/057151 | 11/1999 |

(Continued)

OTHER PUBLICATIONS

Asano et al., "Protein Structure and folding: Highly effective recombinant format of a humanized IGG-like bispecific antibody for cancer immunotherapy with regarging of lymphocytes to tumor cells" J Biol Chem 282:27659-27665 (2007).
(Continued)

*Primary Examiner* — Claire Kaufman

(57) ABSTRACT

The present invention relates to bispecific antibodies comprising at least one antigen binding site specific for DR5 and at least one antigen binding site specific for FAP, antibodies specific for DR5, methods for their production, pharmaceutical compositions containing said antibodies, and uses thereof.

13 Claims, 59 Drawing Sheets

Specification includes a Sequence Listing.

Related U.S. Application Data

(60) Provisional application No. 61/808,128, filed on Apr. 3, 2013.

(51) Int. Cl.
    *C07K 16/30*      (2006.01)
    *A61K 39/00*      (2006.01)
    *C07K 16/40*      (2006.01)

(52) U.S. Cl.
CPC .... *A61K 2039/505* (2013.01); *C07K 16/2875* (2013.01); *C07K 16/40* (2013.01); *C07K 2317/21* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/55* (2013.01); *C07K 2317/624* (2013.01); *C07K 2317/64* (2013.01); *C07K 2317/66* (2013.01); *C07K 2317/73* (2013.01); *C07K 2317/75* (2013.01); *C07K 2317/92* (2013.01); *C07K 2317/94* (2013.01); *C07K 2319/00* (2013.01)

(56) References Cited

U.S. PATENT DOCUMENTS

| | | |
|---|---|---|
| 6,455,677 B1 | 9/2002 | Park et al. |
| 7,632,497 B2 | 12/2009 | Stavenhagen |
| 8,029,783 B2 | 4/2011 | Adams et al. |
| 8,097,704 B2 | 1/2012 | Kim et al. |
| 8,173,128 B2 * | 5/2012 | Nasoff ............... A61P 35/00 424/138.1 |
| 8,242,247 B2 | 8/2012 | Klein et al. |
| 8,568,727 B2 | 10/2013 | Adolf et al. |
| 9,120,855 B2 | 1/2015 | Cromie et al. |
| 8,945,571 B2 | 3/2015 | Moessner et al. |
| 8,969,526 B2 | 3/2015 | Baehner et al. |
| 9,011,847 B2 | 4/2015 | Bacac et al. |
| 9,481,730 B2 | 1/2016 | Bruenker et al. |
| 9,266,938 B2 | 2/2016 | Ast et al. |
| 9,266,967 B2 | 2/2016 | Klein et al. |
| 9,346,872 B2 | 5/2016 | Duerner et al. |
| 9,447,159 B2 | 9/2016 | Ast et al. |
| 2003/0143229 A1 | 7/2003 | Park et al. |
| 2003/0232049 A1 | 12/2003 | Jung |
| 2004/0033511 A1 | 2/2004 | Pfizenmaier et al. |
| 2007/0031414 A1 | 2/2007 | Adams |
| 2010/0316645 A1 | 12/2010 | Imhof-Jung et al. |
| 2011/0064751 A1 | 3/2011 | Mossner et al. |
| 2012/0225071 A1 | 6/2012 | Klein et al. |
| 2012/0184718 A1 | 7/2012 | Bruenker et al. |
| 2013/0078249 A1 | 3/2013 | Ast et al. |
| 2014/0044674 A1 | 2/2014 | Duerner et al. |
| 2014/0370019 A1 | 12/2014 | Bruenker et al. |
| 2016/0060357 A1 | 3/2016 | Bacac et al. |
| 2016/0208017 A1 | 7/2016 | Ast et al. |
| 2016/0159917 A1 | 9/2016 | Bruenker et al. |
| 2016/0263240 A1 | 9/2016 | Ast et al. |
| 2016/0340399 A1 | 11/2016 | Amann et al. |

FOREIGN PATENT DOCUMENTS

| | | |
|---|---|---|
| WO | 01/068708 | 9/2001 |
| WO | 2002/08291 | 1/2002 |
| WO | 2002/085946 | 1/2002 |
| WO | 2005/092927 | 10/2005 |
| WO | 2006/074397 | 7/2006 |
| WO | 2006/083971 A2 | 8/2006 |
| WO | 2007/077173 | 7/2007 |
| WO | 2008/004760 | 1/2008 |
| WO | 2011/020783 | 2/2011 |
| WO | 2011/098520 | 2/2011 |
| WO | 2011/039126 | 4/2011 |
| WO | 2012/020006 A2 | 2/2012 |
| WO | 2013/026833 A1 | 2/2013 |

OTHER PUBLICATIONS

Baum et al., "Single-chain Fv immunoliposomes for the targeting of fibroblast activation protein-expressing tumor stromal cells" Journal of Drug Targeting 15(6):399-406 (Jul. 1, 2007).

Booy et al., "Monoclonal and bispecific antibodies as novel therapeutics" Arch Immunol Ther Exp. 54(2):85-101 ( 2006).

Carter, "Bispecific human IgG by design" J Immunol Methods 248(1-2):7-15 (Feb. 1, 2001).

Casset et al., "A peptide mimetic of an anti-CD4 monoclonal antibody by rational design" Biochem Bioph Res Co(307):198-205 ( 2003).

Chen et al., "Selection and analysis of an optimized anti-VEGF antibody: Crystal structure of an affinity-matured Fab in complex with antigen" J Mol Biol 293:865-881 ( 1991).

De Pascalis et al., "Grafting of 'abbreviated' complementarity-determining regions containing specificity-determining residues essential for ligan contact to engineer a less immunogenic humanized monoclonal antibody" J Immunol 169:3076-3084 ( 2002).

Hermann et al., "Construction of Optimized Bispecific Antibodies for Selective Activation of the Death Receptor CD95" Cancer Res 68(68):1221-1227 (Feb. 15, 2008).

Jung et al., "Target Cell-restricted Triggering of the CD95 (APO-1/Fas) Death Receptor with Bispecific Antibody Fragments" Cancer Res 61(5):1846-1848 ( 2001).

Kriangkum et al., "Bispecific and bifunctional single chain recombinant antibodies" Biomol Eng 18(1):31-40 (Aug. 2001).

Lamminmak et al., "Crystal structure of a recombinant anti-estradiol Fab fragment in complex with 17β-estradiol" Journal of Biological Chemistry 276(39):36687-36694 (Sep. 28, 2001).

Little 'Recombinant Antibodies for Immunotherapy' Cambridge University Press, ( 2009) pp. v-vi, 145-152.

MacCallum et al., "Antibody-antigen interactions: contact analysis and binding site topography" J Mol Biol 262(5):732-745 (Oct. 11, 1996).

MacFarlane et al., "Identification and Molecular Cloning of Two Novel Receptors for the Cytotoxis Ligand TRAIL" Journal of Biological Chemistry 272:25417-25420 ( 1997).

Marsters et al., "A Novel Receptor for Apo2L/TRAIL Contains a Truncated Death Domain" Current Biology 7:1003-1006 (Oct. 6, 1997).

Marvin et al., "Recombinant approaches to IgG-like bispecific antibodies" Acta Pharmacologica Sinica 26(6):649-658 (Jun. 2005).

Melero et al., "Immunostimulatory monoclonal antibodies for cancer therapy" Nat Rev Cancer 7:95-106 ( 2007).

Mersmann, "Human Antibody Derivatives Against the Fibroblast Protein for Tumor Stroma Targeting of Carcinomas" International Journal of Cancer 92(2):240-248 (Apr. 15, 2001).

Michaelson et al., "Anti-tumor activity of stability-engineered IgG-like bispecific antibodies targeting TRAIL-R2 and LTβR." MAbs (e-pub. Mar. 11, 2009), 1(2):128-141 (Mar. 2009).

Nagaoka et al., "Single amino acid substitution in the mouse IgG1 Fc region induces drastic enhancement of the affinity to protein A" Protein Engineering 16(4):243-245 ( 2003).

Ridgway et al., "'Knobs-into-holes' engineering of antibody $C_H3$ domains for heavy chain heterodimerization" Protein Eng 9(7):617-621 ( 1996).

Samel et al., "Generation of a FasL-based Proapoptotic Fusion Protein Devoid of Systemic Toxicity due to Cell-surface Antigen-restricted Activation" J. Biol. Chem. 278(34):32077-32082 (May 28, 2003).

Simonet et al., "Osteoprotegerin: A Novel Secreted Protein Involved in the Regulation of Bone Density" Cell 89:309-319 ( 1997).

Vajdos et al. et al., "Comprehensive functional maps of the antigen-binding site of an anti-ErbB2 antibody obtained with shotgun scanning mutagenesis" J Mol Biol 320(2):415-428 (Jul. 5, 2002).

Wagner et al., "Death-Receptor O-Glycosylation Controls Tumor-Cell Sensitivity to the Proapoptotic Ligand Apo2L/TRAIL" Nature Medicine 13(9):1070-1077 (Sep. 2007).

Wajant et al., "Differential Activation of TRAIL-R1 and -2 by Soluble and Membrane TRAIL Allows Selective Surface Antigen-

(56) References Cited

OTHER PUBLICATIONS directed Activation of TRAIL-R2 by a Soluble TRAIL Derivative" Oncogene 20:4101-4106 (Apr. 19, 2001).

Written Opinion for PCT/EP2014/056511 (mailing date Oct. 3, 2015).

Wu et al. et al., "Humanization of a murine monoclonal antibody by simultaneous optimization of framework and CDR residues" J Mol Biol 294(1):151-162 (Nov. 19, 1999).

Wu et al., "Simultaneous Targeting of multiple disease mediators by a dual-variable-domain immunoglobulin" Nat. Biotech. 25(11):1290-1297 ( 2007).

Wuest et al., "Construction of a bispecific single chain antibody for recruitment of cytotoxic T cells to the tumour stroma associated antigen fibroblast activation protein" J Biotechnol 92:159-168 ( 2001).

Yada et al., "A novel humanized anti-human death receptor 5 antibody CS-1008 induces apoptosis in tumor cells without toxicity in hepatocytes" Annals of Oncology 19:1060-1067 ( 2008).

\* cited by examiner

|  | 5E11 | 22E9 | 174 | 422 | Drozitumab |
|---|---|---|---|---|---|
| 5E11 | 0 | 0 | 0 | 1 | 1 |
| 22E9 | 0 | 0 | 0 | 1 | 1 |
| 174 | 0 | 0 | 0 | 1 | 1 |
| 422 | 0 | 0 | 1 | 0 | 0 |
| Drozitumab | 1 | 1 | 1 | 1 | 0 |

1 = additional binding

0 = no additional binding

FIG. 17

| Bispecific molecule | Structure | Bispecific molecule | Structure |
|---|---|---|---|
| Drozitumab-3F2 VHVL-scFv (HC) pETR6606 | 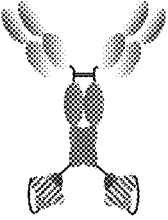 | Drozitumab-FAP (28H1) VHCL pETR9551 2+2 | 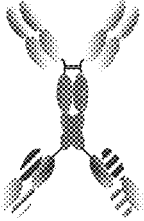 |
| Drozitumab-FAP (4G8) VHVL-scFv (LC) pETR7344 | 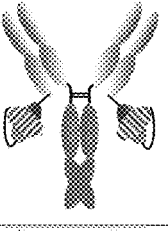 | DR5 (22E9)-FAP (28H1) VHCL pETR9711 2+2 | 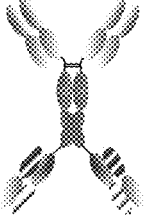 |
| Drozitumab-3F2 VLCL_VHCH1-scFab (HC) pETR7369 | 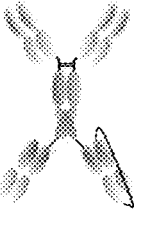 | DR5 (21H3)-FAP (28H1) VHCL pETR10626 2+2 | 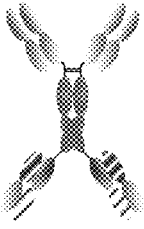 |
| Drozitumab-3F2 VLCL_VHCH1-scFab (LC) pETR7370 | | DR5 (20F2)-FAP (28H1) VHCL pETR10135 2+2 | 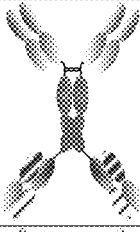 |
| Drozitumab-FAP (4G8) VHCL 2+2 | 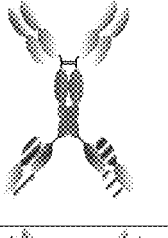 | DR5(5E11)-FAP (28H1) VHCL pETR10334 2+2 | 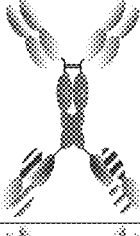 |
| Drozitumab-FAP (4G8) VLCH1 2+2 | 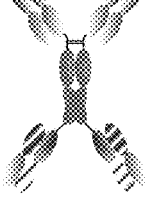 | DR5(5E11)-FAP (28H1) VHCL 2+2 Removal of C-term. Lysine in Fc pETR11052 | 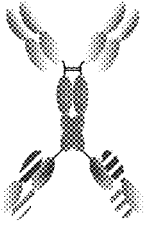 |

*FIG. 50A*

| Bispecific molecule | Structure | Bispecific molecule | Structure |
|---|---|---|---|
| DR5(5E11)-FAP (28H1) VHCL 2+2 Removal of C-term. Lysine in Fc P329G/LALA mut. pETR11025 |  | DR5(5E11)_Fc knob Fab-Fab Head-to-tail 2+1 pETR10662 |  |
| VHVL DR5(5E11)-FAP (28H1) pETR11827 2+2 |  | DR5(18F11)-FAP (28H1) Fc knob VHCL 2+1 pETR9807 |  |
| CH1CL DR5(5E11)-FAP (28H1) pETR11828 2+2 |  | DR5(18F11)-FAP (28H1) VHCL Fc knob 3+1 pETR10333 |  |
| DR5(18F11)-FAP (28H1) VHCL 2+2 |  | FAP (28H1)_Fc hole VHCL pETR10130 |  |
| DR5(5E11)-FAP (28H1) Fc knob VHCL 2+1 pETR10427 |  | DR5 (5E11)_FAP(4B9) VHCL pETR11060 |  |
| DR5(5E11)-DR5(5E11) Fc hole pETR10429 3+1 |  | | |

SEQUENCE LISTING

<160> NUMBER OF SEQ ID NOS: 318

<210> SEQ ID NO 1
<211> LENGTH: 5
<212> TYPE: PRT

```
<213> ORGANISM: Artificial Sequence
<220> FEATURE:
<223> OTHER INFORMATION: DR5 (5E11) binder; CDR1 of VH

<400> SEQUENCE: 1

Ser Tyr Ala Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: DR5 (5E11) binder; CDR2 of VH

<400> SEQUENCE: 2

Ala Ile Ser Gly Ser Gly Gly Ser Thr Tyr Tyr Ala Asp Ser Val Lys
1               5                   10                  15
Gly

<210> SEQ ID NO 3
<211> LENGTH: 8
<212> TYPE: PRT
<213> ORGANISM: Artificial Sequence
<220> FEATURE:
<223> OTHER INFORMATION: DR5 (5E11) binder; CDR3 of VH

<400> SEQUENCE: 3

Gly Val Arg Val Ser Phe Asp Tyr
1               5

<210> SEQ ID NO 4
<211> LENGTH: 12
<212> TYPE: PRT
<213> ORGANISM: Artificial Sequence
<220> FEATURE:
<223> OTHER INFORMATION: DR5 (5E11) binder; CDR1 of VL

<400> SEQUENCE: 4

Arg Ala Ser Gln Ser Val Ser Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: DR5 (5E11) binder; CDR2 of VL

<400> SEQUENCE: 5

Gly Ala Ser Ser Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: DR5 (5E11) binder; CDR3 of VL

<400> SEQUENCE: 6

Gln Gln Gly Thr Thr His Pro Ile Thr
1               5

<210> SEQ ID NO 7
<211> LENGTH: 117
```

```
<212> TYPE: PRT
<213> ORGANISM: Artificial Sequence
<220> FEATURE:
<223> OTHER INFORMATION: DR5(5E11)binder_variable heavy chain (VH)

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: DR5 (5E11) binder_variable light chain (VL)

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Thr Thr His Pro
                85                  90                  95

Ile Thr Phe Gly Gln Gly Thr Lys Val Glu Ile Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: FAP (28H1) binder; CDR1 of VH

<400> SEQUENCE: 9

Ser His Ala Met Ser
1               5

<210> SEQ ID NO 10
<211> LENGTH: 16
<212> TYPE: PRT
```

<213> ORGANISM: Artificial Sequence
<220> FEATURE:
<223> OTHER INFORMATION: FAP(28H1), binder; CDR2 of VH

<400> SEQUENCE: 10

Ala Ile Trp Ala Ser Gly Glu Gln Tyr Tyr Ala Asp Ser Val Lys Gly
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: FAP(28H1) binder; CDR3 of VH

<400> SEQUENCE: 11

Gly Trp Leu Gly Asn Phe Asp Tyr
1               5

<210> SEQ ID NO 12
<211> LENGTH: 12
<212> TYPE: PRT
<213> ORGANISM: Artificial Sequence
<220> FEATURE:
<223> OTHER INFORMATION: FAP(28H1) binder; CDR1 of VL

<400> SEQUENCE: 12

Arg Ala Ser Gln Ser Val Ser Arg Ser Tyr Leu Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: FAP(28H1) binder; CDR2 of VL

<400> SEQUENCE: 13

Gly Ala Ser Thr Arg Ala Thr
1               5

<210> SEQ ID NO 14
<211> LENGTH: 9
<212> TYPE: PRT
<213> ORGANISM: Artificial Sequence
<220> FEATURE:
<223> OTHER INFORMATION: FAP(28H1) binder; CDR3 of VL

<400> SEQUENCE: 14

Gln Gln Gly Gln Val Ile Pro Pro Thr
1               5

<210> SEQ ID NO 15
<211> LENGTH: 116
<212> TYPE: PRT
<213> ORGANISM: Artificial Sequence
<220> FEATURE:
<223> OTHER INFORMATION: FAP(28H1) binder_variable heavy chain (VH)

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

```
Ser Ala Ile Trp Ala Ser Gly Glu Gln Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser
            115

<210> SEQ ID NO 16
<211> LENGTH: 108
<212> TYPE: PRT
<213> ORGANISM: Artificial Sequence
<220> FEATURE:
<223> OTHER INFORMATION: FAP(28H1)binder_variable light chain (VL)

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 17
<211> LENGTH: 5
<212> TYPE: PRT
<213> ORGANISM: Artificial Sequence
<220> FEATURE:
<223> OTHER INFORMATION: DR5 (174-VH7) and (174-VH17) binders; CDR1 of
      VH

<400> SEQUENCE: 17

Arg Tyr Ala Met Ile
1               5

<210> SEQ ID NO 18
<211> LENGTH: 16
<212> TYPE: PRT
<213> ORGANISM: Artificial Sequence
<220> FEATURE:
<223> OTHER INFORMATION: DR5 (174-VH7) binder; CDR2 of VH

<400> SEQUENCE: 18

Phe Ile Thr Ser Asp Gly Ser Thr Tyr Tyr Ala Asp Ser Ala Lys Gly
1               5                   10                  15

<210> SEQ ID NO 19
<211> LENGTH: 9
<212> TYPE: PRT
<213> ORGANISM: Artificial Sequence
```

```
<220> FEATURE:
<223> OTHER INFORMATION: DR5 (174-VH7) and (174-VH17) binders; CDR3 of
      VH

<400> SEQUENCE: 19

Tyr Thr Tyr Ser Asp Gly Thr Asp Leu
1               5

<210> SEQ ID NO 20
<211> LENGTH: 11
<212> TYPE: PRT
<213> ORGANISM: Artificial Sequence
<220> FEATURE:
<223> OTHER INFORMATION: DR5 (174-VL15), (174-VL10), (174-VL3) and
      (174-VL2) binders; CDR1 of VL

<400> SEQUENCE: 20

Arg Ala Ser Gln Ser Ile Ser Thr Tyr Leu Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: DR5 (174-VL15) and (174-VL2) binders; CDR2 of
      VL

<400> SEQUENCE: 21

Lys Ala Ser Ser Leu Ala Ser
1               5

<210> SEQ ID NO 22
<211> LENGTH: 12
<212> TYPE: PRT
<213> ORGANISM: Artificial Sequence
<220> FEATURE:
<223> OTHER INFORMATION: DR5 (174-VL15), (174-VL11), (174-VL10),
      (174-VL3) and (174-VL2) binders; CDR3 of VL

<400> SEQUENCE: 22

Gln Pro Asn Ser Gly Ile Ala Thr Tyr Gly Ala Ala
1               5                   10

<210> SEQ ID NO 23
<211> LENGTH: 117
<212> TYPE: PRT
<213> ORGANISM: Artificial Sequence
<220> FEATURE:
<223> OTHER INFORMATION: DR5 (174-VH7) binder; variable heavy chain (VH)

<400> SEQUENCE: 23

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Arg Tyr
            20                  25                  30

Ala Met Ile Trp Val Arg Gln Ala Pro Gly Lys Gly Leu Glu Tyr Ile
        35                  40                  45

Gly Phe Ile Thr Ser Asp Gly Ser Thr Tyr Tyr Ala Asp Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

Arg Tyr Thr Tyr Ser Asp Gly Thr Asp Leu Trp Gly Arg Gly Thr Leu
            100                 105                 110

Val Thr Val Ser Ser
        115

<210> SEQ ID NO 24
<211> LENGTH: 111
<212> TYPE: PRT
<213> ORGANISM: Artificial Sequence
<220> FEATURE:
<223> OTHER INFORMATION: DR5 (174-VL15) binder; variable light chain
      (VL)

<400> SEQUENCE: 24

Ala Asp Ile Gln Met Thr Gln Ser Pro Ser Thr Leu Ser Ala Ser Val
1               5                   10                  15

Gly Asp Arg Val Thr Ile Thr Cys Arg Ala Ser Gln Ser Ile Ser Thr
            20                  25                  30

Tyr Leu Ser Trp Tyr Gln Gln Lys Pro Gly Lys Ala Pro Lys Arg Leu
        35                  40                  45

Ile Tyr Lys Ala Ser Ser Leu Ala Ser Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Asp Asp Ala Ala Thr Tyr Tyr Cys Gln Pro Asn Ser Gly Ile Ala
                85                  90                  95

Thr Tyr Gly Ala Ala Phe Gly Gly Gly Thr Lys Val Glu Ile Lys
            100                 105                 110

<210> SEQ ID NO 25
<211> LENGTH: 16
<212> TYPE: PRT
<213> ORGANISM: Artificial Sequence
<220> FEATURE:
<223> OTHER INFORMATION: DR5 (174-VH17) binder; CDR2 of VH

<400> SEQUENCE: 25

Phe Ile Thr Ser Asp Ser Ser Ala Tyr Tyr Ala Ser Trp Ala Lys Gly
1               5                   10                  15

<210> SEQ ID NO 26
<211> LENGTH: 117
<212> TYPE: PRT
<213> ORGANISM: Artificial Sequence
<220> FEATURE:
<223> OTHER INFORMATION: DR5 (174-VH17) binder; variable heavy chain

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Ile Ser Arg Tyr
            20                  25                  30

Ala Met Ile Trp Val Arg Gln Ala Pro Gly Lys Gly Leu Glu Tyr Val
        35                  40                  45

Gly Phe Ile Thr Ser Asp Ser Ser Ala Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

```
Arg Tyr Thr Tyr Ser Asp Gly Thr Asp Leu Trp Gly Gln Gly Thr Leu
                100                 105                 110

Val Thr Val Ser Ser
        115

<210> SEQ ID NO 27
<211> LENGTH: 11
<212> TYPE: PRT
<213> ORGANISM: Artificial Sequence
<220> FEATURE:
<223> OTHER INFORMATION: DR5 (174-VL11) binder; CDR1 of VL

<400> SEQUENCE: 27

Gln Ala Ser Gln Ser Ile Ser Thr Tyr Leu Ser
1               5                   10

<210> SEQ ID NO 28
<211> LENGTH: 7
<212> TYPE: PRT
<213> ORGANISM: Artificial Sequence
<220> FEATURE:
<223> OTHER INFORMATION: DR5 (174-VL11), (174-VL10) and (174-VL3)
      binders; CDR2 of VL

<400> SEQUENCE: 28

Lys Ala Ser Thr Leu Ala Ser
1               5

<210> SEQ ID NO 29
<211> LENGTH: 110
<212> TYPE: PRT
<213> ORGANISM: Artificial Sequence
<220> FEATURE:
<223> OTHER INFORMATION: DR5 (174-VL11) binder; variable light chain
      (VL)

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ser Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Pro Asn Ser Gly Ile Ala Thr
                85                  90                  95

Tyr Gly Ala Ala Phe Gly Gly Gly Thr Lys Val Glu Ile Lys
            100                 105                 110

<210> SEQ ID NO 30
<211> LENGTH: 110
<212> TYPE: PRT
<213> ORGANISM: Artificial Sequence
<220> FEATURE:
<223> OTHER INFORMATION: DR5 (174-VL3) binder; variable light chain (VL)

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
```

```
                        20                   25                  30

Leu Ser Trp Tyr Gln Gln Lys Pro Gly Lys Ala Pro Lys Arg Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Pro Asn Ser Gly Ile Ala Thr
                85                  90                  95

Tyr Gly Ala Ala Phe Gly Gly Gly Thr Lys Val Glu Ile Lys
            100                 105                 110

<210> SEQ ID NO 31
<211> LENGTH: 110
<212> TYPE: PRT
<213> ORGANISM: Artificial Sequence
<220> FEATURE:
<223> OTHER INFORMATION: DR5 (174-VL10) binder; variable light chain
      (VL)

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ser Trp Tyr Gln Gln Lys Pro Gly Gln Pro Pro Lys Arg Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Pro Asn Ser Gly Ile Ala Thr
                85                  90                  95

Tyr Gly Ala Ala Phe Gly Gly Gly Thr Lys Val Glu Ile Lys
            100                 105                 110

<210> SEQ ID NO 32
<211> LENGTH: 110
<212> TYPE: PRT
<213> ORGANISM: Artificial Sequence
<220> FEATURE:
<223> OTHER INFORMATION: DR5 (174-VL2) binder; variable light chain (VL)

<400> SEQUENCE: 32

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ser Trp Tyr Gln Gln Lys Pro Gly Lys Ala Pro Lys Arg Leu Ile
            35                  40                  45

Tyr Lys Ala Ser Ser Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Ala Ala Thr Tyr Tyr Cys Gln Pro Asn Ser Gly Ile Ala Thr
                85                  90                  95

Tyr Gly Ala Ala Phe Gly Gly Gly Thr Lys Val Glu Ile Lys
            100                 105                 110
```

<210> SEQ ID NO 33
<211> LENGTH: 5
<212> TYPE: PRT
<213> ORGANISM: Artificial Sequence
<220> FEATURE:
<223> OTHER INFORMATION: FAP(4B9) binder; CDR1 of VH

<400> SEQUENCE: 33

Ser Tyr Ala Met Ser
1               5

<210> SEQ ID NO 34
<211> LENGTH: 17
<212> TYPE: PRT
<213> ORGANISM: Artificial Sequence
<220> FEATURE:
<223> OTHER INFORMATION: FAP(4B9) binder; CDR2 of VH

<400> SEQUENCE: 34

Ala Ile Ile Gly Ser Gly Ala Ser Thr Tyr Tyr Ala Asp Ser Val Lys
1               5                   10                  15

Gly

<210> SEQ ID NO 35
<211> LENGTH: 8
<212> TYPE: PRT
<213> ORGANISM: Artificial Sequence
<220> FEATURE:
<223> OTHER INFORMATION: FAP(4B9) binder; CDR3 of VH

<400> SEQUENCE: 35

Gly Trp Phe Gly Gly Phe Asn Tyr
1               5

<210> SEQ ID NO 36
<211> LENGTH: 12
<212> TYPE: PRT
<213> ORGANISM: Artificial Sequence
<220> FEATURE:
<223> OTHER INFORMATION: FAP(4B9) binder; CDR1 of VL

<400> SEQUENCE: 36

Arg Ala Ser Gln Ser Val Thr Ser Ser Tyr Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: FAP(4B9) binder; CDR2 of VL

<400> SEQUENCE: 37

Val Gly Ser Arg Arg Ala Thr
1               5

<210> SEQ ID NO 38
<211> LENGTH: 9
<212> TYPE: PRT
<213> ORGANISM: Artificial Sequence
<220> FEATURE:
<223> OTHER INFORMATION: FAP(4B9) binder; CDR3 of VL

<400> SEQUENCE: 38

Gln Gln Gly Ile Met Leu Pro Pro Thr

-continued

```
<210> SEQ ID NO 39
<211> LENGTH: 117
<212> TYPE: PRT
<213> ORGANISM: Artificial Sequence
<220> FEATURE:
<223> OTHER INFORMATION: FAP(4B9) binder variable heavy chain (VH)

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Phe Asn Tyr Trp Gly Gln Gly Thr Leu
            100                 105                 110

Val Thr Val Ser Ser
        115

<210> SEQ ID NO 40
<211> LENGTH: 108
<212> TYPE: PRT
<213> ORGANISM: Artificial Sequence
<220> FEATURE:
<223> OTHER INFORMATION: FAP(4B9) binder variable light chain (VL)

<400> SEQUENCE: 40

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105

<210> SEQ ID NO 41
<211> LENGTH: 114
<212> TYPE: PRT
<213> ORGANISM: Artificial Sequence
<220> FEATURE:
<223> OTHER INFORMATION: DR5 (TAA-0005) binder variable heavy chain (VH)

<400> SEQUENCE: 41

Gln Ser Leu Glu Glu Ser Gly Gly Arg Leu Val Thr Pro Gly Thr Pro
1               5                   10                  15
```

Leu Thr Leu Thr Cys Thr Ala Ser Gly Phe Ser Leu Ser Ser Ala Tyr
            20                  25                  30

Met Ser Trp Val Arg Gln Ala Pro Gly Lys Gly Leu Glu Trp Ile Gly
         35                  40                  45

Tyr Ile Tyr Ser Gly Ser Gly Ser Thr Trp Tyr Ala Ser Trp Val Lys
     50                  55                  60

Gly Arg Phe Thr Ile Ser Lys Thr Ser Thr Thr Val Asp Leu Lys Ile
 65                  70                  75                  80

Thr Ser Pro Thr Thr Glu Asp Thr Ala Thr Tyr Phe Cys Ala Arg Gly
                 85                  90                  95

Tyr Ser Thr Met Gly Asp Leu Trp Gly Pro Gly Thr Leu Val Thr Val
            100                 105                 110

Ser Ser

<210> SEQ ID NO 42
<211> LENGTH: 323
<212> TYPE: PRT
<213> ORGANISM: Artificial Sequence
<220> FEATURE:
<223> OTHER INFORMATION: DR5 binder (rabbit) constant heavy chain (CH1)

<400> SEQUENCE: 42

Gly Gln Pro Lys Ala Pro Ser Val Phe Pro Leu Ala Pro Cys Cys Gly
 1               5                  10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
         35                  40                  45

Gly Val Arg Thr Phe Pro Ser Val Arg Gln Ser Ser Gly Leu Tyr Ser
     50                  55                  60

Leu Ser Ser Val Val Ser Val Thr Ser Ser Ser Gln Pro Val Thr Cys
 65                  70                  75                  80

Asn Val Ala His Pro Ala Thr Asn Thr Lys Val Asp Lys Thr Val Ala
                 85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
         115                 120                 125

Ile Ser Arg Thr Pro Glu Val Thr Cys Val Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
         195                 200                 205

Glu Lys Thr Ile Ser Lys Ala Arg Gly Gln Pro Leu Glu Pro Lys Val
     210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Asn Lys Leu Ser Val
        275                 280                 285

Pro Thr Ser Glu Trp Gln Arg Gly Asp Val Phe Thr Cys Ser Val Met
    290                 295                 300

His Glu Ala Leu His Asn His Tyr Thr Gln Lys Ser Ile Ser Arg Ser
305                 310                 315                 320

Pro Gly Lys

<210> SEQ ID NO 43
<211> LENGTH: 5
<212> TYPE: PRT
<213> ORGANISM: Artificial Sequence
<220> FEATURE:
<223> OTHER INFORMATION: DR5 (TAA-0005) binder; CDR1 of VH

<400> SEQUENCE: 43

Ser Ala Tyr Met Ser
1               5

<210> SEQ ID NO 44
<211> LENGTH: 17
<212> TYPE: PRT
<213> ORGANISM: Artificial Sequence
<220> FEATURE:
<223> OTHER INFORMATION: DR5 (TAA-0005) binder; CDR2 of VH

<400> SEQUENCE: 44

Tyr Ile Tyr Ser Gly Ser Gly Ser Thr Trp Tyr Ala Ser Trp Val Lys
1               5                   10                  15

Gly

<210> SEQ ID NO 45
<211> LENGTH: 8
<212> TYPE: PRT
<213> ORGANISM: Artificial Sequence
<220> FEATURE:
<223> OTHER INFORMATION: DR5 (TAA-0005) binder; CDR3 of VH

<400> SEQUENCE: 45

Gly Tyr Ser Thr Met Gly Asp Leu
1               5

<210> SEQ ID NO 46
<211> LENGTH: 108
<212> TYPE: PRT
<213> ORGANISM: Artificial Sequence
<220> FEATURE:
<223> OTHER INFORMATION: DR5 (TAA-0005) binder; variable light chain
      (VL)

<400> SEQUENCE: 46

Gln Val Leu Thr Gln Thr Pro Ser Pro Val Ser Ala Ala Val Gly Gly
1               5                   10                  15

Thr Val Thr Ile Asn Cys Gln Ala Ser Gln Ser Val Tyr Asn Asn Arg
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Gln Cys

```
                65                  70                  75                  80
Asp Asp Ala Ala Thr Tyr Tyr Cys Ala Gly Gly Tyr Ser Gly Asn Ile
                    85                  90                  95

Asn Ala Phe Gly Gly Gly Thr Glu Val Val Val Lys
                100                 105

<210> SEQ ID NO 47
<211> LENGTH: 104
<212> TYPE: PRT
<213> ORGANISM: Artificial Sequence
<220> FEATURE:
<223> OTHER INFORMATION: DR5 (rabbit) binder constant light chain
      (Ckappa)

<400> SEQUENCE: 47

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Ser Val Val
                85                  90                  95

Gln Ser Phe Asn Arg Gly Asp Cys
            100

<210> SEQ ID NO 48
<211> LENGTH: 12
<212> TYPE: PRT
<213> ORGANISM: Artificial Sequence
<220> FEATURE:
<223> OTHER INFORMATION: DR5 (TAA-0005) binder; CDR1 of VL

<400> SEQUENCE: 48

Gln Ala Ser Gln Ser Val Tyr Asn Asn Arg Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: DR5 (TAA-0005) binder; CDR2 of VL

<400> SEQUENCE: 49

Leu Ala Ser Thr Leu Ala Ser
1               5

<210> SEQ ID NO 50
<211> LENGTH: 10
<212> TYPE: PRT
<213> ORGANISM: Artificial Sequence
<220> FEATURE:
<223> OTHER INFORMATION: DR5 (TAA-0005) binder; CDR3 of VL

<400> SEQUENCE: 50

Ala Gly Gly Tyr Ser Gly Asn Ile Asn Ala
1               5                   10
```

<210> SEQ ID NO 51
<211> LENGTH: 117
<212> TYPE: PRT
<213> ORGANISM: Artificial Sequence
<220> FEATURE:
<223> OTHER INFORMATION: DR5 (TAA-0006) binder; variable heavy chain
      (VH)

<400> SEQUENCE: 51

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Asn His
            20                  25                  30

Met Ser Trp Val Arg Gln Ala Pro Gly Lys Gly Leu Glu Trp Ile Gly
        35                  40                  45

Tyr Ile Tyr Ala Gly Ser Gly Ser Ala Tyr Tyr Ala Ser Trp Ala Lys
    50                  55                  60

Gly Arg Phe Thr Ile Ser Arg Thr Ser Thr Val Asp Leu Lys Met
65                  70                  75                  80

Thr Ser Leu Thr Thr Glu Asp Thr Ala Thr Tyr Phe Cys Ala Gly Asp
                85                  90                  95

Ala Gly Ser Ser Tyr Trp Glu Phe Asn Leu Trp Gly Pro Gly Thr Leu
            100                 105                 110

Val Thr Val Ser Ser
        115

<210> SEQ ID NO 52
<211> LENGTH: 5
<212> TYPE: PRT
<213> ORGANISM: Artificial Sequence
<220> FEATURE:
<223> OTHER INFORMATION: DR5 (TAA-0006) binder; CDR1 of VH

<400> SEQUENCE: 52

Ser Asn His Met Ser
1               5

<210> SEQ ID NO 53
<211> LENGTH: 17
<212> TYPE: PRT
<213> ORGANISM: Artificial Sequence
<220> FEATURE:
<223> OTHER INFORMATION: DR5 (TAA-0006) binder; CDR2 of VH

<400> SEQUENCE: 53

Tyr Ile Tyr Ala Gly Ser Gly Ser Ala Tyr Tyr Ala Ser Trp Ala Lys
1               5                   10                  15

Gly

<210> SEQ ID NO 54
<211> LENGTH: 11
<212> TYPE: PRT
<213> ORGANISM: Artificial Sequence
<220> FEATURE:
<223> OTHER INFORMATION: DR5 (TAA-0006) binder; CDR3 of VH

<400> SEQUENCE: 54

Asp Ala Gly Ser Ser Tyr Trp Glu Phe Asn Leu
1               5                   10

<210> SEQ ID NO 55
<211> LENGTH: 110

-continued

```
<212> TYPE: PRT
<213> ORGANISM: Artificial Sequence
<220> FEATURE:
<223> OTHER INFORMATION: DR5 (TAA-0006) binder; variable light chain
      (VL)

<400> SEQUENCE: 55

Leu Val Met Thr Gln Thr Pro Ser Ser Thr Ser Glu Pro Val Gly Gly
1               5                   10                  15

Thr Val Thr Ile Lys Cys Gln Ala Ser Gln Ser Ile Gly Ser Ser Leu
            20                  25                  30

Ser Trp Tyr Gln Gln Lys Pro Gly Gln Pro Pro Lys Leu Leu Ile Tyr
        35                  40                  45

His Ala Ser Thr Leu Ala Ser Gly Val Pro Ser Arg Phe Ser Gly Ser
    50                  55                  60

Arg Ser Gly Ile Gln Thr Thr Leu Thr Ile Ser Gly Val Gln Cys Asp
65                  70                  75                  80

Asp Ala Ala Thr Tyr Tyr Cys Leu Gly Val Ala Asp Ala Arg Arg Asp
                85                  90                  95

Asp Gly Phe Ala Phe Gly Gly Gly Thr Glu Val Val Val Lys
            100                 105                 110

<210> SEQ ID NO 56
<211> LENGTH: 104
<212> TYPE: PRT
<213> ORGANISM: Artificial Sequence
<220> FEATURE:
<223> OTHER INFORMATION: DR5 (TAA-0006) binder; constant light chain
      (ckappa)

<400> SEQUENCE: 56

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 57
<211> LENGTH: 11
<212> TYPE: PRT
<213> ORGANISM: Artificial Sequence
<220> FEATURE:
<223> OTHER INFORMATION: DR5 (TAA-0006) binder; CDR1 of VL

<400> SEQUENCE: 57

Gln Ala Ser Gln Ser Ile Gly Ser Ser Leu Ser
1               5                   10

<210> SEQ ID NO 58
<211> LENGTH: 7
<212> TYPE: PRT
<213> ORGANISM: Artificial Sequence
```

```
<220> FEATURE:
<223> OTHER INFORMATION: DR5 (TAA-0006) binder; CDR2 of VL

<400> SEQUENCE: 58

His Ala Ser Thr Leu Ala Ser
1               5

<210> SEQ ID NO 59
<211> LENGTH: 13
<212> TYPE: PRT
<213> ORGANISM: Artificial Sequence
<220> FEATURE:
<223> OTHER INFORMATION: DR5 (TAA-0006) binder; CDR3 of VL

<400> SEQUENCE: 59

Leu Gly Val Ala Asp Ala Arg Arg Asp Asp Gly Phe Ala
1               5                   10

<210> SEQ ID NO 60
<211> LENGTH: 117
<212> TYPE: PRT
<213> ORGANISM: Artificial Sequence
<220> FEATURE:
<223> OTHER INFORMATION: DR5 (TAA-0010) binder, variable heavy chain
      (VH)

<400> SEQUENCE: 60

Gln Ser Leu Glu Glu Ser Gly Gly Arg Leu Val Lys Pro Asp Glu Thr
1               5                   10                  15

Leu Thr Leu Thr Cys Thr Val Ser Gly Phe Ser Leu Ser Ser Asn Ala
            20                  25                  30

Ile Ser Trp Val Arg Gln Ala Pro Gly Met Gly Leu Glu Trp Ile Gly
        35                  40                  45

Ile Ile Gly Ser Ser Gly Tyr Thr Tyr Tyr Ala Ser Trp Ala Lys Gly
    50                  55                  60

Arg Phe Thr Val Ser Lys Thr Ser Thr Thr Val Asp Leu Glu Ile Ala
65                  70                  75                  80

Ser Pro Thr Thr Glu Asp Thr Ala Thr Tyr Phe Cys Ala Arg Gly Tyr
                85                  90                  95

Ser Gly Ala Ser Asp Tyr Ser Phe Asn Leu Trp Gly Pro Gly Thr Leu
            100                 105                 110

Val Thr Val Ser Ser
        115

<210> SEQ ID NO 61
<211> LENGTH: 5
<212> TYPE: PRT
<213> ORGANISM: Artificial Sequence
<220> FEATURE:
<223> OTHER INFORMATION: DR5 (TAA-0010) binder; CDR1 of VH

<400> SEQUENCE: 61

Ser Asn Ala Ile Ser
1               5

<210> SEQ ID NO 62
<211> LENGTH: 16
<212> TYPE: PRT
<213> ORGANISM: Artificial Sequence
<220> FEATURE:
<223> OTHER INFORMATION: DR5 (TAA-0010) binder; CDR2 of VH

<400> SEQUENCE: 62
```

Ile Ile Gly Ser Ser Gly Tyr Thr Tyr Tyr Ala Ser Trp Ala Lys Gly
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: DR5 (TAA-0010) binder; CDR3 of VH

<400> SEQUENCE: 63

Gly Tyr Ser Gly Ala Ser Asp Tyr Ser Phe Asn Leu
1               5                   10

<210> SEQ ID NO 64
<211> LENGTH: 110
<212> TYPE: PRT
<213> ORGANISM: Artificial Sequence
<220> FEATURE:
<223> OTHER INFORMATION: DR5 (TAA-0010) binder; variable light chain
      (VL)

<400> SEQUENCE: 64

Ala Tyr Asp Met Thr Gln Thr Pro Asp Ser Val Glu Val Ala Val Gly
1               5                   10                  15

Gly Thr Val Thr Ile Lys Cys Gln Ala Ser Gln Thr Ile Gly Asp Ala
                20                  25                  30

Leu Ala Trp Tyr Gln Gln Lys Pro Gly Gln Arg Pro Asn Leu Leu Ile
            35                  40                  45

Tyr Arg Thr Ser Thr Leu Ala Ser Gly Val Pro Ser Arg Phe Ser Gly
    50                  55                  60

Ser Gly Ser Gly Thr His Phe Thr Leu Thr Ile Ser Gly Val Glu Cys
65                  70                  75                  80

Ala Asp Ala Ala Thr Tyr Tyr Cys Gln Gln Gly Ala Thr Tyr Asn Asn
                85                  90                  95

Val Leu Asn Thr Phe Gly Gly Gly Thr Glu Val Val Val Lys
            100                 105                 110

<210> SEQ ID NO 65
<211> LENGTH: 11
<212> TYPE: PRT
<213> ORGANISM: Artificial Sequence
<220> FEATURE:
<223> OTHER INFORMATION: DR5 (TAA-0010) binder; CDR1 of VL

<400> SEQUENCE: 65

Gln Ala Ser Gln Thr Ile Gly Asp Ala Leu Ala
1               5                   10

<210> SEQ ID NO 66
<211> LENGTH: 7
<212> TYPE: PRT
<213> ORGANISM: Artificial Sequence
<220> FEATURE:
<223> OTHER INFORMATION: DR5 (TAA-0010) binder; CDR2 of VL

<400> SEQUENCE: 66

Arg Thr Ser Thr Leu Ala Ser
1               5

<210> SEQ ID NO 67
<211> LENGTH: 12
<212> TYPE: PRT
<213> ORGANISM: Artificial Sequence
<220> FEATURE:
<223> OTHER INFORMATION: DR5 (TAA-0010) binder; CDR3 of VL

<400> SEQUENCE: 67

Gln Gln Gly Ala Thr Tyr Asn Asn Val Leu Asn Thr
1               5                   10

<210> SEQ ID NO 68
<211> LENGTH: 117
<212> TYPE: PRT
<213> ORGANISM: Artificial Sequence
<220> FEATURE:
<223> OTHER INFORMATION: DR5 (TAA-0013) binder; variable heavy chain
      (VH)

<400> SEQUENCE: 68

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr His
            20                  25                  30

Met Ser Trp Val Arg Gln Ala Pro Gly Lys Gly Leu Glu Trp Ile Gly
        35                  40                  45

Tyr Ile Tyr Ala Gly Ser Ala Ser Thr Trp Tyr Ala Ser Trp Val Lys
    50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Asp
                85                  90                  95

Ala Gly Ser Ser Tyr Trp Glu Phe Asn Leu Trp Gly Pro Gly Thr Leu
            100                 105                 110

Val Thr Val Ser Ser
        115

<210> SEQ ID NO 69
<211> LENGTH: 5
<212> TYPE: PRT
<213> ORGANISM: Artificial Sequence
<220> FEATURE:
<223> OTHER INFORMATION: DR5 (TAA-0013) binder; CDR1 of VH

<400> SEQUENCE: 69

Ser Tyr His Met Ser
1               5

<210> SEQ ID NO 70
<211> LENGTH: 17
<212> TYPE: PRT
<213> ORGANISM: Artificial Sequence
<220> FEATURE:
<223> OTHER INFORMATION: DR5 (TAA-0013) binder; CDR2 of VH

<400> SEQUENCE: 70

Tyr Ile Tyr Ala Gly Ser Ala Ser Thr Trp Tyr Ala Ser Trp Val Lys
1               5                   10                  15

Gly

<210> SEQ ID NO 71
<211> LENGTH: 110
<212> TYPE: PRT
<213> ORGANISM: Artificial Sequence
<220> FEATURE:
<223> OTHER INFORMATION: DR5 (TAA-0013) binder;variable light chain (VL)

<400> SEQUENCE: 71

Leu Val Met Thr Gln Thr Pro Ser Ser Thr Ser Glu Pro Val Gly Gly
1               5                   10                  15

Thr Val Thr Ile Lys Cys Gln Ala Ser Gln Ser Ile Gly Ser Ser Leu
            20                  25                  30

Ser Trp Tyr Gln Gln Thr Pro Gly Gln Pro Pro Lys Leu Leu Ile Tyr
        35                  40                  45

Thr Ala Ser Ser Leu Ala Ser Ser Val Pro Lys Arg Phe Ser Gly Ser
    50                  55                  60

Arg Ser Gly Thr Gln Phe Thr Leu Thr Ile Ser Gly Val Gln Cys Ala
65                  70                  75                  80

Asp Ala Ala Thr Tyr Tyr Cys Leu Gly Ile Asp Asp Val Arg Arg Asp
                85                  90                  95

Asp Gly Phe Ala Phe Gly Gly Gly Thr Glu Val Val Val Lys
            100                 105                 110

<210> SEQ ID NO 72
<211> LENGTH: 7
<212> TYPE: PRT
<213> ORGANISM: Artificial Sequence
<220> FEATURE:
<223> OTHER INFORMATION: DR5 (TAA-0013) binder; CDR2 of VL

<400> SEQUENCE: 72

Thr Ala Ser Ser Leu Ala Ser
1               5

<210> SEQ ID NO 73
<211> LENGTH: 13
<212> TYPE: PRT
<213> ORGANISM: Artificial Sequence
<220> FEATURE:
<223> OTHER INFORMATION: DR5 (TAA-0013) binder; CDR3 of VL

<400> SEQUENCE: 73

Leu Gly Ile Asp Asp Val Arg Arg Asp Asp Gly Phe Ala
1               5                   10

<210> SEQ ID NO 74
<211> LENGTH: 117
<212> TYPE: PRT
<213> ORGANISM: Artificial Sequence
<220> FEATURE:
<223> OTHER INFORMATION: DR5 (TAA-0019) binder, variable heavy chain
      (VH)

<400> SEQUENCE: 74

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Met Ser Trp Val Arg Gln Ala Pro Gly Lys Gly Leu Glu Trp Ile Gly
        35                  40                  45

Ile Ile Ser Ser Ser Gly Thr Thr Tyr Tyr Ala Ser Trp Ala Lys Gly
    50                  55                  60

Arg Phe Thr Ile Ser Lys Thr Ser Thr Thr Val Asp Leu Lys Val Thr
65                  70                  75                  80

Ser Pro Thr Thr Glu Asp Thr Ala Thr Tyr Phe Cys Ala Arg Glu Thr
                85                  90                  95

Tyr Tyr Gly Tyr Ser Tyr Ala Ala Gly Leu Trp Gly Pro Gly Thr Leu

Val Thr Val Ser Ser
        115

<210> SEQ ID NO 75
<211> LENGTH: 5
<212> TYPE: PRT
<213> ORGANISM: Artificial Sequence
<220> FEATURE:
<223> OTHER INFORMATION: DR5 (TAA-0019) binder; CDR1 of VH

<400> SEQUENCE: 75

Asn Tyr Ala Met Ser
1               5

<210> SEQ ID NO 76
<211> LENGTH: 16
<212> TYPE: PRT
<213> ORGANISM: Artificial Sequence
<220> FEATURE:
<223> OTHER INFORMATION: DR5 (TAA-0019) binder; CDR2 of VH

<400> SEQUENCE: 76

Ile Ile Ser Ser Ser Gly Thr Thr Tyr Tyr Ala Ser Trp Ala Lys Gly
1               5                   10                  15

<210> SEQ ID NO 77
<211> LENGTH: 12
<212> TYPE: PRT
<213> ORGANISM: Artificial Sequence
<220> FEATURE:
<223> OTHER INFORMATION: DR5 (TAA-0019) binder; CDR3 of VH

<400> SEQUENCE: 77

Glu Thr Tyr Tyr Gly Tyr Ser Tyr Ala Ala Gly Leu
1               5                   10

<210> SEQ ID NO 78
<211> LENGTH: 110
<212> TYPE: PRT
<213> ORGANISM: Artificial Sequence
<220> FEATURE:
<223> OTHER INFORMATION: DR5 (TAA-0019) binder; variable light chain
      (VL)

<400> SEQUENCE: 78

Ala Leu Val Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Phe Gln Gln Lys Pro Gly Gln Pro Pro Lys Leu Leu Ile
        35                  40                  45

Tyr Glu Thr Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Ser Ser Trp His Ser Ile Ser
                85                  90                  95

Thr Asp Cys Ala Phe Gly Gly Gly Thr Glu Val Val Val Lys
            100                 105                 110

<210> SEQ ID NO 79
<211> LENGTH: 11

```
<212> TYPE: PRT
<213> ORGANISM: Artificial Sequence
<220> FEATURE:
<223> OTHER INFORMATION: DR5 (TAA-0019) binder; CDR1 of VL

<400> SEQUENCE: 79

Gln Ala Ser Gln Asn Ile Tyr Ser Asn Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: DR5 (TAA-0019) binder; CDR2 of VL

<400> SEQUENCE: 80

Glu Thr Ser Lys Leu Ala Ser
1               5

<210> SEQ ID NO 81
<211> LENGTH: 12
<212> TYPE: PRT
<213> ORGANISM: Artificial Sequence
<220> FEATURE:
<223> OTHER INFORMATION: DR5 (TAA-0019) binder; CDR3 of VL

<400> SEQUENCE: 81

Gln Ser Ser Trp His Ser Ile Ser Thr Asp Cys Ala
1               5                   10

<210> SEQ ID NO 82
<211> LENGTH: 119
<212> TYPE: PRT
<213> ORGANISM: Artificial Sequence
<220> FEATURE:
<223> OTHER INFORMATION: DR5 (TAA-0016) binder; variable heavy chain
      (VH)

<400> SEQUENCE: 82

Gln Ser Leu Glu Glu Ser Gly Gly Arg Leu Val Lys Pro Asp Glu Thr
1               5                   10                  15

Leu Thr Leu Thr Cys Thr Val Ser Gly Phe Ser Leu Asn Asn Tyr Ala
            20                  25                  30

Met Ser Trp Val Arg Gln Ala Pro Gly Lys Gly Leu Glu Trp Ile Gly
        35                  40                  45

Met Ile Asn Lys Tyr Gly Thr Lys Tyr Ala Thr Trp Thr Lys Gly
    50                  55                  60

Arg Ala Thr Ile Ser Lys Thr Ser Thr Leu Asp Leu Glu Ile Thr
65                  70                  75                  80

Ser Pro Thr Thr Glu Asp Thr Ala Thr Tyr Phe Cys Ala Arg Val Arg
                85                  90                  95

Tyr Ala Gly Asp Asp Tyr Ala Glu Trp Leu Asp Val Trp Gly Gln Gly
            100                 105                 110

Ile Leu Val Thr Val Ser Ser
        115

<210> SEQ ID NO 83
<211> LENGTH: 16
<212> TYPE: PRT
<213> ORGANISM: Artificial Sequence
<220> FEATURE:
<223> OTHER INFORMATION: DR5 (TAA-0016) binder; CDR2 of VH
```

```
<400> SEQUENCE: 83

Met Ile Asn Lys Tyr Gly Thr Lys Tyr Ala Thr Trp Thr Lys Gly
1               5                   10                  15

<210> SEQ ID NO 84
<211> LENGTH: 14
<212> TYPE: PRT
<213> ORGANISM: Artificial Sequence
<220> FEATURE:
<223> OTHER INFORMATION: DR5 (TAA-0016) binder; CDR3 of VH

<400> SEQUENCE: 84

Val Arg Tyr Ala Gly Asp Asp Tyr Ala Glu Trp Leu Asp Val
1               5                   10

<210> SEQ ID NO 85
<211> LENGTH: 113
<212> TYPE: PRT
<213> ORGANISM: Artificial Sequence
<220> FEATURE:
<223> OTHER INFORMATION: DR5 (TAA-0016) binder; variable light chain
      (VL)

<400> SEQUENCE: 85

Ala Asp Ile Val Met Thr Gln Thr Ala Ser Pro Val Ser Ala Val
1               5                   10                  15

Gly Gly Thr Val Thr Ile Asn Cys Gln Ala Ser Gln Ser Ile Ser Ser
                20                  25                  30

Ser Tyr Val Ser Trp Tyr Gln Gln Lys Pro Gly Gln Pro Pro Lys Leu
            35                  40                  45

Leu Ile Tyr Lys Ala Ser Thr Leu Ala Ser Gly Val Pro Ser Arg Phe
    50                  55                  60

Ser Gly Ser Gly Ser Gly Thr Gln Leu Ser Leu Thr Ile Arg Gly Val
65                  70                  75                  80

Gln Cys Asp Asp Ala Ala Thr Tyr Tyr Cys Leu Tyr Gly Tyr Ser Asp
                85                  90                  95

Val Ser Ser Ser Glu Tyr Val Phe Gly Gly Gly Thr Glu Val Val Val
                100                 105                 110

Arg

<210> SEQ ID NO 86
<211> LENGTH: 12
<212> TYPE: PRT
<213> ORGANISM: Artificial Sequence
<220> FEATURE:
<223> OTHER INFORMATION: DR5 (TAA-0016) binder; CDR1 of VL

<400> SEQUENCE: 86

Gln Ala Ser Gln Ser Ile Ser Ser Ser Tyr Val Ser
1               5                   10

<210> SEQ ID NO 87
<211> LENGTH: 13
<212> TYPE: PRT
<213> ORGANISM: Artificial Sequence
<220> FEATURE:
<223> OTHER INFORMATION: DR5 (TAA-0016) binder; CDR3 of VL

<400> SEQUENCE: 87

Leu Tyr Gly Tyr Ser Asp Val Ser Ser Ser Glu Tyr Val
1               5                   10
```

```
<210> SEQ ID NO 88
<211> LENGTH: 114
<212> TYPE: PRT
<213> ORGANISM: Artificial Sequence
<220> FEATURE:
<223> OTHER INFORMATION: DR5 (TAA-0011) binder; variable heavy chain
      (VH)

<400> SEQUENCE: 88

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Ile Ser Arg Tyr Ala
            20                  25                  30

Met Ile Trp Val Arg Gln Ala Pro Gly Glu Gly Leu Glu Tyr Ile Gly
        35                  40                  45

Phe Ile Thr Ser Asp Ser Ser Ala Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Tyr Thr
                85                  90                  95

Tyr Ser Asp Gly Thr Asp Leu Trp Gly Pro Gly Thr Leu Val Thr Val
            100                 105                 110

Ser Ser

<210> SEQ ID NO 89
<211> LENGTH: 111
<212> TYPE: PRT
<213> ORGANISM: Artificial Sequence
<220> FEATURE:
<223> OTHER INFORMATION: DR5 (TAA-0011) binder; variable light chain
      (VL)

<400> SEQUENCE: 89

Ala Asp Ile Val Met Thr Gln Thr Pro Ala Ser Val Ser Glu Pro Val
1               5                   10                  15

Gly Gly Thr Val Thr Ile Lys Cys Gln Ala Ser Gln Ser Ile Ser Thr
            20                  25                  30

Tyr Leu Ser Trp Tyr Gln Gln Lys Pro Gly Gln Pro Pro Lys Arg Leu
        35                  40                  45

Ile Tyr Lys Ala Ser Thr Leu Ala Ser Gly Val Pro Ser Arg Phe Lys
    50                  55                  60

Gly Ser Gly Ser Gly Thr Asp Phe Thr Leu Thr Ile Arg Asp Leu Glu
65                  70                  75                  80

Cys Ala Asp Ala Ala Thr Tyr Tyr Cys Gln Pro Asn Ser Gly Ile Ala
                85                  90                  95

Thr Tyr Gly Ala Ala Phe Gly Gly Gly Thr Glu Val Val Val Lys
            100                 105                 110

<210> SEQ ID NO 90
<211> LENGTH: 114
<212> TYPE: PRT
<213> ORGANISM: Artificial Sequence
<220> FEATURE:
<223> OTHER INFORMATION: DR5 (TAA-0052) binder; variable heavy chain
      (VH)

<400> SEQUENCE: 90

Gln Ser Val Glu Glu Ser Gly Gly Arg Leu Val Thr Pro Gly Thr Pro
1               5                   10                  15
```

```
Leu Thr Leu Thr Cys Thr Val Ser Gly Phe Ser Ile Ser Arg Tyr Ala
            20                  25                  30

Met Ile Trp Val Arg Gln Ala Pro Gly Glu Gly Leu Glu Tyr Ile Gly
        35                  40                  45

Phe Ile Thr Ser Asp Ser Ser Ala Tyr Tyr Ala Ser Trp Ala Lys Gly
    50                  55                  60

Arg Phe Thr Ile Ser Lys Thr Ser Thr Thr Val Asp Leu Lys Met Thr
65                  70                  75                  80

Ser Pro Thr Thr Glu Asp Thr Ala Thr Tyr Phe Cys Ala Arg Tyr Thr
                85                  90                  95

Tyr Ser Asp Gly Thr Asp Leu Trp Gly Pro Gly Thr Leu Val Thr Val
                100                 105                 110

Ser Ser
```

<210> SEQ ID NO 91
<211> LENGTH: 330
<212> TYPE: PRT
<213> ORGANISM: Artificial Sequence
<220> FEATURE:
<223> OTHER INFORMATION: DR5 (TAA-0052) binder; constant heavy chain
      (CH1)

<400> SEQUENCE: 91

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 92
<211> LENGTH: 111
<212> TYPE: PRT
<213> ORGANISM: Artificial Sequence
<220> FEATURE:
<223> OTHER INFORMATION: DR5 (TAA-0052) binder; variable light chain
      (VL)

<400> SEQUENCE: 92

Ala Asp Ile Val Met Thr Gln Thr Pro Ala Ser Val Ser Glu Pro Val
1               5                   10                  15

Gly Gly Thr Val Thr Ile Lys Cys Gln Ala Ser Gln Ser Ile Ser Thr
            20                  25                  30

Tyr Leu Ser Trp Tyr Gln Gln Lys Pro Gly Gln Pro Pro Lys Arg Leu
        35                  40                  45

Ile Tyr Lys Ala Ser Thr Leu Ala Ser Gly Val Pro Ser Arg Phe Lys
    50                  55                  60

Gly Ser Gly Ser Gly Thr Asp Phe Thr Leu Thr Ile Arg Asp Leu Glu
65                  70                  75                  80

Ser Ala Asp Ala Ala Thr Tyr Tyr Cys Gln Pro Asn Ser Gly Ile Ala
                85                  90                  95

Thr Tyr Gly Ala Ala Phe Gly Gly Gly Thr Glu Val Val Val Lys
            100                 105                 110

<210> SEQ ID NO 93
<211> LENGTH: 107
<212> TYPE: PRT
<213> ORGANISM: Artificial Sequence
<220> FEATURE:
<223> OTHER INFORMATION: DR5 (TAA-0052) binder; Constant light chain
      (Ckappa)

<400> SEQUENCE: 93

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

-continued

<210> SEQ ID NO 94
<211> LENGTH: 117
<212> TYPE: PRT
<213> ORGANISM: Artificial Sequence
<220> FEATURE:
<223> OTHER INFORMATION: DR5 (18F11) binder_variable heavy chain (VH)

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Gly Val Arg Lys Lys Phe Asp Tyr Trp Gly Gln Gly Thr Leu
            100                 105                 110

Val Thr Val Ser Ser
        115

<210> SEQ ID NO 95
<211> LENGTH: 108
<212> TYPE: PRT
<213> ORGANISM: Artificial Sequence
<220> FEATURE:
<223> OTHER INFORMATION: DR5(18F11) binder_Variable light chain (VL)

<400> SEQUENCE: 95

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Pro Pro
                85                  90                  95

Ile Thr Phe Gly Gln Gly Thr Lys Val Glu Ile Lys
            100                 105

<210> SEQ ID NO 96
<211> LENGTH: 8
<212> TYPE: PRT
<213> ORGANISM: Artificial Sequence
<220> FEATURE:
<223> OTHER INFORMATION: DR5(22E9) binder; CDR3 of VH

<400> SEQUENCE: 96

Gly Val Arg Ile Ser Phe Asp Tyr
1               5

```
<210> SEQ ID NO 97
<211> LENGTH: 9
<212> TYPE: PRT
<213> ORGANISM: Artificial Sequence
<220> FEATURE:
<223> OTHER INFORMATION: DR5 (18F11) binder; CDR3 of VL

<400> SEQUENCE: 97

Gln Gln Gly Gln Leu Pro Pro Ile Thr
1               5

<210> SEQ ID NO 98
<211> LENGTH: 8
<212> TYPE: PRT
<213> ORGANISM: Artificial Sequence
<220> FEATURE:
<223> OTHER INFORMATION: DR5 (18F11) binder; CDR3 of VH

<400> SEQUENCE: 98

Gly Val Arg Lys Lys Phe Asp Tyr
1               5

<210> SEQ ID NO 99
<211> LENGTH: 9
<212> TYPE: PRT
<213> ORGANISM: Artificial Sequence
<220> FEATURE:
<223> OTHER INFORMATION: DR5 (22E9) binder, CDR3 of VL

<400> SEQUENCE: 99

Gln Gln Gly Ser Asn Gln Pro Val Thr
1               5

<210> SEQ ID NO 100
<211> LENGTH: 117
<212> TYPE: PRT
<213> ORGANISM: Artificial Sequence
<220> FEATURE:
<223> OTHER INFORMATION: DR5(22E9) binder; variable heavy chain (VH)

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Ile Ser Phe Asp Tyr Trp Gly Gln Gly Thr Leu
            100                 105                 110

Val Thr Val Ser Ser
        115

<210> SEQ ID NO 101
<211> LENGTH: 108
<212> TYPE: PRT
<213> ORGANISM: Artificial Sequence
<220> FEATURE:
<223> OTHER INFORMATION: DR5 (22E9) binder; variable light chain (VL)
```

<400> SEQUENCE: 101

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Asn Gln Pro
                85                  90                  95

Val Thr Phe Gly Gln Gly Thr Lys Val Glu Ile Lys
            100                 105

<210> SEQ ID NO 102
<211> LENGTH: 117
<212> TYPE: PRT
<213> ORGANISM: Artificial Sequence
<220> FEATURE:
<223> OTHER INFORMATION: DR5(21H3)binder; variable heavy chain (VH)

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Gly Ala Arg Val Ser Phe Asp Tyr Trp Gly Gln Gly Thr Leu
            100                 105                 110

Val Thr Val Ser Ser
        115

<210> SEQ ID NO 103
<211> LENGTH: 108
<212> TYPE: PRT
<213> ORGANISM: Artificial Sequence
<220> FEATURE:
<223> OTHER INFORMATION: DR5(21H3) binder; variable light chain (VL)

<400> SEQUENCE: 103

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Gln Pro Pro
                85                  90                  95

Ile Thr Phe Gly Gln Gly Thr Lys Val Glu Ile Lys
            100                 105

<210> SEQ ID NO 104
<211> LENGTH: 8
<212> TYPE: PRT
<213> ORGANISM: Artificial Sequence
<220> FEATURE:
<223> OTHER INFORMATION: DR5(21H3) binder; CDR3 of VH

<400> SEQUENCE: 104

Gly Ala Arg Val Ser Phe Asp Tyr
1               5

<210> SEQ ID NO 105
<211> LENGTH: 9
<212> TYPE: PRT
<213> ORGANISM: Artificial Sequence
<220> FEATURE:
<223> OTHER INFORMATION: DR5 (21H3) binder; CDR3 of VL

<400> SEQUENCE: 105

Gln Gln Gly Ser Gln Pro Pro Ile Thr
1               5

<210> SEQ ID NO 106
<211> LENGTH: 117
<212> TYPE: PRT
<213> ORGANISM: Artificial Sequence
<220> FEATURE:
<223> OTHER INFORMATION: DR5(20F2) binder; variable heavy chain (VH)

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Lys Gly Phe Asp Tyr Trp Gly Gln Gly Thr Leu
            100                 105                 110

Val Thr Val Ser Ser
        115

<210> SEQ ID NO 107
<211> LENGTH: 108
<212> TYPE: PRT
<213> ORGANISM: Artificial Sequence
<220> FEATURE:
<223> OTHER INFORMATION: DR5(20F2) binder; variable light chain (VL)

<400> SEQUENCE: 107

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Glu Ser Pro Pro
                85                  90                  95

Pro Thr Phe Gly Gln Gly Thr Lys Val Glu Ile Lys
            100                 105
```

<210> SEQ ID NO 108
<211> LENGTH: 8
<212> TYPE: PRT
<213> ORGANISM: Artificial Sequence
<220> FEATURE:
<223> OTHER INFORMATION: DR5(20F2) binder, CDR3 of VH

<400> SEQUENCE: 108

```
Gly Val Arg Lys Gly Phe Asp Tyr
1               5
```

<210> SEQ ID NO 109
<211> LENGTH: 9
<212> TYPE: PRT
<213> ORGANISM: Artificial Sequence
<220> FEATURE:
<223> OTHER INFORMATION: DR5(20F2) binder; CDR3 of VL

<400> SEQUENCE: 109

```
Gln Gln Gly Glu Ser Pro Pro Pro Thr
1               5
```

<210> SEQ ID NO 110
<211> LENGTH: 107
<212> TYPE: PRT
<213> ORGANISM: Artificial Sequence
<220> FEATURE:
<223> OTHER INFORMATION: Drozitumab_variable light chain (VL)

<400> SEQUENCE: 110

```
Ser Glu Leu Thr Gln Asp Pro Ala Val Ser Val Ala Leu Gly Gln Thr
1               5                   10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ala Asp Ser Ser Gly Asn His Val
                85                  90                  95

Val Phe Gly Gly Gly Thr Lys Leu Thr Val Leu
            100                 105
```

<210> SEQ ID NO 111
<211> LENGTH: 717
<212> TYPE: PRT
<213> ORGANISM: Artificial Sequence
<220> FEATURE:
<223> OTHER INFORMATION: Drozitumab-3F2 VHVL-scFv (HC) pETR6606

<400> SEQUENCE: 111

```
Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Ser Gly Gly Gly Ser Gly Gly Gly Ser Gly Gly
        450                 455                 460

Gly Gly Ser Gly Gly Gly Ser Glu Val Gln Leu Leu Glu Ser Gly
465                 470                 475                 480

Gly Gly Leu Val Gln Pro Gly Gly Ser Leu Arg Leu Ser Cys Ala Ala
                485                 490                 495

Ser Gly Phe Thr Phe Ser Ser Tyr Ala Met Ser Trp Val Arg Gln Ala
            500                 505                 510

Pro Gly Lys Cys Leu Glu Trp Val Ser Ala Ile Ser Gly Ser Gly Gly
        515                 520                 525

Ser Thr Tyr Tyr Ala Asp Ser Val Lys Gly Arg Phe Thr Ile Ser Arg
530                 535                 540

Asp Asn Ser Lys Asn Thr Leu Tyr Leu Gln Met Asn Ser Leu Arg Ala
545                 550                 555                 560

Glu Asp Thr Ala Val Tyr Tyr Cys Ala Lys Gly Trp Phe Gly Gly Phe
                565                 570                 575

Asn Tyr Trp Gly Gln Gly Thr Leu Val Thr Val Ser Ser Gly Gly Gly
            580                 585                 590

Gly Ser Gly Gly Gly Gly Ser Gly Gly Gly Gly Ser Gly Gly Gly Gly
        595                 600                 605

Ser Glu Ile Val Leu Thr Gln Ser Pro Gly Thr Leu Ser Leu Tyr Pro
610                 615                 620

Gly Glu Arg Ala Thr Leu Ser Cys Arg Ala Ser Gln Ser Val Thr Ser
625                 630                 635                 640

Ser Tyr Leu Ala Trp Tyr Gln Gln Lys Pro Gly Gln Ala Pro Arg Leu
                645                 650                 655

Leu Ile Asn Val Gly Ser Arg Arg Ala Thr Gly Ile Pro Asp Arg Phe
            660                 665                 670

Ser Gly Ser Gly Ser Gly Thr Asp Phe Thr Leu Thr Ile Ser Arg Leu
        675                 680                 685

Glu Pro Glu Asp Phe Ala Val Tyr Tyr Cys Gln Gln Gly Ile Met Leu
690                 695                 700

Pro Pro Thr Phe Gly Cys Gly Thr Lys Val Glu Ile Lys
705                 710                 715
```

<210> SEQ ID NO 112
<211> LENGTH: 708
<212> TYPE: PRT
<213> ORGANISM: Artificial Sequence
<220> FEATURE:
<223> OTHER INFORMATION: Drozitumab-FAP (4G8) VHVL-scFv (HC)pETR7342

<400> SEQUENCE: 112

```
Glu Val Gln Leu Val Gln Ser Gly Gly Gly Val Glu Arg Pro Gly Gly
1               5                   10                  15
```

```
Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
```

```
                435                 440                 445
Pro Gly Gly Gly Ser Gly Gly Gly Ser Gly Gly Gly Ser Glu
    450                 455                 460
Val Gln Leu Leu Glu Ser Gly Gly Leu Val Gln Pro Gly Gly Ser
465                 470                 475                 480
Leu Arg Leu Ser Cys Ala Ala Ser Gly Phe Thr Phe Ser Ser Tyr Ala
                485                 490                 495
Met Ser Trp Val Arg Gln Ala Pro Gly Lys Cys Leu Glu Trp Val Ser
            500                 505                 510
Ala Ile Ser Gly Ser Gly Gly Ser Thr Tyr Tyr Ala Asp Ser Val Lys
        515                 520                 525
Gly Arg Phe Thr Ile Ser Arg Asp Asn Ser Lys Asn Thr Leu Tyr Leu
    530                 535                 540
Gln Met Asn Ser Leu Arg Ala Glu Asp Thr Ala Val Tyr Tyr Cys Ala
545                 550                 555                 560
Lys Gly Trp Leu Gly Asn Phe Asp Tyr Trp Gly Gln Gly Thr Leu Val
                565                 570                 575
Thr Val Ser Ser Gly Gly Gly Gly Ser Gly Gly Gly Gly Ser Gly Gly
                580                 585                 590
Gly Gly Ser Gly Gly Gly Gly Ser Glu Ile Val Leu Thr Gln Ser Pro
            595                 600                 605
Gly Thr Leu Ser Leu Ser Pro Gly Glu Arg Ala Thr Leu Ser Cys Arg
    610                 615                 620
Ala Ser Gln Ser Val Ser Arg Ser Tyr Leu Ala Trp Tyr Gln Gln Lys
625                 630                 635                 640
Pro Gly Gln Ala Pro Arg Leu Leu Ile Ile Gly Ala Ser Thr Arg Ala
                645                 650                 655
Thr Gly Ile Pro Asp Arg Phe Ser Gly Ser Gly Ser Gly Thr Asp Phe
            660                 665                 670
Thr Leu Thr Ile Ser Arg Leu Glu Pro Glu Asp Phe Ala Val Tyr Tyr
        675                 680                 685
Cys Gln Gln Gly Gln Val Ile Pro Pro Thr Phe Gly Cys Gly Thr Lys
    690                 695                 700
Val Glu Ile Lys
705

<210> SEQ ID NO 113
<211> LENGTH: 468
<212> TYPE: PRT
<213> ORGANISM: Artificial Sequence
<220> FEATURE:
<223> OTHER INFORMATION: Drozitumab-FAP (4G8)VHVL-scFv (LC)pETR7344

<400> SEQUENCE: 113

Ser Glu Leu Thr Gln Asp Pro Ala Val Ser Val Ala Leu Gly Gln Thr
1               5                   10                  15
Val Arg Ile Thr Cys Ser Gly Asp Ser Leu Arg Ser Tyr Tyr Ala Ser
                20                  25                  30
Trp Tyr Gln Gln Lys Pro Gly Gln Ala Pro Val Leu Val Ile Tyr Gly
            35                  40                  45
Ala Asn Asn Arg Pro Ser Gly Ile Pro Asp Arg Phe Ser Gly Ser Ser
        50                  55                  60
Ser Gly Asn Thr Ala Ser Leu Thr Ile Thr Gly Ala Gln Ala Glu Asp
65                  70                  75                  80
Glu Ala Asp Tyr Tyr Cys Asn Ser Ala Asp Ser Ser Gly Asn His Val
```

```
                85                  90                  95
Val Phe Gly Gly Gly Thr Lys Leu Thr Val Leu Gly Gln Pro Lys Ala
                100                 105                 110

Ala Pro Ser Val Thr Leu Phe Pro Pro Ser Ser Glu Glu Leu Gln Ala
                115                 120                 125

Asn Lys Ala Thr Leu Val Cys Leu Ile Ser Asp Phe Tyr Pro Gly Ala
                130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
                195                 200                 205

Pro Thr Glu Cys Ser Gly Gly Gly Ser Gly Gly Gly Ser Glu
                210                 215                 220

Val Gln Leu Leu Glu Ser Gly Gly Leu Val Gln Pro Gly Gly Ser
225                 230                 235                 240

Leu Arg Leu Ser Cys Ala Ala Ser Gly Phe Thr Phe Ser Ser Tyr Ala
                245                 250                 255

Met Ser Trp Val Arg Gln Ala Pro Gly Lys Cys Leu Glu Trp Val Ser
                260                 265                 270

Ala Ile Ser Gly Ser Gly Gly Ser Thr Tyr Tyr Ala Asp Ser Val Lys
                275                 280                 285

Gly Arg Phe Thr Ile Ser Arg Asp Asn Ser Lys Asn Thr Leu Tyr Leu
                290                 295                 300

Gln Met Asn Ser Leu Arg Ala Glu Asp Thr Ala Val Tyr Tyr Cys Ala
305                 310                 315                 320

Lys Gly Trp Leu Gly Asn Phe Asp Tyr Trp Gly Gln Gly Thr Leu Val
                325                 330                 335

Thr Val Ser Ser Gly Gly Gly Ser Gly Gly Gly Ser Gly Gly
                340                 345                 350

Gly Gly Ser Gly Gly Gly Gly Ser Glu Ile Val Leu Thr Gln Ser Pro
                355                 360                 365

Gly Thr Leu Ser Leu Ser Pro Gly Glu Arg Ala Thr Leu Ser Cys Arg
                370                 375                 380

Ala Ser Gln Ser Val Ser Arg Ser Tyr Leu Ala Trp Tyr Gln Gln Lys
385                 390                 395                 400

Pro Gly Gln Ala Pro Arg Leu Leu Ile Ile Gly Ala Ser Thr Arg Ala
                405                 410                 415

Thr Gly Ile Pro Asp Arg Phe Ser Gly Ser Gly Ser Gly Thr Asp Phe
                420                 425                 430

Thr Leu Thr Ile Ser Arg Leu Glu Pro Glu Asp Phe Ala Val Tyr Tyr
                435                 440                 445

Cys Gln Gln Gly Gln Val Ile Pro Pro Thr Phe Gly Cys Gly Thr Lys
                450                 455                 460

Val Glu Ile Lys
465

<210> SEQ ID NO 114
<211> LENGTH: 942
<212> TYPE: PRT
<213> ORGANISM: Artificial Sequence
```

<220> FEATURE:
<223> OTHER INFORMATION: Drozitumab-3F2VLCL_VHCH1-scFab (HC)pETR7369

<400> SEQUENCE: 114

```
Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Ser Gly Gly Gly Ser Gly Gly Gly Ser Gly Gly
            450                 455                 460

Gly Gly Ser Gly Gly Gly Ser Glu Ile Val Leu Thr Gln Ser Pro
465                 470                 475                 480

Gly Thr Leu Ser Leu Tyr Pro Gly Glu Arg Ala Thr Leu Ser Cys Arg
            485                 490                 495

Ala Ser Gln Ser Val Thr Ser Ser Tyr Leu Ala Trp Tyr Gln Gln Lys
            500                 505                 510

Pro Gly Gln Ala Pro Arg Leu Leu Ile Asn Val Gly Ser Arg Arg Ala
            515                 520                 525

Thr Gly Ile Pro Asp Arg Phe Ser Gly Ser Gly Ser Gly Thr Asp Phe
            530                 535                 540

Thr Leu Thr Ile Ser Arg Leu Glu Pro Glu Asp Phe Ala Val Tyr Tyr
545                 550                 555                 560

Cys Gln Gln Gly Ile Met Leu Pro Pro Thr Phe Gly Gln Gly Thr Lys
            565                 570                 575

Val Glu Ile Lys Arg Thr Val Ala Ala Pro Ser Val Phe Ile Phe Pro
            580                 585                 590

Pro Ser Asp Glu Gln Leu Lys Ser Gly Thr Ala Ser Val Val Cys Leu
            595                 600                 605

Leu Asn Asn Phe Tyr Pro Arg Glu Ala Lys Val Gln Trp Lys Val Asp
            610                 615                 620

Asn Ala Leu Gln Ser Gly Asn Ser Gln Glu Ser Val Thr Glu Gln Asp
625                 630                 635                 640

Ser Lys Asp Ser Thr Tyr Ser Leu Ser Ser Thr Leu Thr Leu Ser Lys
            645                 650                 655

Ala Asp Tyr Glu Lys His Lys Val Tyr Ala Cys Glu Val Thr His Gln
            660                 665                 670

Gly Leu Ser Ser Pro Val Thr Lys Ser Phe Asn Arg Gly Glu Cys Ser
            675                 680                 685

Gly Gly Gly Ser Gly Gly Gly Ser Glu Gly Gly Ser Glu Gly Gly
            690                 695                 700

Gly Ser Glu Gly Gly Ser Glu Gly Gly Ser Gly Gly Gly Ser
705                 710                 715                 720

Gly Glu Val Gln Leu Leu Glu Ser Gly Gly Leu Val Gln Pro Gly
            725                 730                 735

Gly Ser Leu Arg Leu Ser Cys Ala Ala Ser Gly Phe Thr Phe Ser Ser
            740                 745                 750

Tyr Ala Met Ser Trp Val Arg Gln Ala Pro Gly Lys Gly Leu Glu Trp
            755                 760                 765

Val Ser Ala Ile Ser Gly Ser Gly Gly Ser Thr Tyr Tyr Ala Asp Ser
            770                 775                 780

Val Lys Gly Arg Phe Thr Ile Ser Arg Asp Asn Ser Lys Asn Thr Leu
785                 790                 795                 800

Tyr Leu Gln Met Asn Ser Leu Arg Ala Glu Asp Thr Ala Val Tyr Tyr
            805                 810                 815
```

```
Cys Ala Lys Gly Trp Phe Gly Phe Asn Tyr Trp Gly Gln Gly Thr
            820                 825                 830

Leu Val Thr Val Ser Ser Ala Ser Thr Lys Gly Pro Ser Val Phe Pro
        835                 840                 845

Leu Ala Pro Ser Ser Lys Ser Thr Ser Gly Gly Thr Ala Ala Leu Gly
    850                 855                 860

Cys Leu Val Lys Asp Tyr Phe Pro Glu Pro Val Thr Val Ser Trp Asn
865                 870                 875                 880

Ser Gly Ala Leu Thr Ser Gly Val His Thr Phe Pro Ala Val Leu Gln
                885                 890                 895

Ser Ser Gly Leu Tyr Ser Leu Ser Val Val Thr Val Pro Ser Ser
            900                 905                 910

Ser Leu Gly Thr Gln Thr Tyr Ile Cys Asn Val Asn His Lys Pro Ser
        915                 920                 925

Asn Thr Lys Val Asp Lys Lys Val Glu Pro Lys Ser Cys Asp
    930                 935                 940

<210> SEQ ID NO 115
<211> LENGTH: 703
<212> TYPE: PRT
<213> ORGANISM: Artificial Sequence
<220> FEATURE:
<223> OTHER INFORMATION: Drozitumab-3F2VLCL_VHCH1-scFab (LC)pETR7370

<400> SEQUENCE: 115

Ser Glu Leu Thr Gln Asp Pro Ala Val Ser Val Ala Leu Gly Gln Thr
1               5                   10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ala Asp Ser Ser Gly Asn His Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser Gly Gly Gly Gly Ser Gly Gly Gly Gly Ser Gly
    210                 215                 220

Gly Gly Gly Ser Gly Gly Gly Gly Ser Glu Ile Val Leu Thr Gln Ser
225                 230                 235                 240
```

-continued

Pro Gly Thr Leu Ser Leu Tyr Pro Gly Glu Arg Ala Thr Leu Ser Cys
                245                 250                 255

Arg Ala Ser Gln Ser Val Thr Ser Ser Tyr Leu Ala Trp Tyr Gln Gln
            260                 265                 270

Lys Pro Gly Gln Ala Pro Arg Leu Leu Ile Asn Val Gly Ser Arg Arg
        275                 280                 285

Ala Thr Gly Ile Pro Asp Arg Phe Ser Gly Ser Gly Ser Gly Thr Asp
    290                 295                 300

Phe Thr Leu Thr Ile Ser Arg Leu Glu Pro Glu Asp Phe Ala Val Tyr
305                 310                 315                 320

Tyr Cys Gln Gln Gly Ile Met Leu Pro Pro Thr Phe Gly Gln Gly Thr
                325                 330                 335

Lys Val Glu Ile Lys Arg Thr Val Ala Ala Pro Ser Val Phe Ile Phe
            340                 345                 350

Pro Pro Ser Asp Glu Gln Leu Lys Ser Gly Thr Ala Ser Val Val Cys
        355                 360                 365

Leu Leu Asn Asn Phe Tyr Pro Arg Glu Ala Lys Val Gln Trp Lys Val
    370                 375                 380

Asp Asn Ala Leu Gln Ser Gly Asn Ser Gln Glu Ser Val Thr Glu Gln
385                 390                 395                 400

Asp Ser Lys Asp Ser Thr Tyr Ser Leu Ser Ser Thr Leu Thr Leu Ser
                405                 410                 415

Lys Ala Asp Tyr Glu Lys His Lys Val Tyr Ala Cys Glu Val Thr His
            420                 425                 430

Gln Gly Leu Ser Ser Pro Val Thr Lys Ser Phe Asn Arg Gly Glu Cys
        435                 440                 445

Ser Gly Gly Gly Ser Gly Gly Gly Ser Glu Gly Gly Gly Ser Glu Gly
    450                 455                 460

Gly Gly Ser Glu Gly Gly Gly Ser Glu Gly Gly Gly Ser Gly Gly Gly
465                 470                 475                 480

Ser Gly Glu Val Gln Leu Leu Glu Ser Gly Gly Gly Leu Val Gln Pro
                485                 490                 495

Gly Gly Ser Leu Arg Leu Ser Cys Ala Ala Ser Gly Phe Thr Phe Ser
            500                 505                 510

Ser Tyr Ala Met Ser Trp Val Arg Gln Ala Pro Gly Lys Gly Leu Glu
        515                 520                 525

Trp Val Ser Ala Ile Ser Gly Ser Gly Gly Ser Thr Tyr Tyr Ala Asp
    530                 535                 540

Ser Val Lys Gly Arg Phe Thr Ile Ser Arg Asp Asn Ser Lys Asn Thr
545                 550                 555                 560

Leu Tyr Leu Gln Met Asn Ser Leu Arg Ala Glu Asp Thr Ala Val Tyr
                565                 570                 575

Tyr Cys Ala Lys Gly Trp Phe Gly Gly Phe Asn Tyr Trp Gly Gln Gly
            580                 585                 590

Thr Leu Val Thr Val Ser Ser Ala Ser Thr Lys Gly Pro Ser Val Phe
        595                 600                 605

Pro Leu Ala Pro Ser Ser Lys Ser Thr Ser Gly Gly Thr Ala Ala Leu
    610                 615                 620

Gly Cys Leu Val Lys Asp Tyr Phe Pro Glu Pro Val Thr Val Ser Trp
625                 630                 635                 640

Asn Ser Gly Ala Leu Thr Ser Gly Val His Thr Phe Pro Ala Val Leu
                645                 650                 655

Gln Ser Ser Gly Leu Tyr Ser Leu Ser Ser Val Val Thr Val Pro Ser

<210> SEQ ID NO 116
<211> LENGTH: 942
<212> TYPE: PRT
<213> ORGANISM: Artificial Sequence
<220> FEATURE:
<223> OTHER INFORMATION: Drozitumab-FAP (4G8)VLCL_VHCH1-scFab
(HC)pETR7371

<400> SEQUENCE: 116

```
Glu Val Gln Leu Val Gln Ser Gly Gly Gly Val Glu Arg Pro Gly Gly
 1               5                  10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Gly Ile Asn Trp Gln Gly Gly Ser Thr Gly Tyr Ala Asp Ser Val
        50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Ser Gly Gly Gly Gly Ser Gly Gly Gly Gly Ser Gly Gly
    450                 455                 460
Gly Gly Ser Gly Gly Gly Gly Ser Glu Ile Val Leu Thr Gln Ser Pro
465                 470                 475                 480
Gly Thr Leu Ser Leu Ser Pro Gly Glu Arg Ala Thr Leu Ser Cys Arg
                485                 490                 495
Ala Ser Gln Ser Val Ser Arg Ser Tyr Leu Ala Trp Tyr Gln Gln Lys
            500                 505                 510
Pro Gly Gln Ala Pro Arg Leu Leu Ile Ile Gly Ala Ser Thr Arg Ala
        515                 520                 525
Thr Gly Ile Pro Asp Arg Phe Ser Gly Ser Gly Ser Gly Thr Asp Phe
    530                 535                 540
Thr Leu Thr Ile Ser Arg Leu Glu Pro Glu Asp Phe Ala Val Tyr Tyr
545                 550                 555                 560
Cys Gln Gln Gly Gln Val Ile Pro Pro Thr Phe Gly Gln Gly Thr Lys
                565                 570                 575
Val Glu Ile Lys Arg Thr Val Ala Ala Pro Ser Val Phe Ile Phe Pro
            580                 585                 590
Pro Ser Asp Glu Gln Leu Lys Ser Gly Thr Ala Ser Val Val Cys Leu
        595                 600                 605
Leu Asn Asn Phe Tyr Pro Arg Glu Ala Lys Val Gln Trp Lys Val Asp
    610                 615                 620
Asn Ala Leu Gln Ser Gly Asn Ser Gln Glu Ser Val Thr Glu Gln Asp
625                 630                 635                 640
Ser Lys Asp Ser Thr Tyr Ser Leu Ser Ser Thr Leu Thr Leu Ser Lys
                645                 650                 655
Ala Asp Tyr Glu Lys His Lys Val Tyr Ala Cys Glu Val Thr His Gln
            660                 665                 670
Gly Leu Ser Ser Pro Val Thr Lys Ser Phe Asn Arg Gly Glu Cys Ser
        675                 680                 685
Gly Gly Gly Ser Gly Gly Gly Ser Glu Gly Gly Ser Glu Gly Gly
    690                 695                 700
Gly Ser Glu Gly Gly Ser Glu Gly Gly Ser Gly Gly Gly Ser
705                 710                 715                 720
Gly Glu Val Gln Leu Leu Glu Ser Gly Gly Gly Leu Val Gln Pro Gly
                725                 730                 735
Gly Ser Leu Arg Leu Ser Cys Ala Ala Ser Gly Phe Thr Phe Ser Ser
```

```
            740                 745                 750
Tyr Ala Met Ser Trp Val Arg Gln Ala Pro Gly Lys Gly Leu Glu Trp
        755                 760                 765
Val Ser Ala Ile Ser Gly Ser Gly Gly Ser Thr Tyr Tyr Ala Asp Ser
        770                 775                 780
Val Lys Gly Arg Phe Thr Ile Ser Arg Asp Asn Ser Lys Asn Thr Leu
785                 790                 795                 800
Tyr Leu Gln Met Asn Ser Leu Arg Ala Glu Asp Thr Ala Val Tyr Tyr
                805                 810                 815
Cys Ala Lys Gly Trp Leu Gly Asn Phe Asp Tyr Trp Gly Gln Gly Thr
                820                 825                 830
Leu Val Thr Val Ser Ser Ala Ser Thr Lys Gly Pro Ser Val Phe Pro
            835                 840                 845
Leu Ala Pro Ser Ser Lys Ser Thr Ser Gly Gly Thr Ala Ala Leu Gly
        850                 855                 860
Cys Leu Val Lys Asp Tyr Phe Pro Glu Pro Val Thr Val Ser Trp Asn
865                 870                 875                 880
Ser Gly Ala Leu Thr Ser Gly Val His Thr Phe Pro Ala Val Leu Gln
                885                 890                 895
Ser Ser Gly Leu Tyr Ser Leu Ser Ser Val Val Thr Val Pro Ser Ser
                900                 905                 910
Ser Leu Gly Thr Gln Thr Tyr Ile Cys Asn Val Asn His Lys Pro Ser
            915                 920                 925
Asn Thr Lys Val Asp Lys Lys Val Glu Pro Lys Ser Cys Asp
        930                 935                 940

<210> SEQ ID NO 117
<211> LENGTH: 703
<212> TYPE: PRT
<213> ORGANISM: Artificial Sequence
<220> FEATURE:
<223> OTHER INFORMATION: Drozitumab-FAP (4G8)VLCL_VHCH1-scFab
      (LC)pETR7380

<400> SEQUENCE: 117

Ser Glu Leu Thr Gln Asp Pro Ala Val Ser Val Ala Leu Gly Gln Thr
1               5                   10                  15
Val Arg Ile Thr Cys Ser Gly Asp Ser Leu Arg Ser Tyr Tyr Ala Ser
            20                  25                  30
Trp Tyr Gln Gln Lys Pro Gly Gln Ala Pro Val Leu Val Ile Tyr Gly
        35                  40                  45
Ala Asn Asn Arg Pro Ser Gly Ile Pro Asp Arg Phe Ser Gly Ser Ser
    50                  55                  60
Ser Gly Asn Thr Ala Ser Leu Thr Ile Thr Gly Ala Gln Ala Glu Asp
65                  70                  75                  80
Glu Ala Asp Tyr Tyr Cys Asn Ser Ala Asp Ser Ser Gly Asn His Val
                85                  90                  95
Val Phe Gly Gly Gly Thr Lys Leu Thr Val Leu Gly Gln Pro Lys Ala
            100                 105                 110
Ala Pro Ser Val Thr Leu Phe Pro Pro Ser Ser Glu Glu Leu Gln Ala
        115                 120                 125
Asn Lys Ala Thr Leu Val Cys Leu Ile Ser Asp Phe Tyr Pro Gly Ala
    130                 135                 140
Val Thr Val Ala Trp Lys Ala Asp Ser Ser Pro Val Lys Ala Gly Val
145                 150                 155                 160
```

```
Glu Thr Thr Thr Pro Ser Lys Gln Ser Asn Asn Lys Tyr Ala Ala Ser
            165                 170                 175

Ser Tyr Leu Ser Leu Thr Pro Glu Gln Trp Lys Ser His Arg Ser Tyr
        180                 185                 190

Ser Cys Gln Val Thr His Glu Gly Ser Thr Val Glu Lys Thr Val Ala
        195                 200                 205

Pro Thr Glu Cys Ser Gly Gly Gly Gly Ser Gly Gly Gly Gly Ser Gly
    210                 215                 220

Gly Gly Gly Ser Gly Gly Gly Ser Glu Ile Val Leu Thr Gln Ser
225                 230                 235                 240

Pro Gly Thr Leu Ser Leu Ser Pro Gly Glu Arg Ala Thr Leu Ser Cys
                245                 250                 255

Arg Ala Ser Gln Ser Val Ser Arg Ser Tyr Leu Ala Trp Tyr Gln Gln
            260                 265                 270

Lys Pro Gly Gln Ala Pro Arg Leu Leu Ile Ile Gly Ala Ser Thr Arg
        275                 280                 285

Ala Thr Gly Ile Pro Asp Arg Phe Ser Gly Ser Gly Ser Gly Thr Asp
        290                 295                 300

Phe Thr Leu Thr Ile Ser Arg Leu Glu Pro Glu Asp Phe Ala Val Tyr
305                 310                 315                 320

Tyr Cys Gln Gln Gly Gln Val Ile Pro Pro Thr Phe Gly Gln Gly Thr
                325                 330                 335

Lys Val Glu Ile Lys Arg Thr Val Ala Ala Pro Ser Val Phe Ile Phe
            340                 345                 350

Pro Pro Ser Asp Glu Gln Leu Lys Ser Gly Thr Ala Ser Val Val Cys
        355                 360                 365

Leu Leu Asn Asn Phe Tyr Pro Arg Glu Ala Lys Val Gln Trp Lys Val
        370                 375                 380

Asp Asn Ala Leu Gln Ser Gly Asn Ser Gln Glu Ser Val Thr Glu Gln
385                 390                 395                 400

Asp Ser Lys Asp Ser Thr Tyr Ser Leu Ser Ser Thr Leu Thr Leu Ser
                405                 410                 415

Lys Ala Asp Tyr Glu Lys His Lys Val Tyr Ala Cys Glu Val Thr His
            420                 425                 430

Gln Gly Leu Ser Ser Pro Val Thr Lys Ser Phe Asn Arg Gly Glu Cys
        435                 440                 445

Ser Gly Gly Gly Ser Gly Gly Ser Glu Gly Gly Ser Glu Gly
        450                 455                 460

Gly Gly Ser Glu Gly Gly Ser Glu Gly Gly Ser Gly Gly
465                 470                 475                 480

Ser Gly Glu Val Gln Leu Leu Glu Ser Gly Gly Gly Leu Val Gln Pro
                485                 490                 495

Gly Gly Ser Leu Arg Leu Ser Cys Ala Ala Ser Gly Phe Thr Phe Ser
        500                 505                 510

Ser Tyr Ala Met Ser Trp Val Arg Gln Ala Pro Gly Lys Gly Leu Glu
        515                 520                 525

Trp Val Ser Ala Ile Ser Gly Ser Gly Gly Ser Thr Tyr Tyr Ala Asp
        530                 535                 540

Ser Val Lys Gly Arg Phe Thr Ile Ser Arg Asp Asn Ser Lys Asn Thr
545                 550                 555                 560

Leu Tyr Leu Gln Met Asn Ser Leu Arg Ala Glu Asp Thr Ala Val Tyr
                565                 570                 575

Tyr Cys Ala Lys Gly Trp Leu Gly Asn Phe Asp Tyr Trp Gly Gln Gly
```

```
                580             585             590
Thr Leu Val Thr Val Ser Ser Ala Ser Thr Lys Gly Pro Ser Val Phe
            595                 600             605

Pro Leu Ala Pro Ser Ser Lys Ser Thr Ser Gly Gly Thr Ala Ala Leu
610             615                 620

Gly Cys Leu Val Lys Asp Tyr Phe Pro Glu Pro Val Thr Val Ser Trp
625                 630                 635                 640

Asn Ser Gly Ala Leu Thr Ser Gly Val His Thr Phe Pro Ala Val Leu
                645                 650                 655

Gln Ser Ser Gly Leu Tyr Ser Leu Ser Ser Val Val Thr Val Pro Ser
            660                 665                 670

Ser Ser Leu Gly Thr Gln Thr Tyr Ile Cys Asn Val Asn His Lys Pro
            675                 680                 685

Ser Asn Thr Lys Val Asp Lys Lys Val Glu Pro Lys Ser Cys Asp
            690                 695                 700

<210> SEQ ID NO 118
<211> LENGTH: 696
<212> TYPE: PRT
<213> ORGANISM: Artificial Sequence
<220> FEATURE:
<223> OTHER INFORMATION: Drozitumab-FAP (4G8)VHCL2+2

<400> SEQUENCE: 118

Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Gly Ile Asn Trp Gln Gly Gly Ser Thr Gly Tyr Ala Asp Ser Val
    50                  55                  60

Lys Gly Arg Val Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Ile Leu Gly Ala Gly Arg Gly Trp Tyr Phe Asp Tyr Trp Gly
            100                 105                 110

Lys Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
              245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
        290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
        435                 440                 445
Pro Gly Lys Ser Gly Gly Gly Ser Gly Gly Gly Ser Gly Gly
        450                 455                 460
Gly Gly Ser Gly Gly Gly Ser Glu Val Gln Leu Leu Glu Ser Gly
465                 470                 475                 480
Gly Gly Leu Val Gln Pro Gly Gly Ser Leu Arg Leu Ser Cys Ala Ala
                485                 490                 495
Ser Gly Phe Thr Phe Ser Ser Tyr Ala Met Ser Trp Val Arg Gln Ala
                500                 505                 510
Pro Gly Lys Gly Leu Glu Trp Val Ser Ala Ile Ser Gly Ser Gly Gly
            515                 520                 525
Ser Thr Tyr Tyr Ala Asp Ser Val Lys Gly Arg Phe Thr Ile Ser Arg
        530                 535                 540
Asp Asn Ser Lys Asn Thr Leu Tyr Leu Gln Met Asn Ser Leu Arg Ala
545                 550                 555                 560
Glu Asp Thr Ala Val Tyr Tyr Cys Ala Lys Gly Trp Leu Gly Asn Phe
            565                 570                 575
Asp Tyr Trp Gly Gln Gly Thr Leu Val Thr Val Ser Ser Ala Ser Val
            580                 585                 590
Ala Ala Pro Ser Val Phe Ile Phe Pro Pro Ser Asp Glu Gln Leu Lys
            595                 600                 605
Ser Gly Thr Ala Ser Val Val Cys Leu Leu Asn Asn Phe Tyr Pro Arg
        610                 615                 620
Glu Ala Lys Val Gln Trp Lys Val Asp Asn Ala Leu Gln Ser Gly Asn
625                 630                 635                 640
Ser Gln Glu Ser Val Thr Glu Gln Asp Ser Lys Asp Ser Thr Tyr Ser
                645                 650                 655
Leu Ser Ser Thr Leu Thr Leu Ser Lys Ala Asp Tyr Glu Lys His Lys
            660                 665                 670
```

```
Val Tyr Ala Cys Glu Val Thr His Gln Gly Leu Ser Ser Pro Val Thr
        675                 680                 685

Lys Ser Phe Asn Arg Gly Glu Cys
    690                 695

<210> SEQ ID NO 119
<211> LENGTH: 213
<212> TYPE: PRT
<213> ORGANISM: Artificial Sequence
<220> FEATURE:
<223> OTHER INFORMATION: Drozitumab LCpETR7303

<400> SEQUENCE: 119

Ser Glu Leu Thr Gln Asp Pro Ala Val Ser Val Ala Leu Gly Gln Thr
1               5                   10                  15

Val Arg Ile Thr Cys Ser Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Ala Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Ala Asp Ser Ser Gly Asn His Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 120
<211> LENGTH: 214
<212> TYPE: PRT
<213> ORGANISM: Artificial Sequence
<220> FEATURE:
<223> OTHER INFORMATION: FAP(4G8)_VLCH1

<400> SEQUENCE: 120

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
```

```
                50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys Ser Ser Ala Ser
                100                 105                 110

Thr Lys Gly Pro Ser Val Phe Pro Leu Ala Pro Ser Ser Lys Ser Thr
                115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
                180                 185                 190

Cys Asn Val Asn His Lys Pro Ser Asn Thr Lys Val Asp Lys Lys Val
                195                 200                 205

Glu Pro Lys Ser Cys Asp
    210

<210> SEQ ID NO 121
<211> LENGTH: 684
<212> TYPE: PRT
<213> ORGANISM: Artificial Sequence
<220> FEATURE:
<223> OTHER INFORMATION: Drozitumab-FAP (4G8)VLCH12+2

<400> SEQUENCE: 121

Glu Val Gln Leu Val Gln Ser Gly Gly Gly Val Glu Arg Pro Gly Gly
  1               5                  10                  15

Ser Leu Arg Leu Ser Cys Ala Ala Ser Gly Phe Thr Phe Asp Asp Tyr
                 20                  25                  30

Ala Met Ser Trp Val Arg Gln Ala Pro Gly Lys Gly Leu Glu Trp Val
             35                  40                  45

Ser Gly Ile Asn Trp Gln Gly Gly Ser Thr Gly Tyr Ala Asp Ser Val
     50                  55                  60

Lys Gly Arg Val Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Ile Leu Gly Ala Gly Arg Gly Trp Tyr Phe Asp Tyr Trp Gly
                100                 105                 110

Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
```

```
            195                 200                 205
Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Ser Gly Gly Gly Ser Gly Gly Gly Ser Gly Gly
            450                 455                 460

Gly Gly Ser Gly Gly Gly Ser Glu Ile Val Leu Thr Gln Ser Pro
465                 470                 475                 480

Gly Thr Leu Ser Leu Ser Pro Gly Glu Arg Ala Thr Leu Ser Cys Arg
                485                 490                 495

Ala Ser Gln Ser Val Ser Arg Ser Tyr Leu Ala Trp Tyr Gln Gln Lys
            500                 505                 510

Pro Gly Gln Ala Pro Arg Leu Leu Ile Ile Gly Ala Ser Thr Arg Ala
            515                 520                 525

Thr Gly Ile Pro Asp Arg Phe Ser Gly Ser Gly Ser Gly Thr Asp Phe
            530                 535                 540

Thr Leu Thr Ile Ser Arg Leu Glu Pro Glu Asp Phe Ala Val Tyr Tyr
545                 550                 555                 560

Cys Gln Gln Gly Gln Val Ile Pro Pro Thr Phe Gly Gln Gly Thr Lys
                565                 570                 575

Val Glu Ile Lys Ala Ser Thr Lys Gly Pro Ser Val Phe Pro Leu Ala
            580                 585                 590

Pro Ser Ser Lys Ser Thr Ser Gly Gly Thr Ala Ala Leu Gly Cys Leu
            595                 600                 605

Val Lys Asp Tyr Phe Pro Glu Pro Val Thr Val Ser Trp Asn Ser Gly
610                 615                 620
```

```
Ala Leu Thr Ser Gly Val His Thr Phe Pro Ala Val Leu Gln Ser Ser
625                 630                 635                 640

Gly Leu Tyr Ser Leu Ser Ser Val Val Thr Val Pro Ser Ser Ser Leu
            645                 650                 655

Gly Thr Gln Thr Tyr Ile Cys Asn Val Asn His Lys Pro Ser Asn Thr
        660                 665                 670

Lys Val Asp Lys Lys Val Glu Pro Lys Ser Cys Asp
    675                 680
```

<210> SEQ ID NO 122
<211> LENGTH: 224
<212> TYPE: PRT
<213> ORGANISM: Artificial Sequence
<220> FEATURE:
<223> OTHER INFORMATION: FAP(4G8)_VHCL

<400> SEQUENCE: 122

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220
```

<210> SEQ ID NO 123
<211> LENGTH: 695
<212> TYPE: PRT
<213> ORGANISM: Artificial Sequence
<220> FEATURE:
<223> OTHER INFORMATION: Drozitumab-FAP (28H1)VHCLpETR95512+2

<400> SEQUENCE: 123

```
Glu Val Gln Leu Val Gln Ser Gly Gly Gly Val Glu Arg Pro Gly Gly
1               5                   10                  15

Ser Leu Arg Leu Ser Cys Ala Ala Ser Gly Phe Thr Phe Asp Asp Tyr
```

```
                20                  25                  30
Ala Met Ser Trp Val Arg Gln Ala Pro Gly Lys Gly Leu Glu Trp Val
            35                  40                  45
Ser Gly Ile Asn Trp Gln Gly Gly Ser Thr Gly Tyr Ala Asp Ser Val
    50                  55                  60
Lys Gly Arg Val Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Ile Leu Gly Ala Gly Arg Gly Trp Tyr Phe Asp Tyr Trp Gly
            100                 105                 110
Lys Gly Thr Thr Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
```

Pro Gly Lys Ser Gly Gly Gly Ser Gly Gly Gly Ser Gly Gly
            450                 455                 460

Gly Gly Ser Gly Gly Gly Ser Glu Val Gln Leu Leu Glu Ser Gly
465                 470                 475                 480

Gly Gly Leu Val Gln Pro Gly Gly Ser Leu Arg Leu Ser Cys Ala Ala
                485                 490                 495

Ser Gly Phe Thr Phe Ser Ser His Ala Met Ser Trp Val Arg Gln Ala
                500                 505                 510

Pro Gly Lys Gly Leu Glu Trp Val Ser Ala Ile Trp Ala Ser Gly Glu
            515                 520                 525

Gln Tyr Tyr Ala Asp Ser Val Lys Gly Arg Phe Thr Ile Ser Arg Asp
530                 535                 540

Asn Ser Lys Asn Thr Leu Tyr Leu Gln Met Asn Ser Leu Arg Ala Glu
545                 550                 555                 560

Asp Thr Ala Val Tyr Tyr Cys Ala Lys Gly Trp Leu Gly Asn Phe Asp
                565                 570                 575

Tyr Trp Gly Gln Gly Thr Leu Val Thr Val Ser Ser Ala Ser Val Ala
                580                 585                 590

Ala Pro Ser Val Phe Ile Phe Pro Ser Asp Glu Gln Leu Lys Ser
            595                 600                 605

Gly Thr Ala Ser Val Val Cys Leu Leu Asn Asn Phe Tyr Pro Arg Glu
610                 615                 620

Ala Lys Val Gln Trp Lys Val Asp Asn Ala Leu Gln Ser Gly Asn Ser
625                 630                 635                 640

Gln Glu Ser Val Thr Glu Gln Asp Ser Lys Asp Ser Thr Tyr Ser Leu
                645                 650                 655

Ser Ser Thr Leu Thr Leu Ser Lys Ala Asp Tyr Glu Lys His Lys Val
                660                 665                 670

Tyr Ala Cys Glu Val Thr His Gln Gly Leu Ser Ser Pro Val Thr Lys
            675                 680                 685

Ser Phe Asn Arg Gly Glu Cys
    690                 695

<210> SEQ ID NO 124
<211> LENGTH: 214
<212> TYPE: PRT
<213> ORGANISM: Artificial Sequence
<220> FEATURE:
<223> OTHER INFORMATION: FAP(28H1)_VLCH1pETR9537

<400> SEQUENCE: 124

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
                20                  25                  30

Tyr Leu Ala Trp Tyr Gln Gln Lys Pro Gly Gln Ala Pro Arg Leu Leu
            35                  40                  45

Ile Ile Gly Ala Ser Thr Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Ser Ser Ala Ser
            100                 105                 110

```
Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
        130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Gly Leu Tyr Ser Leu Ser
                165                 170                 175

Ser Val Val Thr Val Pro Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys Asp
210
```

<210> SEQ ID NO 125
<211> LENGTH: 691
<212> TYPE: PRT
<213> ORGANISM: Artificial Sequence
<220> FEATURE:
<223> OTHER INFORMATION: DR5 (22E9)-FAP (28H1)VHCLpETR97112+2

<400> SEQUENCE: 125

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Ile Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Ser
        435                 440                 445
Gly Gly Gly Gly Ser Gly Gly Gly Ser Gly Gly Gly Gly Ser Gly
    450                 455                 460
Gly Gly Ser Glu Val Gln Leu Leu Glu Ser Gly Gly Gly Leu Val
465                 470                 475                 480
Gln Pro Gly Gly Ser Leu Arg Leu Ser Cys Ala Ala Ser Gly Phe Thr
                485                 490                 495
Phe Ser Ser His Ala Met Ser Trp Val Arg Gln Ala Pro Gly Lys Gly
            500                 505                 510
Leu Glu Trp Val Ser Ala Ile Trp Ala Ser Gly Glu Gln Tyr Tyr Ala
        515                 520                 525
Asp Ser Val Lys Gly Arg Phe Thr Ile Ser Arg Asp Asn Ser Lys Asn
    530                 535                 540
Thr Leu Tyr Leu Gln Met Asn Ser Leu Arg Ala Glu Asp Thr Ala Val
545                 550                 555                 560
Tyr Tyr Cys Ala Lys Gly Trp Leu Gly Asn Phe Asp Tyr Trp Gly Gln
                565                 570                 575
Gly Thr Leu Val Thr Val Ser Ser Ala Ser Val Ala Ala Pro Ser Val
            580                 585                 590
Phe Ile Phe Pro Pro Ser Asp Glu Gln Leu Lys Ser Gly Thr Ala Ser
        595                 600                 605
Val Val Cys Leu Leu Asn Asn Phe Tyr Pro Arg Glu Ala Lys Val Gln
    610                 615                 620
Trp Lys Val Asp Asn Ala Leu Gln Ser Gly Asn Ser Gln Glu Ser Val
625                 630                 635                 640
Thr Glu Gln Asp Ser Lys Asp Ser Thr Tyr Ser Leu Ser Ser Thr Leu
                645                 650                 655
Thr Leu Ser Lys Ala Asp Tyr Glu Lys His Lys Val Tyr Ala Cys Glu
            660                 665                 670
```

```
Val Thr His Gln Gly Leu Ser Ser Pro Val Thr Lys Ser Phe Asn Arg
        675                 680                 685
Gly Glu Cys
    690

<210> SEQ ID NO 126
<211> LENGTH: 215
<212> TYPE: PRT
<213> ORGANISM: Artificial Sequence
<220> FEATURE:
<223> OTHER INFORMATION: DR5 (22E9) LCpETR9076

<400> SEQUENCE: 126

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Asn Gln Pro
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 127
<211> LENGTH: 691
<212> TYPE: PRT
<213> ORGANISM: Artificial Sequence
<220> FEATURE:
<223> OTHER INFORMATION: DR5 (21H3)-FAP (28H1)VHCLpETR10626 2+2

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Met Ala Val Tyr Tyr Cys
                 85                  90                  95

Ala Lys Gly Ala Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Gly Gly Gly Ser Gly Gly Gly Ser Gly Gly Gly Gly Ser Gly
450                 455                 460

Gly Gly Gly Ser Glu Val Gln Leu Leu Glu Ser Gly Gly Gly Leu Val
465                 470                 475                 480
```

Gln Pro Gly Gly Ser Leu Arg Leu Ser Cys Ala Ala Ser Gly Phe Thr
            485                 490                 495

Phe Ser Ser His Ala Met Ser Trp Val Arg Gln Ala Pro Gly Lys Gly
        500                 505                 510

Leu Glu Trp Val Ser Ala Ile Trp Ala Ser Gly Glu Gln Tyr Tyr Ala
        515                 520                 525

Asp Ser Val Lys Gly Arg Phe Thr Ile Ser Arg Asp Asn Ser Lys Asn
        530                 535                 540

Thr Leu Tyr Leu Gln Met Asn Ser Leu Arg Ala Glu Asp Thr Ala Val
545                 550                 555                 560

Tyr Tyr Cys Ala Lys Gly Trp Leu Gly Asn Phe Asp Tyr Trp Gly Gln
                565                 570                 575

Gly Thr Leu Val Thr Val Ser Ser Ala Ser Val Ala Ala Pro Ser Val
            580                 585                 590

Phe Ile Phe Pro Pro Ser Asp Glu Gln Leu Lys Ser Gly Thr Ala Ser
        595                 600                 605

Val Val Cys Leu Leu Asn Asn Phe Tyr Pro Arg Glu Ala Lys Val Gln
    610                 615                 620

Trp Lys Val Asp Asn Ala Leu Gln Ser Gly Asn Ser Gln Glu Ser Val
625                 630                 635                 640

Thr Glu Gln Asp Ser Lys Asp Ser Thr Tyr Ser Leu Ser Ser Thr Leu
                645                 650                 655

Thr Leu Ser Lys Ala Asp Tyr Glu Lys His Lys Val Tyr Ala Cys Glu
            660                 665                 670

Val Thr His Gln Gly Leu Ser Ser Pro Val Thr Lys Ser Phe Asn Arg
        675                 680                 685

Gly Glu Cys
    690

<210> SEQ ID NO 128
<211> LENGTH: 215
<212> TYPE: PRT
<213> ORGANISM: Artificial Sequence
<220> FEATURE:
<223> OTHER INFORMATION: DR5 (21H3) LCpETR9075

<400> SEQUENCE: 128

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Gln Pro Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 129
<211> LENGTH: 691
<212> TYPE: PRT
<213> ORGANISM: Artificial Sequence
<220> FEATURE:
<223> OTHER INFORMATION: DR5(20F2)-FAP(28H1)VHCLpETR10135 2+2

<400> SEQUENCE: 129

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Lys Gly Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

```
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Ser
        435                 440                 445
Gly Gly Gly Gly Ser Gly Gly Gly Ser Gly Gly Gly Ser Gly
450                 455                 460
Gly Gly Gly Ser Glu Val Gln Leu Leu Glu Ser Gly Gly Gly Leu Val
465                 470                 475                 480
Gln Pro Gly Gly Ser Leu Arg Leu Ser Cys Ala Ala Ser Gly Phe Thr
                485                 490                 495
Phe Ser Ser His Ala Met Ser Trp Val Arg Gln Ala Pro Gly Lys Gly
            500                 505                 510
Leu Glu Trp Val Ser Ala Ile Trp Ala Ser Gly Glu Gln Tyr Tyr Ala
        515                 520                 525
Asp Ser Val Lys Gly Arg Phe Thr Ile Ser Arg Asp Asn Ser Lys Asn
530                 535                 540
Thr Leu Tyr Leu Gln Met Asn Ser Leu Arg Ala Glu Asp Thr Ala Val
545                 550                 555                 560
Tyr Tyr Cys Ala Lys Gly Trp Leu Gly Asn Phe Asp Tyr Trp Gly Gln
                565                 570                 575
Gly Thr Leu Val Thr Val Ser Ser Ala Ser Val Ala Ala Pro Ser Val
            580                 585                 590
Phe Ile Phe Pro Pro Ser Asp Glu Gln Leu Lys Ser Gly Thr Ala Ser
        595                 600                 605
Val Val Cys Leu Leu Asn Asn Phe Tyr Pro Arg Glu Ala Lys Val Gln
610                 615                 620
Trp Lys Val Asp Asn Ala Leu Gln Ser Gly Asn Ser Gln Glu Ser Val
625                 630                 635                 640
Thr Glu Gln Asp Ser Lys Asp Ser Thr Tyr Ser Leu Ser Ser Thr Leu
                645                 650                 655
Thr Leu Ser Lys Ala Asp Tyr Glu Lys His Lys Val Tyr Ala Cys Glu
            660                 665                 670
Val Thr His Gln Gly Leu Ser Ser Pro Val Thr Lys Ser Phe Asn Arg
        675                 680                 685
Gly Glu Cys
690
```

```
<210> SEQ ID NO 130
<211> LENGTH: 215
<212> TYPE: PRT
<213> ORGANISM: Artificial Sequence
<220> FEATURE:
<223> OTHER INFORMATION: DR5 (20F2) LC pETR9061

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Glu Ser Pro Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 131
<211> LENGTH: 691
<212> TYPE: PRT
<213> ORGANISM: Artificial Sequence
<220> FEATURE:
<223> OTHER INFORMATION: DR5(5E11)-FAP (28H1) VHCL pETR10334 2+2

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Val Arg Val Ser Phe Asp Tyr Trp Gly Gln Gly Thr Leu
            100                 105                 110
Val Thr Val Ser Ser Ala Ser Thr Lys Gly Pro Ser Val Phe Pro Leu
            115                 120                 125
Ala Pro Ser Ser Lys Ser Thr Ser Gly Gly Thr Ala Ala Leu Gly Cys
130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Gln Thr Tyr Ile Cys Asn Val Asn His Lys Pro Ser Asn
            195                 200                 205
Thr Lys Val Asp Lys Lys Val Glu Pro Lys Ser Cys Asp Lys Thr His
            210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Ser
            435                 440                 445
Gly Gly Gly Gly Ser Gly Gly Gly Ser Gly Gly Gly Gly Ser Gly Gly
450                 455                 460
Gly Gly Gly Ser Glu Val Gln Leu Leu Glu Ser Gly Gly Gly Leu Val
465                 470                 475                 480
Gln Pro Gly Gly Ser Leu Arg Leu Ser Cys Ala Ala Ser Gly Phe Thr
                485                 490                 495
Phe Ser Ser His Ala Met Ser Trp Val Arg Gln Ala Pro Gly Lys Gly
            500                 505                 510
Leu Glu Trp Val Ser Ala Ile Trp Ala Ser Gly Glu Gln Tyr Tyr Ala
```

```
                515                 520                 525
Asp Ser Val Lys Gly Arg Phe Thr Ile Ser Arg Asp Asn Ser Lys Asn
    530                 535                 540

Thr Leu Tyr Leu Gln Met Asn Ser Leu Arg Ala Glu Asp Thr Ala Val
545                 550                 555                 560

Tyr Tyr Cys Ala Lys Gly Trp Leu Gly Asn Phe Asp Tyr Trp Gly Gln
                565                 570                 575

Gly Thr Leu Val Thr Val Ser Ser Ala Ser Val Ala Ala Pro Ser Val
            580                 585                 590

Phe Ile Phe Pro Pro Ser Asp Glu Gln Leu Lys Ser Gly Thr Ala Ser
        595                 600                 605

Val Val Cys Leu Leu Asn Asn Phe Tyr Pro Arg Glu Ala Lys Val Gln
    610                 615                 620

Trp Lys Val Asp Asn Ala Leu Gln Ser Gly Asn Ser Gln Glu Ser Val
625                 630                 635                 640

Thr Glu Gln Asp Ser Lys Asp Ser Thr Tyr Ser Leu Ser Ser Thr Leu
                645                 650                 655

Thr Leu Ser Lys Ala Asp Tyr Glu Lys His Lys Val Tyr Ala Cys Glu
            660                 665                 670

Val Thr His Gln Gly Leu Ser Ser Pro Val Thr Lys Ser Phe Asn Arg
        675                 680                 685

Gly Glu Cys
    690

<210> SEQ ID NO 132
<211> LENGTH: 215
<212> TYPE: PRT
<213> ORGANISM: Artificial Sequence
<220> FEATURE:
<223> OTHER INFORMATION: DR5(5E11) LCpETR9044

<400> SEQUENCE: 132

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Thr Thr His Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
```

```
                     180                 185                 190
Tyr Ala Cys Glu Val Thr His Gln Gly Leu Ser Ser Pro Val Thr Lys
            195                 200                 205

Ser Phe Asn Arg Gly Glu Cys
            210             215

<210> SEQ ID NO 133
<211> LENGTH: 689
<212> TYPE: PRT
<213> ORGANISM: Artificial Sequence
<220> FEATURE:
<223> OTHER INFORMATION: DR5(5E11)-FAP (28H1)VHCL 2+2 Removal of C-term.
      Lysine in Fc pETR11052

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Ser Gly Gly Gly Ser Gly Gly Gly
    450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Phe Thr Phe Ser
            485                 490                 495

Ser His Ala Met Ser Trp Val Arg Gln Ala Pro Gly Lys Gly Leu Glu
            500                 505                 510

Trp Val Ser Ala Ile Trp Ala Ser Gly Glu Gln Tyr Tyr Ala Asp Ser
            515                 520                 525

Val Lys Gly Arg Phe Thr Ile Ser Arg Asp Asn Ser Lys Asn Thr Leu
    530                 535                 540

Tyr Leu Gln Met Asn Ser Leu Arg Ala Glu Asp Thr Ala Val Tyr Tyr
545                 550                 555                 560

Cys Ala Lys Gly Trp Leu Gly Asn Phe Asp Tyr Trp Gly Gln Gly Thr
            565                 570                 575

Leu Val Thr Val Ser Ser Ala Ser Val Ala Ala Pro Ser Val Phe Ile
            580                 585                 590

Phe Pro Pro Ser Asp Glu Gln Leu Lys Ser Gly Thr Ala Ser Val Val
            595                 600                 605

Cys Leu Leu Asn Asn Phe Tyr Pro Arg Glu Ala Lys Val Gln Trp Lys
            610                 615                 620

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
            645                 650                 655

Ser Lys Ala Asp Tyr Glu Lys His Lys Val Tyr Ala Cys Glu Val Thr
            660                 665                 670

His Gln Gly Leu Ser Ser Pro Val Thr Lys Ser Phe Asn Arg Gly Glu
            675                 680                 685

Cys
```

<210> SEQ ID NO 134
<211> LENGTH: 689
<212> TYPE: PRT
<213> ORGANISM: Artificial Sequence
<220> FEATURE:
<223> OTHER INFORMATION: DR5(5E11)-FAP (28H1)VHCL2+2Removal of C-term.
      Lysine in Fc P329G/LALA mut.pETR11025

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg

```
                        405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Ser Gly Gly Gly Ser Gly Gly Gly
        450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Phe Thr Phe Ser
                485                 490                 495

Ser His Ala Met Ser Trp Val Arg Gln Ala Pro Gly Lys Gly Leu Glu
            500                 505                 510

Trp Val Ser Ala Ile Trp Ala Ser Gly Glu Gln Tyr Tyr Ala Asp Ser
            515                 520                 525

Val Lys Gly Arg Phe Thr Ile Ser Arg Asp Asn Ser Lys Asn Thr Leu
        530                 535                 540

Tyr Leu Gln Met Asn Ser Leu Arg Ala Glu Asp Thr Ala Val Tyr Tyr
545                 550                 555                 560

Cys Ala Lys Gly Trp Leu Gly Asn Phe Asp Tyr Trp Gly Gln Gly Thr
                565                 570                 575

Leu Val Thr Val Ser Ser Ala Ser Val Ala Ala Pro Ser Val Phe Ile
            580                 585                 590

Phe Pro Pro Ser Asp Glu Gln Leu Lys Ser Gly Thr Ala Ser Val Val
            595                 600                 605

Cys Leu Leu Asn Asn Phe Tyr Pro Arg Glu Ala Lys Val Gln Trp Lys
        610                 615                 620

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
                645                 650                 655

Ser Lys Ala Asp Tyr Glu Lys His Lys Val Tyr Ala Cys Glu Val Thr
            660                 665                 670

His Gln Gly Leu Ser Ser Pro Val Thr Lys Ser Phe Asn Arg Gly Glu
            675                 680                 685

Cys

<210> SEQ ID NO 135
<211> LENGTH: 681
<212> TYPE: PRT
<213> ORGANISM: Artificial Sequence
<220> FEATURE:
<223> OTHER INFORMATION: VHVL DR5(5E11)-FAP (28H1) pETR11827 2+2

<400> SEQUENCE: 135

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Gly Thr Thr His Pro
                85                  90                  95
Ile Thr Phe Gly Gln Gly Thr Lys Val Glu Ile Lys Ser Ser Ala Ser
            100                 105                 110
Thr Lys Gly Pro Ser Val Phe Pro Leu Ala Pro Ser Ser Lys Ser Thr
            115                 120                 125
Ser Gly Gly Thr Ala Ala Leu Gly Cys Leu Val Lys Asp Tyr Phe Pro
130                 135                 140
Glu Pro Val Thr Val Ser Trp Asn Ser Gly Ala Leu Thr Ser Gly Val
145                 150                 155                 160
His Thr Phe Pro Ala Val Leu Gln Ser Ser Gly Leu Tyr Ser Leu Ser
                165                 170                 175
Ser Val Val Thr Val Pro Ser Ser Ser Leu Gly Thr Gln Thr Tyr Ile
            180                 185                 190
Cys Asn Val Asn His Lys Pro Ser Asn Thr Lys Val Asp Lys Lys Val
            195                 200                 205
Glu Pro Lys Ser Cys Asp Lys Thr His Thr Cys Pro Pro Cys Pro Ala
            210                 215                 220
Pro Glu Leu Leu Gly Gly Pro Ser Val Phe Leu Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser His Glu Asp Pro Glu Val Lys Phe Asn Trp Tyr Val
            260                 265                 270
Asp Gly Val Glu Val His Asn Ala Lys Thr Lys Pro Arg Glu Glu Gln
            275                 280                 285
Tyr Asn Ser Thr Tyr Arg Val Val Ser Val Leu Thr Val Leu His Gln
            290                 295                 300
Asp Trp Leu Asn Gly Lys Glu Tyr Lys Cys Lys Val Ser Asn Lys Ala
305                 310                 315                 320
Leu Pro Ala Pro Ile Glu Lys Thr Ile Ser Lys Ala Lys Gly Gln Pro
                325                 330                 335
Arg Glu Pro Gln Val Tyr Thr Leu Pro Pro Ser Arg Asp Glu Leu Thr
            340                 345                 350
Lys Asn Gln Val Ser Leu Thr Cys Leu Val Lys Gly Phe Tyr Pro Ser
            355                 360                 365
Asp Ile Ala Val Glu Trp Glu Ser Asn Gly Gln Pro Glu Asn Asn Tyr
370                 375                 380
Lys Thr Thr Pro Pro Val Leu Asp Ser Asp Gly Ser Phe Phe Leu Tyr
385                 390                 395                 400
Ser Lys Leu Thr Val Asp Lys Ser Arg Trp Gln Gln Gly Asn Val Phe
                405                 410                 415
Ser Cys Ser Val Met His Glu Ala Leu His Asn His Tyr Thr Gln Lys
            420                 425                 430
Ser Leu Ser Leu Ser Pro Gly Lys Ser Gly Gly Gly Gly Ser Gly Gly
            435                 440                 445
Gly Gly Ser Gly Gly Gly Gly Ser Gly Gly Gly Gly Ser Glu Val Gln
            450                 455                 460
Leu Leu Glu Ser Gly Gly Gly Leu Val Gln Pro Gly Gly Ser Leu Arg
465                 470                 475                 480
Leu Ser Cys Ala Ala Ser Gly Phe Thr Phe Ser Ser His Ala Met Ser
                485                 490                 495
```

```
Trp Val Arg Gln Ala Pro Gly Lys Gly Leu Glu Trp Val Ser Ala Ile
            500                 505                 510

Trp Ala Ser Gly Glu Gln Tyr Tyr Ala Asp Ser Val Lys Gly Arg Phe
        515                 520                 525

Thr Ile Ser Arg Asp Asn Ser Lys Asn Thr Leu Tyr Leu Gln Met Asn
    530                 535                 540

Ser Leu Arg Ala Glu Asp Thr Ala Val Tyr Tyr Cys Ala Lys Gly Trp
545                 550                 555                 560

Leu Gly Asn Phe Asp Tyr Trp Gly Gln Gly Thr Leu Val Thr Val Ser
                565                 570                 575

Ser Ala Ser Thr Lys Gly Pro Ser Val Phe Pro Leu Ala Pro Ser Ser
            580                 585                 590

Lys Ser Thr Ser Gly Gly Thr Ala Ala Leu Gly Cys Leu Val Lys Asp
        595                 600                 605

Tyr Phe Pro Glu Pro Val Thr Val Ser Trp Asn Ser Gly Ala Leu Thr
    610                 615                 620

Ser Gly Val His Thr Phe Pro Ala Val Leu Gln Ser Ser Gly Leu Tyr
625                 630                 635                 640

Ser Leu Ser Ser Val Val Thr Val Pro Ser Ser Ser Leu Gly Thr Gln
                645                 650                 655

Thr Tyr Ile Cys Asn Val Asn His Lys Pro Ser Asn Thr Lys Val Asp
            660                 665                 670

Lys Lys Val Glu Pro Lys Ser Cys Asp
        675                 680

<210> SEQ ID NO 136
<211> LENGTH: 224
<212> TYPE: PRT
<213> ORGANISM: Artificial Sequence
<220> FEATURE:
<223> OTHER INFORMATION: DR5(5E11) VHCL pETR11484

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175
```

```
Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
            195                 200                 205

Gln Gly Leu Ser Ser Pro Val Thr Lys Ser Phe Asn Arg Gly Glu Cys
            210                 215                 220

<210> SEQ ID NO 137
<211> LENGTH: 215
<212> TYPE: PRT
<213> ORGANISM: Artificial Sequence
<220> FEATURE:
<223> OTHER INFORMATION: FAP (28H1) VLCL pETR9366

<400> SEQUENCE: 137

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 138
<211> LENGTH: 690
<212> TYPE: PRT
<213> ORGANISM: Artificial Sequence
<220> FEATURE:
<223> OTHER INFORMATION: CH1CL DR5(5E11)-FAP(28H1) pETR11828 2+2

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
    130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Gly Gly Gly Ser Gly Gly Gly Ser Gly Gly Gly
    450                 455                 460

```
Ser Gly Gly Gly Gly Ser Glu Val Gln Leu Leu Glu Ser Gly Gly
465                 470                 475                 480

Leu Val Gln Pro Gly Gly Ser Leu Arg Leu Ser Cys Ala Ala Ser Gly
                485                 490                 495

Phe Thr Phe Ser Ser His Ala Met Ser Trp Val Arg Gln Ala Pro Gly
            500                 505                 510

Lys Gly Leu Glu Trp Val Ser Ala Ile Trp Ala Ser Gly Glu Gln Tyr
        515                 520                 525

Tyr Ala Asp Ser Val Lys Gly Arg Phe Thr Ile Ser Arg Asp Asn Ser
    530                 535                 540

Lys Asn Thr Leu Tyr Leu Gln Met Asn Ser Leu Arg Ala Glu Asp Thr
545                 550                 555                 560

Ala Val Tyr Tyr Cys Ala Lys Gly Trp Leu Gly Asn Phe Asp Tyr Trp
                565                 570                 575

Gly Gln Gly Thr Leu Val Thr Val Ser Ser Ala Ser Thr Lys Gly Pro
            580                 585                 590

Ser Val Phe Pro Leu Ala Pro Ser Ser Lys Ser Thr Ser Gly Gly Thr
        595                 600                 605

Ala Ala Leu Gly Cys Leu Val Lys Asp Tyr Phe Pro Glu Pro Val Thr
    610                 615                 620

Val Ser Trp Asn Ser Gly Ala Leu Thr Ser Gly Val His Thr Phe Pro
625                 630                 635                 640

Ala Val Leu Gln Ser Ser Gly Leu Tyr Ser Leu Ser Ser Val Val Thr
                645                 650                 655

Val Pro Ser Ser Ser Leu Gly Thr Gln Thr Tyr Ile Cys Asn Val Asn
            660                 665                 670

His Lys Pro Ser Asn Thr Lys Val Asp Lys Lys Val Glu Pro Lys Ser
        675                 680                 685

Cys Asp
690

<210> SEQ ID NO 139
<211> LENGTH: 214
<212> TYPE: PRT
<213> ORGANISM: Artificial Sequence
<220> FEATURE:
<223> OTHER INFORMATION: DR5(5E11) VLCH1pETR11480

<400> SEQUENCE: 139

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Thr Thr His Pro
                85                  90                  95

Ile Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125
```

```
Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
                195                 200                 205

Glu Pro Lys Ser Cys Asp
    210
```

<210> SEQ ID NO 140
<211> LENGTH: 691
<212> TYPE: PRT
<213> ORGANISM: Artificial Sequence
<220> FEATURE:
<223> OTHER INFORMATION: DR5(18F11)-FAP(28H1)VHCL2+2

<400> SEQUENCE: 140

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Gly Val Arg Lys Lys Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

-continued

```
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys Ser
            435                 440                 445
Gly Gly Gly Gly Ser Gly Gly Gly Ser Gly Gly Gly Gly Ser Gly
450                 455                 460
Gly Gly Gly Ser Glu Val Gln Leu Leu Glu Ser Gly Gly Gly Leu Val
465                 470                 475                 480
Gln Pro Gly Gly Ser Leu Arg Leu Ser Cys Ala Ala Ser Gly Phe Thr
                485                 490                 495
Phe Ser Ser His Ala Met Ser Trp Val Arg Gln Ala Pro Gly Lys Gly
            500                 505                 510
Leu Glu Trp Val Ser Ala Ile Trp Ala Ser Gly Glu Gln Tyr Tyr Ala
            515                 520                 525
Asp Ser Val Lys Gly Arg Phe Thr Ile Ser Arg Asp Asn Ser Lys Asn
530                 535                 540
Thr Leu Tyr Leu Gln Met Asn Ser Leu Arg Ala Glu Asp Thr Ala Val
545                 550                 555                 560
Tyr Tyr Cys Ala Lys Gly Trp Leu Gly Asn Phe Asp Tyr Trp Gly Gln
                565                 570                 575
Gly Thr Leu Val Thr Val Ser Ser Ala Ser Val Ala Ala Pro Ser Val
            580                 585                 590
Phe Ile Phe Pro Pro Ser Asp Glu Gln Leu Lys Ser Gly Thr Ala Ser
            595                 600                 605
Val Val Cys Leu Leu Asn Asn Phe Tyr Pro Arg Glu Ala Lys Val Gln
610                 615                 620
Trp Lys Val Asp Asn Ala Leu Gln Ser Gly Asn Ser Gln Glu Ser Val
625                 630                 635                 640
Thr Glu Gln Asp Ser Lys Asp Ser Thr Tyr Ser Leu Ser Ser Thr Leu
                645                 650                 655
Thr Leu Ser Lys Ala Asp Tyr Glu Lys His Lys Val Tyr Ala Cys Glu
            660                 665                 670
Val Thr His Gln Gly Leu Ser Ser Pro Val Thr Lys Ser Phe Asn Arg
            675                 680                 685
Gly Glu Cys
```

-continued

690

<210> SEQ ID NO 141
<211> LENGTH: 215
<212> TYPE: PRT
<213> ORGANISM: Artificial Sequence
<220> FEATURE:
<223> OTHER INFORMATION: DR5(18F11) LC

<400> SEQUENCE: 141

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Pro Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 142
<211> LENGTH: 689
<212> TYPE: PRT
<213> ORGANISM: Artificial Sequence
<220> FEATURE:
<223> OTHER INFORMATION: DR5(5E11)-FAP(28H1)Fc knobVHCL2+1pETR10427

<400> SEQUENCE: 142

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130             135                 140

Leu Val Lys Asp Tyr Phe Pro Glu Pro Val Thr Val Ser Trp Asn Ser
145             150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
210             215                 220

Thr Cys Pro Pro Cys Pro Ala Pro Glu Leu Leu Gly Gly Pro Ser Val
225             230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290             295                 300

Val Leu Thr Val Leu His Gln Asp Trp Leu Asn Gly Lys Glu Tyr Lys
305             310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385             390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Gly Ser Gly Gly Gly Gly Ser Gly Gly Gly
450                 455                 460

Gly Ser Glu Val Gln Leu Leu Glu Ser Gly Gly Gly Leu Val Gln Pro
465             470                 475                 480

Gly Gly Ser Leu Arg Leu Ser Cys Ala Ala Ser Gly Phe Thr Phe Ser
                485                 490                 495

Ser His Ala Met Ser Trp Val Arg Gln Ala Pro Gly Lys Gly Leu Glu
```

```
                500             505             510
Trp Val Ser Ala Ile Trp Ala Ser Gly Glu Gln Tyr Tyr Ala Asp Ser
                515             520             525

Val Lys Gly Arg Phe Thr Ile Ser Arg Asp Asn Ser Lys Asn Thr Leu
            530             535             540

Tyr Leu Gln Met Asn Ser Leu Arg Ala Glu Asp Thr Ala Val Tyr Tyr
545             550             555             560

Cys Ala Lys Gly Trp Leu Gly Asn Phe Asp Tyr Trp Gly Gln Gly Thr
                565             570             575

Leu Val Thr Val Ser Ser Ala Ser Val Ala Ala Pro Ser Val Phe Ile
            580             585             590

Phe Pro Pro Ser Asp Glu Gln Leu Lys Ser Gly Thr Ala Ser Val Val
        595             600             605

Cys Leu Leu Asn Asn Phe Tyr Pro Arg Glu Ala Lys Val Gln Trp Lys
        610             615             620

Val Asp Asn Ala Leu Gln Ser Gly Asn Ser Gln Glu Ser Val Thr Glu
625             630             635             640

Gln Asp Ser Lys Asp Ser Thr Tyr Ser Leu Ser Ser Thr Leu Thr Leu
            645             650             655

Ser Lys Ala Asp Tyr Glu Lys His Lys Val Tyr Ala Cys Glu Val Thr
            660             665             670

His Gln Gly Leu Ser Ser Pro Val Thr Lys Ser Phe Asn Arg Gly Glu
        675             680             685

Cys

<210> SEQ ID NO 143
<211> LENGTH: 447
<212> TYPE: PRT
<213> ORGANISM: Artificial Sequence
<220> FEATURE:
<223> OTHER INFORMATION: DR5(5E11)Fc holepETR10336

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Cys Thr Leu Pro
        340                 345                 350

Pro Ser Arg Asp Glu Leu Thr Lys Asn Gln Val Ser Leu Ser Cys Ala
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys
    435                 440                 445

<210> SEQ ID NO 144
<211> LENGTH: 687
<212> TYPE: PRT
<213> ORGANISM: Artificial Sequence
<220> FEATURE:
<223> OTHER INFORMATION: DR5(5E11)-DR5(5E11)Fc hole pETR10429 3+1

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

```
Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Gly Gly Gly Ser Gly Gly Gly
    450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Phe Thr Phe Ser
                485                 490                 495

Ser Tyr Ala Met Ser Trp Val Arg Gln Ala Pro Gly Lys Gly Leu Glu
            500                 505                 510
```

```
Trp Val Ser Ala Ile Ser Gly Ser Gly Gly Ser Thr Tyr Tyr Ala Asp
            515                 520                 525

Ser Val Lys Gly Arg Phe Thr Ile Ser Arg Asp Asn Ser Lys Asn Thr
        530                 535                 540

Leu Tyr Leu Gln Met Asn Ser Leu Arg Ala Glu Asp Thr Ala Val Tyr
545                 550                 555                 560

Tyr Cys Ala Lys Gly Val Arg Val Ser Phe Asp Tyr Trp Gly Gln Gly
                565                 570                 575

Thr Leu Val Thr Val Ser Ser Ala Ser Thr Lys Gly Pro Ser Val Phe
            580                 585                 590

Pro Leu Ala Pro Ser Ser Lys Ser Thr Ser Gly Gly Thr Ala Ala Leu
        595                 600                 605

Gly Cys Leu Val Lys Asp Tyr Phe Pro Glu Pro Val Thr Val Ser Trp
    610                 615                 620

Asn Ser Gly Ala Leu Thr Ser Gly Val His Thr Phe Pro Ala Val Leu
625                 630                 635                 640

Gln Ser Ser Gly Leu Tyr Ser Leu Ser Ser Val Val Thr Val Pro Ser
                645                 650                 655

Ser Ser Leu Gly Thr Gln Thr Tyr Ile Cys Asn Val Asn His Lys Pro
            660                 665                 670

Ser Asn Thr Lys Val Asp Lys Lys Val Glu Pro Lys Ser Cys Asp
        675                 680                 685

<210> SEQ ID NO 145
<211> LENGTH: 677
<212> TYPE: PRT
<213> ORGANISM: Artificial Sequence
<220> FEATURE:
<223> OTHER INFORMATION: DR5(5E11)_Fc knob Fab-Fab Head-to-tail2+1
      pETR10662

<400> SEQUENCE: 145

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Gly Gly Gly Gly
    210                 215                 220

Ser Gly Gly Gly Gly Ser Glu Val Gln Leu Leu Glu Ser Gly Gly Gly
225                 230                 235                 240

Leu Val Gln Pro Gly Gly Ser Leu Arg Leu Ser Cys Ala Ala Ser Gly
                245                 250                 255

Phe Thr Phe Ser Ser Tyr Ala Met Ser Trp Val Arg Gln Ala Pro Gly
            260                 265                 270

Lys Gly Leu Glu Trp Val Ser Ala Ile Ser Gly Ser Gly Gly Ser Thr
        275                 280                 285

Tyr Tyr Ala Asp Ser Val Lys Gly Arg Phe Thr Ile Ser Arg Asp Asn
    290                 295                 300

Ser Lys Asn Thr Leu Tyr Leu Gln Met Asn Ser Leu Arg Ala Glu Asp
305                 310                 315                 320

Thr Ala Val Tyr Tyr Cys Ala Lys Gly Val Arg Val Ser Phe Asp Tyr
                325                 330                 335

Trp Gly Gln Gly Thr Leu Val Thr Val Ser Ser Ala Ser Thr Lys Gly
            340                 345                 350

Pro Ser Val Phe Pro Leu Ala Pro Ser Ser Lys Ser Thr Ser Gly Gly
            355                 360                 365

Thr Ala Ala Leu Gly Cys Leu Val Lys Asp Tyr Phe Pro Glu Pro Val
            370                 375                 380

Thr Val Ser Trp Asn Ser Gly Ala Leu Thr Ser Gly Val His Thr Phe
385                 390                 395                 400

Pro Ala Val Leu Gln Ser Ser Gly Leu Tyr Ser Leu Ser Ser Val Val
                405                 410                 415

Thr Val Pro Ser Ser Ser Leu Gly Thr Gln Thr Tyr Ile Cys Asn Val
            420                 425                 430

Asn His Lys Pro Ser Asn Thr Lys Val Asp Lys Lys Val Glu Pro Lys
        435                 440                 445

Ser Cys Asp Lys Thr His Thr Cys Pro Pro Cys Pro Ala Pro Glu Leu
    450                 455                 460

Leu Gly Gly Pro Ser Val Phe Leu Phe Pro Pro Lys Pro Lys Asp Thr
465                 470                 475                 480

Leu Met Ile Ser Arg Thr Pro Glu Val Thr Cys Val Val Val Asp Val
                485                 490                 495

Ser His Glu Asp Pro Glu Val Lys Phe Asn Trp Tyr Val Asp Gly Val
            500                 505                 510

Glu Val His Asn Ala Lys Thr Lys Pro Arg Glu Glu Gln Tyr Asn Ser
        515                 520                 525

Thr Tyr Arg Val Val Ser Val Leu Thr Val Leu His Gln Asp Trp Leu
    530                 535                 540

Asn Gly Lys Glu Tyr Lys Cys Lys Val Ser Asn Lys Ala Leu Pro Ala
545                 550                 555                 560

Pro Ile Glu Lys Thr Ile Ser Lys Ala Lys Gly Gln Pro Arg Glu Pro
                565                 570                 575

Gln Val Tyr Thr Leu Pro Pro Cys Arg Asp Glu Leu Thr Lys Asn Gln
            580                 585                 590

Val Ser Leu Trp Cys Leu Val Lys Gly Phe Tyr Pro Ser Asp Ile Ala
        595                 600                 605
```

```
Val Glu Trp Glu Ser Asn Gly Gln Pro Glu Asn Asn Tyr Lys Thr Thr
    610             615                 620
Pro Pro Val Leu Asp Ser Asp Gly Ser Phe Phe Leu Tyr Ser Lys Leu
625             630                 635                 640
Thr Val Asp Lys Ser Arg Trp Gln Gln Gly Asn Val Phe Ser Cys Ser
                645                 650                 655
Val Met His Glu Ala Leu His Asn His Tyr Thr Gln Lys Ser Leu Ser
            660                 665                 670
Leu Ser Pro Gly Lys
            675

<210> SEQ ID NO 146
<211> LENGTH: 450
<212> TYPE: PRT
<213> ORGANISM: Artificial Sequence
<220> FEATURE:
<223> OTHER INFORMATION: FAP (28H1) _FcholeVHCLpETR10130

<400> SEQUENCE: 146

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser His
            20                  25                  30
Ala Met Ser Trp Val Arg Gln Ala Pro Gly Lys Gly Leu Glu Trp Val
        35                  40                  45
Ser Ala Ile Trp Ala Ser Gly Glu Gln Tyr Tyr Ala Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Lys Gly Trp Leu Gly Asn Phe Asp Tyr Trp Gly Gln Gly Thr Leu Val
            100                 105                 110
Thr Val Ser Ser Ala Ser Val Ala Ala Pro Ser Val Phe Ile Phe Pro
        115                 120                 125
Pro Ser Asp Glu Gln Leu Lys Ser Gly Thr Ala Ser Val Val Cys Leu
    130                 135                 140
Leu Asn Asn Phe Tyr Pro Arg Glu Ala Lys Val Gln Trp Lys Val Asp
145                 150                 155                 160
Asn Ala Leu Gln Ser Gly Asn Ser Gln Glu Ser Val Thr Glu Gln Asp
                165                 170                 175
Ser Lys Asp Ser Thr Tyr Ser Leu Ser Ser Thr Leu Thr Leu Ser Lys
            180                 185                 190
Ala Asp Tyr Glu Lys His Lys Val Tyr Ala Cys Glu Val Thr His Gln
        195                 200                 205
Gly Leu Ser Ser Pro Val Thr Lys Ser Phe Asn Arg Gly Glu Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 147
<211> LENGTH: 691
<212> TYPE: PRT
<213> ORGANISM: Artificial Sequence
<220> FEATURE:
<223> OTHER INFORMATION: DR5(18F11)-FAP (28H1)Fc knobVHCL2+1pETR9807

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Gly Val Arg Lys Lys Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Arg Asp Glu Leu Thr Lys Asn Gln Val Ser Leu Trp Cys Leu
    355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
    435                 440                 445

Gly Gly Gly Gly Ser Gly Gly Gly Gly Ser Gly Gly Gly Gly Ser Gly
450                 455                 460

Gly Gly Ser Glu Val Gln Leu Leu Glu Ser Gly Gly Gly Leu Val
465                 470                 475                 480

Gln Pro Gly Gly Ser Leu Arg Leu Ser Cys Ala Ala Ser Gly Phe Thr
                485                 490                 495

Phe Ser Ser His Ala Met Ser Trp Val Arg Gln Ala Pro Gly Lys Gly
            500                 505                 510

Leu Glu Trp Val Ser Ala Ile Trp Ala Ser Gly Glu Gln Tyr Tyr Ala
    515                 520                 525

Asp Ser Val Lys Gly Arg Phe Thr Ile Ser Arg Asp Asn Ser Lys Asn
    530                 535                 540

Thr Leu Tyr Leu Gln Met Asn Ser Leu Arg Ala Glu Asp Thr Ala Val
545                 550                 555                 560

Tyr Tyr Cys Ala Lys Gly Trp Leu Gly Asn Phe Asp Tyr Trp Gly Gln
                565                 570                 575

Gly Thr Leu Val Thr Val Ser Ser Ala Ser Val Ala Ala Pro Ser Val
            580                 585                 590

Phe Ile Phe Pro Pro Ser Asp Glu Gln Leu Lys Ser Gly Thr Ala Ser
    595                 600                 605

Val Val Cys Leu Leu Asn Asn Phe Tyr Pro Arg Glu Ala Lys Val Gln
```

```
            610                 615                 620
Trp Lys Val Asp Asn Ala Leu Gln Ser Gly Asn Ser Gln Glu Ser Val
625                 630                 635                 640

Thr Glu Gln Asp Ser Lys Asp Ser Thr Tyr Ser Leu Ser Ser Thr Leu
                645                 650                 655

Thr Leu Ser Lys Ala Asp Tyr Glu Lys His Lys Val Tyr Ala Cys Glu
                660                 665                 670

Val Thr His Gln Gly Leu Ser Ser Pro Val Thr Lys Ser Phe Asn Arg
                675                 680                 685

Gly Glu Cys
        690

<210> SEQ ID NO 148
<211> LENGTH: 447
<212> TYPE: PRT
<213> ORGANISM: Artificial Sequence
<220> FEATURE:
<223> OTHER INFORMATION: DR5(18F11) Fc hole pETR9808

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Gly Val Arg Lys Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
```

275                 280                 285
Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 149
<211> LENGTH: 689
<212> TYPE: PRT
<213> ORGANISM: Artificial Sequence
<220> FEATURE:
<223> OTHER INFORMATION: DR5(18F11)-FAP(28H1)VHCLFc knob3+1pETR10333

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Gly Val Arg Lys Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn

```
                195                 200                 205
Thr Lys Val Asp Lys Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
            275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Cys Arg Asp Glu Leu Thr Lys Asn Gln Val Ser Leu Trp Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
                420                 425                 430
His Asn His Tyr Thr Gln Lys Ser Leu Ser Leu Ser Pro Gly Gly Gly
            435                 440                 445
Gly Gly Ser Gly Gly Gly Gly Ser Gly Gly Gly Gly Ser Gly Gly Gly
450                 455                 460
Gly Ser Glu Val Gln Leu Leu Glu Ser Gly Gly Gly Leu Val Gln Pro
465                 470                 475                 480
Gly Gly Ser Leu Arg Leu Ser Cys Ala Ala Ser Gly Phe Thr Phe Ser
                485                 490                 495
Ser His Ala Met Ser Trp Val Arg Gln Ala Pro Gly Lys Gly Leu Glu
            500                 505                 510
Trp Val Ser Ala Ile Trp Ala Ser Gly Glu Gln Tyr Tyr Ala Asp Ser
            515                 520                 525
Val Lys Gly Arg Phe Thr Ile Ser Arg Asp Asn Ser Lys Asn Thr Leu
            530                 535                 540
Tyr Leu Gln Met Asn Ser Leu Arg Ala Glu Asp Thr Ala Val Tyr Tyr
545                 550                 555                 560
Cys Ala Lys Gly Trp Leu Gly Asn Phe Asp Tyr Trp Gly Gln Gly Thr
                565                 570                 575
Leu Val Thr Val Ser Ser Ala Ser Val Ala Ala Pro Ser Val Phe Ile
            580                 585                 590
Phe Pro Pro Ser Asp Glu Gln Leu Lys Ser Gly Thr Ala Ser Val Val
            595                 600                 605
Cys Leu Leu Asn Asn Phe Tyr Pro Arg Glu Ala Lys Val Gln Trp Lys
610                 615                 620
```

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
            645                 650                 655

Ser Lys Ala Asp Tyr Glu Lys His Lys Val Tyr Ala Cys Glu Val Thr
        660                 665                 670

His Gln Gly Leu Ser Ser Pro Val Thr Lys Ser Phe Asn Arg Gly Glu
    675                 680                 685

Cys

<210> SEQ ID NO 150
<211> LENGTH: 687
<212> TYPE: PRT
<213> ORGANISM: Artificial Sequence
<220> FEATURE:
<223> OTHER INFORMATION: DR5(18F11)-DR5(18F11)Fc holepETR10288

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
            85                  90                  95

Ala Lys Gly Val Arg Lys Phe Asp Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Ser Gly Gly Gly Ser Gly Gly Gly
450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Phe Thr Phe Ser
                485                 490                 495

Ser Tyr Ala Met Ser Trp Val Arg Gln Ala Pro Gly Lys Gly Leu Glu
            500                 505                 510

Trp Val Ser Ala Ile Ser Gly Ser Gly Gly Ser Thr Tyr Tyr Ala Asp
        515                 520                 525

Ser Val Lys Gly Arg Phe Thr Ile Ser Arg Asp Asn Ser Lys Asn Thr
    530                 535                 540

Leu Tyr Leu Gln Met Asn Ser Leu Arg Ala Glu Asp Ala Ala Val Tyr
545                 550                 555                 560

Tyr Cys Ala Lys Gly Val Arg Lys Phe Asp Tyr Trp Gly Gln Gly
                565                 570                 575

Thr Leu Val Thr Val Ser Ser Ala Ser Thr Lys Gly Pro Ser Val Phe
            580                 585                 590

Pro Leu Ala Pro Ser Ser Lys Ser Thr Ser Gly Gly Thr Ala Ala Leu
        595                 600                 605

Gly Cys Leu Val Lys Asp Tyr Phe Pro Glu Pro Val Thr Val Ser Trp
610                 615                 620

Asn Ser Gly Ala Leu Thr Ser Gly Val His Thr Phe Pro Ala Val Leu
625                 630                 635                 640

Gln Ser Ser Gly Leu Tyr Ser Leu Ser Ser Val Val Thr Val Pro Ser
                645                 650                 655

Ser Ser Leu Gly Thr Gln Thr Tyr Ile Cys Asn Val Asn His Lys Pro
            660                 665                 670

Ser Asn Thr Lys Val Asp Lys Lys Val Glu Pro Lys Ser Cys Asp
        675                 680                 685

<210> SEQ ID NO 151
<211> LENGTH: 330
<212> TYPE: PRT
```

<213> ORGANISM: Artificial Sequence
<220> FEATURE:
<223> OTHER INFORMATION: hu Fc _wt

<400> SEQUENCE: 151

| | | | | | | | | | | | | | | | |
|---|---|---|---|---|---|---|---|---|---|---|---|---|---|---|---|
| Ala | Ser | Thr | Lys | Gly | Pro | Ser | Val | Phe | Pro | Leu | Ala | Pro | Ser | Ser | Lys |
| 1 | | | | 5 | | | | | 10 | | | | | 15 | |
| Ser | Thr | Ser | Gly | Gly | Thr | Ala | Ala | Leu | Gly | Cys | Leu | Val | Lys | Asp | Tyr |
| | | | 20 | | | | | 25 | | | | | 30 | | |
| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |
| Gly | Val | His | Thr | Phe | Pro | Ala | Val | Leu | Gln | Ser | Ser | Gly | Leu | Tyr | Ser |
| | 50 | | | | | 55 | | | | | 60 | | | | |
| Leu | Ser | Ser | Val | Val | Thr | Val | Pro | Ser | Ser | Ser | Leu | Gly | Thr | Gln | Thr |
| 65 | | | | | 70 | | | | | 75 | | | | | 80 |
| Tyr | Ile | Cys | Asn | Val | Asn | His | Lys | Pro | Ser | Asn | Thr | Lys | Val | Asp | Lys |
| | | | | 85 | | | | | 90 | | | | | 95 | |
| Lys | Val | Glu | Pro | Lys | Ser | Cys | Asp | Lys | Thr | His | Thr | Cys | Pro | Pro | Cys |
| | | | 100 | | | | | 105 | | | | | 110 | | |
| Pro | Ala | Pro | Glu | Leu | Leu | Gly | Gly | Pro | Ser | Val | Phe | Leu | Phe | Pro | Pro |
| | | 115 | | | | | 120 | | | | | 125 | | | |
| Lys | Pro | Lys | Asp | Thr | Leu | Met | Ile | Ser | Arg | Thr | Pro | Glu | Val | Thr | Cys |
| | 130 | | | | | 135 | | | | | 140 | | | | |
| Val | Val | Val | Asp | Val | Ser | His | Glu | Asp | Pro | Glu | Val | Lys | Phe | Asn | Trp |
| 145 | | | | | 150 | | | | | 155 | | | | | 160 |
| Tyr | Val | Asp | Gly | Val | Glu | Val | His | Asn | Ala | Lys | Thr | Lys | Pro | Arg | Glu |
| | | | | 165 | | | | | 170 | | | | | 175 | |
| Glu | Gln | Tyr | Asn | Ser | Thr | Tyr | Arg | Val | Val | Ser | Val | Leu | Thr | Val | Leu |
| | | | 180 | | | | | 185 | | | | | 190 | | |
| His | Gln | Asp | Trp | Leu | Asn | Gly | Lys | Glu | Tyr | Lys | Cys | Lys | Val | Ser | Asn |
| | | 195 | | | | | 200 | | | | | 205 | | | |
| Lys | Ala | Leu | Pro | Ala | Pro | Ile | Glu | Lys | Thr | Ile | Ser | Lys | Ala | Lys | Gly |
| | 210 | | | | | 215 | | | | | 220 | | | | |
| Gln | Pro | Arg | Glu | Pro | Gln | Val | Tyr | Thr | Leu | Pro | Pro | Ser | Arg | Asp | Glu |
| 225 | | | | | 230 | | | | | 235 | | | | | 240 |
| Leu | Thr | Lys | Asn | Gln | Val | Ser | Leu | Thr | Cys | Leu | Val | Lys | Gly | Phe | Tyr |
| | | | | 245 | | | | | 250 | | | | | 255 | |
| Pro | Ser | Asp | Ile | Ala | Val | Glu | Trp | Glu | Ser | Asn | Gly | Gln | Pro | Glu | Asn |
| | | | 260 | | | | | 265 | | | | | 270 | | |
| Asn | Tyr | Lys | Thr | Thr | Pro | Pro | Val | Leu | Asp | Ser | Asp | Gly | Ser | Phe | Phe |
| | | 275 | | | | | 280 | | | | | 285 | | | |
| Leu | Tyr | Ser | Lys | Leu | Thr | Val | Asp | Lys | Ser | Arg | Trp | Gln | Gln | Gly | Asn |
| | 290 | | | | | 295 | | | | | 300 | | | | |
| Val | Phe | Ser | Cys | Ser | Val | Met | His | Glu | Ala | Leu | His | Asn | His | Tyr | Thr |
| 305 | | | | | 310 | | | | | 315 | | | | | 320 |
| Gln | Lys | Ser | Leu | Ser | Leu | Ser | Pro | Gly | Lys | | | | | | |
| | | | | 325 | | | | | 330 | | | | | | |

<210> SEQ ID NO 152
<211> LENGTH: 329
<212> TYPE: PRT
<213> ORGANISM: Artificial Sequence
<220> FEATURE:
<223> OTHER INFORMATION: hu Fc_P329G/LALA

<400> SEQUENCE: 152

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Gly Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Lys
                325

<210> SEQ ID NO 153
<211> LENGTH: 107
<212> TYPE: PRT
<213> ORGANISM: Artificial Sequence
<220> FEATURE:
<223> OTHER INFORMATION: hu kappa light chain

<400> SEQUENCE: 153

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 154
<211> LENGTH: 106
<212> TYPE: PRT
<213> ORGANISM: Artificial Sequence
<220> FEATURE:
<223> OTHER INFORMATION: hu lambda light chain

<400> SEQUENCE: 154

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 155
<211> LENGTH: 439
<212> TYPE: PRT
<213> ORGANISM: Homo sapiens

<400> SEQUENCE: 155

Met Glu Gln Arg Gly Gln Asn Ala Pro Ala Ala Ser Gly Ala Arg Lys
 1               5                  10                  15

Arg His Gly Pro Gly Pro Arg Glu Ala Arg Gly Ala Arg Pro Gly Pro
             20                  25                  30

Arg Val Pro Lys Thr Leu Val Leu Val Val Ala Ala Val Leu Leu Leu
         35                  40                  45

Val Ser Ala Glu Ser Ala Leu Ile Thr Gln Gln Asp Leu Ala Pro Gln
 50                  55                  60

Gln Arg Ala Ala Pro Gln Gln Lys Arg Ser Ser Pro Ser Glu Gly Leu
 65                  70                  75                  80

Cys Pro Pro Gly His His Ile Ser Glu Asp Gly Arg Asp Cys Ile Ser
                 85                  90                  95

Cys Lys Tyr Gly Asp Tyr Ser Thr His Trp Asn Asp Leu Leu Phe Cys
            100                 105                 110

Leu Arg Cys Thr Arg Cys Asp Ser Gly Glu Val Glu Leu Ser Pro Cys
        115                 120                 125

Thr Thr Thr Arg Asn Thr Val Cys Gln Cys Glu Glu Gly Thr Phe Arg
```

```
            130                 135                 140
Glu Asp Ser Pro Glu Met Cys Arg Lys Cys Arg Thr Gly Cys Pro
145                 150                 155                 160

Arg Gly Met Val Lys Val Gly Asp Cys Thr Pro Trp Ser Asp Ile Glu
                165                 170                 175

Cys Val His Lys Glu Ser Gly Thr Lys His Ser Gly Glu Ala Pro Ala
            180                 185                 190

Val Glu Glu Thr Val Thr Ser Ser Pro Gly Thr Pro Ala Ser Pro Cys
        195                 200                 205

Ser Leu Ser Gly Ile Ile Ile Gly Val Thr Val Ala Ala Val Val Leu
    210                 215                 220

Ile Val Ala Val Phe Val Cys Lys Ser Leu Leu Trp Lys Lys Val Leu
225                 230                 235                 240

Pro Tyr Leu Lys Gly Ile Cys Ser Gly Gly Gly Asp Pro Glu Arg
                245                 250                 255

Val Asp Arg Ser Ser Gln Arg Pro Gly Ala Glu Asp Asn Val Leu Asn
            260                 265                 270

Glu Ile Val Ser Ile Leu Gln Pro Thr Gln Val Pro Glu Gln Glu Met
        275                 280                 285

Glu Val Gln Glu Pro Ala Glu Pro Thr Gly Val Asn Met Leu Ser Pro
290                 295                 300

Gly Glu Ser Glu His Leu Leu Glu Pro Ala Glu Ala Glu Arg Ser Gln
305                 310                 315                 320

Arg Arg Arg Leu Leu Val Pro Ala Asn Glu Gly Asp Pro Thr Glu Thr
                325                 330                 335

Leu Arg Gln Cys Phe Asp Asp Phe Ala Asp Leu Val Pro Phe Asp Ser
            340                 345                 350

Trp Glu Pro Leu Met Arg Lys Leu Gly Leu Met Asp Asn Glu Ile Lys
        355                 360                 365

Val Ala Lys Ala Glu Ala Ala Gly His Arg Asp Thr Leu Tyr Thr Met
370                 375                 380

Leu Ile Lys Trp Val Asn Lys Thr Gly Arg Asp Ala Ser Val His Thr
385                 390                 395                 400

Leu Leu Asp Ala Leu Glu Thr Leu Gly Glu Arg Leu Ala Lys Gln Lys
                405                 410                 415

Ile Glu Asp His Leu Leu Ser Ser Gly Lys Phe Met Tyr Leu Glu Gly
            420                 425                 430

Asn Ala Asp Ser Ala Met Ser
            435

<210> SEQ ID NO 156
<211> LENGTH: 748
<212> TYPE: PRT
<213> ORGANISM: Artificial Sequence
<220> FEATURE:
<223> OTHER INFORMATION: Human FAP ectodomain+poly-lys-tag+his6-tag

<400> SEQUENCE: 156

Arg Pro Ser Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
```

```
                50                  55                  60
Ser Asn Arg Thr Met Lys Ser Val Asn Ala Ser Asn Tyr Gly Leu Ser
 65                  70                  75                  80

Pro Asp Arg Gln Phe Val Tyr Leu Glu Ser Asp Tyr Ser Lys Leu Trp
                     85                  90                  95

Arg Tyr Ser Tyr Thr Ala Thr Tyr Tyr Ile Tyr Asp Leu Ser Asn Gly
                    100                 105                 110

Glu Phe Val Arg Gly Asn Glu Leu Pro Arg Pro Ile Gln Tyr Leu Cys
                115                 120                 125

Trp Ser Pro Val Gly Ser Lys Leu Ala Tyr Val Tyr Gln Asn Asn Ile
            130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                    165                 170                 175

Glu Glu Met Leu Ala Thr Lys Tyr Ala Leu Trp Trp Ser Pro Asn Gly
                180                 185                 190

Lys Phe Leu Ala Tyr Ala Glu Phe Asn Asp Thr Asp Ile Pro Val Ile
                195                 200                 205

Ala Tyr Ser Tyr Tyr Gly Asp Glu Gln Tyr Pro Arg Thr Ile Asn Ile
            210                 215                 220

Pro Tyr Pro Lys Ala Gly Ala Lys Asn Pro Val Val Arg Ile Phe Ile
225                 230                 235                 240

Ile Asp Thr Thr Tyr Pro Ala Tyr Val Gly Pro Gln Glu Val Pro Val
                    245                 250                 255

Pro Ala Met Ile Ala Ser Ser Asp Tyr Tyr Phe Ser Trp Leu Thr Trp
                260                 265                 270

Val Thr Asp Glu Arg Val Cys Leu Gln Trp Leu Lys Arg Val Gln Asn
                275                 280                 285

Val Ser Val Leu Ser Ile Cys Asp Phe Arg Glu Asp Trp Gln Thr Trp
            290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                    325                 330                 335

Ser Tyr Tyr Lys Ile Phe Ser Asp Lys Asp Gly Tyr Lys His Ile His
                340                 345                 350

Tyr Ile Lys Asp Thr Val Glu Asn Ala Ile Gln Ile Thr Ser Gly Lys
            355                 360                 365

Trp Glu Ala Ile Asn Ile Phe Arg Val Thr Gln Asp Ser Leu Phe Tyr
370                 375                 380

Ser Ser Asn Glu Phe Glu Glu Tyr Pro Gly Arg Arg Asn Ile Tyr Arg
385                 390                 395                 400

Ile Ser Ile Gly Ser Tyr Pro Pro Ser Lys Lys Cys Val Thr Cys His
                    405                 410                 415

Leu Arg Lys Glu Arg Cys Gln Tyr Tyr Thr Ala Ser Phe Ser Asp Tyr
                420                 425                 430

Ala Lys Tyr Tyr Ala Leu Val Cys Tyr Gly Pro Gly Ile Pro Ile Ser
            435                 440                 445

Thr Leu His Asp Gly Arg Thr Asp Gln Glu Ile Lys Ile Leu Glu Glu
450                 455                 460

Asn Lys Glu Leu Glu Asn Ala Leu Lys Asn Ile Gln Leu Pro Lys Glu
465                 470                 475                 480
```

```
Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His
            740                 745
```

```
<210> SEQ ID NO 157
<211> LENGTH: 749
<212> TYPE: PRT
<213> ORGANISM: Artificial Sequence
<220> FEATURE:
<223> OTHER INFORMATION: Murine FAP ectodomain+poly-lys-tag+his6-tag

<400> SEQUENCE: 157

Arg Pro Ser Arg Val Tyr Lys Pro Glu Gly Asn Thr Lys Arg Ala Leu
1               5                   10                  15

Thr Leu Lys Asp Ile Leu Asn Gly Thr Phe Ser Tyr Lys Thr Tyr Phe
            20                  25                  30

Pro Asn Trp Ile Ser Glu Gln Glu Tyr Leu His Gln Ser Glu Asp Asp
        35                  40                  45

Asn Ile Val Phe Tyr Asn Ile Glu Thr Arg Glu Ser Tyr Ile Ile Leu
    50                  55                  60

Ser Asn Ser Thr Met Lys Ser Val Asn Ala Thr Asp Tyr Gly Leu Ser
65                  70                  75                  80

Pro Asp Arg Gln Phe Val Tyr Leu Glu Ser Asp Tyr Ser Lys Leu Trp
                85                  90                  95
```

```
-continued

Arg Tyr Ser Tyr Thr Ala Thr Tyr Tyr Ile Tyr Asp Leu Gln Asn Gly
            100                 105                 110

Glu Phe Val Arg Gly Tyr Glu Leu Pro Arg Pro Ile Gln Tyr Leu Cys
            115                 120                 125

Trp Ser Pro Val Gly Ser Lys Leu Ala Tyr Val Tyr Gln Asn Asn Ile
130                 135                 140

Tyr Leu Lys Gln Arg Pro Gly Asp Pro Pro Phe Gln Ile Thr Tyr Thr
145                 150                 155                 160

Gly Arg Glu Asn Arg Ile Phe Asn Gly Ile Pro Asp Trp Val Tyr Glu
                165                 170                 175

Glu Glu Met Leu Ala Thr Lys Tyr Ala Leu Trp Trp Ser Pro Asp Gly
            180                 185                 190

Lys Phe Leu Ala Tyr Val Glu Phe Asn Asp Ser Asp Ile Pro Ile Ile
            195                 200                 205

Ala Tyr Ser Tyr Tyr Gly Asp Gly Gln Tyr Pro Arg Thr Ile Asn Ile
            210                 215                 220

Pro Tyr Pro Lys Ala Gly Ala Lys Asn Pro Val Val Arg Val Phe Ile
225                 230                 235                 240

Val Asp Thr Thr Tyr Pro His His Val Gly Pro Met Glu Val Pro Val
                245                 250                 255

Pro Glu Met Ile Ala Ser Ser Asp Tyr Tyr Phe Ser Trp Leu Thr Trp
            260                 265                 270

Val Ser Ser Glu Arg Val Cys Leu Gln Trp Leu Lys Arg Val Gln Asn
            275                 280                 285

Val Ser Val Leu Ser Ile Cys Asp Phe Arg Glu Asp Trp His Ala Trp
            290                 295                 300

Glu Cys Pro Lys Asn Gln Glu His Val Glu Glu Ser Arg Thr Gly Trp
305                 310                 315                 320

Ala Gly Gly Phe Phe Val Ser Thr Pro Ala Phe Ser Gln Asp Ala Thr
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
            355                 360                 365

Trp Glu Ala Ile Tyr Ile Phe Arg Val Thr Gln Asp Ser Leu Phe Tyr
370                 375                 380

Ser Ser Asn Glu Phe Glu Gly Tyr Pro Gly Arg Arg Asn Ile Tyr Arg
385                 390                 395                 400

Ile Ser Ile Gly Asn Ser Pro Ser Lys Cys Val Thr Cys His
                405                 410                 415

Leu Arg Lys Glu Arg Cys Gln Tyr Tyr Thr Ala Ser Phe Ser Tyr Lys
            420                 425                 430

Ala Lys Tyr Tyr Ala Leu Val Cys Tyr Gly Pro Gly Leu Pro Ile Ser
            435                 440                 445

Thr Leu His Asp Gly Arg Thr Asp Gln Glu Ile Gln Val Leu Glu Glu
            450                 455                 460

Asn Lys Glu Leu Glu Asn Ser Leu Arg Asn Ile Gln Leu Pro Lys Val
465                 470                 475                 480

Glu Ile Lys Lys Leu Lys Asp Gly Gly Leu Thr Phe Trp Tyr Lys Met
                485                 490                 495

Ile Leu Pro Pro Gln Phe Asp Arg Ser Lys Lys Tyr Pro Leu Leu Ile
            500                 505                 510
```

```
Gln Val Tyr Gly Gly Pro Cys Ser Gln Ser Val Lys Ser Val Phe Ala
            515                 520                 525

Val Asn Trp Ile Thr Tyr Leu Ala Ser Lys Glu Gly Ile Val Ile Ala
        530                 535                 540

Leu Val Asp Gly Arg Gly Thr Ala Phe Gln Gly Asp Lys Phe Leu His
545                 550                 555                 560

Ala Val Tyr Arg Lys Leu Gly Val Tyr Glu Val Glu Asp Gln Leu Thr
                565                 570                 575

Ala Val Arg Lys Phe Ile Glu Met Gly Phe Ile Asp Glu Glu Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
610                 615                 620

Ser Ser Trp Glu Tyr Tyr Ala Ser Ile Tyr Ser Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
690                 695                 700

Asp Gln Asn His Gly Ile Leu Ser Gly Arg Ser Gln Asn His Leu Tyr
705                 710                 715                 720

Thr His Met Thr His Phe Leu Lys Gln Cys Phe Ser Leu Ser Asp Gly
                725                 730                 735

Lys Lys Lys Lys Lys Gly His His His His His
            740                 745

<210> SEQ ID NO 158
<211> LENGTH: 748
<212> TYPE: PRT
<213> ORGANISM: Artificial Sequence
<220> FEATURE:
<223> OTHER INFORMATION: Cynomolgus FAP ectodomain+poly-lys-tag+his6-tag

<400> SEQUENCE: 158

Arg Pro Pro Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
    50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125
```

```
Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Phe Val Arg Ile Phe Ile
225                 230                 235                 240

Ile Asp Thr Thr Tyr Pro Ala Tyr Val Gly Pro Gln Glu Val Pro Val
                245                 250                 255

Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
        275                 280                 285

Val Ser Val Leu Ser Ile Cys Asp Phe Arg Glu Asp Trp Gln Thr Trp
    290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
        355                 360                 365

Trp Glu Ala Ile Asn Ile Phe Arg Val Thr Gln Asp Ser Leu Phe Tyr
    370                 375                 380

Ser Ser Asn Glu Phe Glu Asp Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415

Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
        435                 440                 445

Thr Leu His Asp Gly Arg Thr Asp Gln Glu Ile Lys Ile Leu Glu Glu
    450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
    530                 535                 540

Leu Val Asp Gly Arg Gly Thr Ala Phe Gln Gly Asp Lys Leu Leu Tyr
```

```
            545                 550                 555                 560
        Ala Val Tyr Arg Lys Leu Gly Val Tyr Glu Val Glu Asp Gln Ile Thr
                        565                 570                 575

Ala Val Arg Lys Phe Ile Glu Met Gly Phe Ile Asp Glu Lys Arg Ile
                        580                 585                 590

Ala Ile Trp Gly Trp Ser Tyr Gly Gly Tyr Val Ser Leu Ala Leu
                        595                 600                 605

Ala Ser Gly Thr Gly Leu Phe Lys Cys Gly Ile Ala Val Ala Pro Val
                        610                 615                 620

Ser Ser Trp Glu Tyr Tyr Ala Ser Val Tyr Thr Glu Arg Phe Met Gly
        625                 630                 635                 640

Leu Pro Thr Lys Asp Asp Asn Leu Glu His Tyr Lys Asn Ser Thr Val
                        645                 650                 655

Met Ala Arg Ala Glu Tyr Phe Arg Asn Val Asp Tyr Leu Leu Ile His
                        660                 665                 670

Gly Thr Ala Asp Asp Asn Val His Phe Gln Asn Ser Ala Gln Ile Ala
                        675                 680                 685

Lys Ala Leu Val Asn Ala Gln Val Asp Phe Gln Ala Met Trp Tyr Ser
                        690                 695                 700

Asp Gln Asn His Gly Leu Ser Gly Leu Ser Thr Asn His Leu Tyr Thr
        705                 710                 715                 720

His Met Thr His Phe Leu Lys Gln Cys Phe Ser Leu Ser Asp Gly Lys
                        725                 730                 735

Lys Lys Lys Lys Lys Gly His His His His His His
                        740                 745

<210> SEQ ID NO 159
<211> LENGTH: 450
<212> TYPE: PRT
<213> ORGANISM: Artificial Sequence
<220> FEATURE:
<223> OTHER INFORMATION: FAP (28H1)_FcholeVHCLpETR10130

<400> SEQUENCE: 159

Glu Val Gln Leu Leu Glu Ser Gly Gly Gly Leu Val Gln Pro Gly Gly
        1               5                   10                  15

Ser Leu Arg Leu Ser Cys Ala Ala Ser Gly Phe Thr Phe Ser Ser His
                        20                  25                  30

Ala Met Ser Trp Val Arg Gln Ala Pro Gly Lys Gly Leu Glu Trp Val
                        35                  40                  45

Ser Ala Ile Trp Ala Ser Gly Glu Gln Tyr Tyr Ala Asp Ser Val Lys
                50                  55                  60

Gly Arg Phe Thr Ile Ser Arg Asp Asn Ser Lys Asn Thr Leu Tyr Leu
        65                  70                  75                  80

Gln Met Asn Ser Leu Arg Ala Glu Asp Thr Ala Val Tyr Tyr Cys Ala
                        85                  90                  95

Lys Gly Trp Leu Gly Asn Phe Asp Tyr Trp Gly Gln Gly Thr Leu Val
                        100                 105                 110

Thr Val Ser Ser Ala Ser Val Ala Ala Pro Ser Val Phe Ile Phe Pro
                        115                 120                 125

Pro Ser Asp Glu Gln Leu Lys Ser Gly Thr Ala Ser Val Val Cys Leu
                        130                 135                 140

Leu Asn Asn Phe Tyr Pro Arg Glu Ala Lys Val Gln Trp Lys Val Asp
        145                 150                 155                 160

Asn Ala Leu Gln Ser Gly Asn Ser Gln Glu Ser Val Thr Glu Gln Asp
```

```
                    165                 170                 175
Ser Lys Asp Ser Thr Tyr Ser Leu Ser Ser Thr Leu Thr Leu Ser Lys
                180                 185                 190

Ala Asp Tyr Glu Lys His Lys Val Tyr Ala Cys Glu Val Thr His Gln
            195                 200                 205

Gly Leu Ser Ser Pro Val Thr Lys Ser Phe Asn Arg Gly Glu Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 160
<211> LENGTH: 214
<212> TYPE: PRT
<213> ORGANISM: Artificial Sequence
<220> FEATURE:
<223> OTHER INFORMATION: FAP (28H1)VLCH1pETR9537

<400> SEQUENCE: 160

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
```

Pro Glu Asp Phe Ala Val Tyr Tyr Cys Gln Gln Gly Gln Val Ile Pro
65                  70                  75                  80

Pro Thr Phe Gly Gln Gly Thr Lys Val Glu Ile Lys Ser Ser Ala Ser
                85                  90                  95

Thr Lys Gly Pro Ser Val Phe Pro Leu Ala Pro Ser Ser Lys Ser Thr
            100                 105                 110

Ser Gly Gly Thr Ala Ala Leu Gly Cys Leu Val Lys Asp Tyr Phe Pro
        115                 120                 125

Glu Pro Val Thr Val Ser Trp Asn Ser Gly Ala Leu Thr Ser Gly Val
130                 135                 140

His Thr Phe Pro Ala Val Leu Gln Ser Gly Leu Tyr Ser Leu Ser
145                 150                 155                 160

Ser Val Val Thr Val Pro Ser Ser Leu Gly Thr Gln Thr Tyr Ile
                165                 170                 175

Cys Asn Val Asn His Lys Pro Ser Asn Thr Lys Val Asp Lys Lys Val
            180                 185                 190

Glu Pro Lys Ser Cys Asp
            195                 200                 205

210

<210> SEQ ID NO 161
<211> LENGTH: 447
<212> TYPE: PRT
<213> ORGANISM: Artificial Sequence
<220> FEATURE:
<223> OTHER INFORMATION: DR5(5E11)-Fcknob

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His

```
            210                 215                 220
Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Cys Arg Asp Glu Leu Thr Lys Asn Gln Val Ser Leu Trp Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 162
<211> LENGTH: 215
<212> TYPE: PRT
<213> ORGANISM: Artificial Sequence
<220> FEATURE:
<223> OTHER INFORMATION: DR5 (5E11)_LCpETR9044

<400> SEQUENCE: 162

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Thr Thr His Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
```

```
            130                 135                 140
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 163
<211> LENGTH: 24
<212> TYPE: DNA
<213> ORGANISM: Artificial Sequence
<220> FEATURE:
<223> OTHER INFORMATION: primer GAB-4039

<400> SEQUENCE: 163
gctggctcct ggacttccat ttcc                                        24

<210> SEQ ID NO 164
<211> LENGTH: 21
<212> TYPE: DNA
<213> ORGANISM: Artificial Sequence
<220> FEATURE:
<223> OTHER INFORMATION: primer GAB4040

<400> SEQUENCE: 164
gacccaggga ggcgcgggga g                                           21

<210> SEQ ID NO 165
<211> LENGTH: 38
<212> TYPE: DNA
<213> ORGANISM: Artificial Sequence
<220> FEATURE:
<223> OTHER INFORMATION: primer GAB-4145

<400> SEQUENCE: 165
gtgcattcca tcacccgaca atccctagat ccccagcg                         38

<210> SEQ ID NO 166
<211> LENGTH: 37
<212> TYPE: DNA
<213> ORGANISM: Artificial Sequence
<220> FEATURE:
<223> OTHER INFORMATION: primer GAB-4146

<400> SEQUENCE: 166
gcgtcgactg attctttgtg gacacactca atgtcac                          37

<210> SEQ ID NO 167
<211> LENGTH: 351
<212> TYPE: DNA
<213> ORGANISM: Artificial Sequence
<220> FEATURE:
<223> OTHER INFORMATION: DR5(22E9)_VH DNA

<400> SEQUENCE: 167
gaggtgcaat tgttggagtc tgggggaggc ttggtacagc ctgggggtc cctgagactc   60 tcctgtgcag cctccggatt cacctttagc agttatgcca tgagctgggt ccgccaggct  120
```

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggtgtg    300
cggatttcgt ttgactactg gggccaagga accctggtca ccgtctcgag t             351
```

<210> SEQ ID NO 168
<211> LENGTH: 15
<212> TYPE: DNA
<213> ORGANISM: Artificial Sequence
<220> FEATURE:
<223> OTHER INFORMATION: DR5(22E9)_ CDRH1 DNA

<400> SEQUENCE: 168

```
agttatgcca tgagc                                                      15
```

<210> SEQ ID NO 169
<211> LENGTH: 51
<212> TYPE: DNA
<213> ORGANISM: Artificial Sequence
<220> FEATURE:
<223> OTHER INFORMATION: DR5 (22E9)_CDRH2 DNA

<400> SEQUENCE: 169

```
gctattagtg gtagtggtgg tagcacatac tacgcagact ccgtgaaggg c              51
```

<210> SEQ ID NO 170
<211> LENGTH: 24
<212> TYPE: DNA
<213> ORGANISM: Artificial Sequence
<220> FEATURE:
<223> OTHER INFORMATION: DR5 (22E9)_CDRH3

<400> SEQUENCE: 170

```
ggtgtgcgga tttcgtttga ctac                                            24
```

<210> SEQ ID NO 171
<211> LENGTH: 324
<212> TYPE: DNA
<213> ORGANISM: Artificial Sequence
<220> FEATURE:
<223> OTHER INFORMATION: DR5 (22E9)_VL DNA

<400> SEQUENCE: 171

```
gaaatcgtgt taacgcagtc tccaggcacc ctgtctttgt ctccagggga aagagccacc     60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggttcta atcagcccgt tacgttcggc    300
caggggacca agtggaaat caaa                                            324
```

<210> SEQ ID NO 172
<211> LENGTH: 36
<212> TYPE: DNA
<213> ORGANISM: Artificial Sequence
<220> FEATURE:
<223> OTHER INFORMATION: DR5 (22E9)_CDRL1 DNA

<400> SEQUENCE: 172

```
agggccagtc agagtgttag cagcagctac ttagcc                               36
```

```
<210> SEQ ID NO 173
<211> LENGTH: 21
<212> TYPE: DNA
<213> ORGANISM: Artificial Sequence
<220> FEATURE:
<223> OTHER INFORMATION: DR5 (22E9)_CDRL2 DNA

<400> SEQUENCE: 173
ggagcatcca gcagggccac t                                              21

<210> SEQ ID NO 174
<211> LENGTH: 27
<212> TYPE: DNA
<213> ORGANISM: Artificial Sequence
<220> FEATURE:
<223> OTHER INFORMATION: DR5 (22E9)_CDRL3 DNA

<400> SEQUENCE: 174
cagcagggtt ctaatcagcc cgttacg                                        27

<210> SEQ ID NO 175
<211> LENGTH: 351
<212> TYPE: DNA
<213> ORGANISM: Artificial Sequence
<220> FEATURE:
<223> OTHER INFORMATION: DR5 (21H3)_VH DNA

<400> SEQUENCE: 175
gaggtgcaat tgttggagtc tgggggaggc ttggtacagc ctggggggtc cctgagactc    60
tcctgtgcag cctccggatt caccttago agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac atggccgtat attactgtgc gaaaggtgct   300 cgtgttttctt tgactactg gggccaagga accctggtca ccgtctcgag t            351

<210> SEQ ID NO 176
<211> LENGTH: 15
<212> TYPE: DNA
<213> ORGANISM: Artificial Sequence
<220> FEATURE:
<223> OTHER INFORMATION: DR5 (21H3)_CDRH1 DNA

<400> SEQUENCE: 176
agttatgcca tgagc                                                     15

<210> SEQ ID NO 177
<211> LENGTH: 51
<212> TYPE: DNA
<213> ORGANISM: Artificial Sequence
<220> FEATURE:
<223> OTHER INFORMATION: DR5 (21H3)_CDRH2 DNA

<400> SEQUENCE: 177
gctattagtg gtagtggtgg tagcacatac tacgcagact ccgtgaaggg c             51

<210> SEQ ID NO 178
<211> LENGTH: 24
<212> TYPE: DNA
<213> ORGANISM: Artificial Sequence
<220> FEATURE:
<223> OTHER INFORMATION: DR5 (21H3)_CDRH3 DNA

<400> SEQUENCE: 178
```

```
ggtgctcgtg tttcttttga ctac                                            24
```

<210> SEQ ID NO 179
<211> LENGTH: 324
<212> TYPE: DNA
<213> ORGANISM: Artificial Sequence
<220> FEATURE:
<223> OTHER INFORMATION: DR5 (21H3)_VL DNA

<400> SEQUENCE: 179

```
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcggtgta ttactgtcag cagggttctc agccgccat tacgttcggc   300
caggggacca agtggaaat caaa                                           324
```

<210> SEQ ID NO 180
<211> LENGTH: 36
<212> TYPE: DNA
<213> ORGANISM: Artificial Sequence
<220> FEATURE:
<223> OTHER INFORMATION: DR5 (21H3)_CDRL1 DNA

<400> SEQUENCE: 180

```
agggccagtc agagtgttag cagcagctac ttagcc                               36
```

<210> SEQ ID NO 181
<211> LENGTH: 21
<212> TYPE: DNA
<213> ORGANISM: Artificial Sequence
<220> FEATURE:
<223> OTHER INFORMATION: DR5 (21H3)_CDRL2 DNA

<400> SEQUENCE: 181

```
ggagcatcca gcagggccac t                                               21
```

<210> SEQ ID NO 182
<211> LENGTH: 27
<212> TYPE: DNA
<213> ORGANISM: Artificial Sequence
<220> FEATURE:
<223> OTHER INFORMATION: DR5 (21H3)_CDRL3 DNA

<400> SEQUENCE: 182

```
cagcagggtt ctcagccgcc cattacg                                         27
```

<210> SEQ ID NO 183
<211> LENGTH: 351
<212> TYPE: DNA
<213> ORGANISM: Artificial Sequence
<220> FEATURE:
<223> OTHER INFORMATION: DR5 (20F2)_VH DNA

<400> SEQUENCE: 183

```
gaggtgcaat gttggagtc tgggggaggc ttggtacagc ctgggggtc cctgagactc      60
tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaaggtgtg   300
```
aggaaggggt tgactactg gggccaagga accctggtca ccgtctcgag t       351

<210> SEQ ID NO 184
<211> LENGTH: 15
<212> TYPE: DNA
<213> ORGANISM: Artificial Sequence
<220> FEATURE:
<223> OTHER INFORMATION: DR5 (20F2)_CDRH1 DNA

<400> SEQUENCE: 184
agttatgcca tgagc                                              15

<210> SEQ ID NO 185
<211> LENGTH: 51
<212> TYPE: DNA
<213> ORGANISM: Artificial Sequence
<220> FEATURE:
<223> OTHER INFORMATION: DR5 (20F2)_CDRH2 DNA

<400> SEQUENCE: 185
gctattagtg gtagtggtgg tagcacatac tacgcagact ccgtgaaggg c       51

<210> SEQ ID NO 186
<211> LENGTH: 24
<212> TYPE: DNA
<213> ORGANISM: Artificial Sequence
<220> FEATURE:
<223> OTHER INFORMATION: DR5 (20F2)_CDRH3 DNA

<400> SEQUENCE: 186
ggtgtgagga aggggtttga ctac                                    24

<210> SEQ ID NO 187
<211> LENGTH: 324
<212> TYPE: DNA
<213> ORGANISM: Artificial Sequence
<220> FEATURE:
<223> OTHER INFORMATION: DR5 (20F2)_VL DNA

<400> SEQUENCE: 187
gaaatcgtgt taacgcagtc tccaggcacc ctgtctttgt ctccagggga aagagccacc    60
ctctcttgca gggccagtca gagtgttagc agcagctact tagcctggta ccagcagaaa   120
cctggccagg ctcccaggct cctcatctat ggagcatcca gcagggccac tggcatccca   180
gacaggttca gtggcagtgg atccgggaca gacttcactc tcaccatcag cagactggag   240
cctgaagatt ttgcagtgta ttactgtcag cagggtgagt cgcctccccc gacgttcggc   300
caggggacca agtggaaat caaa                                          324

<210> SEQ ID NO 188
<211> LENGTH: 36
<212> TYPE: DNA
<213> ORGANISM: Artificial Sequence
<220> FEATURE:
<223> OTHER INFORMATION: DR5 (20F2)_CDRL1 DNA

<400> SEQUENCE: 188
agggccagtc agagtgttag cagcagctac ttagcc                       36

<210> SEQ ID NO 189
<211> LENGTH: 21
<212> TYPE: DNA
<213> ORGANISM: Artificial Sequence
<220> FEATURE:

<223> OTHER INFORMATION: DR5 (20F2)_CDRL2 DNA

<400> SEQUENCE: 189
ggagcatcca gcagggccac t                                              21

<210> SEQ ID NO 190
<211> LENGTH: 27
<212> TYPE: DNA
<213> ORGANISM: Artificial Sequence
<220> FEATURE:
<223> OTHER INFORMATION: DR5 (20F2)_CDRL3 DNA

<400> SEQUENCE: 190
cagcagggtg agtcgcctcc cccgacg                                        27

<210> SEQ ID NO 191
<211> LENGTH: 351
<212> TYPE: DNA
<213> ORGANISM: Artificial Sequence
<220> FEATURE:
<223> OTHER INFORMATION: DR5(5E11)_VH DNA

<400> SEQUENCE: 191
gaggtgcaat tgttggagtc tgggggaggc ttggtacagc ctgggggtc cctgagactc      60 tcctgtgcag cctccggatt cacctttagc agttatgcca tgagctgggt ccgccaggct   120
ccagggaagg gctggagtg gtctcagct attagtggta gtggtggtag cacatactac     180
gcagactccg tgaagggccg gttcaccatc tccagagaca attccaagaa cacgctgtat   240
ctgcagatga acagcctgag agccgaggac acggccgtat attactgtgc gaaagggtg    300 agggtgtctt ttgactactg gggccaagga accctggtca ccgtctcgag t            351

<210> SEQ ID NO 192
<211> LENGTH: 15
<212> TYPE: DNA
<213> ORGANISM: Artificial Sequence
<220> FEATURE:
<223> OTHER INFORMATION: DR5(5E11)_CDRH1 DNA

<400> SEQUENCE: 192
agttatgcca tgagc                                                     15

<210> SEQ ID NO 193
<211> LENGTH: 51
<212> TYPE: DNA
<213> ORGANISM: Artificial Sequence
<220> FEATURE:
<223> OTHER INFORMATION: DR5(5E11)_CDRH2 DNA

<400> SEQUENCE: 193
gctattagtg gtagtggtgg tagcacatac tacgcagact ccgtgaaggg c              51

<210> SEQ ID NO 194
<211> LENGTH: 24
<212> TYPE: DNA
<213> ORGANISM: Artificial Sequence
<220> FEATURE:
<223> OTHER INFORMATION: DR5(5E11)_CDRH3 DNA

<400> SEQUENCE: 194
ggggtgaggg tgtcttttga ctac                                           24

<210> SEQ ID NO 195
<211> LENGTH: 324

```
<212> TYPE: DNA
<213> ORGANISM: Artificial Sequence
<220> FEATURE:
<223> OTHER INFORMATION: DR5(5E11)_VL DNA

<400> SEQUENCE: 195
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtacta ctcatcccat tacgttcggc     300
caggggacca agtggaaat caaa                                             324

<210> SEQ ID NO 196
<211> LENGTH: 36
<212> TYPE: DNA
<213> ORGANISM: Artificial Sequence
<220> FEATURE:
<223> OTHER INFORMATION: DR5(5E11)_CDRL1 DNA

<400> SEQUENCE: 196
agggccagtc agagtgttag cagcagctac ttagcc                                36

<210> SEQ ID NO 197
<211> LENGTH: 21
<212> TYPE: DNA
<213> ORGANISM: Artificial Sequence
<220> FEATURE:
<223> OTHER INFORMATION: DR5(5E11)_CDRL2 DNA

<400> SEQUENCE: 197
ggagcatcca gcagggccac t                                                21

<210> SEQ ID NO 198
<211> LENGTH: 27
<212> TYPE: DNA
<213> ORGANISM: Artificial Sequence
<220> FEATURE:
<223> OTHER INFORMATION: DR5(5E11)_CDRL3 DNA

<400> SEQUENCE: 198
cagcagggta ctactcatcc cattacg                                          27

<210> SEQ ID NO 199
<211> LENGTH: 351
<212> TYPE: DNA
<213> ORGANISM: Artificial Sequence
<220> FEATURE:
<223> OTHER INFORMATION: DR5(18F11)_VH DNA

<400> SEQUENCE: 199
gaggtgcaat tgttggagtc tgggggaggc ttggtacagc ctgggggtc cctgagactc       60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac gcggccgtat attactgtgc gaaggggtg     300 cgtaagaagt ttgactactg gggccaagga accctggtca ccgtctcgag t             351

<210> SEQ ID NO 200
```

```
<210> SEQ ID NO 200
<211> LENGTH: 15
<212> TYPE: DNA
<213> ORGANISM: Artificial Sequence
<220> FEATURE:
<223> OTHER INFORMATION: DR5(18F11)_CDRH1 DNA

<400> SEQUENCE: 200
agttatgcca tgagc                                                      15

<210> SEQ ID NO 201
<211> LENGTH: 51
<212> TYPE: DNA
<213> ORGANISM: Artificial Sequence
<220> FEATURE:
<223> OTHER INFORMATION: DR5(18F11)_CDRH2 DNA

<400> SEQUENCE: 201
gctattagtg gtagtggtgg tagcacatac tacgcagact ccgtgaaggg c              51

<210> SEQ ID NO 202
<211> LENGTH: 24
<212> TYPE: DNA
<213> ORGANISM: Artificial Sequence
<220> FEATURE:
<223> OTHER INFORMATION: DR5(18F11)_CDRH3 DNA

<400> SEQUENCE: 202
ggggtgcgta agaagtttga ctac                                            24

<210> SEQ ID NO 203
<211> LENGTH: 324
<212> TYPE: DNA
<213> ORGANISM: Artificial Sequence
<220> FEATURE:
<223> OTHER INFORMATION: DR5(18F11)_VL DNA

<400> SEQUENCE: 203
gaaatcgtgt taacgcagtc tccaggcacc ctgtctttgt ctccagggga aagagccacc     60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggtcagt tgcctcccat acgttcggc    300 caggggacca agtggaaat caaa                                            324

<210> SEQ ID NO 204
<211> LENGTH: 36
<212> TYPE: DNA
<213> ORGANISM: Artificial Sequence
<220> FEATURE:
<223> OTHER INFORMATION: DR5(18F11)_CDRL1 DNA

<400> SEQUENCE: 204
agggccagtc agagtgttag cagcagctac ttagcc                              36

<210> SEQ ID NO 205
<211> LENGTH: 21
<212> TYPE: DNA
<213> ORGANISM: Artificial Sequence
<220> FEATURE:
<223> OTHER INFORMATION: DR5(18F11)_CDRL2 DNA

<400> SEQUENCE: 205
ggagcatcca gcagggccac t                                              21
```

<210> SEQ ID NO 206
<211> LENGTH: 27
<212> TYPE: DNA
<213> ORGANISM: Artificial Sequence
<220> FEATURE:
<223> OTHER INFORMATION: DR5(18F11)_CDRL3 DNA

<400> SEQUENCE: 206
cagcagggtc agttgcctcc cattacg                                27

<210> SEQ ID NO 207
<211> LENGTH: 348
<212> TYPE: DNA
<213> ORGANISM: Artificial Sequence
<220> FEATURE:
<223> OTHER INFORMATION: FAP (28H1)_VH DNA

<400> SEQUENCE: 207
gaagtgcagc tgctggaatc cggcggaggc ctggtgcagc ctggcggatc tctgagactg    60
tcctgcgccg cctccggctt caccttctcc tcccacgcca tgtcctgggt ccgacaggct   120
cctggcaaag gctggaatg gtgtccgcc atctgggcct ccggcgagca gtactacgcc    180
gactctgtga agggccggtt caccatctcc cggacaacct ccaagaacac cctgtacctg   240
cagatgaact ccctgcgggc cgaggacacc gccgtgtact actgtgccaa gggctggctg   300
ggcaacttcg actactgggg acagggcacc ctggtcaccg tgtccagc              348

<210> SEQ ID NO 208
<211> LENGTH: 324
<212> TYPE: DNA
<213> ORGANISM: Artificial Sequence
<220> FEATURE:
<223> OTHER INFORMATION: FAP (28H1)__VL DNA

<400> SEQUENCE: 208
gagatcgtgc tgacccagtc ccccggcacc ctgtctctga gccctggcga gagagccacc    60
ctgtcctgca gagcctccca gtccgtgtcc ggtcctacc tcgcctggta tcagcagaag   120
cccggccagg cccctcggct gctgatcatc ggcgcctcta ccagagccac cggcatccct   180
gaccggttct ccggctctgg ctccggcacc gacttcaccc tgaccatctc ccggctggaa   240
cccgaggact tcgccgtgta ctactgccag cagggccagg tcatccctcc cacctttggc   300
cagggcacca aggtggaaat caag                                         324

<210> SEQ ID NO 209
<211> LENGTH: 351
<212> TYPE: DNA
<213> ORGANISM: Artificial Sequence
<220> FEATURE:
<223> OTHER INFORMATION: FAP (4B9)__VH DNA

<400> SEQUENCE: 209
gaggtgcaat tgttggagtc tgggggaggc ttggtacagc ctggggggtc cctgagactc    60
tcctgtgcag cctccggatt caccttagc agttatgcta tgagctgggt ccgccaggct   120
ccagggaagg gctggagtg gtctcagct attattggta gtggtgctag cacatactac   180
gcagactccg tgaagggccg gttcaccatc tccagagaca attccaagaa cacgctgtat   240
ctgcagatga acagcctgag agccgaggac acggccgtat attactgtgc gaaagggtgg   300
tttggtggtt ttaactactg gggccaagga accctggtca ccgtctcgag t           351

<210> SEQ ID NO 210
<211> LENGTH: 324
<212> TYPE: DNA
<213> ORGANISM: Artificial Sequence
<220> FEATURE:
<223> OTHER INFORMATION: FAP (4B9)_VL DNA

<400> SEQUENCE: 210

```
gagatcgtgc tgacccagtc ccccggcacc ctgtctctga gccctggcga gagagccacc    60
ctgtcctgca gagcctccca gtccgtgacc tcctcctacc tcgcctggta tcagcagaag   120
cccggccagg cccctcggct gctgatcaac gtgggcagtc ggagagccac cggcatccct   180
gaccggttct ccggctctgg ctccggcacc gacttcaccc tgaccatctc ccggctggaa   240
cccgaggact cgccgtgta ctactgccag cagggcatca tgctgccccc cacctttggc   300
cagggcacca aggtggaaat caag                                          324
```

<210> SEQ ID NO 211
<211> LENGTH: 363
<212> TYPE: DNA
<213> ORGANISM: Artificial Sequence
<220> FEATURE:
<223> OTHER INFORMATION: Drozitumab_VH DNA

<400> SEQUENCE: 211

```
gaagtgcagc tggtgcagtc tggcggcgga gtggaaagac ctggcggcag cctgagactg    60
agctgcgccg ccagcggctt caccttcgac gactacgcca tgtcttgggt ccgccaggcc   120
cctggaaagg gcctggaatg ggtgtccggc atcaactggc agggcggcag caccggctac   180
gccgacagcg tgaagggcag agtgaccatc agccgggaca cgccaagaa cagcctgtac   240
ctgcagatga acagcctgag agccgaggac accgccgtgt actactgcgc caagatcctg   300
ggagccggca gaggctggta cttcgactac tggggcaagg gcaccaccgt gactgtgtct   360
agc                                                                 363
```

<210> SEQ ID NO 212
<211> LENGTH: 324
<212> TYPE: DNA
<213> ORGANISM: Artificial Sequence
<220> FEATURE:
<223> OTHER INFORMATION: Drozitumab_VL DNA

<400> SEQUENCE: 212

```
agcgagctga cccaggatcc tgccgtgtct gtggctctgg ccagaccgt gcggatcacc    60
tgtagcggcg acagcctgcg gagctactac gccagctggt atcagcagaa gcccggccag   120
gctcccgtgc tggtgatcta cggcgccaac aacagaccca gcggcatccc cgacagattc   180
agcggcagca gcagcggcaa taccgccagc ctgaccatca caggcgccca ggccgaggac   240
gaggccgact actactgcaa cagcgccgac agctccggca ccacgtggt gttcggcgga   300
ggcaccaagc tgaccgtcct aggt                                          324
```

<210> SEQ ID NO 213
<211> LENGTH: 2151
<212> TYPE: DNA
<213> ORGANISM: Artificial Sequence
<220> FEATURE:
<223> OTHER INFORMATION: Drozitumab - 3F2 scFv (HC) pETR6606 DNA

<400> SEQUENCE: 213

```
gaggtgcagc tggtgcagag cggcggaggg gtggagaggc ctggcggcag cctgagactg    60
```

```
agctgcgccg ccagcggctt caccttcgac gactacgcca tgagctgggt gcgccaggcc    120
cctggcaagg gcctggaatg ggtgtccggc atcaactggc agggaggcag caccggctac    180
gccgacagcg tgaagggcag agtgaccatc agccgggaca cgccaagaa cagcctgtac     240
ctgcagatga acagcctgcg ggccgaggac acagccgtgt actactgcgc caagatcctg    300
ggagccggca ggggctggta cttcgactac tggggcaagg gcaccaccgt gaccgtgtcc    360
agcgctagca ccaagggccc atcggtcttc cccctggcac cctcctccaa gagcacctct    420
gggggcacag cggccctggg ctgcctggtc aaggactact cccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga agctgcaggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaatccggag cggaggaag tggagggggga   1380
ggatccggag gggcggatc tggcggcgga ggcagcgagg tgcaattgct ggaaagcgga   1440
ggcggactcg tgcagcctgg cggcagcctg agactgagct cgccgccag cggcttcacc   1500
ttcagcagct acgccatgtc ttgggtccgg caggcccctg gaaagtgcct ggaatgggtg   1560
tccgccatca gcggcagcgg cggcagcacc tactacgccg acagcgtgaa gggccggttc   1620
accatcagcc gggacaacag caagaacacc ctgtacctcc agatgaacag cctgagagcc   1680
gaggacaccg ccgtgtacta ctgcgccaag ggatggttcg gcggcttcaa ctactggggc   1740
cagggcaccc tggtcacagt ctcgagtggc ggaggggggat ctggggggagg cggatcagga   1800
ggaggaggaa gcggggagg gggcagcgag atcgtgttaa cgcagagccc cggcaccctg   1860
agcctgtatc ccggcgagag agccaccctg agctgcagag ccagcagag cgtgaccagc   1920
agctacctgg cctggtatca gcagaagccc ggccaggccc cagactgct gatcaacgtg   1980
ggcagcagaa gggccaccgg catccccgac agattcagcg gctccggcag cggcaccgac   2040
ttcaccctga ccatcagcag actggaaccc gaggatttcg ccgtgtatta ttgccagcag   2100
ggcatcatgc tgccccctac cttcggatgc ggcaccaagg tggagatcaa g            2151
```

<210> SEQ ID NO 214  
<211> LENGTH: 2124  
<212> TYPE: DNA  
<213> ORGANISM: Artificial Sequence  
<220> FEATURE:  
<223> OTHER INFORMATION: Drozitumab-FAP (4G8) scFv (HC)pETR7342 DNA

<400> SEQUENCE: 214

```
gaggtgcagc tggtgcagag cggcggaggg gtggagaggc ctggcggcag cctgagactg      60
agctgcgccg ccagcggctt caccttcgac gactacgcca tgagctgggt gcgccaggcc     120
cctggcaagg gcctggaatg ggtgtccggc atcaactggc agggaggcag caccggctac     180
gccgacagcg tgaagggcag agtgaccatc agccgggaca cgccaagaa cagcctgtac      240
ctgcagatga acagcctgcg ggccgaggac acagccgtgt actactgcgc caagatcctg     300
ggagccggca ggggctggta cttcgactac tggggcaagg gcaccaccgt gaccgtgtcc     360
agcgctagca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc      780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt ggcgggtccg gaggcggagg aagtggcggc    1380
ggaggcagcg aagtgcagct gctggaaagc ggcgaggac tggtgcagcc tggcggcagc    1440
ctgagactga gctgcgccgc cagcggcttc accttcagca gctacgccat gtcttgggtc    1500
cgccaggccc ctggaaagtg cctggaatgg gtgtccgcca tcagcggcag cggcggcagc    1560
acctactacg ccgacagcgt gaagggccgg ttcaccatca gccgggacaa cagcaagaac    1620
accctgtacc tgcagatgaa cagcctgaga gccgaggaca ccgccgtgta ctactgcgcc    1680
aagggctggc tgggcaactt cgactactgg ggccagggca ctctggtcac agtgtctagc    1740
ggaggcggcg gatctggcgg aggtggaagc ggaggggag gatcaggggg cggaggctcc    1800
gagatcgtgc tgacccagag ccctggcaca ctgtctctga ccctggcga gagagccacc    1860
ctgagctgca gagccagcca gagcgtgtcc agaagctacc tggcttggta tcagcagaag    1920
cccggccagg cccccagact gctgatcatc ggcgctagca ccagagccac cggcattccc    1980
gacagattca gcggctccgg cagcggcacc gacttcaccc tgaccatcag cagactggaa    2040
cccgaggatt tcgccgtcta ttattgccag cagggccaag tcatccctcc taccttcgga    2100
tgcggcacta aggtggagat caag                                           2124
```

<210> SEQ ID NO 215
<211> LENGTH: 1404
<212> TYPE: DNA
<213> ORGANISM: Artificial Sequence
<220> FEATURE:
<223> OTHER INFORMATION: Drozitumab-FAP (4G8) scFv (LC) DNA

<400> SEQUENCE: 215

| | | |
|---|---|---|
| agcgagctga cccaggaccc cgccgtgagc gtggccctgg acagaccgt gcggatcacc | 60 |
| tgcagcggcg acagcctgcg cagctactac gccagctggt atcagcagaa gcccggccag | 120 |
| gcccccgtgc tggtgatcta cggcgccaac aaccggccca gcggcatccc cgaccggttc | 180 |
| agcggcagca gcagcggcaa caccgccagc ctgaccatca caggcgccca ggccgaggac | 240 |
| gaggccgact actactgcaa cagcgccgac agctccggca ccacgtggt gtttggcggc | 300 |
| ggaacaaagc tgaccgtcct aggtcaaccc aaggctgccc ccagcgtgac cctgttcccc | 360 |
| cccagcagcg aggaactgca ggccaacaag gccaccctgg tctgcctgat cagcgacttc | 420 |
| tacccaggcg ccgtgaccgt ggcctggaag gccgacagca gcccgtgaa ggccggcgtg | 480 |
| gagaccacca cccccagcaa gcagagcaac aacaagtacg ccgccagcag ctacctgagc | 540 |
| ctgacccccg agcagtggaa gagccacagg tcctacagct gccaggtgac ccacgagggc | 600 |
| agcaccgtgg agaaaaccgt ggcccccacc gagtgctccg gaggcggagg aagtggcggc | 660 |
| ggaggcagca agtgcagct gctggaaagc ggcggaggac tggtgcagcc tggcggcagc | 720 |
| ctgagactga gctgcgccgc cagcggcttc accttcagca gctacgccat gtcttgggtc | 780 |
| cgccaggccc ctggaaagtg cctggaatgg gtgtccgcca tcagcggcag cggcggcagc | 840 |
| acctactacg ccgacagcgt gaagggccgg ttcaccatca gccgggacaa cagcaagaac | 900 |
| accctgtacc tgcagatgaa cagcctgaga gccgaggaca ccgccgtgta ctactgcgcc | 960 |
| aagggctggc tgggcaactt cgactactgg ggccagggca ctctggtcac agtgtctagc | 1020 |
| ggaggcggcg gatctggcgg aggtggaagc ggaggggag gatcagggg cggaggctcc | 1080 |
| gagatcgtgc tgacccagag ccctggcaca ctgtctctga gccctggcga gagagccacc | 1140 |
| ctgagctgca gagccagcca gagcgtgtcc agaagctacc tggcttggta tcagcagaag | 1200 |
| cccggccagg ccccagact gctgatcatc ggcgctagca ccagagccac cggcattccc | 1260 |
| gacagattca gcggctccgg cagcggcacc gacttcaccc tgaccatcag cagactggaa | 1320 |
| cccgaggatt tcgccgtcta ttattgccag cagggccaag tcatccctcc taccttcgga | 1380 |
| tgcggcacta aggtggagat caag | 1404 |

<210> SEQ ID NO 216
<211> LENGTH: 2826
<212> TYPE: DNA
<213> ORGANISM: Artificial Sequence
<220> FEATURE:
<223> OTHER INFORMATION: Drozitumab - 3F2 scFab (HC) pETR7369 DNA

<400> SEQUENCE: 216

| | | |
|---|---|---|
| gaggtgcagc tggtgcagag cggcggaggg gtggagaggc ctggcggcag cctgagactg | 60 |
| agctgcgccg ccagcggctt caccttcgac gactacgcca tgagctgggt cgcccaggcc | 120 |
| cctggcaagg gcctggaatg ggtgtccggc atcaactggc agggaggcag caccggctac | 180 |
| gccgacagcg tgaagggcag agtgaccatc agccgggaca cgccaagaa cagcctgtac | 240 |
| ctgcagatga cagcctgcg ggccgaggac acagccgtgt actactgcgc caagatcctg | 300 |
| ggagccggca ggggctggta cttcgactac tggggcaagg gcaccaccgt gaccgtgtcc | 360 |
| agcgctagca ccaagggccc atcggtcttc cccctggcac cctcctccaa gagcacctct | 420 |
| gggggcacag cggccctggg ctgcctggtc aaggactact cccccgaacc ggtgacggtg | 480 |

```
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagccc cgagaaccca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaatccggag cggaggttc cggtggaggc   1380
ggatccggag gaggtggcag cggaggtggt ggctccgaaa tcgtgttaac gcagtctcca   1440
ggcaccctgt ctttgtatcc aggggaaaga gccaccctct cttgcagggc cagtcagagt   1500
gttaccagta gctacttagc ctggtaccag cagaaacctg gccaggctcc caggctcctc   1560
atcaatgtgg gctcccgtag gccactggca tcccagaca ggttcagtgg cagtggatcc   1620
gggacagact tcactctcac catcagcaga ctggagcctg aagattttgc agtgtattac   1680
tgtcagcagg gtattatgct tccccgacg ttcggccagg ggaccaaagt ggaaatcaaa   1740
cgtacggtgg ccgctcccag cgtgttcatc ttcccccca gcgacgagca gctgaagtcc   1800
ggcaccgcca gcgtggtgtg cctgctgaac aacttctacc cccgggaggc caaggtgcag   1860
tggaaggtgg acaacgccct gcagagcggc aacagccagg aaagcgtcac cgagcaggac   1920
agcaaggact ccacctacag cctgtccagc accctgaccc tgagcaaggc cgactacgag   1980
aagcacaagg tgtacgcctg cgaagtgacc caccagggcc tgagcagccc cgtgaccaag   2040
agcttcaacc ggggcgagtg ctccggcgga ggatctgggg gaggaagcga aggaggcgga   2100
tctgagggcg gtggctctga aggcggtgga agtgagggag gcggtagcgg aggtggatcc   2160
ggcgaggtgc aattgttgga gtctggggga ggcttggtac agcctggggg gtccctgaga   2220
ctctcctgtg cagcctccgg attcaccttt agcagttatg ccatgagctg ggtccgccag   2280
gctccaggga aggggctgga gtgggtctca gctattagtg gtagtggtgg tagcacatac   2340
tacgcagact ccgtgaaggg ccggttcacc atctccagag acaattccaa gaacacgctg   2400
tatctgcaga tgaacagcct gagagccgag gacacggccg tatattactg tgcgaagggg   2460
tggtttggtg gttttaacta ctggggccaa ggaaccctgg tcaccgtctc gagtgctagc   2520
acaaagggcc cagcgtgtt ccctctggcc cccagcagca gagcacaag cggcggaaca   2580
gccgccctgg gctgcctggt caaggactac ttccccgagc ccgtgactgt gtcctggaac   2640
agcggtgctc tcacatctgg ggtccacacc tttccagccg tgctccagtc ctcagggctc   2700
tacagcctga gcagcgtcgt cacagtccca tctagcagcc tgggcaccca gacctacatc   2760
tgcaacgtga accacaagcc cagcaacacc aaggtggaca gaaggtgga gcccaagagc   2820
tgtgac                                                              2826
```

<210> SEQ ID NO 217
<211> LENGTH: 2109
<212> TYPE: DNA
<213> ORGANISM: Artificial Sequence
<220> FEATURE:
<223> OTHER INFORMATION: Drozitumab-3F2 scFab (LC) DNA

<400> SEQUENCE: 217

| | | | | | |
|---|---|---|---|---|---|
| agcgagctga | cccaggaccc | cgccgtgagc | gtggccctgg | acagaccgt | gcggatcacc | 60 |
| tgcagcggcg | acagcctgcg | cagctactac | gccagctggt | atcagcagaa | gcccggccag | 120 |
| gcccccgtgc | tggtgatcta | cggcgccaac | aaccggccca | gcggcatccc | cgaccggttc | 180 |
| agcggcagca | gcagcggcaa | caccgccagc | ctgaccatca | caggcgccca | ggccgaggac | 240 |
| gaggccgact | actactgcaa | cagcgccgac | agctccggca | ccacgtggt | gtttggcggc | 300 |
| ggaacaaagc | tgaccgtcct | aggtcaaccc | aaggctgccc | ccagcgtgac | cctgttcccc | 360 |
| cccagcagcg | aggaactgca | ggccaacaag | gccaccctgg | tctgcctgat | cagcgacttc | 420 |
| tacccaggcg | ccgtgaccgt | ggcctggaag | gccgacagca | gccccgtgaa | ggccggcgtg | 480 |
| gagaccacca | cccccagcaa | gcagagcaac | aacaagtacg | ccgccagcag | ctacctgagc | 540 |
| ctgaccccg | agcagtggaa | gagccacagg | tcctacagct | gccaggtgac | ccacgagggc | 600 |
| agcaccgtgg | agaaaaccgt | ggccccacc | gagtgctccg | gaggcggagg | ttccggtgga | 660 |
| ggcggatccg | gaggaggtgg | cagcggaggt | ggtggctccg | aaatcgtgtt | aacgcagtct | 720 |
| ccaggcaccc | tgtctttgta | tccaggggaa | agagccaccc | tctcttgcag | ggccagtcag | 780 |
| agtgttacca | gtagctactt | agcctggtac | cagcagaaac | ctggccaggc | tcccaggctc | 840 |
| ctcatcaatg | tgggctcccg | tagggccact | ggcatcccag | acaggttcag | tggcagtgga | 900 |
| tccgggacag | acttcactct | caccatcagc | agactggagc | ctgaagattt | tgcagtgtat | 960 |
| tactgtcagc | agggtattat | gcttcccccg | acgttcggcc | aggggaccaa | agtggaaatc | 1020 |
| aaacgtacgg | tggccgctcc | cagcgtgttc | atcttccccc | ccagcgacga | gcagctgaag | 1080 |
| tccggcaccg | ccagcgtggt | gtgcctgctg | aacaacttct | accccgggga | ggccaaggtg | 1140 |
| cagtggaagg | tggacaacgc | cctgcagagc | ggcaacagca | ggaaaagcgt | caccgagcag | 1200 |
| gacagcaagg | actccaccta | cagcctgtcc | agcaccctga | ccctgagcaa | ggccgactac | 1260 |
| gagaagcaca | aggtgtacgc | ctgcgaagtg | acccaccagg | gcctgagcag | ccccgtgacc | 1320 |
| aagagcttca | accggggcga | gtgctccggc | ggaggatctg | ggggaggaag | cgaaggaggc | 1380 |
| ggatctgagg | gcggtggctc | tgaaggcggt | ggaagtgagg | gaggcggtag | cggaggtgga | 1440 |
| tccggcgagg | tgcaattgtt | ggagtctggg | ggaggcttgg | tacagcctgg | ggggtccctg | 1500 |
| agactctcct | gtgcagcctc | cggattcacc | tttagcagtt | atgccatgag | ctgggtccgc | 1560 |
| caggctccag | ggaaggggct | ggagtgggtc | tcagctatta | gtggtagtgg | tggtagcaca | 1620 |
| tactacgcag | actccgtgaa | gggccggttc | accatctcca | gagacaattc | caagaacacg | 1680 |
| ctgtatctgc | agatgaacag | cctgagagcc | gaggacacgg | ccgtatatta | ctgtgcgaaa | 1740 |
| gggtggtttg | gtggttttaa | ctactggggc | caaggaaccc | tggtcaccgt | ctcgagtgct | 1800 |
| agcacaaagg | gcccagcgt | gttccctctg | gcccccagca | gcaagagcac | aagcggcgga | 1860 |
| acagccgccc | tgggctgcct | ggtcaaggac | tacttcccg | agcccgtgac | tgtgtcctgg | 1920 |
| aacagcggtg | ctctcacatc | tggggtccac | acctttccag | ccgtgctcca | gtcctcaggg | 1980 |
| ctctacagcc | tgagcagcgt | cgtcacagtc | ccatctagca | gcctgggcac | ccagacctac | 2040 |

| | |
|---|---|
| atctgcaacg tgaaccacaa gcccagcaac accaaggtgg acaagaaggt ggagcccaag | 2100 |
| agctgtgac | 2109 |

<210> SEQ ID NO 218
<211> LENGTH: 2826
<212> TYPE: DNA
<213> ORGANISM: Artificial Sequence
<220> FEATURE:
<223> OTHER INFORMATION: Drozitumab-FAP (4G8) scFab (HC) DNA

<400> SEQUENCE: 218

| | |
|---|---|
| gaggtgcagc tggtgcagag cggcggaggg gtggagaggc ctggcggcag cctgagactg | 60 |
| agctgcgccg ccagcggctt caccttcgac gactacgcca tgagctgggt gcgccaggcc | 120 |
| cctggcaagg gcctggaatg ggtgtccggc atcaactggc agggaggcag caccggctac | 180 |
| gccgacagcg tgaagggcag agtgaccatc agccgggaca cgccaagaa cagcctgtac | 240 |
| ctgcagatga acagcctgcg ggccgaggac acagccgtgt actactgcgc caagatcctg | 300 |
| ggagccggca ggggctggta cttcgactac tggggcaagg gcaccaccgt gaccgtgtcc | 360 |
| agcgctagca ccaagggccc atcggtcttc cccctggcac cctcctccaa gagcacctct | 420 |
| gggggcacag cggccctggg ctgcctggtc aaggactact tccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca ccctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggat | 1080 |
| gagctgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaatccggag gcggaggaag cggaggggga | 1380 |
| ggatcaggcg gcggtggatc aggcggtgga ggatccgaga tcgtgctgac ccagtcccct | 1440 |
| ggcaccctgt ctctgagccc aggcgagaga gccaccctga gctgcagagc cagcagagtg | 1500 |
| tgtccagaa ctatctggc ttggtatcag cagaagcccg gccaggcccc cagactgctg | 1560 |
| atcatcggcg ccagcaccag agccaccggc atccccgaca gattcagcgg cagcggctcc | 1620 |
| ggcaccgact tcaccctgac catctcccgg ctggaacccg aggacttcgc cgtgtactac | 1680 |
| tgccagcagg ccaggtcat ccctcctacc ttcggccagg gcaccaaggt ggagatcaag | 1740 |
| cgtacggtgg ccgctcccag cgtgttcatc ttcccaccca gcgacgagca gctgaagtcc | 1800 |
| ggcacagcca gcgtggtctg cctgctgaac aacttctacc ccggggaggc caaggtgcag | 1860 |
| tggaaggtgg acaacgccct gcagagcggc aacagccagg aaagcgtcac cgagcaggac | 1920 |
| agcaaggact ccacctacag cctgagcagc acactgaccc tgagcaaggc cgactacgag | 1980 |

```
aagcacaagg tgtacgcctg cgaagtgacc caccagggcc tgtccagccc cgtgaccaag    2040
agcttcaacc ggggcgagtg ttctggtggc ggatctggcg gaggcagtga aggcggcgga    2100
agtgagggtg gaggcagcga gggggaggc tctgaagggg gaggaagtgg aggcggttca    2160
ggggaagtgc aattgttgga gtctggggga ggcttggtac agcctggggg gtccctgaga    2220
ctctcctgtg cagcctccgg attcaccttt agcagttatg ccatgagctg ggtccgccag    2280
gctccaggga aggggctgga gtgggtctca gctattagtg gtagtggtgg tagcacatac    2340
tacgcagact ccgtgaaggg ccggttcacc atctccagag acaattccaa gaacacgctg    2400
tatctgcaga tgaacagcct gagagccgag gacacggccg tatattactg tgcgaaaggg    2460
tggctgggta atttttgacta ctggggccaa ggaaccctgg tcaccgtctc gagtgctagc    2520
acaaagggcc ccagcgtgtt ccctctggcc ccagcagca agagcacaag cggcggaaca    2580
gccgccctgg gctgcctggt caaggactac ttccccgagc ccgtgactgt gtcctggaac    2640
agcggtgctc tcacatctgg ggtccacacc tttccagccg tgctccagtc ctcagggctc    2700
tacagcctga gcagcgtcgt cacagtccca tctagcagcc tgggcaccca gacctacatc    2760
tgcaacgtga accacaagcc cagcaacacc aaggtggaca gaaggtggag gcccaagagc    2820
tgtgac                                                              2826

<210> SEQ ID NO 219
<211> LENGTH: 2109
<212> TYPE: DNA
<213> ORGANISM: Artificial Sequence
<220> FEATURE:
<223> OTHER INFORMATION: Drozitumab-FAP (4G8) scFab (LC) DNA

<400> SEQUENCE: 219
agcgagctga cccaggaccc cgccgtgagc gtggccctgg acagaccgt gcggatcacc      60 tgcagcggcg acagcctgcg cagctactac gccagctggt atcagcagaa gcccggccag     120
gcccccgtgc tggtgatcta cggcgccaac aaccggccca gcggcatccc cgaccggttc     180
agcggcagca gcagcggcaa caccgccagc ctgaccatca caggcgccca ggccgaggac     240
gaggccgact actactgcaa cagcgccgac agctccggca ccacgtggt gtttggcggc     300 ggaacaaagc tgaccgtcct aggtcaaccc aaggctgccc ccagcgtgac cctgttcccc     360
cccagcagcg aggaactgca ggccaacaag gccaccctgg tctgcctgat cagcgacttc     420
tacccaggcg ccgtgaccgt ggcctggaag gccgacagca gcccgtgaa ggccggcgtg     480 gagaccacca cccccagcaa gcagagcaac aacaagtacg ccgccagcag ctacctgagc     540
ctgacccccg agcagtggaa gagccacagg tcctacagct gccaggtgac ccacgagggc     600
agcaccgtgg agaaaaccgt ggcccccacc gagtgctccg gaggcggagg aagcggaggg     660
ggaggatcag gcggcggtgg atcaggcggt ggaggatccg agatcgtgct gacccagtcc     720
cctggcaccc tgtctctgag cccaggcgag agagccaccc tgagctgcag agccagccag     780
agcgtgtcca gaagctatct ggcttggtat cagcagaagc ccggccaggc ccccagactg     840
ctgatcatcg gcgccagcac cagagccacc ggcatccccg acagattcag cggcagcggc     900
tccggcaccg acttcaccct gaccatctcc cggctggaac ccgaggactt cgccgtgtac     960
tactgccagc agggccaggt catccctcct accttcggcc agggcaccaa ggtggagatc    1020
aagcgtacgg tggccgctcc cagcgtgttc atcttcccac ccagcgacga gcagctgaag    1080
tccggcacag ccagcgtggt ctgcctgctg aacaacttct acccccggga ggccaaggtg    1140
```

```
cagtggaagg tggacaacgc cctgcagagc ggcaacagcc aggaaagcgt caccgagcag   1200
gacagcaagg actccaccta cagcctgagc agcacactga ccctgagcaa ggccgactac   1260
gagaagcaca aggtgtacgc ctgcgaagtg acccaccagg gcctgtccag ccccgtgacc   1320
aagagcttca accggggcga gtgttctggt ggcggatctg gcggaggcag tgaaggcggc   1380
ggaagtgagg gtggaggcag cgagggggga ggctctgaag ggggaggaag tggaggcggt   1440
tcaggggaag tgcaattgtt ggagtctggg ggaggcttgg tacagcctgg ggggtccctg   1500
agactctcct gtgcagcctc cggattcacc tttagcagtt atgccatgag ctgggtccgc   1560
caggctccag ggaaggggct ggagtgggtc tcagctatta gtggtagtgg tggtagcaca   1620
tactacgcag actccgtgaa gggccggttc accatctcca gagacaattc caagaacacg   1680
ctgtatctgc agatgaacag cctgagagcc gaggacacgg ccgtatatta ctgtgcgaaa   1740
gggtggctgg gtaattttga ctactggggc caaggaaccc tggtcaccgt ctcgagtgct   1800
agcacaaagg gcccagcgt gttccctctg gccccagca gcaagagcac aagcggcgga   1860
acagccgccc tgggctgcct ggtcaaggac tacttccccg agcccgtgac tgtgtcctgg   1920
aacagcggtg ctctcacatc tggggtccac acctttccag ccgtgctcca gtcctcaggg   1980
ctctacagcc tgagcagcgt cgtcacagtc ccatctagca gcctgggcac ccagacctac   2040
atctgcaacg tgaaccacaa gcccagcaac accaaggtgg acaagaaggt ggagcccaag   2100
agctgtgac                                                            2109

<210> SEQ ID NO 220
<211> LENGTH: 2088
<212> TYPE: DNA
<213> ORGANISM: Artificial Sequence
<220> FEATURE:
<223> OTHER INFORMATION: Drozitumab-FAP (4G8) VHCL 2+2 DNA

<400> SEQUENCE: 220
gaagtgcagc tggtgcagtc tggcggcgga gtggaaagac ctggcggcag cctgagactg     60
agctgcgccg ccagcggctt caccttcgac gactacgcca tgtcttgggt ccgccaggcc    120
cctggaaagg gcctggaatg ggtgtccggc atcaactggc agggcggcag caccggctac    180
gccgacagcg tgaagggcag agtgaccatc agccgggaca cgccaagaa cagcctgtac    240 ctgcagatga acagcctgag agccgaggac accgccgtgt actactgcgc caagatcctg    300
ggagccggca gaggctggta cttcgactac tggggcaagg gcaccaccgt gactgtgtct    360
agcgctagca caagggccc aagcgtgttc cctctggccc ccagcagcaa gagcacaagc    420
ggcggaacag ccgccctggg ctgcctggtc aaggactact cccccgagcc cgtgacagtg    480
tcctggaaca gcggagccct gaccagcggc gtgcacacct tccagccgt gctgcagagc    540 agcggcctgt acagcctgag cagcgtggtc acagtgccta gcagcagcct gggcacccag    600
acctacatct gcaacgtgaa ccacaagccc agcaacacca aggtggacaa gaaggtggag    660
cccaagagct gcgacaagac ccacacctgt ccccttgtc ctgcccctga gctgctgggc    720
ggacccagcg tgttcctgtt cccccaaag cccaaggaca ccctgatgat cagccggacc    780
cccgaagtga cctgcgtggt ggtggacgtg tcccacgagg accctgaagt gaagttcaat    840
tggtacgtgg acggcgtgga ggtgcacaat gccaagacca gccccgggga ggaacagtac    900
aacagcacct accgggtggt gtccgtgctg accgtgctgc accaggactg gctgaacggc    960
aaagagtaca agtgcaaggt ctccaacaag gccctgcctg cccccatcga gaaaaccatc   1020
agcaaggcca agggccagcc cagagaaccc caggtgtaca ccctgccccc cagcagagat   1080
```

```
gagctgacca agaaccaggt gtccctgacc tgtctggtca agggcttcta ccccagcgat    1140
atcgccgtgg agtgggagag caacggccag cctgagaaca actacaagac cacccccct    1200 gtgctggaca cgacggcag cttcttcctg tactccaaac tgaccgtgga caagagccgg    1260
tggcagcagg gcaacgtgtt cagctgcagc gtgatgcacg aggccctgca caaccactac    1320
acccagaagt ccctgagcct gagccccggc aagtccggag cggcggaag cggaggagga    1380 ggatccggag gaggggaag tggcggcgga ggatctgagg tgcagctgct ggaatctgga    1440
ggcggcctgg tgcagcctgg cggcagcctg agactgtctt gcgccgccag cggcttcacc    1500
ttcagcagct acgccatgag ctgggtccga caggctcctg gcaagggact ggaatgggtg    1560
tccgccatct ccggcagcgg aggcagcacc tactacgccg acagcgtgaa gggccggttc    1620
accatcagca gagacaacag caagaacacc ctgtacctgc agatgaacag cctgcgggcc    1680
gaggataccg ccgtgtatta ttgcgccaag ggatggctgg gcaacttcga ctactggggc    1740
cagggaaccc tggtgacagt gtccagcgct agcgtggccg ctcccagcgt gttcatcttc    1800
ccacccagcg acgagcagct gaagtccggc acagccagcg tggtgtgcct gctgaacaac    1860
ttctaccccc gcgaggccaa ggtgcagtgg aaggtggaca cgccctgca gagcggcaac    1920 agccaggaat ccgtgaccga gcaggacagc aaggactcca cctacagcct gagcagcacc    1980
ctgaccctga gcaaggccga ctacgagaag cacaaggtgt acgcctgcga agtgacccac    2040
cagggcctgt ccagccccgt gaccaagagc ttcaaccggg gcgagtgc             2088

<210> SEQ ID NO 221
<211> LENGTH: 639
<212> TYPE: DNA
<213> ORGANISM: Artificial Sequence
<220> FEATURE:
<223> OTHER INFORMATION: Drozitumab LC pETR7303 DNA

<400> SEQUENCE: 221
agcgagctga cccaggatcc tgccgtgtct gtggctctgg ccagaccgt gcggatcacc     60 tgtagcggcg acagcctgcg gagctactac gccagctggt atcagcagaa gcccggccag    120
gctcccgtgc tggtgatcta cggcgccaac aacagaccca cgcatccc cgacagattc    180 agcggcagca gcagcggcaa taccgccagc ctgaccatca caggcgccca ggccgaggac    240
gaggccgact actactgcaa cagcgccgac agctccggca ccacgtggt gttcggcgga    300 ggcaccaagc tgaccgtcct aggtcagccc aaagccgccc tagcgtgac cctgttcccc    360 ccaagcagca ggaactgca ggccaacaag gccaccctgg tgtgcctgat cagcgacttc    420
taccctggcg ccgtgacagt ggcctggaag gccgactcta gccctgtgaa ggccggcgtg    480
gagacaacca ccccagcaa gcagagcaac aacaagtacg ccgccagcag ctacctgagc    540
ctgacccccg agcagtggaa gtccacggg tcctacagct gccaggtgac acgagggc     600 agcaccgtgg agaaaaccgt ggcccccacc gagtgcagc                          639

<210> SEQ ID NO 222
<211> LENGTH: 642
<212> TYPE: DNA
<213> ORGANISM: Artificial Sequence
<220> FEATURE:
<223> OTHER INFORMATION: FAP (4G8) _VLCH1 DNA

<400> SEQUENCE: 222
gagatcgtgc tgacccagtc tcccggcacc ctgagcctga gccctggcga gagagccacc     60
```

```
ctgagctgca gagccagcca gagcgtgagc cggagctacc tggcctggta tcagcagaag    120
cccggccagg cccccagact gctgatcatc ggcgccagca cccgggccac cggcatcccc    180
gatagattca gcggcagcgg ctccggcacc gacttcaccc tgaccatcag ccggctggaa    240
cccgaggact cgccgtgta ctactgccag cagggccagg tgatccccc caccttcggc     300 cagggcacca aggtggaaat caagagctcc gctagcacca agggcccctc cgtgtttcct    360 ctggcccca gcagcaagag cacctctggc ggaacagccg ccctgggctg cctggtgaaa    420
gactacttcc ccgagcccgt gaccgtgtcc tggaactctg gcgccctgac cagcggcgtg    480
cacacctttc cagccgtgct gcagagcagc ggcctgtact ccctgagcag cgtggtgaca    540
gtgccctcca gcagcctggg cacccagacc tacatctgca acgtgaacca caagcccagc    600
aacaccaaag tggacaagaa ggtggaaccc aagagctgcg ac                       642
```

<210> SEQ ID NO 223
<211> LENGTH: 2052
<212> TYPE: DNA
<213> ORGANISM: Artificial Sequence
<220> FEATURE:
<223> OTHER INFORMATION: Drozitumab-FAP (4G8) VLCH1 2+2 DNA

<400> SEQUENCE: 223

```
gaagtgcagc tggtgcagtc tggcggcgga gtggaaagac ctggcggcag cctgagactg     60
agctgcgccg ccagcggctt caccttcgac gactacgcca tgtcttgggt ccgccaggcc    120
cctggaaagg gcctggaatg ggtgtccggc atcaactggc agggcggcag caccggctac    180
gccgacagcg tgaagggcag agtgaccatc agccgggaca cgccaagaa cagcctgtac    240 ctgcagatga acagcctgag agccgaggac accgccgtgt actactgcgc caagatcctg    300
ggagccggca gaggctggta cttcgactac tggggcaagg gcaccaccgt gactgtgtct    360
agcgctagca ccaagggccc aagcgtgttc cctctggccc ccagcagcaa gagcacaagc    420
ggcggaacag ccgccctggg ctgcctggtc aaggactact cccccagcc gtgacagtg    480 tcctggaaca gcggagccct gaccagcggc gtgcacacct ttccagccgt gctgcagagc    540
agcggcctgt acagcctgag cagcgtggtc acagtgccta gcagcagcct gggcacccag    600
acctacatct gcaacgtgaa ccacaagccc agcaacacca aggtggacaa gaaggtggag    660
cccaagagct gcgacaagac ccacacctgt cccccttgtc ctgcccctga gctgctgggc    720
ggacccagcg tgttcctgtt ccccccaaag cccaaggaca ccctgatgat cagccggacc    780
cccgaagtga cctgcgtggt ggtggacgtg tcccacgagg accctgaagt gaagttcaat    840
tggtacgtgg acggcgtgga ggtgcacaat gccaagacca gccccgggga ggaacagtac    900
aacagcacct accgggtggt gtccgtgctg accgtgctgc accaggactg gctgaacggc    960
aaagagtaca agtgcaaggt ctccaacaag gccctgcctg cccccatcga gaaaaccatc    1020
agcaaggcca agggccagcc cagagaaccc caggtgtaca ccctgccccc cagcagagat    1080
gagctgacca agaaccaggt gtccctgacc tgtctggtca agggcttcta ccccagcgat    1140
atcgccgtgg agtgggagag caacggccag cctgagaaca actacaagac caccccccct    1200
gtgctggaca gcgacggcag cttcttcctg tactccaaac tgaccgtgga caagagccgg    1260
tggcagcagg gcaacgtgtt cagctgcagc gtgatgcacg aggccctgca caaccactac    1320
acccagaagt ccctgagcct gagccccggc aagtccggag cggcggaag cggaggagga    1380 ggatccggag agggggaag tggcggcgga ggatctgaga tcgtgctgac ccagtctccc    1440
ggcaccctga gcctgagccc tggcgagaga gccaccctga gctgcagagc cagccagagc    1500
```

-continued

```
gtgagccgga gctacctggc ctggtatcag cagaagcccg gccaggcccc cagactgctg    1560
atcatcggcg ccagcacccg ggccaccggc atccccgata gattcagcgg cagcggctcc    1620
ggcaccgact tcaccctgac catcagccgg ctggaacccg aggacttcgc cgtgtactac    1680
tgccagcagg gccaggtgat cccccccacc ttcggccagg gcaccaaggt ggaaatcaag    1740
gctagcacca agggcccctc cgtgtttcct ctggccccca gcagcaagag cacctctggc    1800
ggaacagccg ccctgggctg cctggtgaaa gactacttcc ccgagcccgt gaccgtgtcc    1860
tggaactctg gcgccctgac cagcggcgtg cacacctttc cagccgtgct gcagagcagc    1920
ggcctgtact ccctgagcag cgtggtgaca gtgccctcca gcagcctggg cacccagacc    1980
tacatctgca acgtgaacca caagcccagc aacaccaaag tggacaagaa ggtggaaccc    2040
aagagctgcg ac                                                        2052
```

<210> SEQ ID NO 224
<211> LENGTH: 672
<212> TYPE: DNA
<213> ORGANISM: Artificial Sequence
<220> FEATURE:
<223> OTHER INFORMATION: FAP (4G8) _VHCL DNA

<400> SEQUENCE: 224

```
gaggtgcagc tgctggaatc tggaggcggc ctggtgcagc ctggcggcag cctgagactg     60
tcttgcgccg ccagcggctt caccttcagc agctacgcca tgagctgggt ccgacaggct    120
cctggcaagg gactggaatg ggtgtccgcc atctccggca gcggaggcag cacctactac    180
gccgacagcg tgaagggccg gttcaccatc agcagagaca acagcaagaa caccctgtac    240
ctgcagatga acagcctgcg ggccgaggat accgccgtgt attattgcgc caagggatgg    300
ctgggcaact tcgactactg gggccaggga accctggtga cagtgtccag cgctagcgtg    360
gccgctccca gcgtgttcat cttcccaccc agcgacgagc agctgaagtc cggcacagcc    420
agcgtggtgt gcctgctgaa caacttctac ccccgcgagg ccaaggtgca gtggaaggtg    480
gacaacgccc tgcagagcgg caacagccag gaatccgtga ccgagcagga cagcaaggac    540
tccacctaca gcctgagcag cacccgacc ctgagcaagg ccgactacga aaagcacaag    600
gtgtacgcct gcgaagtgac ccaccagggc ctgtccagcc ccgtgaccaa gagcttcaac    660
cggggcgagt gc                                                        672
```

<210> SEQ ID NO 225
<211> LENGTH: 2085
<212> TYPE: DNA
<213> ORGANISM: Artificial Sequence
<220> FEATURE:
<223> OTHER INFORMATION: Drozitumab-FAP (28H1) VHCLpETR9551 2+2 DNA

<400> SEQUENCE: 225

```
gaagtgcagc tggtgcagtc tggcggcgga gtggaaagac tggcggcag cctgagactg      60 agctgcgccg ccagcggctt caccttcgac gactacgcca tgtcttgggt ccgccaggcc    120
cctggaaagg gcctggaatg ggtgtccggc atcaactggc agggcggcag caccggctac    180
gccgacagcg tgaagggcag agtgaccatc agccgggaca cgccaagaa cagcctgtac    240 ctgcagatga acagcctgag agccgaggac accgccgtgt actactgcgc caagatcctg    300
ggagccggca gaggctggta cttcgactac tggggcaagg gcaccaccgt gactgtgtct    360
agcgctagca ccaagggccc aagcgtgttc cctctggccc ccagcagcaa gagcacaagc    420
```

```
ggcggaacag ccgccctggg ctgcctggtc aaggactact tccccgagcc cgtgacagtg      480
tcctggaaca gcggagccct gaccagcggc gtgcacacct tccagccgt gctgcagagc       540 agcggcctgt acagcctgag cagcgtggtc acagtgccta gcagcagcct gggcacccag      600
acctacatct gcaacgtgaa ccacaagccc agcaacacca aggtggacaa gaaggtggag      660
cccaagagct gcgacaagac ccacacctgt ccccttgtc ctgcccctga gctgctgggc       720
ggacccagcg tgttcctgtt cccccaaag cccaaggaca ccctgatgat cagccggacc       780
cccgaagtga cctgcgtggt ggtggacgtg tcccacgagg accctgaagt gaagttcaat      840
tggtacgtgg acggcgtgga ggtgcacaat gccaagacca gccccgggga ggaacagtac      900
aacagcacct accgggtggt gtccgtgctg accgtgctgc accaggactg gctgaacggc      960
aaagagtaca gtgcaaggt ctccaacaag gccctgcctg cccccatcga gaaaaccatc       1020
agcaaggcca agggccagcc cagagaaccc caggtgtaca cctgccccc cagcagagat       1080 gagctgacca gaaccaggt gtccctgacc tgtctggtca agggcttcta ccccagcgat       1140
atcgccgtgg agtgggagag caacggccag cctgagaaca actacaagac cacccccct       1200 gtgctggaca gcgacggcag cttcttcctg tactccaaac tgaccgtgga caagagccgg      1260
tggcagcagg gcaacgtgtt cagctgcagc gtgatgcacg aggccctgca caaccactac      1320
acccagaagt ccctgagcct gagccccggc aagtccggag cggcggaag cggaggagga      1380 ggatccggag gaggggggaag tggcggcgga ggatctgagg tgcagctgct ggaatccggc      1440
ggaggcctgg tgcagcctgg cggatctctg agactgtcct gcgccgcctc cggcttcacc      1500
ttctcctccc acgccatgtc ctgggtccga caggctcctg gcaaaggcct ggaatgggtg      1560
tccgccatct gggcctccgg cgagcagtac tacgccgact ctgtgaaggg ccggttcacc      1620
atctcccgga caactccaa gaacaccctg tacctgcaga tgaactccct gcgggccgag      1680
gacaccgccg tgtactactg tgccaagggc tggctgggca acttcgacta ctggggccag     1740
ggcaccctgt tcaccgtgtc cagcgctagc gtggccgctc ccagcgtgtt catcttccca      1800
cccagcgacg agcagctgaa gtccggcaca gccagcgtgg tgtgcctgct gaacaacttc      1860 taccccgcg aggccaaggt gcagtggaag gtggacaacg ccctgcagag cggcaacagc      1920
caggaatccg tgaccgagca ggacagcaag gactccacct acagcctgag cagcacctg      1980 accctgagca aggccgacta cgagaagcac aaggtgtacg cctgcgaagt gacccaccag      2040
ggcctgtcca gcccgtgac caagagcttc aaccggggcg agtgc                      2085

<210> SEQ ID NO 226
<211> LENGTH: 642
<212> TYPE: DNA
<213> ORGANISM: Artificial Sequence
<220> FEATURE:
<223> OTHER INFORMATION: FAP(28H1)_VLCH1pETR9537 DNA

<400> SEQUENCE: 226
gagatcgtgc tgacccagtc tcccggcacc ctgagcctga gccctggcga gagagccacc      60
ctgagctgca gagccagcca gagcgtgagc cggagctacc tggcctggta tcagcagaag      120
cccggccagg cccccagact gctgatcatc ggcgccagca cccgggccac ggcatcccc       180 gatagattca gcggcagcgg ctccggcacc gacttcaccc tgaccatcag ccggctggaa      240
cccgaggact tcgccgtgta ctactgccag cagggccagg tgatcccccc caccttcggc      300
cagggcacca aggtggaaat caagagctcc gctagcacca agggcccctc cgtgtttcct      360
ctggccccca gcagcaagag cacctctggc ggaacagccg ccctgggctg cctggtgaaa      420
```

```
gactacttcc ccgagcccgt gaccgtgtcc tggaactctg gcgccctgac cagcggcgtg      480
cacacctttc cagccgtgct gcagagcagc ggcctgtact ccctgagcag cgtggtgaca      540
gtgccctcca gcagcctggg cacccagacc tacatctgca acgtgaacca caagcccagc      600
aacaccaaag tggacaagaa ggtggaaccc aagagctgcg ac                         642

<210> SEQ ID NO 227
<211> LENGTH: 2073
<212> TYPE: DNA
<213> ORGANISM: Artificial Sequence
<220> FEATURE:
<223> OTHER INFORMATION: DR5(22E9)-FAP(28H1)   VHCLpETR9711 2+2 DNA

<400> SEQUENCE: 227
gaggtgcaat tgttggagtc tgggggaggc ttggtacagc ctgggggtc cctgagactc        60 tcctgtgcag cctccggatt cacctttagc agttatgcca tgagctgggt ccgccaggct      120
ccagggaagg ggctggagtg gtctcagct attagtggta gtggtggtag cacatactac       180
gcagactccg tgaagggccg gttcaccatc tccagagaca attccaagaa cacgctgtat      240
ctgcagatga acagcctgag agccgaggac acggccgtat attactgtgc gaaaggtgtg      300
cggatttcgt ttgactactg gggccaagga accctggtca ccgtctcgag tgctagcacc      360
aagggcccaa gcgtgttccc tctggccccc agcagcaaga gcacaagcgg cggaacagcc      420
gccctgggct gcctggtcaa ggactacttc cccgagcccg tgacagtgtc ctggaacagc      480
ggagccctga ccagcggcgt gcacaccttt ccagccgtgc tgcagagcag cggcctgtac      540
agcctgagca gcgtggtcac agtgcctagc agcagcctgg gcacccagac ctacatctgc      600
aacgtgaacc acaagcccag caacaccaag gtggacaaga aggtggagcc caagagctgc      660
gacaagaccc acacctgtcc cccttgtcct gcccctgagc tgctgggcgg acccagcgtg      720
ttcctgttcc ccccaaagcc caaggacacc ctgatgatca gccggacccc cgaagtgacc      780
tgcgtggtgg tggacgtgtc ccacgaggac cctgaagtga agttcaattg gtacgtggac      840
ggcgtggagg tgcacaatgc caagaccaag ccccgggagg aacagtacaa cagcacctac      900
cgggtggtgt ccgtgctgac cgtgctgcac caggactggc tgaacggcaa agagtacaag      960
tgcaaggtct ccaacaaggc cctgcctgcc ccatcgaga aaccatcag caaggccaag     1020 ggccagcccc gagaaccca gtgtacacc ctgccccca gcagagatga gctgaccaag      1080
aaccaggtgt ccctgacctg tctggtcaag ggcttctacc ccagcgatat cgccgtggag      1140
tgggagagca acggccagcc tgagaacaac tacaagacca ccccccctgt gctggacagc      1200
gacggcagct tcttcctgta ctccaaactg accgtggaca agagccggtg gcagcagggc      1260
aacgtgttca gctgcagcgt gatgcacgag gccctgcaca accactacac ccagaagtcc      1320
ctgagcctga gccccggcaa gtccggaggc ggcggaagcg gaggaggagg atccggagga      1380 ggggaagtg gcggcggagg atctgaggtg cagctgctgg aatccggcgg aggcctggtg      1440
cagcctggcg gatctctgag actgtcctgc gccgcctccg gcttcacctt ctcctcccac      1500
gccatgtcct gggtccgaca ggctcctggc aaaggcctgg aatgggtgtc cgccatctgg      1560
gcctccggcg agcagtacta cgccgactct gtgaagggcc ggttcaccat ctcccgggac      1620
aactccaaga acaccctgta cctgcagatg aactccctgc gggccgagga caccgccgtg      1680
tactactgtg ccaagggctg gctgggcaac ttcgactact ggggccaggg caccctggtc      1740
accgtgtcca gcgctagcgt ggccgctccc agcgtgttca tcttcccacc cagcgacgag      1800
```

```
cagctgaagt ccggcacagc cagcgtggtg tgcctgctga caacttcta ccccgcgag      1860 gccaaggtgc agtggaaggt ggacaacgcc ctgcagagcg gcaacagcca ggaatccgtg      1920
accgagcagg acagcaagga ctccacctac agcctgagca gcaccctgac cctgagcaag      1980
gccgactacg agaagcacaa ggtgtacgcc tgcgaagtga cccaccaggg cctgtccagc      2040
cccgtgacca agagcttcaa ccggggcgag tgc                                  2073
```

<210> SEQ ID NO 228
<211> LENGTH: 645
<212> TYPE: DNA
<213> ORGANISM: Artificial Sequence
<220> FEATURE:
<223> OTHER INFORMATION: DR5(22E9) LCpETR9076 DNA

<400> SEQUENCE: 228

```
gaaatcgtgt taacgcagtc tccaggcacc ctgtctttgt ctccagggga aagagccacc       60
ctctcttgca gggccagtca gagtgttagc agcagctact tagcctggta ccagcagaaa      120
cctggccagg ctcccaggct cctcatctat ggagcatcca gcagggccac tggcatccca      180
gacaggttca gtggcagtgg atccgggaca gacttcactc tcaccatcag cagactggag      240
cctgaagatt ttgcagtgta ttactgtcag cagggttcta atcagcccgt tacgttcggc      300
caggggacca aagtggaaat caaacgtacg gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaagagcttc aacaggggag agtgt                     645
```

<210> SEQ ID NO 229
<211> LENGTH: 2073
<212> TYPE: DNA
<213> ORGANISM: Artificial Sequence
<220> FEATURE:
<223> OTHER INFORMATION: DR5(21H3)-FAP(28H1) VHCLpETR10626_2+2 DNA

<400> SEQUENCE: 229

```
gaggtgcaat tgttggagtc tgggggaggc ttggtacagc ctgggggtc cctgagactc       60 tcctgtgcag cctccggatt cacctttagc agttatgcca tgagctgggt ccgccaggct      120
ccagggaagg ggctggagtg gtctcagct attagtggta gtggtggtag cacatactac      180
gcagactccg tgaagggccg gttcaccatc tccagagaca attccaagaa cacgctgtat      240
ctgcagatga acagcctgag agccgaggac atggccgtat attactgtgc gaaaggtgct      300 cgtgttctt ttgactactg gggccaagga accctggtca ccgtctcgag tgctagcacc      360
aagggcccaa gcgtgttccc tctggccccc agcagcaaga gcacaagcgg cggaacagcc      420
gccctgggct gcctggtcaa ggactacttc cccgagcccg tgacagtgtc ctggaacagc      480
ggagccctga ccagcggcgt gcacaccttt ccagccgtgc tgcagagcag cggcctgtac      540
agcctgagca gcgtggtcac agtgcctagc agcagcctgg gcacccagac ctacatctgc      600
aacgtgaacc acaagcccag caacaccaag gtggacaaga aggtggagcc caagagctgc      660
gacaagaccc acacctgtcc cccttgtcct gcccctgagc tgctgggcgg acccagcgtg      720
ttcctgttcc ccccaaagcc caaggacacc ctgatgatca gccggacccc cgaagtgacc      780
tgcgtggtgg tggacgtgtc ccacgaggac cctgaagtga agttcaattg gtacgtggac      840
```

```
ggcgtggagg tgcacaatgc aagaccaag ccccgggagg aacagtacaa cagcacctac      900
cgggtggtgt ccgtgctgac cgtgctgcac caggactggc tgaacggcaa agagtacaag     960
tgcaaggtct ccaacaaggc cctgcctgcc cccatcgaga aaccatcag caaggccaag     1020 ggccagccca gagaaccca ggtgtacacc ctgccccca gcagagatga gctgaccaag     1080
aaccaggtgt ccctgacctg tctggtcaag ggcttctacc ccagcgatat cgccgtggag     1140
tgggagagca cggccagcc tgagaacaac tacaagacca ccccctgt gctggacagc     1200 gacggcagct tcttcctgta ctccaaactg accgtggaca gagccggtg gcagcagggc     1260 aacgtgttca gctgcagcgt gatgcacgag gccctgcaca accactacac ccagaagtcc     1320
ctgagcctga gccccggcaa gtccggaggc ggcggaagcg aggaggagg atccggagga     1380 gggggaagtg gcggcggagg atctgaggtg cagctgctgg aatccggcgg aggcctggtg     1440
cagcctggcg gatctctgag actgtcctgc gccgcctccg gcttcacctt ctcctcccac     1500
gccatgtcct gggtccgaca ggctcctggc aaaggcctgg aatgggtgtc cgccatctgg     1560
gcctccggcg agcagtacta cgccgactct gtgaagggcc ggttcaccat ctcccgggac     1620
aactccaaga acaccctgta cctgcagatg aactccctgc gggccgagga caccgccgtg     1680
tactactgtg ccaagggctg gctgggcaac ttcgactact ggggccaggg caccctggtc     1740
accgtgtcca gcgctagcgt ggccgctccc agcgtgttca tcttcccacc cagcgacgag     1800
cagctgaagt ccggcacagc cagcgtggtg tgcctgctga caacttcta ccccgcgag     1860 gccaaggtgc agtggaaggt ggacaacgcc ctgcagagcg gcaacagcca ggaatccgtg     1920
accgagcagg acagcaagga ctccacctac agcctgagca gcaccctgac cctgagcaag     1980
gccgactacg agaagcacaa ggtgtacgcc tgcgaagtga cccaccaggg cctgtccagc     2040
cccgtgacca agagcttcaa ccggggcgag tgc                                  2073
```

<210> SEQ ID NO 230
<211> LENGTH: 645
<212> TYPE: DNA
<213> ORGANISM: Artificial Sequence
<220> FEATURE:
<223> OTHER INFORMATION: DR5(21H3) LC_pETR9075 DNA

<400> SEQUENCE: 230

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcggtgta ttactgtcag caggttctc agccgcccat tacgttcggc     300
caggggacca agtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacaggggag agtgt                     645
```

<210> SEQ ID NO 231
<211> LENGTH: 2073
<212> TYPE: DNA

<213> ORGANISM: Artificial Sequence
<220> FEATURE:
<223> OTHER INFORMATION: DR5 (20F2)-FAP(28H1) VHCL_pETR10135_2+2 DNA

<400> SEQUENCE: 231

```
gaggtgcaat tgttggagtc tgggggaggc ttggtacagc ctgggggtc cctgagactc        60
tcctgtgcag cctccggatt caccttagc agttatgcca tgagctgggt ccgccaggct       120
ccagggaagg gctggagtg gtctcagct attagtggta gtggtggtag cacatactac        180
gcagactccg tgaagggccg gttcaccatc tccagagaca attccaagaa cacgctgtat      240
ctgcagatga acagcctgag agccgaggac acggccgtat attactgtgc gaaaggtgtg     300
aggaaggggt ttgactactg gggccaagga accctggtca ccgtctcgag tgctagcacc     360
aagggcccaa gcgtgttccc tctggccccc agcagcaaga gcacaagcgg cggaacagcc      420
gccctgggct gcctggtcaa ggactacttc cccgagcccg tgacagtgtc ctggaacagc      480
ggagccctga ccagcggcgt gcacaccttt ccagccgtgc tgcagagcag cggcctgtac      540
agcctgagca gcgtggtcac agtgcctagc agcagcctgg gcacccagac ctacatctgc      600
aacgtgaacc acaagcccag caacaccaag gtggacaaga aggtggagcc caagagctgc      660
gacaagaccc acacctgtcc cccttgtcct gcccctgagc tgctgggcgg acccagcgtg      720
ttcctgttcc ccccaaagcc caaggacacc ctgatgatca gccggacccc cgaagtgacc     780
tgcgtggtgg tggacgtgtc ccacgaggac cctgaagtga agttcaattg gtacgtggac      840
ggcgtggagg tgcacaatgc caagaccaag ccccggggag aacagtacaa cagcacctac      900
cgggtggtgt ccgtgctgac cgtgctgcac caggactggc tgaacggcaa agagtacaag     960
tgcaaggtct ccaacaaggc cctgcctgcc ccatcgaga aaaccatcag caaggccaag     1020
ggccagccca gagaaccca ggtgtacacc ctgcccccca gcagagatga gctgaccaag    1080
aaccaggtgt ccctgacctg tctggtcaag ggcttctacc ccagcgatat cgccgtggag     1140
tgggagagca acggccagcc tgagaacaac tacaagacca ccccccctgt gctggacagc    1200
gacggcagct tcttcctgta ctccaaactg accgtggaca gagccggtg gcagcagggc     1260
aacgtgttca gctgcagcgt gatgcacgag gccctgcaca accactacac ccagaagtcc    1320
ctgagcctga gccccggcaa gtccggaggc ggcggaagcg gaggaggagg atccggagga    1380
ggggggaagtg gcggcggagg atctgaggtg cagctgctgg aatccggcgg aggcctggtg    1440
cagcctggcg gatctctgag actgtcctgc gccgcctccg gcttcacctt ctcctcccac    1500
gccatgtcct gggtccgaca ggctcctggc aaaggcctgg aatgggtgtc cgccatctgg    1560
gcctccggcg agcagtacta cgccgactct gtgaagggcc ggttcaccat ctcccgggac   1620
aactccaaga acaccctgta cctgcagatg aactccctgc gggccgagga caccgccgtg    1680
tactactgtg ccaagggctg gctgggcaac ttcgactact ggggccaggg caccctggtc    1740
accgtgtcca gcgctagcgt ggccgctccc agcgtgttca tcttcccacc cagcgacgag    1800
cagctgaagt ccggcacagc cagcgtggtg tgcctgctga caacttcta cccccgcgag    1860
gccaaggtgc agtggaaggt ggacaacgcc ctgcagagcg gcaacagcca ggaatccgtg    1920
accgagcagg acagcaagga ctccacctac agcctgagca gcaccctgac cctgagcaag    1980
gccgactacg agaagcacaa ggtgtacgcc tgcgaagtga cccaccaggg cctgtccagc    2040
cccgtgacca gagcttcaa ccggggcgag tgc                                  2073
```

<210> SEQ ID NO 232
<211> LENGTH: 645

```
<212> TYPE: DNA
<213> ORGANISM: Artificial Sequence
<220> FEATURE:
<223> OTHER INFORMATION: DR5(20F2) LCpETR9061 DNA

<400> SEQUENCE: 232
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtgagt cgcctccccc gacgttcggc     300
caggggacca agtggaaat caaacgtacg gtggctgcac catctgtctt catcttcccg      360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt                      645

<210> SEQ ID NO 233
<211> LENGTH: 2073
<212> TYPE: DNA
<213> ORGANISM: Artificial Sequence
<220> FEATURE:
<223> OTHER INFORMATION: DR5(5E11)-FAP(28H1) VHCLpETR10334_2+2 DNA

<400> SEQUENCE: 233
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggggtg     300
agggtgtctt ttgactactg ggccaagga acccctggtca ccgtctcgag tgctagcacc     360
aagggcccaa gcgtgttccc tctggccccc agcagcaaga gcacaagcgg cggaacagcc     420
gccctgggct gcctggtcaa ggactacttc cccgagcccg tgacagtgtc ctggaacagc     480
ggagccctga ccagcggcgt gcacaccttt ccagccgtgc tgcagagcag cggcctgtac     540
agcctgagca gcgtggtcac agtgcctagc agcagcctgg gcacccagac ctacatctgc     600
aacgtgaacc acaagcccag caacaccaag gtggacaaga aggtggagcc caagagctgc     660
gacaagaccc acacctgtcc ccttgtcct gcccctgagc tgctgggcgg acccagcgtg     720
ttcctgttcc cccaaagcc caaggacacc ctgatgatca gccggacccc gaagtgacc      780
tgcgtggtgg tggacgtgtc ccacgaggac cctgaagtga agttcaattg gtacgtggac     840
ggcgtggagg tgcacaatgc caagaccaag ccccgggagg aacagtacaa cagcacctac     900
cgggtggtgt ccgtgctgac cgtgctgcac caggactggc tgaacggcaa agagtacaag     960
tgcaaggtct ccaacaaggc cctgcctgcc cccatcgaga aaccatcag caaggccaag    1020
ggccagccca gagaaccca ggtgtacacc ctgcccccca gcagagatga gctgaccaag    1080
aaccaggtgt ccctgacctg tctggtcaag ggcttctacc ccagcgatat cgccgtggag    1140
tgggagagca acggccagcc tgagaacaac tacaagacca ccccccctgt gctggacagc    1200
```

-continued

```
gacggcagct tcttcctgta ctccaaactg accgtggaca agagccggtg gcagcagggc    1260
aacgtgttca gctgcagcgt gatgcacgag gccctgcaca accactacac ccagaagtcc    1320
ctgagcctga gccccggcaa gtccggaggc ggcggaagcg gaggaggagg atccggagga    1380
gggggaagtg gcggcggagg atctgaggtg cagctgctgg aatccggcgg aggcctggtg    1440
cagcctggcg gatctctgag actgtcctgc gccgcctccg gcttcacctt ctcctcccac    1500
gccatgtcct gggtccgaca ggctcctggc aaaggcctgg aatgggtgtc cgccatctgg    1560
gcctccggcg agcagtacta cgccgactct gtgaagggcc ggttcaccat ctcccgggac    1620
aactccaaga cacccctgta cctgcagatg aactccctgc gggccgagga caccgccgtg    1680
tactactgtg ccaagggctg gctgggcaac ttcgactact ggggccaggg cacccctggtc    1740 accgtgtcca gcgctagcgt ggccgctccc agcgtgttca tcttcccacc cagcgacgag    1800
cagctgaagt ccggcacagc cagcgtggtg tgcctgctga caacttctca ccccgcgag    1860 gccaaggtgc agtggaaggt ggacaacgcc ctgcagagcg gcaacagcca ggaatccgtg    1920
accgagcagg acagcaagga ctccacctac agcctgagca gcaccctgac cctgagcaag    1980
gccgactacg agaagcacaa ggtgtacgcc tgcgaagtga cccaccaggg cctgtccagc    2040
cccgtgacca agagcttcaa ccggggcgag tgc                                 2073
```

<210> SEQ ID NO 234
<211> LENGTH: 645
<212> TYPE: DNA
<213> ORGANISM: Artificial Sequence
<220> FEATURE:
<223> OTHER INFORMATION: DR5(5E11) LCpETR9044 DNA

<400> SEQUENCE: 234

```
gaaatcgtgt taacgcagtc tccaggcacc ctgtctttgt ctccagggga aagagccacc     60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggtacta ctcatcccat tacgttcggc    300
caggggacca agtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 235
<211> LENGTH: 2067
<212> TYPE: DNA
<213> ORGANISM: Artificial Sequence
<220> FEATURE:
<223> OTHER INFORMATION: DR5(5E11)-FAP (28H1) VHCL 2+2 Removal of
      C-term. Lysine in Fc pETR11052 DNA

<400> SEQUENCE: 235

```
gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg ggctggagtg gtctcagct attagtggta gtggtggtag cacatactac    180
```

```
gcagactccg tgaagggccg gttcaccatc tccagagaca attccaagaa cacgctgtat    240
ctgcagatga acagcctgag agccgaggac acggccgtat attactgtgc gaaagggtg    300 aggggtgtctt ttgactactg ggccaagga accctggtca ccgtctcgag tgctagcacc    360
aagggcccaa gcgtgttccc tctggccccc agcagcaaga gcacaagcgg cggaacagcc    420
gccctgggct gcctggtcaa ggactacttc cccgagcccg tgacagtgtc ctggaacagc    480
ggagccctga ccagcggcgt gcacaccttt ccagccgtgc tgcagagcag cggcctgtac    540
agcctgagca gcgtggtcac agtgcctagc agcagcctgg gcacccagac ctacatctgc    600
aacgtgaacc acaagcccag caacaccaag gtggacaaga aggtggagcc caagagctgc    660
gacaagaccc acacctgtcc cccttgtcct gcccctgagc tgctgggcgg acccagcgtg    720
ttcctgttcc ccccaaagcc caaggacacc ctgatgatca gccggacccc cgaagtgacc    780
tgcgtggtgg tggacgtgtc ccacgaggac cctgaagtga agttcaattg gtacgtggac    840
ggcgtggagg tgcacaatgc caagaccaag ccccggagg aacagtacaa cagcacctac    900
cgggtggtgt ccgtgctgac cgtgctgcac caggactggc tgaacggcaa agagtacaag    960
tgcaaggtct ccaacaaggc cctgcctgcc cccatcgaga aaaccatcag caaggccaag    1020
ggccagccca gagaacccca ggtgtacacc ctgccccta gcagagatga gctgaccaag    1080
aaccaggtgt ccctgacctg tctcgtgaaa ggcttctacc cctccgatat cgccgtggaa    1140
tgggagagca acggccagcc cgagaacaac tacaagacca cccccctgt gctggactcc    1200 gacggctcat tcttcctgta ctctaagctg acagtggaca gtcccggtg cagcagggc    1260 aacgtgttct cctgctccgt gatgcacgag gccctgcaca accactacac ccagaagtcc    1320
ctgtccctgt ctcccggggg aggcggagga tctggcggag cggatccgg tggtggcgga    1380 tctgggggcg gtggatctga ggtgcagctg ctggaatctg ggggaggact ggtgcagcca    1440
ggcggatctc tgaggctgtc ctgcgctgct tccggctta ccttctccag ccacgccatg    1500
agttgggtgc gccaggcacc cggaaaagga ctggaatggg tgtcagccat ctgggcctcc    1560
ggcgagcagt actacgccga tagcgtgaag gccggttca ccatctctcg ggataacagc    1620
aagaatactc tgtacctgca gatgaactcc ctgcgcgctg aagataccgc tgtgtattac    1680
tgcgccaagg gctggctggg caacttcgat tactggggcc agggaaccct cgtgactgtc    1740
tcgagcgctt ctgtggccgc tccctccgtg ttcatcttcc cacctttcga cgagcagctg    1800
aagtccggca ctgcctctgt cgtgtgcctg ctgaacaact ctaccctcg ggaagccaag    1860 gtgcagtgga aagtggataa cgccctgcag tccggcaact cccaggaatc cgtgaccgag    1920
caggactcca aggacagcac ctactccctg agcagcaccc tgaccctgtc caaggccgac    1980
tacgagaagc acaaggtgta cgcctgtgaa gtgacccacc agggcctgtc cagccccgtg    2040
accaagtcct tcaaccgggg cgagtgc                                       2067
```

<210> SEQ ID NO 236
<211> LENGTH: 2067
<212> TYPE: DNA
<213> ORGANISM: Artificial Sequence
<220> FEATURE:
<223> OTHER INFORMATION: DR5(5E11)-FAP(28H1) VHCL2+2 Removal of C-term.
      Lysine in Fc P329G/LALA mut. pETR11025 DNA

<400> SEQUENCE: 236

```
gaggtgcaat gttggagtc tgggggaggc ttggtacagc ctgggggtc cctgagactc     60 tcctgtgcag cctccggatt caccttttagc agttatgcca tgagctgggt ccgccaggct    120
```

| | |
|---|---:|
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac acggccgtat attactgtgc gaaagggGtg | 300 |
| agggtgtctt ttgactactg gggccaagga accctggtca ccgtctcgag tgctagcacc | 360 |
| aagggcccat ccgtgttccc tctggcccct tccagcaagt ctacctctgg cggcacagcc | 420 |
| gctctgggct gcctcgtgaa ggactacttc cccgagcctg tgacagtgtc ctggaactct | 480 |
| ggcgccctga catccggcgt gcacaccttt ccagctgtgc tgcagtcctc cggcctgtac | 540 |
| tccctgtcct ccgtcgtgac agtgccctcc agctctctgg cacccagac ctacatctgc | 600 |
| aacgtgaacc acaagccctc caacaccaag gtggacaaga aggtggaacc caagtcctgc | 660 |
| gacaagaccc acacctgtcc cccttgtcct gcccctgaag ctgctggcgg ccctagcgtg | 720 |
| ttcctgttcc ccccaaagcc caaggacacc ctgatgatct cccggacccc cgaagtgacc | 780 |
| tgcgtggtgg tggatgtgtc ccacgaggac cctgaagtga agttcaattg gtacgtggac | 840 |
| ggcgtggaag tgcacaatgc caagaccaag cctagagagg aacagtacaa ctccacctac | 900 |
| cgggtggtgt ccgtgctgac cgtgctgcac caggattggc tgaacggcaa agagtacaag | 960 |
| tgcaaggtgt ccaacaaggc cctggagcc cccatcgaaa agaccatctc caaggccaag | 1020 |
| ggccagcctc gcgagcctca ggtgtacacc ctgccccta gcagagatga gctgaccaag | 1080 |
| aaccaggtgt ccctgacctg tctcgtgaaa ggcttctacc cctccgatat cgccgtggaa | 1140 |
| tgggagagca acggccagcc cgagaacaac tacaagacca cccccctgt gctggactcc | 1200 |
| gacggctcat tcttcctgta ctctaagctg acagtggaca agtcccggtg gcagcagggc | 1260 |
| aacgtgttct cctgctccgt gatgcacgag gccctgcaca accactacac ccagaagtcc | 1320 |
| ctgtccctgt ctcccggggg aggcggagga tctggcggag gcggatccgg tggtggcgga | 1380 |
| tctgggggcg gtggatctga ggtgcagctg ctggaatctg ggggaggact ggtgcagcca | 1440 |
| ggcggatctc tgaggctgtc ctgcgctgct tccggctttc ccttctccag ccacgccatg | 1500 |
| agttgggtgc gccaggcacc cggaaaagga ctggaatggg tgtcagccat ctgggcctcc | 1560 |
| ggcgagcagt actacgccga tagcgtgaag ggccggttca ccatctctcg ggataacagc | 1620 |
| aagaatactc tgtacctgca gatgaactcc ctgcgcgctg aagataccgc tgtgtattac | 1680 |
| tgcgccaagg gctggctggg caacttcgat tactgggggcc agggaaccct cgtgactgtc | 1740 |
| tcgagcgctt ctgtggccgc tccctccgtg ttcatcttcc caccttccga cgagcagctg | 1800 |
| aagtccggca ctgcctctgt cgtgtgcctg ctgaacaact tctacccct cg ggaagccaag | 1860 |
| gtgcagtgga aagtggataa cgccctgcag tccggcaact cccaggaatc cgtgaccgag | 1920 |
| caggactcca aggacagcac ctactccctg agcagcaccc tgaccctgtc caaggccgac | 1980 |
| tacgagaagc acaaggtgta cgcctgtgaa gtgacccacc agggcctgtc cagccccgtg | 2040 |
| accaagtcct tcaaccgggg cgagtgc | 2067 |

<210> SEQ ID NO 237
<211> LENGTH: 2043
<212> TYPE: DNA
<213> ORGANISM: Artificial Sequence
<220> FEATURE:
<223> OTHER INFORMATION: VHVL Cross DR5 (5E11)-FAP (28H1) pETR11827 2+2 DNA

<400> SEQUENCE: 237

| | |
|---|---:|
| gaaatcgtgt taacgcagtc tccaggcacc ctgtctttgt ctccagggga aagagccacc | 60 |

```
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggtacta ctcatcccat acgttcggc    300 caggggacca agtggaaat caaaagctcc gctagcacca agggcccaag cgtgttccct    360
ctggccccca gcagcaagag cacaagcggc ggaacagccg ccctgggctg cctggtcaag    420
gactacttcc ccgagcccgt gacagtgtcc tggaacagcg gagccctgac cagcggcgtg    480
cacacctttc cagccgtgct gcagagcagc ggcctgtaca gcctgagcag cgtggtcaca    540
gtgcctagca gcagcctggg cacccagacc tacatctgca acgtgaacca caagcccagc    600
aacaccaagg tggacaagaa ggtggagccc aagagctgcg acaagaccca cctgtccc     660 ccttgtcctg cccctgagct gctgggcgga cccagcgtgt tcctgttccc cccaaagccc    720
aaggacaccc tgatgatcag ccggacccccc gaagtgacct gcgtggtggt ggacgtgtcc    780
cacgaggacc ctgaagtgaa gttcaattgg tacgtggacg gcgtggaggt gcacaatgcc    840
aagaccaagc ccggaggga acagtacaac agcacctacc gggtggtgtc cgtgctgacc    900
gtgctgcacc aggactggct gaacggcaaa gagtacaagt gcaaggtctc caacaaggcc    960
ctgcctgccc ccatcgagaa aaccatcagc aaggccaagg ccagcccag agaaccccag    1020 gtgtacaccc tgcccccccag cagagatgag ctgaccaaga accaggtgtc cctgacctgt    1080
ctggtcaagg gcttctaccc cagcgatatc gccgtggagt gggagagcaa cggccagcct    1140
gagaacaact acaagaccac ccccccctgtg ctggacagcg acggcagctt cttcctgtac    1200
tccaaactga ccgtggacaa gagccggtgg cagcagggca acgtgttcag ctgcagcgtg    1260
atgcacgagg ccctgcacaa ccactacacc cagaagtccc tgagcctgag ccccggcaag    1320
tccggaggcg gcggaagcgg aggaggagga tccggaggag ggggaagtgg cggcggagga    1380
tctgaggtgc agctgctgga atccggcgga ggcctggtgc agcctggcgg atctctgaga    1440
ctgtcctgcg ccgcctccgg cttcaccttc tcctcccacg ccatgtcctg ggtccgacag    1500
gctcctggca aaggcctgga atgggtgtcc gccatctggg cctccggcga gcagtactac    1560
gccgactctg tgaagggccg gttcaccatc tcccgggaca actccaagaa caccctgtac    1620
ctgcagatga ctccctgcg ggccgaggac accgccgtgt actactgtgc caagggctgg    1680
ctgggcaact tcgactactg gggccagggc accctggtca ccgtgtccag cgctagcacc    1740
aagggcccct ccgtgtttcc tctggcccct agctctaaga gcaccagcgg aggaacagcc    1800
gccctgggct gcctcgtgaa agactacttc cccgagcccg tgacagtgtc ttggaactct    1860
ggcgccctga ccagcggcgt gcacacattt ccagctgtgc tgcagtccag cggcctgtac    1920
tctctgagca gcgtcgtgac tgtgcccagc tctagcctgg aacccagac ctacatctgc    1980 aacgtgaacc acaagcccag caacaccaaa gtggataaga aggtggaacc caagagctgc    2040
gac                                                                  2043
```

<210> SEQ ID NO 238
<211> LENGTH: 672
<212> TYPE: DNA
<213> ORGANISM: Artificial Sequence
<220> FEATURE:
<223> OTHER INFORMATION: DR5(5E11)VHCL_pETR11484 DNA

<400> SEQUENCE: 238

```
gaggtgcaat tgttggagtc tgggggaggc ttggtacagc ctggggggtc cctgagactc     60
```

```
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggggtg    300
agggtgtctt ttgactactg gggccaagga accctggtca ccgtctcgag tgctagcgtg    360
gctgcaccat ctgtcttcat cttcccgcca tctgatgagc agttgaaatc tggaactgcc    420
tctgttgtgt gcctgctgaa taacttctat cccagagagg ccaaagtaca gtggaaggtg    480
gataacgccc tccaatcggg taactcccag gagagtgtca cagagcagga cagcaaggac    540
agcacctaca gcctcagcag caccctgacg ctgagcaaag cagactacga gaaacacaaa    600
gtctacgcct gcgaagtcac ccatcagggc ctgagctcgc ccgtcacaaa gagcttcaac    660
aggggagagt gt                                                        672
```

<210> SEQ ID NO 239
<211> LENGTH: 645
<212> TYPE: DNA
<213> ORGANISM: Artificial Sequence
<220> FEATURE:
<223> OTHER INFORMATION: FAP (28H1) VLCL_pETR9366 DNA

<400> SEQUENCE: 239

```
gagatcgtgc tgacccagtc ccccggcacc ctgtctctga gccctggcga gagagccacc     60
ctgtcctgca gagcctccca gtccgtgtcc cggtcctacc tcgcctggta tcagcagaag    120
cccggccagg cccctcggct gctgatcatc ggcgcctcta ccagagccac cggcatccct    180
gaccggttct ccggctctgg ctccggcacc gacttcaccc tgaccatctc ccggctggaa    240
cccgaggact tcgccgtgta ctactgccag cagggccagg tcatccctcc cacctttggc    300
cagggcacca aggtggaaat caagcgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 240
<211> LENGTH: 2070
<212> TYPE: DNA
<213> ORGANISM: Artificial Sequence
<220> FEATURE:
<223> OTHER INFORMATION: CH1CL Cross DR5(5E11)-FAP (28H1) pETR11828 2+2
      DNA

<400> SEQUENCE: 240

```
gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggggtg    300
agggtgtctt ttgactactg gggccaagga accctggtca ccgtctcgag tgctagcgtg    360
gccgctccca gcgtgttcat cttcccacct agcgacgagc agctgaagtc cggcacagcc    420
```

```
tctgtcgtgt gcctgctgaa caacttctac ccccgcgagg ccaaggtgca gtggaaggtg        480
gacaatgccc tgcagagcgg caacagccag gaaagcgtga ccgagcagga cagcaaggac        540
tccacctaca gcctgagcag cacactgacc ctgagcaagg ccgactacga gaagcacaag        600
gtgtacgcct gcgaagtgac ccaccagggc ctgtctagcc ccgtgaccaa gagcttcaac        660
cggggcgagt gcgacaagac ccacacctgc ccccttgtc ctgcccctga actgctggga         720
ggccctagcg tgttcctgtt cccccaaag cccaaggaca cctgatgat cagccggacc          780
cctgaagtga cctgcgtggt ggtggatgtg tcccacgagg acccagaagt gaagttcaat        840
tggtacgtgg acggcgtgga ggtgcacaat gccaagacca gccccggga ggaacagtac         900
aacagcacct accgggtggt gtccgtgctg accgtgctgc accaggactg gctgaacggc        960
aaagagtaca agtgcaaggt ctccaacaag gccctgcctg ccccatcga aaaaccatc        1020
agcaaggcca agggccagcc cagagaaccc caggtgtaca ccctgccccc tagcagagat       1080
gagctgacca gaaccaggt gtccctgacc tgtctcgtga aaggcttcta cccctccgat        1140
atcgccgtgg aatgggagag caacggccag cccgagaaca actacaagac cacccccct        1200
gtgctggact ccgacggctc attcttcctg tactctaagc tgacagtgga caagtcccgg       1260
tggcagcagg gcaacgtgtt ctcctgctcc gtgatgcacg aggccctgca caaccactac       1320
acccagaagt ccctgtccct gtctcccggg ggaggcggag gatctggcgg aggcggatcc       1380
ggaggagggg gaagtggcgg cggaggatct gaggtgcagc tgctggaatc cggcggaggc       1440
ctggtgcagc ctggcggatc tctgagactg tcctgcgccg cctccggctt caccttctcc      1500
tcccacgcca tgtcctgggt ccgacaggct cctggcaaag gctggaatg ggtgtccgcc        1560
atctgggcct ccggcgagca gtactacgcc gactctgtga agggccggtt caccatctcc      1620
cgggacaact ccaagaacac cctgtacctg cagatgaact ccctgcgggc cgaggacacc      1680
gccgtgtact actgtgccaa gggctggctg ggcaacttcg actactgggg ccagggcacc      1740
ctggtcaccg tgtccagcgc tagcaccaag ggcccctccg tgttcctct ggcccctagc        1800
tctaagagca ccagcggagg aacagccgcc ctgggctgcc tcgtgaaaga ctacttcccc      1860
gagcccgtga cagtgtcttg gaactctggc gccctgacca gcggcgtgca cacatttcca     1920
gctgtgctgc agtccagcgg cctgtactct ctgagcagcg tcgtgactgt gcccagctct     1980
agcctgggaa cccagaccta catctgcaac gtgaaccaca gcccagcaa caccaaagtg       2040
gataagaagg tggaacccaa gagctgcgac                                       2070
```

<210> SEQ ID NO 241
<211> LENGTH: 642
<212> TYPE: DNA
<213> ORGANISM: Artificial Sequence
<220> FEATURE:
<223> OTHER INFORMATION: DR5(5E11) VLCH1_pETR11480 DNA

<400> SEQUENCE: 241

```
gaaatcgtgt taacgcagtc tccaggcacc ctgtctttgt ctccagggga agagccacc         60
ctctcttgca gggccagtca gagtgttagc agcagctact tagcctggta ccagcagaaa       120
cctggccagg ctcccaggct cctcatctat ggagcatcca gcagggccac tggcatccca       180
gacaggttca gtggcagtgg atccgggaca gacttcactc tcaccatcag cagactggag       240
cctgaagatt ttgcagtgta ttactgtcag cagggtacta ctcatcccat acgttcggc        300
caggggacca aagtggaaat caaaagctcc gctagcacca agggcccctc cgtgtttcct       360
```

| | |
|---|---|
| ctggccccca gcagcaagag cacctctggc ggaacagccg ccctgggctg cctggtgaaa | 420 |
| gactacttcc ccgagcccgt gaccgtgtcc tggaactctg gcgccctgac cagcggcgtg | 480 |
| cacacctttc cagccgtgct gcagagcagc ggcctgtact ccctgagcag cgtggtgaca | 540 |
| gtgccctcca gcagcctggg cacccagacc tacatctgca acgtgaacca caagcccagc | 600 |
| aacaccaaag tggacaagaa ggtggaaccc aagagctgcg ac | 642 |

<210> SEQ ID NO 242
<211> LENGTH: 2073
<212> TYPE: DNA
<213> ORGANISM: Artificial Sequence
<220> FEATURE:
<223> OTHER INFORMATION: DR5(18F11)-FAP (28H1) VHCL 2+2  pETR9801 DNA

<400> SEQUENCE: 242

| | |
|---|---|
| gaggtgcaat tgttggagtc tgggggaggc ttggtacagc ctgggggggtc cctgagactc | 60 |
| tcctgtgcag cctccggatt cacctttagc agttatgcca tgagctgggt ccgccaggct | 120 |
| ccagggaagg gctggagtg gtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac gcggccgtat attactgtgc gaaggggtg | 300 |
| cgtaagaagt ttgactactg gggccaagga accctggtca ccgtctcgag tgctagcacc | 360 |
| aagggcccaa gcgtgttccc tctggccccc agcagcaaga gcacaagcgg cggaacagcc | 420 |
| gccctgggct gcctggtcaa ggactacttc cccgagcccg tgacagtgtc ctggaacagc | 480 |
| ggagccctga ccagcggcgt gcacaccttt ccagccgtgc tgcagagcag cggcctgtac | 540 |
| agcctgagca gcgtggtcac agtgcctagc agcagcctgg gcacccagac ctacatctgc | 600 |
| aacgtgaacc acaagcccag caacaccaag gtggacaaga aggtggagcc caagagctgc | 660 |
| gacaagaccc acacctgtcc cccttgtcct gcccctgagc tgctgggcgg accagcgtg | 720 |
| ttcctgttcc cccaaagcc caaggacacc ctgatgatca gccggacccc cgaagtgacc | 780 |
| tgcgtggtgg tggacgtgtc cacgaggac cctgaagtga agttcaattg gtacgtggac | 840 |
| ggcgtggagg tgcacaatgc caagaccaag ccccgggagg aacagtacaa cagcacctac | 900 |
| cgggtggtgt ccgtgctgac cgtgctgcac caggactggc tgaacggcaa agagtacaag | 960 |
| tgcaaggtct ccaacaaggc cctgcctgcc cccatcgaga aaaccatcag caaggccaag | 1020 |
| ggccagccca gagaacccca ggtgtacacc ctgccccca gcagagatga gctgaccaag | 1080 |
| aaccaggtgt ccctgacctg tctggtcaag ggcttctacc ccagcgatat cgccgtggag | 1140 |
| tgggagagca acggccagcc tgagaacaac tacaagacca cccccctgt gctggacagc | 1200 |
| gacggcagct tcttcctgta ctccaaactg accgtggaca agagccggtg gcagcagggc | 1260 |
| aacgtgttca gctgcagcgt gatgcacgag gccctgcaca accactacac ccagaagtcc | 1320 |
| ctgagcctga gccccggcaa gtccggaggc ggcggaagcg gaggaggagg atccggagga | 1380 |
| ggggaagtg gcggcggagg atctgaggtg cagctgctgg aatccggcgg aggcctggtg | 1440 |
| cagcctggcg gatctctgag actgtcctgc gccgcctccg gcttcacctt ctcctcccac | 1500 |
| gccatgtcct gggtccgaca ggctcctggc aaaggcctgg aatgggtgtc cgccatctgg | 1560 |
| gcctccggcg agcagtacta cgccgactct gtgaagggcc ggttcaccat ctcccgggac | 1620 |
| aactccaaga acaccctgta cctgcagatg aactccctgc gggccgagga caccgccgtg | 1680 |
| tactactgtg ccaagggctg gctgggcaac ttcgactact ggggccaggg caccctggtc | 1740 |
| accgtgtcca gcgctagcgt ggccgctccc agcgtgttca tcttcccacc cagcgacgag | 1800 |

```
cagctgaagt ccggcacagc cagcgtggtg tgcctgctga caacttcta ccccgcgag     1860 gccaaggtgc agtggaaggt ggacaacgcc ctgcagagcg gcaacagcca ggaatccgtg     1920
accgagcagg acagcaagga ctccacctac agcctgagca gcaccctgac cctgagcaag     1980
gccgactacg agaagcacaa ggtgtacgcc tgcgaagtga cccaccaggg cctgtccagc     2040
cccgtgacca agagcttcaa ccggggcgag tgc                                  2073
```

<210> SEQ ID NO 243
<211> LENGTH: 645
<212> TYPE: DNA
<213> ORGANISM: Artificial Sequence
<220> FEATURE:
<223> OTHER INFORMATION: DR5(18F11) LC_pETR9070 DNA

<400> SEQUENCE: 243

```
gaaatcgtgt taacgcagtc tccaggcacc ctgtctttgt ctccagggga agagccacc      60 ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagggtcagt gcctcccat acgttcggc      300 caggggacca aagtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcccctg     540 acgctgagca agcagactta cgagaaacac aaagtctacg cctgcgaagt cacccatcag    600
ggcctgagct cgcccgtcac aaagagcttc aacaggggag agtgt                    645
```

<210> SEQ ID NO 244
<211> LENGTH: 2067
<212> TYPE: DNA
<213> ORGANISM: Artificial Sequence
<220> FEATURE:
<223> OTHER INFORMATION: DR5(5E11)-FAP (28H1) Fc knob VHCL 2+1 pETR10427
      DNA

<400> SEQUENCE: 244

```
gaggtgcaat tgttggagtc tgggggaggc ttggtacagc ctgggggtc cctgagactc       60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggggtg    300
agggtgtctt ttgactactg gggccaagga accctggtca ccgtctcgag tgctagcacc    360
aagggcccaa gcgtgttccc tctggccccc agcagcaaga gcacaagcgg cggaacagcc    420
gccctgggct gcctggtcaa ggactacttc cccgagcccg tgacagtgtc ctggaacagc    480
ggagccctga ccagcggcgt gcacaccttt ccagccgtgc tgcagagcag cggcctgtac    540
agcctgagca gcgtggtcac agtgcctagc agcagcctgg gcacccagac ctacatctgc    600
aacgtgaacc acaagcccag caacaccaag gtggacaaga aggtggagcc caagagctgc    660
gacaagaccc acacctgtcc cccttgtcct gcccctgagc tgctgggcgg acccagcgtg    720
ttcctgttcc cccaaagcc aaggacacc ctgatgatca gccggacccc cgaagtgacc    780
```

```
tgcgtggtgg tggacgtgtc ccacgaggac cctgaagtga agttcaattg gtacgtggac    840
ggcgtggagg tgcacaatgc caagaccaag ccccgggagg aacagtacaa cagcacctac    900
cgggtggtgt ccgtgctgac cgtgctgcac caggactggc tgaacggcaa agagtacaag    960
tgcaaggtct ccaacaaggc cctgcctgcc cccatcgaga aaaccatcag caaggccaag   1020
ggccagccca gagaacccca ggtgtacacc ctgcccccct gcagagatga gctgaccaag   1080
aaccaggtgt ccctgtggtg tctggtcaag ggcttctacc ccagcgatat cgccgtggag   1140
tgggagagca acggccagcc tgagaacaac tacaagacca cccccctgt gctggacagc    1200 gacggcagct tcttcctgta ctccaaactg accgtggaca gagccggtg gcagcagggc    1260 aacgtgttca gctgcagcgt gatgcacgag gccctgcaca accactacac ccagaagtcc   1320
ctgagcctga gccccggcgg aggcggcgga agcggaggag aggatccgg aggagggga    1380 agtggcggcg gaggatctga ggtgcagctg ctggaatccg gcggaggcct ggtgcagcct   1440
ggcggatctc tgagactgtc ctgcgccgcc tccggcttca ccttctcctc ccacgccatg   1500
tcctgggtcc gacaggctcc tggcaaaggc ctggaatggg tgtccgccat ctgggcctcc   1560
ggcgagcagt actacgccga ctctgtgaag gccggttca ccatctcccg ggacaactcc    1620
aagaacaccc tgtacctgca gatgaactcc ctgcgggccg aggacaccgc cgtgtactac   1680
tgtgccaagg gctggctggg caacttcgac tactggggcc agggcaccct ggtcaccgtg   1740
tccagcgcta gcgtggccgc tcccagcgtg ttcatcttcc cacccagcga cgagcagctg   1800
aagtccggca cagccagcgt ggtgtgcctg ctgaacaact ctacccccg cgaggccaag    1860 gtgcagtgga aggtggacaa cgccctgcag agcggcaaca gccaggaatc cgtgaccgag   1920
caggacagca aggactccac ctacagcctg agcagcaccc tgaccctgag caaggccgac   1980
tacgagaagc acaaggtgta cgcctgcgaa gtgacccacc agggcctgtc cagccccgtg   2040
accaagagct tcaaccgggg cgagtgc                                       2067
```

<210> SEQ ID NO 245
<211> LENGTH: 1341
<212> TYPE: DNA
<213> ORGANISM: Artificial Sequence
<220> FEATURE:
<223> OTHER INFORMATION: DR5(5E11) Fc hole pETR10336 DNA

<400> SEQUENCE: 245

```
gaggtgcaat tgttggagtc tgggggaggc ttggtacagc ctgggggtc cctgagactc      60 tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaagggggtg    300
agggtgtctt ttgactactg gggccaagga accctggtca ccgtctcgag tgctagcacc   360
aagggcccaa gcgtgttccc tctggccccc agcagcaaga gcacaagcgg cggaacagcc   420
gccctgggct gcctggtcaa ggactacttc cccgagcccg tgacagtgtc ctggaacagc   480
ggagccctga ccagcggcgt gcacaccttt ccagccgtgc tgcagagcag cggcctgtac   540
agcctgagca gcgtggtcac agtgcctagc agcagcctgg gcacccagac ctacatctgc   600
aacgtgaacc acaagcccag caacaccaag gtggacaaga aggtggagcc caagagctgc   660
gacaagaccc acacctgtcc cccttgtcct gcccctgagc tgctgggcgg acccagcgtg   720
```

| | |
|---|---|
| ttcctgttcc ccccaaagcc caaggacacc ctgatgatca gccggacccc cgaagtgacc | 780 |
| tgcgtggtgg tggacgtgtc ccacgaggac cctgaagtga agttcaattg gtacgtggac | 840 |
| ggcgtggagg tgcacaatgc caagaccaag ccccgggagg aacagtacaa cagcacctac | 900 |
| cgggtggtgt ccgtgctgac cgtgctgcac caggactggc tgaacggcaa agagtacaag | 960 |
| tgcaaggtct ccaacaaggc cctgcctgcc cccatcgaga aaaccatcag caaggccaag | 1020 |
| ggccagccca gagaacccca ggtgtgcacc ctgcccccca gcagagatga gctgaccaag | 1080 |
| aaccaggtgt ccctgagctg tgccgtcaag ggcttctacc ccagcgatat cgccgtggag | 1140 |
| tgggagagca acggccagcc tgagaacaac tacaagacca cccccctgt gctggacagc | 1200 |
| gacggcagct tcttcctggt gtccaaactg accgtggaca gagccggtg gcagcagggc | 1260 |
| aacgtgttca gctgcagcgt gatgcacgag gccctgcaca accactacac ccagaagtcc | 1320 |
| ctgagcctga gccccggcaa g | 1341 |

<210> SEQ ID NO 246
<211> LENGTH: 2067
<212> TYPE: DNA
<213> ORGANISM: Artificial Sequence
<220> FEATURE:
<223> OTHER INFORMATION: DR5(5E11)-FAP (28H1) Fc knob VHCL 3+1 pETR10427 DNA

<400> SEQUENCE: 246

| | |
|---|---|
| gaggtgcaat tgttggagtc tgggggaggc ttggtacagc ctggggggtc cctgagactc | 60 |
| tcctgtgcag cctccggatt cacctttagc agttatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac acggccgtat attactgtgc gaaaggggtg | 300 |
| agggtgtctt ttgactactg gggccaagga accctggtca ccgtctcgag tgctagcacc | 360 |
| aagggcccaa gcgtgttccc tctggccccc agcagcaaga gcacaagcgg cggaacagcc | 420 |
| gccctgggct gcctggtcaa ggactacttc cccgagcccg tgacagtgtc ctggaacagc | 480 |
| ggagccctga ccagcggcgt gcacaccttt ccagccgtgc tgcagagcag cggcctgtac | 540 |
| agcctgagca gcgtggtcac agtgcctagc agcagcctgg gcacccagac ctacatctgc | 600 |
| aacgtgaacc acaagcccag caacaccaag gtggacaaga aggtggagcc caagagctgc | 660 |
| gacaagaccc acacctgtcc cccttgtcct gcccctgagc tgctgggcgg acccagcgtg | 720 |
| ttcctgttcc ccccaaagcc caaggacacc ctgatgatca gccggacccc cgaagtgacc | 780 |
| tgcgtggtgg tggacgtgtc ccacgaggac cctgaagtga agttcaattg gtacgtggac | 840 |
| ggcgtggagg tgcacaatgc caagaccaag ccccgggagg aacagtacaa cagcacctac | 900 |
| cgggtggtgt ccgtgctgac cgtgctgcac caggactggc tgaacggcaa agagtacaag | 960 |
| tgcaaggtct ccaacaaggc cctgcctgcc cccatcgaga aaaccatcag caaggccaag | 1020 |
| ggccagccca gagaacccca ggtgtacacc ctgcccccct gcagagatga gctgaccaag | 1080 |
| aaccaggtgt ccctgtggtg tctggtcaag ggcttctacc ccagcgatat cgccgtggag | 1140 |
| tgggagagca acggccagcc tgagaacaac tacaagacca cccccctgt gctggacagc | 1200 |
| gacggcagct tcttcctgta ctccaaactg accgtggaca gagccggtg gcagcagggc | 1260 |
| aacgtgttca gctgcagcgt gatgcacgag gccctgcaca accactacac ccagaagtcc | 1320 |
| ctgagcctga gccccggcgg aggcggcgga agcggaggag gaggatccgg aggaggggga | 1380 |

| | |
|---|---|
| agtggcggcg gaggatctga ggtgcagctg ctggaatccg gcggaggcct ggtgcagcct | 1440 |
| ggcggatctc tgagactgtc ctgcgccgcc tccggcttca ccttctcctc ccacgccatg | 1500 |
| tcctgggtcc gacaggctcc tggcaaaggc ctggaatggg tgtccgccat ctgggcctcc | 1560 |
| ggcgagcagt actacgccga ctctgtgaag ggccggttca ccatctcccg ggacaactcc | 1620 |
| aagaacaccc tgtacctgca gatgaactcc ctgcgggccg aggacaccgc cgtgtactac | 1680 |
| tgtgccaagg gctggctggg caacttcgac tactggggcc agggcaccct ggtcaccgtg | 1740 |
| tccagcgcta gcgtggccgc tcccagcgtg ttcatcttcc cacccagcga cgagcagctg | 1800 |
| aagtccggca cagccagcgt ggtgtgcctg ctgaacaact ctacccccg cgaggccaag | 1860 |
| gtgcagtgga aggtggacaa cgccctgcag agcggcaaca gccaggaatc cgtgaccgag | 1920 |
| caggacagca aggactccac ctacagcctg agcagcaccc tgaccctgag caaggccgac | 1980 |
| tacgagaagc acaaggtgta cgcctgcgaa gtgacccacc agggcctgtc cagccccgtg | 2040 |
| accaagagct tcaaccgggg cgagtgc | 2067 |

<210> SEQ ID NO 247
<211> LENGTH: 2061
<212> TYPE: DNA
<213> ORGANISM: Artificial Sequence
<220> FEATURE:
<223> OTHER INFORMATION: DR5(5E11)-DR5(5E11) Fc hole pETR10429 DNA

<400> SEQUENCE: 247

| | |
|---|---|
| gaggtgcaat tgttggagtc tgggggaggc ttggtacagc ctgggggtc cctgagactc | 60 |
| tcctgtgcag cctccggatt cacctttagc agttatgcca tgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac acggccgtat attactgtgc gaaggggtg | 300 |
| agggtgtctt ttgactactg gggccaagga accctggtca ccgtctcgag tgctagcacc | 360 |
| aagggcccaa gcgtgttccc tctggccccc agcagcaaga gcacaagcgg cggaacagcc | 420 |
| gccctgggct gcctggtcaa ggactacttc cccgagcccg tgacagtgtc ctggaacagc | 480 |
| ggagccctga ccagcggcgt gcacaccttt ccagccgtgc tgcagagcag cggcctgtac | 540 |
| agcctgagca gcgtggtcac agtgcctagc agcagcctgg gcacccagac ctacatctgc | 600 |
| aacgtgaacc acaagcccag caacaccaag gtggacaaga aggtggagcc caagagctgc | 660 |
| gacaagaccc acacctgtcc ccctt gtcct gcccctgagc tgctgggcgg acccagcgtg | 720 |
| ttcctgttcc cccaaagcc caaggacacc ctgatgatca gccggacccc cgaagtgacc | 780 |
| tgcgtggtgg tggacgtgtc ccacgaggac cctgaagtga agttcaattg gtacgtggac | 840 |
| ggcgtggagg tgcacaatgc caagaccaag ccccgggagg aacagtacaa cagcacctac | 900 |
| cgggtggtgt ccgtgctgac cgtgctgcac caggactggc tgaacggcaa agagtacaag | 960 |
| tgcaaggtct ccaacaaggc cctgcctgcc cccatcgaga aaaccatcag caaggccaag | 1020 |
| ggccagccca gagaaccca ggtgtgcacc ctgccccca gcagagatga gctgaccaag | 1080 |
| aaccaggtgt ccctgagctg tgccgtcaag ggcttctacc ccagcgatat cgccgtggag | 1140 |
| tgggagagca acggccagcc tgagaacaac tacaagacca cccccctgt gctggacagc | 1200 |
| gacggcagct tcttcctggt gtccaaactg accgtggaca agagccggtg gcagcagggc | 1260 |
| aacgtgttca gctgcagcgt gatgcacgag gccctgcaca accactacac ccagaagtcc | 1320 |
| ctgagcctga gccccggcgg aggcggcgga agcggaggag gaggatccgg aggggaggga | 1380 |

| tctggcggag gcggcagcga ggtgcaattg ttggagtctg ggggaggctt ggtacagcct | 1440 |
| gggggtccc tgagactctc ctgtgcagcc tccggattca cctttagcag ttatgccatg | 1500 |
| agctgggtcc gccaggctcc agggaagggg ctggagtggg tctcagctat tagtggtagt | 1560 |
| ggtggtagca catactacgc agactccgtg aagggccggt tcaccatctc cagagacaat | 1620 |
| tccaagaaca cgctgtatct gcagatgaac agcctgagag ccgaggacac ggccgtatat | 1680 |
| tactgtgcga aaggggtgag ggtgtctttt gactactggg gccaaggaac cctggtcacc | 1740 |
| gtctcgagtg ctagcaccaa ggcccctcc gtgtttcctc tggcccccag cagcaagagc | 1800 |
| acctctggcg aacagccgc cctgggctgc ctggtgaaag actacttccc cgagcccgtg | 1860 |
| accgtgtcct ggaactctgg cgccctgacc agcggcgtgc acacctttcc agccgtgctg | 1920 |
| cagagcagcg gcctgtactc cctgagcagc gtggtgacag tgccctccag cagcctgggc | 1980 |
| acccagacct acatctgcaa cgtgaaccac aagcccagca caccaaagt ggacaagaag | 2040 |
| gtggaaccca agagctgcga c | 2061 |

<210> SEQ ID NO 248
<211> LENGTH: 2031
<212> TYPE: DNA
<213> ORGANISM: Artificial Sequence
<220> FEATURE:
<223> OTHER INFORMATION: DR5(5E11)_Fc knob Fab-Fab Head-to-tail 2+1
      pETR10662 DNA

<400> SEQUENCE: 248

| gaggtgcaat tgttggagtc tgggggaggc ttggtacagc ctgggggtc cctgagactc | 60 |
| tcctgtgcag cctccggatt cacctttagc agttatgcca tgagctgggt ccgccaggct | 120 |
| ccagggaagg gctggagtg gtctcagct attagtggta gtggtggtag cacatactac | 180 |
| gcagactccg tgaagggccg gttcaccatc tccagagaca attccaagaa cacgctgtat | 240 |
| ctgcagatga cagcctgag agccgaggac acggccgtat attactgtgc gaaaggggtg | 300 |
| agggtgtctt ttgactactg gggccaagga accctggtca ccgtctcgag tgctagcacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| ggaggcggag gatccggcgg aggcggatct gaggtgcaat gttggagtc tgggggaggc | 720 |
| ttggtacagc ctggggggtc cctgagactc tcctgtgcag cctccggatt cacctttagc | 780 |
| agttatgcca tgagctgggt ccgccaggct ccagggaagg gctggagtg gtctcagct | 840 |
| attagtggta gtggtggtag cacatactac gcagactccg tgaagggccg gttcaccatc | 900 |
| tccagagaca attccaagaa cacgctgtat ctgcagatga cagcctgag agccgaggac | 960 |
| acggccgtat attactgtgc gaaaggggtg agggtgtctt ttgactactg gggccaagga | 1020 |
| accctggtca ccgtctcgag tgctagcacc aaggcccaa gcgtgttccc tctggccccc | 1080 |
| agcagcaaga gcacaagcgg cggaacagcc gccctgggct gcctggtcaa ggactacttc | 1140 |
| cccgagcccg tgacagtgtc ctggaacagc ggagccctga ccagcggcgt gcacaccttt | 1200 |
| ccagccgtgc tgcagagcag cggcctgtac agcctgagca gcgtggtcac agtgcctagc | 1260 |
| agcagcctgg gcacccagac ctacatctgc aacgtgaacc acaagcccag caacaccaag | 1320 |

```
gtggacaaga aggtggagcc aagagctgc gacaagaccc acacctgtcc cccttgtcct    1380
gccctgagc tgctgggcgg acccagcgtg ttcctgttcc ccccaaagcc caaggacacc    1440
ctgatgatca gccggacccc cgaagtgacc tgcgtggtgg tggacgtgtc ccacgaggac   1500
cctgaagtga agttcaattg gtacgtggac ggcgtggaag tgcacaatgc caagaccaag   1560
ccgcgggagg agcagtacaa cagcacgtac cgtgtggtca gcgtcctcac cgtcctgcac   1620
caggactggc tgaatggcaa ggagtacaag tgcaaggtct ccaacaaagc cctcccagcc   1680
cccatcgaga aaaccatctc caaagccaaa gggcagcccc gagaaccaca ggtgtacacc   1740
ctgcccccat gccgggatga gctgaccaag aaccaggtca gcctgtggtg cctggtcaaa   1800
ggcttctatc ccagcgacat cgccgtggag tgggagagca atgggcagcc ggagaacaac   1860
tacaagacca cgcctcccgt gctggactcc gacggctcct tcttcctcta cagcaagctc   1920
accgtggaca agagcaggtg gcagcagggg aacgtcttct catgctccgt gatgcatgag   1980
gctctgcaca accactacac gcagaagagc ctctccctgt ctccgggtaa a           2031

<210> SEQ ID NO 249
<211> LENGTH: 1350
<212> TYPE: DNA
<213> ORGANISM: Artificial Sequence
<220> FEATURE:
<223> OTHER INFORMATION: FAP(28H1) _Fc hole VHCL Cross pETR10130 DNA

<400> SEQUENCE: 249
gaagtgcagc tgctggaatc cggcggaggc ctggtgcagc ctggcggatc tctgagactg     60
tcctgcgccg cctccggctt caccttctcc tcccacgcca tgtcctgggt ccgacaggct   120
cctggcaaag gctggaatg ggtgtccgcc atctgggcct ccggcgagca gtactacgcc   180
gactctgtga agggccggtt caccatctcc cgggacaact ccaagaacac cctgtacctg   240
cagatgaact ccctgcgggc cgaggacacc gccgtgtact actgtgccaa gggctggctg   300
ggcaacttcg actactgggg acagggcacc ctggtcaccg tgtccagcgc tagcgtggcc   360
gctcccagcg tgttcatctt cccacccagc gacgagcagc tgaagtccgg cacagccagc   420
gtggtgtgcc tgctgaacaa cttctacccc cgcgaggcca aggtgcagtg gaaggtggac   480
aacgccctgc agagcggcaa cagccaggaa tccgtgaccg agcaggacag caaggactcc   540
acctacagcc tgagcagcac cctgaccctg agcaaggccg actacgagaa gcacaaggtg   600
tacgcctgcg aagtgaccca ccagggcctg tccagccccg tgaccaagag cttcaaccgg   660
ggcgagtgcg acaagaccca cacctgtccc cttgccctg cccctgaact gctgggtggc   720
ccttccgtgt tcctgttccc cccaaagccc aaggacaccc tgatgatcag ccggaccccc   780
gaagtgacct gcgtggtggt cgatgtgtcc cacgaggacc ctgaagtgaa gttcaattgg   840
tacgtggacg gcgtggaggt gcacaatgcc aagaccaagc ccgggagga acagtacaac   900
agcacctacc gggtggtgtc cgtgctgacc gtgctgcacc aggactggct gaacggcaaa   960
gagtacaagt gcaaggtctc caacaaggcc ctgcctgccc ccatcgagaa aaccatcagc  1020
aaggccaagg gccagcccag agaacccag gtgtgcaccc tgcccccag cagagatgag   1080
ctgaccaaga accaggtgtc cctgagctgt gccgtcaagg gcttctaccc cagcgatatc  1140
gccgtggagt gggagagcaa cggccagcct gagaacaact acaagaccac cccccctgtg  1200
ctggacagcg acggcagctt cttcctggtg tccaaactga ccgtggacaa gagccggtgg  1260
cagcagggca acgtgttcag ctgcagcgtg atgcacgagg ccctgcacaa ccactacacc  1320
```

<210> SEQ ID NO 250
<211> LENGTH: 2073
<212> TYPE: DNA
<213> ORGANISM: Artificial Sequence
<220> FEATURE:
<223> OTHER INFORMATION: DR5(18F11)-FAP (28H1) Fc knob VHCL 2+1 pETR9807 DNA

<400> SEQUENCE: 250

```
cagaagtccc tgagcctgag ccccggcaag                                    1350
gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac gcggccgtat attactgtgc gaaaggggtg    300
cgtaagaagt ttgactactg gggccaagga accctggtca ccgtctcgag tgctagcacc    360
aagggcccaa gcgtgttccc tctggccccc agcagcaaga gcacaagcgg cggaacagcc    420
gccctgggct gcctggtcaa ggactacttc cccgagcccg tgacagtgtc ctggaacagc    480
ggagccctga ccagcggcgt gcacaccttt ccagccgtgc tgcagagcag cggcctgtac    540
agcctgagca gcgtggtcac agtgcctagc agcagcctgg gcacccagac ctacatctgc    600
aacgtgaacc acaagcccag caacaccaag gtggacaaga aggtggagcc caagagctgc    660
gacaagaccc acacctgtcc ccttgtcct gcccctgagc tgctgggcgg acccagcgtg    720
ttcctgttcc cccaaagcc caaggacacc ctgatgatca gccggacccc cgaagtgacc    780
tgcgtggtgg tggacgtgtc ccacgaggac cctgaagtga agttcaattg gtacgtggac    840
ggcgtggagg tgcacaatgc caagaccaag ccccgggagg aacagtacaa cagcacctac    900
cgggtggtgt ccgtgctgac cgtgctgcac caggactggc tgaacggcaa agagtacaag    960
tgcaaggtct ccaacaaggc cctgcctgcc cccatcgaga aaaccatcag caaggccaag   1020
ggccagccca gagaaccca ggtgtacacc ctgccccct gcagagatga gctgaccaag   1080
aaccaggtgt ccctgtggtg tctggtcaag ggcttctacc ccagcgatat cgccgtggag   1140
tgggagagca cggccagcc tgagaacaac tacaagacca ccccccctgt gctggacagc   1200
gacggcagct tcttcctgta ctccaaactg accgtggaca gagccggtg gcagcagggc   1260
aacgtgttca gctgcagcgt gatgcacgag gccctgcaca accactacac ccagaagtcc   1320
ctgagcctga gccccggcaa gtccggaggc ggcggaagcg aggaggagg atccggagga   1380
gggggaagtg gcggcggagg atctgaggtg cagctgctgg aatccggcgg aggcctggtg   1440
cagcctggcg gatctctgag actgtcctgc gccgcctccg gcttcacctt ctcctcccac   1500
gccatgtcct gggtccgaca ggctcctggc aaaggcctgg aatgggtgtc cgccatctgg   1560
gcctccggcg agcagtacta cgccgactct gtgaagggcc ggttcaccat ctcccgggac   1620
aactccaaga acaccctgta cctgcagatg aactccctgc gggccgagga caccgccgtg   1680
tactactgtg ccaagggctg gctgggcaac ttcgactact ggggccaggg caccctggtc   1740
accgtgtcca gcgctagcgt ggccgctccc agcgtgttca tcttcccacc cagcgacgag   1800
cagctgaagt ccggcacagc cagcgtggtg tgcctgctga caacttcta ccccgcgag   1860
gccaaggtgc agtggaaggt ggacaacgcc ctgcagagcg gcaacagcca ggaatccgtg   1920
accgagcagg acagcaagga ctccacctac agcctgagca gcaccctgac cctgagcaag   1980
```

```
gccgactacg agaagcacaa ggtgtacgcc tgcgaagtga cccaccaggg cctgtccagc    2040
cccgtgacca agagcttcaa ccggggcgag tgc                                2073

<210> SEQ ID NO 251
<211> LENGTH: 1341
<212> TYPE: DNA
<213> ORGANISM: Artificial Sequence
<220> FEATURE:
<223> OTHER INFORMATION: DR5(18F11) Fc hole pETR9808 DNA

<400> SEQUENCE: 251
gaggtgcaat tgttggagtc tgggggaggc ttggtacagc ctgggggtc cctgagactc    60 tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac gcggccgtat attactgtgc gaaaggggtg    300
cgtaagaagt ttgactactg gggccaagga accctggtca ccgtctcgag tgctagcacc    360
aagggcccaa gcgtgttccc tctggccccc agcagcaaga gcacaagcgg cggaacagcc    420
gccctgggct gcctggtcaa ggactacttc cccgagcccg tgacagtgtc ctggaacagc    480
ggagccctga ccagcggcgt gcacaccttt ccagccgtgc tgcagagcag cggcctgtac    540
agcctgagca gcgtggtcac agtgcctagc agcagcctgg gcacccagac ctacatctgc    600
aacgtgaacc acaagcccag caacaccaag gtggacaaga aggtggagcc caagagctgc    660
gacaagaccc acacctgtcc cccttgtcct gcccctgagc tgctgggcgg acccagcgtg    720
ttcctgttcc ccccaaagcc caaggacacc ctgatgatca gccggacccc cgaagtgacc    780
tgcgtggtgg tggacgtgtc ccacgaggac cctgaagtga agttcaattg gtacgtggac    840
ggcgtggagg tgcacaatgc caagaccaag ccccggggag aacagtacaa cagcacctac    900
cgggtggtgt ccgtgctgac cgtgctgcac caggactggc tgaacggcaa agagtacaag    960
tgcaaggtct ccaacaaggc cctgcctgcc cccatcgaga aaaccatcag caaggccaag    1020
ggccagccca gagaacccca ggtgtgcacc ctgcccccca gcagagatga gctgaccaag    1080
aaccaggtgt ccctgagctg tgccgtcaag ggcttctacc ccagcgatat cgccgtggag    1140
tgggagagca acggccagcc tgagaacaac tacaagacca cccccctgt gctggacagc    1200 gacggcagct tcttcctggt gtccaaactg accgtggaca agagccggtg gcagcagggc    1260
aacgtgttca gctgcagcgt gatgcacgag gccctgcaca accactacac ccagaagtcc    1320
ctgagcctga gccccggcaa g                                             1341

<210> SEQ ID NO 252
<211> LENGTH: 2067
<212> TYPE: DNA
<213> ORGANISM: Artificial Sequence
<220> FEATURE:
<223> OTHER INFORMATION: DR5(18F11)-FAP (28H1) VHCL Fcknob 3+1 pETR10333
      DNA

<400> SEQUENCE: 252
gaggtgcaat tgttggagtc tgggggaggc ttggtacagc ctgggggtc cctgagactc    60 tcctgtgcag cctccggatt cacctttagc agttatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
```

```
ctgcagatga acagcctgag agccgaggac gcggccgtat attactgtgc gaaaggggtg      300
cgtaagaagt ttgactactg gggccaagga accctggtca ccgtctcgag tgctagcacc      360
aagggcccaa gcgtgttccc tctggccccc agcagcaaga gcacaagcgg cggaacagcc      420
gccctgggct gcctggtcaa ggactacttc cccgagcccg tgacagtgtc ctggaacagc      480
ggagccctga ccagcggcgt gcacaccttt ccagccgtgc tgcagagcag cggcctgtac      540
agcctgagca gcgtggtcac agtgcctagc agcagcctgg gcacccagac ctacatctgc      600
aacgtgaacc acaagcccag caacaccaag gtggacaaga aggtggagcc caagagctgc      660
gacaagaccc acacctgtcc cccttgtcct gcccctgagc tgctgggcgg acccagcgtg      720
ttcctgttcc ccccaaagcc caaggacacc ctgatgatca gccggacccc cgaagtgacc      780
tgcgtggtgg tggacgtgtc ccacgaggac cctgaagtga agttcaattg gtacgtggac      840
ggcgtggagg tgcacaatgc caagaccaag ccccggggag aacagtacaa cagcacctac      900
cgggtggtgt ccgtgctgac cgtgctgcac caggactggc tgaacggcaa agagtacaag      960
tgcaaggtct ccaacaaggc cctgcctgcc cccatcgaga aaaccatcag caaggccaag     1020
ggccagccca gagaacccca ggtgtacacc ctgccccct gcagagatga gctgaccaag     1080
aaccaggtgt ccctgtggtg tctggtcaag ggcttctacc ccagcgatat cgccgtggag     1140
tgggagagca cggccagcc tgagaacaac tacaagacca cccccctgt gctggacagc     1200 gacggcagct cttcctgta ctccaaactg accgtggaca gagccggtg gcagcagggc     1260 aacgtgttca gctgcagcgt gatgcacgag gccctgcaca accactacac ccagaagtcc     1320
ctgagcctga gccccggcgg aggcggcgga agcggaggag gaggatccgg aggagggga     1380 agtggcggcg gaggatctga ggtgcagctg ctggaatccg gcggaggcct ggtgcagcct     1440
ggcggatctc tgagactgtc ctgcgccgcc tccggcttca ccttctcctc ccacgccatg     1500
tcctgggtcc gacaggctcc tggcaaaggc ctggaatggg tgtccgccat ctgggcctcc     1560
ggcgagcagt actacgccga ctctgtgaag ggccggttca ccatctcccg ggacaactcc     1620
aagaacaccc tgtacctgca gatgaactcc ctgcgggccg aggacaccgc cgtgtactac     1680
tgtgccaagg gctggctggg caacttcgac tactgggggcc agggcaccct ggtcaccgtg     1740
tccagcgcta gcgtggccgc tcccagcgtg ttcatcttcc cacccagcga cgagcagctg     1800
aagtccggca gccagccagt ggtgtgcctg ctgaacaact ctaccccccg cgaggccaag     1860
gtgcagtgga aggtggacaa cgccctgcag agcggcaaca gccaggaatc cgtgaccgag     1920
caggacagca aggactccac ctacagcctg agcagcaccc tgaccctgag caaggccgac     1980
tacgagaagc acaaggtgta cgcctgcgaa gtgacccacc agggcctgtc cagccccgtg     2040
accaagagct caaccggggg cgagtgc                                        2067
```

<210> SEQ ID NO 253
<211> LENGTH: 2061
<212> TYPE: DNA
<213> ORGANISM: Artificial Sequence
<220> FEATURE:
<223> OTHER INFORMATION: DR5(18F11)-DR5(18F11) Fc hole pETR10288 DNA

<400> SEQUENCE: 253

```
gaggtgcaat tgttggagtc tgggggaggc ttggtacagc ctggggggtc cctgagactc       60
tcctgtgcag cctccggatt caccttagc agttatgcca tgagctgggt ccgccaggct      120
ccagggaagg ggctggagtg ggtctcagct attagtggta gtggtggtag cacatactac      180
gcagactccg tgaagggccg gttcaccatc tccagagaca attccaagaa cacgctgtat      240
```

```
ctgcagatga acagcctgag agccgaggac gcggccgtat attactgtgc gaaaggggtg    300
cgtaagaagt ttgactactg gggccaagga accctggtca ccgtctcgag tgctagcacc    360
aagggcccaa gcgtgttccc tctggccccc agcagcaaga gcacaagcgg cggaacagcc    420
gccctgggct gcctggtcaa ggactacttc cccgagcccg tgacagtgtc ctggaacagc    480
ggagccctga ccagcggcgt gcacaccttt ccagccgtgc tgcagagcag cggcctgtac    540
agcctgagca gcgtggtcac agtgcctagc agcagcctgg gcacccagac ctacatctgc    600
aacgtgaacc acaagcccag caacaccaag gtggacaaga aggtggagcc caagagctgc    660
gacaagaccc acacctgtcc cccttgtcct gcccctgagc tgctgggcgg acccagcgtg    720
ttcctgttcc ccccaaagcc caaggacacc ctgatgatca gccggacccc cgaagtgacc    780
tgcgtggtgg tggacgtgtc ccacgaggac cctgaagtga agttcaattg gtacgtggac    840
ggcgtggagg tgcacaatgc caagaccaag ccccggggagg aacagtacaa cagcacctac    900
cgggtggtgt ccgtgctgac cgtgctgcac caggactggc tgaacggcaa agagtacaag    960
tgcaaggtct ccaacaaggc cctgcctgcc cccatcgaga aaaccatcag caaggccaag   1020
ggccagccca gagaaccccca ggtgtgcacc ctgcccccca gcagagatga gctgaccaag   1080
aaccaggtgt ccctgagctg tgccgtcaag ggcttctacc ccagcgatat cgccgtggag   1140
tgggagagca cgccagcc tgagaacaac tacaagacca cccccctgt gctggacagc   1200 gacggcagct tcttcctggt gtccaaactg accgtggaca agagccggtg gcagcagggc   1260
aacgtgttca gctgcagcgt gatgcacgag gccctgcaca accactacac ccagaagtcc   1320
ctgagcctga gccccggcgg aggcggcgga agcggaggag gaggatccgg aggggagga   1380 tctggcggag gcggcagcga ggtgcaattg ttggagtctg ggggaggctt ggtacagcct   1440
ggggggtccc tgagactctc ctgtgcagcc tccggattca cctttagcag ttatgccatg   1500
agctgggtcc gccaggctcc agggaagggg ctggagtggg tctcagctat tagtggtagt    1560
ggtggtagca catactacgc agactccgtg aagggccggt tcaccatctc cagagacaat   1620
tccaagaaca cgctgtatct gcagatgaac agcctgagag ccgaggacgc ggccgtatat   1680
tactgtgcga aggggtgcg taagaagttt gactactggg gccaaggaac cctggtcacc   1740
gtctcgagtg ctagcaccaa gggcccctcc gtgtttcctc tggcccccag cagcaagagc   1800
acctctggcg aacagccgc cctgggctgc ctggtgaaag actacttccc cgagcccgtg   1860
accgtgtcct ggaactctgg cgccctgacc agcggcgtgc acacctttcc agccgtgctg   1920
cagagcagcg gcctgtactc cctgagcagc gtggtgacag tgccctccag cagcctgggc   1980
acccagacct acatctgcaa cgtgaaccac aagcccagca acaccaaagt ggacaagaag   2040
gtggaaccca gagctgcga c                                               2061

<210> SEQ ID NO 254
<211> LENGTH: 990
<212> TYPE: DNA
<213> ORGANISM: Artificial Sequence
<220> FEATURE:
<223> OTHER INFORMATION: hu Fc _wt DNA

<400> SEQUENCE: 254
gctagcacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
```

```
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcggaggga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag gcagccccg agaaccacag gtgtacaccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa                                       990
```

<210> SEQ ID NO 255
<211> LENGTH: 990
<212> TYPE: DNA
<213> ORGANISM: Artificial Sequence
<220> FEATURE:
<223> OTHER INFORMATION: hu Fc_P329G/LALA DNA

<400> SEQUENCE: 255

```
gctagcacca agggcccatc cgtgttccct ctggcccctt ccagcaagtc tacctctggc       60
ggcacagccg ctctgggctg cctcgtgaag gactacttcc ccgagcctgt gacagtgtcc      120
tggaactctg gcgccctgac atccggcgtg cacacctttc cagctgtgct gcagtcctcc      180
ggcctgtact ccctgtcctc cgtcgtgaca gtgccctcca gctctctggg cacccagacc      240
tacatctgca acgtgaacca caagccctcc aacaccaagg tggacaagaa ggtggaaccc      300
aagtcctgcg acaagaccca cacctgtccc ccttgtcctg cccctgaagc tgctggcggc      360
cctagcgtgt tcctgttccc cccaaagccc aaggacaccc tgatgatctc ccggaccccc      420
gaagtgacct gcgtggtggt ggatgtgtcc cacgaggacc ctgaagtgaa gttcaattgg      480
tacgtggacg gcgtggaagt gcacaatgcc aagaccaagc ctagagagga acagtacaac      540
tccacctacc gggtggtgtc cgtgctgacc gtgctgcacc aggattggct gaacggcaaa      600
gagtacaagt gcaaggtgtc caacaaggcc ctgggagccc ccatcgaaaa gaccatctcc      660
aaggccaagg gccagcctcg cgagcctcag gtgtacaccc tgcccctag cagagatgag      720 ctgaccaaga accaggtgtc cctgacctgt ctcgtgaaag gcttctaccc ctccgatatc      780
gccgtggaat gggagagcaa cggccagccc gagaacaact acaagaccac ccccctgtg      840 ctggactccg acggctcatt cttcctgtac tctaagctga cagtggacaa gtcccggtgg      900
cagcagggca acgtgttctc ctgctccgtg atgcacgagg ccctgcacaa ccactacacc      960
cagaagtccc tgtccctgtc tcccgggaaa                                       990
```

<210> SEQ ID NO 256
<211> LENGTH: 321
<212> TYPE: DNA
<213> ORGANISM: Artificial Sequence
<220> FEATURE:
<223> OTHER INFORMATION: hu kappa light chain DNA

<400> SEQUENCE: 256

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                              321
```

<210> SEQ ID NO 257
<211> LENGTH: 318
<212> TYPE: DNA
<213> ORGANISM: Artificial Sequence
<220> FEATURE:
<223> OTHER INFORMATION: hu lambda light chain DNA

<400> SEQUENCE: 257

```
ggtcagccca agccgccccc tagcgtgacc ctgttccccc caagcagcga ggaactgcag    60
gccaacaagg ccaccctggt gtgcctgatc agcgacttct accctggcgc cgtgacagtg   120
gcctggaagg ccgactctag ccctgtgaag gccggcgtgg agacaaccac ccccagcaag   180
cagagcaaca caagtacgc cgccagcagc tacctgagcc tgaccccga gcagtggaag   240
tcccaccggt cctacagctg ccaggtgaca cacgagggca gcaccgtgga gaaaaccgtg   300
gcccccaccg agtgcagc                                                  318
```

<210> SEQ ID NO 258
<211> LENGTH: 1350
<212> TYPE: DNA
<213> ORGANISM: Artificial Sequence
<220> FEATURE:
<223> OTHER INFORMATION: 28H1_Fc hole VHCL pETR10130 DNA

<400> SEQUENCE: 258

```
gaagtgcagc tgctggaatc cggcggaggc ctggtgcagc ctggcggatc tctgagactg    60
tcctgcgccg cctccggctt caccttctcc tcccacgcca tgtcctgggt ccgacaggct   120
cctggcaaag gcctggaatg ggtgtccgca atctgggcct ccggcgagca gtactacgcc   180
gactctgtga agggccggtt caccatctcc cgggacaact ccaagaacac cctgtacctg   240
cagatgaact ccctgcgggc cgaggacacc gccgtgtact actgtgccaa gggctggctg   300
ggcaacttcg actactgggg acagggcacc ctggtcaccg tgtccagcgc tagcgtggcc   360
gctcccagcg tgttcatctt cccacccagc gacgagcagc tgaagtccgg cacagccagc   420
gtggtgtgcc tgctgaacaa cttctacccc cgcgaggcca aggtgcagtg gaaggtggac   480
aacgccctgc agagcggcaa cagccaggaa tccgtgaccg agcaggacag caaggactcc   540
acctacagcc tgagcagcac cctgaccctg agcaaggccg actacgagaa gcacaaggtg   600
tacgcctgcg aagtgaccca ccagggcctg tccagccccg tgaccaagag cttcaaccgg   660
ggcgagtgcg acaagaccca cacctgtccc ccttgccctg ccctgaact gctgggtggc   720
ccttccgtgt tcctgttccc cccaaagccc aaggacaccc tgatgatcag ccggaccccc   780
gaagtgacct gcgtggtggt cgatgtgtcc cacgaggacc ctgaagtgaa gttcaattgg   840
tacgtggacg gcgtggaggt gcacaatgcc aagaccaagc ccggagga acagtacaac   900
agcacctacc gggtggtgtc cgtgctgacc gtgctgcacc aggactggct gaacggcaaa   960
```

```
gagtacaagt gcaaggtctc caacaaggcc ctgcctgccc ccatcgagaa aaccatcagc    1020
aaggccaagg gccagcccag agaacccag gtgtgcaccc tgcccccag cagagatgag     1080 ctgaccaaga accaggtgtc cctgagctgt gccgtcaagg gcttctaccc cagcgatatc   1140
gccgtggagt gggagagcaa cggccagcct gagaacaact acaagaccac ccccctgtg    1200 ctggacagcg acggcagctt cttcctggtg tccaaactga ccgtggacaa gagccggtgg   1260
cagcagggca acgtgttcag ctgcagcgtg atgcacgagg ccctgcacaa ccactacacc   1320
cagaagtccc tgagcctgag ccccggcaag                                   1350
```

<210> SEQ ID NO 259
<211> LENGTH: 642
<212> TYPE: DNA
<213> ORGANISM: Artificial Sequence
<220> FEATURE:
<223> OTHER INFORMATION: 28H1VLCH1pETR9537 DNA

<400> SEQUENCE: 259

```
gagatcgtgc tgacccagtc tcccggcacc ctgagcctga gccctggcga gagagccacc     60
ctgagctgca gagccagcca gagcgtgagc cggagctacc tggcctggta tcagcagaag    120
cccggccagg cccccagact gctgatcatc ggcgccagca cccgggccac cggcatcccc    180
gatagattca gcggcagcgg ctccggcacc gacttcaccc tgaccatcag ccggctggaa    240
cccgaggact tcgccgtgta ctactgccag cagggccagg tgatcccccc caccttcggc    300
cagggcacca aggtggaaat caagagctcc gctagcacca agggcccctc cgtgttccct    360
ctggccccca gcagcaagag cacctctggc ggaacagccg ccctgggctg cctggtgaaa    420
gactacttcc ccgagcccgt gaccgtgtcc tggaactctg gcgccctgac cagcggcgtg    480
cacacctttc cagccgtgct gcagagcagc ggcctgtact ccctgagcag cgtggtgaca    540
gtgccctcca gcagcctggg cacccagacc tacatctgca acgtgaacca caagcccagc    600
aacaccaaag tggacaagaa ggtggaaccc aagagctgcg ac                       642
```

<210> SEQ ID NO 260
<211> LENGTH: 2070
<212> TYPE: DNA
<213> ORGANISM: Artificial Sequence
<220> FEATURE:
<223> OTHER INFORMATION: 5E11_4B9 VHCL pETR11060 DNA

<400> SEQUENCE: 260

```
gaggtgcaat gttggagtc tgggggaggc ttggtacagc ctggggggtc cctgagactc      60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggggtg    300
agggtgtctt ttgactactg gggccaagga accctggtca ccgtctcgag tgctagcacc    360
aagggcccaa gcgtgttccc tctggccccc agcagcaaga gcacaagcgg cggaacagcc    420
gccctgggct gcctggtcaa ggactacttc cccgagcccg tgacagtgtc ctggaacagc    480
ggagccctga ccagcggcgt gcacaccttt ccagccgtgc tgcagagcag cggcctgtac    540
agcctgagca gcgtggtcac agtgcctagc agcagcctgg gcacccagac ctacatctgc    600
aacgtgaacc acaagcccag caacaccaag gtggacaaga aggtggagcc caagagctgc    660
gacaagaccc acacctgtcc cccttgtcct gcccctgagc tgctgggcgg acccagcgtg    720
```

```
ttcctgttcc ccccaaagcc caaggacacc ctgatgatca gccggacccc cgaagtgacc        780
tgcgtggtgg tggacgtgtc ccacgaggac cctgaagtga agttcaattg gtacgtggac        840
ggcgtggagg tgcacaatgc caagaccaag ccccgggagg aacagtacaa cagcacctac        900
cgggtggtgt ccgtgctgac cgtgctgcac caggactggc tgaacggcaa agagtacaag        960
tgcaaggtct ccaacaaggc cctgcctgcc cccatcgaga aaccatcag caaggccaag        1020 ggccagccca gagaacccca ggtgtacacc ctgcccccta gcagagatga gctgaccaag       1080
aaccaggtgt ccctgacctg tctcgtgaaa ggcttctacc cctccgatat cgccgtggaa       1140
tgggagagca acggccagcc cgagaacaac tacaagacca cccccctgt gctggactcc        1200 gacggctcat tcttcctgta ctctaagctg acagtggaca gtcccggtg cagcagggc         1260 aacgtgttct cctgctccgt gatgcacgag gccctgcaca accactacac ccagaagtcc       1320
ctgtccctgt ctcccggggg aggcggagga tctggcggag gcggatccgg aggaggggga       1380
agtggcggcg gaggatctga ggtgcaattg ttggagtctg ggggaggctt ggtacagcct       1440
ggggggtccc tgagactctc ctgtgcagcc tctggattca cctttagcag ttatgctatg       1500
agctgggtcc gccaggctcc agggaagggg ctggagtggg tctcagctat tattggtagt       1560
ggtgccagca catactacgc agactccgtg aagggccggt tcaccatctc cagagacaat       1620
tccaagaaca cgctgtatct gcagatgaac agcctgagag ccgaggacac ggccgtatat       1680
tactgtgcga aagggtggtt tggtggttttt aactactggg gccaaggaac cctggtcacc     1740
gtctcgagtg ctagcgtggc cgctcccagc gtgttcatct cccacccag cgacgagcag       1800 ctgaagtccg gcacagccag cgtggtgtgc ctgctgaaca acttctaccc ccgcgaggcc       1860
aaggtgcagt ggaaggtgga caacgccctg cagagcggca acagccagga atccgtgacc       1920
gagcaggaca gcaaggactc cacctacagc ctgagcagca ccctgaccct gagcaaggcc       1980
gactacgaga gcacaaggt gtacgcctgc gaagtgaccc accagggcct gtccagcccc       2040
gtgaccaaga gcttcaaccg gggcgagtgc                                        2070
```

<210> SEQ ID NO 261
<211> LENGTH: 642
<212> TYPE: DNA
<213> ORGANISM: Artificial Sequence
<220> FEATURE:
<223> OTHER INFORMATION: 4B9_VLCH1_pETR10020 DNA

<400> SEQUENCE: 261

```
gagatcgtgc tgacccagtc ccccggcacc ctgtctctga gccctggcga gagagccacc        60
ctgtcctgca gagcctccca gtccgtgacc tcctcctacc tcgcctggta tcagcagaag       120
cccggccagg cccctcggct gctgatcaac gtgggcagtc ggagagccac cggcatccct       180
gaccggttct ccggctctgg ctccggcacc gacttcaccc tgaccatctc ccggctggaa       240
cccgaggact tcgccgtgta ctactgccag cagggcatca tgctgccccc cacctttggc       300
cagggcacca aggtggaaat caagagctcc gctagcacca agggcccctc cgtgtttcct       360
ctggccccca gcagcaagag cacctctggc ggaacagccg ccctgggctg cctggtgaaa       420
gactacttcc ccgagcccgt gaccgtgtcc tggaactctg gcgccctgac cagcggcgtg       480
cacacctttc cagccgtgct gcagagcagc ggcctgtact ccctgagcag cgtggtgaca       540
gtgccctcca gcagctggg cacccagacc tacatctgca acgtgaacca caagcccagc       600
aacaccaaag tggacaagaa ggtggaaccc aagagctgcg ac                          642
```

<210> SEQ ID NO 262
<211> LENGTH: 690
<212> TYPE: PRT
<213> ORGANISM: Artificial Sequence
<220> FEATURE:
<223> OTHER INFORMATION: DR5 (5E11)__FAP(4B9)VHCL_pETR11060

<400> SEQUENCE: 262

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
        435                 440                 445
Gly Gly Ser Gly Gly Gly Ser Gly Gly Gly Ser Gly Gly Gly
450                 455                 460
Gly Ser Glu Val Gln Leu Leu Glu Ser Gly Gly Gly Leu Val Gln Pro
465                 470                 475                 480
Gly Gly Ser Leu Arg Leu Ser Cys Ala Ala Ser Gly Phe Thr Phe Ser
                485                 490                 495
Ser Tyr Ala Met Ser Trp Val Arg Gln Ala Pro Gly Lys Gly Leu Glu
            500                 505                 510
Trp Val Ser Ala Ile Ile Gly Ser Gly Ala Ser Thr Tyr Tyr Ala Asp
        515                 520                 525
Ser Val Lys Gly Arg Phe Thr Ile Ser Arg Asp Asn Ser Lys Asn Thr
530                 535                 540
Leu Tyr Leu Gln Met Asn Ser Leu Arg Ala Glu Asp Thr Ala Val Tyr
545                 550                 555                 560
Tyr Cys Ala Lys Gly Trp Phe Gly Gly Phe Asn Tyr Trp Gly Gln Gly
                565                 570                 575
Thr Leu Val Thr Val Ser Ser Ala Ser Val Ala Ala Pro Ser Val Phe
            580                 585                 590
Ile Phe Pro Pro Ser Asp Glu Gln Leu Lys Ser Gly Thr Ala Ser Val
        595                 600                 605
Val Cys Leu Leu Asn Asn Phe Tyr Pro Arg Glu Ala Lys Val Gln Trp
610                 615                 620
Lys Val Asp Asn Ala Leu Gln Ser Gly Asn Ser Gln Glu Ser Val Thr
625                 630                 635                 640
Glu Gln Asp Ser Lys Asp Ser Thr Tyr Ser Leu Ser Ser Thr Leu Thr
                645                 650                 655
Leu Ser Lys Ala Asp Tyr Glu Lys His Lys Val Tyr Ala Cys Glu Val
            660                 665                 670
Thr His Gln Gly Leu Ser Ser Pro Val Thr Lys Ser Phe Asn Arg Gly
        675                 680                 685
Glu Cys
    690

<210> SEQ ID NO 263
<211> LENGTH: 214
<212> TYPE: PRT
<213> ORGANISM: Artificial Sequence
<220> FEATURE:
<223> OTHER INFORMATION: FAP(4B9)_VLCH1_pETR10020

<400> SEQUENCE: 263

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
            35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys Ser Ser Ala Ser
                100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
                180                 185                 190

Cys Asn Val Asn His Lys Pro Ser Asn Thr Lys Val Asp Lys Lys Val
            195                 200                 205

Glu Pro Lys Ser Cys Asp
    210

<210> SEQ ID NO 264
<211> LENGTH: 1341
<212> TYPE: DNA
<213> ORGANISM: Artificial Sequence
<220> FEATURE:
<223> OTHER INFORMATION: 5E11-Fc knob DNA

<400> SEQUENCE: 264

```
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaaggggtg     300
agggtgtctt ttgactactg gggccaagga accctggtca ccgtctcgag tgctagcacc     360
aagggcccaa gcgtgttccc tctggccccc agcagcaaga gcacaagcgg cggaacagcc     420
gccctgggct gcctggtcaa ggactacttc cccgagcccg tgacagtgtc ctggaacagc     480
ggagccctga ccagcggcgt gcacaccttt ccagccgtgc tgcagagcag cggcctgtac     540
agcctgagca gcgtggtcac agtgcctagc agcagcctgg gcacccagac ctacatctgc     600
aacgtgaacc acaagcccag caacaccaag gtggacaaga aggtggagcc caagagctgc     660
gacaagaccc acacctgtcc ccttgtcct gccctgagc tgctgggcgg acccagcgtg     720
ttcctgttcc cccaaagcc aaggacacc ctgatgatca gccggacccc cgaagtgacc     780
tgcgtggtgg tggacgtgtc ccacgaggac cctgaagtga agttcaattg gtacgtggac     840
ggcgtggaag tgcacaatgc caagaccaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
```

```
gggcagcccc gagaaccaca ggtgtacacc ctgcccccat gccgggatga gctgaccaag    1080
aaccaggtca gcctgtggtg cctggtcaaa ggcttctatc ccagcgacat cgccgtggaa    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 265
<211> LENGTH: 645
<212> TYPE: DNA
<213> ORGANISM: Artificial Sequence
<220> FEATURE:
<223> OTHER INFORMATION: 5E11_LC pETR9044 DNA

<400> SEQUENCE: 265

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagggtacta ctcatcccat acgttcggc      300 caggggacca agtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt                     645
```

<210> SEQ ID NO 266
<211> LENGTH: 9
<212> TYPE: PRT
<213> ORGANISM: Artificial Sequence
<220> FEATURE:
<223> OTHER INFORMATION: DR5 (1B12)_CDR H3

<400> SEQUENCE: 266

Gly Phe Gly Tyr Trp Tyr Met Asp Tyr
1               5

<210> SEQ ID NO 267
<211> LENGTH: 8
<212> TYPE: PRT
<213> ORGANISM: Artificial Sequence
<220> FEATURE:
<223> OTHER INFORMATION: DR5 (1B12)_CDR L3

<400> SEQUENCE: 267

Gln Gln Ser Gly Arg Arg Gln Thr
1               5

<210> SEQ ID NO 268
<211> LENGTH: 9
<212> TYPE: PRT
<213> ORGANISM: Artificial Sequence
<220> FEATURE:
<223> OTHER INFORMATION: DR5 (19C12)_CDR H3

<400> SEQUENCE: 268

Ser Ile Phe Tyr Ser Thr Leu Asp Tyr
1               5

<210> SEQ ID NO 269
<211> LENGTH: 8
<212> TYPE: PRT
<213> ORGANISM: Artificial Sequence
<220> FEATURE:
<223> OTHER INFORMATION: DR5 (19C12)_CDR L3

<400> SEQUENCE: 269

Gln Gln Gln Gly Trp Phe Gln Thr
1               5

<210> SEQ ID NO 270
<211> LENGTH: 9
<212> TYPE: PRT
<213> ORGANISM: Artificial Sequence
<220> FEATURE:
<223> OTHER INFORMATION: DR5 (19D6)_CDR H3

<400> SEQUENCE: 270

Val Leu Gly Tyr Ala Ser Tyr Asp Tyr
1               5

<210> SEQ ID NO 271
<211> LENGTH: 8
<212> TYPE: PRT
<213> ORGANISM: Artificial Sequence
<220> FEATURE:
<223> OTHER INFORMATION: DR5 (19D6)_CDR L3

<400> SEQUENCE: 271

Gln Gln Gln Gly Trp Ser Thr Thr
1               5

<210> SEQ ID NO 272
<211> LENGTH: 8
<212> TYPE: PRT
<213> ORGANISM: Artificial Sequence
<220> FEATURE:
<223> OTHER INFORMATION: DR5 (20E3)_CDR H3

<400> SEQUENCE: 272

Gly Thr Arg Arg Gly Phe Asp Tyr
1               5

<210> SEQ ID NO 273
<211> LENGTH: 9
<212> TYPE: PRT
<213> ORGANISM: Artificial Sequence
<220> FEATURE:
<223> OTHER INFORMATION: DR5 (20E3)_CDR L3

<400> SEQUENCE: 273

Gln Gln Gly Glu Leu Thr Pro Val Thr
1               5

<210> SEQ ID NO 274
<211> LENGTH: 681
<212> TYPE: PRT
<213> ORGANISM: Artificial Sequence
<220> FEATURE:
<223> OTHER INFORMATION: 118265E11 (VLCL)-Fc-28H1 (VHCH1)

<400> SEQUENCE: 274

-continued

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Thr Thr His Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415
```

```
Val Phe Ser Cys Ser Val Met His Glu Ala Leu His Asn His Tyr Thr
            420                 425                 430

Gln Lys Ser Leu Ser Leu Ser Pro Gly Gly Gly Gly Ser Gly Gly
        435                 440                 445

Gly Gly Ser Gly Gly Gly Ser Gly Gly Gly Ser Glu Val Gln
    450                 455                 460

Leu Leu Glu Ser Gly Gly Gly Leu Val Gln Pro Gly Gly Ser Leu Arg
465                 470                 475                 480

Leu Ser Cys Ala Ala Ser Gly Phe Thr Phe Ser Ser His Ala Met Ser
                485                 490                 495

Trp Val Arg Gln Ala Pro Gly Lys Gly Leu Glu Trp Val Ser Ala Ile
            500                 505                 510

Trp Ala Ser Gly Glu Gln Tyr Tyr Ala Asp Ser Val Lys Gly Arg Phe
            515                 520                 525

Thr Ile Ser Arg Asp Asn Ser Lys Asn Thr Leu Tyr Leu Gln Met Asn
            530                 535                 540

Ser Leu Arg Ala Glu Asp Thr Ala Val Tyr Tyr Cys Ala Lys Gly Trp
545                 550                 555                 560

Leu Gly Asn Phe Asp Tyr Trp Gly Gln Gly Thr Leu Val Thr Val Ser
                565                 570                 575

Ser Ala Ser Thr Lys Gly Pro Ser Val Phe Pro Leu Ala Pro Ser Ser
            580                 585                 590

Lys Ser Thr Ser Gly Gly Thr Ala Ala Leu Gly Cys Leu Val Lys Asp
            595                 600                 605

Tyr Phe Pro Glu Pro Val Thr Val Ser Trp Asn Ser Gly Ala Leu Thr
610                 615                 620

Ser Gly Val His Thr Phe Pro Ala Val Leu Gln Ser Ser Gly Leu Tyr
625                 630                 635                 640

Ser Leu Ser Ser Val Val Thr Val Pro Ser Ser Ser Leu Gly Thr Gln
                645                 650                 655

Thr Tyr Ile Cys Asn Val Asn His Lys Pro Ser Asn Thr Lys Val Asp
                660                 665                 670

Lys Lys Val Glu Pro Lys Ser Cys Asp
            675                 680

<210> SEQ ID NO 275
<211> LENGTH: 221
<212> TYPE: PRT
<213> ORGANISM: Artificial Sequence
<220> FEATURE:
<223> OTHER INFORMATION: 11478_5E11 VHCH1

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp
    210                 215                 220

<210> SEQ ID NO 276
<211> LENGTH: 681
<212> TYPE: PRT
<213> ORGANISM: Artificial Sequence
<220> FEATURE:
<223> OTHER INFORMATION: 11829 5E11-28H1 VHCH1

<400> SEQUENCE: 276

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

-continued

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
        260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Gly Ser Gly Gly Gly Gly Ser Gly Gly Gly
450                 455                 460

Gly Ser Glu Ile Val Leu Thr Gln Ser Pro Gly Thr Leu Ser Leu Ser
465                 470                 475                 480

Pro Gly Glu Arg Ala Thr Leu Ser Cys Arg Ala Ser Gln Ser Val Ser
                485                 490                 495

Arg Ser Tyr Leu Ala Trp Tyr Gln Gln Lys Pro Gly Gln Ala Pro Arg
        500                 505                 510

Leu Leu Ile Ile Gly Ala Ser Thr Arg Ala Thr Gly Ile Pro Asp Arg
        515                 520                 525

Phe Ser Gly Ser Gly Ser Gly Thr Asp Phe Thr Leu Thr Ile Ser Arg
        530                 535                 540

Leu Glu Pro Glu Asp Phe Ala Val Tyr Tyr Cys Gln Gln Gly Gln Val
545                 550                 555                 560

Ile Pro Pro Thr Phe Gly Gln Gly Thr Lys Val Glu Ile Lys Arg Thr
                565                 570                 575

Val Ala Ala Pro Ser Val Phe Ile Phe Pro Pro Ser Asp Glu Gln Leu
            580                 585                 590

Lys Ser Gly Thr Ala Ser Val Val Cys Leu Leu Asn Asn Phe Tyr Pro
        595                 600                 605

Arg Glu Ala Lys Val Gln Trp Lys Val Asp Asn Ala Leu Gln Ser Gly
    610                 615                 620

Asn Ser Gln Glu Ser Val Thr Glu Gln Asp Ser Lys Asp Ser Thr Tyr
625                 630                 635                 640

Ser Leu Ser Ser Thr Leu Thr Leu Ser Lys Ala Asp Tyr Glu Lys His
                645                 650                 655

Lys Val Tyr Ala Cys Glu Val Thr His Gln Gly Leu Ser Ser Pro Val

```
                     660                 665                 670
Thr Lys Ser Phe Asn Arg Gly Glu Cys
        675                 680

<210> SEQ ID NO 277
<211> LENGTH: 220
<212> TYPE: PRT
<213> ORGANISM: Artificial Sequence
<220> FEATURE:
<223> OTHER INFORMATION: 11830 28H1 VHCH1

<400> SEQUENCE: 277

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp
    210                 215                 220

<210> SEQ ID NO 278
<211> LENGTH: 680
<212> TYPE: PRT
<213> ORGANISM: Artificial Sequence
<220> FEATURE:
<223> OTHER INFORMATION: 12207 5E11-28H1 (VLCH1)

<400> SEQUENCE: 278

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Val Arg Val Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
        435                 440                 445

Gly Gly Ser Gly Gly Gly Gly Ser Gly Gly Gly Gly Ser Gly Gly Gly
    450                 455                 460

Gly Ser Glu Ile Val Leu Thr Gln Ser Pro Gly Thr Leu Ser Leu Ser
465                 470                 475                 480

Pro Gly Glu Arg Ala Thr Leu Ser Cys Arg Ala Ser Gln Ser Val Ser
```

```
                        485                 490                 495
Arg Ser Tyr Leu Ala Trp Tyr Gln Gln Lys Pro Gly Gln Ala Pro Arg
                500                 505                 510

Leu Leu Ile Ile Gly Ala Ser Thr Arg Ala Thr Gly Ile Pro Asp Arg
            515                 520                 525

Phe Ser Gly Ser Gly Ser Gly Thr Asp Phe Thr Leu Thr Ile Ser Arg
        530                 535                 540

Leu Glu Pro Glu Asp Phe Ala Val Tyr Tyr Cys Gln Gln Gly Gln Val
545                 550                 555                 560

Ile Pro Pro Thr Phe Gly Gln Gly Thr Lys Val Glu Ile Lys Ser Ser
                565                 570                 575

Ala Ser Thr Lys Gly Pro Ser Val Phe Pro Leu Ala Pro Ser Ser Lys
                580                 585                 590

Ser Thr Ser Gly Gly Thr Ala Ala Leu Gly Cys Leu Val Lys Asp Tyr
            595                 600                 605

Phe Pro Glu Pro Val Thr Val Ser Trp Asn Ser Gly Ala Leu Thr Ser
        610                 615                 620

Gly Val His Thr Phe Pro Ala Val Leu Gln Ser Ser Gly Leu Tyr Ser
625                 630                 635                 640

Leu Ser Ser Val Val Thr Val Pro Ser Ser Ser Leu Gly Thr Gln Thr
                645                 650                 655

Tyr Ile Cys Asn Val Asn His Lys Pro Ser Asn Thr Lys Val Asp Lys
                660                 665                 670

Lys Val Glu Pro Lys Ser Cys Asp
            675                 680

<210> SEQ ID NO 279
<211> LENGTH: 223
<212> TYPE: PRT
<213> ORGANISM: Artificial Sequence
<220> FEATURE:
<223> OTHER INFORMATION: 12152 28H1 (VHCL)

<400> SEQUENCE: 279

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Leu Gly Asn Phe Asp Tyr Trp Gly Gln Gly Thr Leu Val
            100                 105                 110

Thr Val Ser Ser Ala Ser Val Ala Ala Pro Ser Val Phe Ile Phe Pro
        115                 120                 125

Pro Ser Asp Glu Gln Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
```

```
                165                 170                 175
Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
    210                 215                 220

<210> SEQ ID NO 280
<211> LENGTH: 218
<212> TYPE: PRT
<213> ORGANISM: Artificial Sequence
<220> FEATURE:
<223> OTHER INFORMATION: Construct DR5TAA-0061  (1+1 chimeric Crossmab
      containing 4B9 and DR5TAA-0011) LC (DR5)

<400> SEQUENCE: 280

Ala Asp Ile Val Met Thr Gln Thr Pro Ala Ser Val Ser Glu Pro Val
1               5                   10                  15

Gly Gly Thr Val Thr Ile Lys Cys Gln Ala Ser Gln Ser Ile Ser Thr
            20                  25                  30

Tyr Leu Ser Trp Tyr Gln Gln Lys Pro Gly Gln Pro Pro Lys Arg Leu
        35                  40                  45

Ile Tyr Lys Ala Ser Thr Leu Ala Ser Gly Val Pro Ser Arg Phe Lys
    50                  55                  60

Gly Ser Gly Ser Gly Thr Asp Phe Thr Leu Thr Ile Arg Asp Leu Glu
65                  70                  75                  80

Cys Ala Asp Ala Ala Thr Tyr Tyr Cys Gln Pro Asn Ser Gly Ile Ala
                85                  90                  95

Thr Tyr Gly Ala Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 281
<211> LENGTH: 214
<212> TYPE: PRT
<213> ORGANISM: Artificial Sequence
<220> FEATURE:
<223> OTHER INFORMATION: Construct DR5TAA-0061  (1+1 chimeric Crossmab
      containing 4B9 and DR5TAA-0011) Crossed LC (FAP)

<400> SEQUENCE: 281

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
```

```
                20                  25                  30
Tyr Leu Ala Trp Tyr Gln Gln Lys Pro Gly Gln Ala Pro Arg Leu Leu
             35                  40                  45

Ile Asn Val Gly Ser Arg Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Ile Met Leu Pro
                 85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp
    210
```

<210> SEQ ID NO 282
<211> LENGTH: 444
<212> TYPE: PRT
<213> ORGANISM: Artificial Sequence
<220> FEATURE:
<223> OTHER INFORMATION: Construct DR5TAA-0061  (1+1 chimeric Crossmab
      containing 4B9 and DR5TAA-0011) HC (DR5)

<400> SEQUENCE: 282

```
Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Ile Ser Arg Tyr Ala
             20                  25                  30

Met Ile Trp Val Arg Gln Ala Pro Gly Glu Gly Leu Glu Tyr Ile Gly
         35                  40                  45

Phe Ile Thr Ser Asp Ser Ser Ala Tyr Tyr Ala Ser Trp Ala Lys Gly
 50                  55                  60

Arg Phe Thr Ile Ser Lys Thr Ser Thr Thr Val Asp Leu Lys Met Thr
 65                  70                  75                  80

Ser Pro Thr Thr Glu Asp Thr Ala Thr Tyr Phe Cys Ala Arg Tyr Thr
                 85                  90                  95

Tyr Ser Asp Gly Thr Asp Leu Trp Gly Pro Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160
```

```
Thr Ser Gly Val His Thr Phe Pro Ala Val Leu Gln Ser Ser Gly Leu
            165                 170                 175
Tyr Ser Leu Ser Ser Val Val Thr Val Pro Ser Ser Leu Gly Thr
        180                 185                 190
Gln Thr Tyr Ile Cys Asn Val Asn His Lys Pro Ser Asn Thr Lys Val
        195                 200                 205
Asp Lys Lys Val Glu Pro Lys Ser Cys Asp Lys Thr His Thr Cys Pro
        210                 215                 220
Pro Cys Pro Ala Pro Glu Ala Ala Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
                260                 265                 270
Asn Trp Tyr Val Asp Gly Val Glu Val His Asn Ala Lys Thr Lys Pro
            275                 280                 285
Arg Glu Glu Gln Tyr Asn Ser Thr Tyr Arg Val Val Ser Val Leu Thr
        290                 295                 300
Val Leu His Gln Asp Trp Leu Asn Gly Lys Glu Tyr Lys Cys Lys Val
305                 310                 315                 320
Ser Asn Lys Ala Leu Gly Ala Pro Ile Glu Lys Thr Ile Ser Lys Ala
                325                 330                 335
Lys Gly Gln Pro Arg Glu Pro Gln Val Cys Thr Leu Pro Pro Ser Arg
                340                 345                 350
Asp Glu Leu Thr Lys Asn Gln Val Ser Leu Ser Cys Ala Val Lys Gly
            355                 360                 365
Phe Tyr Pro Ser Asp Ile Ala Val Glu Trp Glu Ser Asn Gly Gln Pro
        370                 375                 380
Glu Asn Asn Tyr Lys Thr Thr Pro Pro Val Leu Asp Ser Asp Gly Ser
385                 390                 395                 400
Phe Phe Leu Val Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
            435                 440

<210> SEQ ID NO 283
<211> LENGTH: 451
<212> TYPE: PRT
<213> ORGANISM: Artificial Sequence
<220> FEATURE:
<223> OTHER INFORMATION: Construct DR5TAA-0061 (1+1 chimeric Crossmab
      containing 4B9 and DR5TAA-0011) Crossed HC (FAP)

<400> SEQUENCE: 283

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ile Gly Ser Gly Ala Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Val Ala Ala Pro Ser Val Phe Ile Phe
        115                 120                 125

Pro Pro Ser Asp Glu Gln Leu Lys Ser Gly Thr Ala Ser Val Val Cys
130                 135                 140

Leu Leu Asn Asn Phe Tyr Pro Arg Glu Ala Lys Val Gln Trp Lys Val
145                 150                 155                 160

Asp Asn Ala Leu Gln Ser Gly Asn Ser Gln Glu Ser Val Thr Glu Gln
                165                 170                 175

Asp Ser Lys Asp Ser Thr Tyr Ser Leu Ser Ser Thr Leu Thr Leu Ser
            180                 185                 190

Lys Ala Asp Tyr Glu Lys His Lys Val Tyr Ala Cys Glu Val Thr His
        195                 200                 205

Gln Gly Leu Ser Ser Pro Val Thr Lys Ser Phe Asn Arg Gly Glu Cys
210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
        355                 360                 365

Leu Trp Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 284
<211> LENGTH: 216
<212> TYPE: PRT
<213> ORGANISM: Artificial Sequence
<220> FEATURE:

<223> OTHER INFORMATION: Construct DR5TAA-0032 (2+2 chimeric CrossMab
containing 28H1 and DR5TAA-0005) LC (DR5)

<400> SEQUENCE: 284

```
Ala Gln Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Asn Asn
            20                  25                  30

Arg Leu Ala Trp Tyr Gln Gln Lys Pro Gly Gln Pro Pro Lys Leu Leu
        35                  40                  45

Ile Tyr Leu Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Leu Gln
65                  70                  75                  80

Cys Asp Asp Ala Ala Thr Tyr Tyr Cys Ala Gly Tyr Ser Gly Asn
                85                  90                  95

Ile Asn Ala Phe Gly Gly Gly Thr Glu Val Val Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 285
<211> LENGTH: 214
<212> TYPE: PRT
<213> ORGANISM: Artificial Sequence
<220> FEATURE:
<223> OTHER INFORMATION: Construct DR5TAA-0032 (2+2 chimeric CrossMab
containing 28H1 and DR5TAA-0005) Crossed LC (FAP)

<400> SEQUENCE: 285

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Ser Ser Ala Ser
            100                 105                 110
```

```
Thr Lys Gly Pro Ser Val Phe Pro Leu Ala Pro Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp
    210
```

```
<210> SEQ ID NO 286
<211> LENGTH: 688
<212> TYPE: PRT
<213> ORGANISM: Artificial Sequence
<220> FEATURE:
<223> OTHER INFORMATION: Construct DR5TAA-0032  (2+2 chimeric CrossMab
      containing 28H1 and DR5TAA-0005) HC (DR5 - crossed FAP

<400> SEQUENCE: 286

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Ala Tyr
            20                  25                  30

Met Ser Trp Val Arg Gln Ala Pro Gly Lys Gly Leu Glu Trp Ile Gly
        35                  40                  45

Tyr Ile Tyr Ser Gly Ser Gly Ser Thr Trp Tyr Ala Ser Trp Val Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Tyr Ser Thr Met Gly Asp Leu Trp Gly Pro Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

```
Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
                340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys Ser Gly Gly Gly
            435                 440                 445

Gly Ser Gly Gly Gly Gly Ser Gly Gly Gly Gly Ser Gly Gly Gly Gly
    450                 455                 460

Ser Glu Val Gln Leu Leu Glu Ser Gly Gly Gly Leu Val Gln Pro Gly
465                 470                 475                 480

Gly Ser Leu Arg Leu Ser Cys Ala Ala Ser Gly Phe Thr Phe Ser Ser
                485                 490                 495

His Ala Met Ser Trp Val Arg Gln Ala Pro Gly Lys Gly Leu Glu Trp
            500                 505                 510

Val Ser Ala Ile Trp Ala Ser Gly Glu Gln Tyr Tyr Ala Asp Ser Val
            515                 520                 525

Lys Gly Arg Phe Thr Ile Ser Arg Asp Asn Ser Lys Asn Thr Leu Tyr
        530                 535                 540

Leu Gln Met Asn Ser Leu Arg Ala Glu Asp Thr Ala Val Tyr Tyr Cys
545                 550                 555                 560

Ala Lys Gly Trp Leu Gly Asn Phe Asp Tyr Trp Gly Gln Gly Thr Leu
                565                 570                 575

Val Thr Val Ser Ser Ala Ser Val Ala Ala Pro Ser Val Phe Ile Phe
            580                 585                 590

Pro Pro Ser Asp Glu Gln Leu Lys Ser Gly Thr Ala Ser Val Val Cys
            595                 600                 605

Leu Leu Asn Asn Phe Tyr Pro Arg Glu Ala Lys Val Gln Trp Lys Val
        610                 615                 620

Asp Asn Ala Leu Gln Ser Gly Asn Ser Gln Glu Ser Val Thr Glu Gln
625                 630                 635                 640

Asp Ser Lys Asp Ser Thr Tyr Ser Leu Ser Ser Thr Leu Thr Leu Ser
                645                 650                 655

Lys Ala Asp Tyr Glu Lys His Lys Val Tyr Ala Cys Glu Val Thr His
                660                 665                 670
```

Gln Gly Leu Ser Ser Pro Val Thr Lys Ser Phe Asn Arg Gly Glu Cys
        675                 680                 685

<210> SEQ ID NO 287
<211> LENGTH: 218
<212> TYPE: PRT
<213> ORGANISM: Artificial Sequence
<220> FEATURE:
<223> OTHER INFORMATION: Construct DR5TAA-0033 (2+2 chimeric CrossMab
      containing 28H1 and DR5TAA-0011)LC (DR5)

<400> SEQUENCE: 287

Ala Asp Ile Val Met Thr Gln Thr Pro Ala Ser Val Ser Glu Pro Val
1               5                   10                  15

Gly Gly Thr Val Thr Ile Lys Cys Gln Ala Ser Gln Ser Ile Ser Thr
            20                  25                  30

Tyr Leu Ser Trp Tyr Gln Gln Lys Pro Gly Gln Pro Pro Lys Arg Leu
        35                  40                  45

Ile Tyr Lys Ala Ser Thr Leu Ala Ser Gly Val Pro Ser Arg Phe Lys
    50                  55                  60

Gly Ser Gly Ser Gly Thr Asp Phe Thr Leu Thr Ile Arg Asp Leu Glu
65                  70                  75                  80

Cys Ala Asp Ala Ala Thr Tyr Tyr Cys Gln Pro Asn Ser Gly Ile Ala
                85                  90                  95

Thr Tyr Gly Ala Ala Phe Gly Gly Gly Thr Glu Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 288
<211> LENGTH: 214
<212> TYPE: PRT
<213> ORGANISM: Artificial Sequence
<220> FEATURE:
<223> OTHER INFORMATION: Construct DR5TAA-0033 (2+2 chimeric CrossMab
      containing 28H1 and DR5TAA-0011)Crossed LC (FAP)

<400> SEQUENCE: 288

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp
    210
```

<210> SEQ ID NO 289
<211> LENGTH: 688
<212> TYPE: PRT
<213> ORGANISM: Artificial Sequence
<220> FEATURE:
<223> OTHER INFORMATION: Construct DR5TAA-0033  (2+2 chimeric CrossMab
      containing 28H1 and DR5TAA-0011)HC (DR5 - crossed FAP)

<400> SEQUENCE: 289

```
Gln Ser Val Glu Glu Ser Gly Gly Arg Leu Val Thr Pro Gly Thr Pro
  1               5                  10                  15

Leu Thr Leu Thr Cys Thr Val Ser Gly Phe Ser Ile Ser Arg Tyr Ala
                 20                  25                  30

Met Ile Trp Val Arg Gln Ala Pro Gly Glu Gly Leu Glu Tyr Ile Gly
             35                  40                  45

Phe Ile Thr Ser Asp Ser Ser Ala Tyr Tyr Ala Ser Trp Ala Lys Gly
 50                  55                  60

Arg Phe Thr Ile Ser Lys Thr Ser Thr Thr Val Asp Leu Lys Met Thr
 65                  70                  75                  80

Ser Pro Thr Thr Glu Asp Thr Ala Thr Tyr Phe Cys Ala Arg Tyr Thr
                 85                  90                  95

Tyr Ser Asp Gly Thr Asp Leu Trp Gly Pro Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205
```

-continued

```
Asp Lys Lys Val Glu Pro Lys Ser Cys Asp Lys Thr His Thr Cys Pro
    210                 215                 220
Pro Cys Pro Ala Pro Glu Leu Leu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser His Glu Asp Pro Glu Val Lys Phe
            260                 265                 270
Asn Trp Tyr Val Asp Gly Val Glu Val His Asn Ala Lys Thr Lys Pro
        275                 280                 285
Arg Glu Glu Gln Tyr Asn Ser Thr Tyr Arg Val Val Ser Val Leu Thr
    290                 295                 300
Val Leu His Gln Asp Trp Leu Asn Gly Lys Glu Tyr Lys Cys Lys Val
305                 310                 315                 320
Ser Asn Lys Ala Leu Pro Ala Pro Ile Glu Lys Thr Ile Ser Lys Ala
                325                 330                 335
Lys Gly Gln Pro Arg Glu Pro Gln Val Tyr Thr Leu Pro Pro Ser Arg
            340                 345                 350
Asp Glu Leu Thr Lys Asn Gln Val Ser Leu Thr Cys Leu Val Lys Gly
        355                 360                 365
Phe Tyr Pro Ser Asp Ile Ala Val Glu Trp Glu Ser Asn Gly Gln Pro
    370                 375                 380
Glu Asn Asn Tyr Lys Thr Thr Pro Pro Val Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
            420                 425                 430
Tyr Thr Gln Lys Ser Leu Ser Leu Ser Pro Gly Lys Ser Gly Gly Gly
        435                 440                 445
Gly Ser Gly Gly Gly Gly Ser Gly Gly Gly Ser Gly Gly Gly Gly
    450                 455                 460
Ser Glu Val Gln Leu Leu Glu Ser Gly Gly Gly Leu Val Gln Pro Gly
465                 470                 475                 480
Gly Ser Leu Arg Leu Ser Cys Ala Ala Ser Gly Phe Thr Phe Ser Ser
                485                 490                 495
His Ala Met Ser Trp Val Arg Gln Ala Pro Gly Lys Gly Leu Glu Trp
            500                 505                 510
Val Ser Ala Ile Trp Ala Ser Gly Glu Gln Tyr Tyr Ala Asp Ser Val
        515                 520                 525
Lys Gly Arg Phe Thr Ile Ser Arg Asp Asn Ser Lys Asn Thr Leu Tyr
    530                 535                 540
Leu Gln Met Asn Ser Leu Arg Ala Glu Asp Thr Ala Val Tyr Tyr Cys
545                 550                 555                 560
Ala Lys Gly Trp Leu Gly Asn Phe Asp Tyr Trp Gly Gln Gly Thr Leu
                565                 570                 575
Val Thr Val Ser Ser Ala Ser Val Ala Ala Pro Ser Val Phe Ile Phe
            580                 585                 590
Pro Pro Ser Asp Glu Gln Leu Lys Ser Gly Thr Ala Ser Val Val Cys
        595                 600                 605
Leu Leu Asn Asn Phe Tyr Pro Arg Glu Ala Lys Val Gln Trp Lys Val
    610                 615                 620
```

```
Asp Asn Ala Leu Gln Ser Gly Asn Ser Gln Glu Ser Val Thr Glu Gln
625                 630                 635                 640

Asp Ser Lys Asp Ser Thr Tyr Ser Leu Ser Ser Thr Leu Thr Leu Ser
                645                 650                 655

Lys Ala Asp Tyr Glu Lys His Lys Val Tyr Ala Cys Glu Val Thr His
                660                 665                 670

Gln Gly Leu Ser Ser Pro Val Thr Lys Ser Phe Asn Arg Gly Glu Cys
            675                 680                 685

<210> SEQ ID NO 290
<211> LENGTH: 218
<212> TYPE: PRT
<213> ORGANISM: Artificial Sequence
<220> FEATURE:
<223> OTHER INFORMATION: Construct DR5TAA-0034  (2+2 chimeric CrossMab
      containing 28H1 and DR5TAA-0013) LC (DR5)

<400> SEQUENCE: 290

Ala Leu Val Met Thr Gln Thr Pro Ser Ser Thr Ser Glu Pro Val Gly
1               5                   10                  15

Gly Thr Val Thr Ile Lys Cys Gln Ala Ser Gln Ser Ile Gly Ser Ser
                20                  25                  30

Leu Ser Trp Tyr Gln Gln Thr Pro Gly Gln Pro Pro Lys Leu Leu Ile
            35                  40                  45

Tyr Thr Ala Ser Ser Leu Ala Ser Ser Val Pro Lys Arg Phe Ser Gly
    50                  55                  60

Ser Arg Ser Gly Thr Gln Phe Thr Leu Thr Ile Ser Gly Val Gln Cys
65                  70                  75                  80

Ala Asp Ala Ala Thr Tyr Tyr Cys Leu Gly Ile Asp Asp Val Arg Arg
                85                  90                  95

Asp Asp Gly Phe Ala Phe Gly Gly Gly Thr Glu Val Val Val Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
    210                 215

<210> SEQ ID NO 291
<211> LENGTH: 214
<212> TYPE: PRT
<213> ORGANISM: Artificial Sequence
<220> FEATURE:
<223> OTHER INFORMATION: Construct DR5TAA-0034  (2+2 chimeric CrossMab
      containing 28H1 and DR5TAA-0013) Crossed LC (FAP)

<400> SEQUENCE: 291

Glu Ile Val Leu Thr Gln Ser Pro Gly Thr Leu Ser Leu Ser Pro Gly
1               5                   10                  15
```

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp
    210

<210> SEQ ID NO 292
<211> LENGTH: 691
<212> TYPE: PRT
<213> ORGANISM: Artificial Sequence
<220> FEATURE:
<223> OTHER INFORMATION: Construct DR5TAA-0034 (2+2 chimeric CrossMab
      containing 28H1 and DR5TAA-0013) HC (DR5 - crossed FAP)

<400> SEQUENCE: 292

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr His
            20                  25                  30

Met Ser Trp Val Arg Gln Ala Pro Gly Lys Gly Leu Glu Trp Ile Gly
        35                  40                  45

Tyr Ile Tyr Ala Gly Ser Ala Ser Thr Trp Tyr Ala Ser Trp Val Lys
    50                  55                  60

Gly Arg Phe Thr Ile Ser Lys Thr Ser Thr Thr Val Asp Leu Lys Met
65                  70                  75                  80

Thr Ser Leu Thr Thr Glu Asp Thr Ala Thr Tyr Phe Cys Ala Arg Asp
                85                  90                  95

Ala Gly Ser Ser Tyr Trp Glu Phe Asn Leu Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Val His Thr Phe Pro Ala Val Leu Gln Ser
            165             170             175

Ser Gly Leu Tyr Ser Leu Ser Ser Val Val Thr Val Pro Ser Ser
            180             185             190

Leu Gly Thr Gln Thr Tyr Ile Cys Asn Val Asn His Lys Pro Ser Asn
            195             200             205

Thr Lys Val Asp Lys Lys Val Glu Pro Lys Ser Cys Asp Lys Thr His
210             215             220

Thr Cys Pro Pro Cys Pro Ala Pro Glu Leu Leu Gly Gly Pro Ser Val
225             230             235             240

Phe Leu Phe Pro Pro Lys Pro Lys Asp Thr Leu Met Ile Ser Arg Thr
            245             250             255

Pro Glu Val Thr Cys Val Val Val Asp Val Ser His Glu Asp Pro Glu
            260             265             270

Val Lys Phe Asn Trp Tyr Val Asp Gly Val Glu Val His Asn Ala Lys
            275             280             285

Thr Lys Pro Arg Glu Glu Gln Tyr Asn Ser Thr Tyr Arg Val Val Ser
            290             295             300

Val Leu Thr Val Leu His Gln Asp Trp Leu Asn Gly Lys Glu Tyr Lys
305             310             315             320

Cys Lys Val Ser Asn Lys Ala Leu Pro Ala Pro Ile Glu Lys Thr Ile
            325             330             335

Ser Lys Ala Lys Gly Gln Pro Arg Glu Pro Gln Val Tyr Thr Leu Pro
            340             345             350

Pro Ser Arg Asp Glu Leu Thr Lys Asn Gln Val Ser Leu Thr Cys Leu
            355             360             365

Val Lys Gly Phe Tyr Pro Ser Asp Ile Ala Val Glu Trp Glu Ser Asn
            370             375             380

Gly Gln Pro Glu Asn Asn Tyr Lys Thr Thr Pro Pro Val Leu Asp Ser
385             390             395             400

Asp Gly Ser Phe Phe Leu Tyr Ser Lys Leu Thr Val Asp Lys Ser Arg
            405             410             415

Trp Gln Gln Gly Asn Val Phe Ser Cys Ser Val Met His Glu Ala Leu
            420             425             430

His Asn His Tyr Thr Gln Lys Ser Leu Ser Leu Ser Pro Gly Lys Ser
            435             440             445

Gly Gly Gly Gly Ser Gly Gly Gly Ser Gly Gly Gly Gly Ser Gly
450             455             460

Gly Gly Gly Ser Glu Val Gln Leu Leu Glu Ser Gly Gly Gly Leu Val
465             470             475             480

Gln Pro Gly Gly Ser Leu Arg Leu Ser Cys Ala Ala Ser Gly Phe Thr
            485             490             495

Phe Ser Ser His Ala Met Ser Trp Val Arg Gln Ala Pro Gly Lys Gly
            500             505             510

Leu Glu Trp Val Ser Ala Ile Trp Ala Ser Gly Glu Gln Tyr Tyr Ala
            515             520             525

Asp Ser Val Lys Gly Arg Phe Thr Ile Ser Arg Asp Asn Ser Lys Asn
            530             535             540

Thr Leu Tyr Leu Gln Met Asn Ser Leu Arg Ala Glu Asp Thr Ala Val
545             550             555             560

Tyr Tyr Cys Ala Lys Gly Trp Leu Gly Asn Phe Asp Tyr Trp Gly Gln
            565             570             575

-continued

```
Gly Thr Leu Val Thr Val Ser Ala Ser Val Ala Pro Ser Val
            580                 585                 590

Phe Ile Phe Pro Pro Ser Asp Glu Gln Leu Lys Ser Gly Thr Ala Ser
        595                 600                 605

Val Val Cys Leu Leu Asn Asn Phe Tyr Pro Arg Glu Ala Lys Val Gln
    610                 615                 620

Trp Lys Val Asp Asn Ala Leu Gln Ser Gly Asn Ser Gln Glu Ser Val
625                 630                 635                 640

Thr Glu Gln Asp Ser Lys Asp Ser Thr Tyr Ser Leu Ser Ser Thr Leu
                645                 650                 655

Thr Leu Ser Lys Ala Asp Tyr Glu Lys His Lys Val Tyr Ala Cys Glu
        660                 665                 670

Val Thr His Gln Gly Leu Ser Ser Pro Val Thr Lys Ser Phe Asn Arg
    675                 680                 685

Gly Glu Cys
    690

<210> SEQ ID NO 293
<211> LENGTH: 220
<212> TYPE: PRT
<213> ORGANISM: Artificial Sequence
<220> FEATURE:
<223> OTHER INFORMATION: Construct DR5TAA-0035  (2+2 chimeric CrossMab
      containing 28H1 and DR5TAA-0016) LC (DR5)

<400> SEQUENCE: 293

Ala Asp Ile Val Met Thr Gln Thr Ala Ser Pro Val Ser Ala Ala Val
1               5                   10                  15

Gly Gly Thr Val Thr Ile Asn Cys Gln Ala Ser Gln Ser Ile Ser Ser
            20                  25                  30

Ser Tyr Val Ser Trp Tyr Gln Gln Lys Pro Gly Gln Pro Pro Lys Leu
        35                  40                  45

Leu Ile Tyr Lys Ala Ser Thr Leu Ala Ser Gly Val Pro Ser Arg Phe
    50                  55                  60

Ser Gly Ser Gly Ser Gly Thr Gln Leu Ser Leu Thr Ile Arg Gly Val
65                  70                  75                  80

Gln Cys Asp Asp Ala Ala Thr Tyr Tyr Cys Leu Tyr Gly Tyr Ser Asp
                85                  90                  95

Val Ser Ser Glu Tyr Val Phe Gly Gly Gly Thr Glu Val Val Val
            100                 105                 110

Arg Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 294
```

```
<211> LENGTH: 214
<212> TYPE: PRT
<213> ORGANISM: Artificial Sequence
<220> FEATURE:
<223> OTHER INFORMATION: Construct DR5TAA-0035  (2+2 chimeric CrossMab
      containing 28H1 and DR5TAA-0016) Crossed LC (FAP)

<400> SEQUENCE: 294
```

| | | | | | | | | | | | | | | |
|---|---|---|---|---|---|---|---|---|---|---|---|---|---|---|
| Glu | Ile | Val | Leu | Thr | Gln | Ser | Pro | Gly | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Ser | Arg | Ser |
| | | | 20 | | | | | 25 | | | | | 30 | | |
| Tyr | Leu | Ala | Trp | Tyr | Gln | Gln | Lys | Pro | Gly | Gln | Ala | Pro | Arg | Leu | Leu |
| | | | 35 | | | | 40 | | | | | 45 | | | |
| Ile | Ile | Gly | Ala | Ser | Thr | Arg | Ala | Thr | Gly | Ile | Pro | Asp | Arg | Phe | Ser |
| 50 | | | | | 55 | | | | | 60 | | | | | |
| Gly | Ser | Gly | Ser | Gly | Thr | Asp | Phe | Thr | Leu | Thr | Ile | Ser | Arg | Leu | Glu |
| 65 | | | | | 70 | | | | | 75 | | | | | 80 |
| Pro | Glu | Asp | Phe | Ala | Val | Tyr | Tyr | Cys | Gln | Gln | Gly | Gln | Val | Ile | Pro |
| | | | | 85 | | | | | 90 | | | | | 95 | |
| Pro | Thr | Phe | Gly | Gln | Gly | Thr | Lys | Val | Glu | Ile | Lys | Ser | Ser | Ala | Ser |
| | | | 100 | | | | | 105 | | | | | 110 | | |
| Thr | Lys | Gly | Pro | Ser | Val | Phe | Pro | Leu | Ala | Pro | Ser | Ser | Lys | Ser | Thr |
| | | | 115 | | | | | 120 | | | | | 125 | | |
| Ser | Gly | Gly | Thr | Ala | Ala | Leu | Gly | Cys | Leu | Val | Lys | Asp | Tyr | Phe | Pro |
| | 130 | | | | | 135 | | | | | 140 | | | | |
| Glu | Pro | Val | Thr | Val | Ser | Trp | Asn | Ser | Gly | Ala | Leu | Thr | Ser | Gly | Val |
| 145 | | | | | 150 | | | | | 155 | | | | | 160 |
| His | Thr | Phe | Pro | Ala | Val | Leu | Gln | Ser | Ser | Gly | Leu | Tyr | Ser | Leu | Ser |
| | | | | 165 | | | | | 170 | | | | | 175 | |
| Ser | Val | Val | Thr | Val | Pro | Ser | Ser | Ser | Leu | Gly | Thr | Gln | Thr | Tyr | Ile |
| | | | | 180 | | | | | 185 | | | | | 190 | |
| Cys | Asn | Val | Asn | His | Lys | Pro | Ser | Asn | Thr | Lys | Val | Asp | Lys | Lys | Val |
| | | | | 195 | | | | | 200 | | | | | 205 | |
| Glu | Pro | Lys | Ser | Cys | Asp | | | | | | | | | | |
| | 210 | | | | | | | | | | | | | | |

```
<210> SEQ ID NO 295
<211> LENGTH: 693
<212> TYPE: PRT
<213> ORGANISM: Artificial Sequence
<220> FEATURE:
<223> OTHER INFORMATION: Construct DR5TAA-0035  (2+2 chimeric CrossMab
      containing 28H1 and DR5TAA-0016) HC (DR5 - crossed FAP)

<400> SEQUENCE: 295
```

| | | | | | | | | | | | | | | |
|---|---|---|---|---|---|---|---|---|---|---|---|---|---|---|
| Gln | Ser | Leu | Glu | Glu | Ser | Gly | Gly | Arg | Leu | Val | Lys | Pro | Asp | Glu | Thr |
| 1 | | | | 5 | | | | | 10 | | | | | 15 | |
| Leu | Thr | Leu | Thr | Cys | Thr | Val | Ser | Gly | Phe | Ser | Leu | Asn | Asn | Tyr | Ala |
| | | | 20 | | | | | 25 | | | | | 30 | | |
| Met | Ser | Trp | Val | Arg | Gln | Ala | Pro | Gly | Lys | Gly | Leu | Glu | Trp | Ile | Gly |
| | | | 35 | | | | 40 | | | | | 45 | | | |
| Met | Ile | Asn | Lys | Tyr | Gly | Thr | Lys | Tyr | Tyr | Ala | Thr | Trp | Thr | Lys | Gly |
| 50 | | | | | 55 | | | | | 60 | | | | | |
| Arg | Ala | Thr | Ile | Ser | Lys | Thr | Ser | Thr | Leu | Asp | Leu | Glu | Ile | Thr |
| 65 | | | | | 70 | | | | | 75 | | | | | 80 |
| Ser | Pro | Thr | Thr | Glu | Asp | Thr | Ala | Thr | Tyr | Phe | Cys | Ala | Arg | Val | Arg |
| | | | | 85 | | | | | 90 | | | | | 95 | |

```
Tyr Ala Gly Asp Asp Tyr Ala Glu Trp Leu Asp Val Trp Gly Gln Gly
                100                 105                 110

Ile Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Ser Gly Gly Gly Gly Ser Gly Gly Gly Ser Gly Gly Gly Gly Gly
    450                 455                 460

Ser Gly Gly Gly Gly Ser Glu Val Gln Leu Leu Glu Ser Gly Gly Gly
465                 470                 475                 480

Leu Val Gln Pro Gly Gly Ser Leu Arg Leu Ser Cys Ala Ala Ser Gly
                485                 490                 495

Phe Thr Phe Ser Ser His Ala Met Ser Trp Val Arg Gln Ala Pro Gly
            500                 505                 510
```

```
Lys Gly Leu Glu Trp Val Ser Ala Ile Trp Ala Ser Gly Glu Gln Tyr
            515                 520                 525

Tyr Ala Asp Ser Val Lys Gly Arg Phe Thr Ile Ser Arg Asp Asn Ser
            530                 535                 540

Lys Asn Thr Leu Tyr Leu Gln Met Asn Ser Leu Arg Ala Glu Asp Thr
545                 550                 555                 560

Ala Val Tyr Tyr Cys Ala Lys Gly Trp Leu Gly Asn Phe Asp Tyr Trp
                565                 570                 575

Gly Gln Gly Thr Leu Val Thr Val Ser Ser Ala Ser Val Ala Ala Pro
            580                 585                 590

Ser Val Phe Ile Phe Pro Pro Ser Asp Glu Gln Leu Lys Ser Gly Thr
            595                 600                 605

Ala Ser Val Val Cys Leu Leu Asn Asn Phe Tyr Pro Arg Glu Ala Lys
            610                 615                 620

Val Gln Trp Lys Val Asp Asn Ala Leu Gln Ser Gly Asn Ser Gln Glu
625                 630                 635                 640

Ser Val Thr Glu Gln Asp Ser Lys Asp Ser Thr Tyr Ser Leu Ser Ser
                645                 650                 655

Thr Leu Thr Leu Ser Lys Ala Asp Tyr Glu Lys His Lys Val Tyr Ala
            660                 665                 670

Cys Glu Val Thr His Gln Gly Leu Ser Ser Pro Val Thr Lys Ser Phe
            675                 680                 685

Asn Arg Gly Glu Cys
    690

<210> SEQ ID NO 296
<211> LENGTH: 217
<212> TYPE: PRT
<213> ORGANISM: Artificial Sequence
<220> FEATURE:
<223> OTHER INFORMATION: Construct DR5TAA-0036  (2+2 chimeric CrossMab
      containing 28H1 and DR5TAA-0019) LC (DR5)

<400> SEQUENCE: 296

Ala Leu Val Met Thr Gln Thr Pro Ser Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Phe Gln Gln Lys Pro Gly Gln Pro Pro Lys Leu Leu Ile
        35                  40                  45

Tyr Glu Thr Ser Lys Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Ser Ser Trp His Ser Ile Ser
                85                  90                  95

Thr Asp Cys Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175
```

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 297
<211> LENGTH: 214
<212> TYPE: PRT
<213> ORGANISM: Artificial Sequence
<220> FEATURE:
<223> OTHER INFORMATION: Construct DR5TAA-0036 (2+2 chimeric CrossMab
      containing 28H1 and DR5TAA-0019) Crossed LC (FAP)

<400> SEQUENCE: 297

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp
    210

<210> SEQ ID NO 298
<211> LENGTH: 691
<212> TYPE: PRT
<213> ORGANISM: Artificial Sequence
<220> FEATURE:
<223> OTHER INFORMATION: Construct DR5TAA-0036 (2+2 chimeric CrossMab
      containing 28H1 and DR5TAA-0019) HC (DR5 - crossed FAP)

<400> SEQUENCE: 298

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

```
Met Ser Trp Val Arg Gln Ala Pro Gly Lys Gly Leu Glu Trp Ile Gly
        35                  40                  45

Ile Ile Ser Ser Ser Gly Thr Thr Tyr Tyr Ala Ser Trp Ala Lys Gly
50                      55                  60

Arg Phe Thr Ile Ser Lys Thr Ser Thr Thr Val Asp Leu Lys Val Thr
65                      70                  75                  80

Ser Pro Thr Thr Glu Asp Thr Ala Thr Tyr Phe Cys Ala Arg Glu Thr
                85                  90                  95

Tyr Tyr Gly Tyr Ser Tyr Ala Ala Gly Leu Trp Gly Pro Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                     135                 140

Leu Val Lys Asp Tyr Phe Pro Glu Pro Val Thr Val Ser Trp Asn Ser
145                     150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                     230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                     310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                     375                 380

Gly Gln Pro Glu Asn Asn Tyr Lys Thr Thr Pro Val Leu Asp Ser
385                     390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Ser
        435                 440                 445
```

```
Gly Gly Gly Ser Gly Gly Gly Ser Gly Gly Gly Ser Gly
    450                 455                 460
Gly Gly Gly Ser Glu Val Gln Leu Leu Glu Ser Gly Gly Leu Val
465                 470                 475                 480
Gln Pro Gly Gly Ser Leu Arg Leu Ser Cys Ala Ala Ser Gly Phe Thr
                485                 490                 495
Phe Ser Ser His Ala Met Ser Trp Val Arg Gln Ala Pro Gly Lys Gly
            500                 505                 510
Leu Glu Trp Val Ser Ala Ile Trp Ala Ser Gly Glu Gln Tyr Tyr Ala
        515                 520                 525
Asp Ser Val Lys Gly Arg Phe Thr Ile Ser Arg Asp Asn Ser Lys Asn
    530                 535                 540
Thr Leu Tyr Leu Gln Met Asn Ser Leu Arg Ala Glu Asp Thr Ala Val
545                 550                 555                 560
Tyr Tyr Cys Ala Lys Gly Trp Leu Gly Asn Phe Asp Tyr Trp Gly Gln
                565                 570                 575
Gly Thr Leu Val Thr Val Ser Ser Ala Ser Val Ala Ala Pro Ser Val
            580                 585                 590
Phe Ile Phe Pro Pro Ser Asp Glu Gln Leu Lys Ser Gly Thr Ala Ser
        595                 600                 605
Val Val Cys Leu Leu Asn Asn Phe Tyr Pro Arg Glu Ala Lys Val Gln
    610                 615                 620
Trp Lys Val Asp Asn Ala Leu Gln Ser Gly Asn Ser Gln Glu Ser Val
625                 630                 635                 640
Thr Glu Gln Asp Ser Lys Asp Ser Thr Tyr Ser Leu Ser Ser Thr Leu
                645                 650                 655
Thr Leu Ser Lys Ala Asp Tyr Glu Lys His Lys Val Tyr Ala Cys Glu
            660                 665                 670
Val Thr His Gln Gly Leu Ser Ser Pro Val Thr Lys Ser Phe Asn Arg
        675                 680                 685
Gly Glu Cys
    690

<210> SEQ ID NO 299
<211> LENGTH: 218
<212> TYPE: PRT
<213> ORGANISM: Artificial Sequence
<220> FEATURE:
<223> OTHER INFORMATION: Construct DR5TAA-0117  (2+2 humanized CrossMab
      containing 28H1 and DR5TAA-0067) LC (DR5)

<400> SEQUENCE: 299

Ala Asp Ile Gln Met Thr Gln Ser Pro Ser Thr Leu Ser Ala Ser Val
1               5                   10                  15
Gly Asp Arg Val Thr Ile Thr Cys Arg Ala Ser Gln Ser Ile Ser Thr
            20                  25                  30
Tyr Leu Ser Trp Tyr Gln Gln Lys Pro Gly Lys Ala Pro Lys Arg Leu
        35                  40                  45
Ile Tyr Lys Ala Ser Ser Leu Ala Ser Gly Val Pro Ser Arg Phe Ser
    50                  55                  60
Gly Ser Gly Ser Gly Thr Glu Phe Thr Leu Thr Ile Ser Ser Leu Gln
65                  70                  75                  80
Pro Asp Asp Ala Ala Thr Tyr Tyr Cys Gln Pro Asn Ser Gly Ile Ala
                85                  90                  95
Thr Tyr Gly Ala Ala Phe Gly Gly Gly Thr Lys Val Glu Ile Lys Arg
            100                 105                 110
```

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 300
<211> LENGTH: 214
<212> TYPE: PRT
<213> ORGANISM: Artificial Sequence
<220> FEATURE:
<223> OTHER INFORMATION: Construct DR5TAA-0117 (2+2 humanized CrossMab
      containing 28H1 and DR5TAA-0067) Crossed LC (FAP)

<400> SEQUENCE: 300

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys Asp
    210

<210> SEQ ID NO 301
<211> LENGTH: 689
<212> TYPE: PRT

<213> ORGANISM: Artificial Sequence
<220> FEATURE:
<223> OTHER INFORMATION: Construct DR5TAA-0117 (2+2 humanized CrossMab containing 28H1 and DR5TAA-0067) HC (DR5 - crossed FAP)

<400> SEQUENCE: 301

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Arg Tyr
            20                  25                  30

Ala Met Ile Trp Val Arg Gln Ala Pro Gly Lys Gly Leu Glu Tyr Ile
        35                  40                  45

Gly Phe Ile Thr Ser Asp Gly Ser Thr Tyr Tyr Ala Asp Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Thr Tyr Ser Asp Gly Thr Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

-continued

```
Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Gly Gly
            435                 440                 445

Gly Gly Ser Gly Gly Gly Ser Gly Gly Gly Ser Gly Gly Gly
450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Phe Thr Phe Ser
            485                 490                 495

Ser His Ala Met Ser Trp Val Arg Gln Ala Pro Gly Lys Gly Leu Glu
        500                 505                 510

Trp Val Ser Ala Ile Trp Ala Ser Gly Glu Gln Tyr Tyr Ala Asp Ser
            515                 520                 525

Val Lys Gly Arg Phe Thr Ile Ser Arg Asp Asn Ser Lys Asn Thr Leu
530                 535                 540

Tyr Leu Gln Met Asn Ser Leu Arg Ala Glu Asp Thr Ala Val Tyr Tyr
545                 550                 555                 560

Cys Ala Lys Gly Trp Leu Gly Asn Phe Asp Tyr Trp Gly Gln Gly Thr
            565                 570                 575

Leu Val Thr Val Ser Ser Ala Ser Val Ala Ala Pro Ser Val Phe Ile
        580                 585                 590

Phe Pro Pro Ser Asp Glu Gln Leu Lys Ser Gly Thr Ala Ser Val Val
            595                 600                 605

Cys Leu Leu Asn Asn Phe Tyr Pro Arg Glu Ala Lys Val Gln Trp Lys
610                 615                 620

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
            645                 650                 655

Ser Lys Ala Asp Tyr Glu Lys His Lys Val Tyr Ala Cys Glu Val Thr
        660                 665                 670

His Gln Gly Leu Ser Ser Pro Val Thr Lys Ser Phe Asn Arg Gly Glu
            675                 680                 685

Cys

<210> SEQ ID NO 302
<211> LENGTH: 218
<212> TYPE: PRT
<213> ORGANISM: Artificial Sequence
<220> FEATURE:
<223> OTHER INFORMATION: Construct DR5TAA-0118  (2+2 humanized CrossMab
      containing 28H1 and DR5TAA-0071) LC (DR5)

<400> SEQUENCE: 302

Ala Asp Ile Gln Met Thr Gln Ser Pro Ser Thr Leu Ser Ala Ser Val
1               5                   10                  15

Gly Asp Arg Val Thr Ile Thr Cys Arg Ala Ser Gln Ser Ile Ser Thr
            20                  25                  30

Tyr Leu Ser Trp Tyr Gln Gln Lys Pro Gly Lys Ala Pro Lys Arg Leu
        35                  40                  45
```

```
Ile Tyr Lys Ala Ser Ser Leu Ala Ser Gly Val Pro Ser Arg Phe Ser
     50                  55                  60

Gly Ser Gly Ser Gly Thr Glu Phe Thr Leu Thr Ile Ser Ser Leu Gln
 65                  70                  75                  80

Pro Asp Asp Ala Ala Thr Tyr Tyr Cys Gln Pro Asn Ser Gly Ile Ala
                 85                  90                  95

Thr Tyr Gly Ala Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 303
<211> LENGTH: 214
<212> TYPE: PRT
<213> ORGANISM: Artificial Sequence
<220> FEATURE:
<223> OTHER INFORMATION: Construct DR5TAA-0118  (2+2 humanized CrossMab
      containing 28H1 and DR5TAA-0071) Crossed LC (FAP)

<400> SEQUENCE: 303

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Arg Ser
             20                  25                  30

Tyr Leu Ala Trp Tyr Gln Gln Lys Pro Gly Gln Ala Pro Arg Leu Leu
         35                  40                  45

Ile Ile Gly Ala Ser Thr Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Gly Gln Val Ile Pro
                 85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
            115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190
```

Cys Asn Val Asn His Lys Pro Ser Asn Thr Lys Val Asp Lys Lys Val
            195                 200                 205

Glu Pro Lys Ser Cys Asp
    210

<210> SEQ ID NO 304
<211> LENGTH: 689
<212> TYPE: PRT
<213> ORGANISM: Artificial Sequence
<220> FEATURE:
<223> OTHER INFORMATION: Construct DR5TAA-0118  (2+2 humanized CrossMab
      containing 28H1 and DR5TAA-0071) HC (DR5 - crossed FAP)

<400> SEQUENCE: 304

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Ile Ser Arg Tyr
            20                  25                  30

Ala Met Ile Trp Val Arg Gln Ala Pro Gly Lys Gly Leu Glu Tyr Val
        35                  40                  45

Gly Phe Ile Thr Ser Asp Ser Ser Ala Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Thr Tyr Ser Asp Gly Tyr Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile

```
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Gly Gly
            435                 440                 445
Gly Gly Ser Gly Gly Gly Gly Ser Gly Gly Gly Gly Ser Gly Gly Gly
        450                 455                 460
Gly Ser Glu Val Gln Leu Leu Glu Ser Gly Gly Gly Leu Val Gln Pro
465                 470                 475                 480
Gly Gly Ser Leu Arg Leu Ser Cys Ala Ala Ser Gly Phe Thr Phe Ser
                485                 490                 495
Ser His Ala Met Ser Trp Val Arg Gln Ala Pro Gly Lys Gly Leu Glu
            500                 505                 510
Trp Val Ser Ala Ile Trp Ala Ser Gly Glu Gln Tyr Tyr Ala Asp Ser
            515                 520                 525
Val Lys Gly Arg Phe Thr Ile Ser Arg Asp Asn Ser Lys Asn Thr Leu
        530                 535                 540
Tyr Leu Gln Met Asn Ser Leu Arg Ala Glu Asp Thr Ala Val Tyr Tyr
545                 550                 555                 560
Cys Ala Lys Gly Trp Leu Gly Asn Phe Asp Tyr Trp Gly Gln Gly Thr
                565                 570                 575
Leu Val Thr Val Ser Ser Ala Ser Val Ala Ala Pro Ser Val Phe Ile
            580                 585                 590
Phe Pro Pro Ser Asp Glu Gln Leu Lys Ser Gly Thr Ala Ser Val Val
            595                 600                 605
Cys Leu Leu Asn Asn Phe Tyr Pro Arg Glu Ala Lys Val Gln Trp Lys
        610                 615                 620
Val Asp Asn Ala Leu Gln Ser Gly Asn Ser Gln Glu Ser Val Thr Glu
625                 630                 635                 640
Gln Asp Ser Lys Asp Ser Thr Tyr Ser Leu Ser Ser Thr Leu Thr Leu
                645                 650                 655
Ser Lys Ala Asp Tyr Glu Lys His Lys Val Tyr Ala Cys Glu Val Thr
            660                 665                 670
His Gln Gly Leu Ser Ser Pro Val Thr Lys Ser Phe Asn Arg Gly Glu
            675                 680                 685
Cys

<210> SEQ ID NO 305
<211> LENGTH: 217
<212> TYPE: PRT
<213> ORGANISM: Artificial Sequence
<220> FEATURE:
<223> OTHER INFORMATION: Construct DR5TAA-0119  (2+2 humanized CrossMab
      containing 28H1 and DR5TAA-0075) LC (DR5)
```

```
<400> SEQUENCE: 305

Asp Ile Gln Met Thr Gln Ser Pro Ser Leu Ser Ala Ser Val Gly
1               5                   10                  15

Asp Arg Val Thr Ile Thr Cys Gln Ala Ser Gln Ser Ile Ser Thr Tyr
            20                  25                  30

Leu Ser Trp Tyr Gln Gln Lys Pro Gly Gln Pro Pro Lys Arg Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Pro Asn Ser Gly Ile Ala Thr
                85                  90                  95

Tyr Gly Ala Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 306
<211> LENGTH: 214
<212> TYPE: PRT
<213> ORGANISM: Artificial Sequence
<220> FEATURE:
<223> OTHER INFORMATION: Construct DR5TAA-0119  (2+2 humanized CrossMab
      containing 28H1 and DR5TAA-0075) Crossed LC (FAP)

<400> SEQUENCE: 306

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Ser Ser Ala Ser
            100                 105                 110

Thr Lys Gly Pro Ser Val Phe Pro Leu Ala Pro Ser Ser Lys Ser Thr
        115                 120                 125
```

```
Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys Asp
    210

<210> SEQ ID NO 307
<211> LENGTH: 689
<212> TYPE: PRT
<213> ORGANISM: Artificial Sequence
<220> FEATURE:
<223> OTHER INFORMATION: Construct DR5TAA-0119  (2+2 humanized CrossMab
      containing 28H1 and DR5TAA-0075) HC (DR5 - crossed FAP)

<400> SEQUENCE: 307

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Val Ser Arg Tyr
            20                  25                  30

Ala Met Ile Trp Val Arg Gln Ala Pro Gly Lys Gly Leu Glu Tyr Ile
        35                  40                  45

Gly Phe Ile Thr Ser Asp Gly Ser Thr Tyr Tyr Ala Asp Ser Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Thr Tyr Ser Asp Gly Thr Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Gly Gly
            435                 440                 445

Gly Gly Ser Gly Gly Gly Gly Ser Gly Gly Gly Gly Ser Gly Gly Gly
    450                 455                 460

Gly Ser Glu Val Gln Leu Leu Glu Ser Gly Gly Gly Leu Val Gln Pro
465                 470                 475                 480

Gly Gly Ser Leu Arg Leu Ser Cys Ala Ala Ser Gly Phe Thr Phe Ser
                485                 490                 495

Ser His Ala Met Ser Trp Val Arg Gln Ala Pro Gly Lys Gly Leu Glu
            500                 505                 510

Trp Val Ser Ala Ile Trp Ala Ser Gly Glu Gln Tyr Tyr Ala Asp Ser
    515                 520                 525

Val Lys Gly Arg Phe Thr Ile Ser Arg Asp Asn Ser Lys Asn Thr Leu
    530                 535                 540

Tyr Leu Gln Met Asn Ser Leu Arg Ala Glu Asp Thr Ala Val Tyr Tyr
545                 550                 555                 560

Cys Ala Lys Gly Trp Leu Gly Asn Phe Asp Tyr Trp Gly Gln Gly Thr
                565                 570                 575

Leu Val Thr Val Ser Ser Ala Ser Val Ala Ala Pro Ser Val Phe Ile
            580                 585                 590

Phe Pro Pro Ser Asp Glu Gln Leu Lys Ser Gly Thr Ala Ser Val Val
    595                 600                 605

Cys Leu Leu Asn Asn Phe Tyr Pro Arg Glu Ala Lys Val Gln Trp Lys
    610                 615                 620

Val Asp Asn Ala Leu Gln Ser Gly Asn Ser Gln Glu Ser Val Thr Glu
625                 630                 635                 640

Gln Asp Ser Lys Asp Ser Thr Tyr Ser Leu Ser Ser Thr Leu Thr Leu
                645                 650                 655

Ser Lys Ala Asp Tyr Glu Lys His Lys Val Tyr Ala Cys Glu Val Thr
            660                 665                 670

His Gln Gly Leu Ser Ser Pro Val Thr Lys Ser Phe Asn Arg Gly Glu
    675                 680                 685

Cys

<210> SEQ ID NO 308
<211> LENGTH: 467
<212> TYPE: PRT
<213> ORGANISM: Artificial Sequence
<220> FEATURE:
<223> OTHER INFORMATION: huFc-VH007

<400> SEQUENCE: 308

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser Gly Gly Gly Gly
225                 230                 235                 240

Ser Gly Gly Gly Gly Ser Glu Val Gln Leu Val Glu Thr Gly Gly Gly
                245                 250                 255

Leu Ile Gln Pro Gly Gly Ser Leu Arg Leu Ser Cys Ala Ala Ser Gly
            260                 265                 270

Phe Thr Val Ser Arg Tyr Ala Met Ile Trp Val Arg Gln Ala Pro Gly
        275                 280                 285

Lys Gly Leu Glu Tyr Ile Gly Phe Ile Thr Ser Asp Gly Ser Thr Tyr
    290                 295                 300

Tyr Ala Asp Ser Ala Lys Gly Arg Phe Thr Ile Ser Arg Asp Asn Ser
305                 310                 315                 320

Lys Asn Thr Leu Tyr Leu Gln Met Asn Ser Leu Arg Ala Glu Asp Thr
                325                 330                 335

Ala Val Tyr Tyr Cys Ala Arg Tyr Thr Tyr Ser Asp Gly Thr Asp Leu
            340                 345                 350

Trp Gly Arg Gly Thr Leu Val Thr Val Ser Ser Ala Ser Thr Lys Gly
```

```
                355                 360                 365
Pro Ser Val Phe Pro Leu Ala Pro Ser Ser Lys Ser Thr Ser Gly Gly
    370                 375                 380

Thr Ala Ala Leu Gly Cys Leu Val Lys Asp Tyr Phe Pro Glu Pro Val
385                 390                 395                 400

Thr Val Ser Trp Asn Ser Gly Ala Leu Thr Ser Gly Val His Thr Phe
                405                 410                 415

Pro Ala Val Leu Gln Ser Ser Gly Leu Tyr Ser Leu Ser Ser Val Val
                420                 425                 430

Thr Val Pro Ser Ser Ser Leu Gly Thr Gln Thr Tyr Ile Cys Asn Val
                435                 440                 445

Asn His Lys Pro Ser Asn Thr Lys Val Asp Lys Lys Val Glu Pro Lys
            450                 455                 460

Ser Cys Asp
465

<210> SEQ ID NO 309
<211> LENGTH: 217
<212> TYPE: PRT
<213> ORGANISM: Artificial Sequence
<220> FEATURE:
<223> OTHER INFORMATION: hVL015

<400> SEQUENCE: 309

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Ser Trp Tyr Gln Gln Lys Pro Gly Lys Ala Pro Lys Arg Leu Ile
        35                  40                  45

Tyr Lys Ala Ser Ser Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Ala Ala Thr Tyr Tyr Cys Gln Pro Asn Ser Gly Ile Ala Thr
                85                  90                  95

Tyr Gly Ala Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 310
<211> LENGTH: 467
<212> TYPE: PRT
```

<213> ORGANISM: Artificial Sequence
<220> FEATURE:
<223> OTHER INFORMATION: huFc-VH017

<400> SEQUENCE: 310

| | | | | | | | | | | | | | | |
|---|---|---|---|---|---|---|---|---|---|---|---|---|---|---|
| Asp | Lys | Thr | His | Thr | Cys | Pro | Pro | Cys | Pro | Ala | Pro | Glu | Leu | Leu | Gly |
| 1 | | | | 5 | | | | | 10 | | | | | 15 | |
| Gly | Pro | Ser | Val | Phe | Leu | Phe | Pro | Pro | Lys | Pro | Lys | Asp | Thr | Leu | Met |
| | | | 20 | | | | | 25 | | | | | 30 | | |
| Ile | Ser | Arg | Thr | Pro | Glu | Val | Thr | Cys | Val | Val | Val | Asp | Val | Ser | His |
| | | 35 | | | | | 40 | | | | | 45 | | | |
| Glu | Asp | Pro | Glu | Val | Lys | Phe | Asn | Trp | Tyr | Val | Asp | Gly | Val | Glu | Val |
| | 50 | | | | | 55 | | | | | 60 | | | | |
| His | Asn | Ala | Lys | Thr | Lys | Pro | Arg | Glu | Glu | Gln | Tyr | Asn | Ser | Thr | Tyr |
| 65 | | | | | 70 | | | | | 75 | | | | | 80 |
| Arg | Val | Val | Ser | Val | Leu | Thr | Val | Leu | His | Gln | Asp | Trp | Leu | Asn | Gly |
| | | | | 85 | | | | | 90 | | | | | 95 | |
| Lys | Glu | Tyr | Lys | Cys | Lys | Val | Ser | Asn | Lys | Ala | Leu | Pro | Ala | Pro | Ile |
| | | | 100 | | | | | 105 | | | | | 110 | | |
| Glu | Lys | Thr | Ile | Ser | Lys | Ala | Lys | Gly | Gln | Pro | Arg | Glu | Pro | Gln | Val |
| | | 115 | | | | | 120 | | | | | 125 | | | |
| Tyr | Thr | Leu | Pro | Pro | Ser | Arg | Asp | Glu | Leu | Thr | Lys | Asn | Gln | Val | Ser |
| | 130 | | | | | 135 | | | | | 140 | | | | |
| Leu | Thr | Cys | Leu | Val | Lys | Gly | Phe | Tyr | Pro | Ser | Asp | Ile | Ala | Val | Glu |
| 145 | | | | | 150 | | | | | 155 | | | | | 160 |
| Trp | Glu | Ser | Asn | Gly | Gln | Pro | Glu | Asn | Asn | Tyr | Lys | Thr | Thr | Pro | Pro |
| | | | | 165 | | | | | 170 | | | | | 175 | |
| Val | Leu | Asp | Ser | Asp | Gly | Ser | Phe | Phe | Leu | Tyr | Ser | Lys | Leu | Thr | Val |
| | | | 180 | | | | | 185 | | | | | 190 | | |
| Asp | Lys | Ser | Arg | Trp | Gln | Gln | Gly | Asn | Val | Phe | Ser | Cys | Ser | Val | Met |
| | | 195 | | | | | 200 | | | | | 205 | | | |
| His | Glu | Ala | Leu | His | Asn | His | Tyr | Thr | Gln | Lys | Ser | Leu | Ser | Leu | Ser |
| | 210 | | | | | 215 | | | | | 220 | | | | |
| Pro | Gly | Gly | Gly | Gly | Ser | Gly | Gly | Gly | Gly | Ser | Gly | Gly | Gly | Gly | Gly |
| 225 | | | | | 230 | | | | | 235 | | | | | 240 |
| Ser | Gly | Gly | Gly | Gly | Ser | Gln | Val | Gln | Leu | Val | Glu | Ser | Gly | Gly | Gly |
| | | | | 245 | | | | | 250 | | | | | 255 | |
| Leu | Val | Gln | Pro | Gly | Gly | Ser | Leu | Arg | Leu | Ser | Cys | Ser | Ala | Ser | Gly |
| | | | 260 | | | | | 265 | | | | | 270 | | |
| Phe | Ser | Ile | Ser | Arg | Tyr | Ala | Met | Ile | Trp | Val | Arg | Gln | Ala | Pro | Gly |
| | | 275 | | | | | 280 | | | | | 285 | | | |
| Lys | Gly | Leu | Glu | Tyr | Val | Gly | Phe | Ile | Thr | Ser | Asp | Ser | Ser | Ala | Tyr |
| | 290 | | | | | 295 | | | | | 300 | | | | |
| Tyr | Ala | Ser | Trp | Ala | Lys | Gly | Arg | Phe | Thr | Ile | Ser | Arg | Asp | Asn | Ser |
| 305 | | | | | 310 | | | | | 315 | | | | | 320 |
| Lys | Asn | Thr | Leu | Tyr | Leu | Gln | Met | Asn | Ser | Leu | Arg | Ala | Glu | Asp | Thr |
| | | | | 325 | | | | | 330 | | | | | 335 | |
| Ala | Val | Tyr | Tyr | Cys | Ala | Arg | Tyr | Thr | Tyr | Ser | Asp | Gly | Thr | Asp | Leu |
| | | | 340 | | | | | 345 | | | | | 350 | | |
| Trp | Gly | Gln | Gly | Thr | Leu | Val | Thr | Val | Ser | Ser | Ala | Ser | Thr | Lys | Gly |
| | | 355 | | | | | 360 | | | | | 365 | | | |
| Pro | Ser | Val | Phe | Pro | Leu | Ala | Pro | Ser | Ser | Lys | Ser | Thr | Ser | Gly | Gly |
| | 370 | | | | | 375 | | | | | 380 | | | | |
| Thr | Ala | Ala | Leu | Gly | Cys | Leu | Val | Lys | Asp | Tyr | Phe | Pro | Glu | Pro | Val |

```
                385                 390                 395                 400
Thr Val Ser Trp Asn Ser Gly Ala Leu Thr Ser Gly Val His Thr Phe
                405                 410                 415

Pro Ala Val Leu Gln Ser Ser Gly Leu Tyr Ser Leu Ser Ser Val Val
                420                 425                 430

Thr Val Pro Ser Ser Leu Gly Thr Gln Thr Tyr Ile Cys Asn Val
                435                 440                 445

Asn His Lys Pro Ser Asn Thr Lys Val Asp Lys Val Glu Pro Lys
450                 455                 460

Ser Cys Asp
465

<210> SEQ ID NO 311
<211> LENGTH: 217
<212> TYPE: PRT
<213> ORGANISM: Artificial Sequence
<220> FEATURE:
<223> OTHER INFORMATION: hVL011

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Thr Tyr
                20                  25                  30

Leu Ser Trp Tyr Gln Gln Lys Pro Gly Gln Pro Lys Arg Leu Ile
            35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Pro Asn Ser Gly Ile Ala Thr
                85                  90                  95

Tyr Gly Ala Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 312
<211> LENGTH: 1401
<212> TYPE: DNA
<213> ORGANISM: Artificial Sequence
<220> FEATURE:
<223> OTHER INFORMATION: huFc-hVH007 DNA

<400> SEQUENCE: 312
```

```
gacaagaccc acacctgtcc cccttgtcct gccctgagc tgctgggcgg acccagcgtg      60
ttcctgttcc cccaaagcc caaggacacc ctgatgatca gccggacccc cgaagtgacc     120
tgcgtggtgg tggacgtgtc ccacgaggac cctgaagtga agttcaattg gtacgtggac    180
ggcgtggagg tgcacaatgc caagaccaag ccccgggagg aacagtacaa cagcacctac    240
cgggtggtgt ccgtgctgac cgtgctgcac caggactggc tgaacggcaa agagtacaag    300
tgcaaggtct ccaacaaggc cctgcctgcc cccatcgaga aaaccatcag caaggccaag    360
ggccagccca gagaaccca ggtgtacacc ctgcccccca gcagagatga gctgaccaag    420
aaccaggtgt ccctgacctg tctggtcaag ggcttctacc ccagcgatat cgccgtggag    480
tgggagagca acggccagcc tgagaacaac tacaagacca cccccctgt gctggacagc     540
gacggcagct tcttcctgta ctccaaactg accgtggaca gagccggtg gcagcagggc     600
aacgtgttca gctgcagcgt gatgcacgag gccctgcaca accactacac ccagaagtcc    660
ctgagcctga ccccggcgg aggaggcgga agtggaggcg gaggatccgg aggggagga    720
tctggcggag gcgcagcga agtgcagctt gtcgaaccg gcgggggact catccagccc    780
ggcggtagcc tgaggctttc ctgcgccgct tctgggttca cagtgtcaag atacgccatg   840
atttgggtcc gccaggcccc tggcaaggga ctggagtata tcggttttat taccagcgac   900
ggctccactt actatgctga ttctgcaaaa gggcggttca caatcagtag ggacaacagc   960
aagaataccc tctacctcca gatgaactcc ttgagagccg aggatactgc tgtgtactat  1020
tgtgcacgct acacctattc tgacggaaca gacctgtggg gccgggggaac cctcgtcact  1080
gtctcctcag ctagcaccaa gggccctcc gtgtttcctc tggcccccag cagcaagagc    1140
acctctggcg gaacagccgc cctgggctgc ctggtgaaag actacttccc cgagcccgtg    1200
accgtgtcct ggaactctgg cgccctgacc agcggcgtgc acacctttcc agccgtgctg    1260
cagagcagcg gcctgtactc cctgagcagc gtggtgacag tgccctccag cagcctgggc    1320
acccagacct acatctgcaa cgtgaaccac aagcccagca caccaaagt ggacaagaag   1380
gtggaaccca gagctgcga c                                              1401
```

<210> SEQ ID NO 313
<211> LENGTH: 651
<212> TYPE: DNA
<213> ORGANISM: Artificial Sequence
<220> FEATURE:
<223> OTHER INFORMATION: hVL015 DNA

<400> SEQUENCE: 313

```
gacatccaga tgacccagag cccctccaca ctgtctgctt cagtgggcga tagggtcacc    60
attacttgca gagcaagcca gtccatctct acatacctca gttggtatca gcaaaagcct   120
gggaaagccc caaagcgcct gatttacaag gccagctccc ttgcatctgg agtgccctca    180
cggttcagcg gctccggttc tgggaccgag tttactctga ccatcagtag cctccagcct    240
gacgatgccg ctacatatta ctgtcagcca aactccggca tagcaaccta cggagccgct    300
ttcggtggcg ggacaaaagt cgaaatcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t            651
```

<210> SEQ ID NO 314
<211> LENGTH: 1401
<212> TYPE: DNA
<213> ORGANISM: Artificial Sequence
<220> FEATURE:
<223> OTHER INFORMATION: huFc-hVH017(DNA

<400> SEQUENCE: 314

```
gacaagaccc acacctgtcc cccttgtcct gccccctgagc tgctgggcgg acccagcgtg      60
ttcctgttcc ccccaaagcc caaggacacc ctgatgatca gccggacccc cgaagtgacc     120
tgcgtggtgg tggacgtgtc ccacgaggac cctgaagtga agttcaattg gtacgtggac     180
ggcgtggagg tgcacaatgc caagaccaag ccccggggagg aacagtacaa cagcacctac     240
cgggtggtgt ccgtgctgac cgtgctgcac caggactggc tgaacggcaa agagtacaag     300
tgcaaggtct ccaacaaggc cctgcctgcc cccatcgaga aaaccatcag caaggccaag     360
ggccagccca gagaacccca ggtgtacacc ctgccccca gcagagatga gctgaccaag     420
aaccaggtgt ccctgacctg tctggtcaag ggcttctacc ccagcgatat cgccgtggag     480
tgggagagca acggccagcc tgagaacaac tacaagacca ccccccctgt gctggacagc     540
gacggcagct tcttcctgta ctccaaactg accgtggaca gagccggtg gcagcagggc     600
aacgtgttca gctgcagcgt gatgcacgag gccctgcaca accactacac ccagaagtcc     660
ctgagcctga gccccggcgg aggaggcgga agtggaggcg gaggatccgg aggggaggga     720
tctggcggag gcggcagcca agtgcagctc gtcgagagcg gcggggggact cgtgcagccc     780
ggcggttccc tgaggctttc ttgctcagcc agcgggttct ccatctccag atacgctatg     840
atttgggtcc gccaggcacc tggcaaggga ctggaatatg tggttttat caccagtgac     900
agctccgcct actatgcttc ttgggcaaaa ggccggttca caatttcaag ggataacagc     960
aagaatatcc tctaccttca aatgaactcc ttgagagccg aggacactgc tgtttactat    1020
tgtgcacgct acacatattc tgatgggacc gacctgtggg gacagggcac tctcgtcact    1080
gtctcctcag ctagcaccaa gggcccctcc gtgtttcctc tggccccag cagcaagagc    1140
acctctggcg gaacagccgc cctgggctgc ctggtgaaag actacttccc cgagcccgtg    1200
accgtgtcct ggaactctgg cgccctgacc agcggcgtgc acacctttcc agccgtgctg    1260
cagagcagcg gcctgtactc cctgagcagc gtggtgacag tgccctccag cagcctgggc    1320
acccagacct acatctgcaa cgtgaaccac aagcccagca caccaaagt ggacaagaag    1380
gtggaaccca gagctgcga c                                                1401
```

<210> SEQ ID NO 315
<211> LENGTH: 651
<212> TYPE: DNA
<213> ORGANISM: Artificial Sequence
<220> FEATURE:
<223> OTHER INFORMATION: hVL011 DNA

<400> SEQUENCE: 315

```
gacatccaga tgacccagag cccctcctct ctgtcagcca gcgtgggcga tagggtcaca      60
attacctgtc aggcttccca atctatcagt acttacctga gctggtatca acagaagcct     120
ggccagccac ccaaaagact gatttacaag gcatccacac ttgcctctgg agtgccttca     180
cgcttcagcg gctccggttc tgggaccgac tttactctga ccatcagtag cctccagcca     240
gaggatttcg ctacatatta ctgtcaaccc aactccggca tagcaaccta cggagccgct     300
```

```
tttggtggcg ggacaaaggt cgaaatcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 316
<211> LENGTH: 412
<212> TYPE: PRT
<213> ORGANISM: Artificial Sequence
<220> FEATURE:
<223> OTHER INFORMATION: Hu DR5 (ECD)-AcTev-Fc-Avi

<400> SEQUENCE: 316

```
Ile Thr Gln Gln Asp Leu Ala Pro Gln Gln Arg Ala Ala Pro Gln Gln
1               5                   10                  15

Lys Arg Ser Ser Pro Ser Glu Gly Leu Cys Pro Pro Gly His His Ile
            20                  25                  30

Ser Glu Asp Gly Arg Asp Cys Ile Ser Cys Lys Tyr Gly Gln Asp Tyr
        35                  40                  45

Ser Thr His Trp Asn Asp Leu Leu Phe Cys Leu Arg Cys Thr Arg Cys
    50                  55                  60

Asp Ser Gly Glu Val Glu Leu Ser Pro Cys Thr Thr Arg Asn Thr
65                  70                  75                  80

Val Cys Gln Cys Glu Glu Gly Thr Phe Arg Glu Glu Asp Ser Pro Glu
                85                  90                  95

Met Cys Arg Lys Cys Arg Thr Gly Cys Pro Arg Gly Met Val Lys Val
            100                 105                 110

Gly Asp Cys Thr Pro Trp Ser Asp Ile Glu Cys Val His Lys Glu Ser
        115                 120                 125

Gly Thr Lys His Ser Gly Glu Ala Pro Ala Val Glu Glu Thr Val Thr
    130                 135                 140

Ser Ser Pro Gly Thr Pro Ala Ser Val Asp Glu Gln Leu Tyr Phe Gln
145                 150                 155                 160

Gly Gly Ser Pro Lys Ser Ala Asp Lys Thr His Thr Cys Pro Pro Cys
                165                 170                 175

Pro Ala Pro Glu Leu Leu Gly Gly Pro Ser Val Phe Leu Phe Pro Pro
            180                 185                 190

Lys Pro Lys Asp Thr Leu Met Ile Ser Arg Thr Pro Glu Val Thr Cys
        195                 200                 205

Val Val Val Asp Val Ser His Glu Asp Pro Glu Val Lys Phe Asn Trp
    210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
            260                 265                 270

Lys Ala Leu Pro Ala Pro Ile Glu Lys Thr Ile Ser Lys Ala Lys Gly
        275                 280                 285

Gln Pro Arg Glu Pro Gln Val Tyr Thr Leu Pro Pro Ser Arg Asp Glu
    290                 295                 300
```

```
Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
            325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
    370                 375                 380

Gln Lys Ser Leu Ser Leu Ser Pro Gly Gly Ser Gly Gly Leu Asn
385                 390                 395                 400

Asp Ile Phe Glu Ala Gln Lys Ile Glu Trp His Glu
                405                 410

<210> SEQ ID NO 317
<211> LENGTH: 388
<212> TYPE: PRT
<213> ORGANISM: Artificial Sequence
<220> FEATURE:
<223> OTHER INFORMATION: Cynom. DR5 (ECD)-AcTev-Fc-Avi

<400> SEQUENCE: 317

Ile Thr Arg Gln Ser Leu Asp Pro Gln Arg Ala Ala Pro Gln Gln
1               5                   10                  15

Lys Arg Ser Ser Pro Thr Glu Gly Leu Cys Pro Pro Gly His His Ile
            20                  25                  30

Ser Glu Asp Ser Arg Glu Cys Ile Ser Cys Lys Tyr Gly Gln Asp Tyr
        35                  40                  45

Ser Thr His Trp Asn Asp Phe Leu Phe Cys Leu Arg Cys Thr Lys Cys
    50                  55                  60

Asp Ser Gly Glu Val Glu Val Asn Ser Cys Thr Thr Thr Arg Asn Thr
65                  70                  75                  80

Val Cys Gln Cys Glu Glu Gly Thr Phe Arg Glu Glu Asp Ser Pro Glu
                85                  90                  95

Ile Cys Arg Lys Cys Arg Thr Gly Cys Pro Arg Gly Met Val Lys Val
            100                 105                 110

Lys Asp Cys Thr Pro Trp Ser Asp Ile Glu Cys Val His Lys Glu Ser
        115                 120                 125

Val Asp Glu Gln Leu Tyr Phe Gln Gly Gly Ser Pro Lys Ser Ala Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255
```

```
Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
        290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Gly Gly Ser Gly Gly Leu Asn Asp Ile Phe Glu Ala Gln Lys Ile
        370                 375                 380

Glu Trp His Glu
385

<210> SEQ ID NO 318
<211> LENGTH: 16
<212> TYPE: PRT
<213> ORGANISM: Artificial Sequence
<220> FEATURE:
<223> OTHER INFORMATION: peptide linker

<400> SEQUENCE: 318

Glu Pro Lys Ser Cys Asp Gly Gly Gly Ser Gly Gly Gly Gly Ser
1               5                   10                  15
```

ANTIBODIES SPECIFIC FOR DR5 AND METHODS OF USE

CROSS REFERENCE TO RELATED APPLICATIONS

This application is a continuation of U.S. patent application Ser. No. 14/231,933, filed Apr. 1, 2014, which claims the benefit of U.S. Provisional Application No. 61/808,128, filed Apr. 3, 2013. The disclosure of each of the foregoing applications is herein incorporated by reference in its entirety.

SEQUENCE LISTING

The present application contains a Sequence Listing which has been submitted in ASCII format via EFS-Web and is hereby incorporated by reference in its entirety. Said ASCII copy, created on Mar. 2, 2018, is named SeqListing_P31434_US_2.txt and is 572,523 bytes in size.

FIELD OF THE INVENTION

The present invention relates to bispecific antibodies comprising a first antigen binding site specific for Death Receptor 5 (DR5) and a second antigen binding site specific for Fibroblast Activation Protein (FAP), antibodies specific for DR5, methods for their production, pharmaceutical compositions containing said antibodies, and uses thereof.

BACKGROUND

Monoclonal antibodies are powerful therapeutic agents in the treatment of cancer since they selectively target antigens which are differentially expressed on cancer cells. Targeting of the TRAIL (TNF related apoptosis inducing ligand) death receptors on cancer cells with agonistic monoclonal antibodies represents a new generation of monoclonal antibody therapy, as they are able to directly induce apoptosis of targeted cells.

Upon binding of TRAIL, death receptors of the TNFR-SF family such as DR4 and DR5 become trimerized. The trimerization induces the extrinsic apoptotic pathway and a complex cascade of events including Caspase activation, which finally result in the killing of the target cells. Apoptosis induction is further enhanced if hyperclustering of DR5 (i.e. the clustering of multiple trimers) takes place. Although death receptors are widely expressed on a variety of cell types, induction of apoptosis via the extrinsic pathway is restricted to tumor cells. Since agonistic DR4 or DR5 binding antibodies are able to cross-link death receptors and hence induce apoptosis, these receptors are interesting targets in cancer therapy. At least eight death receptor targeting molecules entered clinical development and have been assessed in clinical trials for possible treatment of different indications such as advanced solid tumors like colorectal or lung cancers. In addition there have been attempts to treat other indications such as lymphoma and/or multiple myeloma.

Drozitumab, a fully human DR5 agonistic antibody described in US2007/0031414 A1 and WO2006/083971, shows some in vitro apoptotic activity in the absence of cross-linking at high concentrations. However, in vivo data revealed a different mode of action: In FcγR mutant mice (or when antibody variants were used in which FcγR binding was inhibited) Drozitumab was inactive indicating that the in vivo activity of this molecule is mainly dependent on FcγR mediated cross-linking. This molecule was tested up to clinical phase II, seemed to be save (no MTD up to 20 mg/kg was reached) but did not demonstrate any significant efficacy.

Conatumumab (described in EP1922337A), is another fully human DR5 agonistic antibody. The activity of Conatumumab is strictly dependent on cross-linking via Fc receptors. In contrast to Drozitumab this antibody is non-ligand blocking. Also this molecule only showed very limited efficacy in clinical trials.

LBY-135, a chimeric DR5 antibody, exhibits similar characteristics as Conatumumab with respect to cross-linking dependent activity and non-ligand blocking property and did not demonstrate any significant efficacy in monotherapy. In addition, LBY-135 showed signs of immunogenicity in part of the enrolled patients of a phase I trial.

Dulanermin, a recombinantly produced natural ligand of DR4 and DR5 (TRAIL), only showed limited objective responses in clinical trials. The use of the natural ligand has somehow disadvantageous: TRAIL targets multiple receptors including both the death receptors and decoy receptors and, therefore, selectivity is a concern. In addition, TRAIL has a much shorter blood half-life compared with monoclonal anti-DR antibodies, a factor which affects dose and schedule parameters. The very short blood half-life of TRAIL requires large and frequent doses compared with monoclonal anti-DR antibodies. In addition recombinant TRAIL is very difficult and tedious to produce.

The development of all three DR5 agonistic antibodies and the ligand described above was discontinued.

Two additional fully human antibodies, Mapatumumab (anti DR4) and Lexatumumab (anti DR5) are still in development although also these molecules did not exhibit promising efficacy in monotherapy.

Tigatuzumab is a humanized DR5 agonistic antibody which is described as being active in vitro (already at low concentrations) in the absence of secondary cross-linking which of course bears the risk of systemic toxicity issues. However, as all the other described agonistic DR5 antibodies, also this molecule has not demonstrated convincing efficacy in Ph I/Ph II studies so far and the maximally tolerated dose MTD only was demonstrated up to 8 mg/kg.

A different approach to induce apoptosis by targeting a death receptor is pursued with the molecule TAS266, a tetrameric DR5 binding nanobody (WO2011098520A1). Due to the tetravalent configuration of DR5 binding moieties, it is thought that DR5 cross-linking is increased compared to standard bivalent antibodies, which may result in increased activity. However, due to their small size, these molecules have the disadvantage of a rather short half-life (compared to antibodies). In addition there is an increased risk of systemic toxicity since this tetrameric molecule is not targeted to the tumor.

Combining the DR5 antibody Drozitumab with a tumor antigen binding moiety or an antigen present in the stroma surrounding the tumor in a bispecific antibody platform has been described by the inventors of the present application as a new approach to achieve two effects: firstly the DR5 binding antibody can be targeted to the tumor site which could avoid potential systemic toxicity issues (especially when using a DR5 antibody exhibiting cross-linking independent activity). Secondly, this tumor or tumor stroma targeting moiety then also serves as the cross-linking unit to induce DR5 hyperclustering and subsequently tumor site specific apoptosis. The basic concept has been demonstrated using Drozitumab_scFv fusion molecules targeting different tumor types (see WO 2011/039126).

Of particular interest therein were bispecific antibodies binding DR5 and Human Fibroblast Activation Protein (FAP; GenBank Accession Number AAC51668). Human FAP was originally identified in cultured fibroblasts using the monoclonal antibody (mAb) F19 (described in WO 93/05804, ATCC Number HB 8269). Homologues of the protein were found in several species, including mice (Niedermeyer et al., Int J Cancer 71, 383-389 (1997), Niedermeyer et al., Eur J Biochem 254, 650-654 (1998); GenBank Accession Number AAH19190). FAP has a unique tissue distribution: its expression was found to be highly upregulated on reactive stromal fibroblasts of more than 90% of all primary and metastatic epithelial tumors, including lung, colorectal, bladder, ovarian and breast carcinomas, while it is generally absent from normal adult tissues (Rettig et al., Proc Natl Acad Sci USA 85, 3110-3114 (1988); Garin-Chesa et al., Proc Natl Acad Sci USA 87, 7235-7239 (1990)). Subsequent reports showed that FAP is not only expressed in stromal fibroblasts but also in some types of malignant cells of epithelial origin, and that FAP expression directly correlates with the malignant phenotype (Jin et al., Anticancer Res 23, 3195-3198 (2003)). Surprisingly the inventors found that a bispecific antibody targeting FAP in the stroma and DR5 on the tumor cell actually induces apoptosis despite the targets being situated on different cells.

Upon further investigation the inventors of the present application found that the scFv containing bispecific molecules described in WO2011/039126 all have some intrinsic issues with respect to productivity, stability and aggregate formation leading to suboptimal, non-specific activity.

In the present application, novel bispecific antibodies targeting FAP and DR5 are provided. The inventors of the present application developed novel DR5 binding moieties that are only active after crosslinking. Hence induction of tumor cell apoptosis is dependent on DR5 hypercrosslinking via FAP and is independent on Fc/FcR interactions. Therefore in addition to bispecific antibodies specific for FAP and DR5, also novel antibodies binding to DR5 are provided therein.

In contrast, the activity of conventional DR5 targeting molecules as described above is dependent on Fc Receptor (FcR) mediated hyperclustering, and is influenced by the immune infiltration and activation status in the tumor (Li and Ravetch, PNAS 2012; Wilson, Cancer Cell 2011; WO2011098520A1). The Fc/FcR interactions can be impaired by physiological human IgG levels. Thus the activity of conventional DR5 targeting molecules is often limited to a few infiltrating cells (Moessner, Blood 2010). By using a bispecific antibody targeting both DR5 and FAP, the percentage of sensitive tumor cells can be significantly increased by hypercrosslinking via FAP and the risk of an intrinsic resistance to DR5 agonists is decreased. The novel DR5 binding moieties are only active after crosslinking with FAP, which could result in an improved safety and toxicology profile compared to the DR5 binders Apomab and Tigatuzumab. The DR5 agonists that have been tested so far were safe in the clinic, however, these clinical programs have been impeded by a low efficacy of the DR5 targeting molecules.

In addition, the preferred novel DR5 binding moieties bind to a different epitope than Drozitumab.

Importantly the novel DR5 binding moieties can be employed in many bispecific DR5-FAP targeting antibody formats, including both novel and established bispecific formats. In contrast, only C-terminal fusions of a FAP binding moiety are possible with Drozitumab-based bispecific DR5-FAP targeting antibody formats, as any N-terminal fusion to Drozitumab results in inactive molecules. The provision of the new DR5 binding moieties thus significantly expands the possibilities of employing the DR5 targeting moiety in various bispecific DR5-FAP targeting antibody formats. This is particularly important as some bispecific antibody formats have superior characteristics in terms of producability and activity.

Provided therein are novel bispecific antibodies comprising novel DR5 binding moieties and a affinity matured FAP binding moiety.

The bispecific antibodies of the present invention are provided in a bispecific antibody format, wherein one or more crossover-Fab fragments are fused to an IgG molecule. Crossover Fab fragments are Fab fragments wherein either the variable regions or the constant regions of the heavy and light chain are exchanged. Bispecific antibody formats comprising crossover Fab fragments have been described, for example, in WO2009080252, WO2009080253, WO2009080251, WO2009080254, WO2010/136172, WO2010/145792 and WO2013/026831.

So far, only DR5-FAP bispecific antibodies in a scFv containing format have been described (WO2011/039126). In addition to the advantageous properties of the novel DR5 binders disclosed therein, use of a crossover-Fab based bispecific format results in improved yield and less aggregates and side-products during production. In addition, scFv- and scFab-based DR5-FAP targeting bispecific antibodies demonstrated the tendency to form aggregates and therefore bear a higher risk to non-specifically crosslink DR5 even in absence of FAP. Hence these formats have the disadvantage of potentially inducing apoptosis in non-target cells (i.e. healthy cells).

The DR5 and FAP binding moieties of the novel bispecific antibodies provided herein exhibit superior in vivo efficacy compared to conventional DR5 antibodies. The preferred bispecific antibodies of the present invention bind with a high affinity to FAP on the tumor stroma and with a lower affinity to DR5 on the tumor cell. Moreover, the DR5 and FAP targeting bispecific antibodies provided herein do not crossreact with closely related proteins DR4, DcR1, DcR2 (closely related to DR5) and DPPIV (closely related to FAP). In addition it is now for the first time possible to provide a DR5-FAP bispecific antibody in various bispecific formats with no limitation as to the number of valencies of each binding specifity.

To summarize, the novel bispecific DR5-FAP antibodies provided therein are highly specific and potent: They selectively induce apoptosis by DR5 hyperclustering in tumor cells in a FAP dependent manner, with low binding to normal cells.

SUMMARY

The present invention relates to bispecific antibodies combining a Death Receptor 5 (DR5) targeting antigen binding site with a second antigen binding site that targets Fibroblast Activation Protein (FAP). By that the death receptors become cross linked and apoptosis of the targeted tumor cell is induced. The advantage of these bispecific death receptor agonistic antibodies over conventional death receptor targeting antibodies is the specificity of induction of apoptosis only at the site where FAP is expressed as well as the higher potency of these bispecific antibodies due to the induction of DR5 hyperclustering. In addition, novel antibodies binding to DR5 are provided. As outlined above the inventors of the present invention developed novel DR5 binding moieties with superior properties compared to known DR5 binders that are incorporated into novel and advantageous DR5-FAP bispecific antibodies.

In one embodiment, the invention provides a bispecific antibody that binds to death receptor 5 (DR5) and Fibroblast Activation Protein (FAP), comprising at least one antigen binding site specific for DR5, comprising
- (a) a heavy chain CDR1 consisting of SEQ ID NO.:1, SEQ ID NO.:17 and SEQ ID NO.:75;
- (b) a heavy chain CDR2 of SEQ ID NO.:2, SEQ ID NO.:18, SEQ ID NO.:25 and SEQ ID NO.:83;
- (c) a heavy chain CDR3 of SEQ ID NO.:3, SEQ ID NO.:19, SEQ ID NO.:84, SEQ ID NO.:96, SEQ ID NO.:98, SEQ ID NO.:104 and SEQ ID NO.:108;
- (d) a light chain CDR1 of SEQ ID NO.:4, SEQ ID NO.:20, SEQ ID NO.:27 and SEQ ID NO.:86;
- (e) a light chain CDR2 of SEQ ID NO.:5, SEQ ID NO.:21 and SEQ ID NO.:28; and
- (f) a light chain CDR3 of SEQ ID NO.:6, SEQ ID NO.:22, SEQ ID NO.:87, SEQ ID NO.:99, SEQ ID NO.:105, SEQ ID NO.:109 and SEQ ID NO.:97;

and at least one antigen binding site specific for FAP, comprising
- (a) a heavy chain CDR1 of SEQ ID NO.:9 and SEQ ID NO.:33;
- (b) a heavy chain CDR2 of SEQ ID NO.:10 and SEQ ID NO.:34;
- (c) a heavy chain CDR3 of SEQ ID NO.:11 and SEQ ID NO.:35;
- (d) a light chain CDR1 of SEQ ID NO.:12 and SEQ ID NO.:36;
- (e) a light chain CDR2 of SEQ ID NO.:13 and SEQ ID NO.:37;
- (f) a light chain CDR3 of SEQ ID NO.:14 and SEQ ID NO.:38.

In one embodiment, the invention provides a bispecific antibody wherein the antigen binding site specific for DR5 comprises
- (a) a heavy chain CDR1 of SEQ ID NO.:1;
- (b) a heavy chain CDR2 of SEQ ID NO.:2;
- (c) a heavy chain CDR3 of SEQ ID NO.:3;
- (d) a light chain CDR1 of SEQ ID NO.:4;
- (e) a light chain CDR2 of SEQ ID NO.:5;
- (f) a light chain CDR3 of SEQ ID NO.:6 and the antigen binding site specific for FAP comprises
- (a) a heavy chain CDR1 of SEQ ID NO.:9;
- (b) a heavy chain CDR2 of SEQ ID NO.:10;
- (c) a heavy chain CDR3 of SEQ ID NO.:11;
- (d) a light chain CDR1 of SEQ ID NO.:12;
- (e) a light chain CDR2 of SEQ ID NO.:13;
- (f) a light chain CDR3 of SEQ ID NO.:14.

In one embodiment, the bispecific antibody comprises at least one antigen binding site specific for DR5 comprising a variable heavy chain and a variable light chain comprising an amino acid sequence of: SEQ ID NO.:7 and SEQ ID NO.:8; SEQ ID NO.:23 and SEQ ID NO.:24; SEQ ID NO.:26 and SEQ ID NO.:24; SEQ ID NO.:23 and SEQ ID NO.:29; SEQ ID NO.:23 and SEQ ID NO.:30; SEQ ID NO.:26 and SEQ ID NO.:31; SEQ ID NO.:26 and SEQ ID NO.:32; SEQ ID NO.:26 and SEQ ID NO.:30; SEQ ID NO.:23 and SEQ ID NO.:31; SEQ ID NO.:82 and SEQ ID NO.:85; SEQ ID NO.:100 and SEQ ID NO.:101; SEQ ID NO.:102 and SEQ ID NO.:103; SEQ ID NO.:106 and SEQ ID NO.:107; SEQ ID NO.:94 and SEQ ID NO.: 95; and at least one antigen binding site specific for FAP comprising a variable heavy chain comprising an amino acid sequence of SEQ ID NO.:15 and SEQ ID NO.:39; and a variable light chain comprising an amino acid sequence of SEQ ID NO.:16 and SEQ ID NO.:40.

In one embodiment, the bispecific antibody comprises at least one antigen binding site specific for DR5 comprising a variable heavy chain comprising an amino acid sequence of SEQ ID NO.:7 and a variable light chain comprising an amino acid sequence of SEQ ID NO.:8; and at least one antigen binding site specific for FAP comprising a heavy chain variable region comprising an amino acid sequence of SEQ ID NO.:15 and a light chain variable region comprising an amino acid sequence of SEQ ID NO.:16. Preferably said bispecific antibody is human or humanized. In one embodiment, the bispecific antibody comprises an Fc domain, at least one Fab fragment comprising the antigen binding site specific for DR5, and at least one Fab fragment comprising the antigen binding site specific for FAP.

In one embodiment, the bispecific antibody comprises an Fc domain, at least one Fab fragment comprising the antigen binding site specific for DR5, and at least one Fab fragment comprising the antigen binding site specific for FAP, wherein at least one of the Fab fragments is connected to the first or second subunit of the Fc domain via the light chain (VLCL) and at least one Fab fragment is connected to the first or second subunit of the Fc domain via the heavy chain (VHCH1).

In one embodiment, the bispecific antibody comprises
a) an Fc domain,
b) two Fab fragments comprising an antigen binding site specific for DR5,
wherein said Fab fragments are connected at the C-terminus of the constant light chain (CL) to the first or second subunit of the Fc domain,
c) two Fab fragments comprising the antigen binding site specific for FAP, wherein the two Fab fragments are connected at the C-terminus of the constant heavy chain (CH1) to the first or second subunit of the Fc domain.

In one embodiment, the bispecific antibody comprises
a) an Fc domain,
b) two Fab fragments comprising an antigen binding site specific for DR5, wherein said Fab fragments are connected at the C-terminus of the constant heavy chain (CH1) to the first or second subunit of the Fc domain,
c) two Fab fragments comprising the antigen binding site specific for FAP, wherein the two Fab fragments are connected at the C-terminus of the constant light chain (CL) to the first or second subunit of the Fc domain.

In one embodiment, the bispecific antibody comprises an Fc domain, at least one Fab fragment comprising the antigen binding site specific for DR5, and at least one Fab fragment comprising the antigen binding site specific for FAP, wherein either the variable regions or the constant regions of the heavy and light chain of at least one Fab fragment are exchanged.

In one embodiment, the bispecific antibody comprises an Fc domain, two Fab fragments comprising each an antigen binding site specific for DR5, and two Fab fragments comprising each an antigen binding site specific for FAP, wherein either the variable regions or the constant regions of the heavy and light chain of at least one Fab fragment are exchanged.

In one embodiment said bispecific antibody is bivalent both for DR5 and FAP. In one embodiment, the bispecific antibody comprises an Fc domain, two Fab fragments comprising each an antigen binding site specific for DR5, and one Fab fragment comprising an antigen binding site specific for FAP, wherein either the variable regions or the constant regions of the heavy and light chain of at least one Fab fragment are exchanged.

In one embodiment said bispecific antibody is bivalent for DR5 and monovalent for FAP.

In one embodiment, the bispecific antibody comprises an Fc domain, three Fab fragments comprising each an antigen binding site specific for DR5, and one Fab fragment comprising an antigen binding site specific for FAP, wherein either the variable regions or the constant regions of the heavy and light chain of at least one Fab fragment are exchanged.

In one embodiment said bispecific antibody is trivalent for DR5 and monovalent for FAP. In one embodiment, the bispecific antibody comprises an Fc domain, one Fab fragment comprising an antigen binding site specific for DR5, and one Fab fragment comprising an antigen binding site specific for FAP, wherein either the variable regions or the constant regions of the heavy and light chain of at least one Fab fragment are exchanged.

In one embodiment said bispecific antibody is monovalent for DR5 and monovalent for FAP. In one embodiment said bispecific antibody comprises an Fc domain, at least one Fab fragment comprising the antigen binding site specific for DR5, and at least one Fab fragment comprising the antigen binding site specific for FAP, wherein either the variable regions or the constant regions of the heavy and light chain of the Fab fragment(s) comprising an antigen binding site specific for FAP are exchanged. In one embodiment at least one of said Fab fragments is connected to the Fc domain via a peptide linker.

In one embodiment said bispecific antibody comprises an Fc domain, which comprises one or more amino acid substitution that reduces binding to Fc receptors and/or effector function. In one embodiment said one or more amino acid substitution is at one or more positions selected from the group of L234, L235, and P329. In one embodiment each subunit of the Fc domain comprises three amino acid substitutions that abolish binding to an activating or inhibitory Fc receptor and/or effector function wherein said amino acid substitutions are L234A, L235A and P329G.

In one embodiment a bispecific antibody is provided wherein the Fc part of the first heavy chain comprises a first dimerization module and the Fc part of the second heavy chain comprises a second dimerization module allowing a heterodimerization of the two heavy chains of the antibody. In one embodiment the first dimerization module comprises knobs and the second dimerization module comprises holes according to the knobs into holes strategy.

In a further embodiment an antibody that specifically binds to DR5 is provided, comprising
(a) a heavy chain complementarity determining region 1 (CDR1) selected from the group consisting of SEQ ID NO.:1, SEQ ID NO.:17 and SEQ ID NO.:75;
(b) a heavy chain complementarity determining region 2(CDR2) selected from the group of SEQ ID NO.:2, SEQ ID NO.:18, SEQ ID NO.:25 and SEQ ID NO.:83;
(c) a heavy chain complementarity determining region 3 (CDR3) selected from the group of SEQ ID NO.:3, SEQ ID NO.:19, SEQ ID NO.:84, SEQ ID NO.:96, SEQ ID NO.:98, SEQ ID NO.:104 and SEQ ID NO.:108;
(d) a light chain CDR1 selected from the group of SEQ ID NO.:4, SEQ ID NO.:20, SEQ ID NO.:27 and SEQ ID NO.:86;
(e) a light chain CDR2 selected from the group of SEQ ID NO.:5, SEQ ID NO.:21 and SEQ ID NO.:28; and
(f) a light chain CDR3 selected from the group of SEQ ID NO.:6, SEQ ID NO.:22, SEQ ID NO.:87, SEQ ID NO.:99, SEQ ID NO.:105, SEQ ID NO.:109 and SEQ ID NO.:97.

In a further embodiment an antibody that specifically binds to DR5 is provided, comprising (a) a heavy chain CDR1 of SEQ ID NO.:1; (b) a heavy chain CDR2 of SEQ ID NO.:2; (c) a heavy chain CDR3 of SEQ ID NO.:3; (d) a light chain CDR1 of SEQ ID NO.:4; (e) a light chain CDR2 of SEQ ID NO.:5; (f) a light chain CDR3 of SEQ ID NO.:6.

In a further embodiment an antibody that specifically binds to DR5 is provided, comprising a variable heavy chain and a variable light chain comprising an amino acid sequence selected from the group of: SEQ ID NO.:7 and SEQ ID NO.:8; SEQ ID NO.:23 and SEQ ID NO.:24; SEQ ID NO.:26 and SEQ ID NO.:24; SEQ ID NO.:23 and SEQ ID NO.:29; SEQ ID NO.:23 and SEQ ID NO.:30; SEQ ID NO.:26 and SEQ ID NO.:31; SEQ ID NO.:26 and SEQ ID NO.:32; SEQ ID NO.:26 and SEQ ID NO.:30; SEQ ID NO.:23 and SEQ ID NO.:31; SEQ ID NO.:82 and SEQ ID NO.:85; SEQ ID NO.:100 and SEQ ID NO.:101; SEQ ID NO.:102 and SEQ ID NO.:103; SEQ ID NO.:106 and SEQ ID NO.:107; SEQ ID NO.:94 and SEQ ID NO.:95;

In a further embodiment an antibody that specifically binds to DR5 is provided comprising a variable heavy chain comprising an amino acid sequence of SEQ ID NO.:7 and a variable light chain comprising an amino acid sequence of SEQ ID NO.:8.

In a second object the present invention relates to a pharmaceutical composition comprising a bispecific antibody or the antibody that specifically binds to DR5 of the present invention.

In a third object the present invention relates to a bispecific antibody targeting DR5 and FAP or an antibody that specifically binds to DR5 of the present invention for the treatment of cancer. In one preferred embodiment said cancer is pancreatic cancer or colorectal carcinoma. In another embodiment, use of the bispecific antibody or an antibody that specifically binds to DR5 as a medicament is provided. Preferably said use is for the treatment of cancer, preferably pancreatic cancer or colorectal carcinoma.

In further objects the present invention relates to a nucleic acid sequence comprising a sequence encoding a heavy chain of a bispecific antibody or an antibody that specifically binds to DR5 of the present invention, a nucleic acid sequence comprising a sequence encoding a light chain of a bispecific antibody or an antibody that specifically binds to DR5 of the present invention, an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

BRIEF DESCRIPTION OF THE FIGURES

(FIG. 9A) Induction of apoptosis was detected after 24 hrs using a cell death detection ELISA. All tested constructs were used in concentrations of 7 nM and 0.7 nM. Apoptosis induction of target and effector cells is compared to apoptosis of target cells alone. (FIG. 9B) Comparison of co-culture bystander apoptosis induction in Cell Death Detection ELISA (DNA fragmentation) with Drozitumab (+/−Fc cross-linking) vs. bispecific DR5-FAP molecules consisting of a FAP Cross-Fab fused to the C-terminus of Drozitumab heavy chain. The molecule containing the affinity matured FAP binding moiety (28H1) shows superior activity compared to the molecule containing the lower affinity FAP binder.

FIG. 10 shows the results of apoptosis induction on MDA-MB-231 cells by CrossFab molecules cross-linked by recombinant human FAP coated to an ELISA plate. While the control molecule (Drozitumab cross-linked via anti Fc antibody) shows similar apoptosis induction, independent on coating of FAP or an unrelated control protein, the bispecific constructs only exhibited significant apoptosis activity when FAP was coated. With coating of the control plasmid only at highest construct concentration (7 nM) apoptosis could be detected which probably is due to the basal FAP expression of the MDA-MB-231 cell line. Apoptosis activity was similar for both tested CrossFab molecules and in the same range as observed with hyper-cross-linked Drozitumab.

FIG. 17: Results of epitope binding experiments by Surface Plasmon Resonance (Biacore). After binding of a first antibody to human DR5 further binding of additional antibodies to be tested was analyzed. With the exception of clone 422, which might overlap with the Drozitumab epitope, none of the tested new DR5 binders seem to bind to a region on DR5 that overlaps with Drozitumab epitope while among each other they might share at least overlapping epitopes.

FIG. 22A: DR5 binders derived from phage display FIG. 22B: Humanized DR5 binders derived from immunization.

FIG. 26B: 18F11-28H1) in different formats as measured by Cell Death Detection ELISA for DNA fragmentation in MDA-MB-231 cells co-cultured with GM05489 fibroblasts. The standard 2+2 format of Drozitumab-28H1 was compared to the 5E11-28H1 and 18F11-28H1 molecules in 2+2, 2+1 and 3+1 formats at three different concentrations.

| | |
|---|---|
| A: C-terminal crossing of 28H1 (CH1CL) | B: Crossing of entire N-terminal 5E11 Fab |
| C: N-terminal VHVL crossing of 5E11 | D: N-terminal CH1CL crossing of 5E11 |
| E: Complete crossing of C-terminal 28H1 Fab (VHVL) | F: Crossing of C-terminal 28H1 Fab |

Figure 29:
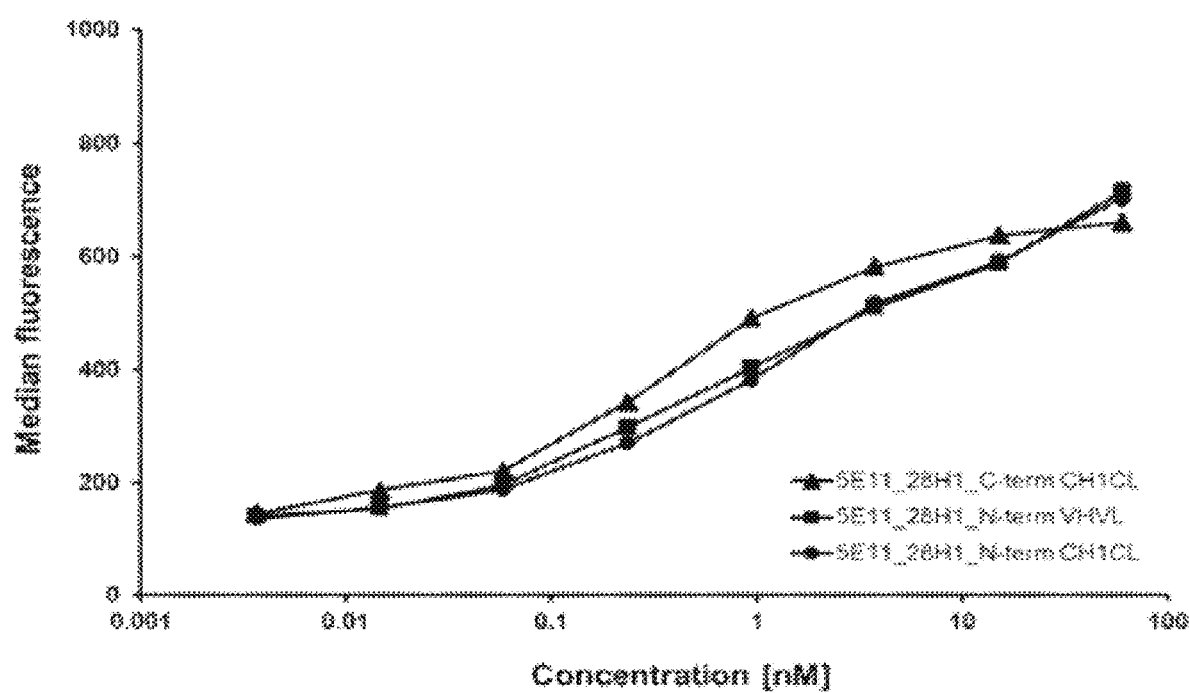

FIG. 29: FACS binding results with 5E11-28H1 Cross-Fabs in three different formats on MDA-MB-231 over a concentration range from 0.0037 to 60 nM. A PE conjugated goat-anti-human Fc (Fab)$_2$ was used for detection.

Figure 30A:
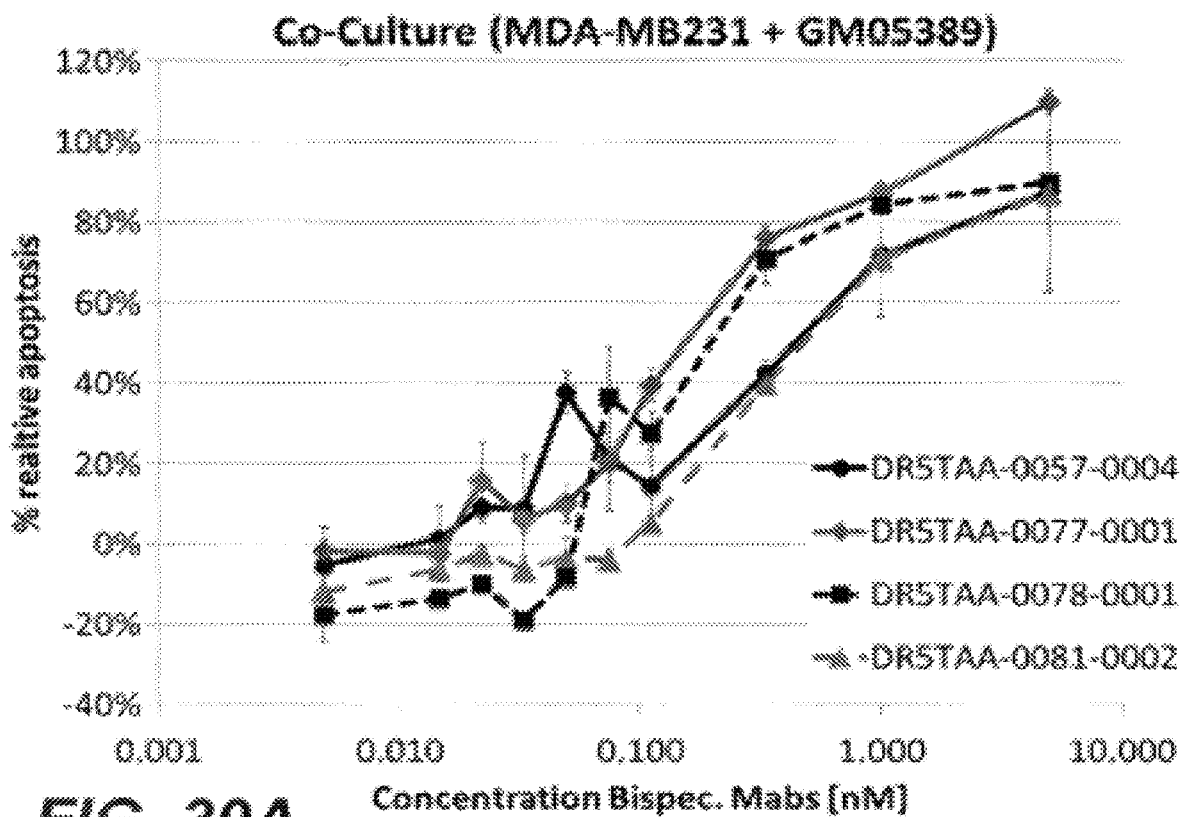
Figure 30B:
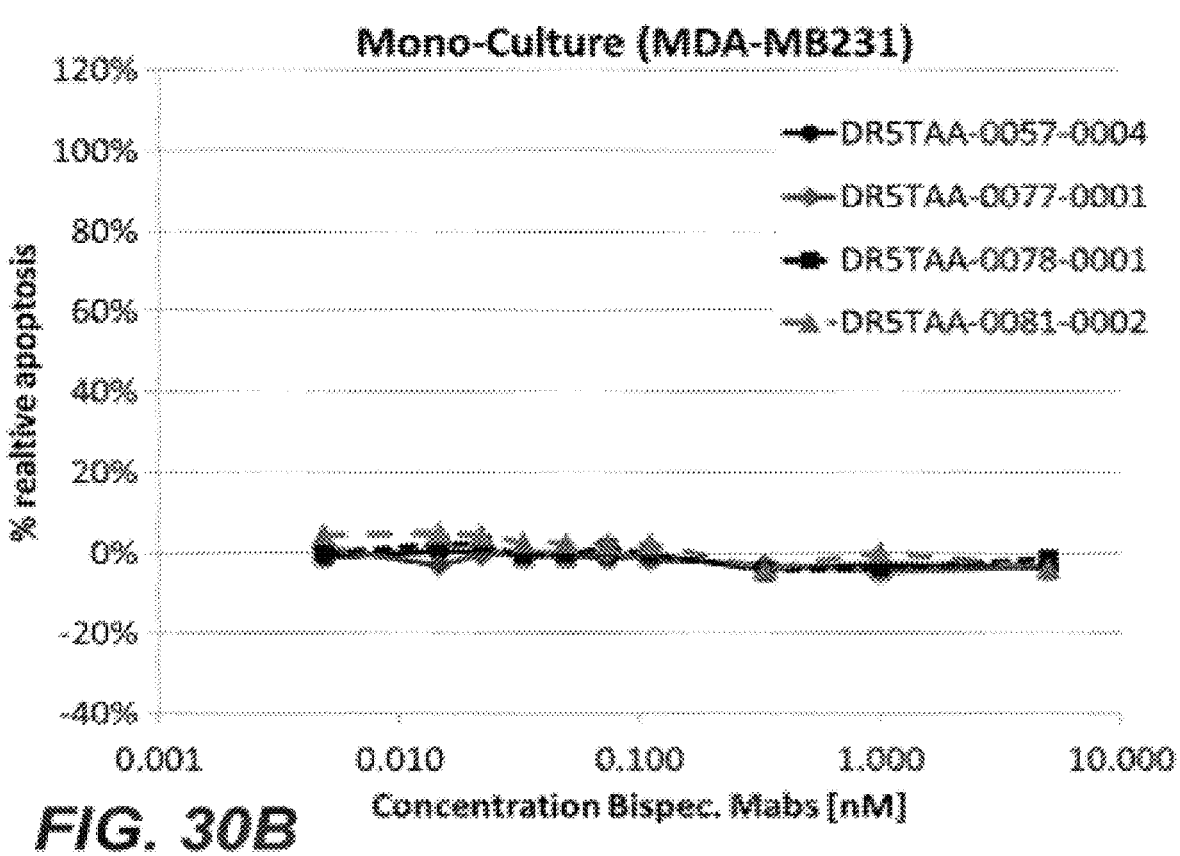
Figure 30C:
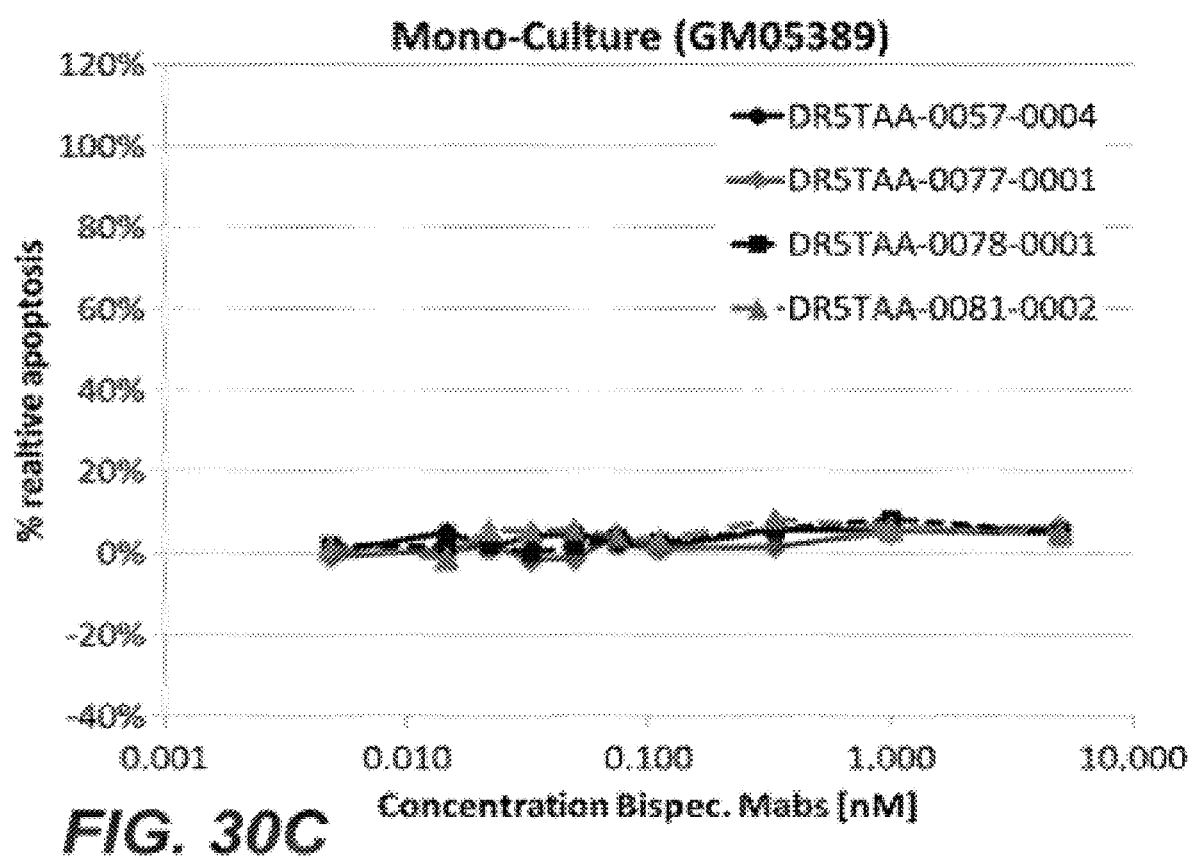

FIGS. 30A-30C: DNA fragmentation ELISA assay for detection of apoptosis. Induction of apoptosis of 4 different CrossMab variants in co- (FIG. 30A) and mono-culture (FIGS. 30B, 30C) settings as detected by DNA fragmentation. All 4 different variants induce apoptosis in tumor cells in the co-culture setting in a comparable dose-dependent manner. In mono-culture settings no apoptosis is induced neither in MDA-MB231 tumor cell line nor in GM05389 fibroblast cell line, pointing out the specificity and FAP-dependency of apoptosis induction of all 4 variants.

Figure 31A:
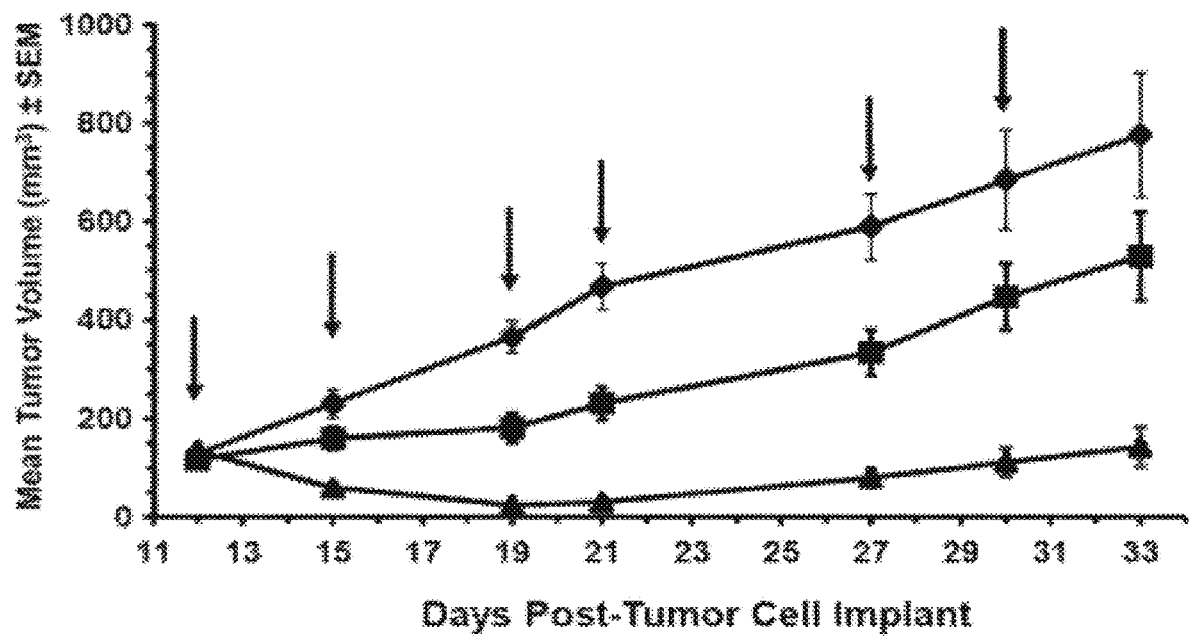
Figure 31B:
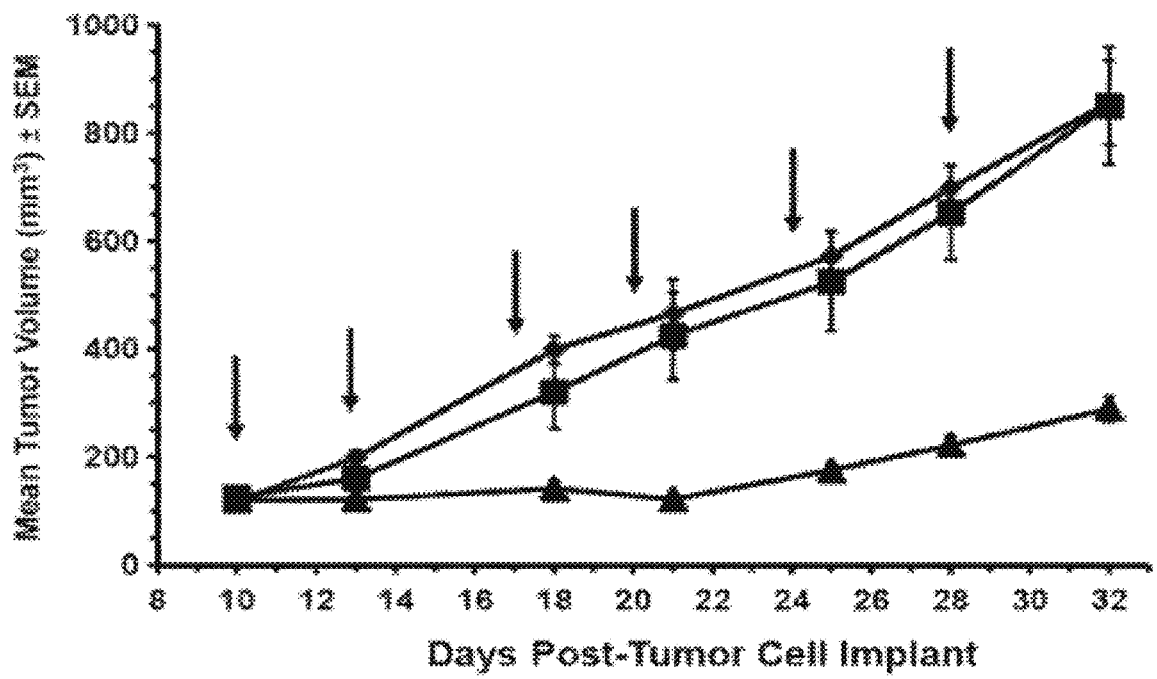

FIGS. 31A and 31B: In vivo efficacy in mouse xenograft tumor models in which DLD-1 (FIG. 31A; nude mice) or MDA-MB-231 (FIG. 31B; SCID-beige mice) cells were co-injected with mu FAP expressing 3T3 fibroblasts to ensure FAP expression in the tumor stroma. After the tumors have been engrafted treatment at 10 mg/kg was performed by i.v. injection of the bispecific Drozitumab-28H1 molecule (triangle) or Drozitumab alone (square) or the vehicle control diamond). Efficacy was determined by means of tumor growth inhibition (TGI) compared to the vehicle control.

Figure 32:
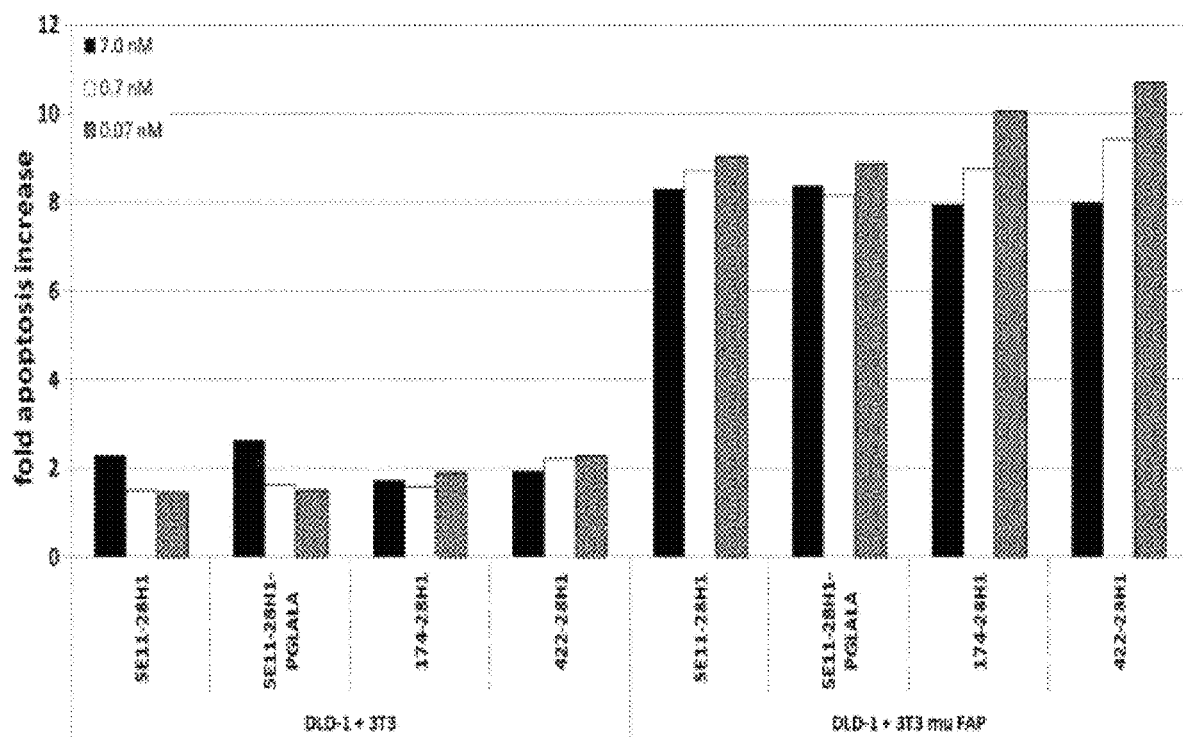

FIG. 32: Evaluation of bispecific DR5-FAP molecules produced for in vivo efficacy experiments for their apoptosis induction activity. The four different molecules were tested in a Cell Death Detection ELISA for DNA fragmentation of DLD-1 cells. 3T3 or recombinant 3T3 cells expressing murine FAP wereused in the co-culture assay for cross-linking. Fold increase of apoptosis in comparison to untreated cells are shown.

Figure 33:
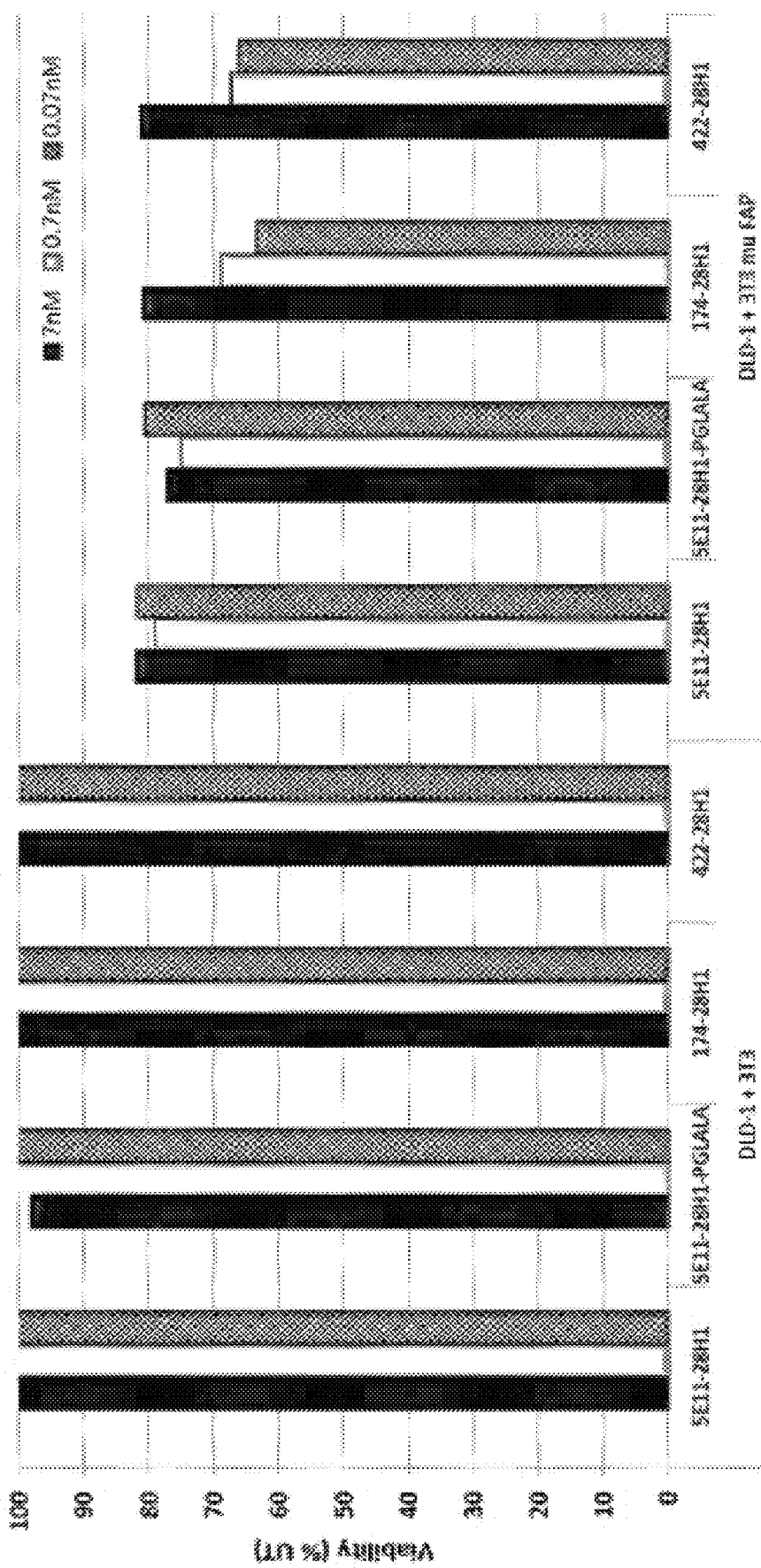

FIG. 33: Viability of DLD-1 cells after treatment with DR5-FAP bispecific antibodies after co-culture assay with 3T3 cells or 3T3 cells expressing murine FAP (Cell Titer-Glo). Percentage of viability compared to an untreated control is given.

Figure 34A:
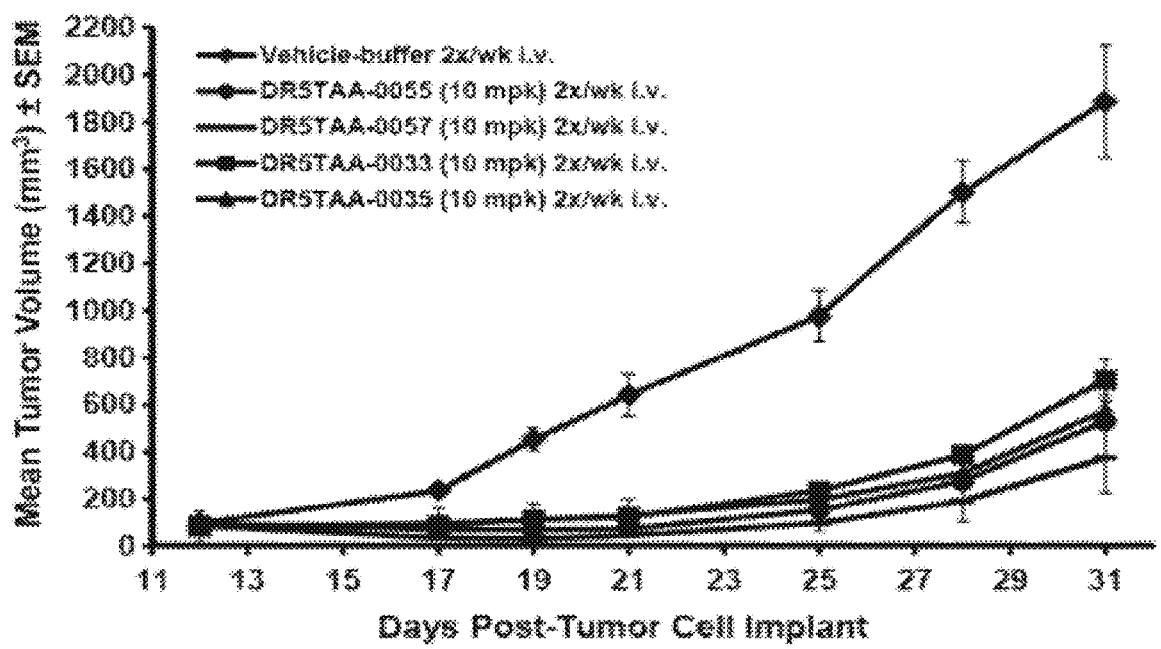
Figure 34B:
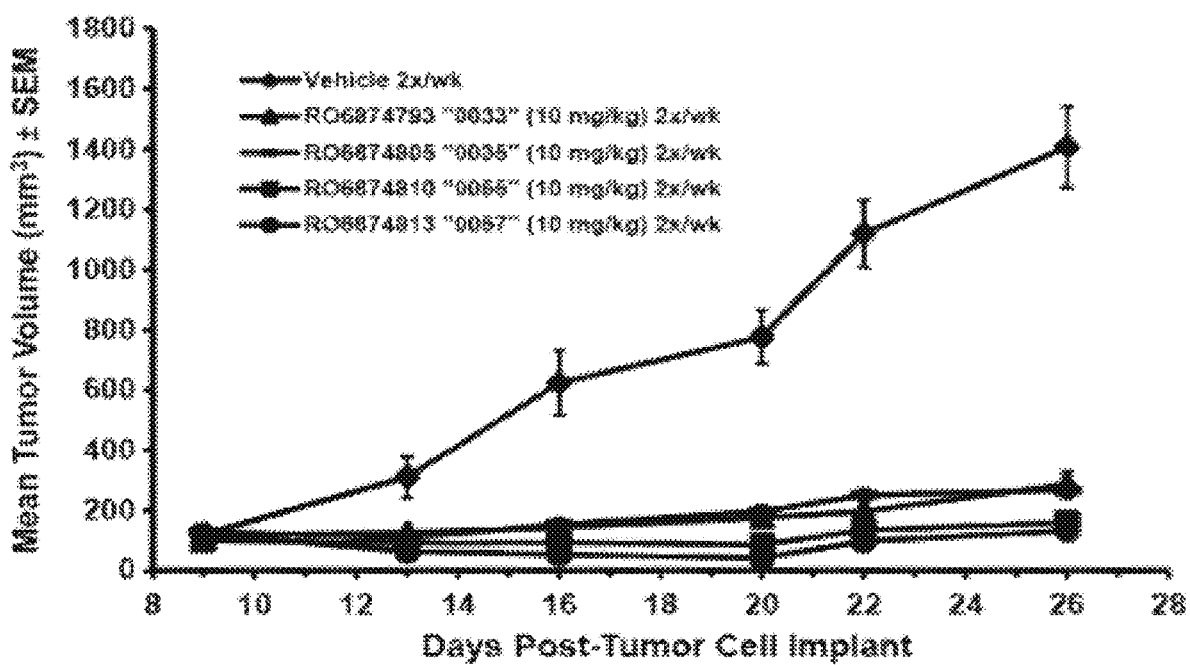

FIGS. 34A and 34B: Mouse xenograft models in which different DR5-FAP bispecific molecules (10 mg/kg) in the 2+2 format were compared to a vehicle control. All constructs contained the 28H1 FAP CrossFab fused to different DR5 binders: 5E11, 174 and 422. In addition one molecule (5E11-28H1) was included in which the Fc carried mutations to inhibit any FcγR interaction (PGLALA). Efficacy was determined as tumor growth inhibition (TGI).

Figure 35A:
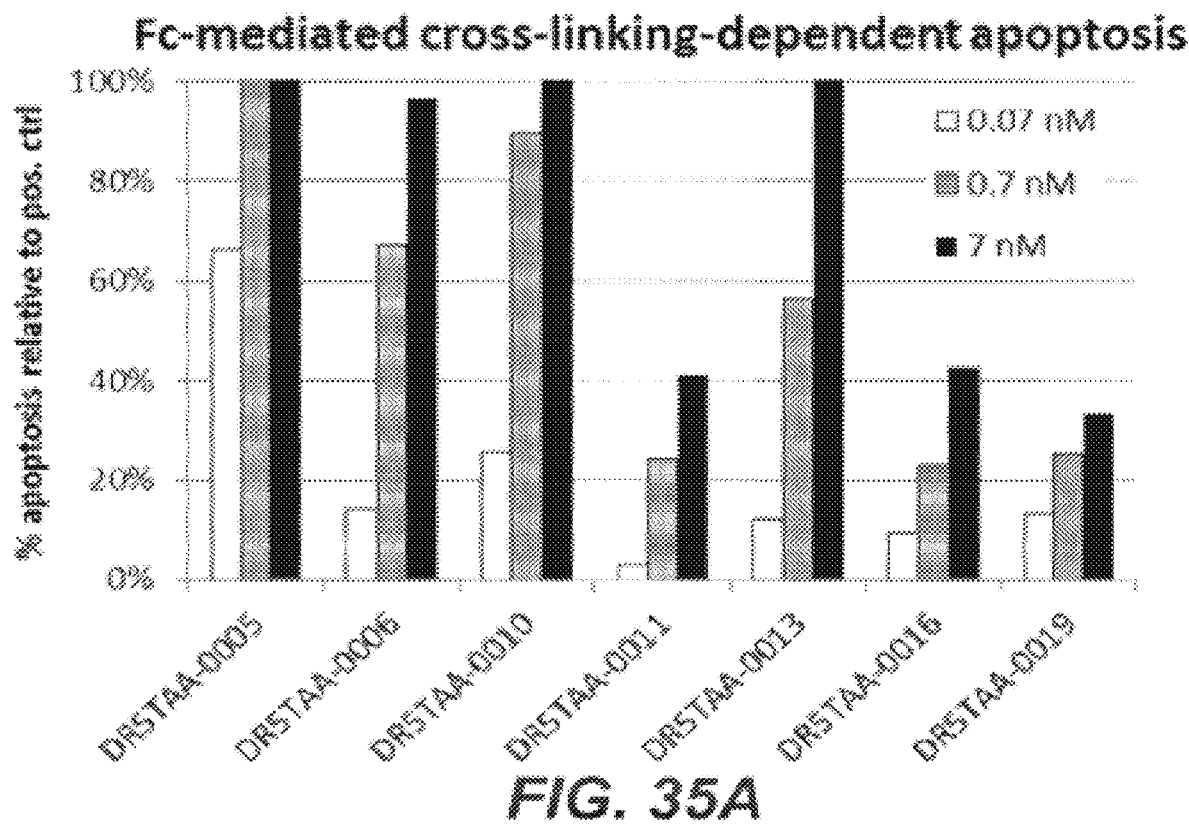
Figure 35B:
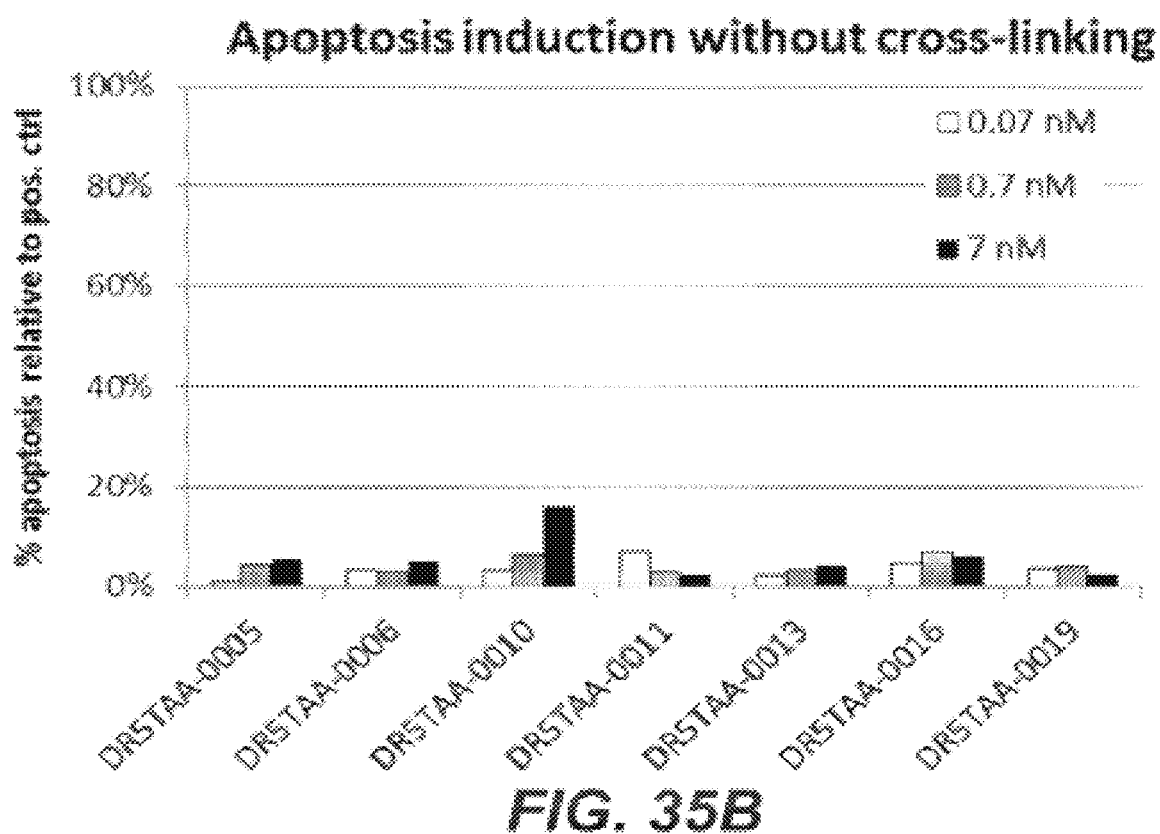

FIGS. 35A and 35B: DNA fragmentation assay. Anti-DR5 antibodies induce cell death upon receptor hyperclustering in a dose-dependent manner. The generated rabbit anti-DR5 antibodies were able to induce apoptosis of MDA-MB231 cells with different potencies but always in a dose-dependent fashion and only after Fc-mediated cross-linking of the DR5 molecules (FIG. 35A). In the absence of an anti-rabbit Fc-specific secondary antibody, no significant cell death was detected (FIG. 35B).

Figure 36A:
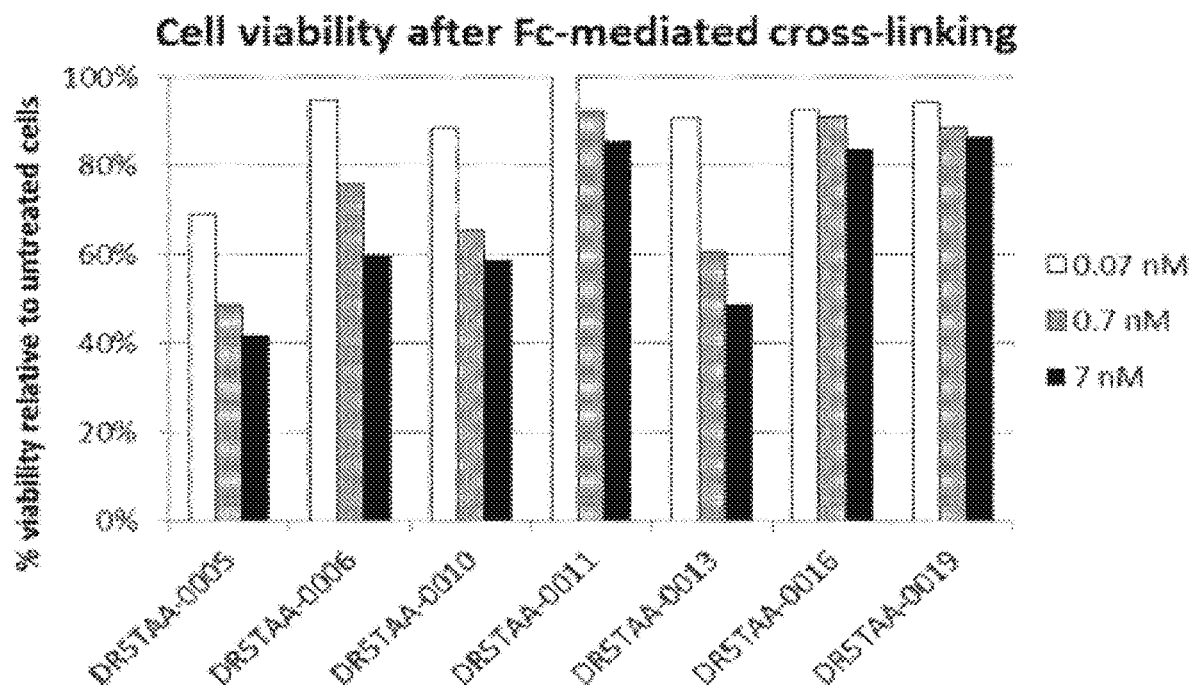
Figure 36B:
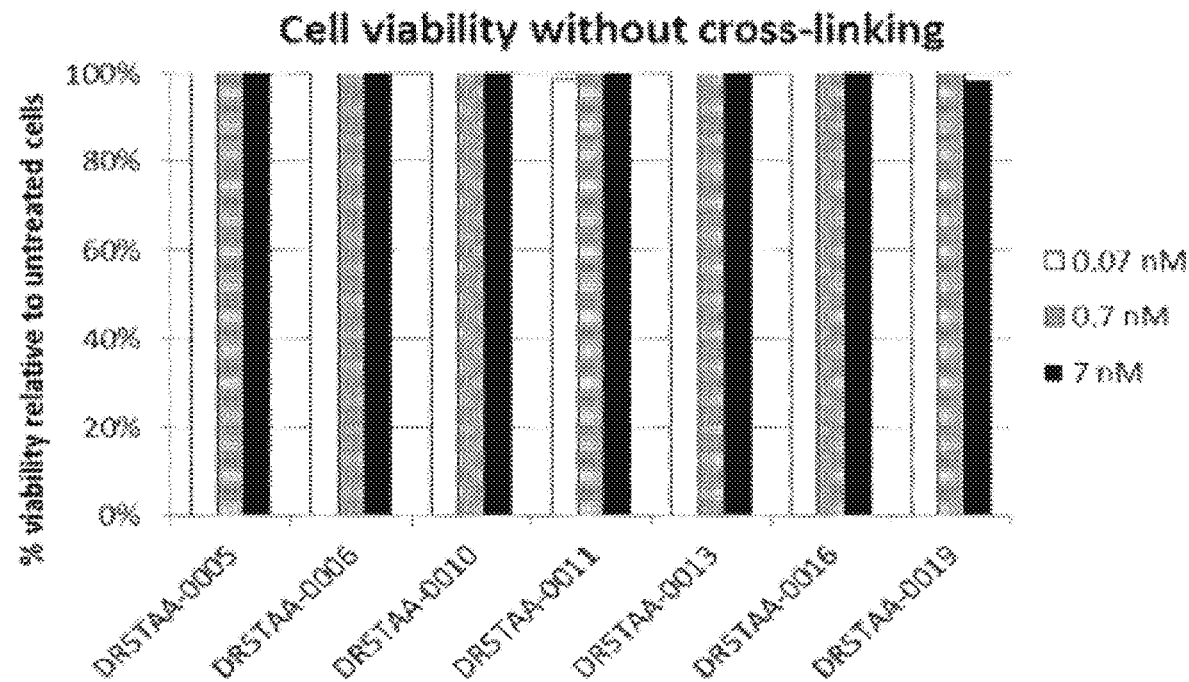

FIGS. 36A and 36B: Cell viability is diminished by anti-DR5 antibodies upon receptor hyperclustering in a dose-dependent manner. The generated rabbit anti-DR5 antibodies were able to decrease the viability of MDA-MB231 cells with varying potencies but always in a dose-dependent fashion and only after Fc-mediated cross-linking of the DR5 molecules (FIG. 36A). In the absence of an anti-rabbit Fc-specific secondary antibody, the cell viability was not affected at any antibody concentration (FIG. 36B).

Figure 37:
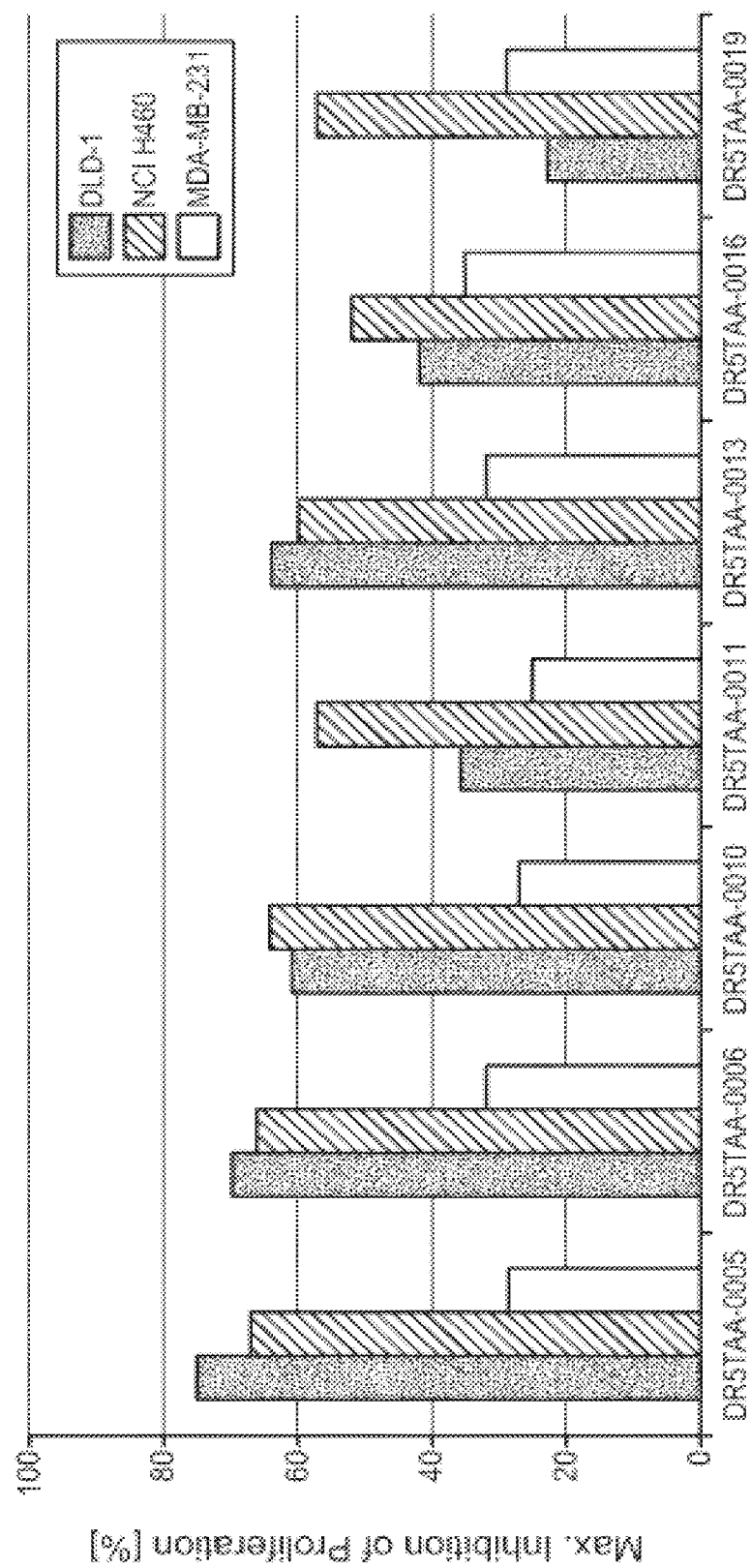

FIG. 37: Analysis of inhibition of cell proliferation (Cell TiterGlo Assay) of three different human tumor cells (DLD-1, NCI H460 and MDA-MB-231) upon treatment with different, cross-linked DR5 antibodies at a concentration of 7 nM.

Figure 38:
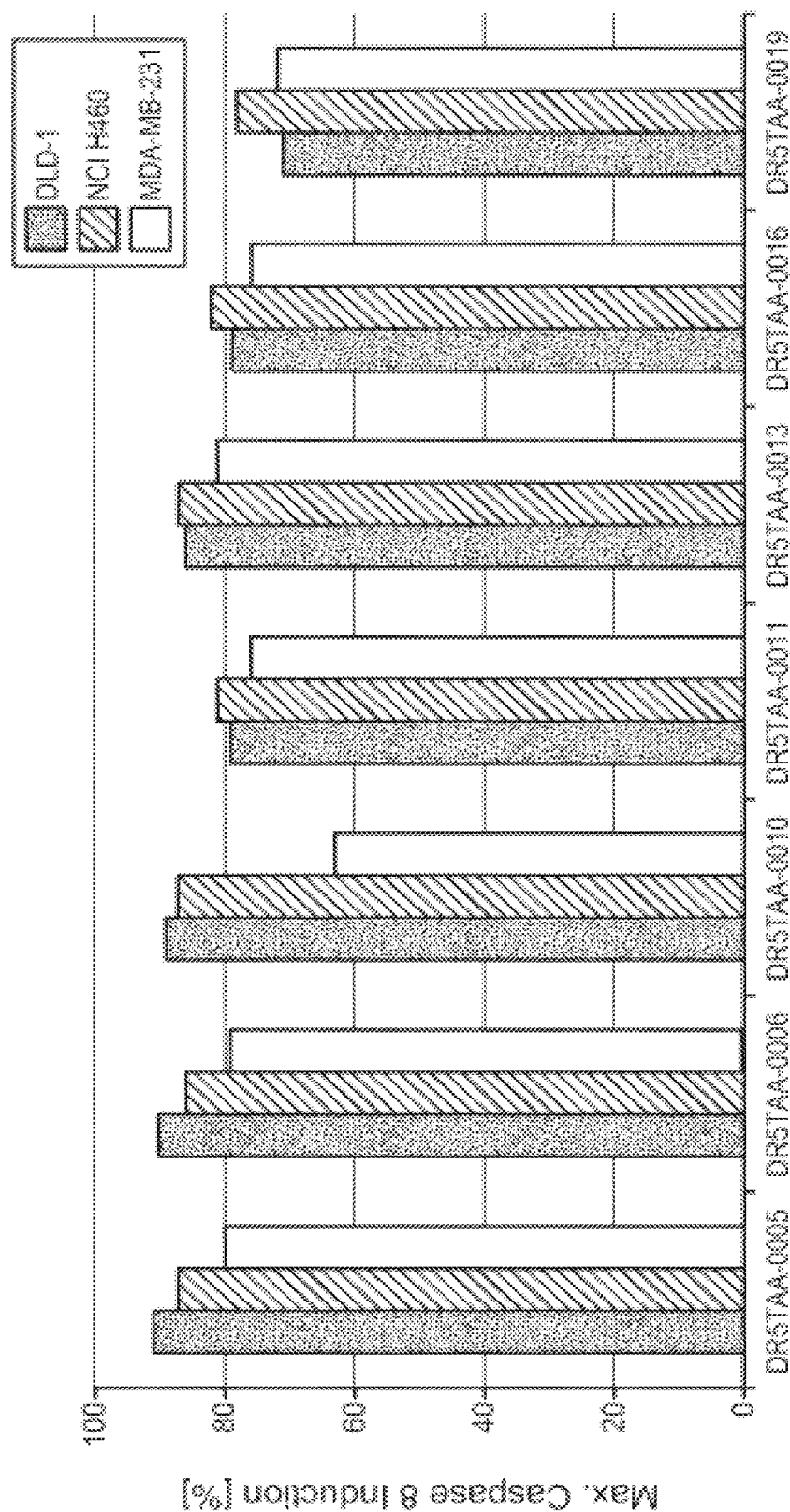

FIG. 38: Evaluation of apoptosis induction measured by Caspase 8 activation in three human tumor cell lines (DLD-1, NCI H460 and MDA-MB-231) after treatment with cross-linked DR5 antibodies at a concentration of 7 nM.

Figure 39:
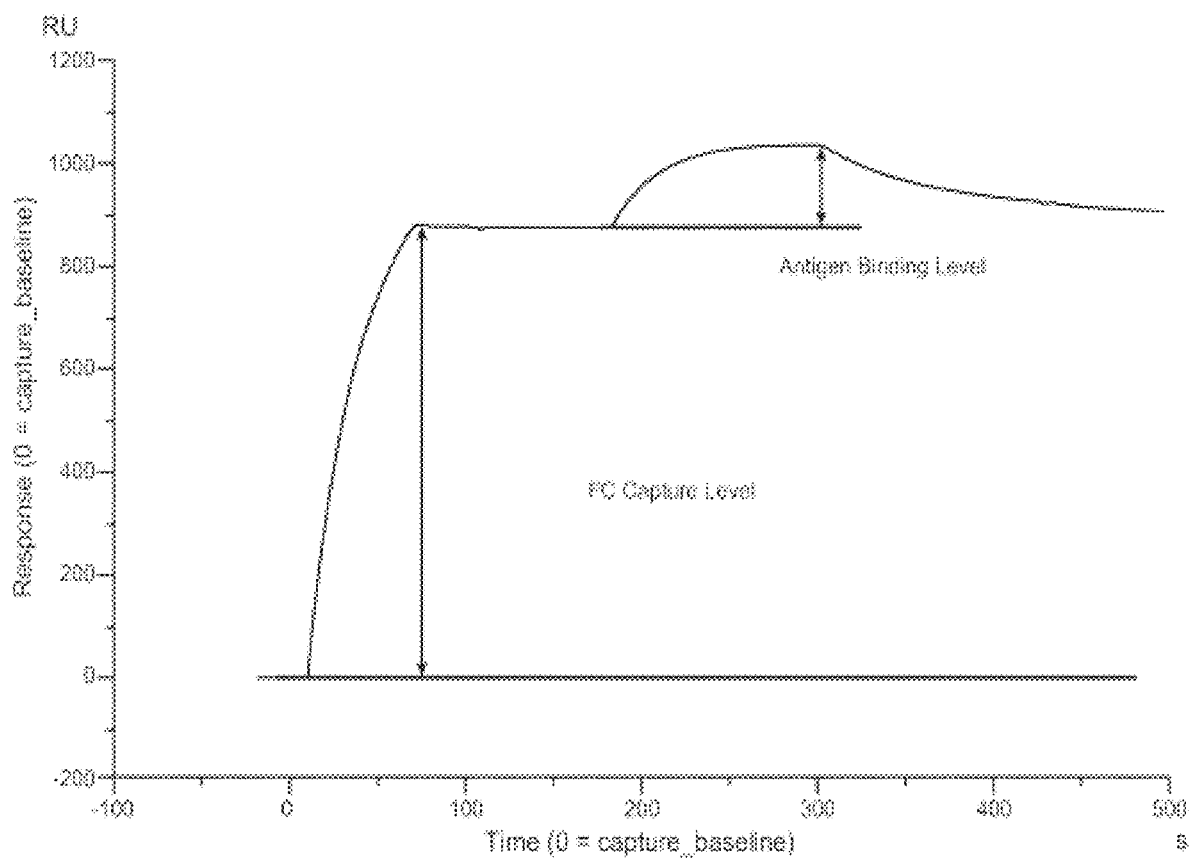

FIG. 39: Relative active concentration of stressed DR5 antibody samples: Exemplary response curve.

Figure 40:
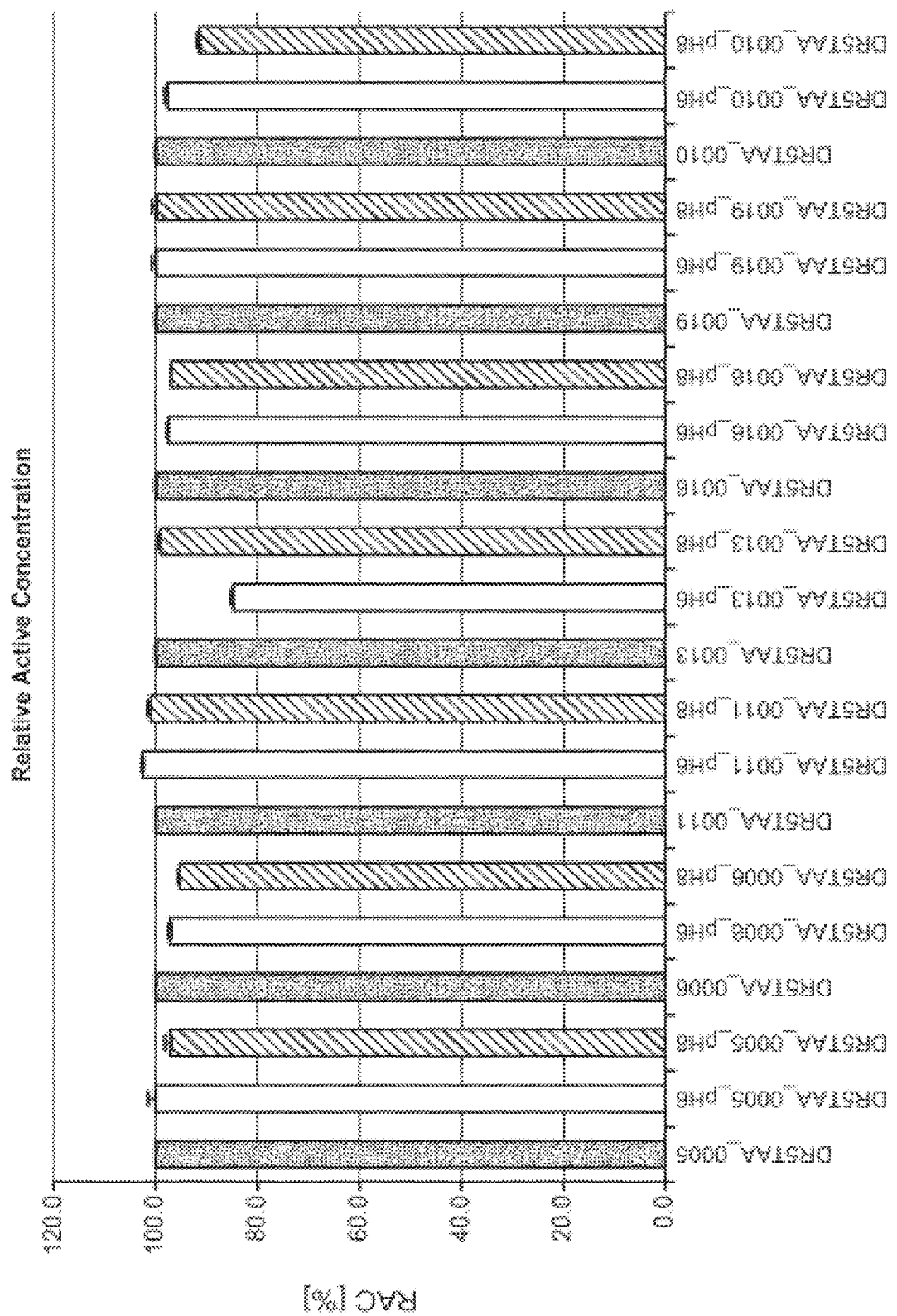

FIG. 40: Relative active concentrations of original and stressed DR5 antibodies derived from immunization.

Figure 41:
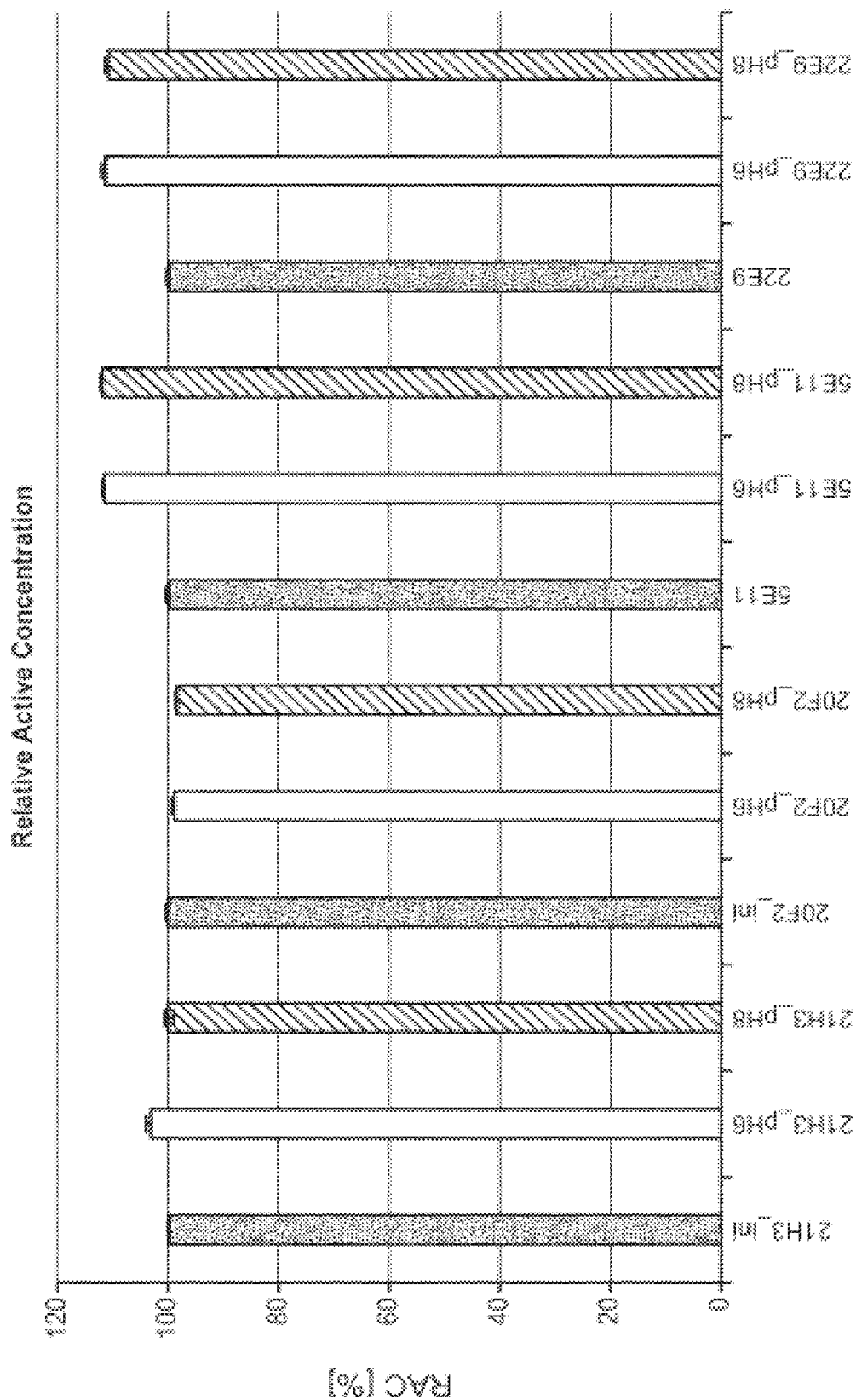

FIG. 41: Relative active concentrations of original and stressed DR5 antibodies derived from phage display.

Figure 42:
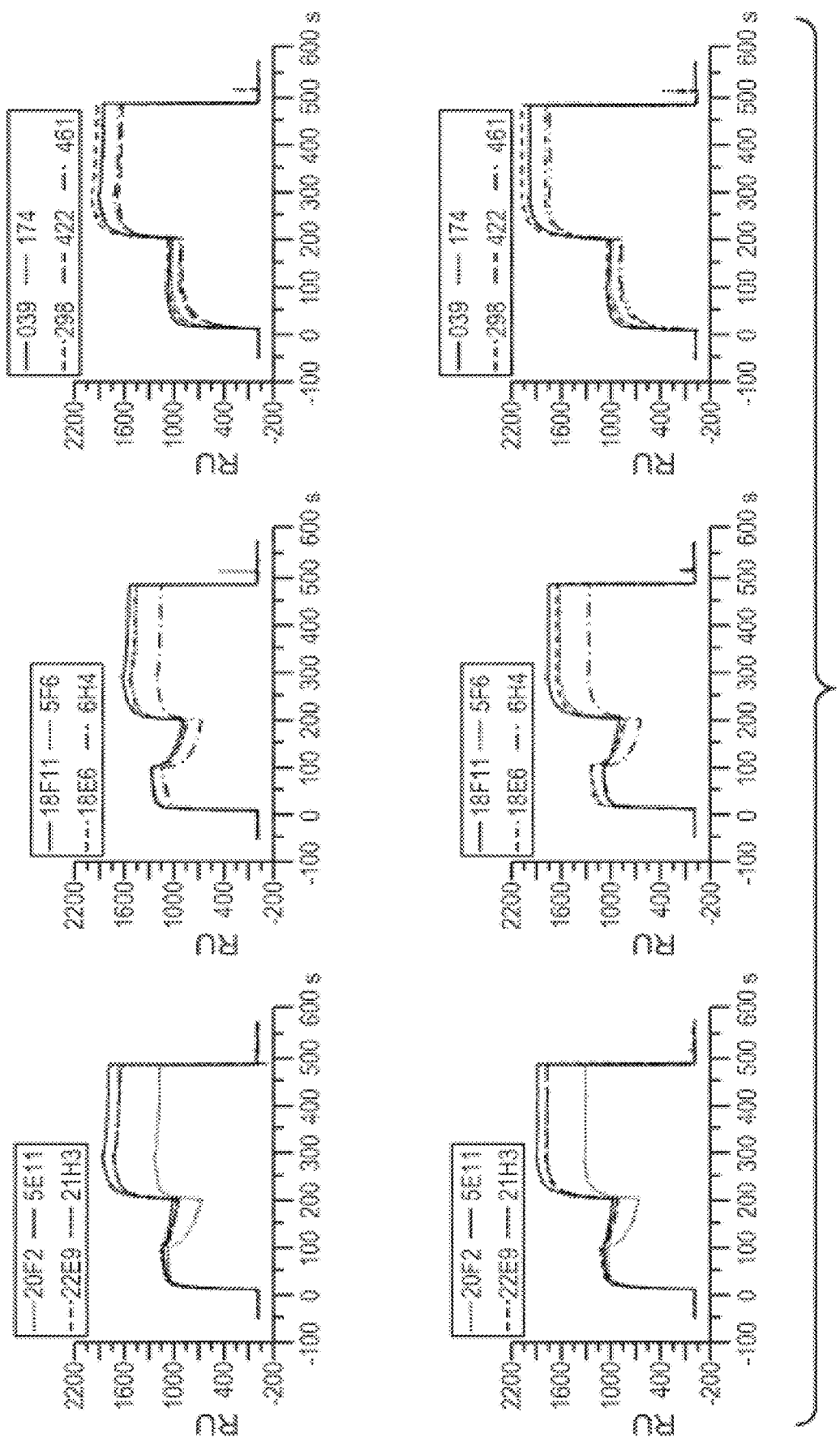

FIG. 42: Surface plasmon resonance (SPR, Biacore) analysis of simultaneous binding of different DR5-FAP bispecific antibodies to both recombinant targets. In a first reaction binding of the bispecific antibodies to recombinant human DR5-Fc was determined, followed by analysis of binding to recombinant human (upper panels) or murine FAP (lower panelS).

Figure 43A:
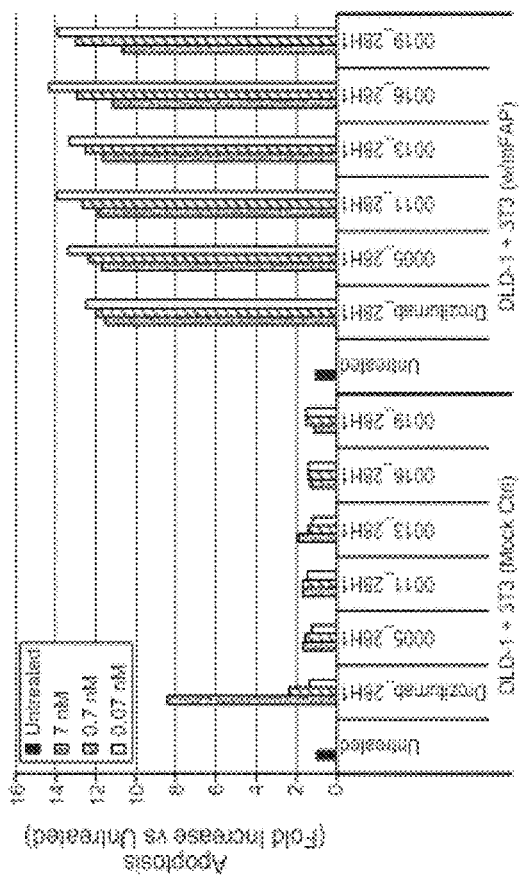
Figure 43B:
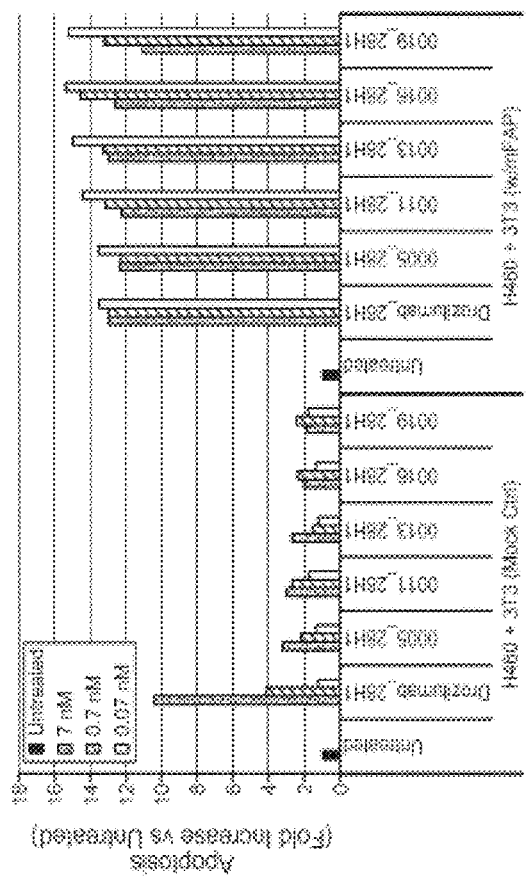

FIGS. 43A and 43B: Induction of apoptosis in DLD-1 and H460 tumor cell lines by 2+2 bispecific constructs in co-culture assays as detected by DNA fragmentation. While a bispecific construct containing Drozitumab as DR5-binding component already induces apoptosis in the absence of FAP, all constructs containing new DR5 binders derived by immunization only induce apoptosis in the presence of FAP. Constructs with newly developed DR5 binders, such as 0011-28H1 and 0016-28H1, are able to induce apoptosis to a higher extent especially at low concentrations as compared to the Drozitumab containing bispecific construct.

Figure 44A:
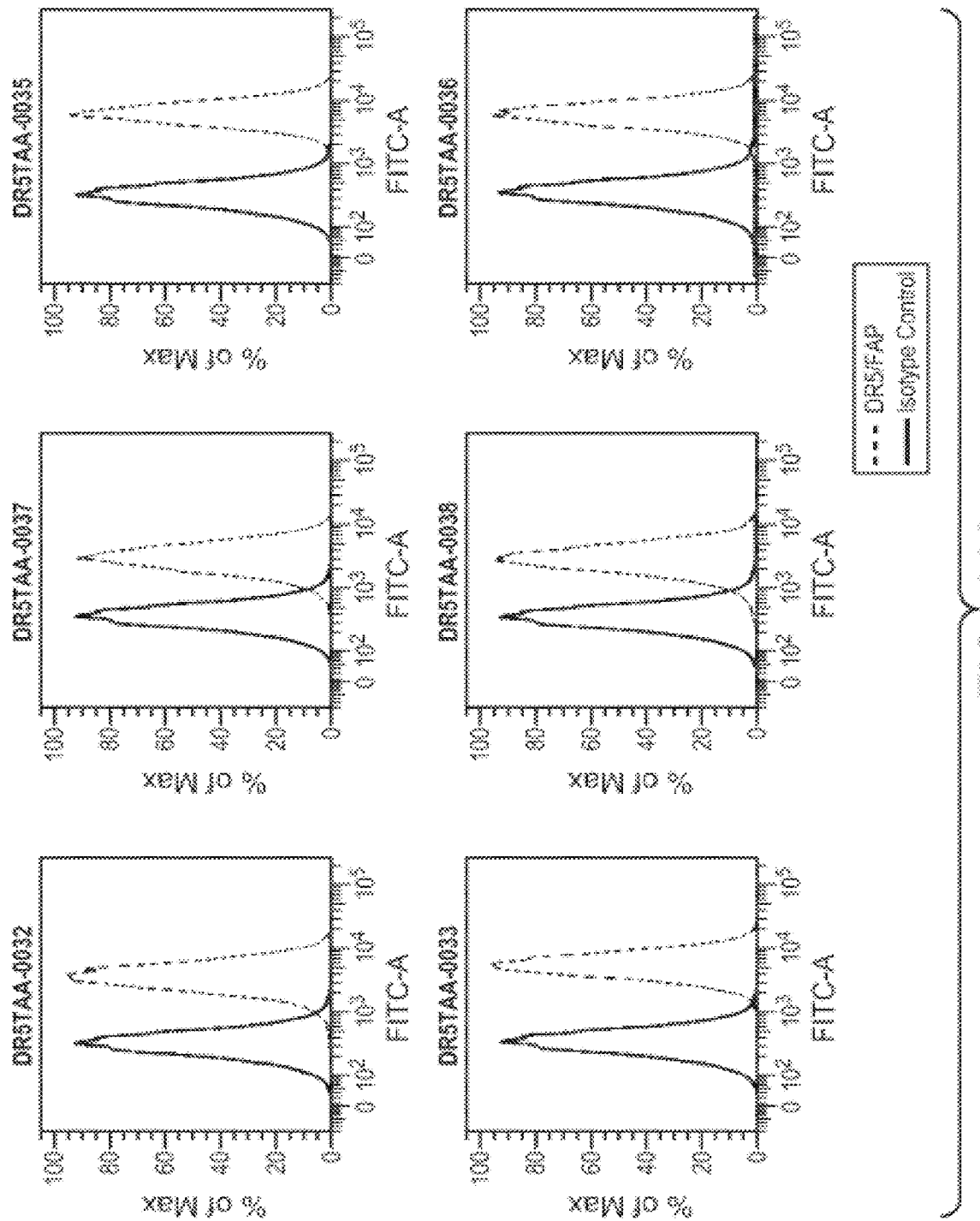
Figure 44B:
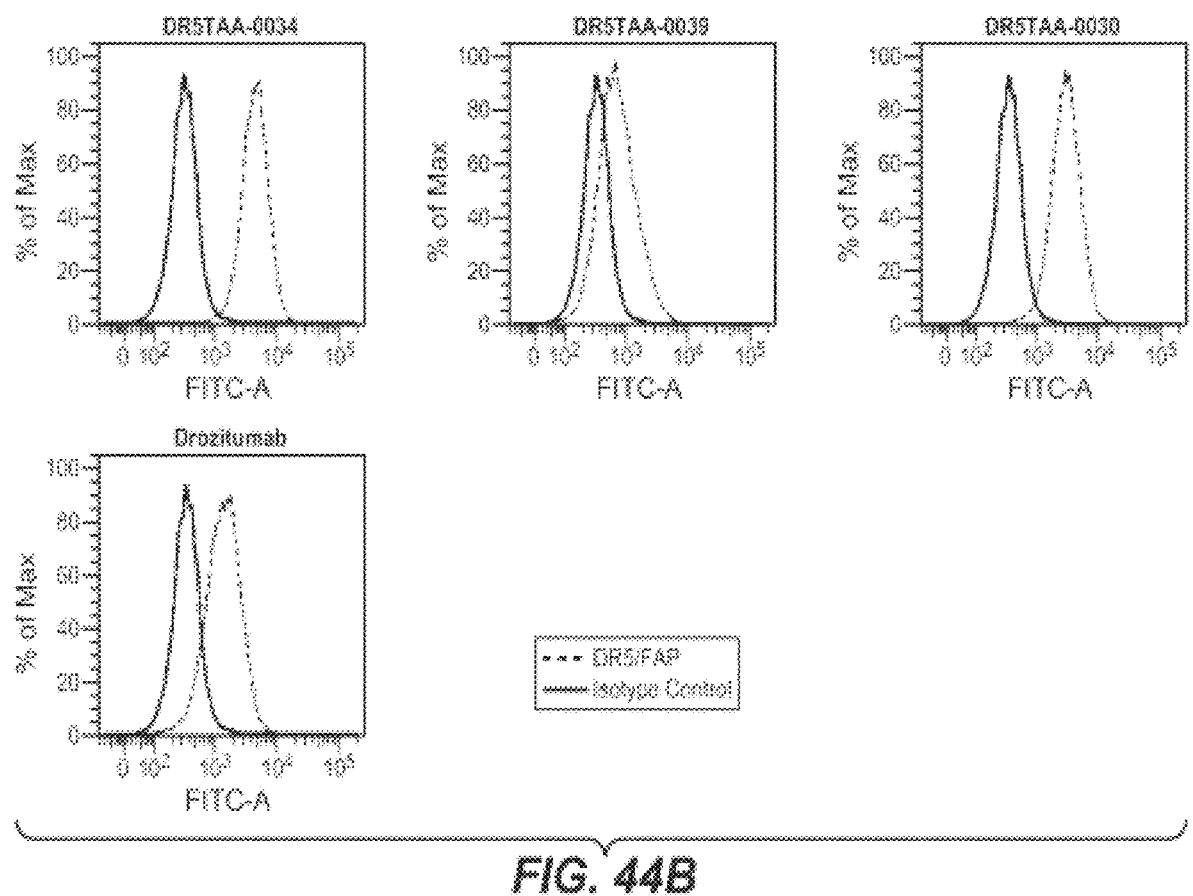

FIGS. 44A and 44B: Binding of anti-DR5-FAP bispecific 2+2 constructs to the DR5-expressing tumor cell line MDA-MB-231 as measured by flow cytometry analysis.

Figures 1, 45A:
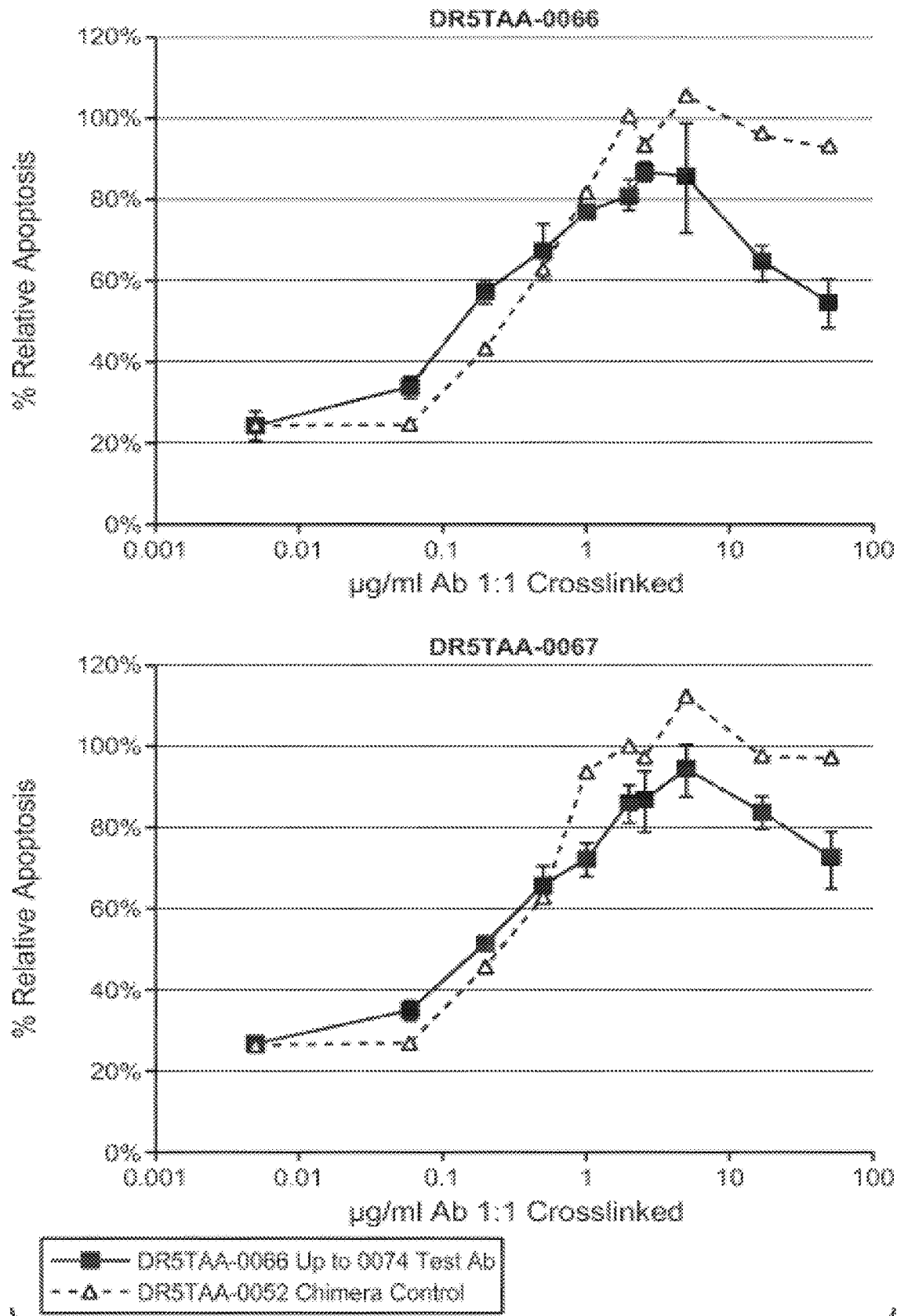
Figures 2, 45A:
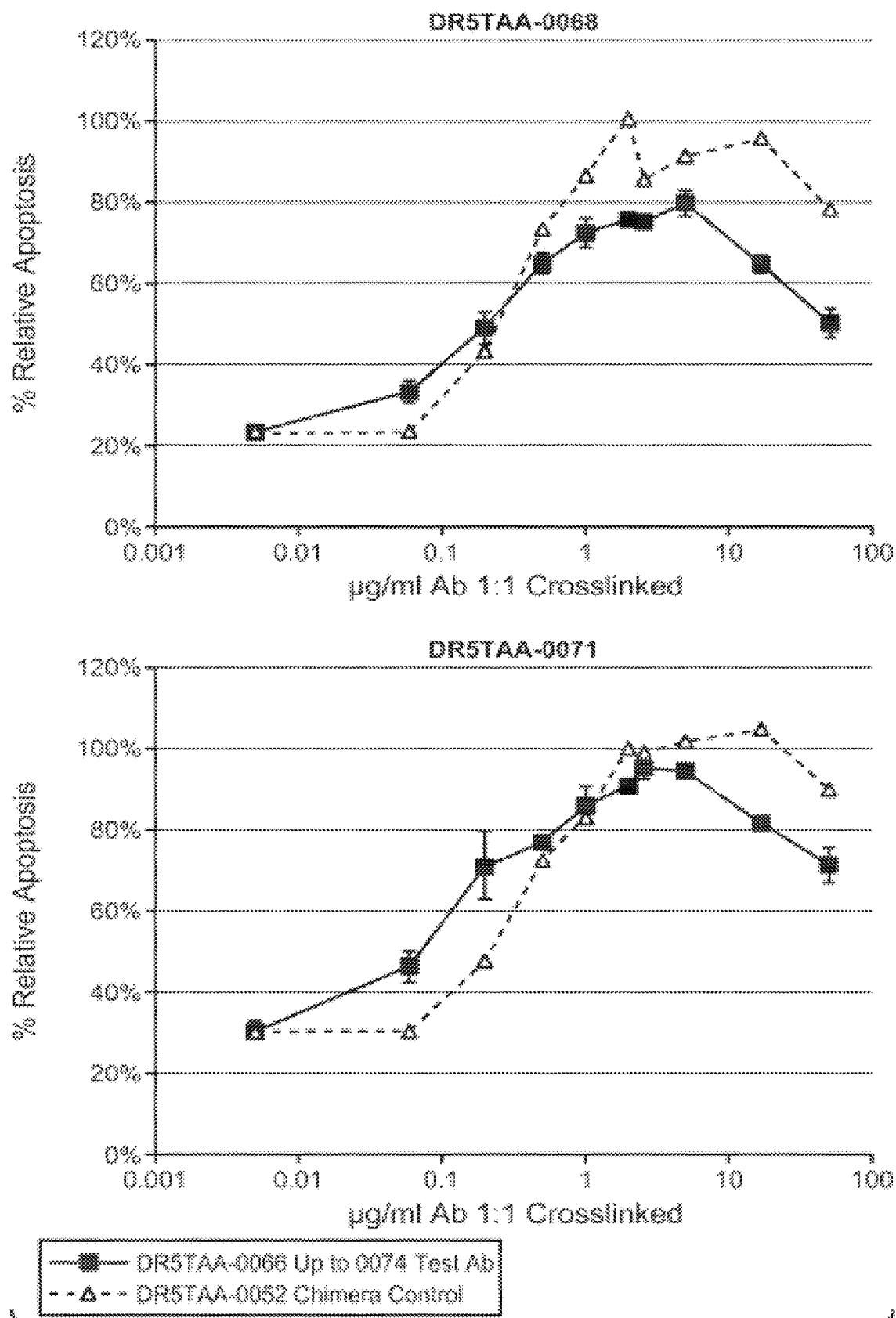
Figures 3, 45A:
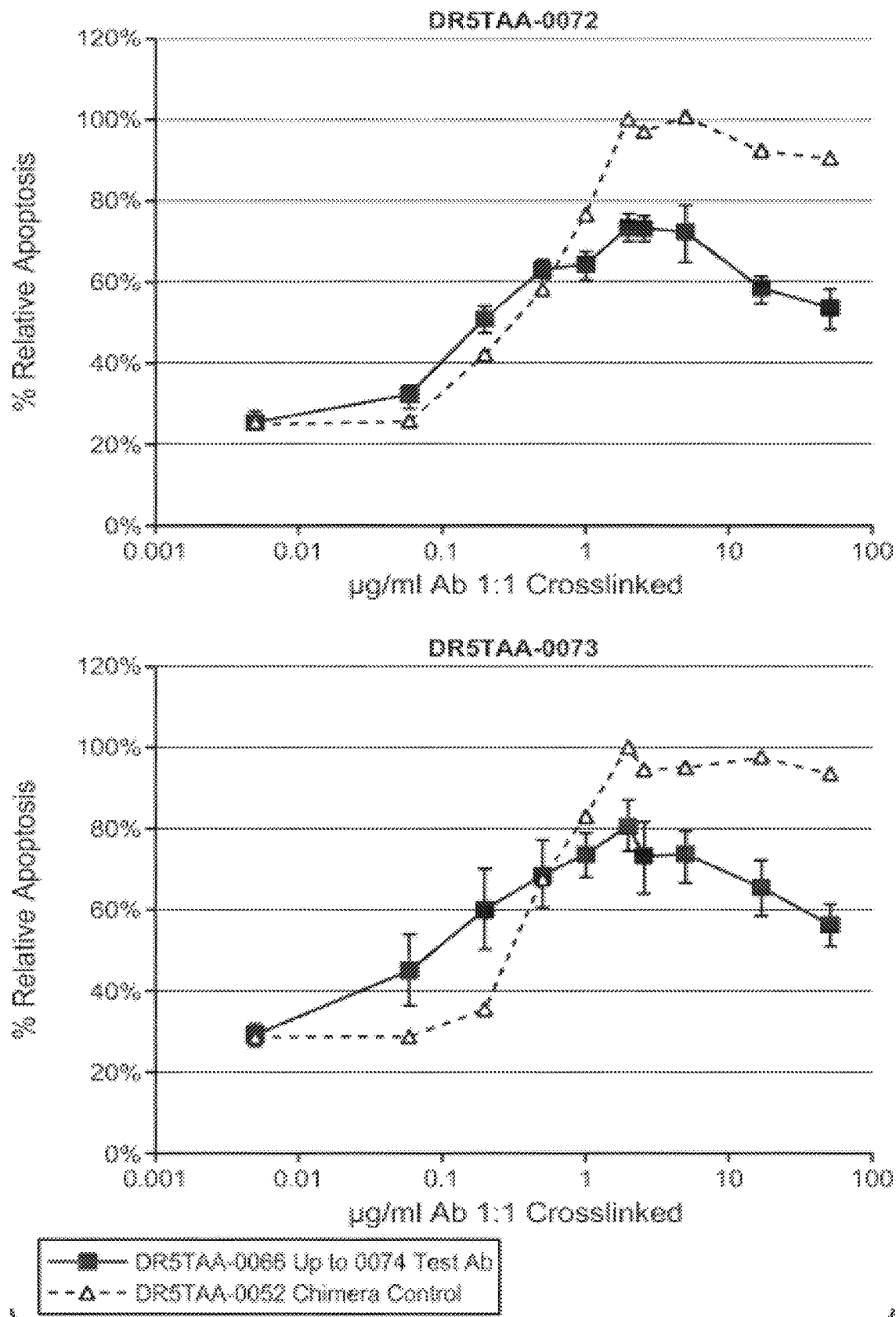
Figures 4, 45A:
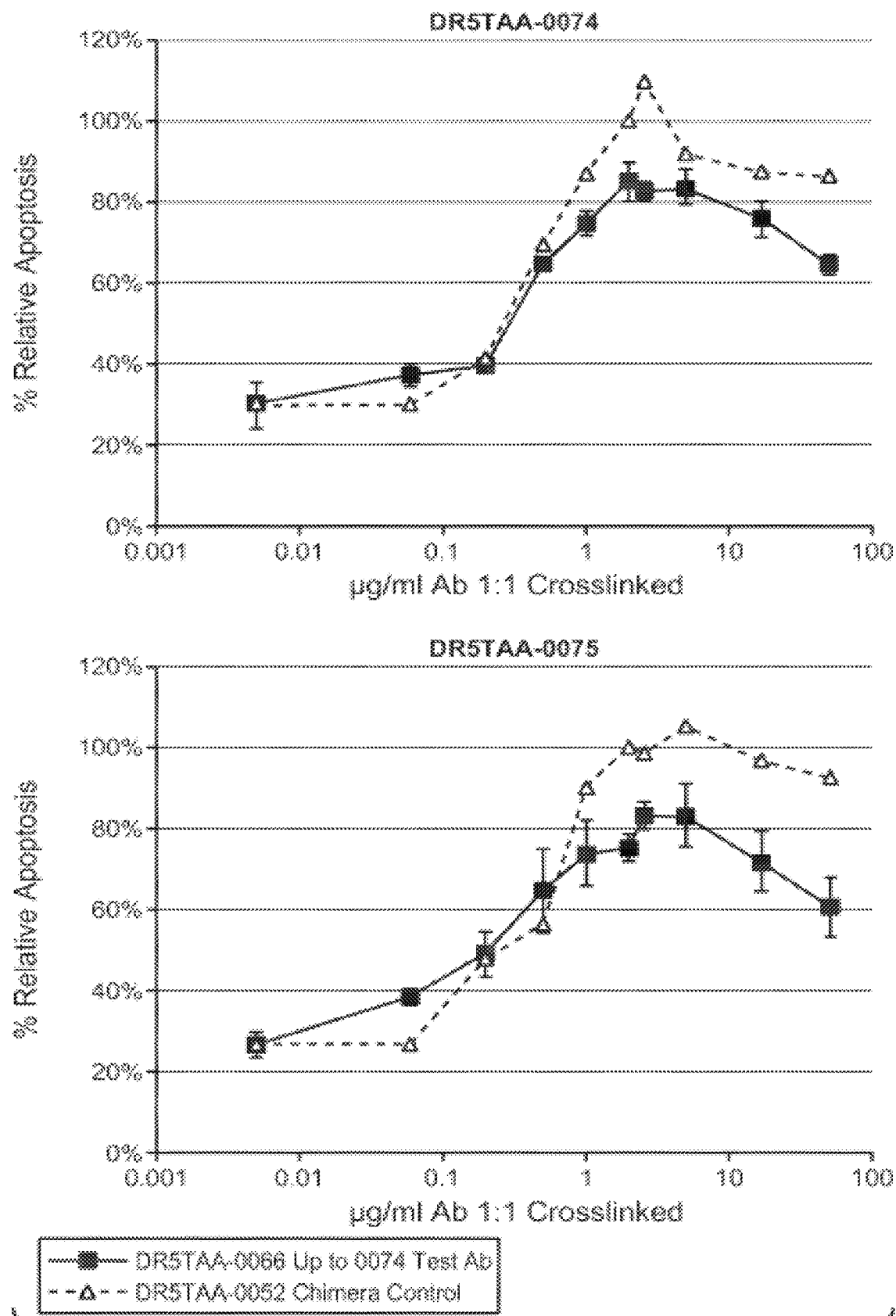
Figure 45B:
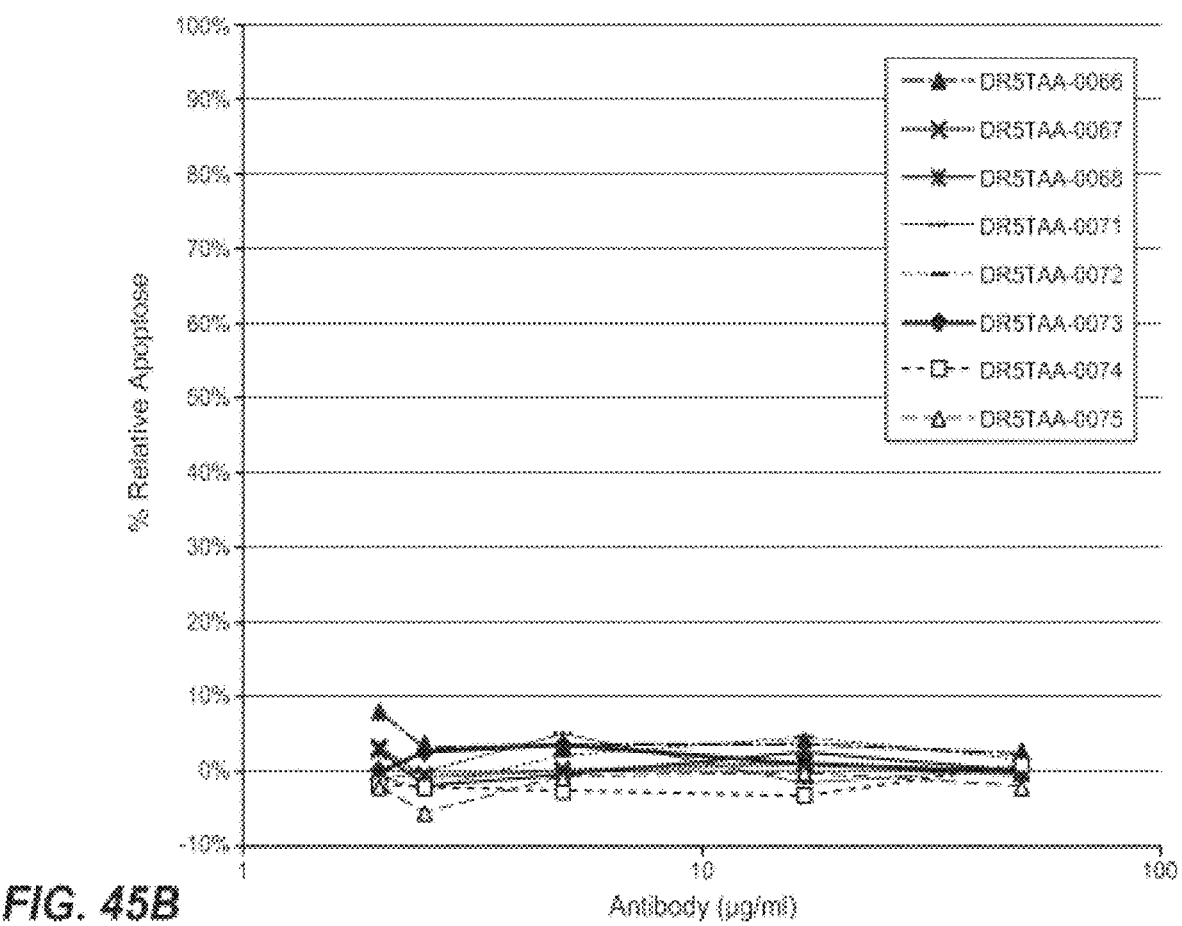

FIGS. 45A-1 to 45A-4: Induction of apoptosis of humanized variants after crosslinking as detected by DNA fragmentation (Cell Death Detection ELISA): Humanized Variants of DR5TAA-0011 (DR5TAA-0066-DR5TAA-0075, black lines) induce apoptosis upon crosslinking with secondary antibody in a dose-dependent manner. Several humanized variants, such as DR5TAA-0067, DR5TAA-0071, DR5TAA-0074 and DR5TAA-0075, are able to induce apoptosis in a similar manner concerning maximum of induction and dose-dependency as compared to the chimeric variant (DR5TAA-0052, grey lines). FIG. 45B: Absence of induction of apoptosis of humanized variants without additional crosslinking as detected by DNA fragmentation (Cell Death Detection ELISA): Humanized Variants of DR5TAA-0011 (DR5TAA-0066-DR5TAA-0075) induce no apoptosis if not crosslinked by a secondary antibody.

Figure 46:
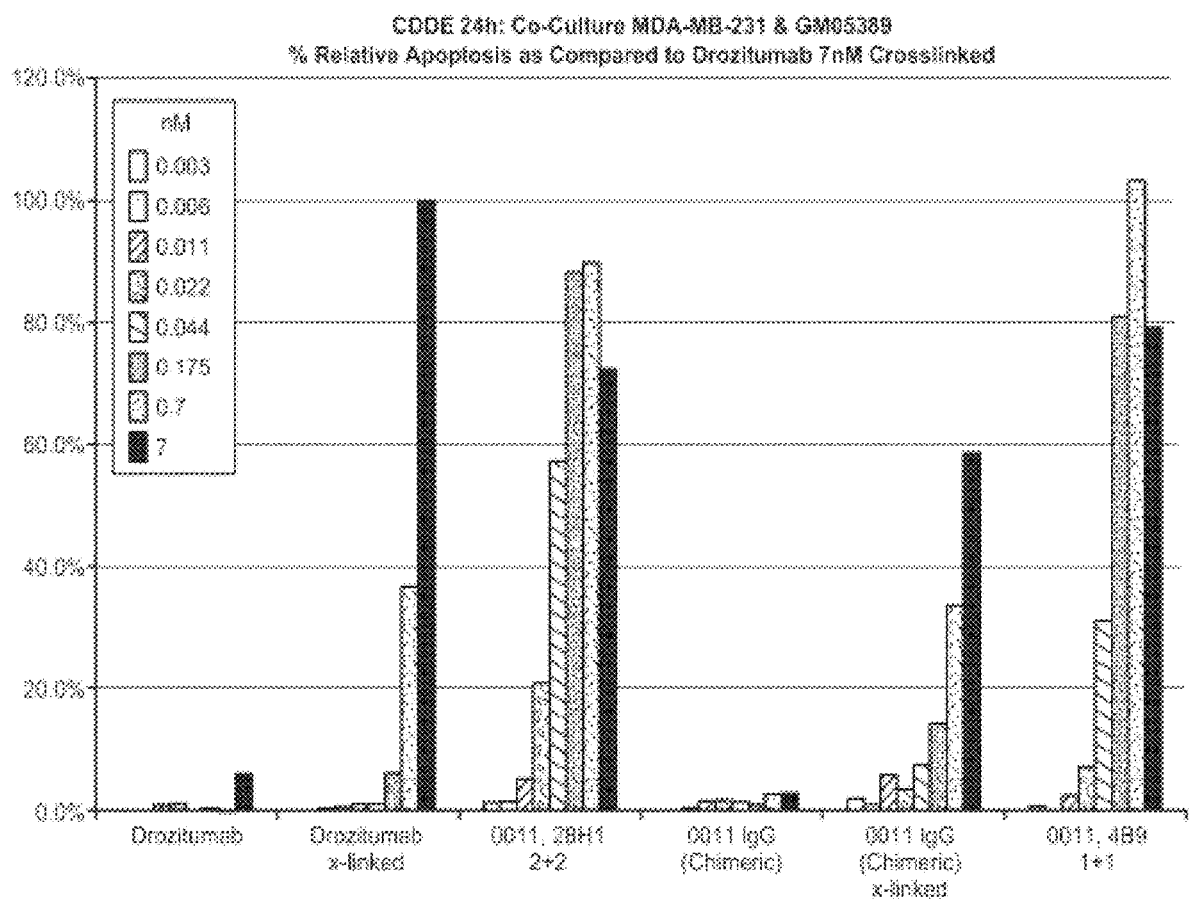

FIG. 46: Comparable induction of cell death in a co-culture system by bispecific anti-DR5-FAP antibodies in 1+1 and 2+2 formats.

Figure 47A:
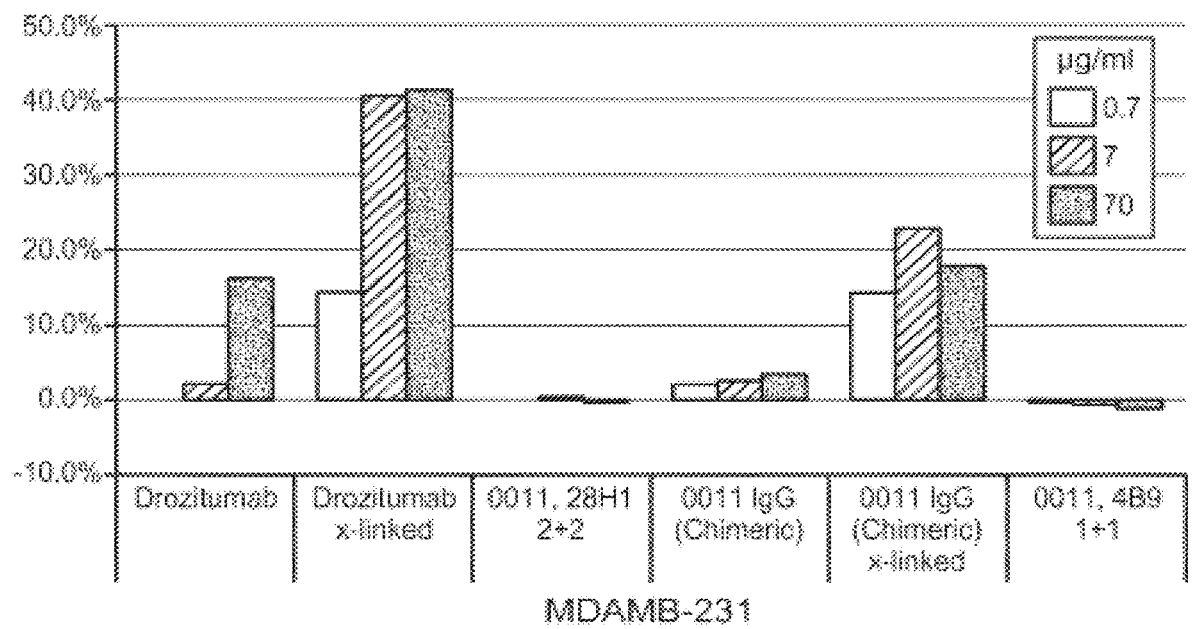
Figure 47B:
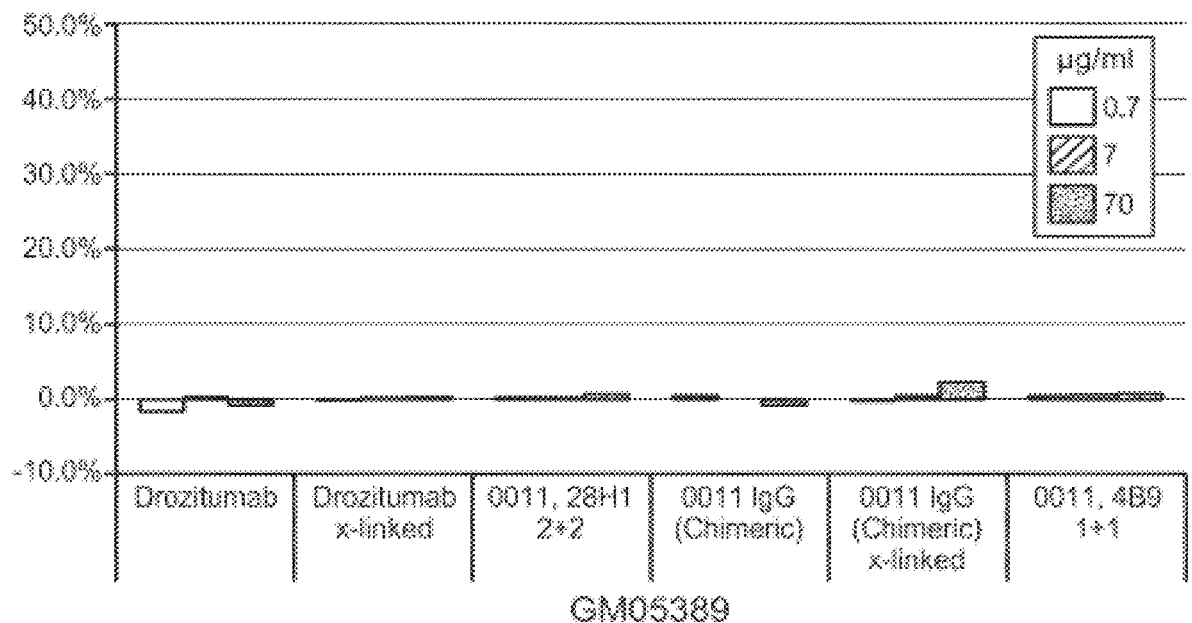

FIGS. 47A and 47B: Great specificity of bispecific anti-DR5-FAP antibodies at inducing cell death only in the presence of both tumor cells and fibroblasts.

Figure 48:
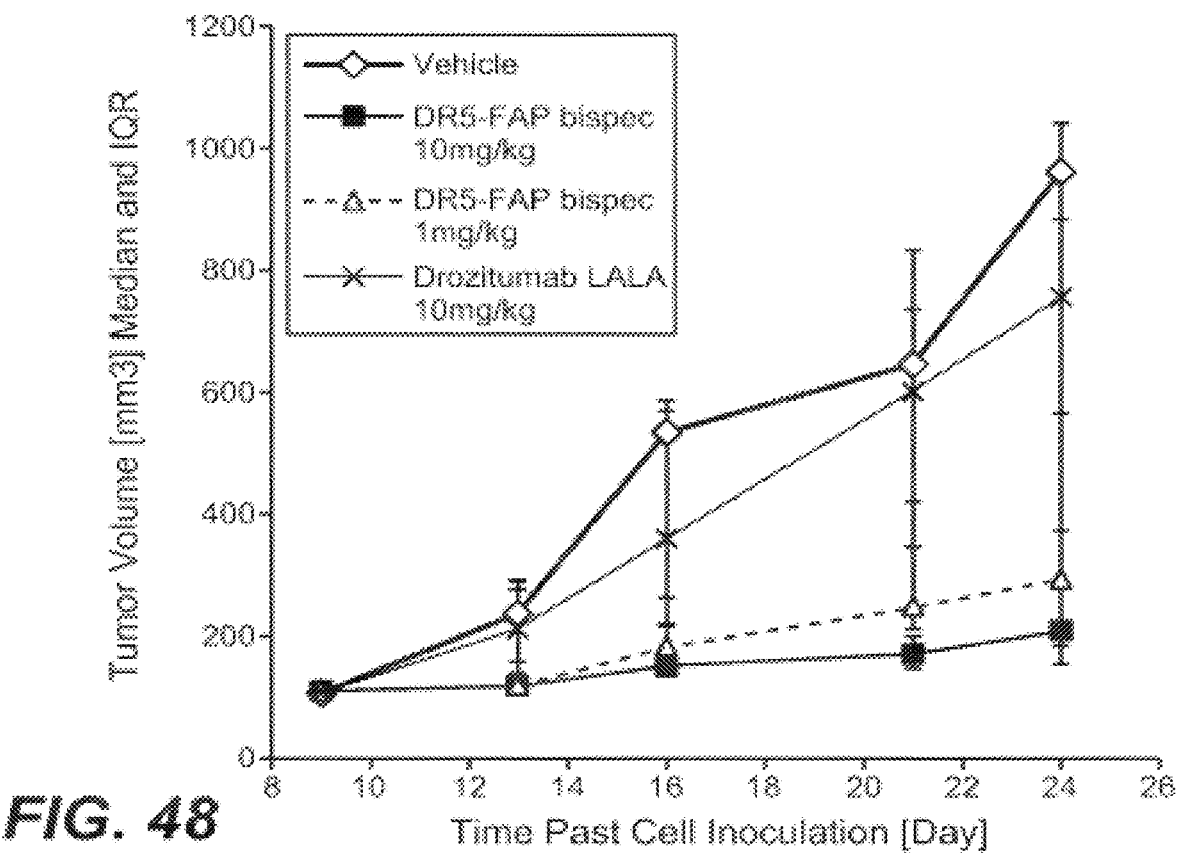
Figure 49:
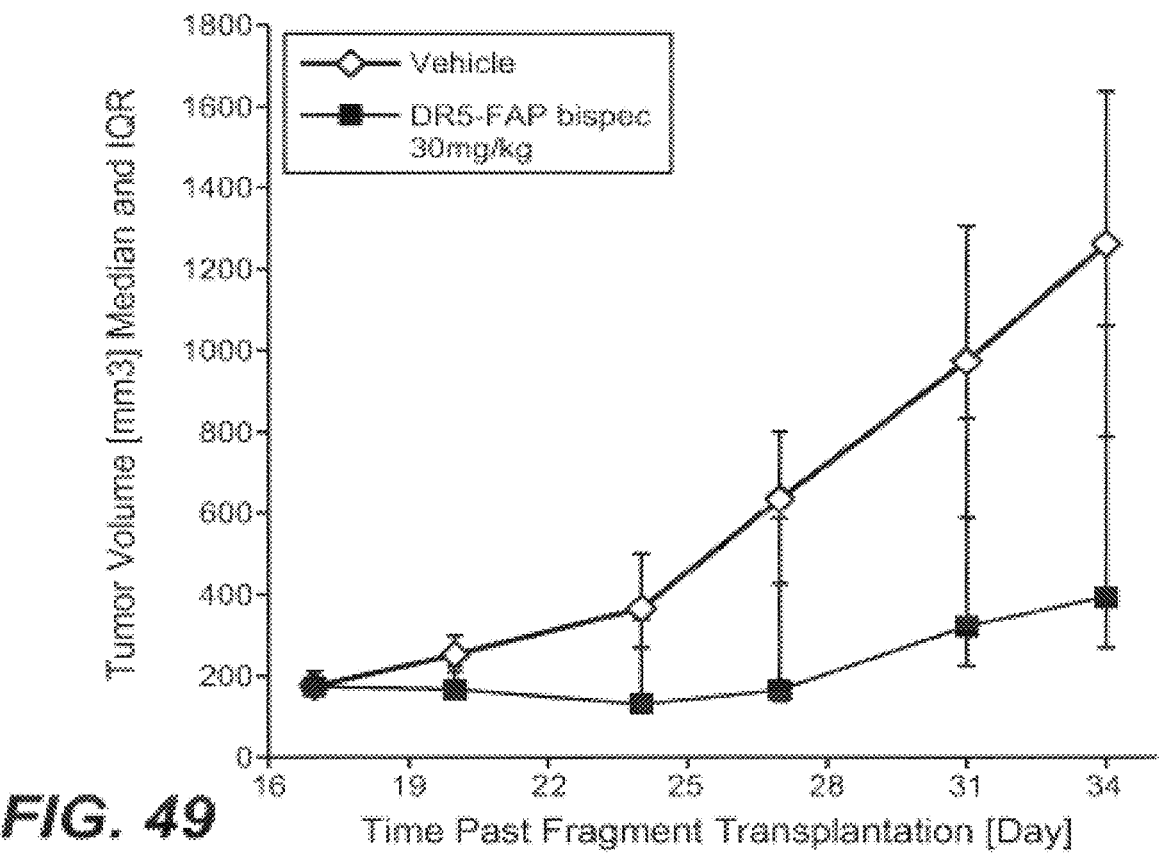

FIG. 48: Efficacy of bispecific anti-DR5-FAP (DR5 binder: VH SEQ ID NO.:7, VL SEQ ID NO.: 8, FAP binder: VH SEQ ID NO.:15, VL SEQ ID NO.: 16) in DLD-1 CRC co-injection cell line based xenograft model FIG. 49: Efficacy of bispecific anti-DR5-FAP (DR5 binder: VH SEQ ID NO.:7, VL SEQ ID NO.: 8, FAP binder: VH SEQ ID NO.:15, VL SEQ ID NO.: 16) in Co5896 CRC fragment based patient derived xenograft model (PDX)

Figure 50B:
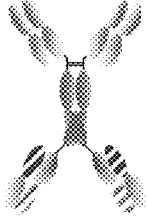
Figure 50B:
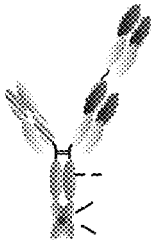
Figure 50B:
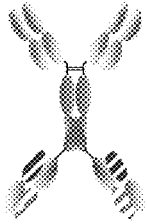
Figure 50B:
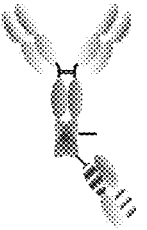
Figure 50B:
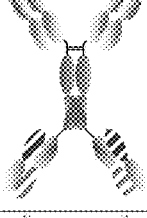
Figure 50B:
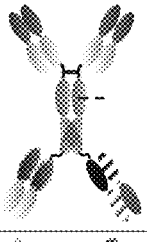
Figure 50B:
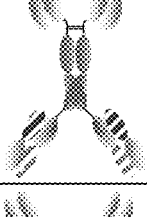
Figure 50B:
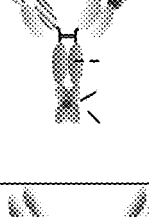
Figure 50B:
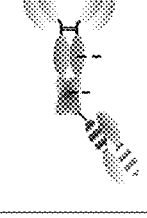
Figure 50B:
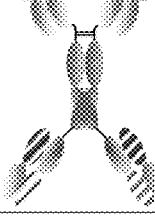
Figure 50B:
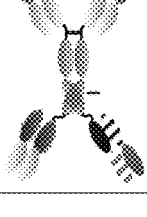

FIGS. 50A and 50B: Illustrative structures of bispecific molecules that are DR5 binders.

DETAILED DESCRIPTION OF EMBODIMENTS OF THE INVENTION

I. Definitions

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "A bispecific antibody that specifically binds death receptor 5 (DR5) and Fibroblast Activation Protein (FAP)" refers to a bispecific antibody that is capable of binding DR5 and FAP with sufficient affinity such that the antibody is useful as a diagnostic and/or therapeutic agent in targeting cells expressing DR5 and FAP). Specifically "A bispecific antibody that specifically binds death receptor 5 (DR5) and Fibroblast Activation Protein (FAP)" refers to a bispecific antibody targeting DR5 on a tumor cell and FAP in the stroma surrounding said tumor. In one embodiment, the extent of binding of a bispecific antibody that specifically binds death receptor 5 (DR5) and Fibroblast Activation Protein (FAP) to an unrelated, non-FAP or non-DR5 protein is less than about 10% of the binding of the antibody to DR5 or FAP as measured, e.g., by a Enzyme-linked immunosorbent assay (ELISA), surface plasmon resonance (SPR) based assays (e.g. Biacore) or flow cytometry (FACS). In certain embodiments, a bispecific antibody that specifically binds death receptor 5 (DR5) and Fibroblast Activation Protein (FAP) has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain embodiments, a bispecific antibody that specifically binds death receptor 5 (DR5) and Fibroblast Activation Protein (FAP) binds to an epitope of DR5 or FAP that is conserved among DR5 or FAP from different species. Preferably said bispecific antibody binds to human and cynomolgus monkey DR5 and to human, cynomolgus monkey and mouse FAP.

The terms "An antibody that specifically binds death receptor 5 (DR5)" refers to an antibody that is capable of binding DR5 with sufficient affinity such that the antibody is useful as a diagnostic and/or therapeutic agent in targeting cells expressing DR5. In one embodiment, the extent of binding of an antibody that specifically binds death receptor 5 (DR5) to an unrelated non-DR5 protein is less than about 10% of the binding of the antibody to DR5 as measured, e.g., by a radioimmunoassay (RIA) or flow cytometry (FACS). In certain embodiments, an antibody that specifically binds death receptor 5 (DR5) has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain embodiments, an antibody that specifically binds death receptor 5 (DR5) binds to an epitope of DR5 that is conserved among DR5 from different species. Preferably said antibody binds to human and cynomolgus monkey DR5. The term "An antibody that specifically binds death receptor 5 (DR5)" also encompasses bispecific antibodies that are capable of binding DR5 and a second antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies, cross-Fab fragments; linear antibodies; single-chain antibody molecules (e.g. scFv); and multispecific antibodies formed from antibody fragments. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

As used herein, "Fab fragment" refers to an antibody fragment comprising a light chain fragment comprising a VL domain and a constant domain of a light chain (CL), and a VH domain and a first constant domain (CH1) of a heavy chain. In one embodiment the bispecific antibodies of the invention comprise at least one Fab fragment, wherein either the variable regions or the constant regions of the heavy and light chain are exchanged. Due to the exchange of either the variable regions or the constant regions, said Fab fragment is also referred to as "cross-Fab fragment" or "xFab fragment" or "crossover Fab fragment". Two different chain compositions of a crossover Fab molecule are possible and comprised in the bispecific antibodies of the invention:

On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction:
a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments a) VH-CH1-linker-VL-CL, b) VL-CL-linker-VH-CH1, c) VH-CL-linker-VL-CH1 and d) VL-CH1-linker-VH-CL, are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering). The term "N-terminus denotes the last amino acid of the N-terminus. The term "C-terminus denotes the last amino acid of the C-terminus. By "fused" or "connected" is meant that the components (e.g. a Fab molecule and an Fc domain subunit) are linked by peptide bonds, either directly or via one or more peptide linkers.

The term "linker" as used herein refers to a peptide linker and is preferably a peptide with an amino acid sequence with a length of at least 5 amino acids, preferably with a length of 5 to 100, more preferably of 10 to 50 amino acids. In one embodiment said peptide linker is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide linker is $(G_4S)_2$.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $γ_1$ (IgG$_1$), $γ_2$ (IgG$_2$), $γ_3$ (IgG$_3$), $γ_4$ (IgG$_4$), $α_1$ (IgA$_1$) and $α_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "antigen binding domain" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "chimeric" antibody refers to an antibody in which a portion of the heavy and/or light chain is derived from a particular source or species, while the remainder of the heavy and/or light chain is derived from a different source or species, usually prepared by recombinant DNA techniques. Chimeric antibodies comprising a rabbit variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See e.g. Morrison, S. L., et al., Proc. Natl. Acad. Sci. USA 81 (1984) 6851-6855; U.S. Pat. Nos. 5,202,238 and 5,204,244.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cellular phagocytosis (ADCP), cytokine secretion, immune complex-mediated antigen uptake by antigen presenting cells; down regulation of cell surface receptors (e.g. B cell receptor); and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, G329, P329G, or Pro329Gly.

An "effective amount" of an agent, e.g., a pharmaceutical formulation, refers to an amount effective, at dosages and for periods of time necessary, to achieve the desired therapeutic or prophylactic result.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. As also mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.)

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., J. Mol. Biol. 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
| --- | --- | --- | --- |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front. Biosci. 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding a bispecific antibody that specifically binds DR5 and FAP antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"No substantial cross-reactivity" means that a molecule (e.g., an antibody) does not recognize or specifically bind an antigen different from the actual target antigen of the molecule (e.g. an antigen closely related to the target antigen), particularly when compared to that target antigen. For example, an antibody may bind less than about 10% to less than about 5% to an antigen different from the actual target antigen, or may bind said antigen different from the actual target antigen at an amount consisting of less than about 10%, 9%, 8% 7%, 6%, 5%, 4%, 3%, 2%, 1%, 0.5%, 0.2%, or 0.1%, preferably less than about 2%, 1%, or 0.5%, and most preferably less than about 0.2% or 0.1% antigen different from the actual target antigen.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "death receptor 5 (DR5)", as used herein, refers to any native DR5 from any vertebrate source, including mammals such as primates (e.g. humans) and rodents (e.g., mice and rats), unless otherwise indicated. The term encompasses "full-length," unprocessed DR5 as well as any form of DR5 that results from processing in the cell. The term also encompasses naturally occurring variants of DR5, e.g., splice variants or allelic variants. The amino acid sequence of an exemplary human DR5 is shown in SEQ ID NO.:155.

The term "Fibroblast activation protein (FAP)", as used herein, refers to any native FAP from any vertebrate source, including mammals such as primates (e.g. humans) and rodents (e.g., mice and rats), unless otherwise indicated. The term encompasses "full-length," unprocessed FAP as well as any form of FAP that results from processing in the cell. The term also encompasses naturally occurring variants of FAP, e.g., splice variants or allelic variants. Preferably, an anti-FAP antibody of the invention binds to the extracellular domain of FAP. The amino acid sequence of exemplary human, mouse and cynomolgus monkey FAP ectodomains (with a C-terminal poly-lysine and 6x His-tag) are shown in SEQ ID NO.:156, SEQ ID NO.:157, and SEQ ID NO.:158 respectively.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "antigen-binding site of an antibody" when used herein refer to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

Antibody specificity refers to selective recognition of the antibody for a particular epitope of an antigen. Natural antibodies, for example, are monospecific. "Bispecific antibodies" according to the invention are antibodies which have two different antigen-binding specificities. Antibodies of the present invention are specific for two different antigens, i.e. DR5 as first antigen and FAP as second antigen.

The term "monospecific" antibody as used herein denotes an antibody that has one or more binding sites each of which bind to the same epitope of the same antigen.

The term "bispecific" antibody as used herein denotes an antibody that has at least two binding sites each of which bind to different epitopes of the same antigen or a different antigen.

The antibody provided herein is a multispecific antibody, e.g. a bispecific antibody. Multispecific antibodies are monoclonal antibodies that have binding specificities for at least two different sites. Provided herein is a bispecific antibody, with binding specificities for FAP and DR5. In certain embodiments, bispecific antibodies may bind to two different epitopes of DR5. Bispecific antibodies may also be used to localize cytotoxic agents to cells which express DR5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising at least one antigen binding site that binds to FAP or DR5 as well as another, different antigen (see, US 2008/0069820, for example).

The term "valent" as used within the current application denotes the presence of a specified number of binding sites in an antibody molecule. As such, the terms "bivalent", "tetravalent", and "hexavalent" denote the presence of two binding sites, four binding sites, and six binding sites, respectively, in an antibody molecule. The bispecific antibodies according to the invention are at least "bivalent" and may be "trivalent" or "multivalent" (e.g. "tetravalent" or "hexavalent").

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

As used herein, the term "binding" or "specifically binding" refers to the binding of the antibody to an epitope of the antigen in an in-vitro assay, preferably in a surface plasmon resonance assay (SPR, BIAcore, GE-Healthcare Uppsala, Sweden). The affinity of the binding is defined by the terms ka (rate constant for the association of the antibody from the antibody/antigen complex), kD (dissociation constant), and KD (kD/ka). Binding or specifically binding means a binding affinity (KD) of 10-8 mol/l or less, preferably 10-9 M to 10-13 mol/l.

Binding of the antibody to the death receptor can be investigated by a BIAcore assay (GE-Healthcare Uppsala, Sweden). The affinity of the binding is defined by the terms ka (rate constant for the association of the antibody from the antibody/antigen complex), kD (dissociation constant), and KD (kD/ka)

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

As used herein, the terms "engineer, engineered, engineering," particularly with the prefix "glyco-," as well as the term "glycosylation engineering" are considered to include any manipulation of the glycosylation pattern of a naturally occurring or recombinant polypeptide or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity.

II. Compositions and Methods

In one aspect, the invention is based on bispecific antibodies comprising a first antigen binding site specific for TRAIL death receptor 5 (DR5) and a second antigen binding site specific for Fibroblast Activation Protein (FAP). In another embodiment novel antibodies targeting DR5 are provided. Antibodies of the invention are useful, e.g., for the treatment or diagnosis of cancer.

A. Exemplary Bispecific Antibodies that Bind to DR5 and FAP

In one aspect, the invention provides isolated bispecific antibodies that bind to DR5 and FAP. FAP binding moieties have been described in WO 2012/020006, which is included by reference in its entirety. FAP binding moieties of particular interest to be used in the DR5-FAP bispecific antibodies are outlined in the embodiments below.

In certain embodiments, a bispecific antibody that binds to DR5 and FAP specifically crosslinks the death receptors and apoptosis of the target cell is induced. The advantage of these bispecific death receptor agonistic antibodies over conventional death receptor targeting antibodies is the specificity of induction of apoptosis only at the site where FAP is expressed. As outlined above the inventors of the present invention developed novel DR5 binding moieties with superior properties compared to known DR5 binders that can be incorporated into novel and advantageous DR5-FAP bispecific antibodies.

In one aspect, the invention provides a bispecific antibody that binds to death receptor 5 (DR5) and Fibroblast Activation Protein (FAP) comprising at least one antigen binding site specific for DR5, comprising
(a) a heavy chain CDR1 consisting of SEQ ID NO.:1, SEQ ID NO.:17 and SEQ ID NO.:75;
(b) a heavy chain CDR2 of SEQ ID NO.:2, SEQ ID NO.:18, SEQ ID NO.:25 and SEQ ID NO.:83;
(c) a heavy chain CDR3 of SEQ ID NO.:3, SEQ ID NO.:19, SEQ ID NO.:84, SEQ ID NO.:96, SEQ ID NO.:98, SEQ ID NO.:104 and SEQ ID NO.:108;
(d) a light chain CDR1 of SEQ ID NO.:4, SEQ ID NO.:20, SEQ ID NO.:27 and SEQ ID NO.:86;
(e) a light chain CDR2 of SEQ ID NO.:5, SEQ ID NO.:21 and SEQ ID NO.:28; and
(f) a light chain CDR3 of SEQ ID NO.:6, SEQ ID NO.:22, SEQ ID NO.:87, SEQ ID NO.:99, SEQ ID NO.:105, SEQ ID NO.:109 and SEQ ID NO.:97;
and at least one antigen binding site specific for FAP, comprising
(a) a heavy chain CDR1 of SEQ ID NO.:9 and SEQ ID NO.:33;
(b) a heavy chain CDR2 of SEQ ID NO.:10 and SEQ ID NO.:34;
(c) a heavy chain CDR3 of SEQ ID NO.:11 and SEQ ID NO.:35;
(d) a light chain CDR1 of SEQ ID NO.:12 and SEQ ID NO.:36;
(e) a light chain CDR2 of SEQ ID NO.:13 and SEQ ID NO.:37;
(f) a light chain CDR3 of SEQ ID NO.:14 and SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 SEQ ID NO.:2;
(c) a heavy chain CDR3 of SEQ ID NO.:3;
(d) a light chain CDR1 of SEQ ID NO.:4;
(e) a light chain CDR2 of SEQ ID NO.:5;
(f) a light chain CDR3 of SEQ ID NO.:6
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:3;
(d) a light chain CDR1 of SEQ ID NO.:4;
(e) a light chain CDR2 of SEQ ID NO.:5;
(f) a light chain CDR3 of SEQ ID NO.:6
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:20;
(e) a light chain CDR2 of SEQ ID NO.:21; and
(f) a light chain CDR3 of SEQ ID NO.:22
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:20;
(e) a light chain CDR2 of SEQ ID NO.:21; and
(f) a light chain CDR3 of SEQ ID NO.:22
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:20;
(e) a light chain CDR2 of SEQ ID NO.:21; and
(f) a light chain CDR3 of SEQ ID NO.:22
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:20;
(e) a light chain CDR2 of SEQ ID NO.:21; and
(f) a light chain CDR3 of SEQ ID NO.:22
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:27;
(e) a light chain CDR2 of SEQ ID NO.:28; and
(f) a light chain CDR3 of SEQ ID NO.:22
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:27;
(e) a light chain CDR2 of SEQ ID NO.:28; and
(f) a light chain CDR3 of SEQ ID NO.:22
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:20;
(e) a light chain CDR2 of SEQ ID NO.:28; and
(f) a light chain CDR3 of SEQ ID NO.:22
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:20;
(e) a light chain CDR2 of SEQ ID NO.:28; and
(f) a light chain CDR3 of SEQ ID NO.:22
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:20;
(e) a light chain CDR2 of SEQ ID NO.:28; and
(f) a light chain CDR3 of SEQ ID NO.:22
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:20;
(e) a light chain CDR2 of SEQ ID NO.:28; and
(f) a light chain CDR3 of SEQ ID NO.:22
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;

(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:75;
(b) a heavy chain CDR2 of SEQ ID NO.:83;
(c) a heavy chain CDR3 of SEQ ID NO.:84;
(d) a light chain CDR1 of SEQ ID NO.:86;
(e) a light chain CDR2 of SEQ ID NO.:28;
(f) a light chain CDR3 of SEQ ID NO.:87
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:75;
(b) a heavy chain CDR2 of SEQ ID NO.:83;
(c) a heavy chain CDR3 of SEQ ID NO.:84;
(d) a light chain CDR1 of SEQ ID NO.:86;
(e) a light chain CDR2 of SEQ ID NO.:28;
(f) a light chain CDR3 of SEQ ID NO.:87
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:96;
(d) a light chain CDR1 of SEQ ID NO.:4;
(e) a light chain CDR2 of SEQ ID NO.:5;
(f) a light chain CDR3 of SEQ ID NO.:99;
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:96;
(d) a light chain CDR1 of SEQ ID NO.:4;
(e) a light chain CDR2 of SEQ ID NO.:5;
(f) a light chain CDR3 of SEQ ID NO.:99;
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:104;
(d) a light chain CDR1 of SEQ ID NO.:4;
(e) a light chain CDR2 of SEQ ID NO.:5;
(f) a light chain CDR3 of SEQ ID NO:105;
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:104;
(d) a light chain CDR1 of SEQ ID NO.:4;
(e) a light chain CDR2 of SEQ ID NO.:5;
(f) a light chain CDR3 of SEQ ID NO:105;
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:108;
(d) a light chain CDR1 of SEQ ID NO.:4;
(e) a light chain CDR2 of SEQ ID NO.:5;
(f) a light chain CDR3 of SEQ ID NO:109;
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:108;
(d) a light chain CDR1 of SEQ ID NO.:4;
(e) a light chain CDR2 of SEQ ID NO.:5;
(f) a light chain CDR3 of SEQ ID NO:109;
and at least one antigen binding site specific for FAP, comprising
(a) a heavy chain CDR1 of SEQ ID NO.:33;
(b) a heavy chain CDR2 of SEQ ID NO.:34;

(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:98;
(d) a light chain CDR1 of SEQ ID NO.:4;
(e) a light chain CDR2 of SEQ ID NO.:5;
(f) a light chain CDR3 of SEQ ID NO.:97;
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:1;
(b) a heavy chain CDR2 of SEQ ID NO.:2;
(c) a heavy chain CDR3 of SEQ ID NO.:98;
(d) a light chain CDR1 of SEQ ID NO.:4;
(e) a light chain CDR2 of SEQ ID NO.:5;
(f) a light chain CDR3 of SEQ ID NO.:97;
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:27;
(e) a light chain CDR2 of SEQ ID NO.:28;
(f) a light chain CDR3 of SEQ ID NO.:22;
and at least one antigen binding site specific for FAP, comprising
(a) a heavy chain CDR1 of SEQ ID NO.:9;
(b) a heavy chain CDR2 of SEQ ID NO.:10;
(c) a heavy chain CDR3 of SEQ ID NO.:11;
(d) a light chain CDR1 of SEQ ID NO.:12;
(e) a light chain CDR2 of SEQ ID NO.:13;
(f) a light chain CDR3 of SEQ ID NO.:14.

In one aspect, the invention provides a bispecific antibody that binds to DR5 and FAP comprising at least one antigen binding site specific for DR5, comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:27;
(e) a light chain CDR2 of SEQ ID NO.:28;
(f) a light chain CDR3 of SEQ ID NO.:22;
and at least one antigen binding site specific for FAP, comprising
(a) a heavy chain CDR1 of SEQ ID NO.:33;
(b) a heavy chain CDR2 of SEQ ID NO.:34;
(c) a heavy chain CDR3 of SEQ ID NO.:35;
(d) a light chain CDR1 of SEQ ID NO.:36;
(e) a light chain CDR2 of SEQ ID NO.:37;
(f) a light chain CDR3 of SEQ ID NO.:38.

In one embodiment, the bispecific antibody comprises at least one antigen binding site specific for DR5 comprising a variable heavy chain and a variable light chain comprising an amino acid sequence selected from the group of: SEQ ID NO.:7 and SEQ ID NO.:8; SEQ ID NO.:23 and SEQ ID NO.:24; SEQ ID NO.:26 and SEQ ID NO.:24; SEQ ID NO.:23 and SEQ ID NO.:29; SEQ ID NO.:23 and SEQ ID NO.:30; SEQ ID NO.:26 and SEQ ID NO.:31; SEQ ID NO.:26 and SEQ ID NO.:32; SEQ ID NO.:26 and SEQ ID NO.:30; SEQ ID NO.:23 and SEQ ID NO.:31; SEQ ID NO.:82 and SEQ ID NO.:85; SEQ ID NO.:100 and SEQ ID NO.:101; SEQ ID NO.:102 and SEQ ID NO.:103; SEQ ID NO.:106 and SEQ ID NO.:107; SEQ ID NO.:94 and SEQ ID NO.:95; and at least one antigen binding site specific for FAP comprisings a variable heavy chain comprising an amino acid sequence selected from the group of: SEQ ID NO.:15 and SEQ ID NO.:39; and a light chain variable region comprising an amino acid sequence selected from the group of SEQ ID NO.:16 and SEQ ID NO.:40.

In one embodiment, the bispecific antibody comprises at least one antigen binding site specific for DR5, comprising a variable heavy chain comprising an amino acid sequence of SEQ ID NO.:7 and a variable light chain comprising an amino acid sequence of SEQ ID NO.:8; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:7 and a variable light chain comprising an amino acid sequence of SEQ ID NO.:8; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:24; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:24; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:24; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:24; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:29; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:29; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:30; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:30; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:31; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:31; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:32; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:32; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:30; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:26 and a variable light chain comprising an amino acid sequence of SEQ ID NO.:30; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:31; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:23 and a variable light chain comprising an amino acid sequence of SEQ ID NO.:31; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:82 and a variable light chain comprising an amino acid sequence of SEQ ID NO.:85; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:82 and a variable light chain comprising an amino acid sequence of SEQ ID NO.:85; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:100 and a variable light chain comprising an amino acid sequence of SEQ ID NO.:101; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:100 and a variable light chain comprising an amino acid sequence of SEQ ID NO.:101; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:102 and a variable light chain comprising an amino acid sequence of SEQ ID NO.:103; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:102 and a variable light chain comprising an amino acid sequence of SEQ ID NO.:103; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:106 and a variable light chain comprising an amino acid sequence of SEQ ID NO.:107; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:106 and a variable light chain comprising an amino acid sequence of SEQ ID NO.:107; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody comprises at least one antigen binding site specific for DR5, comprising a variable heavy chain comprising an amino acid sequence of SEQ ID NO.:94 and a variable light chain comprising an amino acid sequence of SEQ ID NO.:95; and at least one antigen binding site specific for FAP, comprising a heavy chain variable region comprising an amino acid sequence of SEQ ID NO.:15 and a light chain variable region comprising an amino acid sequence of SEQ ID NO.:16.

In one embodiment, the bispecific antibody comprises at least one antigen binding site specific for DR5, comprising a variable heavy chain comprising an amino acid sequence of SEQ ID NO.:94 and a variable light chain comprising an amino acid sequence of SEQ ID NO.:95; and at least one antigen binding site specific for FAP, comprising a heavy chain variable region comprising an amino acid sequence of SEQ ID NO.:39 and a light chain variable region comprising an amino acid sequence of SEQ ID NO.:40.

In one embodiment, the bispecific antibody of the invention comprises a heavy chain constant region comprising the amino acid sequence of SEQ ID NO.:151.

In one embodiment, the bispecific antibody of the invention comprises a heavy chain constant region comprising the amino acid sequence of SEQ ID NO.:152.

In another embodiment the bispecific antibody of the invention comprises a light chain constant region comprising the amino acid sequence of SEQ ID NO.:153.

In one embodiment, the bispecific antibody of the invention comprises a heavy chain constant region comprising the amino acid sequence of SEQ ID NO.:151, wherein the C-terminal Lysine has been removed.

In one embodiment, the bispecific antibody of the invention comprises a heavy chain constant region comprising the amino acid sequence of SEQ ID NO.:152, wherein the C-terminal Lysine has been removed.

In one embodiment the bispecific antibody of the invention comprises a first antibody comprising at least one antigen binding site specific for DR5, said first antibody comprising a variable heavy chain of SEQ ID NO.:7 and a variable light chain of SEQ ID NO.:8, and a heavy chain constant region comprising the amino acid sequence selected from of SEQ ID NO.:151 or SEQ ID NO.:152, and a light chain constant region comprising the amino acid sequence of SEQ ID NO.:153, and a second antibody specific for FAP comprising one or more amino acid sequences as defined in any of the embodiments above. In one embodiment the C-terminal Lysine of the amino acid sequence of said heavy chain constant region has been removed.

In one embodiment the bispecific antibody of the invention comprises a first antibody comprising at least one antigen binding site specific for DR5, said first antibody comprising a variable heavy chain of SEQ ID NO.:7 and a variable light chain of SEQ ID NO.:8, and a heavy chain constant region comprising the amino acid sequence selected from of SEQ ID NO.:151 or SEQ ID NO.:152, and a light chain constant region comprising the amino acid sequence of SEQ ID NO.:153, and a second antibody specific for FAP comprising a variable heavy chain of SEQ ID NO.:15 and a variable light chain of SEQ ID NO.:16.

In one embodiment a bispecific antibody is provided comprising SEQ ID NO.:131, SEQ ID NO.:132 and SEQ ID NO.:124.

In one embodiment a bispecific antibody is provided comprising SEQ ID NO.:133, SEQ ID NO.:132 and SEQ ID NO.:124.

In one preferred embodiment a bispecific antibody is provided comprising SEQ ID NO.:134, SEQ ID NO.:132 and SEQ ID NO.:124.

In one embodiment a bispecific antibody is provided comprising SEQ ID NO.:262, SEQ ID NO.:263 and SEQ ID NO.:132.

In one embodiment a bispecific antibody is provided comprising SEQ ID NO.:135, SEQ ID NO.:136 and SEQ ID NO.:137.

In one embodiment a bispecific antibody is provided comprising SEQ ID NO.:138, SEQ ID NO.:139 and SEQ ID NO.:137.

In one embodiment a bispecific antibody is provided comprising SEQ ID NO.:274, SEQ ID NO.:275, and SEQ ID NO.:137.

In one embodiment a bispecific antibody is provided comprising SEQ ID NO.:276, SEQ ID NO.:277, and SEQ ID NO.:132.

In one embodiment a bispecific antibody is provided comprising SEQ ID NO.:278, SEQ ID NO.:279 and SEQ ID NO.:132.

In one embodiment a bispecific antibody is provided comprising SEQ ID NO.:142, SEQ ID NO.:143, SEQ ID NO.:124 and SEQ ID NO.:132.

In one embodiment a bispecific antibody is provided comprising SEQ ID NO.:145, SEQ ID NO.:146, SEQ ID NO.:124 and SEQ ID NO.:132.

In one embodiment a bispecific antibody is provided comprising SEQ ID NO.:144, SEQ ID NO.:143, SEQ ID NO.:124 and SEQ ID NO.:132.

In one embodiment a bispecific antibody is provided comprising SEQ ID NO.:159, SEQ ID NO.:160, SEQ ID NO.:161 and SEQ ID NO.:162.

In another aspect, a bispecific antibody that binds to DR5 and FAP comprises at least one antigen binding site specific for DR5 comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO.:7, and at least one antigen binding site specific for FAP comprising a variable heavy chain of SEQ ID NO.:15 and a variable light chain of SEQ ID NO.:16.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to FAP and DR5. In certain embodiments, a total of 1 to 10 amino acids have been substituted, inserted and/or deleted in SEQ ID NO.:7. In certain embodiments, substitutions, insertions, or deletions occur in regions outside the HVRs (i.e., in the FRs). Optionally, the bispecific antibody that binds to DR5 and FAP comprises the VH sequence in SEQ ID NO.:7, including post-translational modifications of that sequence.

In another aspect, a bispecific antibody that binds to DR5 and FAP comprises at least one antigen binding site specific for DR5 comprising a light chain variable domain (VL) sequence having at least 90%, 91%, 92%, 93%, 94%, 95%, 96%, 97%, 98%, 99%, or 100% sequence identity to the amino acid sequence of SEQ ID NO.:8, and at least one antigen binding site specific for FAP comprising a variable heavy chain of SEQ ID NO.:15 and a variable light chain of SEQ ID NO.:16.

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to DR5 and FAP. In certain embodiments, a total of 1 to 10 amino acids have been substituted, inserted and/or deleted in SEQ ID NO.:8. In certain embodiments, the substitutions, insertions, or deletions occur in regions outside the HVRs (i.e., in the FRs). Optionally, the bispecific antibody that binds to DR5 and FAP comprises the VL sequence in SEQ ID NO:8, including post-translational modifications of that sequence.

In another aspect, a bispecific antibody that binds to DR5 and FAP is provided, comprising at least one antigen binding site specific for DR5 comprising a variable light chain of SEQ ID NO.:8 and a variable heavy chain of SEQ ID NO.:7; and at least one antigen binding site specific for FAP, comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO.:15. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to FAP and DR5. In certain embodiments, a total of 1 to 10 amino acids have been substituted, inserted and/or deleted in SEQ ID NO.:15. In certain embodiments, substitutions, insertions, or deletions occur in regions outside the HVRs (i.e., in the FRs). Optionally, the bispecific antibody that binds to DR5 and FAP comprises the VH sequence in SEQ ID NO.:15, including post-translational modifications of that sequence.

In another aspect, a bispecific antibody that binds to DR5 and FAP is provided, comprising at least one antigen binding site specific for DR5, comprising a variable light chain of SEQ ID NO.:8 and a variable heavy chain of SEQ ID NO.:7, and at least one antigen binding site specific for FAP, comprising a light chain variable domain (VL) having at least 90%, 91%, 92%, 93%, 94%, 95%, 96%, 97%, 98%, 99%, or 100% sequence identity to the amino acid sequence of SEQ ID NO.:16. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but a bispecific antibody that binds to DR5 and FAP comprising that sequence retains the ability to bind to DR5 and FAP. In certain embodiments, a total of 1 to 10 amino acids have been substituted, inserted and/or deleted in SEQ ID NO.:16. In certain embodiments, the substitutions, insertions, or deletions occur in regions outside the HVRs (i.e., in the FRs). Optionally, the bispecific antibody that binds to DR5 and FAP comprises the VL sequence in SEQ ID NO:16, including post-translational modifications of that sequence.

In another aspect, a a bispecific antibody that binds to DR5 and FAP is provided, wherein the antibody comprises a VH as in any of the embodiments provided above, and a VL as in any of the embodiments provided above. In one embodiment, the antibody comprises the VH and VL sequences in SEQ ID NO:7 and SEQ ID NO:8, and SEQ ID NO:15 and SEQ ID NO:16, respectively, including post-translational modifications of those sequences.

In a further aspect of the invention, a bispecific antibody that binds to DR5 and FAP according to any of the above embodiments is a monoclonal antibody, including a chimeric, humanized or human antibody. In one embodiment said bispecific antibody that binds to DR5 and FAP according to any of the above embodiments is a human antibody.

B. Exemplary Antibodies that Bind to DR5

In one aspect, the invention provides isolated antibodies and antibody fragments that bind to DR5. These death receptor agonistic antibodies have superior properties compared to known DR5 binders that can be incorporated into novel and advantageous bispecific antibodies targeting DR5 and a second antigen.

In one aspect, the invention provides an antibody that binds to death receptor 5 (DR5), comprising
(a) a heavy chain CDR1 consisting of SEQ ID NO.:1, SEQ ID NO.:17 and SEQ ID NO.:75;
(b) a heavy chain CDR2 of SEQ ID NO.:2, SEQ ID NO.:18, SEQ ID NO.:25 and SEQ ID NO.:83;
(c) a heavy chain CDR3 of SEQ ID NO.:3, SEQ ID NO.:19, SEQ ID NO.:84, SEQ ID NO.:96, SEQ ID NO.:98, SEQ ID NO.:104 and SEQ ID NO.:108;
(d) a light chain CDR1 of SEQ ID NO.:4, SEQ ID NO.:20, SEQ ID NO.:27 and SEQ ID NO.:86;
(e) a light chain CDR2 of SEQ ID NO.:5, SEQ ID NO.:21 and SEQ ID NO.:28; and
(f) a light chain CDR3 of SEQ ID NO.:6, SEQ ID NO.:22, SEQ ID NO.:87, SEQ ID NO.:99, SEQ ID NO.:105, SEQ ID NO.:109 and SEQ ID NO.:97.

In one aspect, the invention provides an antibody that binds to death receptor 5 (DR5), comprising
(a) a heavy chain CDR1 of SEQ ID NO.:1;
(b) a heavy chain CDR2 SEQ ID NO.:2;
(c) a heavy chain CDR3 of SEQ ID NO.:3;
(d) a light chain CDR1 of SEQ ID NO.:4;
(e) a light chain CDR2 of SEQ ID NO.:5;
(f) a light chain CDR3 of SEQ ID NO.:6.

In one aspect, the invention provides an antibody that binds to death receptor 5 (DR5), comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:20;
(e) a light chain CDR2 of SEQ ID NO.:21; and
(f) a light chain CDR3 of SEQ ID NO.:22.

In one aspect, the invention provides an antibody that binds to death receptor 5 (DR5), comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:20;
(e) a light chain CDR2 of SEQ ID NO.:21; and
(f) a light chain CDR3 of SEQ ID NO.:22.

In one aspect, the invention provides an antibody that binds to death receptor 5 (DR5), comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:27;
(e) a light chain CDR2 of SEQ ID NO.:28; and
(f) a light chain CDR3 of SEQ ID NO.:22.

In one aspect, the invention provides an antibody that binds to death receptor 5 (DR5), comprising
(a) a heavy chain CDR1 of SEQ ID NO.:17;
(b) a heavy chain CDR2 of SEQ ID NO.:18;
(c) a heavy chain CDR3 of SEQ ID NO.:19;
(d) a light chain CDR1 of SEQ ID NO.:20;
(e) a light chain CDR2 of SEQ ID NO.:28; and
(f) a light chain CDR3 of SEQ ID NO.:22.

In one aspect, the invention provides an antibody that binds to death receptor 5 (DR5), comprising
(a) a heavy chain CDR1 of SEQ ID NO.:17;
(b) a heavy chain CDR2 of SEQ ID NO.:25;
(c) a heavy chain CDR3 of SEQ ID NO.:19;
(d) a light chain CDR1 of SEQ ID NO.:20;
(e) a light chain CDR2 of SEQ ID NO.:28; and
(f) a light chain CDR3 of SEQ ID NO.:22.

In one aspect, the invention provides an antibody that binds to death receptor 5 (DR5), comprising
(a) a heavy chain CDR1 of SEQ ID NO.:75;
(b) a heavy chain CDR2 of SEQ ID NO.:83;
(c) a heavy chain CDR3 of SEQ ID NO.:84;
(d) a light chain CDR1 of SEQ ID NO.:86;
(e) a light chain CDR2 of SEQ ID NO.:28;
(f) a light chain CDR3 of SEQ ID NO.:87.

In one aspect, the invention provides an antibody that binds to death receptor 5 (DR5), comprising
(a) a heavy chain CDR1 of SEQ ID NO.:1;
(b) a heavy chain CDR2 of SEQ ID NO.:2;
(c) a heavy chain CDR3 of SEQ ID NO.:96;
(d) a light chain CDR1 of SEQ ID NO.:4;
(e) a light chain CDR2 of SEQ ID NO.:5;
(f) a light chain CDR3 of SEQ ID NO.:99.

In one aspect, the invention provides an antibody that binds to death receptor 5 (DR5), comprising
(a) a heavy chain CDR1 of SEQ ID NO.:1;
(b) a heavy chain CDR2 of SEQ ID NO.:2;
(c) a heavy chain CDR3 of SEQ ID NO.:104;
(d) a light chain CDR1 of SEQ ID NO.:4;
(e) a light chain CDR2 of SEQ ID NO.:5;
(f) a light chain CDR3 of SEQ ID NO:105.

In one aspect, the invention provides an antibody that binds to death receptor 5 (DR5), comprising
(a) a heavy chain CDR1 of SEQ ID NO.:1;
(b) a heavy chain CDR2 of SEQ ID NO.:2;
(c) a heavy chain CDR3 of SEQ ID NO.:108;
(d) a light chain CDR1 of SEQ ID NO.:4;
(e) a light chain CDR2 of SEQ ID NO.:5;
(f) a light chain CDR3 of SEQ ID NO:109.

In one aspect, the invention provides an antibody that binds to death receptor 5 (DR5), comprising
(a) a heavy chain CDR1 of SEQ ID NO.:1;
(b) a heavy chain CDR2 of SEQ ID NO.:2;
(c) a heavy chain CDR3 of SEQ ID NO.:98;
(d) a light chain CDR1 of SEQ ID NO.:4;
(e) a light chain CDR2 of SEQ ID NO.:5;
(f) a light chain CDR3 of SEQ ID NO.:97.

In one embodiment, the antibody that binds to death receptor 5 (DR5) comprises a variable heavy chain and a variable light chain comprising an amino acid sequence selected from the group of: SEQ ID NO.:7 and SEQ ID NO.:8; SEQ ID NO.:23 and SEQ ID NO.:24; SEQ ID NO.:26 and SEQ ID NO.:24; SEQ ID NO.:23 and SEQ ID NO.:29; SEQ ID NO.:23 and SEQ ID NO.:30; SEQ ID NO.:26 and SEQ ID NO.:31; SEQ ID NO.:26 and SEQ ID NO.:32; SEQ ID NO.:26 and SEQ ID NO.:30; SEQ ID NO.:23 and SEQ ID NO.:31; SEQ ID NO.:82 and SEQ ID NO.:85; SEQ ID NO.:100 and SEQ ID NO.:101; SEQ ID NO.:102 and SEQ ID NO.:103; SEQ ID NO.:106 and SEQ ID NO.:107; SEQ ID NO.:94 and SEQ ID NO.:95.

In one embodiment, the antibody that binds to death receptor 5 (DR5) comprises a variable heavy chain comprising an amino acid sequence of SEQ ID NO.:7 and a variable light chain comprising an amino acid sequence of SEQ ID NO.:8.

In one embodiment, the antibody that binds to death receptor 5 (DR5) comprises a variable heavy chain comprising an amino acid sequence of SEQ ID NO.:23 and a variable light chain comprising an amino acid sequence of SEQ ID NO.:24.

In one embodiment, the antibody that binds to death receptor 5 (DR5) comprises a variable heavy chain comprising an amino acid sequence of SEQ ID NO.:26 and a variable light chain comprising an amino acid sequence of SEQ ID NO.:24.

In one embodiment, the antibody that binds to death receptor 5 (DR5) comprises a variable heavy chain comprising an amino acid sequence of SEQ ID NO.:23 and a variable light chain comprising an amino acid sequence of SEQ ID NO.:29.

In one embodiment, the antibody that binds to death receptor 5 (DR5) comprises a variable heavy chain comprising an amino acid sequence of SEQ ID NO.:23 and a variable light chain comprising an amino acid sequence of SEQ ID NO.:30.

In one embodiment, the antibody that binds to death receptor 5 (DR5) comprises a variable heavy chain comprising an amino acid sequence of SEQ ID NO.:26 and a variable light chain comprising an amino acid sequence of SEQ ID NO.:31.

In one embodiment, the antibody that binds to death receptor 5 (DR5) comprises a variable heavy chain comprising an amino acid sequence of SEQ ID NO.:26 and a variable light chain comprising an amino acid sequence of SEQ ID NO.:32.

In one embodiment, the antibody that binds to death receptor 5 (DR5) comprises a variable heavy chain comprising an amino acid sequence of SEQ ID NO.:26 and a variable light chain comprising an amino acid sequence of SEQ ID NO.:30.

In one embodiment, the antibody that binds to death receptor 5 (DR5) comprises a variable heavy chain comprising an amino acid sequence of SEQ ID NO.:23 and a variable light chain comprising an amino acid sequence of SEQ ID NO.:31.

In one embodiment, the antibody that binds to death receptor 5 (DR5) comprises a variable heavy chain comprising an amino acid sequence of SEQ ID NO.:82 and a variable light chain comprising an amino acid sequence of SEQ ID NO.:85.

In one embodiment, the antibody that binds to death receptor 5 (DR5) comprises a variable heavy chain comprising an amino acid sequence of SEQ ID NO.:100 and a variable light chain comprising an amino acid sequence of SEQ ID NO.:101.

In one embodiment, the antibody that binds to death receptor 5 (DR5) comprises a variable heavy chain comprising an amino acid sequence of SEQ ID NO.:102 and a variable light chain comprising an amino acid sequence of SEQ ID NO.:103.

In one embodiment, the antibody that binds to death receptor 5 (DR5) comprises a variable heavy chain comprising an amino acid sequence of SEQ ID NO.:106 and a variable light chain comprising an amino acid sequence of SEQ ID NO.:107.

In one embodiment, the antibody that binds to death receptor 5 (DR5) comprises a variable heavy chain comprising an amino acid sequence of SEQ ID NO.:94 and a variable light chain comprising an amino acid sequence of SEQ ID NO.:95.

In another aspect, the antibody that binds to death receptor 5 (DR5) comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO.:7.

In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but the antibody that binds to DR5 comprising that sequence retains the ability to bind to DR5. In certain embodiments, a total of 1 to 10 amino acids have been substituted, inserted and/or deleted in SEQ ID NO.:7. In certain embodiments, substitutions, insertions, or deletions occur in regions outside the HVRs (i.e., in the FRs). Optionally, the antibody that binds to DR5 comprises the VH sequence in SEQ ID NO.:7, including post-translational modifications of that sequence.

In another aspect the antibody that binds to death receptor 5 (DR5) a light chain variable domain (VL) sequence having at least 90%, 91%, 92%, 93%, 94%, 95%, 96%, 97%, 98%, 99%, or 100% sequence identity to the amino acid sequence of SEQ ID NO.:8.

In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody that binds to DR5 comprising that sequence retains the ability to bind to DR5. In certain embodiments, a total of 1 to 10 amino acids have been substituted, inserted and/or deleted in SEQ ID NO.:8. In certain embodiments, the substitutions, insertions, or deletions occur in regions outside the HVRs (i.e., in the FRs). Optionally, the antibody that binds to DR5 comprises the VL sequence in SEQ ID NO:8, including post-translational modifications of that sequence.

In another aspect, a bispecific antibody that binds to DR5 and a second antigen is provided, wherein the antibody comprises a VH as in any of the embodiments provided above, and a VL as in any of the embodiments provided above. In one embodiment, the antibody comprises the VH and VL sequences in SEQ ID NO:7 and SEQ ID NO:8, respectively, including post-translational modifications of those sequences. In one embodiment a bispecific antibody is provided that binds to DR5 and a second antigen, wherein the antibody comprises a VH as in any of the embodiments provided above, and a VL as in any of the embodiments provided above and wherein the antibody has a format as outlined for the DR5-FAP bispecific antibodies in section C below. In another embodiment said bispecific antibody that binds to DR5 and a second antigen is provided which comprises a VH as in any of the embodiments provided above, and a VL as in any of the embodiments provided above, and which comprises one or more Fc domain modifications as outlined for the DR5-FAP bispecific antibodies in sections D and E below.

In a further aspect of the invention, an antibody that binds to DR5 according to any of the above embodiments is a monoclonal antibody, including a chimeric, humanized or human antibody. In one embodiment said antibody that binds to DR5 according to any of the above embodiments is a human antibody.

C. Exemplary Formats of Bispecific Antibodies Binding to DR5 and FAP

In one embodiment, a bispecific antibody that binds to DR5 and FAP comprises an antibody fragment, e.g., a Fv, Fab, Fab', scFv, xFab, scFab, diabody, or F(ab')$_2$ fragment. In another embodiment, the antibody comprises a full length antibody, e.g., an intact IgG1 antibody or other antibody class or isotype as defined herein.

The bispecific antibodies according to the invention are at least bivalent and can be trivalent or multivalent e.g. tetravalent or hexavalent.

The bispecific antibody of the invention comprise an Fc domain, at least one Fab fragment comprising an antigen binding site specific for DR5, and at least one Fab fragment comprising an antigen binding site specific for FAP, wherein either the variable regions or the constant regions of the heavy and light chain of at least one Fab fragment are exchanged.

In another embodiment, the bispecific antibody comprises an Fc domain, at least one Fab fragment comprising an antigen binding site specific for DR5, and at least one Fab fragment comprising an antigen binding site specific for FAP, wherein at least one of the Fab fragments is connected to the first or second subunit of the Fc domain via the light chain (VLCL) and at least one Fab fragment is connected to the first or second subunit of the Fc domain via the heavy chain (VHCH1).

In any of the embodiments, the Fab fragments may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$, $(SG_4)_n$, $(G_4S)_n$ or $G_4(SG_4)_n$ peptide linkers. "n" is generally a number between 1 and 10, typically between 2 and 4. A particularly suitable peptide linker for fusing the Fab light chains of the first and the second antigen binding moiety to each other is $(G_4S)_2$. An exemplary peptide linker suitable for connecting the Fab heavy chains of the first and the second antigen binding moiety is EPKSC(D)-$(G_4S)_2$ (SEQ ID NO.: 318). Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

Preferably said bispecific antibodies are tetravalent with two binding sites each targeting FAP and DR5, respectively (2+2 format). In another embodiment said bispecific antibodies are tetravalent with three binding sites for DR5 and one binding site for FAP (3+1 format). The 3+1 format can be achieved, for example, through fusing one Fab fragment targeting FAP and one Fab fragment targeting DR5 to the C-terminus of the heavy chain of an IgG molecule that has two DR5 binding sites. This is outlined in more detail below.

In another preferred embodiment said bispecific antibodies are trivalent (2+1 format) with two binding sites each targeting DR5 and one binding site targeting FAP. The 2+1 format can be achieved, for example, through fusing a Fab fragment targeting FAP to the C-terminus of the heavy chain of an IgG molecule that has two DR5 binding sites, wherein the Fc part of the first antibody is modified according to the knobs-into hole strategy as outlined below.

In another preferred embodiment said bispecific antibodies are bivalent (1+1 format), i.e. monovalent for each DR5 and FAP. Bivalent antibodies of the invention have one binding site targeting DR5 and one binding site targeting FAP. The 1+1 format can be achieved, for example, by the Crossmab technology described in Schaefer et al. Proc Natl Acad Sci USA 2011; 108:11187-92 and as outlined below.

Figure 25:
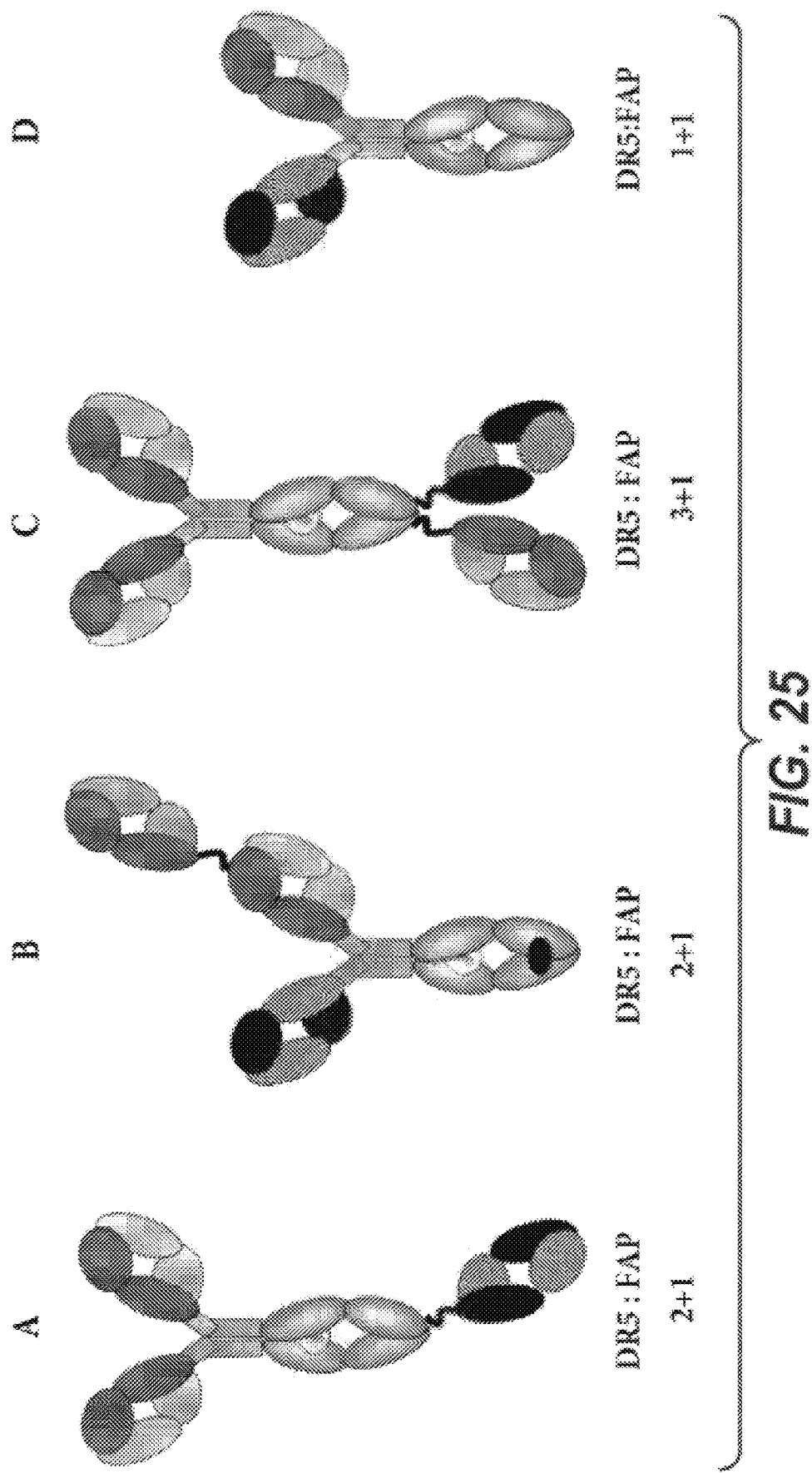
FIG. 25: Schematic representation of the additional bispecific DR5-FAP CrossFab formats that were evaluated with respect to productivity and quality. These four molecules differ in the position and valency of DR5 and FAP binding moieties: two 2+1 molecules, one 3+1 and one 1+1 construct were evaluated. One 2+1 molecule contains one FAP (28H1) CrossFab fused to the C-terminus of a DR5 (5E11) heavy chain (A) whereas a second 2+1 format consists of two DR5 (5E11) Fabs fused to the N-terminus of an Fc with the 28H1 CrossMab counterpart (B). The third molecule (C) contains three DR5 targeting Fabs and one 28H1 CrossFab fused at the C-terminus of a heavy chain. In the 1+1 format (D) the DR5 binder #174 is combined with the FAP binding moiety 4B9 in CrossFab arrangement. All constructs depend on hetero-dimerization using the knob-into-hole technology.
Figure 28:
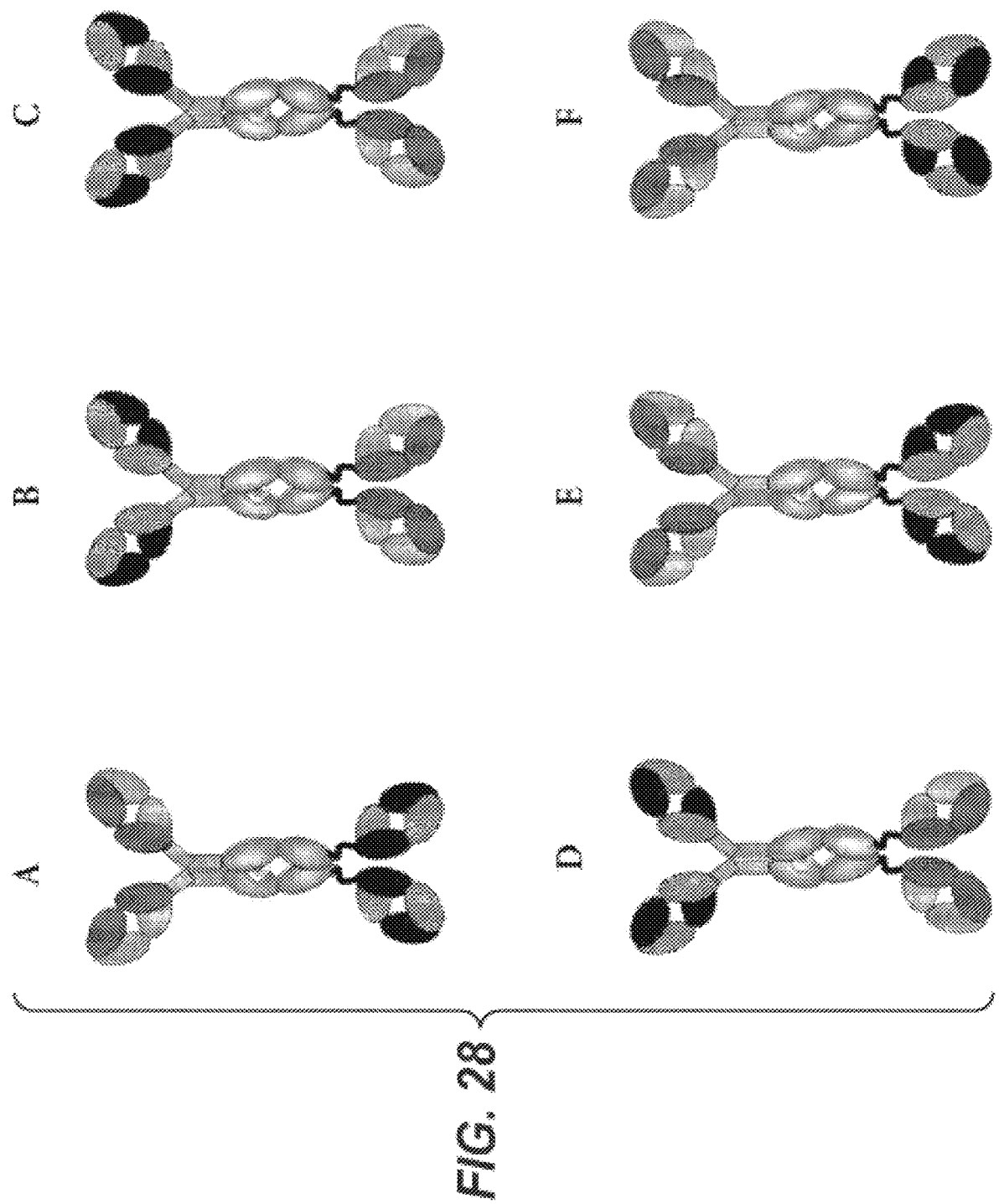
FIG. 28: New bispecific 5E11-28H1 formats (2+2) for evaluation of productivity, side product profile and activity. The molecules differ in site and type of crossing.

Exemplary formats of bispecific antibodies of the invention are given in FIGS. 25 and 28.

Provided therein are different bispecific antibody formats that are binding to DR5 and
FAP comprising any of the sequences according to any of the above embodiments.

1. Bispecific DR5-FAP Antibodies in a 2+2 Format

In one preferred embodiment a bispecific antibody that binds to DR5 and FAP according to any of the above embodiments comprises
an Fc domain,
two Fab fragments comprising each an antigen binding site specific for DR5,
and two Fab fragments comprising each an antigen binding site specific for FAP, wherein either the variable regions or the constant regions of the heavy and light chain of at least one Fab fragment are exchanged.

Since the above bispecific antibody is bivalent both for FAP and DR5, with 2 binding sites each for FAP and DR5, this format is also referred to as "2+2" format. Exemplary structures of bispecific antibodies with a 2+2 format are depicted in FIG. 28. Due to the exchange of either the variable regions or the constant regions, the Fab fragments above are also referred to as "cross-Fab fragment" or "xFab fragment" or "crossover Fab fragment".

In one preferred embodiment a bispecific antibody that binds to DR5 and FAP according to any of the above embodiments comprises
an Fc domain,
two Fab fragments comprising each an antigen binding site specific for DR5,
and two Fab fragments comprising each an antigen binding site specific for FAP, wherein either the variable regions or the constant regions of the heavy and light chain of both Fab fragments comprising an antigen binding site specific for FAP are exchanged.

In another embodiment a bispecific antibody that binds to DR5 and FAP according to any of the above embodiments comprises
an Fc domain,
two Fab fragments comprising each an antigen binding site specific for DR5,
and two Fab fragments comprising each an antigen binding site specific for FAP,
wherein either the variable regions or the constant regions of the heavy and light chain of both Fab fragments comprising an antigen binding site specific for DR5 are exchanged.

In one preferred embodiment a bispecific antibody that binds to DR5 and FAP according to any of the above embodiments comprises
an Fc domain,
two Fab fragments comprising each an antigen binding site specific for DR5,
and two Fab fragments comprising each an antigen binding site specific for FAP, wherein the variable regions of the heavy and light chain of both Fab fragments comprising an antigen binding site specific for FAP are exchanged.

In another embodiment a bispecific antibody that binds to DR5 and FAP according to any of the above embodiments comprises
an Fc domain,
two Fab fragments comprising each an antigen binding site specific for DR5,
and two Fab fragments comprising each an antigen binding site specific for FAP,
wherein the variable regions of the heavy and light chain of both Fab fragments comprising an antigen binding site specific for DR5 are exchanged.

Due to the exchange of the variable regions of the Fab heavy and light chain the crossover Fab fragments specific for FAP each comprise a peptide chain composed of the light chain variable region (VL) and the heavy chain constant region (CH1), and a peptide chain composed of the heavy chain variable region (VH) and the light chain constant region (CL). These crossover Fab fragments are also referred to as CrossFab$_{(VLVH)}$ and each comprise a VLCH1 and a VHCL chain.

In one preferred embodiment a bispecific antibody that binds to DR5 and FAP according to any of the above embodiments comprises an Fc domain, two Fab fragments comprising each an antigen binding site specific for DR5, and two Fab fragments comprising each an antigen binding site specific for FAP, wherein the constant regions of the heavy and light chain of both Fab fragments comprising an antigen binding site specific for FAP are exchanged.

In another embodiment a bispecific antibody that binds to DR5 and FAP according to any of the above embodiments comprises an Fc domain, two Fab fragments comprising each an antigen binding site specific for DR5, and two Fab fragments comprising each an antigen binding site specific for FAP, wherein the constant regions of the heavy and light chain of both Fab fragments comprising an antigen binding site specific for DR5 are exchanged.

Due to the exchange of the constant regions of the Fab heavy and light chain the crossover Fab fragments specific for FAP each comprise a peptide chain composed of the heavy chain variable region (VH) and the light chain constant region (CL), and a peptide chain composed of the light chain variable region (VL) and the heavy chain constant region (CH1). These crossover Fab fragments are also referred to as CrossFab$_{(CLCH1}$ and comprise a VHCL and a VLCH1 chain.

In one embodiment said bispecific antibody that binds to DR5 and FAP according to any of the above embodiments comprises an Fc domain to which two Fab fragments are fused to the N-terminus and two Fab fragments are fused to the C-terminus, wherein either the variable regions or the constant regions of the heavy and light chain of at least one Fab fragment are exchanged. In one embodiment two Fab fragments are fused to the N-terminus of the Fc domain through an immunoglobulin hinge region. In one embodiment, the immunoglobulin hinge region is a human IgG1 hinge region. In one embodiment the two Fab fragments comprising an antigen binding site specific for DR5 and the Fc domain are part of an immunoglobulin molecule. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

In one embodiment two Fab fragments comprising the antigen binding site specific for FAP are connected to the Fc domain via a peptide linker. In one embodiment two Fab fragments comprising an antigen binding site specific for FAP are connected to the C-terminus of the first or second subunit of the Fc domain via a peptide linker. In one such embodiment said Fab fragments comprising an antigen binding site specific for FAP are connected to the C-terminus of the second subunit (CH3 chain) of the Fc domain via a peptide linker.

In one embodiment said bispecific antibody that binds to DR5 and FAP according to any of the above embodiments comprises a) an Immunoglobulin G (IgG) molecule with two binding sites specific for DR5 (i.e. two Fab fragments specific for DR5) and b) two Fab fragments specific for FAP, wherein either the variable regions or the constant regions of the heavy and light chain are exchanged.

In another embodiment a bispecific antibody that binds to DR5 and FAP according to any of the above embodiments comprises a) an Immunoglobulin G (IgG) molecule with two binding sites (Fab fragments) specific for DR5 wherein either the variable regions or the constant regions of the heavy and light chain are exchanged and b) two Fab fragments specific for FAP.

In one embodiment a bispecific antibody that binds to DR5 and FAP according to any of the above embodiments comprises a) an Immunoglobulin G (IgG) molecule with two binding sites specific for DR5 and b) two Fab fragments specific for FAP, wherein the variable regions of the Fab heavy and light chain are exchanged.

In one embodiment a bispecific antibody that binds to DR5 and FAP according to any of the above embodiments comprises a) an Immunoglobulin G (IgG) molecule with two binding sites specific for DR5 and b) two Fab fragments specific for FAP, wherein the constant regions of the Fab heavy and light chain are exchanged.

In one embodiment a bispecific antibody that binds to DR5 and FAP according to any of the above embodiments comprises a) an Immunoglobulin G (IgG) molecule with two binding sites specific for DR5 and b) two Fab fragments specific for FAP, wherein either the variable regions or the constant regions of the heavy and light chain are exchanged, wherein the two Fab fragments are fused to the constant heavy chain of said IgG molecule.

In one embodiment said two Fab fragments are fused to the C-terminus of the constant heavy chain of said IgG molecule. In one embodiment said two Fab fragments are fused to the C-terminus of the constant heavy chain (CH1) to the first or second subunit of the Fc domain of said IgG molecule.

In one embodiment said two Fab fragments are fused to the C-terminus of the second subunit (CH3) of the Fc domain of said IgG molecule.

In one embodiment a bispecific antibody that binds to DR5 and FAP according to any of the above embodiments comprises a) an Immunoglobulin G (IgG) molecule with two binding sites specific for DR5 and b) two Fab fragments specific for FAP, wherein the variable regions of the Fab heavy and light chain are exchanged, wherein the two Fab fragments are fused to the constant heavy chain of said IgG molecule.

In one embodiment said two Fab fragments are fused to the C-terminus of the constant heavy chain of said IgG molecule. In one embodiment said two Fab fragments are fused to the C-terminus of the constant heavy chain (CH1) to the first or second subunit of the Fc domain of said IgG molecule. In one embodiment said two Fab fragments are fused to the C-terminus of the second subunit (CH3) of the Fc domain of said IgG molecule.

In one embodiment a bispecific antibody that binds to DR5 and FAP according to any of the above embodiments comprises a) an Immunoglobulin G (IgG) molecule with two binding sites specific for DR5 and
b) two Fab fragments specific for FAP, wherein the constant regions of the Fab heavy and light chain are exchanged, wherein the two Fab fragments are fused to the constant heavy chain of said IgG molecule.

In one embodiment said two Fab fragments are fused to the C-terminus of the constant heavy chain of said IgG molecule. In one embodiment said two Fab fragments are fused to the C-terminus of the constant heavy chain (CH1) to the first or second subunit of the Fc domain of said IgG molecule. In one embodiment said two Fab fragments are fused to the C-terminus of the second subunit (CH3) of the Fc domain of said IgG molecule.

In a further preferred embodiment, the two Fab fragments specific for FAP are fused to the IgG molecule by a peptide linker, preferably a peptide linker having a length of about 10-30 amino acids. Preferably said peptide linker is a (G4S)2 or (G4S)4 linker.

In one embodiment a bispecific antibody that binds to DR5 and FAP according to any of the above embodiments comprises
a) an Immunoglobulin G (IgG) molecule with two binding sites specific for DR5 and
b) two Fab fragments specific for FAP, wherein the variable regions of the Fab heavy and light chain are exchanged, wherein the two Fab fragments are fused to the constant heavy chain of said IgG molecule by a peptide linker.

In one embodiment said two Fab fragments are fused to the C-terminus of the constant heavy chain of said IgG molecule by a peptide linker. In one embodiment said two Fab fragments are fused to the C-terminus of the constant heavy chain (CH1) to the first or second subunit of the Fc domain of said IgG molecule by a peptide linker.

In one embodiment said two Fab fragments are fused to the C-terminus of the second subunit (CH3) of the Fc domain of said IgG molecule by a peptide linker.

In one embodiment a bispecific antibody that binds to DR5 and FAP according to any of the above embodiments comprises
a) an Immunoglobulin G (IgG) molecule with two binding sites specific for DR5 and
b) two Fab fragments specific for FAP, wherein the constant regions of the Fab heavy
and light chain are exchanged, wherein the two Fab fragments are fused to the constant heavy chain of said IgG molecule by a peptide linker.

In one embodiment said two Fab fragments are fused to the C-terminus of the constant heavy chain of said IgG molecule by a peptide linker.

In one embodiment said two Fab fragments are fused to the C-terminus of the constant heavy chain (CH1) to the first or second subunit of the Fc domain of said IgG molecule by a peptide linker.

In one embodiment said two Fab fragments are fused to the C-terminus of the second subunit (CH3) of the Fc domain of said IgG molecule by a peptide linker.

In one embodiment, the bispecific antibody comprises an Fc domain, at least one Fab fragment comprising the antigen binding site specific for DR5, and at least one Fab fragment comprising the antigen binding site specific for FAP, wherein at least one of the Fab fragments is connected to the first or second subunit of the Fc domain via the light chain (VLCL) and at least one Fab fragment is connected to the first or second subunit of the Fc domain via the heavy chain (VHCH1).

In one embodiment, the bispecific antibody comprises an Fc domain, two Fab fragments comprising the antigen binding site specific for DR5, and two Fab fragments comprising the antigen binding site specific for FAP, wherein at least one of the Fab fragments is fused to the first or second subunit of the Fc domain via the light chain (VLCL) and at least one Fab fragment is connected to the first or second subunit of the Fc domain via the heavy chain (VHCH1).

In one embodiment, the bispecific antibody comprises
a) an Fc domain,
b) two Fab fragments comprising an antigen binding site specific for DR5,
wherein said Fab fragments are connected at the C-terminus of the constant light chain (CL) to the first or second subunit of the Fc domain,
c) two Fab fragments comprising the antigen binding site specific for FAP, wherein the two Fab fragments are connected at the C-terminus of the constant heavy chain (CH1) to the first or second subunit of the Fc domain.

In one embodiment, the bispecific antibody comprises
a) an Fc domain,
b) two Fab fragments comprising an antigen binding site specific for DR5,
wherein said Fab fragments are connected at the C-terminus of the constant light chain (CL) to the N-terminus of the first subunit of the Fc domain,
c) two Fab fragments comprising the antigen binding site specific for FAP, wherein the two Fab fragments are connected at the C-terminus of the constant heavy chain (CH1) to the second subunit (CH3) of the Fc domain.

In one embodiment, said two Fab fragments comprising an antigen binding site specific for DR5 are each fused to the Fc domain through an immunoglobulin hinge region. In a specific embodiment, the immunoglobulin hinge region is a human IgG1 hinge region. In one embodiment the two Fab fragments comprising an antigen binding site specific for DR5 and the Fc domain are part of an immunoglobulin molecule. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

In one embodiment two Fab fragments comprising the antigen binding site specific for FAP are connected to the Fc domain via a peptide linker.

In one embodiment, the bispecific antibody comprises
a) an Fc domain,
b) two Fab fragments comprising an antigen binding site specific for DR5,
wherein said Fab fragments are connected at the C-terminus of the constant heavy chain (CH1) to the first or second subunit of the Fc domain,
c) two Fab fragments comprising the antigen binding site specific for FAP, wherein the two Fab fragments are connected at the N-terminus of the constant light chain (CL) to the first or second subunit of the Fc domain.

In one embodiment, the bispecific antibody comprises
a) an Fc domain,
b) two Fab fragments comprising an antigen binding site specific for DR5, wherein said Fab fragments are connected at the C-terminus of the constant heavy chain (CH1) to the N-terminus of the first subunit of the Fc domain,
  c) two Fab fragments comprising the antigen binding site specific for FAP, wherein the two Fab fragments are connected at the N-terminus of the constant light chain (CL) to the N-terminus of the second subunit of the Fc domain.

In one embodiment, said two Fab fragments comprising an antigen binding site specific for DR5 are each fused to the Fc domain through an immunoglobulin hinge region. In a specific embodiment, the immunoglobulin hinge region is a human IgG1 hinge region. In one embodiment the two Fab fragments comprising an antigen binding site specific for DR5 and the Fc domain are part of an immunoglobulin molecule. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

Exemplary Antibodies with a 2+2 Format

In one embodiment a bispecific antibody that binds to DR5 and FAP according to any of the above embodiments comprises
  a) an Immunoglobulin G (IgG) molecule with two binding sites specific for DR5, comprising
  a heavy chain CDR1 of SEQ ID NO.:1;
  a heavy chain CDR2 of SEQ ID NO.:2;
  a heavy chain CDR3 of SEQ ID NO.:3;
  a light chain CDR1 of SEQ ID NO.:4;
  a light chain CDR2 of SEQ ID NO.:5;
  a light chain CDR3 of SEQ ID NO.:6; and
  b) two Fab fragments specific for FAP, comprising
  a heavy chain CDR1 of SEQ ID NO.:9;
  a heavy chain CDR2 of SEQ ID NO.:10;
  a heavy chain CDR3 of SEQ ID NO.:11;
  a light chain CDR1 of SEQ ID NO.:12;
  a light chain CDR2 of SEQ ID NO.:13;
  a light chain CDR3 of SEQ ID NO.:14;
wherein the constant regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
  a) an Immunoglobulin G (IgG) molecule with two binding sites specific for DR5, comprising
  a heavy chain CDR1 of SEQ ID NO.:1;
  a heavy chain CDR2 of SEQ ID NO.:2;
  a heavy chain CDR3 of SEQ ID NO.:3;
  a light chain CDR1 of SEQ ID NO.:4;
  a light chain CDR2 of SEQ ID NO.:5;
  a light chain CDR3 of SEQ ID NO.:6; and
  b) two Fab fragments specific for FAP, comprising
  a heavy chain CDR1 of SEQ ID NO.:9;
  a heavy chain CDR2 of SEQ ID NO.:10;
  a heavy chain CDR3 of SEQ ID NO.:11;
  a light chain CDR1 of SEQ ID NO.:12;
  a light chain CDR2 of SEQ ID NO.:13;
  a light chain CDR3 of SEQ ID NO.:14;
wherein the variable regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
  a) an Immunoglobulin G (IgG) molecule with two binding sites specific for DR5, comprising a variable heavy chain of SEQ ID NO.:7 and a variable light chain of SEQ ID NO.:8; and
  b) two Fab fragments specific for FAP, comprising a heavy chain variable region comprising an amino acid sequence of SEQ ID NO.:15 and a light chain variable region comprising an amino acid sequence of SEQ ID NO.:16; wherein the constant regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
  a) an Immunoglobulin G (IgG) molecule with two binding sites specific for DR5, comprising a variable heavy chain of SEQ ID NO.:7 and a variable light chain of SEQ ID NO.:8; and
  b) two Fab fragments specific for FAP, comprising a heavy chain variable region comprising an amino acid sequence of SEQ ID NO.:15 and a light chain variable region comprising an amino acid sequence of SEQ ID NO.:16; wherein the variable regions of the Fab heavy and light chain are exchanged, wherein the two Fab fragments are fused to the constant heavy chain of said IgG molecule by a peptide linker.

In another embodiment said bispecific antibody of the invention comprises a modification in the Fc part of the IgG molecule, as outlined below.

In one embodiment a bispecific antibody with a 2+2 format as described above is provided comprising two $VH_{(DR5)}$-Fc part-$VH_{(FAP)}$-CL chains of SEQ ID NO.:131, two VL (DR5)-kappa light chains of SEQ ID NO.:132 and two VLCH1 (FAP) chains of SEQ ID NO.:124.

In one embodiment a bispecific antibody with a 2+2 format as described above is provided comprising two $VH_{(DR5)}$-Fc part-$VH_{(FAP)}$-CL chains of SEQ ID NO.:133, two VL (DR5)-kappa light chains of SEQ ID NO.:132 and two VLCH1 (FAP) chains of SEQ ID NO.:124.

In one embodiment a bispecific antibody with a 2+2 format as described above is provided comprising two $VH_{(DR5)}$-Fc part-$VH_{(FAP)}$-CL chains of SEQ ID NO.:134, two VL (DR5)-kappa light chains of SEQ ID NO.:132 and two VLCH1 (FAP) chains of SEQ ID NO.:124.

In one embodiment a bispecific antibody with a 2+2 format as described above is provided comprising two $VL_{(DR5)}$-CH1-Fc part-$VH_{(FAP)}$-CH1 chains of SEQ ID NO. 135, two $VH_{(DR5)}$-CL chains of SEQ ID NO.:136 and two $VL_{(FAP)}$-kappa light chains of SEQ ID NO.:137.

In one embodiment a bispecific antibody with a 2+2 format as described above is provided, comprising two $VH_{(DR5)}$ CL-Fc-peptide linker-$VH_{(FAP)}$-CH1 chains of SEQ ID NO.:138, two $VL_{(DR5)}$-CH1 chains of SEQ ID NO.:139 and two $VL_{(FAP)}$-kappa light chains of SEQ ID NO.:137.

2. Bispecific DR5-FAP Antibodies in a 2+1 Format

In one embodiment a bispecific antibody that binds to DR5 and FAP according to any of the above embodiments comprises an Fc domain, two Fab fragments comprising an antigen binding site specific for DR5, and one Fab fragment comprising the antigen binding site specific for FAP, wherein either the variable regions or the constant regions of the heavy and light chain of at least one Fab fragment are exchanged.

Since the above bispecific antibodies are trivalent with one binding site for FAP and two binding sites for DR5, this format is also referred to as "2+1" format. Hence the bispecific antibodies provided in this section are bivalent for DR5 and monovalent for FAP.

An exemplary structure of a bispecific antibodies with a 2+1 format are depicted in FIGS. 25 A and B. Due to the exchange of either the variable regions or the constant regions, the Fab fragments above are also referred to as "cross-Fab fragment" or "xFab fragment" or "crossover Fab fragment".

In one embodiment a bispecific antibody that binds to DR5 and FAP according to any of the above embodiments comprises an Fc domain, two Fab fragments comprising each an antigen binding site specific for DR5, and one Fab fragment comprising an antigen binding site specific for FAP, wherein either the variable regions or the constant regions of the heavy and light chain of the Fab fragments comprising an antigen binding site specific for FAP are exchanged.

In one embodiment a bispecific antibody that binds to DR5 and FAP according to any of the above embodiments comprises an Fc domain, two Fab fragments comprising each an antigen binding site specific for DR5, and one Fab fragment comprising an antigen binding site specific for FAP, wherein the variable regions of the heavy and light chain of the Fab fragment comprising an antigen binding site specific for FAP are exchanged.

Due to the exchange of the variable regions of the Fab heavy and light chain the crossover Fab fragment specific for FAP each comprise a peptide chain composed of the light chain variable region (VL) and the heavy chain constant region (CH1), and a peptide chain composed of the heavy chain variable region (VH) and the light chain constant region (CL). These crossover Fab fragment is also referred to as CrossFab$_{(VLVH)}$ and comprises a VLCH1 and a VHCL chain.

In one embodiment a bispecific antibody that binds to DR5 and FAP according to any of the above embodiments comprises an Fc domain, two Fab fragments comprising each an antigen binding site specific for DR5, and one Fab fragment comprising an antigen binding site specific for FAP, wherein the constant regions of the heavy and light chain of both Fab fragments comprising the antigen binding site specific for FAP are exchanged.

Due to the exchange of the constant regions of the Fab heavy and light chain the crossover Fab fragment specific for FAP each comprise a peptide chain composed of the heavy chain variable region (VH) and the light chain constant region (CL), and a peptide chain composed of the light chain variable region (VL) and the heavy chain constant region (CH1). These crossover Fab fragments is also referred to as CrossFab$_{(CLCH1)}$ and comprises a VHCL and a VLCH1 chain.

In one embodiment said bispecific antibody that binds to DR5 and FAP according to any of the above embodiments comprises an Fc domain to which two Fab fragments are fused to the N-terminus.

In one embodiment two Fab fragments are fused to the N-terminus of the Fc domain through an immunoglobulin hinge region. In one embodiment, the immunoglobulin hinge region is a human IgG1 hinge region. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

Bispecific DR5-FAP Antibodies in a 2+1 Format with FAP Binder Fused to C-Terminus In one embodiment the two Fab fragments comprising an antigen binding site specific for DR5 and the Fc domain are part of an immunoglobulin molecule. In one embodiment one Fab fragment comprising the antigen binding site specific for FAP is fused to the C-terminus of the first or second subunit of the Fc domain via a peptide linker. In one such embodiment said Fab fragment comprising an antigen binding site specific for FAP is fused to the C-terminus of the second subunit (CH3 chain) of the Fc domain via a peptide linker. An exemplary structure of a bispecific DR5-FAP antibody in a 2+1 Format with the FAP binder fused to C-terminus is depicted in FIG. 25 A.

In one embodiment a bispecific antibody that binds to DR5 and FAP according to any of the above embodiments comprises a) an Immunoglobulin G (IgG) molecule with two binding sites (Fab fragments) specific for DR5 and b) one Fab fragment specific for FAP, wherein either the variable regions or the constant regions of the heavy and light chain are exchanged.

In one embodiment a bispecific antibody that binds to DR5 and FAP according to any of the above embodiments comprises a) an Immunoglobulin G (IgG) molecule with two binding sites specific for DR5 and b) one Fab fragment specific for FAP, wherein the variable regions of the Fab heavy and light chain are exchanged.

In one embodiment a bispecific antibody that binds to DR5 and FAP according to any of the above embodiments comprises a) an Immunoglobulin G (IgG) molecule with two binding sites specific for DR5 and b) one Fab fragment specific for FAP, wherein the constant regions of the Fab heavy and light chain are exchanged.

In one preferred embodiment a bispecific antibody that binds to DR5 and FAP according to any of the above embodiments comprises a) an Immunoglobulin G (IgG) molecule with two binding sites specific for DR5 and b) one Fab fragment specific for FAP, wherein either the variable regions or the constant regions of the heavy and light chain are exchanged, wherein the Fab fragment is fused to the constant heavy chain of said IgG molecule.

In one embodiment said Fab fragment specific for FAP of b) is fused to the C-terminus of the first or second subunit of the Fc domain of said IgG molecule. In one embodiment said Fab fragment of b) is fused to the C-terminus of the second subunit (CH3) of the Fc domain of said IgG molecule.

In one embodiment a bispecific antibody that binds to DR5 and FAP according to any of the above embodiments comprises
- a) an Immunoglobulin G (IgG) molecule with two binding sites specific for DR5 and
- b) one Fab fragment specific for FAP, wherein the variable regions of the Fab heavy and light chain are exchanged, wherein the Fab fragment is fused to the constant heavy chain of said IgG molecule.

In one embodiment said Fab fragment specific for FAP of b) is fused to the C-terminus of the first or second subunit of the Fc domain of said IgG molecule. In one embodiment said Fab fragment of b) is fused to the C-terminus of the second subunit (CH3) of the Fc domain of said IgG molecule.

In one embodiment a bispecific antibody that binds to DR5 and FAP according to any of the above embodiments comprises
- a) an Immunoglobulin G (IgG) molecule with two binding sites specific for DR5 and
- b) one Fab fragment specific for FAP, wherein the constant regions of the Fab heavy and light chain are exchanged, wherein the Fab fragment is fused to the constant heavy chain of said IgG molecule.

In one embodiment said Fab fragment specific for FAP of b) is fused to the C-terminus of the first or second subunit of the Fc domain of said IgG molecule. In one embodiment said Fab fragment of b) is fused to the C-terminus of the second subunit (CH3) of the Fc domain of said IgG molecule.

Bispecific DR5-FAP Antibodies in a 2+1 Format with FAP Binder Fused to the N-Terminus In another embodiment one Fab fragment comprising an antigen binding site specific for DR5, one Fab fragment comprising an antigen binding site specific for FAP and the Fc domain are part of an immunoglobulin molecule. In one embodiment another Fab fragment comprising an antigen binding site specific for DR5 is fused to the N-terminus of the Fab fragment comprising an antigen binding site specific for DR5 of the IgG molecule via a peptide linker. An exemplary structure of a bispecific DR5-FAP antibody in a 2+1 Format with the FAP binder fused to N-terminus is depicted in FIG. 25 B.

In one embodiment a bispecific antibody that binds to DR5 and FAP according to any of the above embodiments comprises
- a) an Immunoglobulin G (IgG) molecule with one binding site (Fab fragment) specific for DR5 and one binding site (Fab fragment) specific for FAP, wherein the Fab fragment specific for FAP is a Crossfab fragment (i.e. either the variable regions or the constant regions of the heavy and light chain are exchanged).
- b) one Fab fragment specific for DR5.

In one embodiment a bispecific antibody that binds to DR5 and FAP according to any of the above embodiments comprises
- a) an Immunoglobulin G (IgG) molecule with one binding site specific for DR5 and one binding site specific for FAP, wherein the Fab fragment specific for FAP is a CrossFab$_{(VLVH)}$ fragment (i.e. the variable regions of the heavy and light chain are exchanged).
- b) one Fab fragment specific for DR5.

In one embodiment a bispecific antibody that binds to DR5 and FAP according to any of the above embodiments comprises
- a) an Immunoglobulin G (IgG) molecule with one binding site specific for DR5 and one binding site specific for FAP, wherein the Fab fragment specific for FAP is a CrossFab$_{(CLCH1)}$ fragment (i.e. the constant regions of the heavy and light chain are exchanged).
- b) one Fab fragment specific for DR5.

In one embodiment a bispecific antibody that binds to DR5 and FAP according to any of the above embodiments comprises
- a) an Immunoglobulin G (IgG) molecule with one binding site specific for DR5 and one binding site specific for FAP, wherein the Fab fragment specific for FAP is a Crossfab fragment (i.e. either the variable regions or the constant regions of the heavy and light chain are exchanged).
- b) one Fab fragment specific for DR5, wherein said Fab fragment is fused to the N-terminus of the variable heavy or light chain of the IgG molecule.

In one embodiment a bispecific antibody that binds to DR5 and FAP according to any of the above embodiments comprises
- a) an Immunoglobulin G (IgG) molecule with one binding site (Fab fragment) specific for DR5 and one binding site specific for FAP, wherein the Fab fragment specific for FAP is a CrossFab$_{(VLVH)}$ fragment (i.e. the variable regions of the heavy and light chain are exchanged).
- b) one Fab fragment specific for DR5, wherein said Fab fragment is fused to the N-terminus of the variable heavy or light chain of the IgG molecule.

In one embodiment, the Fab fragment specific for DR5 of b) is fused to the N-terminus of the variable heavy or light chain of the Fab fragment specific for DR5 of a).

In one embodiment a bispecific antibody that binds to DR5 and FAP according to any of the above embodiments comprises
- a) an Immunoglobulin G (IgG) molecule with one binding site specific for DR5 and one binding site specific for FAP, wherein the Fab fragment specific for FAP is a CrossFab$_{(CLCH1)}$ fragment (i.e. the constant regions of the heavy and light chain are exchanged).
- b) one Fab fragment specific for DR5, wherein said Fab fragment is fused to the N-terminus of the variable heavy or light chain of the IgG molecule.

In one embodiment, the Fab fragment specific for DR5 of b) is fused to the N-terminus of the variable heavy or light chain of the Fab fragment specific for DR5 of a).

In a further preferred embodiment, the Fab fragment specific for DR5 is fused to the IgG molecule by a peptide linker, preferably a peptide linker having a length of about 10-30 amino acids. Preferably said peptide linker is a (G4S)2 or (G4S)4 linker.

In another embodiment said bispecific antibody of the invention comprises a modification in the Fc part of the IgG molecule, as outlined below.

3. Bispecific DR5-FAP Antibodies in a 3+1 Format

In one embodiment a bispecific antibody that binds to DR5 and FAP according to any of the above embodiments comprises
an Fc domain,
three Fab fragments comprising each an antigen binding site specific for DR5,
and one Fab fragment comprising an antigen binding site specific for FAP, wherein either the variable regions or the constant regions of the heavy and light chain of at least one Fab fragment are exchanged.

Since the above bispecific antibody is tetravalent with one binding site for FAP and three binding sites for DR5, this format is also referred to as "3+1" format. Hence the bispecific molecules described in this section are trivalent for DR5 and monovalent for FAP.

An exemplary structure of a bispecific antibody with a 3+1 format is depicted in FIG. 25 C. Due to the exchange of either the variable regions or the constant regions, the Fab fragments above are also referred to as "cross-Fab fragment" or "xFab fragment" or "crossover Fab fragment".

In one embodiment a bispecific antibody that binds to DR5 and FAP according to any of the above embodiments comprises
an Fc domain,
three Fab fragments comprising each an antigen binding site specific for DR5,
and one Fab fragment comprising an antigen binding site specific for FAP, wherein either the variable regions or the constant regions of the heavy and light chain of the Fab fragments comprising an antigen binding site specific for FAP are exchanged.

In one embodiment a bispecific antibody that binds to DR5 and FAP according to any of the above embodiments comprises
an Fc domain,
three Fab fragments comprising each an antigen binding site specific for DR5,
and one Fab fragment comprising an antigen binding site specific for FAP, wherein the variable regions of the heavy and light chain of the Fab fragment comprising an antigen binding site specific for FAP are exchanged.

Due to the exchange of the variable regions of the Fab heavy and light chain the crossover Fab fragment specific for FAP comprises a peptide chain composed of the light chain variable region (VL) and the heavy chain constant region (CH1), and a peptide chain composed of the heavy chain variable region (VH) and the light chain constant region (CL). This crossover Fab fragments is also referred to as CrossFab$_{(VLVH)}$ and comprises a VLCH1 and a VHCL chain.

In one embodiment a bispecific antibody that binds to DR5 and FAP according to any of the above embodiments comprises
an Fc domain,
three Fab fragments comprising each an antigen binding site specific for DR5,
and one Fab fragment comprising an antigen binding site specific for FAP, wherein the constant regions of the heavy and light chain of the Fab fragment comprising the antigen binding site specific for FAP are exchanged.

Due to the exchange of the constant regions of the Fab heavy and light chain the crossover Fab fragment specific for FAP each comprise a peptide chain composed of the heavy chain variable region (VH) and the light chain constant region (CL), and a peptide chain composed of the light chain variable region (VL) and the heavy chain constant region (CH1). This crossover Fab fragment is also referred to as CrossFab$_{(CLCH1)}$ and comprise a VHCL and a VLCH1 chain.

In one embodiment said bispecific antibody that binds to DR5 and FAP according to any of the above embodiments comprises an Fc domain to which two Fab fragments are fused to the N terminus and two Fab fragments are fused to the C-terminus, wherein either the variable regions or the constant regions of the heavy and light chain of the one Fab fragment specific for FAP are exchanged.

In one embodiment two Fab fragments are fused to the N-terminus of the Fc domain through an immunoglobulin hinge region. In one embodiment, the immunoglobulin hinge region is a human IgG1 hinge region. In one embodiment the two Fab fragments comprising an antigen binding site specific for DR5 and the Fc domain are part of an immunoglobulin molecule. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

In one embodiment a bispecific antibody that binds to DR5 and FAP according to any of the above embodiments comprises
a) an Immunoglobulin G (IgG) molecule with two binding sites (Fab fragments) specific for DR5 and
b) one Fab fragment specific for FAP, wherein either the variable regions or the constant regions of the heavy and light chain are exchanged.
c) one Fab fragment specific for DR5.

In one embodiment a bispecific antibody that binds to DR5 and FAP according to any of the above embodiments comprises
a) an Immunoglobulin G (IgG) molecule with two binding sites (Fab fragments) specific for DR5 and
b) one Fab fragment specific for FAP, wherein the variable regions of the Fab heavy and light chain are exchanged.
c) one Fab fragment specific for DR5.

In one embodiment a bispecific antibody that binds to DR5 and FAP according to any of the above embodiments comprises
a) an Immunoglobulin G (IgG) molecule with two binding sites (Fab fragments) specific for DR5 and
b) one Fab fragment specific for FAP, wherein the constant regions of the Fab heavy and light chain are exchanged.
c) one Fab fragment specific for DR5.

In one preferred embodiment a bispecific antibody that binds to DR5 and FAP according to any of the above embodiments comprises
a) an Immunoglobulin G (IgG) molecule with two binding sites (Fab fragments) specific for DR5 and
b) one Fab fragment specific for FAP, wherein either the variable regions or the constant regions of the heavy and light chain are exchanged.
c) one Fab fragment specific for DR5,
wherein the Fab fragments of b) and c) are fused to the C-terminus of the first or second subunit of the Fc domain of said IgG molecule.

In one embodiment said two Fab fragments of b) and c) are fused to the C-terminus of the second subunit (CH3) of the Fc domain of said IgG molecule.

In one embodiment a bispecific antibody that binds to DR5 and FAP according to any of the above embodiments comprises
a) an Immunoglobulin G (IgG) molecule with two binding sites (Fab fragments) specific for DR5 and
b) one Fab fragment specific for FAP, wherein the variable regions of the Fab heavy and light chain are exchanged.
c) one Fab fragment specific for DR5, wherein the Fab fragments of b) and c) are fused to the first or second subunit of the Fc domain of said IgG molecule.

In one embodiment said two Fab fragments of b) and c) are fused to the C-terminus of the second subunit (CH3) of the Fc domain of said IgG molecule.

In one embodiment a bispecific antibody that binds to DR5 and FAP according to any of the above embodiments comprises
- a) an Immunoglobulin G (IgG) molecule with two binding sites (Fab fragments) specific for DR5 and
- b) one Fab fragment specific for FAP, wherein the constant regions of the Fab heavy and light chain are exchanged.
- c) one Fab fragment specific for DR5, wherein the Fab fragments of b) and c) are fused to the first or second subunit of the Fc domain of said IgG molecule.

In one embodiment said two Fab fragments of b) and c) are fused to the C-terminus of the second subunit (CH3) of the Fc domain of said IgG molecule.

In a further preferred embodiment, the two Fab fragments of b) and c) of any of the embodiments described in this section are fused to the IgG molecule by a peptide linker, preferably a peptide linker having a length of about 10-30 amino acids. Preferably said peptide linker is a (G4S)2 or (G4S)4 linker.

In another embodiment said bispecific antibody of the invention comprises a modification in the Fc part of the IgG molecule, as outlined below.

4. Bispecific DR5-FAP Antibodies in a 1+1 Format

In one embodiment a bispecific antibody that binds to DR5 and FAP according to any of the above embodiments comprises
an Fc domain,
one Fab fragment comprising an antigen binding site specific for DR5,
and one Fab fragment comprising an antigen binding site specific for FAP,
wherein either the variable regions or the constant regions of the heavy and light chain of at least one Fab fragment are exchanged.

Since the above bispecific antibody is bivalent with one binding site for FAP and one binding site for DR5, this format is also referred to as "1+1" format. Hence the bispecific antibodies described in this section are monovalent for DR5 and monovalent for FAP. An exemplary structure of a bispecific antibody with a 1+1 format is depicted in FIG. 25 D. Due to the exchange of either the variable regions or the constant regions, the Fab fragment above is also referred to as "cross-Fab fragment" or "xFab fragment" or "crossover Fab fragment". The IgG molecule in a 1+1 format is also referred to as Crossmab format (see Schaefer et al. Proc Natl Acad Sci USA 2011; 108:11187-92).

In one embodiment a bispecific antibody that binds to DR5 and FAP according to any of the above embodiments comprises
an Fc domain,
one Fab fragment comprising an antigen binding site specific for DR5, wherein either the variable regions or the constant regions of the heavy and light chain of the Fab fragment comprising an antigen binding site specific for DR5 are exchanged.
and one Fab fragment comprising an antigen binding site specific for FAP.

In one embodiment a bispecific antibody that binds to DR5 and FAP according to any of the above embodiments comprises
an Fc domain,
one Fab fragment comprising an antigen binding site specific for DR5,
and one Fab fragment comprising an antigen binding site specific for FAP, wherein either the variable regions or the constant regions of the heavy and light chain of the Fab fragment comprising an antigen binding site specific for FAP are exchanged.

In one embodiment a bispecific antibody that binds to DR5 and FAP according to any of the above embodiments comprises
an Fc domain,
one Fab fragment comprising an antigen binding site specific for DR5,
and one Fab fragment comprising an antigen binding site specific for FAP, wherein the variable regions of the heavy and light chain of the Fab fragment comprising an antigen binding site specific for FAP are exchanged.

In one embodiment a bispecific antibody that binds to DR5 and FAP according to any of the above embodiments comprises
an Fc domain,
one Fab fragments comprising an antigen binding site specific for DR5,
and one Fab fragment comprising an antigen binding site specific for FAP, wherein the constant regions of the heavy and light chain of the Fab fragment comprising the antigen binding site specific for FAP are exchanged.

In one embodiment said bispecific antibody that binds to DR5 and FAP according to any of the above embodiments comprises an Fc domain to which two Fab fragments are fused to the N-terminus, wherein either the variable regions or the constant regions of the heavy and light chain of at least one Fab fragment are exchanged. In one embodiment the two Fab fragments are fused to the N-terminus of the Fc domain through an immunoglobulin hinge region. In one embodiment, the immunoglobulin hinge region is a human IgG1 hinge region. In one embodiment the Fab fragment comprising an antigen binding site specific for DR5, the Fab fragment comprising an antigen binding site specific for FAP and the Fc domain are part of an immunoglobulin molecule. In a particular embodiment the immunoglobulin molecule is an IgG class immunoglobulin. In an even more particular embodiment the immunoglobulin is an IgG1 subclass immunoglobulin. In another embodiment the immunoglobulin is an IgG4 subclass immunoglobulin. In a further particular embodiment the immunoglobulin is a human immunoglobulin. In other embodiments the immunoglobulin is a chimeric immunoglobulin or a humanized immunoglobulin.

In one embodiment a bispecific antibody that binds to DR5 and FAP according to any of the above embodiments comprises an Immunoglobulin G (IgG) molecule with one binding site specific for DR5 and one binding site specific for FAP, wherein either the variable regions or the constant regions of the heavy and light chain of one arm (Fab fragment) of the IgG molecule are exchanged.

In one embodiment a bispecific antibody that binds to DR5 and FAP according to any of the above embodiments comprises an Immunoglobulin G (IgG) molecule with one binding site specific for DR5 and one binding site specific for FAP, wherein the variable regions of the heavy and light chain of one arm (Fab fragment) of the IgG molecule are exchanged. This antibody format is also referred to as CrossMab$_{(VHVL)}$.

In one embodiment the variable regions of the heavy and light chain of the one arm (Fab fragment) of the IgG molecule which comprises the binding site specific for FAP are exchanged.

In one embodiment a bispecific antibody that binds to DR5 and FAP according to any of the above embodiments comprises an Immunoglobulin G (IgG) molecule with one binding site specific for DR5 and one binding site specific for FAP, wherein the constant regions of the heavy and light chain of one arm (Fab fragment) of the IgG molecule are exchanged. This antibody format is also referred to as CrossMab$_{(CH1CL)}$.

In one embodiment the constant regions of the heavy and light chain of the one arm (Fab fragment) of the IgG molecule which comprises the binding site specific for FAP are exchanged.

In one embodiment a bispecific antibody that binds to DR5 and FAP according to any of the above embodiments comprises an Immunoglobulin G (IgG) molecule with one binding site specific for DR5 and one binding site specific for FAP, wherein the complete VH-CH1 and VL-CL domains of one arm (Fab fragment) of the IgG molecule are exchanged. This means that at least one of the Fab fragments is fused to the N-terminus of the Fc domain via the light chain (VLCL). In one embodiment the other Fab fragment is fused to the the N-terminus of the Fc domain via the heavy chain (VHCH1).

This antibody format is also referred to as CrossMab$_{Fab}$. In one embodiment both Fab fragments are fused to the N-terminus of the Fc domain through an immunoglobulin hinge region.

D. Fc Domain Modifications Reducing Fc Receptor Binding and/or Effector Function In one preferred embodiment a bispecific antibody that binds to DR5 and FAP according to any of the above embodiments comprises an Immunoglobulin G (IgG) molecule wherein the Fc part is modified. The modified Fc part has a reduced binding affinity for the Fcγ receptors compared to a wildtype Fc part.

The Fc domain of the bispecific antibodies of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

In one embodiment according to the invention the Fc domain of the bispecific antibodies of the invention is an IgG Fc domain. In a particular embodiment the Fc domain is an IgG1 Fc domain. In another embodiment the Fc domain is an IgG4 Fc domain. In a more specific embodiment, the Fc domain is an IgG4 Fc domain comprising an amino acid substitution at position S228 (Kabat numbering), particularly the amino acid substitution S228P. In a more specific embodiment, the Fc domain is an IgG4 Fc domain comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)). In a further particular embodiment the Fc domain is human. An exemplary sequence of a human IgG$_1$ Fc region is given in SEQ ID NO.:151.

The Fc domain confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc domain of the the bispecific antibodies of the invention exhibits reduced binding affinity to an Fc receptor and/or reduced effector function, as compared to a native IgG$_1$ Fc domain. In one such embodiment the Fc domain (or the bispecific antibodies of the invention comprising said Fc domain) exhibits less than 50%, preferably less than 20%, more preferably less than 10% and most preferably less than 5% of the binding affinity to an Fc receptor, as compared to a native IgG$_1$ Fc domain (or a bispecific antibodies of the invention comprising a native IgG$_1$ Fc domain), and/or less than 50%, preferably less than 20%, more preferably less than 10% and most preferably less than 5% of the effector function, as compared to a native IgG$_1$ Fc domain domain (or a bispecific antibodies of the invention comprising a native IgG$_1$ Fc domain). In one embodiment, the Fc domain (or the bispecific antibodies of the invention comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the Fc receptor is an inhibitory Fc receptor. In a specific embodiment the Fc receptor is an inhibitory human Fcγ receptor, more specifically human FcgRIIB. In one embodiment the effector function is one or more of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native IgG$_1$ Fc domain domain. Substantially similar binding to FcRn is achieved when the Fc domain (or the bispecific antibodies of the invention comprising said Fc domain) exhibits greater than about 70%, particularly greater than about 80%, more particularly greater than about 90% of the binding affinity of a native IgG$_1$ Fc domain (or the bispecific antibodies of the invention comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the bispecific antibodies of the invention comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the bispecific antibodies of the invention comprising an engineered Fc domain exhibits less than 20%, particularly less than 10%, more particularly less than 5% of the binding affinity to an Fc receptor as compared to a bispecific antibodies of the invention comprising a non-engineered Fc domain. In a particular embodiment the Fc receptor is an Fcγ receptor. In some embodiments the Fc receptor is a human Fc receptor. In one embodiment the Fc receptor is an inhibitory Fc receptor. In a specific embodiment the Fc receptor is an inhibitory human Fcγ receptor, more specifically human FcgRIIB. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the bispecific antibodies of the invention comprising said Fc domain) exhibits greater than about 70% of the binding affinity of a non-engineered form of the Fc domain (or the bispecific antibodies of the invention comprising said non-engineered form of the Fc domain) to FcRn. The Fc domain, or the bispecific antibodies of the invention of the invention comprising said Fc domain, may exhibit greater than about 80% and even greater than about 90% of such affinity. In certain embodiments the Fc domain of the bispecific antibodies of the invention is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming. In one embodiment the reduced effector function is one or more of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a bispecific antibody of the invention comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position of E233, L234, L235, N297, P331 and P329. In a more specific embodiment the Fc domain comprises an amino acid substitution at a position of L234, L235 and P329. In some embodiments the Fc domain comprises the amino acid substitutions L234A and L235A. In one such embodiment, the Fc domain is an IgG$_1$ Fc domain, particularly a human IgG$_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an IgG1 Fc domain, particularly a human IgG1 Fc domain. The "P329G LALA" combination of amino acid substitutions almost completely abolishes Fcγ receptor binding of a human IgG1 Fc domain, as described in PCT patent application no. PCT/EP2012/055393, incorporated herein by reference in its entirety. PCT/EP2012/055393 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the bispecific antibodies of the invention is an IgG$_4$ Fc domain, particularly a human IgG$_4$ Fc domain. In one embodiment the IgG$_4$ Fc domain comprises amino acid substitutions at position S228, specifically the amino acid substitution S228P. To further reduce its binding affinity to an Fc receptor and/or its effector function, in one embodiment the IgG4 Fc domain comprises an amino acid substitution at position L235, specifically the amino acid substitution L235E. In another embodiment, the IgG4 Fc domain comprises an amino acid substitution at position P329, specifically the amino acid substitution P329G. In a particular embodiment, the IgG4 Fc domain comprises amino acid substitutions at positions S228, L235 and P329, specifically amino acid substitutions S228P, L235E and P329G. Such IgG4 Fc domain mutants and their Fcγ receptor binding properties are described in PCT patent application no. PCT/EP2012/055393, incorporated herein by reference in its entirety.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G.

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D).

In addition to the Fc domains described hereinabove and in PCT patent application no. PCT/EP2012/055393, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or bispecific antibodies of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the bispecific antibodies of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

The following section describes preferred embodiments of the bispecific antibodies of the invention comprising Fc domain modifications reducing Fc receptor binding and/or effector function.

In one preferred embodiment a bispecific antibody that binds to DR5 and FAP according to any of the above embodiments comprises
   a) an Immunoglobulin G (IgG) molecule with two binding sites specific for DR5, wherein the Fc domain exhibits reduced binding affinity to an Fc receptor and/or reduced effector function, as compared to a native IgG1 Fc domain and
   b) two Fab fragments specific for FAP, wherein either the variable regions or the constant regions of the heavy and light chain are exchanged.

In one preferred embodiment a bispecific antibody that binds to DR5 and FAP according to any of the above embodiments comprises
   a) an Immunoglobulin G (IgG) molecule with two binding sites specific for DR5, wherein the Fc domain comprises one or more amino acid substitution that reduces binding to an Fc receptor and/or effector function.
   b) two Fab fragments specific for FAP, wherein either the variable regions or the constant regions of the heavy and light chain are exchanged.

In one preferred embodiment a bispecific antibody that binds to DR5 and FAP according to any of the above embodiments comprises
   a) an Immunoglobulin G (IgG) molecule with two binding sites specific for DR5, wherein said one or more amino acid substitution is at one or more position of L234, L235, and P329
   b) two Fab fragments specific for FAP, wherein either the variable regions or the constant regions of the heavy and light chain are exchanged.

In one preferred embodiment a bispecific antibody that binds to DR5 and FAP according to any of the above embodiments comprises
   a) an Immunoglobulin G (IgG) molecule with two binding sites specific for DR5, wherein each subunit of the Fc domain comprises three amino acid substitutions that reduce binding to an activating or inhibitory Fc receptor and/or effector function wherein said amino acid substitutions are L234A, L235A and P329G.
   b) two Fab fragments specific for FAP, wherein either the variable regions or the constant regions of the heavy and light chain are exchanged.

In one preferred embodiment a bispecific antibody that binds to DR5 and FAP according to any of the above embodiments comprises
   a) an Immunoglobulin G (IgG) molecule with two binding sites specific for DR5, wherein each subunit of the Fc domain comprises three amino acid substitutions that reduce binding to an activating or inhibitory Fc receptor and/or effector function wherein said amino acid substitutions are L234A, L235A and P329G.
   b) two Fab fragments specific for FAP, wherein the variable regions of the Fab heavy and light chain are exchanged.

In one preferred embodiment a bispecific antibody that binds to DR5 and FAP according to any of the above embodiments comprises
   a) an Immunoglobulin G (IgG) molecule with two binding sites specific for DR5, wherein each subunit of the Fc domain comprises three amino acid substitutions that reduce binding to an activating or inhibitory Fc receptor and/or effector function wherein said amino acid substitutions are L234A, L235A and P329G.
   b) two Fab fragments specific for FAP, wherein the constant regions of the Fab heavy and light chain are exchanged.

In one embodiment a bispecific antibody that binds to DR5 and FAP according to any of the above embodiments comprises
   a) an Immunoglobulin G (IgG) molecule with two binding sites specific for DR5, wherein each subunit of the Fc domain comprises three amino acid substitutions that reduce binding to an activating or inhibitory Fc receptor and/or effector function wherein said amino acid substitutions are L234A, L235A and P329G and
   b) two Fab fragments specific for FAP, wherein the variable regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
   a) an Immunoglobulin G (IgG) molecule with two binding sites specific for DR5, wherein each subunit of the Fc domain comprises three amino acid substitutions that reduce binding to an activating or inhibitory Fc receptor and/or effector function wherein said amino acid substitutions are L234A, L235A and P329G and b) two Fab fragments specific for FAP, wherein the constant regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
a) an Immunoglobulin G (IgG) molecule with two binding sites specific for DR5, comprising
a heavy chain CDR1 consisting of SEQ ID NO.:1;
a heavy chain CDR2 of SEQ ID NO.:2;
a heavy chain CDR3 of SEQ ID NO.:3;
a light chain CDR1 of SEQ ID NO.:4;
a light chain CDR2 of SEQ ID NO.:5;
a light chain CDR3 of SEQ ID NO.:6;
wherein each subunit of the Fc domain comprises three amino acid substitutions that reduce binding to activating and inhibitory Fc receptors and/or effector function wherein said amino acid substitutions are L234A, L235A and P329G and
b) two Fab fragments specific for FAP, comprising
a heavy chain CDR1 of SEQ ID NO.:9;
a heavy chain CDR2 of SEQ ID NO.:10;
a heavy chain CDR3 of SEQ ID NO.:11;
a light chain CDR1 of SEQ ID NO.:12;
a light chain CDR2 of SEQ ID NO.:13;
a light chain CDR3 of SEQ ID NO.:14;
wherein either the variable regions or the constant regions of the heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
a) an Immunoglobulin G (IgG) molecule with two binding sites specific for DR5, comprising
a heavy chain CDR1 consisting of SEQ ID NO.:1;
a heavy chain CDR2 of SEQ ID NO.:2;
a heavy chain CDR3 of SEQ ID NO.:3;
a light chain CDR1 of SEQ ID NO.:4;
a light chain CDR2 of SEQ ID NO.:5;
a light chain CDR3 of SEQ ID NO.:6;
wherein each subunit of the Fc domain comprises three amino acid substitutions that reduce binding to an activating or inhibitory Fc receptor and/or effector function wherein said amino acid substitutions are L234A, L235A and P329G and
b) two Fab fragments specific for FAP, comprising
a heavy chain CDR1 of SEQ ID NO.:9;
a heavy chain CDR2 of SEQ ID NO.:10;
a heavy chain CDR3 of SEQ ID NO.:11;
a light chain CDR1 of SEQ ID NO.:12;
a light chain CDR2 of SEQ ID NO.:13;
a light chain CDR3 of SEQ ID NO.:14;
wherein the constant regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
a) an Immunoglobulin G (IgG) molecule with two binding sites specific for DR5, comprising
a heavy chain CDR1 consisting of SEQ ID NO.:1;
a heavy chain CDR2 of SEQ ID NO.:2;
a heavy chain CDR3 of SEQ ID NO.:3;
a light chain CDR1 of SEQ ID NO.:4;
a light chain CDR2 of SEQ ID NO.:5;
a light chain CDR3 of SEQ ID NO.:6;
wherein each subunit of the Fc domain comprises three amino acid substitutions that reduce binding to an activating or inhibitory Fc receptor and/or effector function wherein said amino acid substitutions are L234A, L235A and P329G and
b) two Fab fragments specific for FAP, comprising
a heavy chain CDR1 of SEQ ID NO.:9;
a heavy chain CDR2 of SEQ ID NO.:10;
a heavy chain CDR3 of SEQ ID NO.:11;
a light chain CDR1 of SEQ ID NO.:12;
a light chain CDR2 of SEQ ID NO.:13;
a light chain CDR3 of SEQ ID NO.:14;
wherein the variable regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
a) an Immunoglobulin G (IgG) molecule with two binding sites specific for DR5, comprising a variable heavy chain of SEQ ID NO.:7 and a variable light chain of SEQ ID NO.:8;
wherein each subunit of the Fc domain comprises three amino acid substitutions that reduce binding to an activating or inhibitory Fc receptor and/or effector function wherein said amino acid substitutions are L234A, L235A and P329G and
b) two Fab fragments specific for FAP, comprising a heavy chain variable region comprising an amino acid sequence of SEQ ID NO.:15 and a light chain variable region comprising an amino acid sequence of SEQ ID NO.:16, wherein either the variable regions or the constant regions of the heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
a) an Immunoglobulin G (IgG) molecule with two binding sites specific for DR5, comprising a variable heavy chain of SEQ ID NO.:7 and a variable light chain of SEQ ID NO.:8;
wherein each subunit of the Fc domain comprises three amino acid substitutions that reduce binding to an activating or inhibitory Fc receptor and/or effector function wherein said amino acid substitutions are L234A, L235A and P329G and
b) two Fab fragments specific for FAP, comprising a heavy chain variable region comprising an amino acid sequence of SEQ ID NO.:15 and a light chain variable region comprising an amino acid sequence of SEQ ID NO.:16 wherein the constant regions of the Fab heavy and light chain are exchanged, wherein the two Fab fragments are fused to the constant heavy chain of said IgG molecule by a peptide linker.

In one embodiment a bispecific antibody that binds to DR5 and FAP according to any of the above embodiments comprises
a) an Immunoglobulin G (IgG) molecule with two binding sites specific for DR5,
comprising a variable heavy chain of SEQ ID NO.:7 and a variable light chain of SEQ ID NO.:8;

wherein each subunit of the Fc domain comprises three amino acid substitutions that reduce binding to an activating or inhibitory Fc receptor and/or effector function wherein said amino acid substitutions are L234A, L235A and P329G and b) two Fab fragments specific for FAP, comprising a heavy chain variable region comprising an amino acid sequence of SEQ ID NO.:15 and a light chain variable region comprising an amino acid sequence of SEQ ID NO.:16, wherein the variable regions of the Fab heavy and light chain are exchanged, wherein the two Fab fragments are fused to the constant heavy chain of said IgG molecule by a peptide linker.

E. Fc Domain Modifications Promoting Heterodimerization

The bispecific DR5-FAP antibodies of the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc domain of the bispecific antibodies of the invention a modification promoting the association of the desired polypeptides.

Accordingly, in particular embodiments the Fc domain of the bispecific antibodies of the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain. The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the bispecific antibodies of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

In one embodiment a bispecific antibody that binds to DR5 and FAP according to any of the above embodiments comprises an Immunoglobulin G (IgG) molecule with two binding sites specific for DR5, wherein the Fc part of the first heavy chain comprises a first dimerization module and the Fc part of the second heavy chain comprises a second dimerization module allowing a heterodimerization of the two heavy chains of the IgG molecule.

In a further preferred embodiment, the first dimerization module comprises knobs and the second dimerization module comprises holes according to the knobs into holes strategy (see Carter P.; Ridgway J. B. B.; Presta L. G.: Immunotechnology, Volume 2, Number 1, February 1996, pp. 73-73(1)).

F. Nucleic Acid Sequences, Vectors and Methods of

The invention further provides isolated polynucleotides encoding a bispecific antibody or an antibody binding to DR5 as described herein or a fragment thereof. The polynucleotides encoding bispecific antibodies or the antibodies binding to DR5 of the invention may be expressed as a single polynucleotide that encodes the entire bispecific antigen binding molecule or the entire antibody binding to DR5 or as multiple (e.g., two or more) polynucleotides that are co-expressed. Polypeptides encoded by polynucleotides that are co-expressed may associate through, e.g., disulfide bonds or other means to form a functional bispecific antibody or an antibody binding to DR5. For example, the light chain portion of a Fab fragment may be encoded by a separate polynucleotide from the portion of the bispecific antibody or the antibody binding to DR5 comprising the heavy chain portion of the Fab fragment, an Fc domain subunit and optionally (part of) another Fab fragment. When co-expressed, the heavy chain polypeptides will associate with the light chain polypeptides to form the Fab fragment. In another example, the portion of the bispecific antibody or the antibody binding to DR5 provided therein comprising one of the two Fc domain subunits and optionally (part of) one or more Fab fragments could be encoded by a separate polynucleotide from the portion of the bispecific antibody or the antibody binding to DR5 provided therein comprising the the other of the two Fc domain subunits and optionally (part of) a Fab fragment. When co-expressed, the Fc domain subunits will associate to form the Fc domain.

In one embodiment, the present invention is directed to an isolated polynucleotide encoding a bispecific antibody of the invention or a fragment thereof, wherein the polynucleotide comprises a sequence that encodes a variable heavy chain sequence as shown in SEQ ID NOs 167, 175, 183, 191, 199, 207 and 209.

In one embodiment, the present invention is directed to an isolated polynucleotide encoding a bispecific antibody of the invention or a fragment thereof, wherein the polynucleotide comprises a sequence that encodes a variable light chain sequence as shown in SEQ ID NOs 171, 179, 187, 195, 203, 208 and 210.

In another embodiment, the present invention is directed to an isolated polynucleotide encoding a bispecific antibody or fragment thereof, wherein the polynucleotide comprises a sequence that encodes a polypeptide sequence as shown in SEQ ID NOs 222, 224, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 258, 259, 260, 261, 264 and 265.

In one embodiment, the present invention is directed to an isolated polynucleotide encoding an antibody binding to DR5 of the invention or a fragment thereof, wherein the polynucleotide comprises a sequence that encodes a variable heavy chain sequence as shown in SEQ ID NOs 167, 175, 183, 191 and 199.

In one embodiment, the present invention is directed to an isolated polynucleotide encoding an antibody binding to DR5 of the invention or a fragment thereof, wherein the polynucleotide comprises a sequence that encodes a variable light chain sequence as shown in SEQ ID NOs 171, 179, 187, 195 and 203.

In another embodiment, the invention is directed to an isolated polynucleotide encoding a bispecific antibody of the invention or a fragment thereof, wherein the polynucleotide comprises a sequence that encodes a variable heavy chain sequence that is at least about 80%, 85%, 90%, 95%, 96%, 97%, 98%, or 99% identical to an amino acid sequence in SEQ ID NOs 167, 175, 183, 191, 199, 207 or 209.

In another embodiment, the invention is directed to an isolated polynucleotide encoding a bispecific antibody of the invention or a fragment thereof, wherein the polynucleotide comprises a sequence that encodes a variable lightchain sequence that is at least about 80%, 85%, 90%, 95%, 96%, 97%, 98%, or 99% identical to an amino acid sequence in SEQ ID NOs 171, 179, 187, 195, 203, 208 or 210.

In another embodiment, the invention is directed to an isolated polynucleotide encoding an antibody binding to DR5 of the invention or a fragment thereof, wherein the polynucleotide comprises a sequence that encodes a variable heavy chain sequence that is at least about 80%, 85%, 90%, 95%, 96%, 97%, 98%, or 99% identical to an amino acid sequence in SEQ ID NOs 167, 175, 183, 191 or 199.

In another embodiment, the invention is directed to an isolated polynucleotide encoding an antibody binding to DR5 of the invention or a fragment thereof, wherein the polynucleotide comprises a sequence that encodes a variable light chain sequence that is at least about 80%, 85%, 90%, 95%, 96%, 97%, 98%, or 99% identical to an amino acid sequence in SEQ ID NOs 171, 179, 187, 195 or 203.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

In further objects the present invention relates to an expression vector comprising a nucleic acid sequence of the present invention and to a prokaryotic or eukaryotic host cell comprising a vector of the present invention. In addition a method of producing an antibody comprising culturing the host cell so that the antibody is produced is provided.

G. Antibody Variants

In certain embodiments, amino acid sequence variants of the bispecific antibodies and antibodies binding to DR5 provided herein are contemplated, in addition to those described above. For example, it may be desirable to improve the binding affinity and/or other biological properties of the bispecific antibody or the antibody binding to DR5. Amino acid sequence variants of a bispecific antibody or an antibody binding to DR5 may be prepared by introducing appropriate modifications into the nucleotide sequence encoding the bispecific antibody or the antibody binding to DR5, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

1. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table B under the heading of "conservative substitutions." More substantial changes are provided in Table B under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE B

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |

TABLE B-continued

| Original Residue | Exemplary Substitutions | Preferred Substitutions |
|---|---|---|
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

2. Glycosylation Variants

In certain embodiments, a bispecific antibody or an antibody binding to DR5 provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the bispecific antibody or the antibody binding to DR5 comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in a bispecific antibody or an antibody binding to DR5 of the invention may be made in order to create antibody variants with certain improved properties.

In one embodiment, bispecific antibody variants or variants of antibodies binding to DR5 are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Bispecific antibodies variants or variants of antibodies binding to DR5 are further provided with bisected oligosaccharides, e.g., in which a biantennary oligosaccharide attached to the Fc region of the bispecific antibody or the antibody binding to DR5 is bisected by GlcNAc. Such bispecific antibody variants or variants of antibodies binding to DR5 may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

3. Cysteine Engineered Antibody Variants

In certain embodiments, it may be desirable to create cysteine engineered bispecific antibodies or antibodies binding to DR5, e.g., "thioMAbs," in which one or more residues of a bispecific antibody or antibodies binding to DR5 are substituted with cysteine residues. In particular embodiments, the substituted residues occur at accessible sites of the bispecific antibody or the antibody binding to DR5. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

H. Recombinant Methods and Compositions

Bispecific antibodies and antibodies binding to DR5 of the invention may be obtained, for example, by solid-state peptide synthesis (e.g. Merrifield solid phase synthesis) or recombinant production. For recombinant production one or more polynucleotide encoding the bispecific antibodies or antibodies binding to DR5 (or fragments), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a bispecific antibody (fragment) or an antibody (fragment) binding to DR5 along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the bispecific antibody (fragment) or an antibody (fragment) binding to DR5 (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antibody (fragment) or an antibody (fragment) binding to DR5 of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antibody or the antibody binding to DR5 is desired, DNA encoding a signal sequence may be placed upstream of the nucleic acid encoding a bispecific antibody of the invention or the antibody binding to DR5 of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the bispecific antibody or the antibody binding to DR5 may be included within or at the ends of the bispecific antibody (fragment) or the antibody (fragment) binding to DR5 encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a bispecific antibody or an antibody binding to DR5 of the invention. As used herein, the term "host cell" refers to any kind of cellular system which can be engineered to generate the bispecific antibodies or an antibody binding to DR5 of the invention or fragments thereof. Host cells suitable for replicating and for supporting expression of bispecific antibodies or of antibodies binding to DR5 are well known in the art. Such cells may be transfected or transduced as appropriate with the particular expression vector and large quantities of vector containing cells can be grown for seeding large scale fermenters to obtain sufficient quantities of the bispecific antibody or of the antibodies binding to DR5 for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a bispecific antibody or an antibody binding to DR5 according to the invention is provided, wherein the method comprises culturing a host cell comprising a polynucleotide encoding the bispecific antibody or the antibody binding to DR5, as provided herein, under conditions suitable for expression of the bispecific antibody or the antibody binding to DR5, and recovering the bispecific antibody or the antibody binding to DR5 from the host cell (or host cell culture medium).

The components of the bispecific antibody or the antibody binding to DR5 are genetically fused to each other. Bispecific antibodies or the antibodies binding to DR5 can be designed such that its components are fused directly to each other or indirectly through a linker sequence. The composition and length of the linker may be determined in accordance with methods well known in the art and may be tested for efficacy. Examples of linker sequences between different components of bispecific antibodies are found in the sequences provided herein. Additional sequences may also be included to incorporate a cleavage site to separate the individual components of the fusion if desired, for example an endopeptidase recognition sequence.

In certain embodiments the Fab fragments forming part of the bispecific antibody or the antibody binding to DR5 comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the bispecific antibodies or the antibodies binding to DR5 of the invention. Non-limiting antibodies, antibody fragments, antigen binding domains or variable regions useful in the present invention can be of murine, primate, or human origin. If the bispecific antibody or the antibody binding to DR5 is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain embodiments, the Fab fragments useful in the present invention are engineered to have enhanced binding affinity according to, for example, the methods disclosed in U.S. Pat. Appl. Publ. No. 2004/0132066, the entire contents of which are hereby incorporated by reference. The ability of the bispecific antibody or the antibody binding to DR5 of the invention to bind to a specific antigenic determinant can be measured either through an enzyme-linked immunosorbent assay (ELISA) or other techniques familiar to one of skill in the art, e.g. surface plasmon resonance technique (analyzed on a BIACORE T100 system) (Liljeblad, et al., Glyco J 17, 323-329 (2000)), and traditional binding assays (Heeley, Endocr Res 28, 217-229 (2002)). Competition assays may be used to identify an antibody, antibody fragment, antigen binding domain or variable domain that competes with a reference antibody for binding to a particular antigen. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols,"

in Methods in Molecular Biology vol. 66 (Humana Press, Totowa, N.J.). In an exemplary competition assay, immobilized antigen is incubated in a solution comprising a first labeled antibody that binds to the antigen and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch.14 (Cold Spring Harbor Laboratory, Cold Spring Harbor, N.Y.).

Bispecific antibodies or antibodies binding to DR5 prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antibody or the antibody binding to DR5 binds. For example, for affinity chromatography purification of bispecific antibodies of the invention, a matrix with protein A or protein G may be used. Sequential Protein A or G affinity chromatography and size exclusion chromatography can be used to isolate a bispecific antibody essentially as described in the Examples. The purity of the bispecific antibody or the antibody binding to DR5 can be determined by any of a variety of well known analytical methods including gel electrophoresis, high pressure liquid chromatography, and the like.

I. Assays

Bispecific antibodies that bind to DR5 and FAP and antibodies binding to DR5 provided herein may be identified, screened for, or characterized for their physical/chemical properties and/or biological activities by various assays known in the art 1. Affinity Assays The affinity of the bispecific antibody and the antibody binding to DR5 provided therein for DR5 and/or FAP can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of bispecific antibody and the antibody binding to DR5 provided therein to DR5 and/or FAP may be evaluated using cell lines expressing the particular receptor or target antigen, for example by flow cytometry (FACS). A specific illustrative and exemplary embodiment for measuring binding affinity is described in the following and in the Examples below.

According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody is diluted with 10 mM sodium acetate, pH 5.0, to 40 µm/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody. The final amount of coupled protein is is approximately 12000 R U. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

2. Binding Assays and Other Assays

In one aspect, a bispecific antibody or an antibody that binds to DR5 of the invention is tested for its antigen binding activity, e.g., by known methods such as ELISA, Western blot, etc.

In another aspect, competition assays may be used to identify an antibody that competes with a specific anti-FAP antibody or a specific anti-DR5 antibody for binding to FAP or DR5 respectively. In certain embodiments, such a competing antibody binds to the same epitope (e.g., a linear or a conformational epitope) that is bound by a specific anti-FAP antibody or a specific anti-DR5 antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.). Further methods are described in the example section.

3. Activity Assays

In one aspect, assays are provided for identifying bispecific antibodies that bind to DR5 and FAP or antibodies that binds to DR5 thereof having biological activity. Biological activity may include, e.g., DNA fragmentation, induction of apoptosis and lysis of targeted cells. Antibodies having such biological activity in vivo and/or in vitro are also provided.

In certain embodiments, a bispecific antibody or an antibody that binds to DR5 of the invention is tested for such biological activity. Assays for detecting cell lysis (e.g. by measurement of LDH release) or apoptosis (e.g. using the TUNEL assay) are well known in the art. Assays for measuring ADCC or CDC are also described in WO 2004/065540 (see Example 1 therein), the entire content of which is incorporated herein by reference.

J. Pharmaceutical Formulations

Pharmaceutical formulations of a bispecific antibody that binds to DR5 and FAP or an antibody that binds to DR5 as described herein are prepared by mixing such bispecific antibody or antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

K. Therapeutic Methods and Compositions

Any of the bispecific antibodies that bind to DR5 and FAP and the novel antibodies binding to DR5 provided herein may be used in therapeutic methods.

In one aspect, a bispecific antibody that binds to DR5 and FAP for use as a medicament is provided. In further aspects, a bispecific antibody that binds to DR5 and FAP use in treating cancer is provided. In certain embodiments, a bispecific antibody that binds to DR5 and FAP for use in a method of treatment is provided. In certain embodiments, the invention provides a bispecific antibody that binds to DR5 and FAP for use in a method of treating an individual having cancer comprising administering to the individual an effective amount of the bispecific antibody that binds to DR5 and FAP. In one such embodiment, the method further comprises administering to the individual an effective amount of at least one additional therapeutic agent, e.g., as described below. An "individual" according to any of the above embodiments is preferably a human. In one preferred embodiment said cancer is pancreatic cancer or colorectal carcinoma.

In one aspect, an antibody that binds to DR5 for use as a medicament is provided. In further aspects, an antibody that binds to DR5 use in treating cancer is provided. In certain embodiments, an antibody that binds to DR5 for use in a method of treatment is provided. In certain embodiments, the invention provides an antibody that binds to DR5 for use in a method of treating an individual having cancer comprising administering to the individual an effective amount of the antibody that binds to DR5. In one such embodiment, the method further comprises administering to the individual an effective amount of at least one additional therapeutic agent, e.g., as described below. An "individual" according to any of the above embodiments is preferably a human. In one preferred embodiment said cancer is pancreatic cancer or colorectal carcinoma.

In a further aspect, the invention provides for the use of a bispecific antibody that binds to DR5 and FAP in the manufacture or preparation of a medicament. In another aspect, the invention provides for the use of an antibody that binds to DR5 in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating cancer. In one embodiment, the method comprises administering to an individual having cancer an effective amount of a bispecific antibody that binds to DR5 and FAP or of a novel antibody binding to DR5. In one such embodiment, the method further comprises administering to the individual an effective amount of at least one additional therapeutic agent, as described below. An "individual" according to any of the above embodiments may be a human. In one preferred embodiment said cancer is pancreatic cancer or colorectal carcinoma.

In a further aspect, the invention provides pharmaceutical formulations comprising any of the bispecific antibodies that bind to DR5 and FAP provided herein, e.g., for use in any of the above therapeutic methods. In one embodiment, a pharmaceutical formulation comprises any of the bispecific antibodies that bind to DR5 and FAP provided herein and a pharmaceutically acceptable carrier. In another embodiment, a pharmaceutical formulation comprises any of the bispecific antibodies that bind to DR5 and FAP provided herein and at least one additional therapeutic agent, e.g., as described below.

In a further aspect, the invention provides pharmaceutical formulations comprising any of the antibodies that bind to DR5 provided herein, e.g., for use in any of the above therapeutic methods. In one embodiment, a pharmaceutical formulation comprises any of the antibodies that bind to DR5 provided herein and a pharmaceutically acceptable carrier. In another embodiment, a pharmaceutical formulation comprises any of the antibodies that bind to DR5 provided herein and at least one additional therapeutic agent, e.g., as described below.

A bispecific antibody or a novel antibody binding to DR5 of the invention can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Bispecific antibodies or novel antibodies binding to DR5 of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The bispecific antibody or the novel antibody binding to DR5 need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a bispecific antibody or a novel antibody binding to DR5 of the invention will depend on the type of disease to be treated, the type of antibody, the severity and course of the disease, whether the bispecific antibody or the novel antibody binding to DR5 is administered for preventive or therapeutic purposes, previous therapy, the patient's clinical history and response to the bispecific antibody or to the novel antibody binding to DR5, and the discretion of the attending physician. The bispecific antibody or the novel antibody binding to DR5 is suitably administered to the patient at one time or over a series of treatments. Depending on the type and severity of the disease, about 1 mg/kg to 15 mg/kg (e.g. 0.1 mg/kg-10 mg/kg) of the bispecific antibody or the novel antibody binding to DR5 can be an initial candidate dosage for administration to the patient, whether, for example, by one or more separate administrations, or by continuous infusion. One typical daily dosage might range from about 1 mg/kg to 100 mg/kg or more, depending on the factors mentioned above. For repeated administrations over several days or longer, depending on the condition, the treatment would generally be sustained until a desired suppression of disease symptoms occurs. One exemplary dosage of the bispecific antibody or the novel antibody binding to DR5 would be in the range from about 0.05 mg/kg to about 10 mg/kg. Thus, one or more doses of about 0.5 mg/kg, 2.0 mg/kg, 4.0 mg/kg or 10 mg/kg may be administered to the patient. Such doses may be administered intermittently, e.g. every week or every three weeks (e.g. such that the patient receives from about two to about twenty, or e.g. about six doses of the bispecific antibody or of the novel antibody binding to DR5). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a bispecific antibody that binds to DR5 and FAP or a novel antibody binding to DR5 of the invention.

L. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a bispecific antibody or a novel antibody binding to DR5 of the invention. The label or package insert indicates that the composition is used for treating the condition of choice. Moreover, the article of manufacture may comprise (a) a first container with a composition contained therein, wherein the composition comprises a bispecific antibody or a novel antibody binding to DR5 of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to a bispecific antibody that binds to DR5 and FAP or a novel antibody binding to DR5 of the invention.

III. Examples

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1: A DR5-FAP Death Receptor Agonistic Bispecific Antibody is Able to Mediate Apoptosis of One Cell Line Via Cross-Linking by a Second Cell Line One approach of induction of apoptosis by cross-linking of death receptors as DR5 (apart from cross-linking via an antigen expressed by the tumor cell), is targeting the stroma surrounding the tumor. In that case the targeted antigen is not displayed directly by the tumor cells but by a second, different cell type. One example for this kind of antigen would be FAP (fibroblast activation protein). This protein is expressed on activated fibroblast as they are found in the tumor stroma.

To investigate the possibilities of tumor targeted induction of apoptosis using bispecific death receptor agonistic antibodies targeting human DR5 and an antigen from the tumor stroma, bispecific molecules were generated that consist of an IgG1 part that recognizes DR5 and a FAP binding scFv that is fused to the C-terminus of the heavy chain of the antibody. The sequence of the DR5 targeting IgG was taken from the Drozitumab sequence as described in US2007/0031414 A1. The sequence of variable heavy and light chain of the FAP binding scFv moieties were taken from Fab anti FAP molecules (3F2 or 4G8) isolated by phage display as described in WO2012/020006A1. The FAP scFvs are fused by a $(G_4S)_2$ connector to the C-terminus of the anti DR5 IgG heavy chain or light chain. Both anti FAP antibodies bind to different epitopes on fibroblast activation protein (FAP) and are cross-reactive with the human, murine and cynomolgus antigens.

TABLE 1

Description of tested bispecific DR5-FAP molecules with C-terminal fusion of FAP binding scFv's to DR5 heavy or light chain. Linker and connector length and purification yields are given.

| Molecule | Description | Connector | Linker in scFv | Yield [mg/L] |
|---|---|---|---|---|
| 3F2-scFv_HC (SEQ ID NO.: 111) | Fusion of disulfide stabilized scFv (H44L100) to C-terminus of Drozitumab heavy chain | $(G_4S)_2$ | $(G_4S)_4$ | 2.53 |
| 4G8-scFv_HC (SEQ ID NO.: 112) | Fusion of disulfide stabilized scFv (H44L100) to C-terminus of Drozitumab heavy chain | $(G_4S)_2$ | $(G_4S)_4$ | 4.29 |
| 4G8-scFv_LC (SEQ ID NO.: 113) | Fusion of disulfide stabilized scFv (H44L100) to C-terminus of Drozitumab light chain | $(G_4S)_2$ | $(G_4S)_4$ | 2.15 |

In this kind of setting two different cell lines have to be used for the in vitro activity assays: one cell line (the target cell line) should express human DR5, has to be apoptosis competent but does not need to express FAP. The second cell line (the effector cell line) has to be apoptosis negative (either by apoptosis resistance or by not expressing DR5) but needs to express FAP on the surface.

Figure 1A:
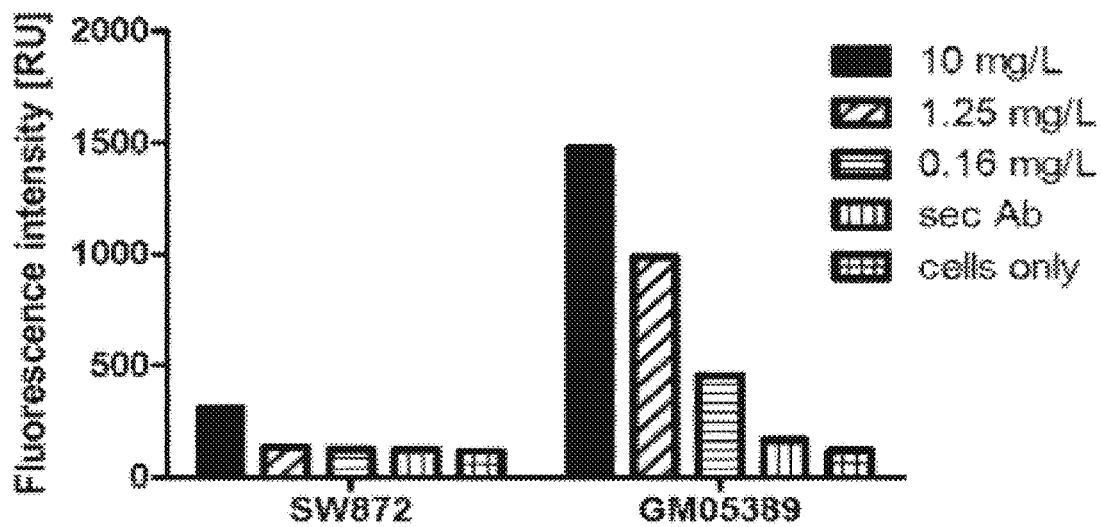
FIGS. 1A and 1B: FACS binding analysis of two different cell lines (SW872 and GM05389) for expression levels of human fibroblast activation protein (FAP) (FIG. 1A). The fluorescence intensity measured with different concentrations of an anti FAP antibody is shown over a range of three magnitudes (black, grey and hatched bars). Negative control reactions as secondary antibody and cells only are shown as stippled and white bars, respectively. While the GM05389 cells demonstrate expression of FAP over all tested antibody concentrations that was above background, with the SW872 cells FAP expression only could be detected with the highest antibody concentration used (10 µg/ml), indicating that these cells are not suitable for FAP based binding/apoptosis induction experiments. In addition it is shown that this cell line hardly undergoes Drozitumab mediated apoptosis (FIG. 1B). Drozitumab alone or another, commercially available anti DR5 antibody did not induce relevant DNA fragmentation. Only when Drozitumab is cross-linked with an anti-human Fc antibody a detectable low level apoptosis induction can be observed.
Figure 1B:
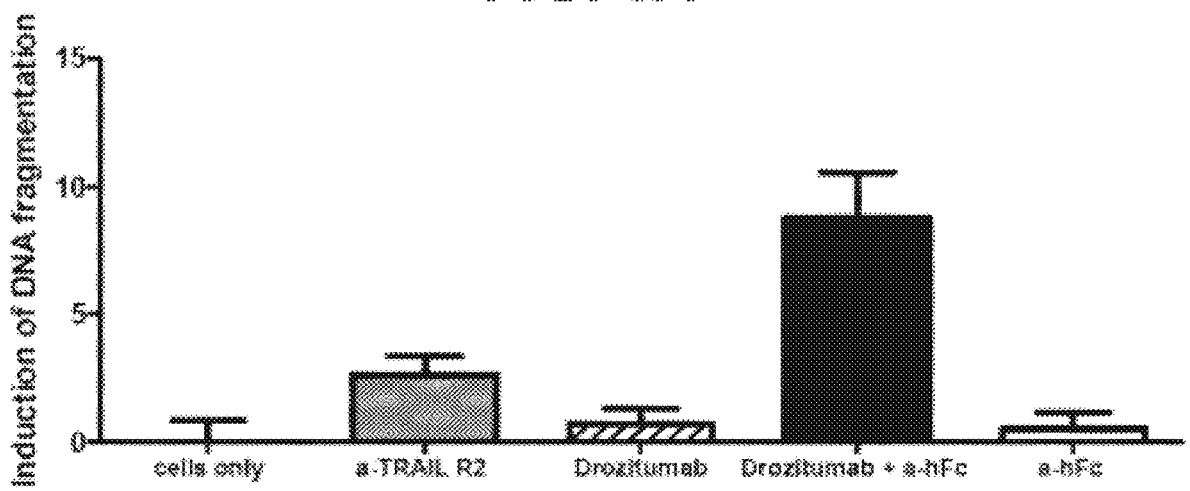

One possible effector cell line that fulfills the desired criteria is the human fibroblast cell line GM05389. As shown in FIG. 1A this cell line expresses significant levels of FAP compared to the cell line SW872 which only showed FAP expression with the highest tested antibody concentration (10 µg/ml) but does not undergo apoptosis by non-cross-linked Drozitumab as seen in FIG. 1B. Therefore this cell line seems to be a potential effector cell line in an apoptosis assay where DNA fragmentation of a target cell line is induced by cross-linking via an antigen expressed on a second cell line.

Figure 2:
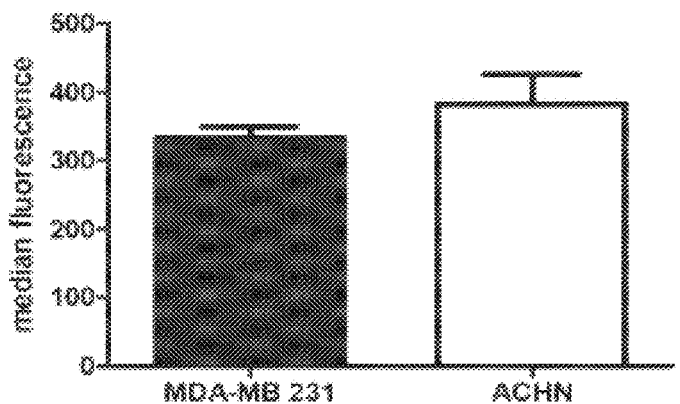
FIG. 2: Detection of DR5 expression on two different human tumor cell lines (breast cancer cell line MDA-MB-231 and the renal carcinoma cell line ACHN) via FACS binding with Drozitumab and subsequent detection with a labeled anti Fc antibody. Both cell lines show comparable, low expression levels of human DR5.
Figure 3A:
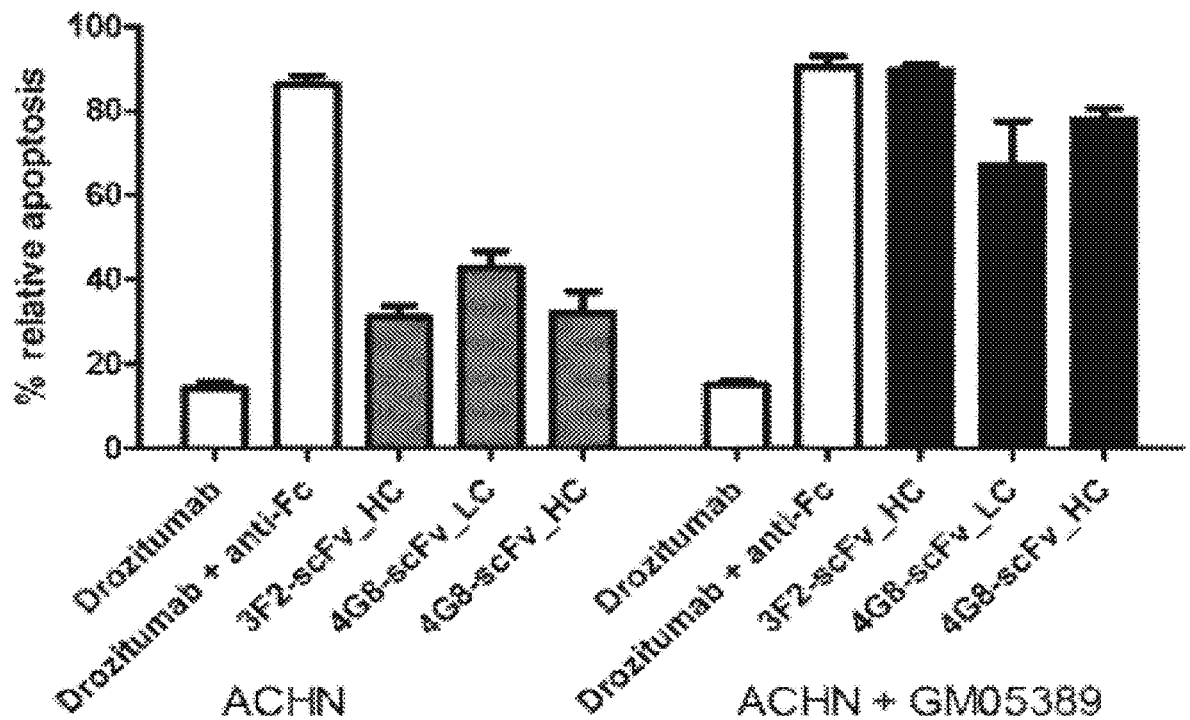
FIGS. 3A and 3B: DNA fragmentation ELISA assay for detection of apoptosis. ACHN (A) or MDA-MB-231 (B) target cells were either cultivated alone or in presence of an equal number of FAP expressing GM05389 fibroblasts. DR5-FAP bispecific antibodies (scFv fusions) were added at a concentration of 0.1 µg/ml (FIG. 3A) and 0.7 nM, respectively (FIG. 3B) and cells were incubated for 24 h prior to detection of DNA fragmentation. For cross-linking of Drozitumab, 0.1 µg/ml secondary anti Fc antibody was used.
Figure 3B:
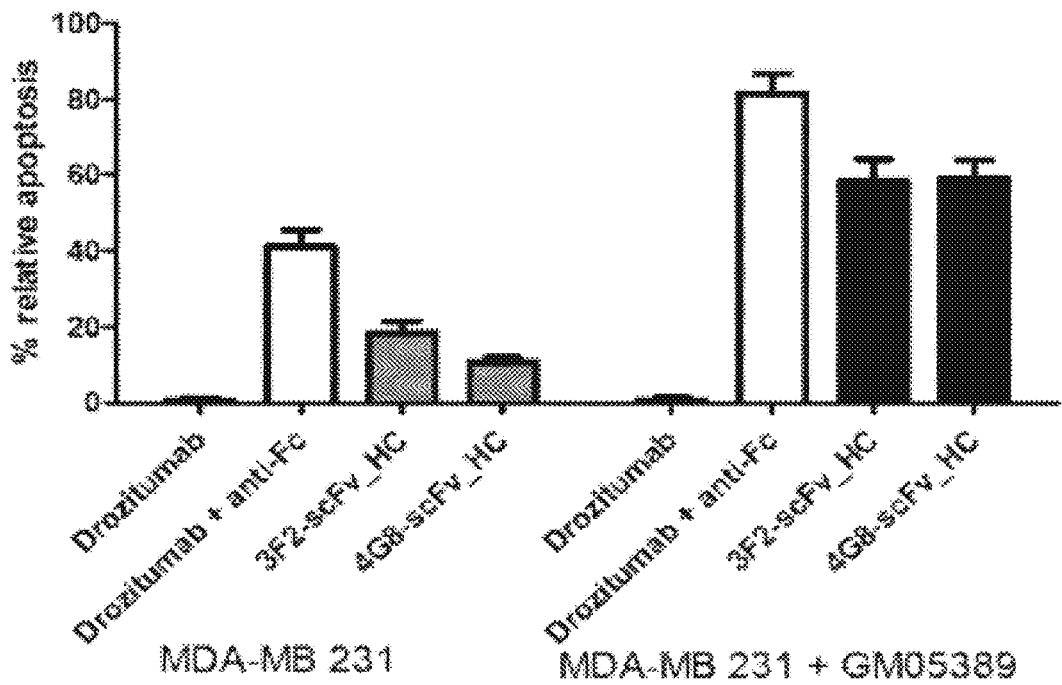

As a target cell line the human kidney-adenocarcinoma cell line ACHN or the human breast cancer cell line MDA-MB-231 were used. They express comparable, low levels of DR5 (FIG. 2) and are sensitive to DR5 mediated apoptosis induction. In FIGS. 3A and 3B the results of induction of DNA fragmentation of ACHN cells compared to the combination of ACHN and GM05389 cell lines by tumor targeted cross-linking of DR5 via FAP is summarized. The control antibody (Drozitumab) induces apoptosis upon cross-linking via a secondary antibody that targets the Fc part (white bars) in both cell lines, but shows also some activity without crosslinking. The bispecific DR5-FAP molecules show significant induction of apoptosis in the presence of both—target and effector cell line (black bars). In the absence of FAP expressing fibroblasts (GM05389) there is a slightly increased apoptosis compared to non-cross-linked Drozitumab (grey bars). We interpret this result in a way that the DR5 receptors on ACHN cells are cross-linked upon binding to the FAP antigen expressed by the fibroblast cell line GM05389. All molecules show comparable maximal apoptosis activity.

Example 2: DR5 Bispecific Agonistic Antibodies with Cross-Reactive FAP Binders in scFab Format Fused to Drozitumab Demonstrate Apoptosis Activity in Co-Culture Assays As demonstrated in example 1 DR5-FAP bispecific agonistic antibodies in which the FAP targeting moiety in scFv format is fused to the C-terminus of the Drozitumab heavy or light chain (2×2 format) are able to induce apoptosis in a two cell line co-culture setting in which one cell line expresses FAP (effector cells) while the second cell line serves as the DR5 receptor target.

Since these molecules containing an scFv fusion showed some disadvantageous properties (low production yield and tendency to form aggregates), constructs were generated in which the FAP binding unit was replaced by single chain Fab entities (scFab), fused to the C-terminus of either the heavy or light chain of Drozitumab leading to the production of four different molecules as described in table 2. The connection of the scFab units to the IgG part of the bispecific molecules occurs via a $(G_4S)_4$ sequence whereas the scFab internal linker consists of 32 amino acids.

These molecules were transiently produced by standard recombinant technologies and purified in sufficient amounts and good quality for detailed testing of FAP and DR5 binding (FACS; Biacore, not shown).

TABLE 2

Description and characterization of the different Drozitumab-FAP (scFab) fusions. In all molecules the anti FAP scFab is fused by a 20 mer connector ($(G_4S)_4$) to Drozitumab.

| Name | Description | Yield [mg/L] | Connector |
|---|---|---|---|
| GA803_A01_B01A_004 3F2_scFab_HC (SEQ ID NO.: 114) | scFab: 3F2; VLCL-VHCH1 C-terminal fusion to Drozitumab heavy chain (2 × 2) | 3.9 | $(G_4S)_4$ |
| GA803_A01_B01B_005 3F2_scFab_LC (SEQ ID NO.: 115) | scFab: 3F2; VLCL-VHCH1 C-terminal fusion to Drozitumab light chain (2 × 2) | 4.9 | $(G_4S)_4$ |
| GA803_A01_B02A_001 4G8_scFab_HC (SEQ ID NO.: 116) | scFab: 4G8; VLCL-VHCH1 C-terminal fusion to Drozitumab heavy chain (2 × 2) | 2.0 | $(G_4S)_4$ |
| GA803_A01_B02B_002 4G8_scFab_LC (SEQ ID NO.: 117) | scFab: 4G8; VLCL-VHCH1 C-terminal fusion to Drozitumab light chain (2 × 2) | 2.5 | $(G_4S)_4$ |

Figure 4A:
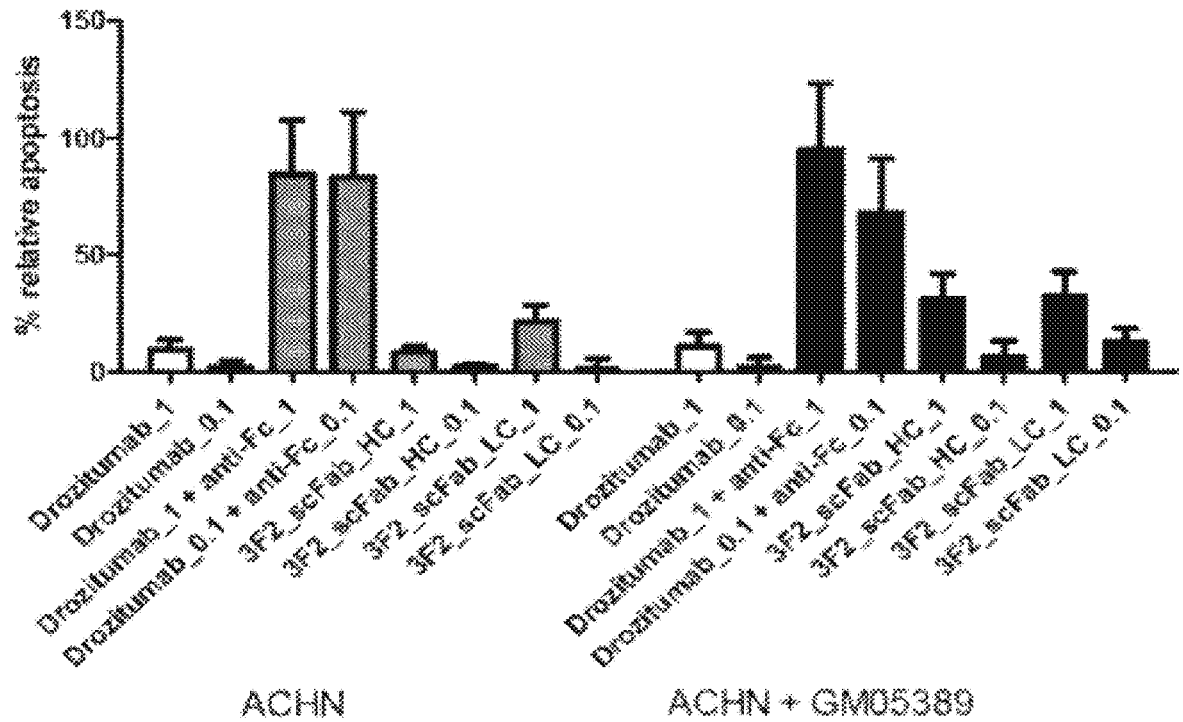
FIGS. 4A and 4B: DNA fragmentation ELISA assay for detection of apoptosis. Apoptosis induction on ACHN cells by bispecific DR5-FAP antibodies (Drozitumab with fused scFab) in the presence or absence of FAP expressing fibroblasts (GM05389). Activity of bispecific molecules with different FAP binding moieties are compared to Drozitumab with or without cross-linking by a secondary anti Fc antibody. Antibodies were used in two different concentrations (1.0 µg/ml and 0.1 µg/ml). In these settings bispecific molecules containing the 4G8 scFab fusion (FIG. 4B) showed superior apoptosis induction activity in a DNA fragmentation assay compared to the 3F2 scFab containing molecules (FIG. 4A).
Figure 4B:
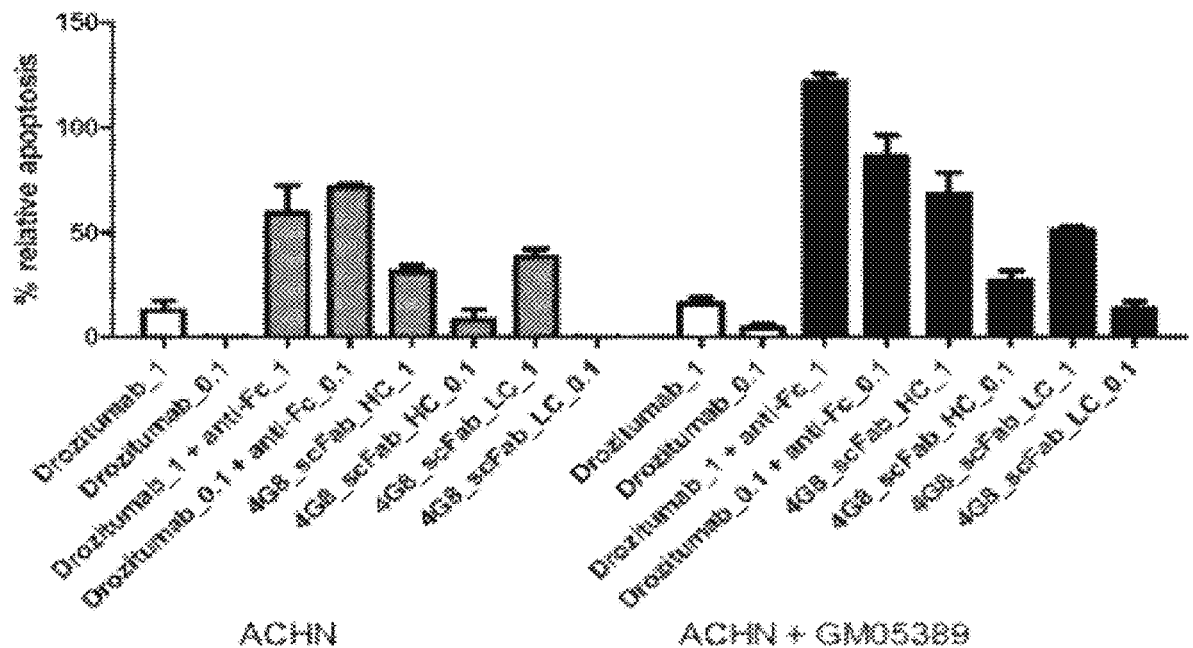

Analysis of apoptosis induction of a DR5 expressing target cell line (e.g. the renal carcinoma cell line ACHN) in the presence and absence of a second, FAP expressing 'effector' cell line (e.g. fibroblast line GM05389) is shown in FIGS. 4A and 4B. The apoptosis induction was analysed with a DNA fragmentation assay. In the assays a ratio of target to effector cells of 1:1 was used and DNA fragmentation after 24 hrs of co-culture in the presence of Drozitumab, hyper-cross-linked Drozitumab or the bispecific constructs (all used in concentrations of 1 μg/ml and 0.1 μg/ml) was analyzed.

For all tested constructs it could be demonstrated that the bispecific molecules, independent of the used FAP binder (either 3F2 or 4G8) as scFabs fused to Drozitumab show increased apoptosis induction in ACHN target cells only in the presence of the fibroblast effector cell line. However, at high concentrations of the bispecific molecules a low degree of apoptosis activity could be observed in the absence of FAP expressing fibroblasts. In general and independent on the used FAP binder, molecules with scFab fusion to the C-terminus of the heavy chain were more active as molecules where the scFabs were fused to the C-terminus of the light chain. In addition, 4G8 containing constructs seemed to be more potent than 3F2 containing molecules. However, activity of scFab based formats was lower compared to the analogous scFv based constructs.

Drozitumab without additional cross-linking by anti Fc antibodies showed a low apoptosis induction. However, Drozitumab hyper-cross-linked via a secondary anti Fc antibody alone—a highly artificial situation—revealed the highest apoptosis activity which could not been reached by any of the tested molecules.

Figure 5:
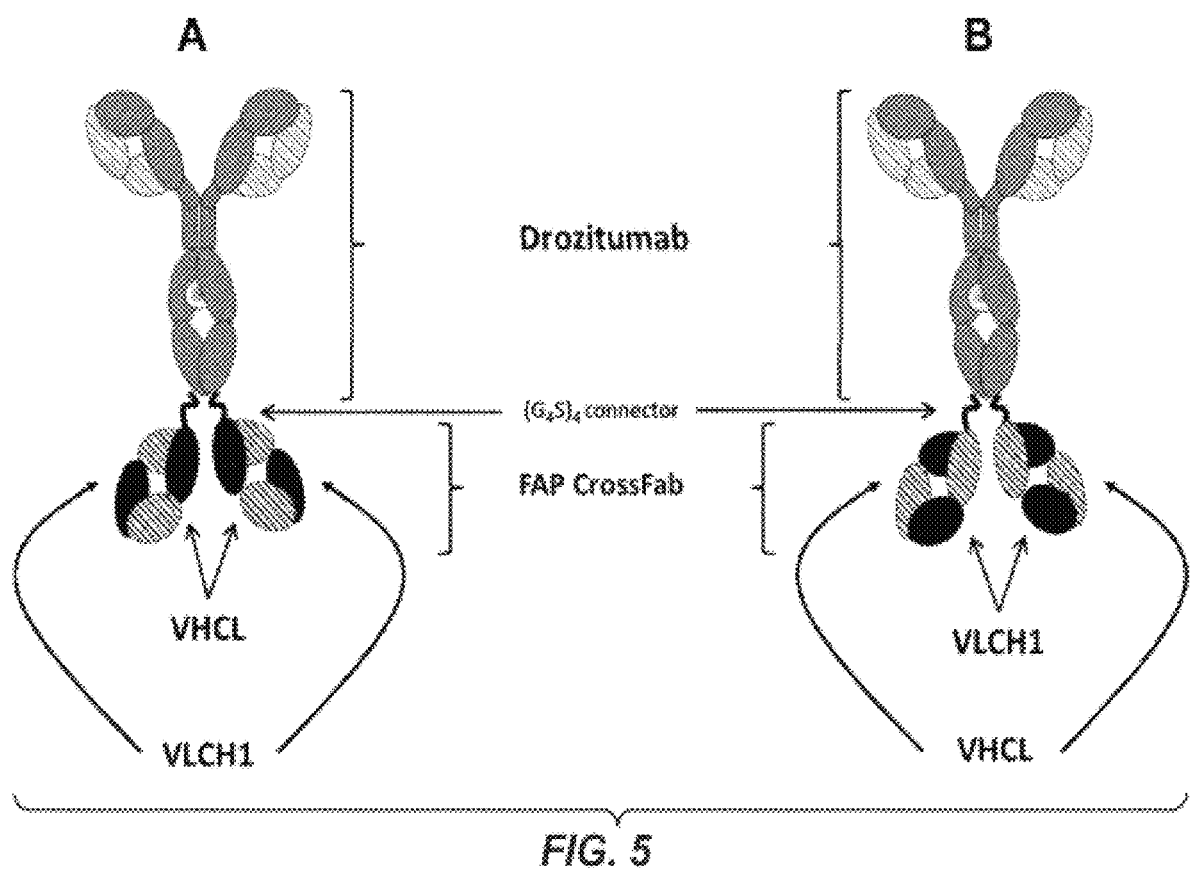
FIG. 5: Schematic representation of two different bispecific DR5-FAP molecules in which the anti FAP CrossFab moiety by a standard $(G_4S)_4$ linker is fused to the C-terminus of Drozitumab IgG. In one case (A) the VHCL CrossFab is fused to Drozitumab IgG while in (B) the VLCH1 chain is connected to the IgG as indicated. These two molecules are only examples for possible formats using IgG-CrossFab combinations which also were used for the bispecific molecules containing newly isolated DR5 binders. Other possibilities include the crossing in the IgG part of the molecule, the implementation of salt bridges and charged residues to stabilize the CrossFabs or the use of different linker lengths and sequences.

Example 3: DR5-FAP Bispecific Agonistic Antibodies in CrossFab Format Demonstrate Superior Characteristics Over scFab Containing Molecules Since the evaluated scFab containing bispecific molecules still showed some disadvantageous characteristics (e.g. low expression yield, optimizable apoptosis activity) a novel format that should overcome these liabilities was analyzed: fusion of a FAP binder (4G8) in CrossFab format to the C-terminus of Drozitumab heavy chain. In this format the FAP binding moiety is used in a 'crossover' exchange of variable regions in the Fab fragment as described in table 3 and shown in FIG. 5. The CrossFab molecules are linked via a 20mer connector ($(G_4S)_4$) to the Drozitumab heavy chain.

TABLE 3

Description and production yields of bispecific Drozitumab-FAP CrossFab constructs in two different formats.

| FIG. | Name | Description | Yield [mg/L] Monomer [%] |
|---|---|---|---|
| 5 A | GA803_A01_E02A_014 Drozitumab-X-FAP_A (2 + 2) (SEQ ID NO.: 118, 119, 120) | Fusion of 4G8 VH-CL to C-terminus of Drozitumab heavy chain (SEQ ID NO.: 118) Separate VL-CH1 cassette (SEQ ID NO.: 120) Separate Drozitumab light chain cassette (SEQ ID NO.: 119) | 36.1 100.0 |
| 5 B | GA803_A01_E02A_015 Drozitumab-X-FAP_B (2 + 2) (SEQ ID NO.: 121, 122, 119) | Fusion of 4G8 VL-CH1 to C-terminus of Drozitumab heavy chain (SEQ ID NO.: 121) Separate VH-CL cassette (SEQ ID NO.: 122) Separate Drozitumab light chain cassette (SEQ ID NO.: 119) | 16.7 100.0 |

Both CrossFab molecules (also see FIG. 5 for organization of the constructs) were transiently produced in HEK293 EBNA cells (either in adherent or suspension cells) and purified with standard methods. Compared to scFab and scFv containing bispecific constructs the CrossFab molecules exhibited significantly increased expression levels leading to approximately 10-fold higher product yields with acceptable low aggregate contents as shown in table 4.

Figure 6A:
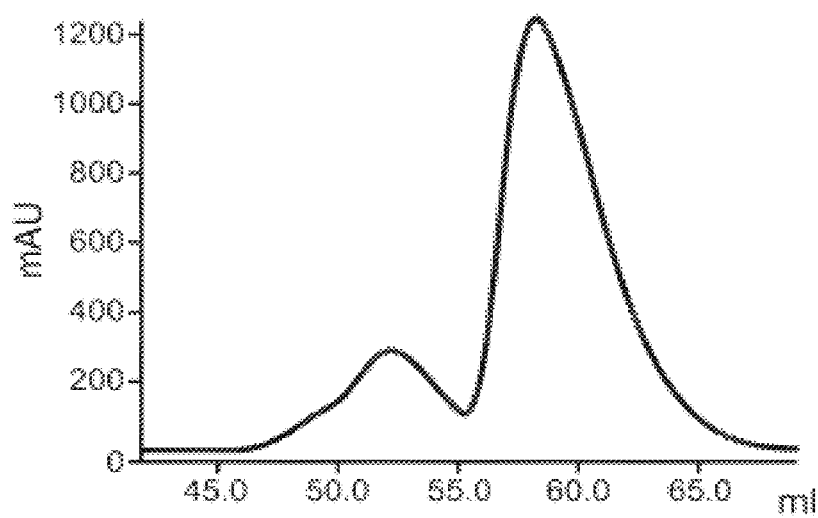
FIGS. 6A-6C: Comparison of aggregate contents during purification of different bispecific DR5-FAP antibody formats. All formats consist of Drozitumab IgG with a FAP binding domain (clone 4G8) fused to the C-terminus. FAP binding moieties consist of either a disulfide stabilized scFv (FIG. 6A), a scFab (FIG. 6B) or a CrossFab (FIG. 6C). The chromatograms of the preparative size exclusion chromatography showed clear differences between the three constructs. While the production of the scFv and CrossFab molecules was comparable, the scFab containing construct showed lower yield and higher aggregate content. From this comparison the CrossFab containing molecule looked most promising.
Figure 6B:
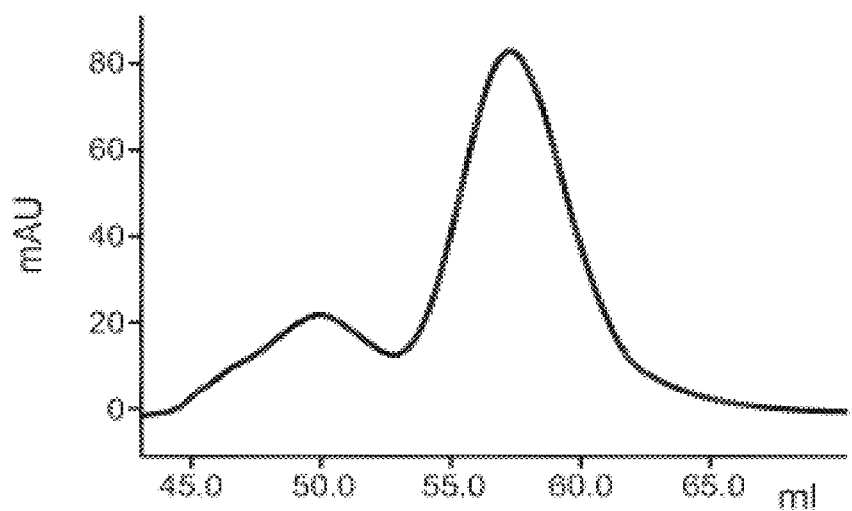
Figure 6C:
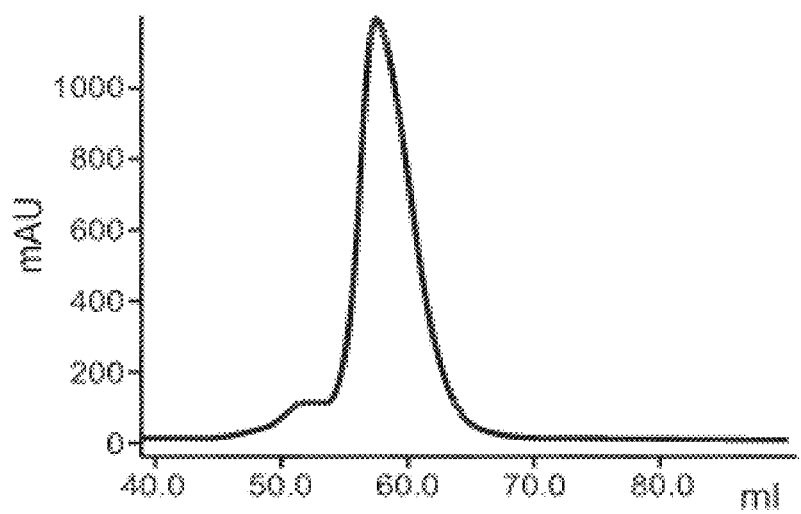

FIGS. 6A-6C demonstrate the aggregate content during production of different bispecific DR5-FAP molecules. Chromatograms from preparative size exclusion chromatography during purification are shown for the scFv (FIG. 6A), scFab (FIG. 6B) and CrossFab (FIG. 6C) fusion to the C-terminus of Drozitumab heavy chain. The scFv and scFab fusion constructs show significantly higher aggregate contents compared to the CrossFab containing molecule. Removal of these aggregates during purification leads to huge loss of material which can easily be seen from the yields obtained after purification.

Figure 7:
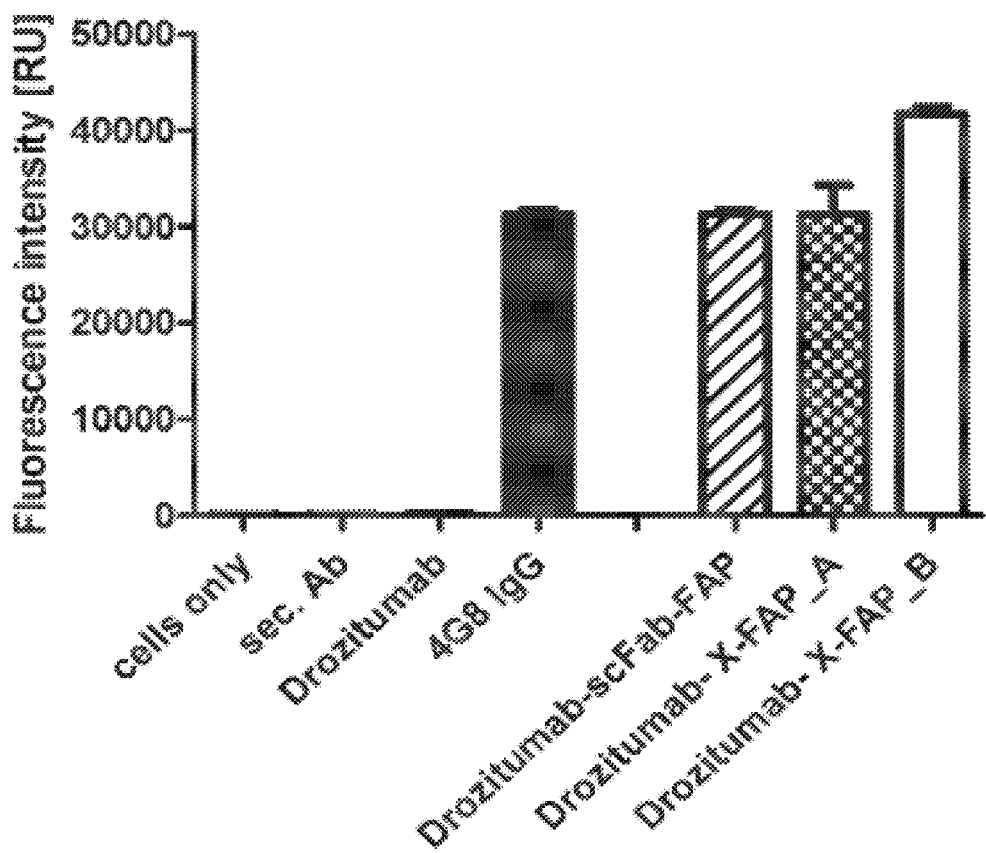
FIG. 7: Analysis of FACS binding on recombinant, human FAP expression HEK293 cells. DR5-FAP bispecific molecules in the new CrossFab format were compared to the scFab molecule, the parental 4G8 IgG and an unrelated negative control, Drozitumab. The two CrossFab molecules were shown to bind to FAP at least in the same range as the IgG control.
Figure 8A:
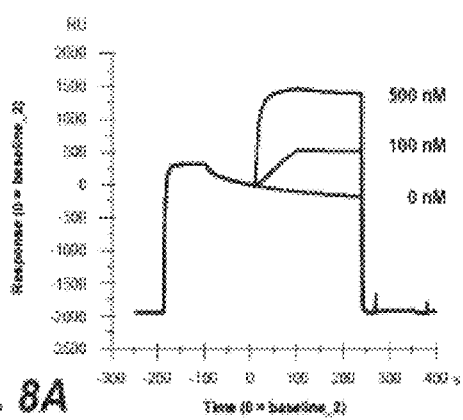
FIGS. 8A-8D: Surface plasmon resonance (SPR, Biacore) analysis of simultaneous binding of bispecific Drozitumab-FAP molecules (CrossFabs) to recombinant human DR5 and FAP. Biotinylated human DR5-Fc as the ligand was immobilized onto a streptavidin chip followed by injection of the first analyte (bispecific CrossFab molecules). After binding to DR5-Fc (90 sec association) and a short dissociation period (10 sec), recombinant soluble FAP (human or murine) in different concentrations (100 nM, 500 nM) was added as the second analyte and the additional response was measured. Binding of Drozitumab-X-FAP_A format (FIGS. 8A and 8B) was compared to Drozitumab-X-FAP_B (FIGS. 8C and 8D). Each construct was measured for binding DR5 and human (FIGS. 8A, 8C) or murine FAP (FIGS. 8B, 8D). By this analysis for all tested molecules a simultaneous binding to DR5 and human/murine FAP could be demonstrated.
Figure 8B:
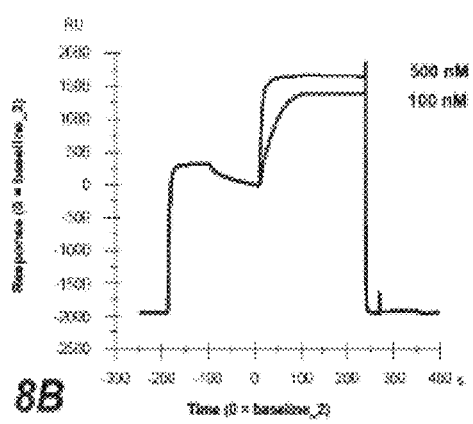
Figure 8C:
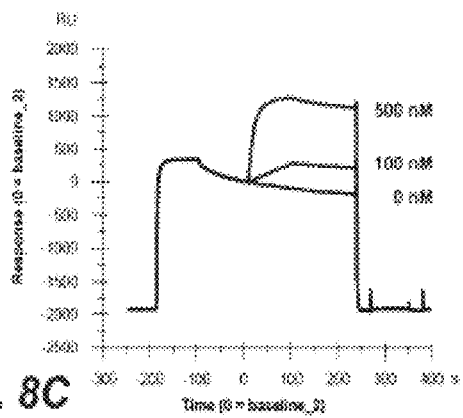
Figure 8D:
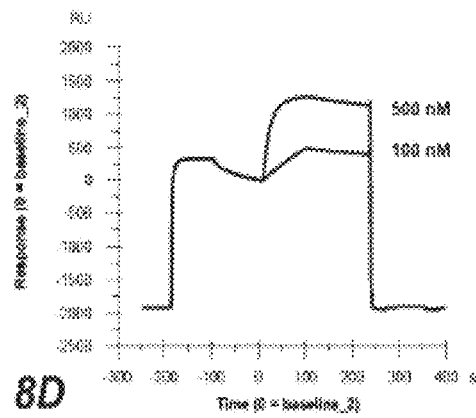

Binding of the molecules to human FAP, expressed on recombinant HEK293 cells was detected by FACS analysis. FIG. 7 shows the FACS binding results of two Drozitumab-CrossFab molecules (Drozitumab-X-FAP_A, dotted bar and Drozitumab-X-FAP_B, white bar) compared to an analogous scFab construct (hatched bar) or the corresponding FAP (4G8) IgG molecule (black bar). All three bispecific molecules in which the 4G8 FAP binding moiety is fused to the C-terminus of the Drozitumab heavy chain are binding similar or in a similar range to the human FAP expressed on the membranes of recombinant HEK cells as the IgG construct indicating that this fusion position does not have an N-terminal blocking effect on the tested FAP binder. The used negative control molecules in this assay (secondary detection antibody and Drozitumab) do not bind in a detectable manner to FAP expressing HEK cells.

TABLE 4

Comparison of yield and quality of all different tested bispecific DR5-FAP molecules.

| | Molecule | Yield [mg/L] | Aggregates [%] before after SEC | | Low molecular weight content [%] | Monomer [%] |
|---|---|---|---|---|---|---|
| 1 | 3F2 scFv_HC (SEQ ID NO.: 111) | 2.53 | 59 | 0.00 | 4.13 | 96.34 |
| 2 | 4G8 scFv_HC (SEQ ID NO.: 112) | 4.29 | n.d. | 0.00 | 1.50 | 98.50 |
| 3 | 4G8 scFv_LC (SEQ ID NO.: 113) | 2.15 | 73 | 0.00 | 0.00 | 100.00 |
| 4 | 3F2 scFab_HC (SEQ ID NO.: 114) | 3.99 | 72 | 0.00 | 0.00 | 100.00 |
| 5 | 3F2 scFab_LC (SEQ ID NO.: 115) | 4.99 | n.d. | 0.00 | 0.00 | 100.00 |
| 6 | 4G8 scFab_HC (SEQ ID NO.: 116) | 2.03 | 78 | 0.00 | 0.00 | 100.00 |
| 7 | 4G8 scFab_LC (SEQ ID NO.: 117) | 2.47 | 66 | 0.00 | 0.00 | 100.00 |
| 8 | 4G8-X-Fab_A (SEQ ID NO.: 118, 119, 120) | 36.10 | 90 | 0.00 | 0.00 | 100.00 |
| 9 | 4G8-X-Fab_B (SEQ ID NO.: 121, 122, 119) | 16.67 | 94 | 0.00 | 0.00 | 100.00 |

In FIGS. 8A-8D the results of Surface Plasmon Resonance analysis (SPR, Biacore) are shown in which the simultaneous binding of the bispecific CrossFab molecules to DR5 and FAP was evaluated. For this assay the antigen (human DR5 as Fc fusion, SEQ ID NO.:316) was coupled to the Biacore chip followed by injection of the CrossFab molecules as first analyte. After binding of the scFab molecules to DR5, recombinant soluble human or murine FAP (SEQ ID NO.:156 and 157) was used as the second analyte. For all tested bispecific molecules concentration dependent simultaneous binding to DR5 and human and murine FAP was demonstrated, as indicated by the increase of the overall response rate after injection of the first analyte, obtained upon injection of the second analyte. Both tetravalent bispecific CrossFab molecules (2×2; Drozitumab-X-FAP_A and Drozitumab-X-FAP_B) showed similar binding to DR5 and human and murine FAP (FIGS. 8A-8D).

Figure 9A:
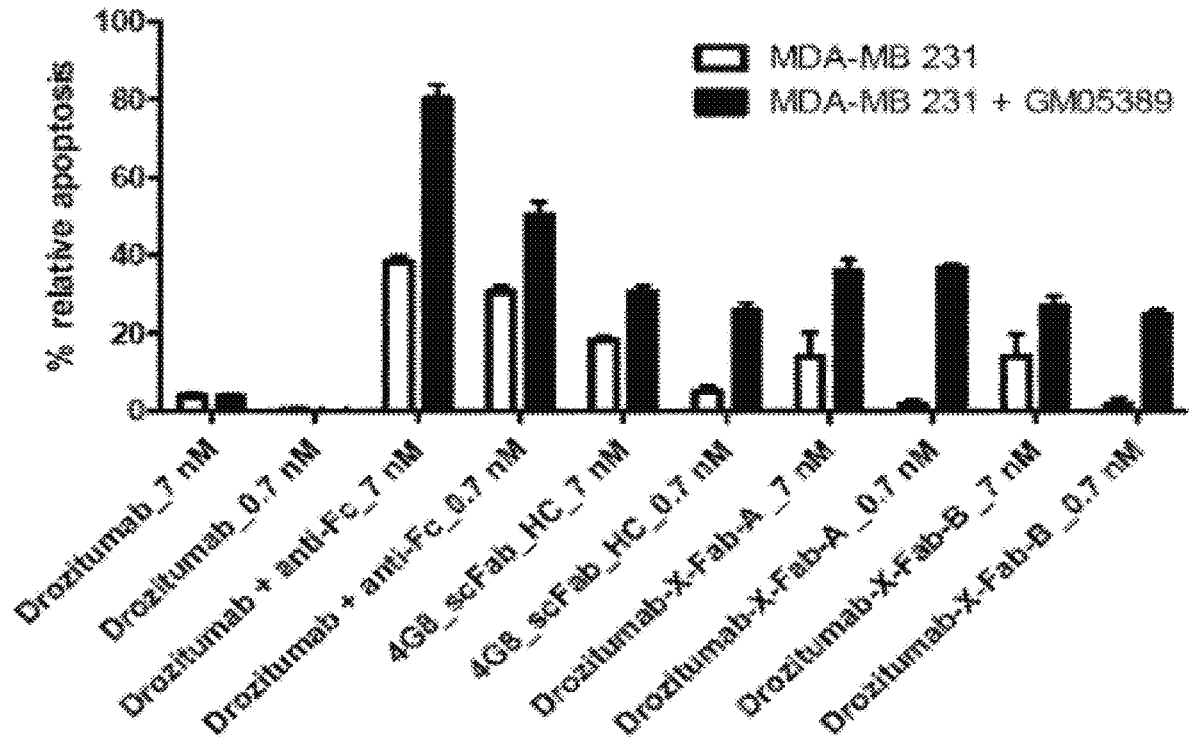
FIGS. 9A and 9B: DNA fragmentation ELISA assay for detection of apoptosis. Results of an apoptosis induction experiment in which two CrossFab molecules (Drozitumab-X-Fab-A and Drozitumab-X-Fab-B) were compared to Drozitumab and hyper-cross-linked Drozitumab in a two cell line (MDA-MB-231 and GM05389) co-culture assay.
Figure 9B:
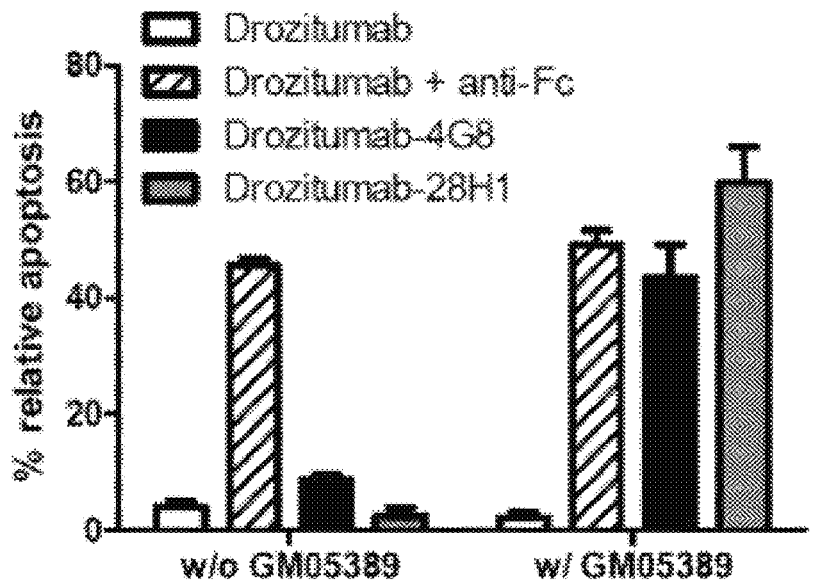

FIGS. 9A and 9B shows the induction of apoptosis as determined by DNA fragmentation assay after 24 hrs of Drozitumab vs. two different bispecific Drozitumab-X-FAP molecules and one Drozitumab_4G8_scFab construct on the breast carcinoma cell line MDA-MB-231 in the absence or presence of FAP expressing fibroblast cells GM05389. Under the applied conditions, hyper-cross-linked Drozitumab and the bispecific DR5-FAP molecules exhibit concentration dependent induction of apoptosis. While the bispecific constructs at low concentrations seemed to be dependent on the so-called bystander apoptosis (apoptosis activity only with DR5 and FAP expressing cell lines present) they also induced apoptosis of MDA-MB-231 cells alone at high concentrations. Hyper-cross-linked Drozitumab induced high levels of apoptosis also at low concentrations when only MDA-MB-231 cells were present. Both bispecific molecules exhibited maximal apoptosis induction already at a concentration of 0.7 nM.

Figure 10:
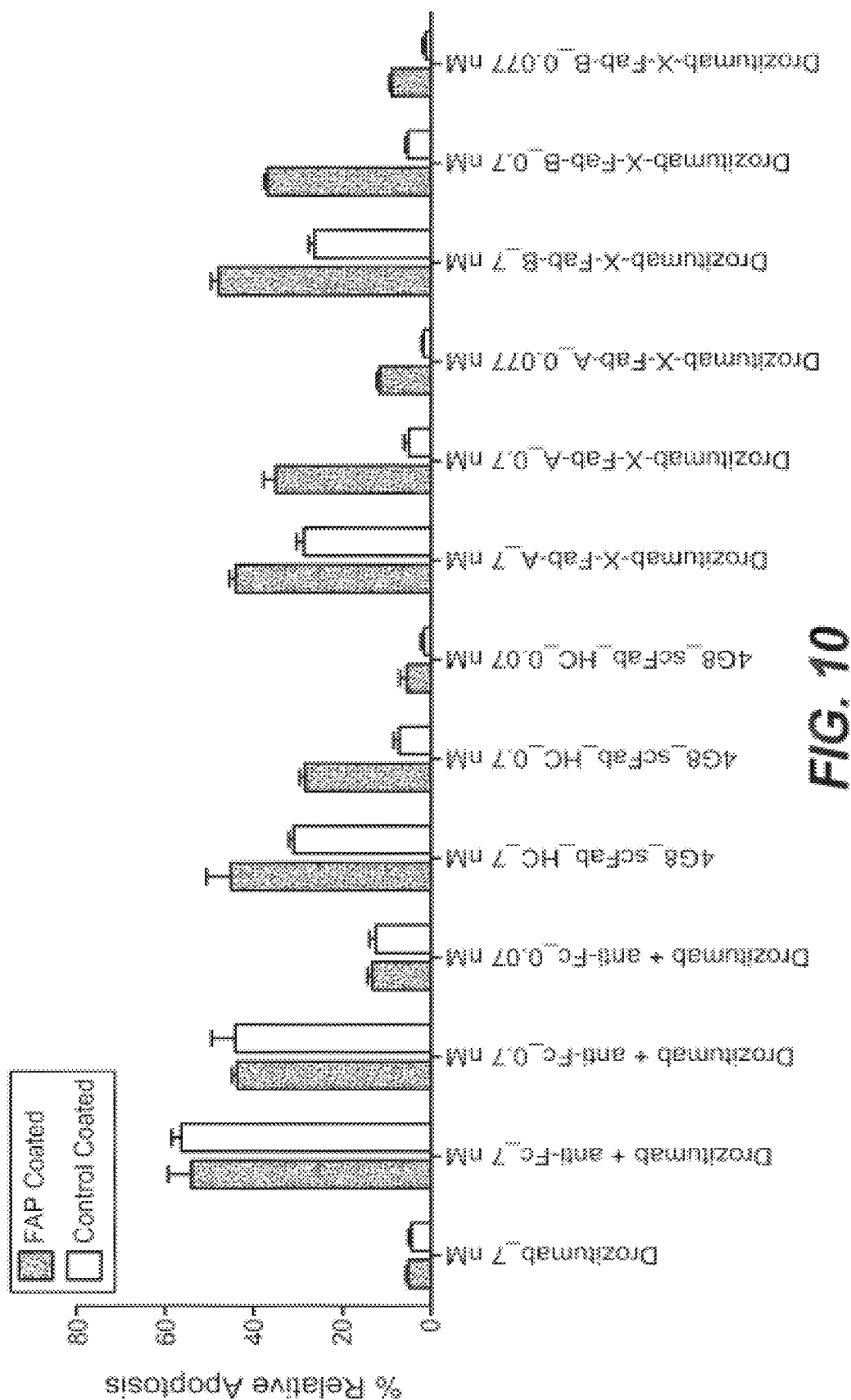
FIG. 10: DNA fragmentation ELISA assay for detection of apoptosis. Induction of apoptosis via bispecific Drozitumab-FAP CrossFab molecules is dependent on cross-linking via FAP.
Figure 11:
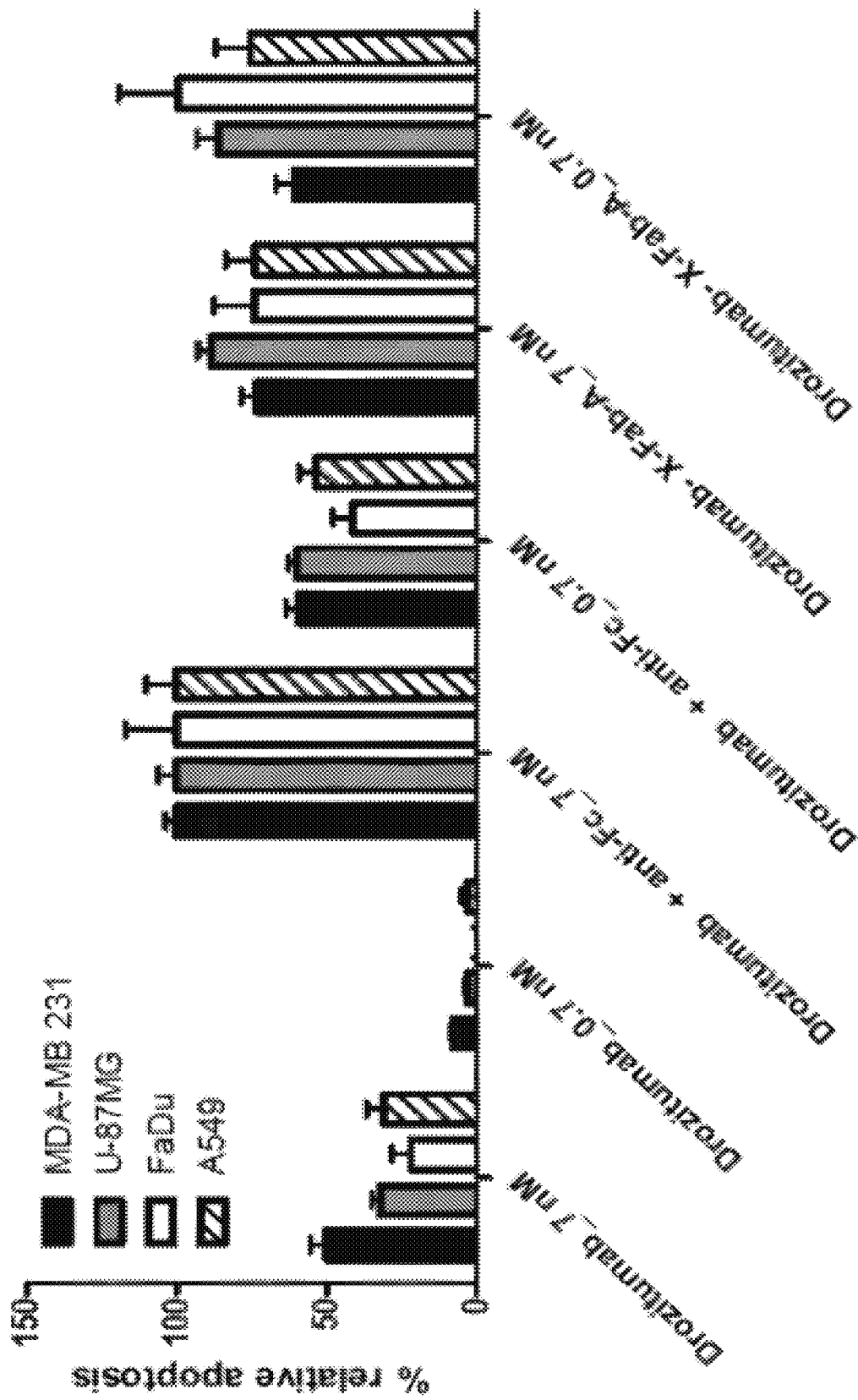
FIG. 11: Comparison of apoptosis induction (DNA fragmentation) on different human tumor cell lines in a co-culture experiment with FAP expressing human fibroblasts GM05389. Drozitumab and hyper-cross-linked Drozitumab is compared to a bispecific Drozitumab-4G8 CrossFab molecule (all at concentrations of 7.0 and 0.7 nM). Used tumor cell lines were MDA-MB-231 (breast cancer), U-87MG (glioblastoma), FaDu (squamous carcinoma) or A549 (lung carcinoma). Apoptosis induction at a concentration of 7 nM was similar for all four cell lines while at 0.7 nM a more pronounced difference between the cell lines was observed.

To test the specificity of the bispecific constructs for their apoptosis induction activity being dependent on cross-linking via FAP a different assay set up was chosen (FIG. 10). In this setting recombinant human FAP or an unrelated control protein (white bars) were coated onto ELISA plates. These proteins were incubated with the bispecific molecules or the relevant controls before target cells (MDA-MB-231) were added and incubated for 24 hrs. A concentration dependent DNA fragmentation indicative for apoptosis induction could be demonstrated for the hyper-cross-linked Drozitumab (grey bars), a bispecific scFab molecule (hatched bars) and the bispecific CrossFab molecules (black bars) as shown in FIG. 10. While apoptosis induction with cross-linked Drozitumab always was in the same range with FAP or the control protein coated (over the entire tested concentration range) the apoptosis activity of CrossFab molecules was higher when FAP was coated onto the plates compared to the control protein. At concentrations of 0.7 nM and below significant apoptosis only could be detected in the presence of coated FAP, indicating specific cross-linking of DR5 on the target MDA-MB-231 cells. The bispecific Drozitumab-FAP constructs containing the FAP moiety fused as a CrossFab to the C-terminus of the Drozitumab heavy chain exhibit superior apoptosis induction over Drozitumab alone at the tested concentrations for different tumor cell lines analyzed in co-culture apoptosis assays (DNA fragmentation assay) over 24 hrs as shown in FIG. 11. In this assay FAP expressing fibroblasts (GM05389) were co-cultured with a series of different tumor cell lines (MDA-MB-231, breast cancer, black bars; U-87MG, glioblastoma, grey bars; FaDu, head and neck, white bars and A549, lung cancer, hatched bars) in the presence of either Drozitumab, Drozitumab cross-linked with anti-Fc antibody, or Drozitumab-X-FAP construct (all at concentrations of 7 nM and 0.7 nM). Apoptosis induction of cross-linked Drozitumab at a concentration of 7 nM was set to 100% and the activities of the other tested molecules were calculated accordingly. While Drozitumab alone at a concentration of 7 nM showed up to 50% activity (depending on the tested tumor cell line), the CrossFab molecule exhibited apoptosis induction in the range of 75-90% of hyper cross-linked Drozitumab with all tested cell lines. Drozitumab alone at 0.7 nM demonstrated low activity while the bispecific molecule displayed significant apoptosis induction activity (up to 100% with FaDu cells, between 60 and 90% with the other tested cell lines).

Figure 12:
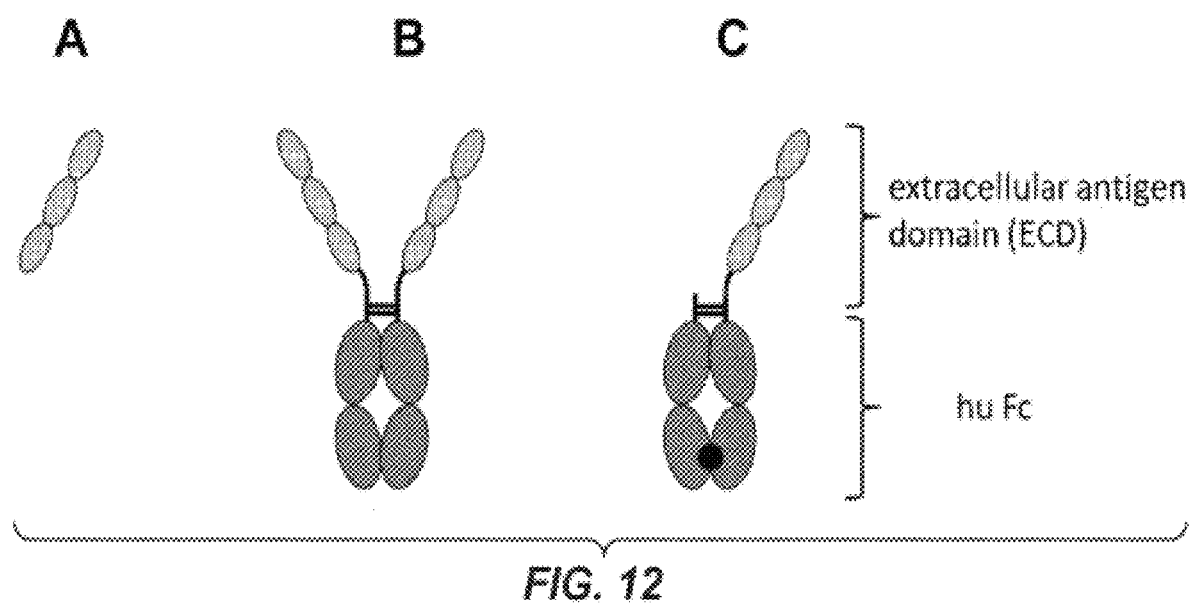
FIG. 12: Schematic representation of the human DR5 antigen constructs used for isolation, screening and characterization of novel DR5 binders. For all constructs the same DR5 domain (extracellular domain, ECD; aa 56-207) was used either alone (A) as dimeric Fc fusion (B) or as monomeric Fc fusion (C) using the knob-into-hole technology. All antigens were transiently transfected and produced in HEK293 EBNA cells.
Figure 13A:
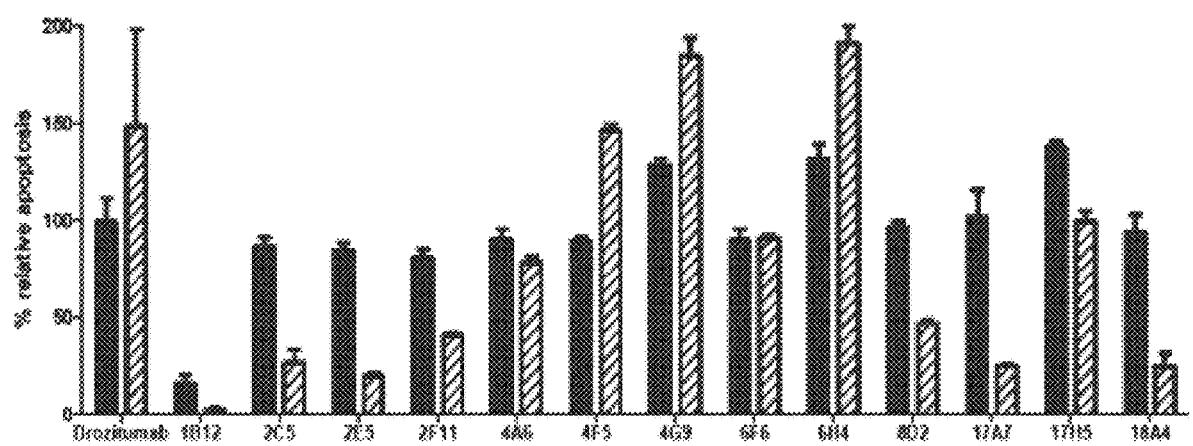
FIGS. 13A-13D: Screening of 46 unique DR5 binders (isolated by phage display) for induction of apoptosis on MDA-MB-231 cells (DNA fragmentation assay) after hyper-cross-linking with secondary anti Fc antibody. Antibodies were used at concentrations of 7 nM (black bars) and 0.7 nM (hatched bars). The vast majority of DR5 binders (42/46) were able to induce DNA fragmentation to different degrees after hyper-cross-linking.
Figure 13B:
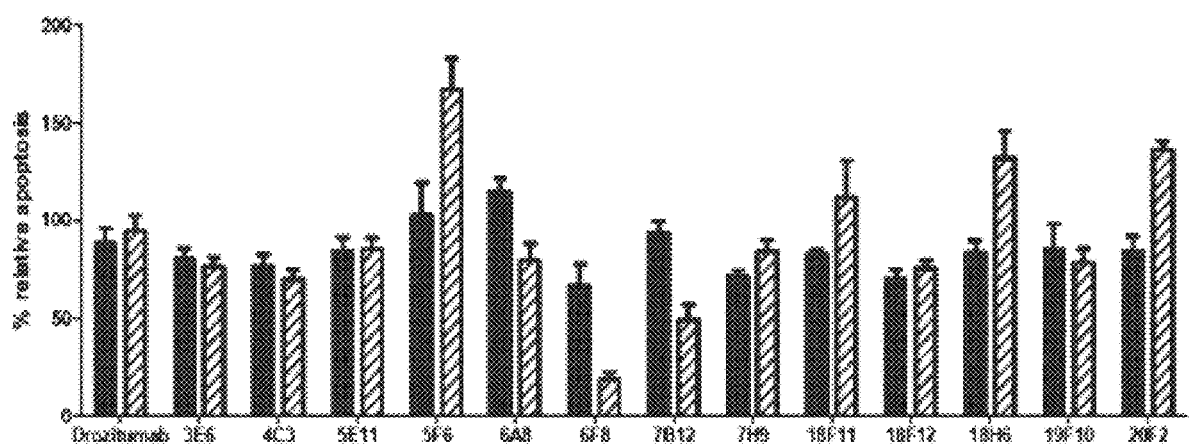
Figure 13C:
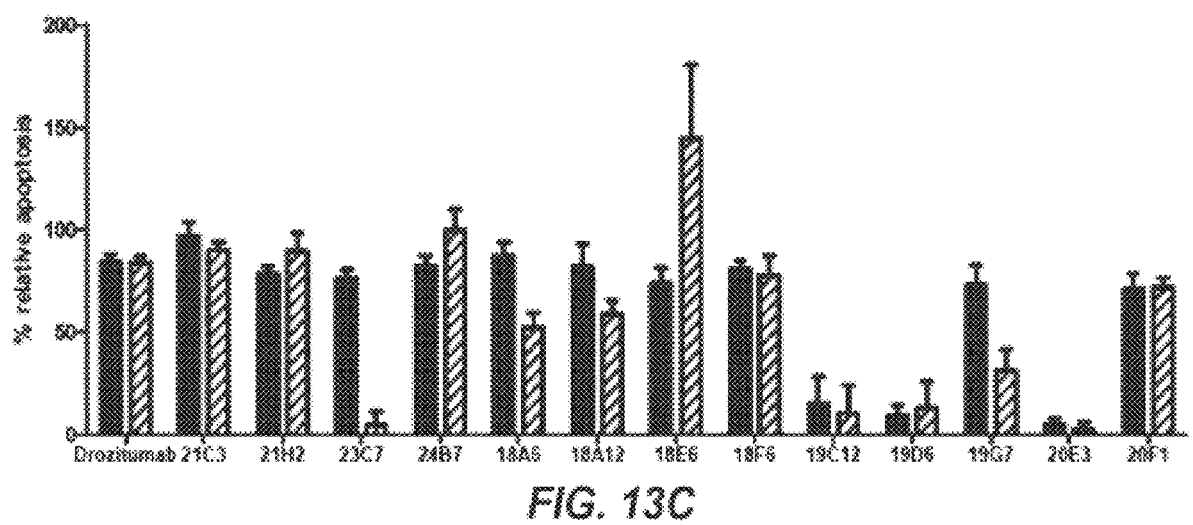
Figure 13D:
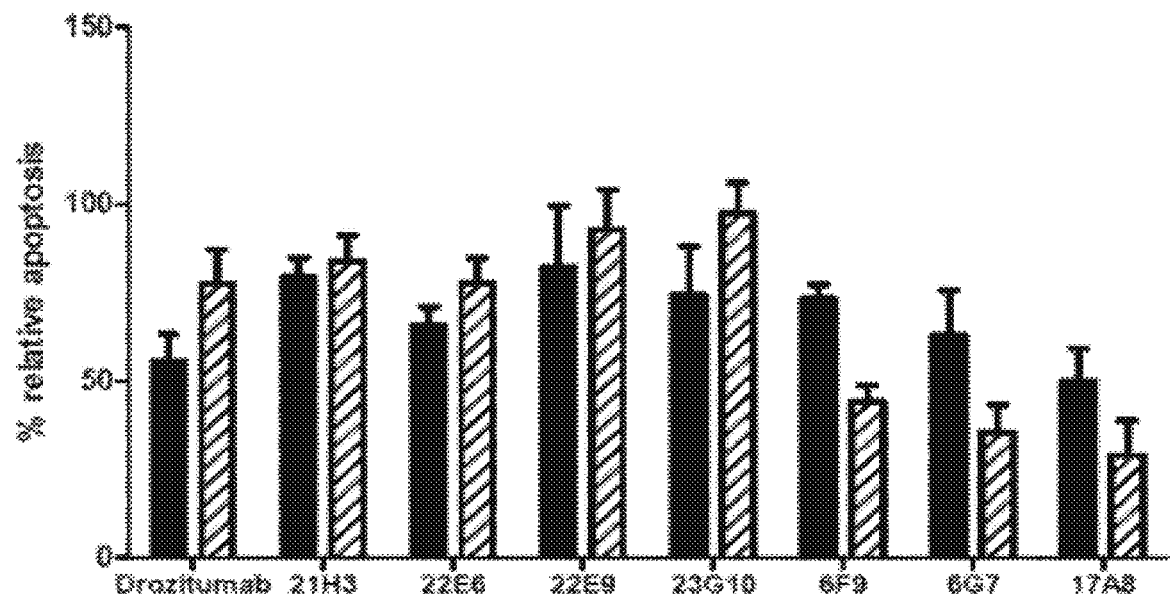

Example 4: Preparation of Antigens and Screening Tools for the Generation of Novel DR5 Binders Due to some suboptimal properties of Drozitumab in bispecific format (low productivity, active without cross-linking, N-terminal fusion inactivates the antibody) new DR5 antibodies were isolated which overcome these liabilities. For generation of suitable antigens to be used in isolation of novel DR5 binders and for screening and selection of those, a series of fusion proteins have been constructed. From each receptor gene the extracellular domain (ECD) encoding region was amplified by PCR and fused to a generic protein partner to generate the following formats (as depicted in FIG. 12):
1. Extracellular domain (ECD) fused in frame to Avi-tag and Hexahis-tag
2. ECD fused to Fc of human IgG1 consisting of the hinge region and CH2 and CH3 domains followed by an Avi tag. Between ECD and Fc an AcTev protease cleavage site was inserted (—(resulting in a dimeric antigen)
3. As in 2 but the ECD is fused to an Fc with knob-into-hole mutations. The antigen-Fc fusion is co-expressed with the Fc-hole counterpart to obtain monomeric antigens While the sequences of human DR5 and murine DR5 were known and annotated in the SwissProt database, the sequence of the cynomolgus homolog has not been described there. Based on homologies among human and rhesus DR5 gene sequences primers have been designed that were used for isolation of the cynomolgus antigen from RNA prepared from cynomolgus PBMCs. In brief, RNA was isolated from freshly isolated cynomolgus blood using the RNeasy Kit from Qiagen. After DNAseI digestion and elution of the RNA the OneStep RT-PCR kit (cDNA synthesis and amplification) from Qiagen (catalog number 210212) was used to amplify the cynomolgus DR5 gene with GAB-4039 (GCTGGCTCCTGGACTTCCATTTCC, SEQ ID NO 163) and GAB4040 (GACCCAGG-GAGGCGCGGGGAG; SEQ ID NO 164) as primers, designed according to the known rhesus DR5 sequence. The PCR product was cloned into pCR2.1 Topo (Invitrogen) for sequencing. Analysis of the sequence revealed 89% homology to the human DR5 extracellular domain. Using the primers GAB-4145 (GTGCATTCCAT-CACCCGACAATCCCTAGATCCCCAGCG; SEQ ID NO 165) and GAB-4146 (GCGTCGACTGAT-TCTTTGTGGACACACTCAATGTCAC; SEQ ID NO 166) the extracellular domain of the cynomolgus DR5 gene was cloned into a generic expression vector in fusion with human Fc.

Expression of the desired genes occurs under control of a MPSV promoter. In addition a 3' polyadenylation site is included and an oriP sequence for stable maintenance of the plasmids in EBV nuclear antigen (EBNA) expressing HEK293 cells.

For production of the antigens relevant expression vectors were transfected into HEK293 EBNA cells (either $Ca_2PO_4$ mediated or PEI dependent transfection). After 5-7 days of cultivation supernatants were harvested and purified via Protein A binding (Fc containing antigens) or by $NI^{2+}$ affinity chromatography (Histag containing molecules) and subsequent size exclusion chromatography (SEC). If necessary the proteins were biotinylated via the C-terminal Avi tag. This could either be performed in vivo, by co-transfection/co-expression of a birA encoding plasmid or after purification of the antigen in vitro using a biotinylation kit from Avidity Cat No. BIRA. The following antigens were produced by transient gene expression in HEK293 EBNA:

TABLE 5

Antigen constructs and screening tools for isolation of antibodies against human DR5

| # | Antigen | Amino acid | Format | Source | Acc. No |
|---|---|---|---|---|---|
| 1 | human DR5 | 56-207 | ECD-Avi-his | Open Biosystems BC001281.1 | O14763 |
| 2 | human DR5 | 56-207 | ECD-AcTev-hu Fc-Avi | as above | O14763 |
| 3 | human DR5 | 56-207 | ECD-AcTev-hu Fc knob-Avi | as above | O14763 |
| 4 | murine DR5 | 53-153 | ECD-AcTev-hu Fc-Avi | Open Biosystems BC065141.1 | Q9QZM4 |
| 5 | cynom. DR5 | 58-185 | ECD-AcTev-hu Fc-Avi | described herein and WO 2004/101608 A2 | SEQ ID NO. 317 | n.a.: not applicable

Recombinant human DR4-Fc (Cat No. 347-DR/CF), DcR1-Fc (Cat No. 630-TR/CF), DcR2-Fc/Cat No. 633-TR/CF) and OPG-Fc (Cat No. 805-=S/CF) were purchased from R&D Biosystems.

Example 5: Isolation of Novel Anti DR5 Binders from Generic Fab Libraries

Antibodies with specificity for human DR5 were selected from a generic phage-displayed antibody library in the Fab format (DP47-3). This library was constructed on the basis of human germline genes using the V-domain pairing Vk3_20 (kappa light chain) and VH3_23 (heavy chain) comprising randomized sequence space in CDR3 of the light chain (L3) and CDR3 of the heavy chain (H3). Library generation was performed by assembly of 3 PCR-amplified fragments by splicing by overlapping extension (SOE) PCR. Fragment 1 comprises the the 5' end of the antibody gene including randomized L3, fragment 2 is a central constant fragment spanning from L3 to H3 whereas fragment 3 comprises randomized H3 and the 3' portion of the antibody gene. The following primer combinations were used to generate these library fragments for DP47-3 library: fragment 1 (LMB3-LibL1b_new), fragment 2 (MS63-MS64) and fragment 3 (Lib2H-fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the 3 fragments as template, parameters were 3 min initial denaturation at 94° C. and 5 cycles of 30 s 94° C., 1 min 58° C., 2 min 72° C. At this stage, outer primers were added and additional 20 cycles were performed prior to a terminal elongation for 10 min at 72° C. After assembly of sufficient amounts of full length randomized Fab constructs, they were digested NcoI/NotI alongside with similarly treated acceptor phagemid vector. 22.8 µg of Fab library were ligated with 16.2 µg of phagemid vector. Purified ligations were used for 68 transformations to obtain a final library size of $4.2 \times 10^{10}$. Phagemid particles displaying the Fab library were rescued and purified by PEG/NaCl purification to be used for selections.

Selections were carried out against HEK293-expressed monomeric or dimeric human DR5 fused to the Fc-portion of a human IgG1 antibody. For the generation of the monomeric antigen, the Fc knob-into-holes format was applied for heterodimerization of two different CH2-CH3 chains (only one of which carrying human DR5 ectodomain as N-terminal fusion). The antigens were enzymatically biotinylated via an avi-tag. Panning rounds were performed in solution according to the following pattern: 1. Preclearing of $\sim 10^{12}$ phagemid particles using hu IgG1 coated at 10 µm/ml onto NUNC maxisorp plates to avoid Fc-binders, 2. binding of non-Fc binding phagemid particles from the supernatant of the pre-clearing reaction to 100 nM biotinylated human DR5 for 0.5 h in a total volume of 1 ml, 3. capture of biotinylated hu DR5 and attached specifically binding phage by incubation on neutravidin-coated microtiter plates for 10 min, 4. washing of beads using 5×1 ml PBS/Tween20 and 5×1 ml PBS, 5. elution of phage particles by addition of 1 ml 100 mM TEA (triethylamine) for 10 min and neutralization by addition of 500 µl 1 M Tris/HCl pH 7.4, 6. post-clearing step of eluted phage particles on human DcR2 to avoid cross-reactive binders and 7. re-infection of log-phase E. coli TG1 cells with the phage particles in the supernatant, infection with helperphage VCSM13 and subsequent PEG/NaCl precipitation of phagemid particles to be used in subsequent selection rounds. Selections were carried out over 3 rounds using constant antigen concentrations at 100 nM. In round 2, capture of antigen: phage complexes was performed by addition of $5.4 \times 10^{7}$ streptavidin-coated magnetic beads for 10 min instead of capture on neutravidin-coated microtiter plates. Specific binders were identified by ELISA as follows: 100 µl of 50 nM biotinylated human DR5 or DcR2 per well were coated on neutravidin plates. Moreover, 10 µg/ml human IgG1 were coated on NUNC maxisorp plates. Fab-containing bacterial supernatants were added and binding Fabs were detected via their Flag-tags by using an anti-Flag/HRP secondary antibody. Clones exhibiting signals on human DR5 but none on human DcR2 and human IgG1 were short-listed for further analyses.

Affinity ($K_D$) of selected Fab clones was measured by surface plasmon resonance using a ProteOn XPR36 instrument (Biorad) at 25° C. with biotinylated mono- or bivalent DR5 antigens immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute at varying contact times, to achieve immobilization levels of 200, 400 or 800 response units (RU) in vertical orientation. Injection of analytes: For one-shot kinetics measurements, injection direction was changed to horizontal orientation, two-fold dilution series of purified Fab (varying concentration ranges between 100 and 3.125 nM) were injected simultaneously at 50, 60 or 100 µl/min along separate channels 1-5, with association times of 120, 180 or 200 s, and dissociation times of 200 or 240 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Regeneration was performed in horizontal orientation using 50 mM NaOH at a flow rate of 100 µl/min for a contact time of 18 s.

Example 6: Selected DR5 Binders are Capable of Inducing Apoptosis Upon Cross-Linking To identify DR5 binders which are able to induce apoptosis of selected target cells only upon cross-linking the antibodies isolated from a Fab library were converted into the corresponding hu IgG1 format. In brief, the variable heavy and variable light chains of 46 unique DR5 binders from phage display were amplified by standard PCR reactions using the Fab clones as the template. The PCR products were purified and inserted (either by restriction endonuclease and ligase based cloning, or by 'recombineering' using the InFusion kit from Invitrogen) into suitable expression vectors in which they are fused to the appropriate human constant heavy or human constant light chain. The expression cassettes in these vectors consist of a chimeric MPSV promoter and a synthetic polyadenylation site. In addition, the plasmids contain the oriP region from the Epstein Barr virus for the stable maintenance of the plasmids in HEK293 cells harboring the EBV nuclear antigen (EBNA). Antibodies were transiently produced in 50 ml scale in HEK293 EBNA cells as described. For a fast and high throughput purification, supernatants were neutralized and incubated with ProteinA Sepharose Fast Flow beads (GE Healthcare Cat No. 17-5138-01) for 16 h. The supernatant/bead mixture was then passed over an empty, equilibrated PD-10 column (GE Healthcare Cat No. 17-0435-01) by gravity flow. The retained beads were washed twice and the antibody eluted with a low pH step. Finally, the eluted protein was neutralized and its concentration calculated using the asorbance at 280 nm and the molar extinction coefficient. The aggregate content of the antibody sample was analysed by analytical size exclusion chromatography using a Zorbax GF-250 column (Agilent Cat No PSMO 845006).

The results of this purification procedure are summarized in table 6

TABLE 6

Summary of purification results, SEQ ID NOs see Table 8

| anti DR5 mAb | Titer [mg/ml] | Yield [mg/ml] | Monomer content [%] |
|---|---|---|---|
| 3E6 | 47.3 | 32.9 | 100 |
| 4C3 | 43.6 | 21.2 | 100 |
| 5E11 | 38.2 | 29.9 | 100 |
| 5F6 | 40.4 | 38.0 | 100 |
| 6A8 | 41.9 | 28.1 | 100 |
| 6F8 | 64.4 | 45.1 | 99 |
| 7B12 | 75.1 | 44.6 | 100 |
| 7H9 | 54.7 | 38.5 | 99 |
| 18F11 | 77.6 | 54.4 | 100 |
| 18F12 | 66.6 | 33.4 | 99 |
| 18H6 | 54.6 | 48.5 | 100 |
| 19F10 | 61.1 | 36.7 | 100 |
| 20F2 | 65.9 | 41.0 | 99 |
| 21C3 | 51.4 | 40.6 | 97 |
| 2I2 | 53.6 | 27.1 | 99 |
| 23C7 | 49.8 | 27.2 | 100 |
| 24B7 | 38.5 | 28.9 | 100 |
| 1B12 | 179.3 | 78.1 | 100 |
| 2C5 | 116.2 | 48.7 | 98 |
| 2E5 | 144.3 | 67.7 | 100 |

TABLE 6-continued

Summary of purification results, SEQ ID NOs see Table 8

| anti DR5 mAb | Titer [mg/ml] | Yield [mg/ml] | Monomer content [%] |
|---|---|---|---|
| 2F11 | 146.2 | 67.3 | 100 |
| 4A6 | 148.0 | 83.2 | 100 |
| 4F5 | 110.5 | 48.7 | 100 |
| 4G9 | 128.1 | 80.9 | 100 |
| 6F6 | 161.3 | 86.3 | 100 |
| 6H4 | 128.1 | 65.8 | 100 |
| 8D2 | 136.6 | 65.8 | 100 |
| 17A7 | 136.1 | 62.7 | 100 |
| 17H5 | 155.7 | 77.1 | 100 |
| 18A4 | 138.9 | 67.1 | 100 |
| 18A6 | 103.9 | 54.7 | 100 |
| 18A12 | 118.1 | 63.3 | 100 |
| 18E6 | 90.8 | 44.3 | 100 |
| 18F6 | 99.3 | 36.0 | 100 |
| 19C12 | 192.6 | 70.6 | 92 |
| 19D6 | 144.9 | 81.7 | 97 |
| 19G7 | 117.0 | 63.1 | 100 |
| 20E3 | 116.4 | 51.7 | 100 |
| 20F1 | 75.5 | 40.7 | 100 |
| 21H3 | 127.1 | 45.1 | 98 |
| 22E6 | 130.9 | 61.2 | 98 |
| 22E9 | 137.5 | 60.2 | 100 |
| 23G10 | 127.9 | 43.5 | 100 |
| 6F9 | 96.8 | 48.2 | 100 |
| 6G7 | 114.7 | 59.3 | 100 |
| 17A8 | 102.1 | 60.0 | 100 |

This small scale transfection and production followed by purification via ProteinA beads yielded in reasonable amounts of pure antibodies with very low aggregate content. In FIGS. 13A-13D the results of a standard DNA fragmentation ELISA assay for detection of apoptosis are summarized. Each antibody was tested in two different concentrations (1.0 µg/ml: black bars and 0.1 µg/ml: hatched bars with 1.0 and 0.1 µg/ml of anti-Fc antibody for cross-linking, respectively). The obtained data were normalized to the maximal activity of cross-linked Drozitumab (at 1.0 µg/ml) which was set to 100%. The majority of analyzed antibodies were able to induce concentration dependent induction of apoptosis in MDA-MB-231 cells after cross-linking. Seven of 46 binders (15.2%) clearly showed higher activity as Drozitumab at both concentrations. Fifteen antibodies (32.6%) were in the same activity range as Drozitumab and twenty of the tested molecules (43.5%) did induce apoptosis upon cross-linking but to a much lower degree compared to Drozitumab. The remaining four binders ("20E3", "19E6", 1B12" and "19C12", 8.7%) were inactive and did not induce apoptosis, even after cross-linking via a secondary anti Fc antibody.

Example 7: Characterization of Novel DR5 Binders

Based on the results of apoptosis activity screen twelve of 46 evaluated DR5 antibodies were selected for additional, more detailed analysis and characterization. These antibodies were re-produced in transiently transfected HEK293 EBNA cells and purified using standard ProteinA affinity columns followed by size exclusion chromatography as described. Yield and monomer/aggregate content were determined (table 7). The purified antibodies were characterized with respect to target specificity, species cross-reactivity and affinity (table 8). In addition thermal stability was analyzed by DLS and the apoptosis induction activity was compared in the presence or absence of a secondary cross-linking anti-human Fc antibody.

TABLE 7

Series of selected DR5 antibodies, SEQ ID NOs see Table 8

| Antibody | SEQ ID NO. VH | SEQ ID NO. VL | Yield [mg/L] | Monomer [%] | Specificity | Cross-reactivity |
|---|---|---|---|---|---|---|
| 18F11 | 94 | 95 | 33.00 | 100.0 | specific for DR5 no binding to DR4, DcR1, DcR2 or OPG | Human and cyno-molgous monkey DR5 no binding to murine DR5 |
| 18H6 | | | 8.40 | 71.2 | as above | as above |
| 18E6 | | | 31.50 | 100.0 | as above | as above |
| 6H4 | | | 30.30 | 100.0 | as above | as above |
| 5F6 | | | 42.18 | 100.0 | as above | as above |
| 20F2 | 106 | 107 | 30.00 | 100.0 | as above | as above |
| 4G9 | | | 42.90 | 100.0 | as above | as above |
| 22E9 | 100 | 101 | 39.96 | 100.0 | as above | as above |
| 21H3 | 102 | 103 | 32.35 | 100.0 | as above | as above |
| 4F5 | | | 36.63 | 100.0 | as above | as above |
| 5E11 | 7 | 8 | 31.68 | 100.0 | as above | as above |
| 24B7 | | | 19.73 | 100.0 | as above | as above |

TABLE 8

Characterization of novel DR5 binders

| Antibody | SEQ ID NO. VH/VL | Affinity [nM] | Avidity [nM] | Aggregation temperature [° C.] |
|---|---|---|---|---|
| 18F11 | 94/95 | 504 | 1.1 | 64 |
| 18H6 | | 555 | 2.7 | n.d. |
| 18E6 | | 471 | 2.2 | 66 |
| 6H4 | | 773 | 8.9 | 65 |
| 5F6 | | 552 | 1.5 | 66 |
| 20F2 | 106/107 | 431 | 4.8 | 66 |
| 4G9 | | 478 | 6.4 | 65 |
| 22E9 | 100/101 | 217 | 1.5 | 64 |
| 21H3 | 102/103 | 259 | 1.6 | 64 |
| 4F5 | | 575 | 4.4 | n.d. |

TABLE 8-continued

Characterization of novel DR5 binders

| Antibody | SEQ ID NO. VH/VL | Affinity [nM] | Avidity [nM] | Aggregation temperature [° C.] |
|---|---|---|---|---|
| 5E11 | 7/8 | 162 | 1.1 | 65 |
| 24B7 |  | 300 | 2.3 | 65 |

All analyzed antibodies specifically recognize human DR5 and do not bind to the closest human homologs from the TNFR super family such as DR4, decoy receptors (DcR1 and DcR2) and osteoprotegerin (OPG). All DR5 antibodies are cross-reactive with human and cynomolgus DR5 but do not recognize the murine counterpart (which is not unexpected due to a sequence homology of only about 30%). While the affinities to human DR5 are in a quite wide range (from 162 to 773 nM) all measured avidities are in the low (one digit) nanomolar range. All tested DR5 binders reveal a high thermal stability with aggregation temperatures well above 60° C. as measured by Dynamic Light Scattering (DLS) experiments.

Figure 14A:
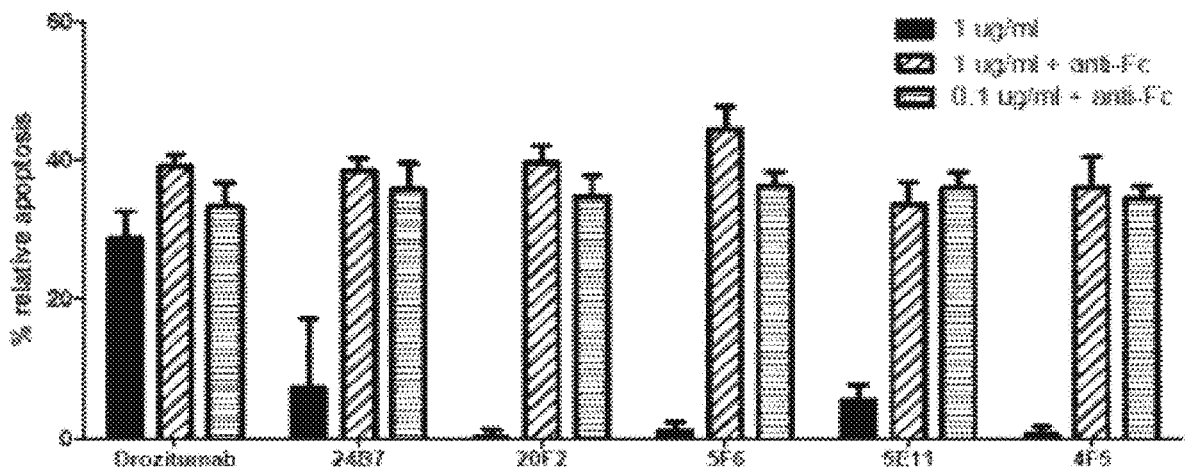
FIGS. 14A-14C: Apoptosis induction in MDA-MB-231 cells measured via DNA fragmentation ELISA assay by a selected series of novel DR5 binders in the presence or absence of secondary, cross-linking anti Fc antibody to evaluate if the new DR5 antibodies exhibit apoptosis activity without secondary cross-linking. The new DR5 binders were compared to Drozitumab, an antibody known to be active to a certain degree without cross-linking.
Figure 14B:
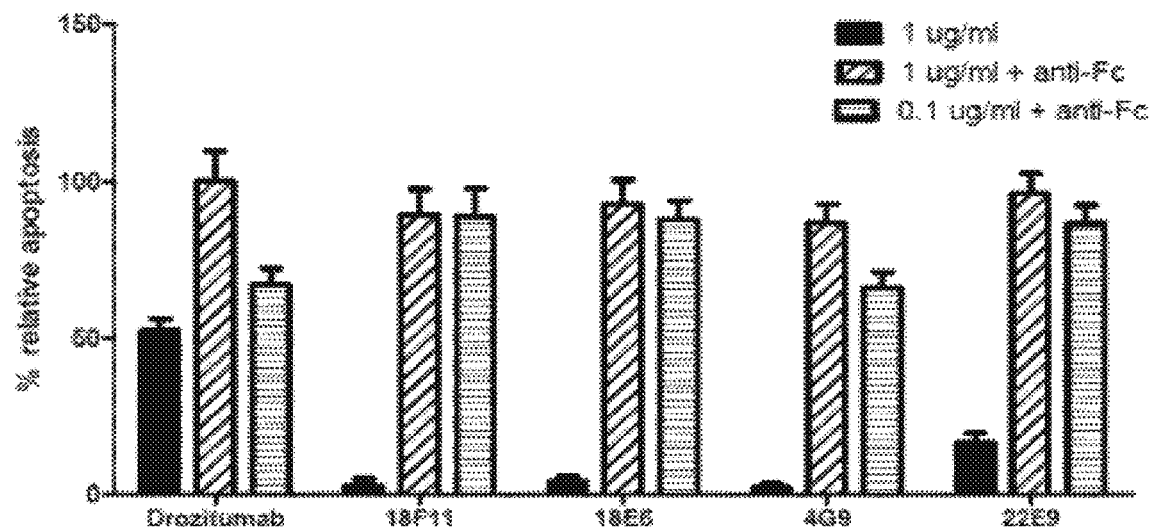
Figure 14C:
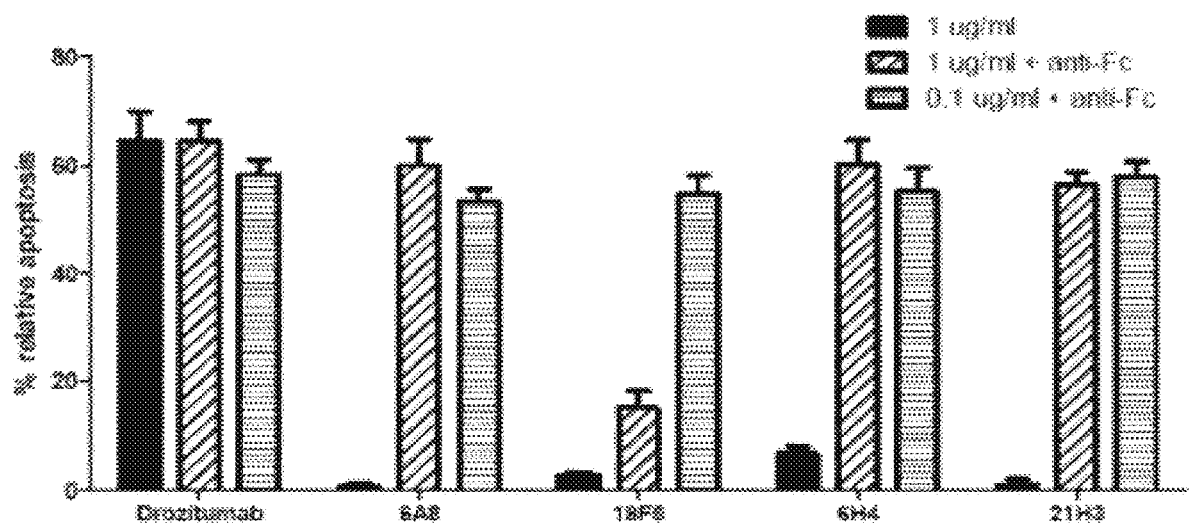

To determine functional activity of a series of selected DR5 binders, apoptosis induction was analyzed using a Cell Death Detection ELISA assay (Roche; #11 774 425 001) which specifically detects DNA fragmentation. Antibodies were used at a concentration of 1.0 and 0.1 µg/ml in the presence of the same concentration of secondary anti human Fc antibody for cross-linking. For comparison antibodies were used at 1.0 µg/ml in the absence of the secondary antibody to evaluate if the activity of the selected DR5 binders depends on cross-linking or if they are already active on their own. The human breast cancer cell line MDA-MB-231 was used as the target cell line. In FIGS. 14A-14C the results of the apoptosis induction of different DR5 binders are summarized. After cross-linking all of the newly isolated DR5 antibodies induce apoptosis in the same range as the control antibody Drozitumab. However, unlike Drozitumab which already exhibits significant apoptosis induction activity without cross-linking, activity of the novel DR5 binders strictly depends on cross-linking via a secondary antibody. The apoptotic activity does not seem to be correlated to the affinity of the DR5 binder to its target since this was similar for antibodies with both the highest and the lowest affinity to human DR5.

Figure 15:
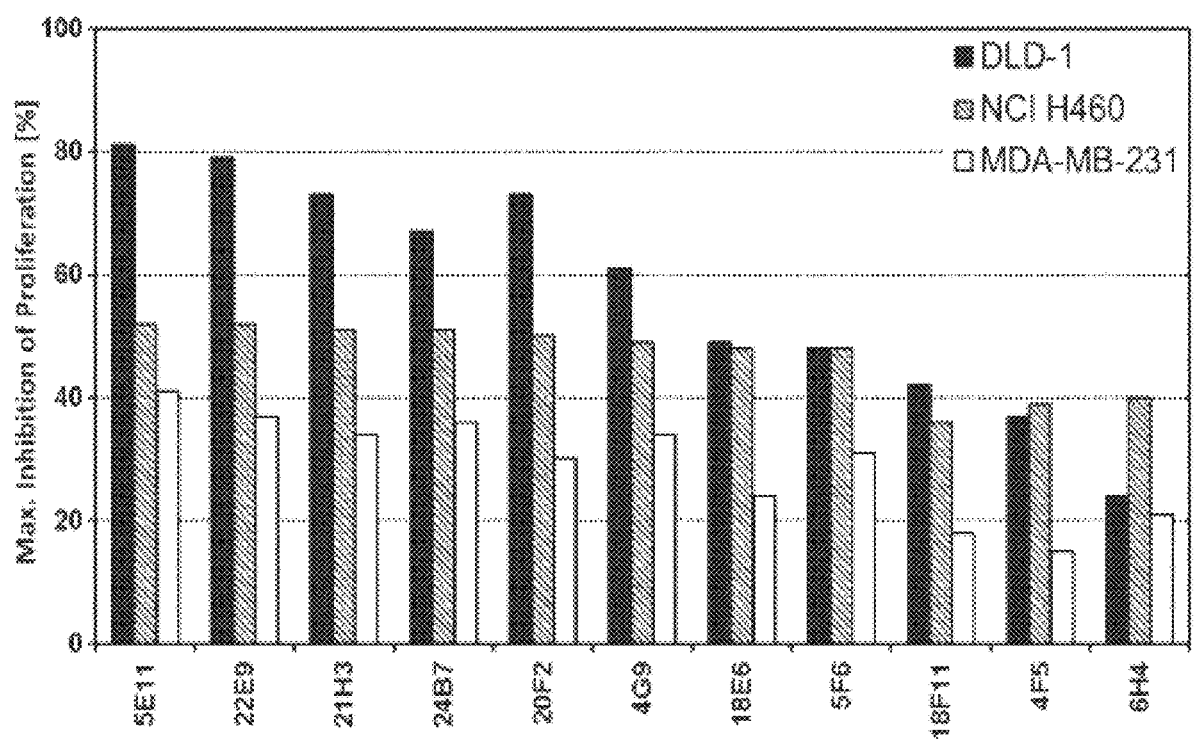
FIG. 15: Analysis of inhibition of cell proliferation (Cell TiterGlo Assay) of three different human tumor cells (DLD-1, NCI H460 and MDA-MB-231) upon treatment with different, cross-linked DR5 antibodies at a concentration of 7 nM.

Two additional assays were used to evaluate the activity of selected DR5 binders: Inhibition of proliferation upon treatment with cross-linked antibodies was measured with a CellTiter-Glo assay (Promega #TB288). In addition, induction of Caspase 8 was determined by a Caspase8-Glo assay (Promega #G8202). FIG. 15 shows the maximal inhibition of proliferation at a concentration of 7 nM of DR5 binders cross-linked via secondary anti Fc antibody of three different tumor cell lines. The effect on the human colorectal adenocarcinoma cell line DLD-1 (black bars) was compared to the large cell lung cancer line HCI-H460 (hatched bars) and the human breast cancer cell line MDA-MB-231 (white bars). For all three cell lines significant inhibition of proliferation could be detected. While the inhibition of proliferation of DLD-1 at 7 nM seems to correlate with the affinity of the DR5 antibody this is not the case for NCI-H460 and only to a certain degree for MDA-MB-231.

TABLE 9

Calculated IC50 values for inhibition of proliferation using the CellTiter-Glo assay

| Antibody | SEQ ID NO. VH/VL | DLD-1 | NCI-H460 | MDA-MB-231 |
|---|---|---|---|---|
| 5E11 | 7/8 | 0.50 | 3.91 | >7.00 |
| 22E9 | 100/101 | 0.56 | 4.00 | >7.00 |
| 21H3 | 102/103 | 1.57 | 6.20 | >7.00 |
| 24B7 |  | 1.86 | 5.00 | >7.00 |
| 20F2 | 106/107 | 2.01 | 6.53 | >7.00 |
| 4G9 |  | 4.30 | >7.00 | >7.00 |
| 18E6 |  | 4.62 | 6.89 | >7.00 |
| 5F6 |  | 6.39 | >7.00 | >7.00 |
| 18F11 | 94/95 | >7.00 | >7.00 | >7.00 |
| 4F5 |  | >7.00 | >7.00 | >7.00 |
| 6H4 |  | >7.00 | >7.00 | >7.00 |

Figure 16:
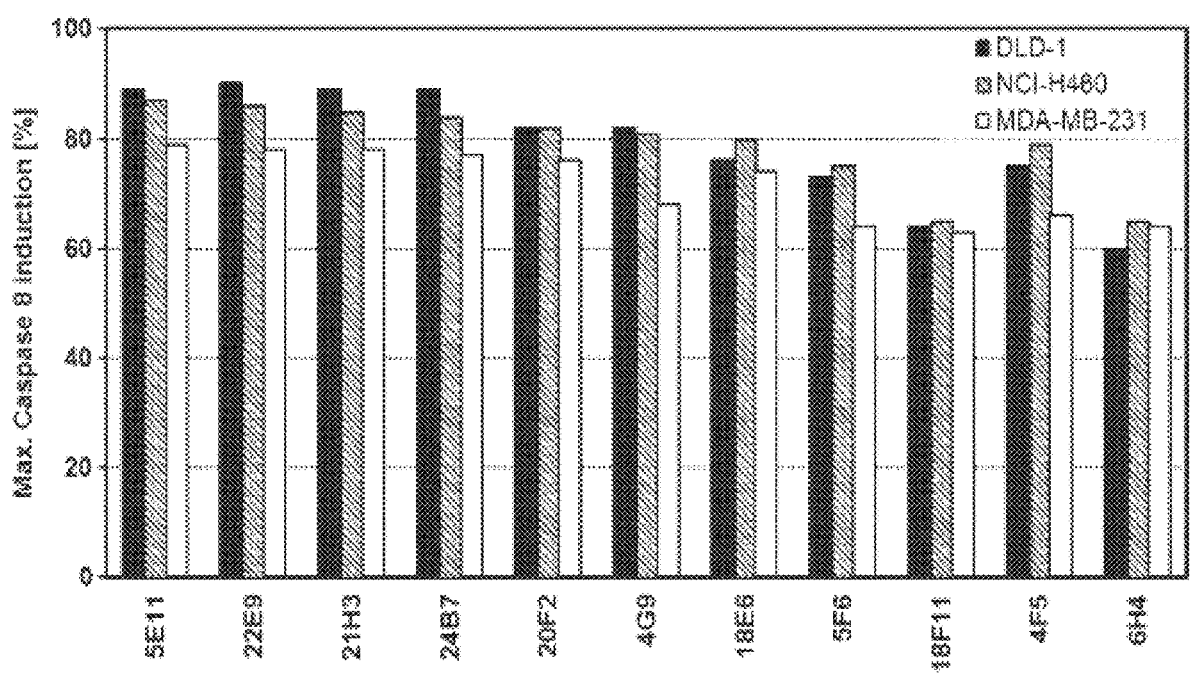
FIG. 16: Evaluation of apoptosis induction measured by Caspase 8 activation in three human tumor cell lines (DLD-1, NCI H460 and MDA-MB-231) after treatment with cross-linked DR5 antibodies at a concentration of 7 nM.

FIG. 16 summarizes the results of Caspase 8 activation upon treatment with anti Fc cross-linked DR5 antibodies. The maximal Caspase 8 activation in three different tumor cell lines (DLD-1, black bars; NCI-H460, hatched bars; and MDA-MB-231, white bars) is shown at a concentration of 7 nM. For all antibodies high level of Caspase 8 activation could be detected in all three cell lines. Induction of Caspase 8 was in the same range for the different cell lines but the correlation of Caspase 8 induction level with the affinity of the antibodies was not as pronounced as seen in the CellTiter-Glo Assay for inhibition of proliferation.

TABLE 10

Calculated EC50 values for induction of Caspase 8 using the Caspase 8-Glo assay

| Antibody | SEQ ID NO. VH/VL | DLD-1 | NCI-H460 | MDA-MB-231 |
|---|---|---|---|---|
| 5E11 | 7/8 | 0.13 | 0.03 | 0.14 |
| 22E9 | 100/101 | 0.15 | 0.05 | 0.24 |
| 21H3 | 102/103 | 0.20 | 0.09 | 0.31 |
| 24B7 |  | 0.21 | 0.09 | 0.26 |
| 20F2 | 106/107 | 0.31 | 0.13 | 0.33 |
| 4G9 |  | 0.48 | 0.38 | 1.04 |
| 18E6 |  | 0.33 | 0.13 | 0.35 |
| 5F6 |  | 0.76 | 0.28 | 1.00 |
| 18F11 | 94/95 | 0.36 | 0.37 | 0.43 |
| 4F5 |  | 0.49 | 0.16 | 0.89 |
| 6H4 |  | 1.84 | 0.70 | 0.99 |

Example 8: Epitope Analysis

To characterize the kind and relative localization of the epitopes recognized by the newly isolated DR5 binders in more detail, Western/Dot Blot analysis and Biacore measurements have been performed with purified IgGs. Comparison of Western Blot vs. Dot Blot results would show if the antibodies recognize a linear or a conformational epitope while Biacore competition experiments would hint to different, identical or partially overlapping epitopes.

To differentiate between linear or conformational epitopes human DR5 was separated by SDS-PAGE, blotted onto a Nitrocellulose membrane, incubated with the different DR5 binders and detected with a secondary anti-huFc-HRP antibody (Sigma A0170). In parallel human DR5 was spotted onto a membrane, DR5 antibody was added and detected with the same secondary antibody. Binding of the antigen only in the Dot Blot experiment would hint to a conformational epitope since in this setting the antigen is analyzed in its natural three dimensional conformation whereas in the Western Blot experiment the antigen has been denatured and only linear epitopes should be accessible.

TABLE 11

Summary of results from Western/Dot Blot analysis

| Anti DR5 mAb | SEQ ID NO. VH/VL | Signal in Western Blot | Signal in Dot Blot |
|---|---|---|---|
| 4G9 | | + | +++ |
| 6H4 | | + | ++ |
| 5F6 | | +++ | +++ |
| 18F11 | 94/95 | ++ | +++ |
| 18H6 | | ++ | +++ |
| 20F2 | 106/107 | + | +++ |
| 18E6 | | + | +++ |
| 22E9 | 100/101 | − | ++ |
| 21H3 | 102/103 | − | +++ |
| 4F5 | | − | ++ |
| 5E11 | 7/8 | − | +++ |
| 24B7 | | +++ | +++ |

Based on these results it could be concluded that the majority of the analyzed antibodies recognize a conformational epitope on hu DR5 while only two antibodies (5F6, 24B7) clearly bind to the denatured antigen in Western Blot analysis indicating binding to a linear epitope. Strong binding in Dot Blot and weak binding in Western Blot also hint to a conformational epitope but this probably contains linear stretches that are recognized (18F11, 18H6).

Binding competition assays by Surface Plasmon Resonance (SPR, Biacore) were performed in two different settings. In the classical sandwich assay a first DR5 binder is immobilized on a chip followed by addition and binding of hu DR5. Then the second DR5 antibody is injected and analyzed for additional binding to DR5. In the tandem assay hu DR5 is immobilized on a chip followed by addition of a first DR5 binder. Then the second DR5 binder is injected and additional binding is analyzed. FIG. 17 summarizes the results of these binding competition assays assays (comparison of four new DR5 antibodies with Drozitumab). From these competition assays it could be concluded that the clones 5E11, 22E9 and 174 (VH SEQ ID NO.:88, VL SEQ ID NO.:89, see e.g. Example 26) probably share a common epitope since once one of these has been bound to DR5 none of the two others could bind to the antigen. These three antibodies clearly recognize a different epitope as Drozitumab. The binding site of clone 422 (VH SEQ ID NO:82, VL SEQ ID NO.:85 see e.g. Example 26) might overlap with the epitope of 5E11, 22E9 and Drozitumab but definitely not with the one from clone 174. A clear answer to the question of the recognized epitope might come from co-crystallization experiments (DR5+mAb) followed by structure analysis.

Figure 18A:
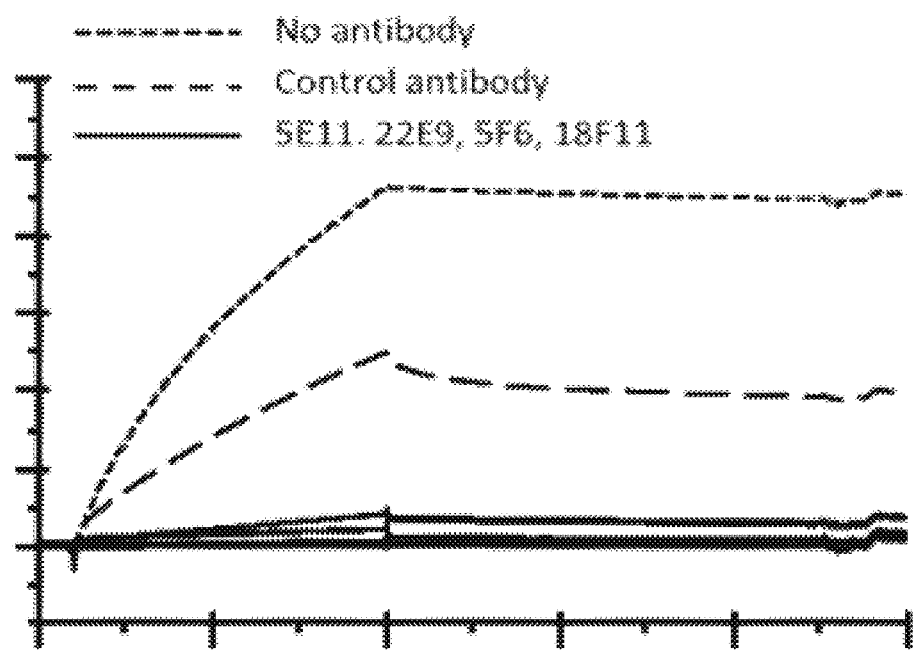
FIGS. 18A and 18B: TRAIL competition assay to determine ligand blocking vs. ligand non-blocking antibodies. Human TRAIL was immobilized on a CM5 chip. Then a complex consisting of human DR5-Fc and DR5 antibody was used as the analyte and binding of the complex to immobilized TRAIL was analyzed. While most of the new binders from phage display were TRAIL blocking molecules, a number of DR5 antibodies from rabbit immunization were of the non-blocking kind.
Figure 18B:
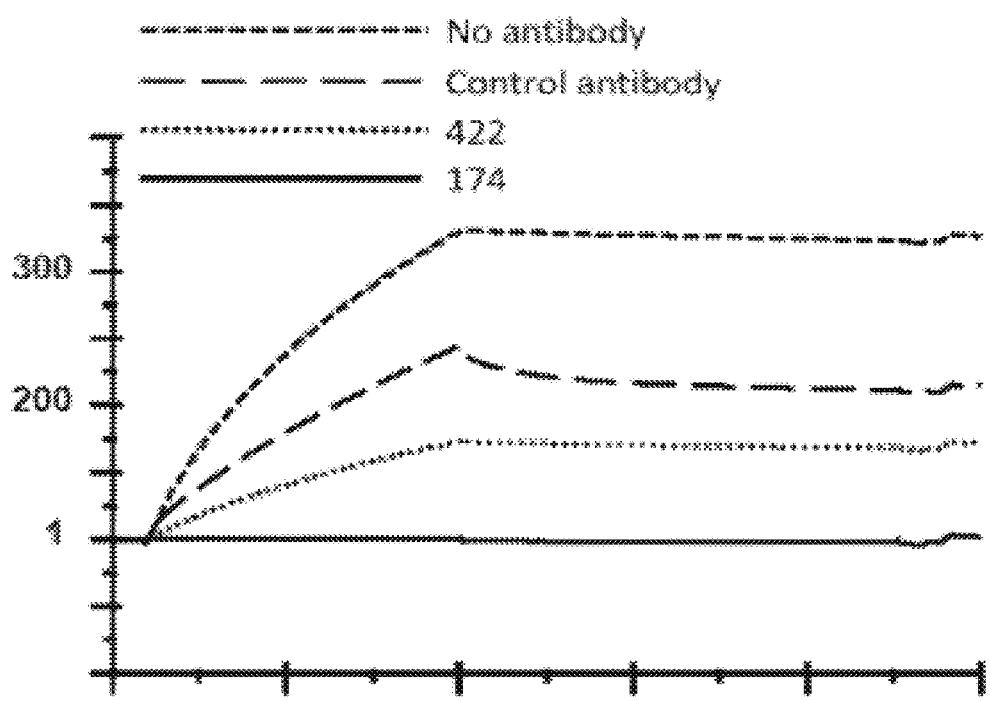

To evaluate if the DR5 antibodies recognize an epitope that is similar or overlaps with the DR5 ligand binding site a TRAIL competition assay in Biacore was set up. For that purpose recombinant hu TRAIL (Preprotech No 310-04) was immobilized on a CM5 chip. A preformed complex consisting of human DR5-Fc and the DR5 binder was used as analyte and binding to the immobilized TRAIL was determined. In FIGS. 18A and 18B the results of the TRAIL competition experiment are shown. With the exception of clone 422 (dotted line in FIG. 18B) all newly isolated DR5 binders seem to bind to an epitope that at least overlaps with the TRAIL binding site on DR5 since none of the tested complexes is able to bind to immobilized hu TRAIL (all solid lines). In contrast to that, DR5 alone (dashed line) or a complex of DR5 with a control antibody (short dashes) showed clear binding to the immobilized ligand.

Example 9: Non-Ligand Competing DR5 Antibodies Demonstrate Increased In Vitro Apoptosis Activity in the Presence of TRAIL Compared to Ligand Competing Binders During isolation and screening of new DR5 binders, antibodies were isolated which recognize different epitopes on human DR5. One possible criterion to classify the antibodies is to group them in ligand blocking and ligand non-blocking molecules. Among the selected binders one representative for each of these groups was chosen: clone 5E11 was identified to block TRAIL binding to DR5, while clone 422 is a ligand non-blocking antibody (FIGS. 18A and 18B).

Figure 19:
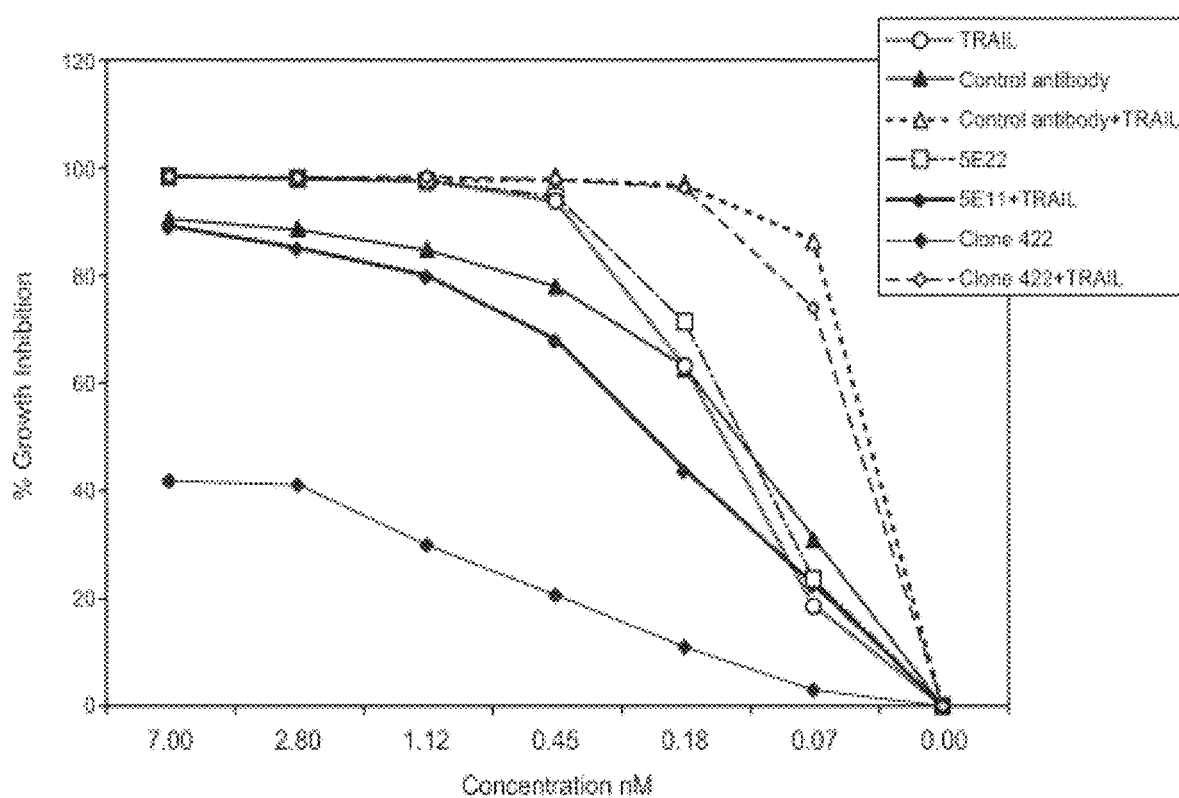
FIG. 19: Effect of human TRAIL on inhibition of proliferation of DLD-1 target cells upon treatment with different DR5 agonistic antibodies. DLD-1 target cells were incubated with cross-linked DR5 antibodies in the absence (solid lines) or presence (stippled lines) of different concentrations of human TRAIL. Depending on the epitope recognized by the DR5 antibodies addition of TRAIL did (non-ligand blocking) or did not (ligand blocking) increase inhibition of cell growth. TRAIL alone and an antibody known to not block TRAIL were included as controls.

To evaluate the impact of binding to an epitope that at least overlaps with TRAIL binding, these two candidates were analyzed for inhibition of proliferation of DLD-1 CRC target cells after cross-linking with secondary anti Fc antibodies in the presence or absence of human TRAIL. 4000 DLD-1 target cells per well were incubated over night at 37° C. before cross-linked antibodies were added: the antibodies 5E11, 422 and a control antibody that does not block TRAIL were used in six different concentrations (starting from 6.67 nM in 2.5 fold dilution steps down to 0.068 nM). Cross-linking was achieved by addition of equimolar concentration of anti Fc secondary antibody. TRAIL was added in concentrations of 10, 4, 1.6, 0.64, 0.256 and 0.102 nM to the respective antibody concentration. After 48 hrs incubation Cell TiterGlo reagent was added. The results of this growth inhibition assay are shown in FIG. 19. It was demonstrated that clone 422, the non-ligand blocking antibody exhibited significantly increased anti proliverative activity upon addition of human TRAIL compared to clone 5E11 which binds to a TRAIL binding site overlapping epitope. Addition of cross-linked 5E11 antibody had no additive effect on growth inhibition by TRAIL alone. In contrast, using cross-linked clone 422 in combination with human TRAIL showed a significant additive effect on activity.

Similar results were observed with a relevant control antibody known to not block TRAIL binding on DR5. If this effect observed in an in vitro assay can be translated into in vivo settings remains to be evaluated.

Example 10: Conversion in Bispecific 2+2 Format

In order to evaluate whether the novel DR5 binders can be used for the generation of bispecific antibodies for the targeted induction of apoptosis of tumor cells by hyper-cross-linking of DR5, a set of DR5 antibodies were converted into tetravalent bispecific molecules. These bispecific antibodies contain two binding moieties, each for DR5 and FAP (fibroblast activation protein). Different, selected DR5 antibodies were combined with the FAP antibody 28H1, a high affinity, human/murine/cynomolgous monkey (hu/mu/cy) cross-reactive FAP binder isolated and affinity matured by phage display. In the used 2+2 format the 28H1 CrossFab domain (VHCL) was fused to the C-terminus of the anti DR5 heavy chain using a $(G_4S)_4$ connector. Schematic structures of the 2+2 format are shown in FIG. 28). Below are exemplary chains of the bispecific antibodies in the 2+2 format.

TABLE 12a

Bispecific, tetravalent DR5-FAP CrossMab molecules (all with 28H1 CrossFab domain (VHCL) fused to the C-terminus of the anti DR5 heavy chain using a $(G_4S)_4$ connector, FAP binder: VH SEQ ID NO.: 15, VL SEQ ID NO.: 16)

| DR5 Binder | SEQ ID NO VH/VL (DR5) | Name | Description |
|---|---|---|---|
| 22E9 | 100/101 | DR5 (22E9)-28H1 VHCL 2 + 2 | 28H1 CrossFab domain (VHCL) fused to the C-terminus of the anti DR5 (22E9) heavy chain using a $(G_4S)_4$ connector: VH $_{(DR5)}$-Fc part-VH $_{(FAP)}$-CL chain (SEQ ID NO.: 125) VL (DR5)-kappa light chain (SEQ ID NO.: 126) VLCH1 (FAP) chain (SEQ ID NO.: 124). |
| 21H3 | 102/103 | DR5 (21H3)-28H1 VHCL 2 + 2 | 28H1 CrossFab domain (VHCL) fused to the C-terminus of the anti DR5 (21H3) heavy chain using a $(G_4S)_4$ connector: VH $_{(DR5)}$-Fc part-VH $_{(FAP)}$-CL chain (SEQ ID NO.: 125) VL (DR5)-kappa light chain (SEQ ID NO.: 128) VLCH1 (FAP) chain (SEQ ID NO.: 124). |
| 20F2 | 106/107 | DR5 (20F2)-28H1 VHCL 2 + 2 | 28H1 CrossFab domain (VHCL) fused to the C-terminus of the anti DR5 (20F2) heavy chain using a $(G_4S)_4$ connector: VH $_{(DR5)}$-Fc part-VH $_{(FAP)}$-CL chain (SEQ ID NO.: 129) VL (DR5)-kappa light chain (SEQ ID NO.: 130) VLCH1 (FAP) chain (SEQ ID NO.: 124). |
| 5E11 | 7/8 | DR5(5E11)-28H1 VHCL 2 + 2 | 28H1 CrossFab domain (VHCL) fused to the C-terminus of the anti DR5 (5E11) heavy chain using a $(G_4S)_4$ connector: VH $_{(DR5)}$-Fc part-VH $_{(FAP)}$-CL chain (SEQ ID NO.: 131) VL (DR5)-kappa light chain (SEQ ID NO.: 132) VLCH1 (FAP) chain (SEQ ID NO.: 124). |
| 5E11 | 7/8 | DR5(5E11)-28H1 VHCL 2 + 2 P329GLALA | As above, and removal of C-term. Lysine and P329G/LALA mutation in Fc VH $_{(DR5)}$-Fc part-VH $_{(FAP)}$-CL chain (SEQ ID NO.: 134) VL (DR5)-kappa light chain (SEQ ID NO.: 132) VLCH1 (FAP) chain (SEQ ID NO.: 124). |
| 18F11 | 94/95 | DR5(18F11)-28H1 VHCL 2 + 2 | 28H1 CrossFab domain (VHCL) fused to the C-terminus of the anti DR5 (18F11) heavy chain using a $(G_4S)_4$ connector: VH $_{(DR5)}$-Fc part-VH $_{(FAP)}$-CL chain (SEQ ID NO.: 140) VL (DR5)-kappa light chain (SEQ ID NO.: 141) VLCH1 (FAP) chain (SEQ ID NO.: 124). |

TABLE 12b

Production data of bispecific, tetravalent DR5-AP CrossMab molecules

| DR5 binder | Production yield [mg/L] | Final monomer [%] | Apoptosis induction |
|---|---|---|---|
| 5E11 | 20.3 | 96.7 | +++ |
| 22E9 | 18.1 | 99.0 | +++ |
| 21H3 | 7.6 | 96.3 | +++ |
| 20F2 | 19.3 | 100.0 | +++ |
| 18E6 | 25.1 | 100.0 | ++ |
| 5F6 | 18.9 | 99.4 | + |
| 18F11 | 22.3 | 96.7 | + |
| 6H4 | 18.5 | 100.0 | ++ |
| 18H6 | 17.5 | 99.6 | — |

All DR5-FAP bispecific molecules were produced in transiently transfected HEK293 EBNA cells and were purified via Protein A and size exclusion chromatography. The obtained product yields were in a reasonable range (around 20 mg/L). The monomer content after the final purification step was above 96% for all molecules.

Target binding analysis by surface plasmon resonance (Biacore) revealed that all selected bispecific antibodies in the 2+2 format were able to simultaneously bind to recombinant DR5 and FAP (human and murine) as depicted in FIG. 42.

Figure 20A:
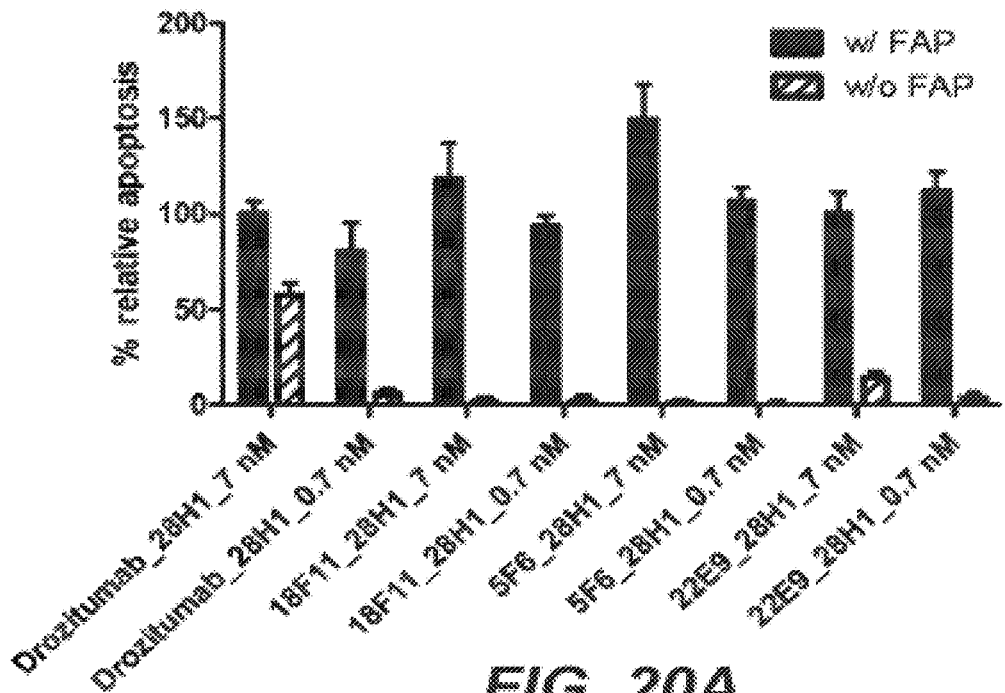
FIGS. 20A and 20B: DNA fragmentation ELISA assay for detection of apoptosis. Apoptosis induction activity of different DR5-FAP bispecific antibodies (FAP clone 28H1) on MDA-MB-231 as the target cell line in the presence or absence of recombinant human FAP coated on a 96 well plate. In this setting the coated FAP should mimic FAP expressed in the tumor stroma. Bispecific antibodies were tested at two concentrations (7.0 and 0.7 nM). For the bispecific molecules containing the novel DR5 binders a concentration dependent induction of apoptosis only was detected in the presence of FAP whereas the control molecule containing Drozitumab also showed some activity in the absence of FAP, confirming that the activity of the new DR5 antibodies is strictly dependent on cross-linking.
Figure 20B:
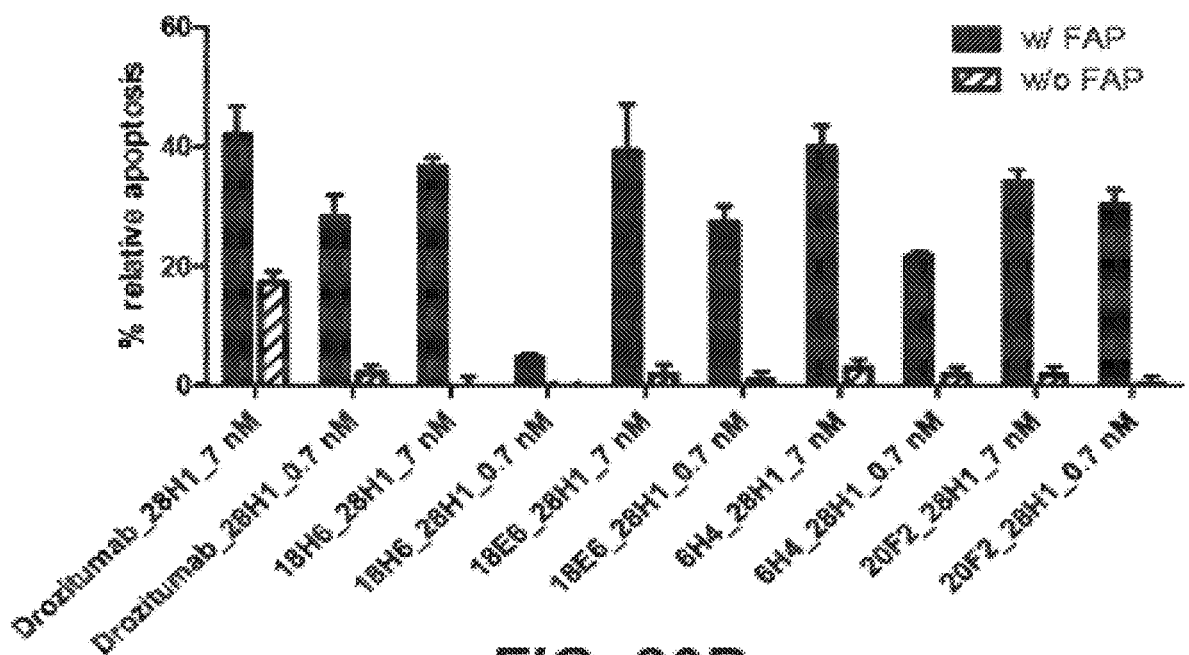

To evaluate if the DR5-FAP bispecific molecules are able to induce apoptosis of the MDA-MB-231 target cell line, 96 well plates were coated with recombinant human FAP for cross-linking of DR5 on the target cells via the subsequently added bispecific antibodies. After addition of the target cells (MDA-MB 231) and incubation for 24 hrs apoptosis induction was determined by the standard DNA fragmentation ELISA assay. FIGS. 20A and 20B shows the comparison of apoptosis induction of seven bispecific antibodies containing newly isolated DR5 binders and the C-terminally fused 28H1 FAP CrossFab compared to Drozitumab at two different concentrations (7.0 nM and 0.7 nM). All molecules were tested in the presence and absence of FAP. As expected, at high concentration the Drozitumab based bispecific molecule induced apoptosis already in the absence of cross-linking FAP to a significant degree. In contrast, the DR5-FAP bispecific molecules using the new DR5 binders only exhibited apoptosis induction activity in the presence of FAP coated on the plates indicating that this activity is dependent on the cross-linking via recombinant FAP.

Figure 21:
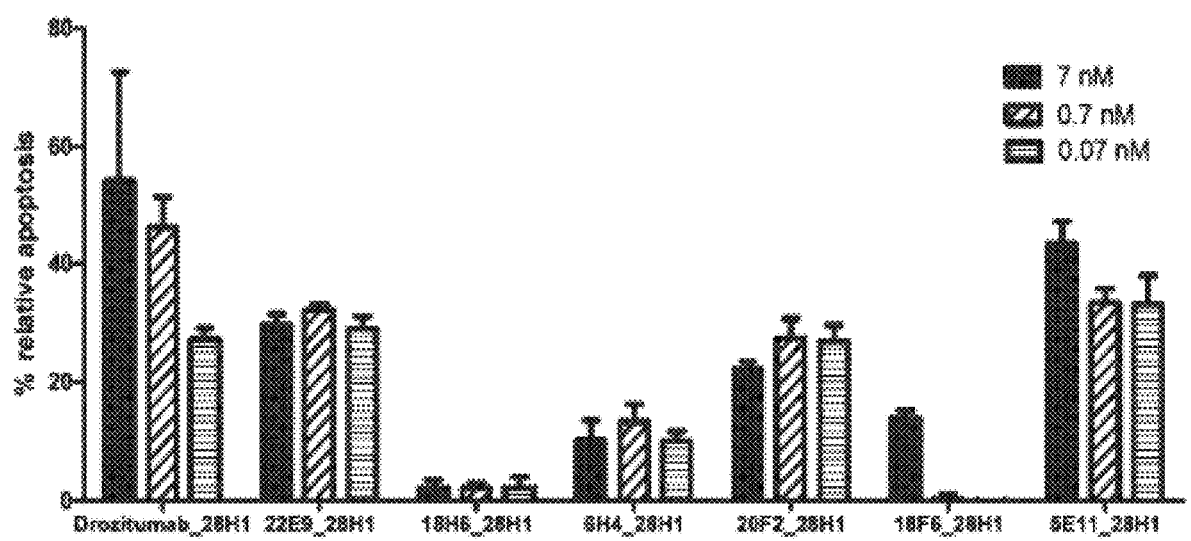
FIG. 21: Bystander apoptosis induction activity of bispecific DR5-FAP molecules (2+2 CrossFab format) in a co-culture assay using MDA-MB-231 as DR5 expressing target cells and GM05389 (FAP$^+$ fibroblasts) for cross-linking. Molecules containing different newly isolated DR5 binders were compared to Drozitumab containing constructs at three concentrations (7.0, 0.7 and 0.07 nM). Under these conditions not all tested bispecific constructs exhibited the same activity compared to cross-linking via anti Fc mAb or via recombinant FAP. This shows that not every antibody that can principally induce apoptosis after cross-linking also would do that under more natural conditions (in which the antigens-DR5 and FAP—are expressed on different cell types).

To determine if the bispecific molecules also could be efficiently cross-linked via FAP expressed on a different cell line than DR5 and thereby induce apoptosis, a so-called bystander co-culture assay was set up. FIG. 21 shows the results of apoptosis induction in a tumor cell line (MDA-MB-231) and FAP expressing fibroblast (GM05389) co-culture experiment with three different concentrations of bispecific molecules (7.0, 0.7 and 0.07 nM). The three bispecific constructs containing the DR5 binding moieties from 5E11, 22E9 and 20F2, respectively fused to the 28H1 FAP CrossFab show a comparable degree of induction of apoptosis as it also was observed with the corresponding, anti Fc cross-linked IgG molecules. In contrast to that the molecule containing 6H4 as the DR5 binding part exhibited reduced activity compared to cross-linked IgG. One of the tested molecules (18H6-28H1) was completely inactive at all concentrations (in contrast to the cross-linked IgG), indicating that not all DR5 binders are suitable for generation of bispecific molecules to hyper-cross-link DR5 on tumor cells. Therefore a careful evaluation of epitope and bispecific activity is necessary to choose the right DR5 antibody for the approach of targeted induction of apoptosis. In this regard DR5 binders which display a rather low affinity to DR5 and a high avidity in the 2+2 bispecific format are particularly advantageous. The low affinity for DR5 prevents binding of the bispecific antibodies to normal cells and hence increases the selectivity for inducing apoptosis in tumor cells in a FAP dependent manner. One binder having these characteristics is for example the DR5 binder 5E11.

Figure 22A:
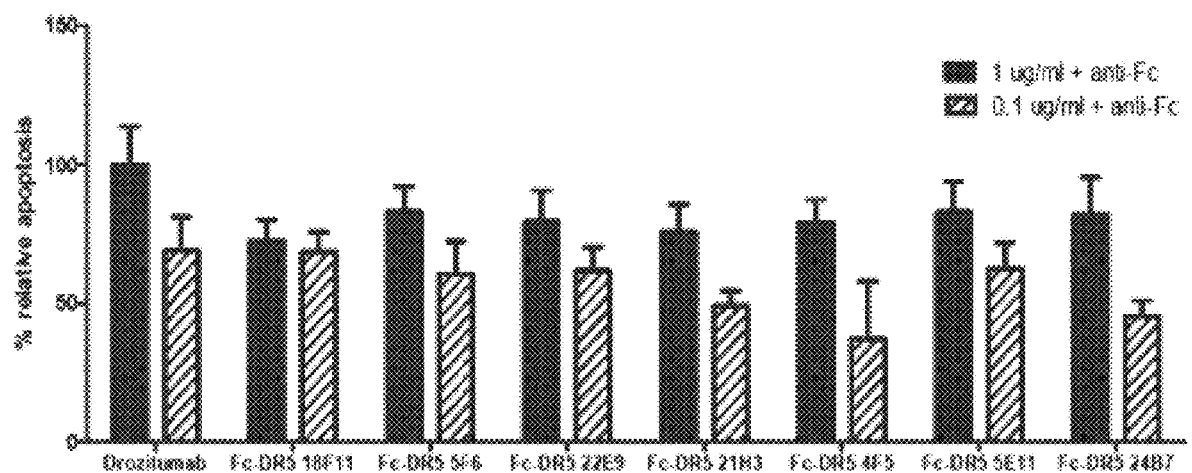
FIGS. 22A and 22B: Cell death detection ELISA (DNA fragmentation) with MDA-MB-231 target cells treated with new DR5 binding Fabs fused to the C-terminus of human Fc, compared to Drozitumab, all after cross-linking with anti Fc antibody. All tested Fc fusion molecules are able to confer apoptosis induction on target cells in the same range as cross-linked Drozitumab, indicating that their binding and activity capacity is not blocked by positioning of the Fc to their N-terminus.
Figure 22B:
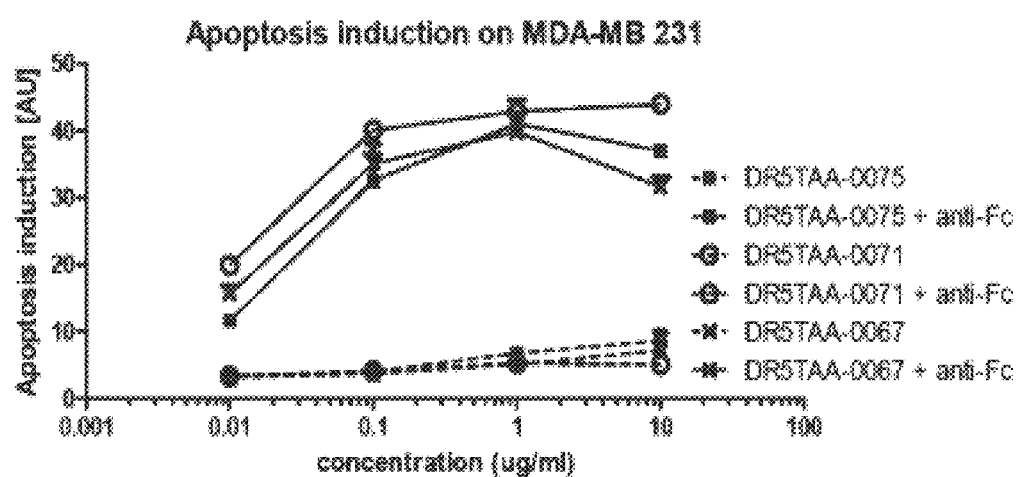

As described, one of the disadvantages of Drozitumab, which limits its use in bispecific formats, is the fact that this antibody does not allow for N-terminal fusion of a second binding moiety. This configuration leads to the blocking of Drozitumab's N-terminus which inhibits proper binding to DR5 and thereby induction of apoptosis is prevented. To test if the newly isolated DR5 antibodies can be used in this kind of format, Fc-fusion molecules were generated, in which the Fabs of selected DR5 binders were fused C-terminally to a human Fc region via a $(G_4S)_4$ connector. These molecules were transiently produced in HEK293 EBNA cells, purified via ProteinA beads and tested in an apoptosis induction assay. In FIGS. 22A and 22B the results of the DNA fragmentation assay in MDA-MB-231 cells with these Fc-DR5 fusion molecules after cross-linking with secondary anti Fc IgG are summarized. All tested molecules are able to induce apoptosis of the target cell line, indicating that the chosen DR5 binders are not N-terminally blocked which opens a wider range of formats that can be used with these binders.

Example 11: Characterization of Thermal Stability of 2+2 Bispecific Format Containing Phage Display Derived DR5 Binder Thermal stability of phage display derived DR5 binder converted into the 2+2 bispecific format was measured using an Optim1000 system (Avacta Group plc) as the change in scattered light intensity. In a micro cuvette array, 9 µL of the samples in 20 mM Histidine, 140 mM NaCl, pH 6.0 at a concentration of 1 mg/mL were heated from 25° C. to 90° C. at a rate of 0.1° C./min. Scattered light intensity (266 nm laser) was recorded every 0.4° C. and processed with the software IgorPro, Version 6.23 (Avacta Group plc). The aggregation onset temperature is defined as the temperature at which the scattering intensity starts to increase.

TABLE 13

Aggregation onset temperatures of bispecific antibodies (2 + 2 format) containing phage display derived DR5 binders as a measure for thermal stability of the bispecific constructs

| TheraPS Name Bispec Antibody | Alias Bispec Antibody | SEQ ID NOs | Optim1000 Tagg (° C.) |
|---|---|---|---|
| DR5TAA-0030 | 5E11-28H1 | 131, 132, 124 | 64 |
| DR5TAA-0037 | 22E9_28H1 | 124, 125, 126 | 63 |
| DR5TAA-0038 | 21H3_28H1 | 127, 128, 124 | 63 |
| DR5TAA-0039 | 20F2_28H1 | 129, 130, 124 | 64 |

All tested DR5 antibodies reveal a high thermal stability with aggregation temperatures well above 60° C. also when cloned into 2+2 bispecific constucts.

Figure 23A:
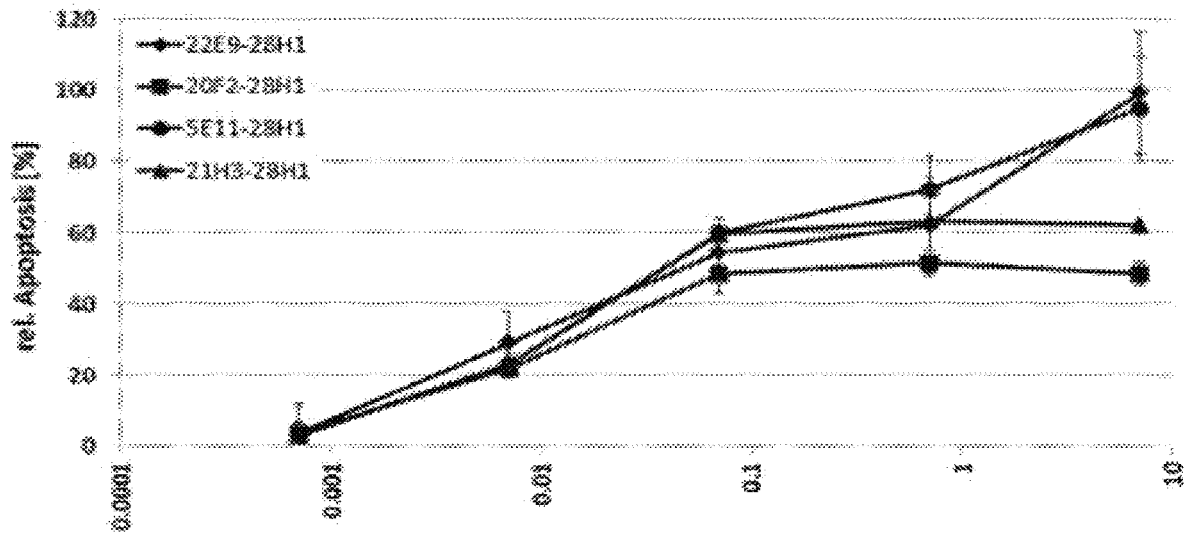
FIGS. 23A and 23B: Comparison of bispecific DR5-FAP antibodies (new DR5 binders with C-terminal 28H1 CrossFab fusion) for apoptosis induction on MDA-MB-231 as the target cell line in a co-culture assay using GM05389 fibroblasts (DNA fragmentation ELISA assay for detection of apoptosis).
Figure 23B:
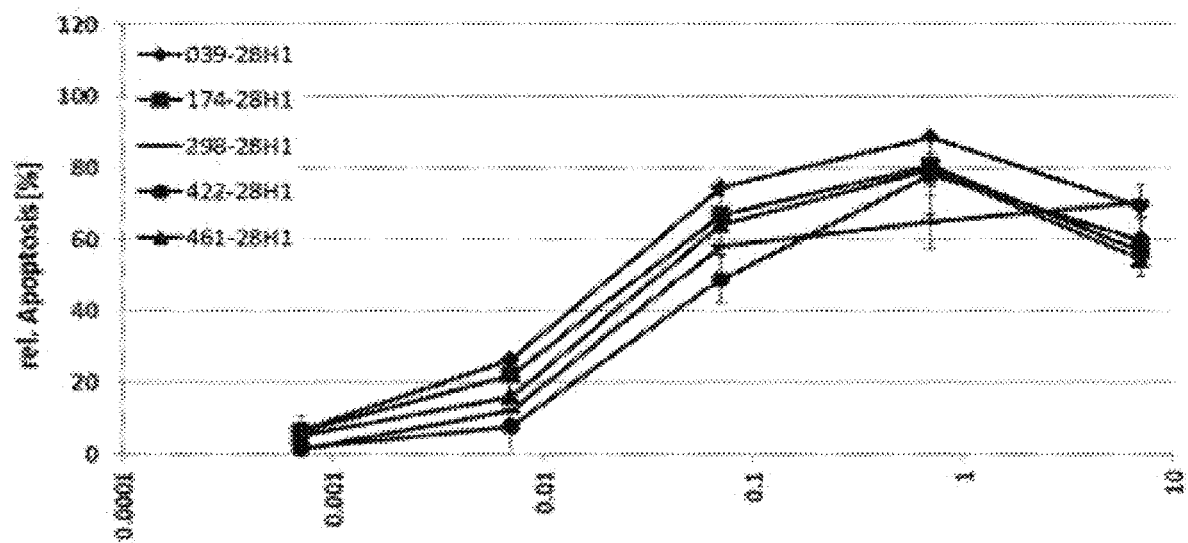
Figure 24A:
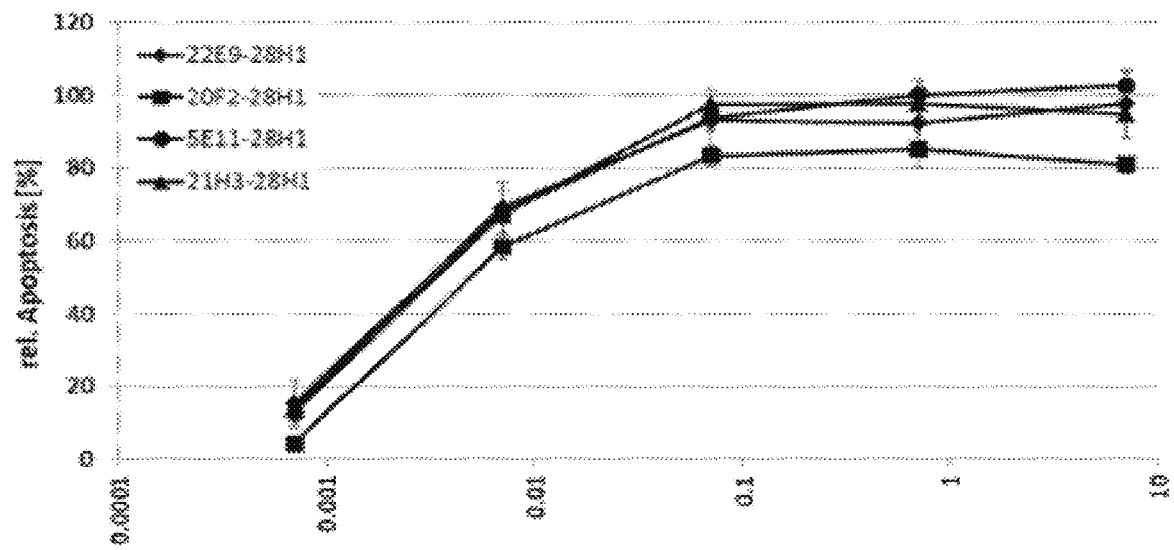
FIGS. 24A and 24B: Bispecific DR5-FAP antibodies induce apoptosis on G401 cells in a bystander assay as determined by DNA fragmentation in a Cell Death Detection ELISA.
Figure 24B:
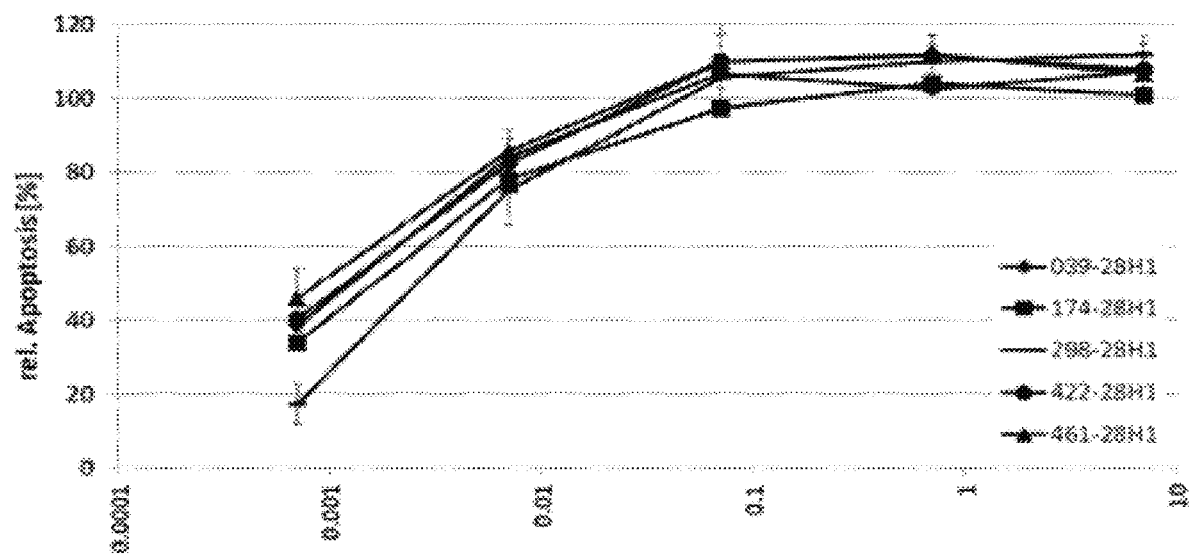

Example 12: DR5-FAP Bispecific Antibodies are Able to Induce Apoptosis on Different Target Cells Nine DR5-FAP bispecific antibodies in the 2+2 format comprising newly isolated DR5 binders (four isolated by phage display, five derived from rabbit immunization as depicted in examples 22 to 25) fused to the FAP 28H1 CrossFab moiety were compared in a side-by-side experiment for induction of apoptosis on two different cell lines (MDA-MB-231 and G401) in a co-culture assay with GM05389 human FAP fibroblasts. The bispecific antibodies were tested over a concentration range from 0.0007-7 nM. The results of the DNA fragmentation assay are summarized in FIGS. 23A and 23B (MDA-MB-231) and FIGS. 24A and 24B (G401). All bispecific antibodies tested demonstrated good apoptosis induction activity on both cell lines. According to the results obtained with the MDA-MB-231 cells the antibodies could be divided into two groups. The one obtained from rabbit immunization showed the maximum of apoptosis induction at a concentration of 0.7 nM and with further increasing antibody concentration the activity decreased slightly. In contrast, the phage display derived binders in the bispecific 2+2 format did not show the decline in activity at high concentrations but stayed constant or even more increased up to the highest concentration. In the experiment with G401 cell in co-culture with GM05389 fibroblasts for both sets of bispecific antibodies the maximum of apoptosis induction was reached already at a concentration of 0.07 nM and then stayed constant. In this setting all molecules performed similarly in terms of apoptosis induction levels.

Example 13: Comparison of Different Bispecific Formats

It has been demonstrated that DR5-FAP bispecific molecules in the 2+2 CrossFab format produce well in a very good quality and are able to mediate concentration-dependent specific induction of apoptosis in a two cell line co-culture setting. The degree of apoptosis induction of these bispecific molecules is in the same range as observed with the corresponding DR5 binders that were hyper-cross-linked via a secondary anti Fc antibody. To evaluate additional, different DR5-FAP bispecific molecules for their apoptosis induction capacity, the following constructs have been generated in which DR5 and FAP binding entities are combined in different formats and with different valences as shown in FIG. 25.

As summarized in table 15 these additional formats seem to be more difficult to be produced and purified compared to the 2+2 formats. Except one (B16_E11A_001), all show

TABLE 14

Description of alternative DR5-FAP bispecific formats

| | Description | Valency | DR5 | FAP |
|---|---|---|---|---|
| 1 | Fusion of FAP binder as CrossFab (VHCL) to the C-terminus of DR5 heavy chain (knob). B24_E11A_001<br>DR5(5E11)-28H1Fc knob VHCL 2 + 1 (SEQ ID NO. 142)<br>DR5(5E11) Fc hole (SEQ ID NO. 143)<br>FAP (28H1) VLCH1 (SEQ ID NO. 124)<br>DR5(5E11) LC (SEQ ID NO. 132)<br>Comment: Knob-into-hole; (G4S)4 connector, FIG. 25, A | 2 + 1 | 5E11 | 28H1 |
| 2 | FAP CrossFab (VHCL) on Fc-hole. DR5 Fabs (head-to-tail) fused to Fc-knob. B24_E11E_001<br>DR5(5E11) Fc knob Fab-Fab Head-to-tail 2 + 1 (SEQ ID NO. 145)<br>FAP (28H1)_Fc holeVHCL (SEQ ID NO. 146)<br>FAP (28H1) VLCH1 (SEQ ID NO. 124)<br>DR5(5E11) LC (SEQ ID NO. 132)<br>Comment: Knob-into-hole; (G4S)2 connector, FIG. 25, B | 2 + 1 | 5E11 | 28H1 |
| 3 | FAP CrossFab (VHCL) fused to the C-terminus of DR5 Fc-hole. DR5 Fab fused to C-terminus of DR5 Fc-knob. B24_E11A_002<br>DR5(5E11)-28H1 Fc knobVHCL 3 + 1 (SEQ ID NO. 143)<br>DR5(5E11)-DR5(5E11) Fc hole 3 + 1 (SEQ ID NO. 144)<br>FAP (28H1) VLCH1 (SEQ ID NO. 124)<br>DR5(5E11) LC (SEQ ID NO. 132)<br>Comment: Knob-into-hole; (G4S)4 connector, FIG. 25, C | 3 + 1 | 5E11 | 28H1 |
| 4 | Fusion of FAP binder as CrossFab (VHCL) to the C-terminus of DR5 heavy chain (knob). B16_E11A_001<br>DR5(18F11)-28H1Fc knobVHCL 2 + 1 (SEQ ID NO. 147)<br>DR5(18F11) Fc hole (SEQ ID NO. 148)<br>FAP (28H1) VLCH1 (SEQ ID NO. 124)<br>DR5(18F11) LC (SEQ ID NO. 141)<br>Comment: Knob-into-hole; (G4S)4 connector, FIG. 25, A | 2 + 1 | 18F11 | 28H1 |
| 5 | FAP CrossFab (VHCL) fused to the C-terminus of DR5 Fc-hole. DR5 fused to C-terminus of DR5 Fc-knob. B16_E11A_002<br>DR5(18F11)-28H1VHCLFc knob 3 + 1 (SEQ ID NO. 149)<br>DR5(18F11)-DR5(18F11) Fc hole (SEQ ID NO. 150)<br>FAP (28H1) VLCH1 (SEQ ID NO. 124)<br>DR5(18F11) LC (SEQ ID NO. 141)<br>Comment: Knob-into-hole; (G4S)4 connector, FIG. 25, C | 3 + 1 | 18F11 | 28H1 |

All molecules were transiently produced in HEK293 EBNA cells and were purified according to standard Protein A and size exclusion chromatography protocols. Side product profile and quality of the molecules were analyzed by SDS-PAGE, SEC and Caliper analysis.

lower expression yields as the analogous 2+2 molecules. However, the aggregate contents were rather low (<2%) but in most cases also lower molecular weight species could be detected which might be due to purification or degradation of the molecules.

TABLE 15

Summary of production results of additional bispecific DR5-FAP molecules

| | Construct | Description | Yield [mg/ml] | Aggregates [%] | Monomer [%] | Low molecular weight species [%] |
|---|---|---|---|---|---|---|
| 1 | B24_E11E_001 | 5E11_28H1;<br>2 + 1 C-terminal on Fc-knob | 5.42 | 1.55 | 95.2 | 3.25 |
| 2 | B24_E11A_001 | 5E11_28H1;<br>head-to-tail on Fc-knob | 5.99 | 0.74 | 98.08 | 0.74 |
| 3 | B24_E11A_002 | 5E11_28H1;<br>3 + 1 C-terminal on Fc-knob | 5.39 | 1.80 | 98.20 | 0.00 |
| 4 | B16_E11A_001 | 5E11_28H1;<br>2 + 1 C-terminal on Fc-knob | 18.34 | 1.50 | 98.50 | 0.00 |
| 5 | B16_E11A_002 | 5E11_28H1;<br>3 + 1 C-terminal on Fc-knob | 3.32 | 0.90 | 99.10 | 0.00 |

Figure 26A:
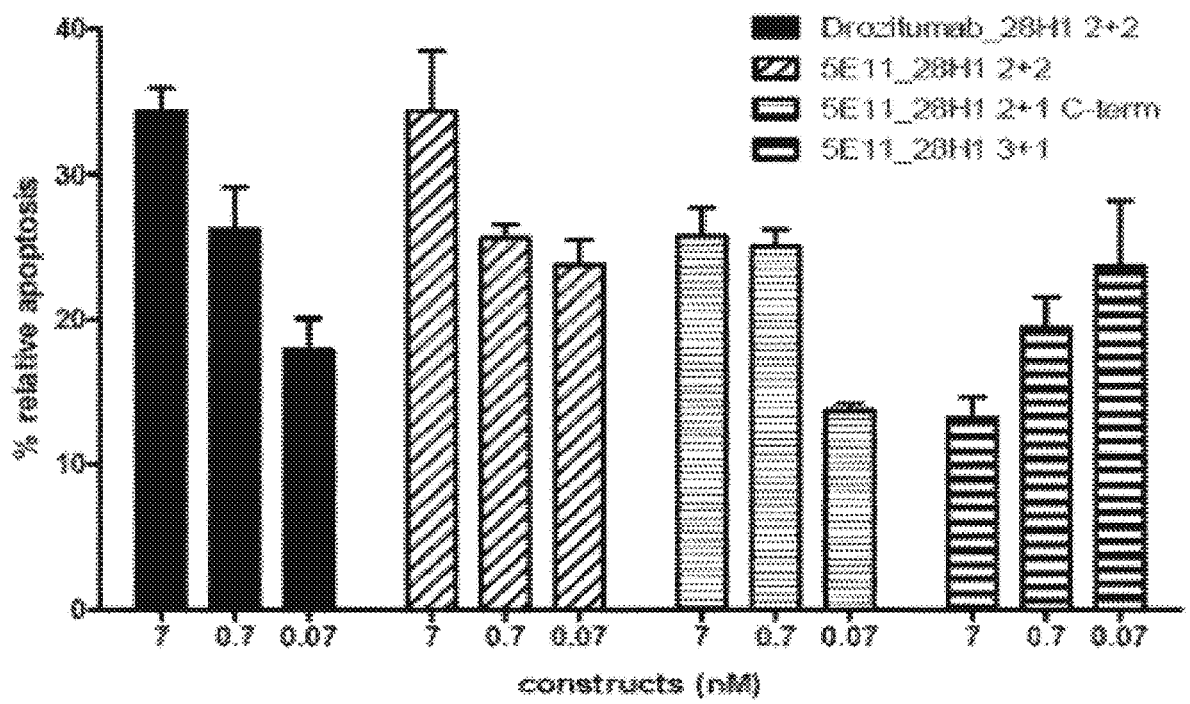
FIGS. 26A and 26B: Apoptosis activity of bispecific DR5-FAP molecules (FIG. 26A: 5E11-28H1.
Figure 26B:
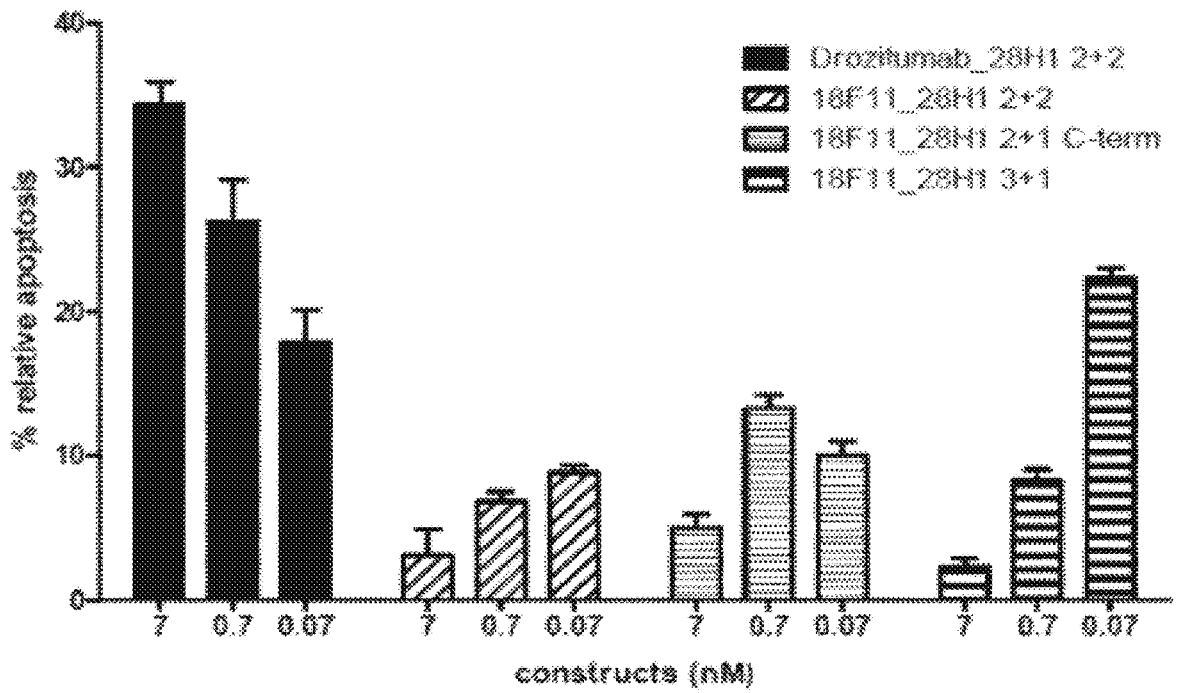

Apoptosis induction activity on MDA-MB-231 was tested in the fibroblast co-culture assay (DNA fragmentation) at different concentrations (7.0; 0.7 and 0.07 nM). FIGS. 26A and 26B show the results of apoptosis activity of three different formats (2+2; 2+1 and 3+1) compared to bispecific Drozitumab in the 2+2 format. In this setting the 5E11-28H1 bispecific molecule in the 2+2 format overall showed similar activity compared to the Drozitumab control. At the lowest concentration, the 5E11-28H1 bispecific molecule in the 2+2 format had displayed even higher activity compared to the Drozitumab control. In contrast, the 2+1 and the 3+1 formats seemed to be less active compared to both 2+2 formats (Drozitumab and 5E11). If the same formats are analyzed with a different DR5 binder (18F11) all three molecules show reduced apoptosis induction activity as compared to the Drozitumab bispecific antibody. However, with the 18F11 bispecific molecule the maximal apoptosis induction occurred at lower concentrations (0.07 nM) whereas the Drozitumab based molecule exhibits higher activity with increasing concentration.

Figure 27:
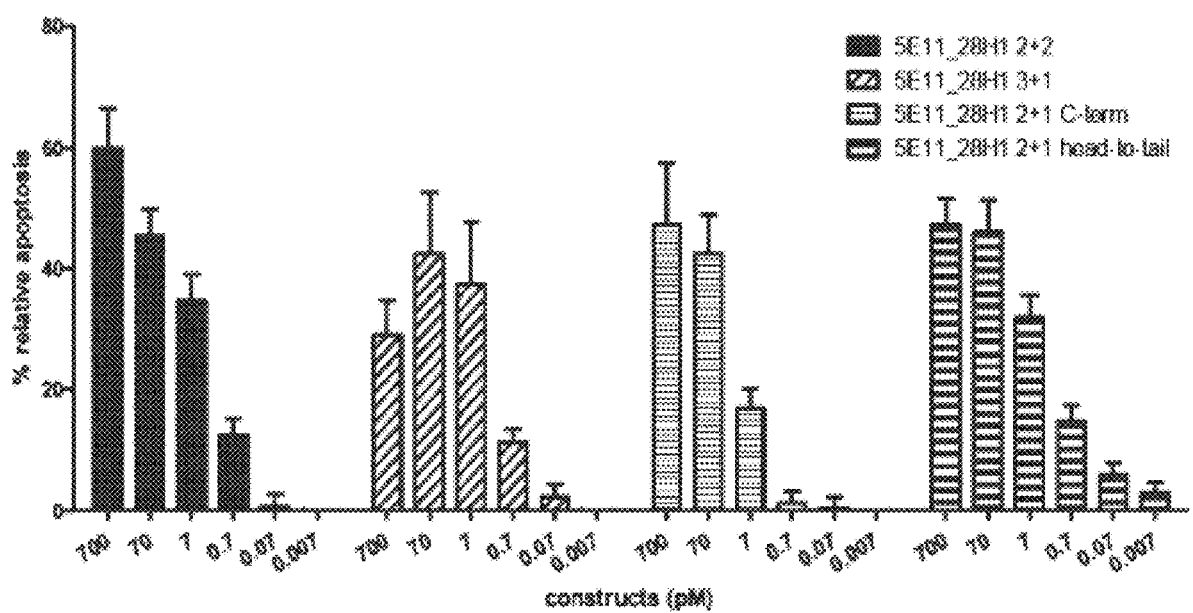
FIG. 27: Bystander apoptosis induction of the 5E11-28H1 molecule (2+2 format) compared to three additional bispecific formats: 2+1, novel 2+1 (head-to-tail fusion) and 3+1. MDA-MB-231 were used as target cells, GM05389 fibroblasts were co-cultured for FAP dependent cross-linking and the bispecific antibodies were evaluated at concentrations from 700-0.007 nM.

In a second set of molecules an additional 2+1 format was evaluated for the 5E11-28H1 bispecific antibody in which two DR5 binding moieties are fused head-to-tail to an Fc-knob part while the FAP targeting Fab is combined with an Fc-hole counterpart. All four formats were compared over a broad range of concentrations (ranging from 7.0 to 0.0007 nM) in a DNA fragmentation assay for apoptosis induction of MDA-MB-231 in co-culture with GM05389 fibroblasts (FIG. 27). Both 2+1 molecules had the highest apoptosis activity at a concentration of 0.7 nM while the 3+1 molecule showed maximal induction of apoptosis already at a 10 fold lower concentration. However, none of the new formats seemed to be superior over the conventional 2+2 format.

Example 14: Test of Functional Activity of a 1+1 Bispecific Format in a Co-Culture Assay System Besides the different format and valency variants described in example 12, another construct has been generated in a 1+1 format (as depicted in FIG. 25 D) with the DR5 binder 0011 (=clone 174) in the uncrossed Fab and the FAP binder 4B9 in the crossed Fab (SEQ ID NOs. 280-282). Functional activity of the 1+1 format was compared to a 2+2 format (as depicted in FIG. 28 A, containing 0011 as DR5 binder and 28H1 as FAP binder; SEQ ID NOs 287-289) and to the chimeric IgG of 0011 (SEQ ID NOs 90-93) with or without secondary crosslinking.

Apoptosis induction was measured by Cell Death Detection ELISA (CDDE, Roche #11 774 425 001) upon treatment of cells with anti-DR5 and anti-DR5-FAP bispecific antibodies in the presence or absence of a cross-linking secondary antibody in a co-culture system consisting of tumor cells (MDA-MB-231) and fibroblasts (GM05389).
Day 1: Preparation of cells. The adherent MDA-MB-231 cell line (human breast adenocarcinoma) was grown in DMEM medium (PAN) supplemented with 10% fetal calf serum (Gibco) and 2 mM L-glutamine (PAA), and normally split twice per week 1:20. The GM05389 fibroblasts were grown in MEM+Earle's medium (Gibco) supplemented with 15% fetal calf serum (Gibco), 1×NEAS (PAN) and 2 mM L-glutamine (PAA), and normally split twice per week 1:3.
For co-culture assays fibroblast were seeded on day 1 at a density of $1 \times 10^4$ cells/1000/well in 96-well plates and incubated overnight at 37° C., 5% CO2. Tumor cells and antibodies were added on day 2.
For monoculture assays cell lines were seeded on different plates at the same density, incubated overnight and treated with antibodies the next day.
Day 2: Induction of apoptosis. Medium was aspirated and antibodies (anti-DR5 IgGs or anti-DR5-FAP bispecific antibodies) were added to the cells at different final concentrations (see FIGS.) alone or together with the cross-linking antibody (goat anti-human IgG, Sigma #I2136) in a 1:1 ratio in 1000 medium.
For co-culture assays tumor cells were immediately added ($1 \times 10^4$ cells/100 µl/well) on the fibroblasts after the antibodies to reach a final volume of 100 µl.
Cultures were incubated at 37° C. for 24 hs.
Day 3: Cell Death Detection Elisa (CDDE). The immunoassay was performed according to the manufacturer's instructions (Roche) with slight changes. Briefly, cells were lysed with 100 µl/well 2×-lyse buffer for 15 minutes at RT. A master mix consisting of anti-histone and anti-DNA antibodies was prepared according to the manufacturer's instructions and mixed with 1:4 diluted lysates on 96-well streptavidin-coated flat-bottomed microtiter plates (Roche). After a 2-hour incubation at RT, wells were washed, ABTS substrate added and incubated at RT until color development sufficient for photometric analysis (10-30 min). Absorbance was read at 405 nm with a Tecan Spectra Rainbow Reader. Results are shown in FIGS. 46, 47A and 47B.

While the monospecific anti-DR5 antibodies (both chimeric 0011 and Drozitumab) did not induce significant apoptosis by their own, hyperclustering of the DR5 molecules on the cell surface with a secondary antibody led to cell death at concentrations around 0.7 mM. However, best apoptosis induction was achieved when anti-DR5-FAP bispecific antibodies (in either format 1+1 or 2+2) were added to the co-culture leading to DR5 hyperclustering on the tumor cells via the second moiety which binds to FAP present on the surface of fibroblasts (FIG. 46).

While the monospecific anti-DR5 antibodies induced apoptosis of MDA-MB-231 cells upon cross-linking, bispecific molecules against DR5 and FAP were only functional in the presence of DR5-expressing tumor cells and FAP-expressing tumor associated fibroblasts. In addition, none of the molecules showed any effect on the viability of fibroblasts. (Relative apoptosis as compared to internal assay positive control, see FIGS. 47A and 47B).

This activity data demonstrates that FAP specific apoptosis induction can also be achieved with a DR5-FAP bispecific antibody in a 1+1 format with one valency for each target in a comparable efficacy as with a 2+2 format.

Example 15: The 2+2 Bispecific Format as a Generic Platform Technology

The bispecific DR5-FAP CrossFab molecules in the 2+2 format in which the 28H1 VHCL is fused to the C-terminus of the 5E11 heavy chain has been proven to be a very good format. For different DR5 binders it has demonstrated to be producible at reasonable product titers, it is stable, exhibits only low amounts of missing or wrongly paired light chains and reproducibly shows good activity. Nevertheless, to extend the format platform, additional bispecific 5E11-28H1 molecules have been generated which differ in the kind and location of the crossing point. The five additional formats evaluated and the parental molecule are depicted in FIG. 28. Four of the five additional molecules do not contain a crossed 28H1 Fab anymore but a standard Fab domain fused to the C-terminus of the DR5 (5E11) heavy chain (either VHCH1 or VLCL which is fused by a $(G_4S)_4$ connector).

TABLE 16

| FIG. 28 scetch | B | C | D | E | F |
|---|---|---|---|---|---|
| Kind of Crossing | N-terminal Fab | N-terminal VHVL | N-terminal CH1CL | C-terminal Fab | C-terminal VHVL |
| 5E11 IgG | VLCL-Fc | VLCH1-Fc | VHCL-Fc | VHCH1-Fc | VHCH1-Fc |
| 28G1 Fab (fusion to heavy chain C-terminus) | VHCH1 | VHCH1 | VHCH1 | VLCL | VLCH1 |

TABLE 17

Exemplary sequences of additional DR5-FAP CrossFab molecules

| | |
|---|---|
| VLCL DR5 (5E11)_ 28H1 2 + 2 (molecule B in FIG. 28) | Anti FAP 28H1 Fab (VHCH1) fused to the C-terminus of the DR5 (5E11) heavy chain by a (G4S)4 connector with entire Fab crossed (VLCL-Fc) VLCL (DR5)-Fc-VHCH1 (FAP) (Seq ID NO. 274) VHCH1 (DR5) (SEQ ID NO. 275) VLCL (FAP 28H1) (SEQ ID NO. 137) |
| VHVL DR5(5E11)- 28H1 2 + 2 (molecule C in FIG. 28) | Anti FAP 28H1 Fab (VHCH1) fused to the C-terminus of the DR5 (5E11) heavy chain by a (G45)4 connector with crossing in Fab (VLCH1-Fc) VL (DR5)-CH1-Fc part-VH(FAP)-CH1 chain (SEQ ID NO. 135) VH(DR5)-CL ( SEQ ID NO.: 136) VL (FAP)-kappa light chain (SEQ ID NO.: 137). |
| CH1CL DR5(5E11)- 28H1 2 + 2 (molecule D in FIG. 28) | Anti FAP 28H1 Fab (VHCH1) fused to the C-terminus of the DR5 (5E11) heavy chain by a (G45)4 connector with crossing in Fab (VHCL1-Fc) VH (DR5) CL-Fc--VH(FAP)-CH1 chain (SEQ ID NO.: 138) VL(DR5)-CH1 chains (SEQ ID NO.: 139) VL (FAP)-kappa light chains (SEQ ID NO.: 137) |
| DR5 (5E11)- 28H1 (VLCL) 2 + 2 (molecule E in FIG. 28) | Anti FAP (28H1) Fab (VLCL) fused by a (G45)4 connector to C-terminus of DR5 (5E11) Fc VH (DR5)-CH1-Fc-VL (FAP)-CL (SEQ ID NO. 276) VL (DR5)-CL (SEQ ID NO 132) VH (FAP)-CH1 (SEQ ID NO. 277) |
| DR5 (5E11)- 28H1 (VLCH1) 2 + 2 (molecule F in FIG. 28) | Anti FAP (28H1) CrossFab (VLCH1) fused by a (G45)4 connector to the C-terminus of DR5 (5E11) Fc VH (DR5)-CH1-Fc-VL (FAP)-CL (SEQ ID NO. 278) VL (DR5)-CL (SEQ ID NO. 132) VH (FAP)-CL (SEQ ID NO. 279) |

All molecules were transiently produced in 200 ml scale in HEK293 EBNA cells, purified by standard ProteinA and size exclusion chromatography and finally analyzed and characterized in comparison with the original format (C-terminal CH1CL crossing of 28H1 fused to 5E11 heavy chain, (molecule A, FIG. 28).

As summarized in table 16 the five molecules can be divided into two groups: one contains the two formats in which the entire Fab's are crossed (B+E). These two molecules gave very low product titers and even after purification they still contained high amounts of aggregate. Therefore these two molecules were not further evaluated. The other three (crossing of 5E11 VHVL or CH1CL and crossing of the C-terminal 28H1 as VHVL) exhibited much better product quality with respect to yield and aggregate content. The molecules C, and D also were tested for target binding on MDA-MB-231 cells by FACS in comparison to molecule A as shown in FIG. 29. Furthermore functionaly activity in terms of apoptosis induction, simultaneous and independent target binding, stability and aggregation tendency as well as side product patterns of molecules C, D, and F were compared to format A (Examples 22 to 25)

Example 16: Test of Functional Activity of 2+2 Bispecific Format Variants in a Coculture Assay System The four different 2+2 format variants (format A, C, D, F of FIG. 28) were compared for their functional activity to induce apoptosis as measured by Cell Death Detection ELISA (CDDE, Roche #11 774 425 001) upon treatment of cells with the constructs in a co-culture system consisting of tumor cells (MDA-MB-231) and fibroblasts (GM05389).

Day 1: Preparation of Cells.

The adherent MDA-MB-231 cell line (human breast adenocarcinoma) was grown in DMEM medium (PAN) supplemented with 10% fetal calf serum (Gibco) and 2 mM L-glutamine (PAA), and normally split twice per week 1:20. The GM05389 fibroblasts were grown in MEM+Earle's medium (Gibco) supplemented with 15% fetal calf serum (Gibco), lx NEAS (PAN) and 2 mM L-glutamine (PAA), and normally split twice per week 1:3.

For co-culture assays fibroblast and tumor cells were seeded on the same day each at a density of $1 \times 10^4$ cells/100 μl/well in 96-well plates and incubated overnight at 37° C., 5% $CO_2$. For monoculture assays cell lines were seeded on different plates at the same density.

Day 2: Induction of Apoptosis.

Medium was aspirated and bispecific antibodies were added to the cells at different final concentrations (see FIGS.) in 100 μl medium.

Cultures were incubated at 37° C. for 24 hs.

Day 3: Cell Death Detection ELISA (CDDE).

The immunoassay was performed according to the manufacturer's instructions (Roche) with slight changes. Briefly, cells were lysed with 100 μl/well 2x-lyse buffer for 15 minutes at RT. A master mix consisting of anti-histone and anti-DNA antibodies was prepared according to the manufacturer's instructions and mixed with 1:4 diluted lysates on 96-well streptavidin-coated flat-bottomed microtiter plates (Roche). After a 2-hour incubation at RT, wells were washed, ABTS substrate added and incubated at RT until color development sufficient for photometric analysis (10-30 min). Absorbance was read at 405 nm with a Tecan Spectra Rainbow Reader.

Results are shown in FIGS. 30A-30C. Induction of apoptosis of 4 different CrossMab variants in co- (FIG. 30A) and mono-culture (FIGS. 30B, 30C) settings as detected by DNA fragmentation. All 4 different variants induce apoptosis in tumor cells in the co-culture setting in a comparable dose-dependent manner. In mono-culture settings no apoptosis is induced neither in MDA-MB231 tumor cell line nor in GM05389 fibroblast cell line, pointing out the specificity and FAP-dependency of apoptosis induction of all 4 variants. This functional activity data demonstrates that the bispecific 2+2 format can be used in different configurations with respect to type and site of crossing.

Example 17: Test of Independent and Simultaneous Target Binding of 2+2 Bispecific Format Variants The four different 2+2 format variants (format A, C, D, F of FIG. 28) were compared additionally for their ability to bind both targets independently and simultaneously by SPR assays.

Assessment of Independent DR5- and FAP-Binding to Different Crossmab Variants

Around 3000 resonance units (RU) of the capturing system (5 µg/ml anti human IgG (Fc); GE Healthcare, BR-1008-39) were coupled on a CM5 chip (GE Healthcare BR-1005-30) at pH 5.0 by using an amine coupling kit supplied by the GE Healthcare. The sample and system buffer was PBS-T (10 mM phosphate buffered saline including 0.05% Tween20) pH 7.4. The temperature of the flow cell was set to 25° C. and of the sample block to 12° C. Before capturing, the flow cell was primed with running buffer twice.

The bispecific antibody was captured by injecting a 5 µg/ml solution for 60 sec at a flow of 5 µl/min. Independent binding of each ligand to the bispecific antibody was analysed by determining the active binding capacity for each ligand, either added sequentially or simultaneously (flow of 10 µl/min):

1. Injection of human DR5 with a concentration of 5 µg/ml for 180 sec (identifies the single binding of the antigen).
2. Injection of human FAP with a concentration of 5 µg/ml for 180 sec (identifies single binding of the antigen).
3. Injection of human DR5 with a concentration of 5 µg/ml and of human FAP with a concentration of 5 µg/ml for 180 sec (identifies the binding of DR5 and of FAP at the same time).

The surface was regenerated by 60 sec washing with a 3 m MgCl2 solution at a flow rate of 30 µl/min. Bulk refractive index differences were corrected by subtracting the response obtained from an anti human IgG surface.

The bispecific antibody is able to bind both antigens mutual independently if the resulting final signal of the approach 3 equals the sum of the individual final signals of the approaches 1 and 2.

TABLE 18

Quantitative Assessment of the independent DR5- and FAP-binding of 4 different Crossmab variants

| | SEQ ID NO | DR5 [RU max] | FAP [RU max] | expected signal DR5 + FAP [RU max] | measured signal Mix: DR5 + FAP [RU max] | ratio expected measured [%] |
|---|---|---|---|---|---|---|
| DR5TAA-0057 format A | 134, 132, 124 | 37.1 | 40.8 | 77.9 | 76.7 | 98 |
| DR5TAA-0077 format C | 135, 136, 137 | 33.0 | 41.9 | 74.9 | 73.1 | 98 |
| DR5TAA-0078 format D | 138, 139, 137 | 27.1 | 38.4 | 65.5 | 63.6 | 97 |
| DR5TAA-0081 format F | 278, 132, 279 | 26.7 | 7.2 | 34 | 33 | 97 |

All 4 different Crossmab variants are able to bind DR5 & FAP mutually independent.

Assessment of Simultaneous DR5- and FAP-Binding to the Crossmab First, around 600 resonance units (RU) of DR5 (20 µg/ml) were coupled on a CM5 chip (GE Healthcare BR-1005-30) at pH 5.0 by using an amine coupling kit supplied by the GE Healthcare. The sample and system buffer was PBS-T (10 mM phosphate buffered saline including 0.05% Tween 20) pH 7.4. Flow cell was set to 25° C. and sample block to 12° C. and primed with running buffer twice. Second, 10 µg/ml solution of the bispecific antibody was injected for 30 sec at a flow of 30 µl/min. Third, hFAP (10 µg/ml) was injected for 30 sec at a flow of 30 µl/min. The binding response of hFAP depends from the amount of the bispecific antibody bound to hDR5 and shows simultaneous binding. The surface was regenerated by 70 sec washing with a Glycine pH2 solution (GE Healthcare BR-1003-55) at a flow rate of 30 µl/min. Simultaneous binding is shown by an additional specific binding signal of hFAP to the previous DR5 bound Crossmab.

Assessment of the simultaneous DR5- and FAP-binding of four Crossmab formats (DR5TAA-0057, DR5TAA-0078, DR5TAA-0077 and DR5TAA-0081) showed that all 4 different Crossmab variants are able to bind FAP and DR5 simultaneously.

Example 18: Test of Thermal Stability and Aggregation Tendency of 2+2 Bispecific Format Variants The four different 2+2 format variants (format A, C, D, F of FIG. 28) were furthermore analyzed for their thermal stability and for their tendency to form aggregates.

Thermal Stability

Aggregation onset temperature: Samples were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffin oil. The hydrodynamic radius is measured repeatedly by dynamic light scattering while the samples are heated with a rate of 0.05° C./min from 25° C. to 80° C. The aggregation onset temperature is defined as the temperature at which the hydrodynamic radius starts to increase.

Aggregation Tendency

Samples were dialyzed into formulation buffer (20 mM His/HisCl, 240 mM Trehalose, pH 6.0) and adjusted to a concentration of 1 mg/mL. After sterile filtration over 0.22 µm centrifugal filter devices (Millipore), samples were stored for 2 weeks at 40° C., while a control sample was maintained at −80° C. Aggregate formation was monitored by SE-HPLC using a TSK3000 SWXL column (Tosoh) and reported as the difference between the 40° C. and the −80° C. sample.

TABLE 19

Assessment of the thermal stability and aggregation tendency of 4 different Crossmab formats.

| | DR5TAA-0057 (SEQ ID NOs 134, 132, 124) Format A | DR5TAA-0077 (SEQ ID NOs 135, 136, 137) Format C | DR5TAA-0078 (SEQ ID NOs 138, 139, 137) Format D | DR5TAA-0081 (SEQ ID NOs 278, 132, 279) Format F |
|---|---|---|---|---|
| Stability by DLS [Tagg, ° C.] | 64 | 61 | 60 | 61 |
| Aggregate formation during storage @ 40° C. in formulation buffer [% increase] | 0.4 | 0.3 | 2.2 | 0.5 |

Thermal stability was slightly reduced in the formats C, D and F as compared to the parental format A but with 61° C. and 60° C. still in a good range.

Aggregation tendency was very low for formats A, C and F and slightly increased for format D.

Example 19: Evaluation of Side-Product Profile of 2+2 Bispecific Format Variants by Mass Spectrometry Finally, the four different 2+2 format variants (format A, C, D, F of FIG. 28) were furthermore analyzed for their side-product profile by mass spectrometry.

The deglycosylated total mass of the different constructs was determined and confirmed via electrospray ionization mass spectrometry (ESI-MS). Moreover potential side products such as LC overrepresentation were detected and relatively quantified. Briefly, 100 μg purified antibodies at a protein concentration of up to 3 mg/ml were deglycosylated with 14 U N-Glycosidase F (Roche) in 100 mM $NaH_2PO_4$/$Na_2HPO_4$, pH 7 at 37° C. for 2 h and subsequently desalted via HPLC on a Sephadex G25 column (GE Healthcare). The deglycosylated total mass was determined via ESI-MS on a maXis UHR-TOF (Broker) MS system equipped with a TriVersa NanoMate (Advion) source.

The different DR5-FAP bispecific antibody constructs were analyzed by mass spectrometry in their deglycosylated form to evaluate the product identity and integrity. The identity could be confirmed for all evaluated constructs. Moreover the different constructs showed several side products for example with overrepresentation of one LC type or with loss of one or two LCs. All constructs had qualitatively and quantitatively similar byproducts profiles.

All results from examples 13 and 30-33 clearly show that the bispecific 2+2 format can be used in different configurations with respect to type and site of crossing. This makes the 2+2 CrossFab format a broadly applicable platform technology.

Example 20: Drozitumab-FAP Bispecific Molecules Exhibit Superior In Vivo Efficacy Over Untargeted Drozitumab It has been demonstrated in in vitro activity assays that bispecific Drozitumab-FAP exhibit superior apoptosis induction activity compared to Drozitumab alone which is not cross-linked. To evaluate if this also translates into in vivo efficacy in relevant mouse tumor models different xenograft models have been set up. One problem with the standard mouse tumor models is that the FAP expression usually is very low and does not reflect the human situation at all. To establish models that more closely resemble the FAP expression in human tumor stroma, engineered murine fibroblasts (3T3 cells) that recombinantly express mouse FAP were co-injected with the respective tumor cell lines (colorectal carcinoma cell line DLD-1 in nude mice and breast cancer line MDA-MB-231 in SCID mice). For this purpose 3T3 fibroblasts were stably transfected with a plasmid that carries an expression cassette for the full length murine FAP gene under control of the MPSV promoter. For selection of stable clones the vector further carries an additional expression cassette for a puromycin acetyltransferase which confers resistance to puromycin. Several clones expressing different levels of murine FAP as judged by FACS binding experiments have been selected. One selected mu FAP-3T3 cell line was co-injected with tumor cell line DLD-1 leading to significantly enhanced tumor growth as compared to DLD-1 cells injected without mu FAP expressing 3T3 cells. Also, IHC analysis using human/mouse cross-reactive anti FAP antibodies has demonstrated high levels of FAP expression in the tumor surrounding stroma for both cell lines, as expected. Therefore this co-grafted subcutaneous xenograft model was used to assess the in vivo efficacy of bispecific Drozitumab-FAP molecule compared to the original untargeted Drozitumab antibody. $2 \times 10^6$ tumor cells were co-implanted with 20% of 3T3 fibroblast expressing murine FAP. Twelve (DLD-1) and ten days (MDA-MB-231) after tumor cell implantation therapy was started. The animals were injected (i.v.) either buffer, Drozitumab (10 mg/kg) or Drozitumab-FAP (10 mg/kg). To compensate for the molecular weight difference of Drozitumab vs. bispecific Drozitumab (Drozitumab is only 60% of the molecular mass of the bispecific molecule) the latter was administered twice weekly while Drozitumab was only given once a week. In FIGS. 31A and 31B, the increase of mean tumor volumes in $mm^3$ over time are summarized. FIG. 31A shows in vivo efficacy of Drozitumab-FAP compared to Drozitumab and the buffer control in the DLD-1/mu FAP-3T3 co-injection model. While Drozitumab only demonstrated a moderate anti-tumor efficacy, resulting in a tumor growth inhibition (TGI) of 36% compared to the control, the bispecific molecule exhibited a tumor growth inhibition of 99% at the end of the study (day 33). In the MDA-MB-231/mu FAP-3T3 co-injection model this difference is even more pronounced since in this model Drozitumab alone did not show any efficacy better than the buffer control whereas the Drozitumab-FAP bispecific antibody exhibited a tumor growth inhibition of 77% at the end of the study at day 32 (FIG. 31B). This result might indicate that the MDA-MB-231 cell line is more resistant to apoptosis induction as the DLD-1 cell line.

Example 21: Evaluation of Anti-Tumor Activity of DR5-FAP Bispecific Molecules Using Newly Isolated DR5 Binders in Combination with 28H1 FAP CrossFab In vivo efficacy of three different DR5 binders (5E11, 174 and 422) in bispecific format fused to the anti FAP antibody 28H1 as CrossFab was compared side-by-side in the DLD-1 and MDA-MB-231 xenograft models each co-injected with 3T3 fibroblast expressing murine FAP. A fourth molecule consisting of 5E11-28H1 CrossFab with mutations in the Fc region that completely abolish binding to Fcγ receptors (while affinity to FcRn is unchanged) was included. For this purpose large scale transient transfections and productions were conducted to generate sufficient material in HEK cells.

TABLE 20

Production of bispecific antibodies for in vivo experiments. All materials exhibited acceptable endotoxin content of <0.23 EU/mg.

| | Sample | Fc region | Titer [mg/L] | Yield [mg] | Aggregate [%] |
|---|---|---|---|---|---|
| 1 | DR5(5E11)-FAP(28H1)VHCL 2 + 2 | wt | 60 | 75 | <2 |
| 2 | DR5(5E11)-FAP(28H1)VHCL 2 + 2 | PG_LALA* | 80 | 100 | <2 |
| 3 | DR5(174)-FAP(28H1)VHCL 2 + 2 | wt | n.d. | 65 | <1 |
| 4 | DR5(422)-FAP(28H1)VHCL 2 + 2 | wt | n.d. | 96 | <1 |

*L234A; L235A; P329G

All molecules were produced at good yields with excellent quality with respect to aggregate and endotoxin content. Binding to the relevant antigens was analyzed by different methods (SPR and FRET) as summarized in table 21.

TABLE 21 a: Affinities/Avidities of DR5-FAP bispecific molecules to human and cynomolgus antigens

| Sample | Fc region | Affinity [nM]* hu DR5 | Affinity [nM]* cy DR5 | Avidity [nM]* hu DR5 | Avidity [nM]* cy DR5 | Avidity [nM]+ hu DR5 | Avidity [nM]+ cy DR5 |
|---|---|---|---|---|---|---|---|
| 1 DR5(5E11)-FAP(28H1) VHCL 2 + 2 | wt | 146.0 | 9.6 | 0.16 | 0.29 | 1.2 | 0.4 |
| 2 DR5(5E11)-FAP(28H1) VHCL 2 + 2 | PG_LALA | 147.0 | 11.9 | 0.14 | 0.26 | 1.9 | 0.6 |
| 3 DR5(174)-FAP(28H1) VHCL 2 + 2 | wt | 9.8 | 20.2 | 0.10 | 3.72 | 1.1 | 0.3 |
| 4 DR5(422)-FAP(28H1) VHCL 2 + 2 | wt | 5.1 | 2.0 | 0.08 | n.d. | 0.8 | 0.7 |

*Biacore measurements
+TagLite

Before in vivo experiments were initiated the materials were first tested for in vitro apoptosis induction activity. FIG. 32 summarizes the results of a Cell Death Detection ELISA in which four different DR5-FAP bispecific molecules were compared at concentrations of 7.0, 0.7 and 0.07 nM. The assay was set up as a co-culture assay in which DLD-1 cells were used as targeted cells and 3T3 or recombinant 3T3 cells expressing murine FAP served as the effector cells for cross-linking. In the DLD-1-3T3 co-culture experiment hardly any induction of apoptosis was detectable in DLD-1 cells whereas in the setting with the FAP expressing 3T3 cells a 10 fold increase in apoptosis induction was observed indicating that this activity is due to the cross-linking via FAP on the surface of the recombinant 3T3 cells. A similar experiment was performed in which the same bispecific molecules, target and effector cells were used to determine cell viability upon treatment with the bispecific agonistic DR5-FAP antibodies. The results of this experiment are summarized in FIG. 33. Here, a significant reduction of cell viability of DLD-1 cells only was observed in the presence of FAP expressing 3T3 cells while with unmodified 3T3 cells (which do not express murine FAP) no reduction of viability was seen.

All four bispecific DR5-FAP molecules were used for evaluation of in vivo efficacy in two different tumor models, both co-injected with 20% of murine FAP expressing 3T3 fibroblasts. The results of these in vivo efficacy experiments are shown in FIGS. 34A and 34B. After engraftment of the tumor and fibroblast cells treatment started with 10 mg/kg administered twice weekly intravenously (i.v.). Definitely, all four molecules were able to control tumor growth in both models as demonstrated by significant tumor growth inhibition (TGI) compared to the vehicle control. The absolute percentage of tumor growth inhibition at the end of the study was in a similar range for all four molecules. The following results were obtained for the DLD-1 and MDA-MB-231 model, respectively: 5E11_28H1 (wt Fc): 75%/95%; 5E11_28H1 (PGLALA): 83%/99%; clone 174: 66%/87% and clone 422: 73%/89%. All molecules were slightly more potent in the MDA-MB-231 model than in the DLD-1 experiment.

TABLE 21b

Summary of characteristics of preferred DR5-FAP bispecific antibody

| Clone Name | DR5 5E11 (VH: SEQ ID NO.: 7 VL: SEQ ID NO.: 8) | FAP 28H1 (VH: SEQ ID NO.: 15 VL: SEQ ID NO.: 16) |
|---|---|---|
| Affinity human [nM] | 165 (IgG) | 2.6 (IgG) |
| Affinity Cyno [nM] | 1.02 (IgG) | 3.7 (IgG) |
| Avidity Human [nM] | 0.06 (IgG) | 0.25 (IgG) |
| Avidity Cyno [nM] | 0.06 (IgG) | 0.06 (IgG) |
| Binding Mode | agonistic (only upon crosslinking) TRAIL competitive, conformational epitope | No interference with signaling/protease function, conformational epitope |
| Specificity | No binding to huDR4, DcR1/2, OPG | No binding to hu DPP-IV (CD26, closest FAP homologue) |
| Species Cross-Reactivity | Human, cyno | Human, cyno, murine |

Examples 22 to 25: Generation and Characterization of New DR5 Binding Moieties by Immunization Besides selection of new DR5 antibodies with improved properties from a phage display library (as described above) new DR5 antibodies were generated also by immunization of rabbits (examples 22-25) followed by intensive characterization (examples 26-28).

Example 22: Immunization of Rabbits

One set of rabbits was immunized with 400 µg of recombinant human DR5 (monomeric Fc fusion), emulsified with complete Freund's adjuvant, at day 0 by intradermal application, and with 200 µg each of DR5-huFc, emulsified with complete Freund's adjuvant, at days 7, 14, 35, 63 and 91, by alternating intramuscular and subcutaneous applications. Blood (10% of estimated total blood volume) was taken at days 21, 41, 69 and 97. Serum was prepared, which was used for titer determination by ELISA (see below), and peripheral mononuclear cells were isolated, which were used as a source of antigen-specific B cells in the B cell cloning process (Example 17).

Another set of rabbits was immunized genetically, using a plasmid expression vector coding for human DR5 lacking the intracellular death domain, by intradermal application of 400 µg vector DNA, followed by Electroporation (5 square pulses of 750 V/cm, duration 10 ms, interval 1 s). Rabbits received 6 consecutive immunizations at days 0, 14, 28, 49, 77 and 105. Blood (10% of estimated total blood volume) was taken at days 35, 56, 84 and 112. Serum was prepared, which was used for titer determination by ELISA (see below), and peripheral mononuclear cells were isolated, which were used as a source of antigen-specific B cells in the B cell cloning process (Example 23).

Determination of Serum Titers

Human DR5 (monomeric Fc fusion), was immobilized on a 96-well NUNC Maxisorp plate at 0.3125 µg/ml, 100 µl/well, in PBS, followed by blocking of the plate with 2% Crotein C in PBS, 200 µl/well; application of serial dilutions of antisera, in duplicates, in 0.5% Crotein C in PBS, 100

µl/well; detection with HRP-conjugated donkey anti-rabbit IgG antibody (Jackson Immunoresearch) diluted 1:16 000 in 0.5% Crotein C in PBS, 100 µl/well. For all steps, plates were incubated for 1 h at 37° C. Between all steps, plates were washed 3 times with 0.05% Tween 20 in PBS. Signal was developed by addition of BM Blue POD Substrate soluble (Roche), 100 µl/well; and stopped by addition of 1 M HCl, 100 µl/well. Absorbance was read out at 450 nm, against 690 nm as reference. Titer was defined as dilution of antisera resulting in half-maximal signal.

Example 23: B-Cell Cloning from Rabbits

Isolation of Rabbit Peripheral Blood Mononuclear Cells (PBMC)

Three rabbits (described in the Example "Immunization of rabbits") were used as a source of blood. EDTA containing whole blood was diluted twofold with 1×PBS (PAA, Pasching, Austria) before density centrifugation using lympholyte mammal (Cedarlane Laboratories, Burlington, Ontario, Canada) according to the specifications of the manufacturer. The PBMCs were washed twice with 1×PBS.

EL-4 B5 Medium

RPMI 1640 (Pan Biotech, Aidenbach, Germany) supplemented with 10% FCS (Hyclone, Logan, Utah, USA), 2 mM Glutamin, 1% penicillin/streptomycin solution (PAA, Pasching, Austria), 2 mM sodium pyruvate, 10 mM HEPES (PAN Biotech, Aidenbach, Germany) and 0.05 mM b-mercaptoethanole (Gibco, Paisley, Scotland)

Depletion of Macrophages/Monocytes

Sterile 6-well plates (cell culture grade) were used to deplete macrophages and monocytes through unspecific adhesion. Each well was filled at maximum with 4 ml medium and up to $6 \times 10^6$ PBMCs from the immunized rabbit and allowed to bind for 1 h at 37° C. in the incubator. The cells in the supernatant (peripheral blood lymphocytes (PBLs)) were used for the antigen panning step.

Coating of Plates

For panning on protein sterile streptavidin coated 6-well plates (Microcoat, Bernried, Germany) were coated with 2 µg/ml biotinylated recombinant human DR5 (monomeric Fc fusion) in PBS for 3 h at room temperature. For panning on human surface DR5-positive cells G401 cells were seeded in sterile cell culture 6-well plates and cultivated to generate a confluent cell monolayer. Prior to the panning these 6-well plates were washed with sterile PBS three times.

Enrichment of B Cells on the Human DR5 Protein 6-well tissue culture plates coated with human DR5 protein or covered with human DR5-positive G401 cells were seeded with up to $6 \times 10^6$ PBLs per 4 ml medium and allowed to bind for 1 h at 37° C. in the incubator. After the enrichment step on the DR5 antigen non-adherent cells were removed by carefully washing the wells 1-2 times with 1×PBS. The remaining sticky cells were detached by trypsin for 10 min at 37° C. in the incubator. Trypsination was stopped with EL-4 B5 medium. The cells were kept on ice until the immune fluorescence staining.

Immune Fluorescence Staining and Flow Cytometry

The anti-IgG FITC (AbD Serotec, Düsseldorf, Germany) was used for single cell sorting. For surface staining, cells from the depletion and enrichment step were incubated with the anti-IgG FITC antibody in PBS and incubated for 45 min in the dark at 4° C. After staining the PBMCs were washed two fold with ice cold PBS. Finally the PBMCs were resuspended in ice cold PBS and immediately subjected to the FACS analyses. Propidium iodide in a concentration of 5 µg/ml (BD Pharmingen, San Diego, Calif., USA) was added prior to the FACS analyses to discriminate between dead and live cells. A Becton Dickinson FACSAria equipped with a computer and the FACSDiva software (BD Biosciences, USA) were used for single cell sort.

B-Cell Cultivation

The cultivation of the rabbit B cells was prepared by a method similar to that described by Zubler et al. (1985). Briefly, single sorted rabbit B cells were incubated in 96-well plates with 200 µl/well EL-4 B5 medium containing Pansorbin Cells (1:100000) (Calbiochem (Merck), Darmstadt, Deutschland), 5% rabbit thymocyte supernatant (charge TSN-M13 (10242), MicroCoat, Bernried, Germany) and gamma-irradiated murine EL-4-B5 thymoma cells ($2.5 \times 10^4$/well) for 7 days at 37° C. in an atmosphere of 5% CO2 in the incubator. The supernatants of the B-cell cultivation were removed for screening and the remaining cells were harvested immediately and were frozen at –80° C. in 100 µl RLT buffer (Qiagen, Hilden, Germany).

Example 24: B-Cell PCR and Recombinant Expression

Isolation of Ribonucleic Acid (RNA)

The cells from which the RNA had to be isolated were at first pelleted by centrifugation. The cell pellet was lysed by the addition of 100 µl RLT-buffer with 10 µl/ml beta-mercaptoethanol. The cells were resuspended by multiple mixing with a pipette and transferred to a multi well plate. The plate was shortly centrifugated at 200×g and frozen at –20° C. The isolation of the RNA was performed with the NucleoSpin® 96 RNA kit (Macherey & Nagel) according to the manufacturer's instructions.

Reverse Transcription Polymerase Chain Reaction

The reverse transcription was carried out with SuperScript III First-Strand Synthesis SuperMix (Invitrogen) according to the manufacturer's instructions.

Polymerase Chain Reaction

The polymerase chain reaction was carried out with AccuPrime Pfx SuperMix (Invitrogen) according to the manufacturer's instructions. Light chain and heavy chain variable regions were amplified in separate reactions. PCR-primers were used with 25 bp overlaps to target antibody expression vectors. PCR-products were purified by Nucleo-Spin® 96 Extract II kit (Macherey & Nagel).

Sequencing and SLIC Cloning

The PCR products were sequenced to determine the DNA-sequences of the variable regions of heavy and light chains. The PCR-products were cloned into expression vectors by the so called SLIC-cloning method, which is described by Haun, R. S., et al., in BioTechniques 13 (1992) pp. 515-518 and Li, M. Z., et al., in Nature Methods 4 (2007) pp. 251-256. The plasmids for the antibody expression were linearized by restriction anzyme digestion. The linearized plasmids were purified by preparative agarose electrophoresis and extracted from the gel (Qiaquick Gel Extraction Kit/Qiagen). The purified plasmids were added to a PCR-protocol using overlapping primers (bay 25 bp) for the PCR-product to be cloned. Both the vector and insert were treated with T4 DNA polymerase (Roche Applied Sciences) in the absence of dNTPs to generate overhangs, then vector and insert were incubated with RecA (New England Biolabs) protein and ATP to promote recombination. Products were transformed into *E. coli*. Plasmid DNAs for light chain and heavy chains were isolated and each couple was combined for transient transfections.

Transient Transfection for Antibody Expression in HEK293 Cells

HEK293 cells (Invitrogen) were grown in F17-media (Gibco) to 1×10e6 cells/ml. 2×10e6 HEK293 cells were transfected with 1 µg HC+LC plasmids suspended in 293-free (Novagen) and OptiMEM® (Gibco). After 7 days incubation supernatants were harvested, purified via Protein A and analyzed.

Example 25: Screening of DR5 Antibodies Derived from Immunization

B-cell culture supernatants were screened by multiple parallel ELISA-based binding assays in 384 well microtiter plates. Antibodies binding to the DR5-expressing cells G401 and to biotinylated recombinant human DR5 (monomeric Fc fusion) and cynomolgus DR5 (dimeric Fc fusion), but not to human DR4 (TNFRSF10A; R&D Systems Cat. No. 347-DR-100) and human IgG1, were selected as primary hits. In a secondary screening, micropurified antibodies recombinantly expressed in HEK cells were tested again for binding to human and cynomolgus DR5 and additionally for absence of binding to human DR4, human DcR1 (inhouse), human Dc R 2 (in house) or human Osteoprotegerin (OPG; R&D Systems Cat. No. 805-05-100). Furthermore antibodies were tested in a functional apoptosis assay (Cell Death Detection Elisa) on G401 cells in the presence or absence of a cross-linking anti-human Fc antibody. Only those antibodies able to induce apoptosis upon Fc-mediated cross-linking (but not in its absence) were selected for further characterization and development.

Sequences of antibodies selected after secondary screening and cloned in expression plasmids by the SLIC cloning procedure were verified by subcloning and re-sequencing of the variable light and variable heavy chains.

These subcloned and sequence-verified expression plasmids were then used for larger scale transient transfections of HEK293F cells followed by Protein A purification allowing further more intensified characterization steps.

Example 26: Characterization of Binding Properties of DR5 Antibodies Derived from Immunization Selected DR5 antibodies from rabbit immunization were characterized for their binding properties, species cross-reactivity and specificity by binding ELISA and SPR analysis.

Binding of Monoclonal Antibodies to TRAIL Binding Receptors (Immunoassay)

Antigen binding immunoassays were performed at room temperature on 384 well streptavidin coated microtiter plates (MicroCoat Biotechnologie GmbH) with PBS buffer supplemented with 0.05% Tween®-20 and 0.5% BSA (Roche Diagnostics GmbH). 125 ng/ml biotinylated human DR5 (monomeric Fc fusion) protein (inhouse) or 63 ng/ml biotinylated hFc cynomolgus DR5 protein (inhouse) or 63 ng/ml biotinylated DcR2 (TNFRSF10D) protein (inhouse) were added to the wells containing a mixture of 1:3000 diluted anti-rabbit Fc-HRP conjugate (GE Healthcare) and 1:50 diluted B-cell supernatants. After 90 min incubation the plate was washed 6 times with PBST (phosphate buffered saline with 0.2% Tween®-20) and developed with BM Blue® HRP substrate solution (BM Blue®: 3,3'-5,5'-Tetramethylbenzidine, Roche Diagnostics GmbH) for 30 minutes at RT. Absorbance was measured at 370 nm. The blank value was defined without addition of supernatant.

For negative selection against the hFc tag of the immunogen an immunoassay with a mixture of biotinylated anti-human IgG (Fab specific) from Jackson ImmunoResearch (Cat. No. 109-066-006), human IgG1 (inhouse) and anti-rabbit Fc-HRP conjugate was used and processed as described. For testing binding to related Trail binding receptors like human DR4 (TNFRSF10A; R&D Systems Cat. No. 347-DR-100), human Osteoprotegerin (OPG; R&D Systems Cat. No. 805-05-100) and human DcR 1 (TNFRSF10C; R&D Systems Cat. No. 630-TR-100) an immunoassay was established by capturing the respective protein—hFc chimera with anti-human Fc antibody (Jackson ImmunoResearch, Cat. No. 109-006-098) on a MaxiSorp 384 well microtiter plate (Sigma-Aldrich, Nunc).

TABLE 22

Binding of DR5 antibodies (rabbit IgG) derived by immunization to human DR5 (monomeric Fc Fusion) and cynomolgus DR5 as detected by biochemical ELISA (EC50 [ng/mL]).
No significant binding to mouse DR5, human DR4, DcR1, DcR2, and Osteoprotegerin was detected (data not shown)

| DR5 Antibody Clone Name | DR5 Antibody Clone Alias | EC50 human DR5 [ng/mL] | EC50 cynomolgus DR5 [ng/mL] | SEQ ID NO VH/VL |
|---|---|---|---|---|
| DR5TAA-0005 | 039 | 2.5 | 3.7 | 41/46 |
| DR5TAA-0006 | 058 | 2.0 | 1.6 | 51/55 |
| DR5TAA-0010 | 481 | 2.8 | 8.7 | 60/64 |
| DR5TAA-0013 | 298 | 2.1 | 2.1 | 68/71 |
| DR5TAA-0019 | 461 | 3.5 | 2.2 | 74/78 |
| DR5TAA-0016 | 422 | 4.0 | 2.7 | 82/85 |
| DR5TAA-0011 | 174 | 2.0 | 4.3 | 88/89 |

Selected DR5 antibodies from rabbit immunization show good and comparable binding properties to human and cynomolgus DR5 in ELISA while they do not recognize murine DR5. All selected antibodies are highly specific for DR5 as they did not give significant signals in binding ELISA to human DR4, DcR1, DcR2, and Osteoprotegerin.

DR5 Kinetic Affinity

Around 3000-5000 resonance units (RU) of the capturing system (10 µg/ml goat anti rabbit; ordering code JIR111-005-046; Jackson Immuno Research) were coupled on a CM5 chip (GE Healthcare BR-1005-30) at pH 5.0 by using an amine coupling kit supplied by the GE Healthcare. The sample and system buffer was PBS-T (10 mM phosphate buffered saline including 0.05% Tween20) pH 7.4. The flow cell was set to 25° C.—and the sample block set to 12° C.—and primed with running buffer twice.

The DR5 antibodies were captured by injecting a 1 µg/ml solution for 30 sec at a flow of 10 µl/min. Association was measured by injection of recombinant human DR5 (monomeric His-Avi fusion protein, in house) in various concentrations in solution for 120 sec at a flow of 30 µl/min starting with 100 nM down to 0.41 nM in 1:3 dilutions. The dissociation phase was monitored for up to 300 sec and triggered by switching from the sample solution to running buffer. The surface was regenerated by 60 sec washing with a 100 mM H3PO4 (phosphoric acid) solution at a flow rate of 30 µl/min. Bulk refractive index differences were corrected by subtracting the response obtained from a blank surface. Buffer injections are also subtracted (=double referencing). For calculation of KD and other kinetic parameters the Langmuir 1:1 model was used.

TABLE 23

Kinetic affinities of DR5 antibodies (rabbit IgG) derived by immunization

| DR5 Antibody Clone Name | DR5 Antibody Clone Alias | ka [nM] | kd [nM] | KD [nM] | SEQ ID NO VH/VL |
|---|---|---|---|---|---|
| DR5TAA-0005 | 039 | 1.60E+06 | 2.14E−02 | 1.33E−08 | 41/46 |
| DR5TAA-0006 | 058 | 3.12E+06 | 1.85E−03 | 5.92E−09 | 51/55 |
| DR5TAA-0010 | 481 | 1.11E+06 | 1.77E−02 | 1.59E−08 | 60/64 |
| DR5TAA-0011 | 174 | 4.55E+05 | 1.93E−03 | 4.24E−09 | 88/89 |
| DR5TAA-0013 | 298 | 4.07E+05 | 3.71E−03 | 9.12E−09 | 68/71 |
| DR5TAA-0016 | 422 | 3.46E+05 | 5.02E−04 | 1.45E−09 | 82/85 |
| DR5TAA-0019 | 461 | 9.00E+05 | 6.07E−04 | 6.75E−10 | 74/78 |

Example 27: Functional Characterization of DR5 Antibodies Derived from Immunization DNA Fragmentation and Cell Viability DR5 antibodies were functionally characterized by evaluating apoptosis and cell viability as measured by Cell Death Detection ELISA (CDDE, Roche #11 774 425 001) and Cell Titer Glo (CTG, Promega #G7573), respectively, upon treatment with anti-DR5 antibodies in the presence or absence of a cross-linking antibody.

Preparation of cells: the adherent MDA-MB-231 cell line (human breast adenocarcinoma) was grown in DMEM medium (PAN) supplemented with 10% fetal calf serum (Gibco) and 2 mM L-glutamine (PAA), and normally split twice per week 1:10. For the assay, cells were washed with PBS, detached from the flask with Accutase (PAA), seeded in 96-well flat-bottomed microtiter plates (Costar) at a density of $1 \times 10^4$ cells/well (CDDE) or $0.25 \times 10^4$ cells/well (CTG) in 500 and incubated overnight at 37° C., 5% CO2.

Induction of apoptosis by rabbit anti-DR5 antibodies: samples (rabbit anti-DR5 IgGs, DR5-TAA-#) were added to the cells at different concentrations alone or together with the cross-linking antibody (goat anti-rabbit IgG, Jackson Immunoresearch) in a 1:1 ratio in 50 µl in PBS, to induce crosslinking of the DR5 receptors leading to apoptosis. Cells were incubated at 37° C. for 24 hs (CDDE) or 48 hs (CTG).

A) Cell Death Detection Elisa (CDDE): the immunoassay was performed according to the manufacturer's instructions (Roche). Briefly, supernatants were carefully aspirated and cells lysed with 200 µl/well lyse buffer for 30 minutes at RT. A master mix consisting of anti-histone and anti-DNA antibodies was prepared according to the manufacturer's instructions and mixed with the 1:4-diluted lysates on 96-well streptavidin-coated flat-bottomed microtiter plates (Roche). After a 2-hour incubation at RT, wells were washed, ABTS substrate added and incubated at RT until color development sufficient for photometric analysis (10-30 min). Absorbance was read at 405 nm with a Tecan Spectra Rainbow Reader.

FIGS. 35A and 35B shows the results of this experiment: The generated rabbit anti-DR5 antibodies were able to induce apoptosis of MDA-MB231 cells with different potencies but always in a dose-dependent fashion and only after Fc-mediated cross-linking of the DR5 molecules. In the absence of an anti-rabbit Fc-specific secondary antibody, no significant cell death was detected.

B) Cell Titer Glo (CTG): the immunoassay was performed according to the manufacturer's instructions (Promega). Briefly, cells were first lysed in the buffer containing the luminescence substrate (100 µl). After a 10-minute incubation period on a shaker luminescence was measured with the TECAN Infinite Plus reader.

FIGS. 36A and 36B shows the results of this experiment: Cell viability is diminished by anti-DR5 antibodies upon receptor hyperclustering in a dose-dependent manner. The generated rabbit anti-DR5 antibodies were able to decrease the viability of MDA-MB231 cells with varying potencies but always in a dose-dependent fashion and only after Fc-mediated cross-linking of the DR5 molecules. In the absence of an anti-rabbit Fc-specific secondary antibody, the cell viability was not affected at any antibody concentration.

Cell Viability & Caspase 8 Activation

Caspase8-Glo Caspase 8 activation assays (Promega cat #G8202) and CellTiter-Glo cell viability assays (Promega cat #TB288) were carried out according to the manufacture's instructions.

For Caspase 8 activation assays, 10,000 cancer cells were seeded in 75 µl per well in opaque white 96 well plates (BD Falcon cat #BD353296) and incubated at 37° C. with 5% CO2 overnight. Then anti-DR5 antibodies were added together with anti-rabbitFc antibodies (equal molar concentration of DR5 and rabbitFc antibodies in 25 µl) in 6 serial dilutions. Antibodies were incubated on the cells at 37° C. with 5% CO2 for 3 hours. Then 100 µl of caspase 8 substrate in lysis buffer was added to each well and mixed well. After incubation of another 30 minutes at 37° C. luminescence signal was read in a Spectra Max M5 plate.

For Cell Viability assays, 4,000 cancer cells were seeded per well in black/clear bottom 96 well plates (BD Falcon cat #BD353220) and incubated at 37° C. with 5% CO2 overnight. Then anti-DR5 antibodies were added together with anti-rabbitFc antibodies (equal molar concentration of DR5 and rabbitFc antibodies in 25 µl) in 6 serial dilutions. Antibodies were incubated on the cells at 37° C. with 5% CO2 for 48 hours. Then 100 µl CellTiter-Glo reagent was added to each well and mixed well. After incubation of another 10 minutes at room temperature luminescence signal was read in a Spectra Max M5 plate reader.

FIG. 37 shows the analysis of inhibition of cell proliferation (Cell TiterGlo Assay) of three different human tumor cells (DLD-1, NCI H460 and MDA-MB-231) upon treatment with different, cross-linked DR5 antibodies at a concentration of 7 nM. FIG. 38 shows apoptosis induction measured by Caspase 8 activation in three human tumor cell lines (DLD-1, NCI H460 and MDA-MB-231) after treatment with cross-linked DR5 antibodies at a concentration of 7 nM. All tested DR5 antibodies induce high caspase 8 activation in all tested tumor cell lines. DR5 antibodies were able to decrease the viability of all tested cell lines with varying potencies.

Example 28: Evaluation of Chemical Stability of DR5 Antibodies Derived by Phage Display and Immunization Generation of Stressed DR5 Antibody Samples To test the chemical stability of DR5 antibodies, stressed samples were generated and functionally characterized with regard to DR5 binding. High-pH stress induces—among others—deamidation of reactive Asn hotspots, whereas at pH 6.0 e.g. succinimide formation from reactive Asn and Asp residues may be induced. For high-pH stress, samples were transferred in 20 mM Na-phosphate, pH 8.0 and incubated for 5 days at 40° C. For low-pH stress, samples were transferred into in 20 mM His/HisCl, 140 mM NaCl, pH 6.0 and incubated for 3 weeks at 40° C. A control sample was kept at −80° C.

Determination of the Relative Active Concentration of Stressed DR5 Antibody Samples Around 5000 resonance units (RU) of the capturing system (20 µg/ml goat anti rabbit; ordering code M111-005-046; Jackson Immuno Research) were coupled on a CM5 chip (GE Healthcare BR-1005-30) at pH 5.0 by using an amine coupling kit supplied by the GE Healthcare. The sample and system buffer was PBS-T (10 mM phosphate buffered saline including 0.05% Tween20) pH 7.4. The temperature of the flow cell was set to 25° C. and of the sample block to 12° C. Before capturing, the flow cell was primed with running buffer twice.

The bispecific antibody was captured by injecting a 50 nM solution for 60 sec at a flow of 10 µl/min. Association was measured by injection of human DR5 in solution for 90 sec at a flow of 30 µl/min at a concentration of 200 nM. The dissociation phase was monitored for up to 90 sec and triggered by switching from the sample solution to running buffer. The surface was regenerated by 60 sec washing with a 0.85% H3PO4 (phosphoric acid) solution at a flow rate of 30 µl/min. Bulk refractive index differences were corrected by subtracting the response obtained from a blank surface.

The relative active concentration of the stressed antibody is the ratio calculated from the capture level and binding level (RU binding divided by RU capture, in comparison to the unstressed reference sample).

FIG. 39 shows an exemplary response curve used for the determination of the relative active concentration of stressed DR5 antibody samples. FIGS. 40 and 41 show relative active concentrations of original and stressed DR5 antibodies derived from immunization and from phage display. Besides antibodies DR5TAA-0013 and DR5TAA-0010 that showed slightly deminished relative active concentrations after stress at pH6 and pH8, respectively, all other DR5 antibodies did not show any relevant reduction of relative active concentrazion after pH stress.

Example 29: Functional Characterization of DR5-Binder Derived by Immunization and Phage Display in 2+2 Bispecific Format in Co-Culture Assays In order to evaluate whether the novel DR5 binders derived by immunization can be used for the generation of bispecific antibodies for the targeted induction of apoptosis of tumor cells by hyper-cross-linking of DR5, a set of DR5 antibodies were converted into 2+2 bispecific molecules (as depicted in FIG. 28 A) in combination with the FAP antibody 28H1. Bispecific constructs were tested for their apoptosis inducing activity in a co-culture assay.

DLD-1 or H460 tumor cells (10,000 cells/well) are seeded to 96-well plates in co-culture with 3T3 cells or with 3T3 cells transfected to express murine FAP 2,500 cells/well) in a total volume of 150 µl to allow for triplicate samples for each treatment. After 24 h, cells are treated with 50 µl antibodies (4× concentration) for 24 h (untreated control: 50 µl medium).

Cell Death Detection ELISA:

(Roche Applied Science Cat. No. 11774 425 001): Procedure is followed exactly as stated in manufacturer's protocol. Vmax values are extrapolated from the measurement of abs at 405 nm (minus reference wavelength value at 490 nm) every minute for 10 minutes. An average of triplicate background values (lysis buffer alone) are subtracted from all samples. Data is expressed as fold increase over apoptosis in untreated samples.

FIGS. 43A and 43B show induction of apoptosis in DLD-1 and H460 tumor cell lines by 2+2 bispecific constructs in co-culture assays as detected by DNA fragmentation. While a bispecific construct containing Drozitumab as DR5-binding component already induces apoptosis in the absence of FAP, all constructs containing new DR5 binders derived by immunization only induce apoptosis in the presence of FAP. Constructs with newly developed DR5 binders, such as 0011-28H1 and 0016-28H1, are able to induce apoptosis to a higher extent especially at low concentrations as compared to the Drozitumab containing bispecific construct.

Example 30: Characterization of Cellular Binding of DR5-Binder Derived by Immunization and Phage Display in 2+2 Bispecific Format Cells were stained (5×10$^4$/50 µl) with 24 µg/ml of each DR5-FAP construct or Drozitumab in staining buffer (PBS+ 5% FCS) for 1 h on ice. After washing twice the secondary antibody goat anti-human IgG-AF488 (Invitrogen #A11013) was added at 10 µg/ml and cells were again incubated 1 h on ice protected from direct light. After two more washing steps cells were measured at FACS Canto.

All tested constructs show binding to MDA-MB-231 with varying intensities (see FIGS. 44A and 44B).

Example 31: Humanization of the VH and VL Domains of DR5 Antibodies Derived by Immunization The rabbit DR5-binding antibody DR5TAA-0011 was humanized using frameworks identical to human germline sequences. The human germline sequences hVH_3_64 (GenBank accession No. M99682) and hVH3_16 (GenBank accession No P01767) were the 2 acceptors for the VH humanized variants and the human germline sequences hVK1_93 (Accession No. P04431) and hVK1_5 (GeneBank accession No. P01602) were the acceptors for VL humanization. Eight humanized DR5 antibodies comprising a heavy chain variable region construct selected from SEQ ID NOs. 23 and 26, and a light chain variable region construct selected from SEQ ID NOs 24, 29, 30, 31, and 32 were obtained and further characterized (Examples 27 to 29).

TABLE 24

Humanized DR5 binders derived by immunization

| Variant | HC variant | SEQ ID NO. | LC variant | SEQ ID NO. |
| --- | --- | --- | --- | --- |
| DR5TAA-0066 | VH7 | 23 | VL3 | 30 |
| DR5TAA-0067 | VH7 | 23 | VL15 | 24 |
| DR5TAA-0068 | VH17 | 26 | VL10 | 31 |
| DR5TAA-0071 | VH17 | 26 | VL15 | 24 |
| DR5TAA-0072 | VH17 | 26 | VL2 | 32 |
| DR5TAA-0073 | VH17 | 26 | VL3 | 30 |
| DR5TAA-0074 | VH7 | 23 | VL10 | 31 |
| DR5TAA-0075 | VH7 | 23 | VL11 | 29 |

Example 32: Functional Characterization of Humanized DR5-Binder Derived by Immunization Humanized DR5 antibodies were functionally characterized by evaluating apoptosis as measured by Cell Death Detection ELISA (CDDE, Roche #11 774 425 001) upon treatment with humanized anti-DR5 antibodies in the presence or absence of a cross-linking antibody. Preparation of cells: the adherent MDA-MB-231 cell line (human breast adenocarcinoma) was grown in DMEM medium (PAN) supplemented with 10% fetal calf serum (Gibco) and 2 mM L-glutamine (PAA), and normally split twice per week 1:10. For the assay, cells were washed with PBS, detached from the flask with Accutase (PAA), seeded in 96-well flat-bottomed microtiter plates (Costar) at a density of $1\times10^4$ cells/well (CDDE) in 50 µl and incubated overnight at 37° C., 5% $CO_2$.

Induction of apoptosis by humanized anti-DR5 antibodies: samples (humanized anti-DR5 IgGs, DR5-TAA-#) were added to the cells at different concentrations alone or together with the cross-linking antibody (goat anti-human IgG, Sigma #12136) in a 1:1 ratio in 50 µl in PBS, to induce crosslinking of the DR5 receptors leading to apoptosis. Cells were incubated at 37° C. for 24 hs (CDDE).

Cell Death Detection Elisa (CDDE): the immunoassay was performed according to the manufacturer's instructions (Roche). Briefly, supernatants were carefully aspirated and cells lysed with 200 µl/well lyse buffer for 30 minutes at RT. A master mix consisting of anti-histone and anti-DNA antibodies was prepared according to the manufacturer's instructions and mixed with the 1:4-diluted lysates on 96-well streptavidin-coated flat-bottomed microtiter plates (Roche). After a 2-hour incubation at RT, wells were washed, ABTS substrate added and incubated at RT until color development sufficient for photometric analysis (10-30 min). Absorbance was read at 405 nm with a Tecan Spectra Rainbow Reader. Apoptosis signals were normalized to the apoptosis of the chimeric anti-DR5 antibody at a concentration of 2 µg/ml. Results are shown in FIGS. 45A-1-45A-4 Humanized Variants of DR5TAA-0011 (DR5TAA-0066-DR5TAA-0075, black lines) induce apoptosis upon cross-linking with secondary antibody in a dose-dependent manner. Several humanized variants, such as DR5TAA-0067, DR5TAA-0071, DR5TAA-0074 and DR5TAA-0075, are able to induce apoptosis in a similar manner concerning maximum of induction and dose-dependency as compared to the chimeric variant (DR5TAA-0052, grey lines). FIG. 45B Humanized Variants of DR5TAA-0011 (DR5TAA-0066-DR5TAA-0075) induce no apoptosis if not crosslinked by a secondary antibody. Thus, also the humanized variants are suited to be used in bispecific formats to specifically induce apoptosis only in the presence of FAP.

The Fabs of selected humanized variants were were fused C-terminally to a human Fc region via a $(G_4S)_4$ connector. These molecules were transiently produced in HEK293 EBNA cells, purified via ProteinA beads and tested in an apoptosis induction assay. In FIG. 22B the results of the DNA fragmentation assay in MDA-MB-231 cells with these Fc-DR5 fusion molecules after cross-linking with secondary anti Fc IgG are summarized. All tested molecules are able to induce apoptosis of the target cell line, indicating that the chosen DR5 binders are not N-terminally blocked which opens a wider range of formats that can be used with these binders.

Example 33: Characterization of Binding Affinities of Humanized DR5-Binder Derived by Immunization Humanized DR5-binder were characterization for their binding affinities by SPR analysis. BIAcore characterization: A BIAcore 3000 instrument (GE Healthcare) was used with a CM5 sensor mounted into the system. The sensor was preconditioned by a 1 min injection at 100 µl/min of 0.1% SDS, 50 mM NaOH, 10 mM HCl and 100 mM $H_3PO_4$. System buffer was 10 mM HEPES pH 7.4, 150 mM NaCl, 0.05% TWEEN 20. The sample buffer was the system buffer supplemented with 1 mg/mL carboxymethyldextran (Sigma). An anti-human antibody capture system was established on the biosensor surface. 8000 relative response units of a goat anti-human Fcγ fragment-specific polyclonal antibody (Jackson Laboratories) were immobilized according to the manufacturer's instructions using EDC/NHS chemistry. The sensor was deactivated using 1M ethanolamine.

20 nM of the respective antibody sample were captured for 1 min at a flow rate of 10 µl/min. As a reference, 20 nM polyclonal human normal IgG (Roche, Ident. 11717570) were captured on the reference flow cell 1 and subtractive signals were monitored.

In one embodiment, the 23.3 kDa analyte DR5 was injected at 30 µl/min for 3 min association time in concentration series at 0 nM, 3.3 nM, 11 nM, 2×33 nM, 100 nM and 300 nM. The complex dissociation was monitored for 5 min.

The system was regenerated at 30 µl/min by a 1 min injection of 10 mM glycine buffer pH 1.5 followed by a two consecutive 1 min injections of 10 mM glycine buffer pH 1.7. Kinetic parameters were evaluated using the Biacore Evaluation Software according to the manufacturer's instructions.

The association rate constant $k_a$(1/Ms), the dissociation rate constant $k_d$ (1/s) and the dissociation constant $K_D$ were calculated according to a Langmuir model with $R_{MAX}$ global.

TABLE 25

Kinetic affinities to monomeric human DR5 of humanized variants of DR5TAA-0011 (DR5TAA-0067 to DR5TAA-0075) as compared to chimeric form of DR5TAA-0011 (DR5TAA-0052)

| Construct | SEQ ID No VH/VL | ka (1/Ms) | kd (1/s) | KD (nM) |
|---|---|---|---|---|
| DR5TAA-0067 | 23/24 | 2.6E05 | 5.2E-03 | 20 |
| DR5TAA-0074 | 23/31 | 2.7E05 | 5.6E-03 | 21 |
| DR5TAA-0071 | 26/24 | 3.0E05 | 4.6E-03 | 15 |
| DR5TAA-0075 | 23/29 | 3.2E05 | 5.6E-03 | 17 |
| DR5TAA-0052 | 90/92 | 3.5E05 | 2.4E-03 | 7 |

Kinetic binding properties of humanized variants were maintained within a factor of approx. 3 for KD and kd and within a factor of approx. 2 for ka as compared to the chimeric variant.

Example 34: Characterization of Thermal and Chemical Stability of Humanized DR5-Binder Derived by Immunization Humanized DR5-binder were characterized for their thermal and chemical stability. Samples were prepared at a concentration of 1 mg/mL in 20 mM Histidine/Histidine chloride, 140 mM NaCl, pH 6.0, transferred into an optical 384-well plate by centrifugation through a 0.4 µm filter plate and covered with paraffin oil. The hydrodynamic radius is measured repeatedly by dynamic light scattering while the samples are heated with a rate of 0.05° C./min from 25° C. to 80° C. The aggregation onset temperature is defined as the temperature at which the hydrodynamic radius starts to increase.

TABLE 26

Aggregation Onset temperatures of humanized variants
of DR5TAA-0011 (DR5TAA-0066-DR5TAA-0075)
as a measure for thermal stability of the antibodies.

| Construct | SEQ ID No VH/VL | Tagg [° C.] |
|---|---|---|
| DR5TAA-0071 | 26/24 | 71 |
| DR5TAA-0067 | 23/24 | 70 |
| DR5TAA-0074 | 23/31 | 68 |
| DR5TAA-0073 | 26/30 | 72 |
| DR5TAA-0068 | 26/31 | 69 |
| DR5TAA-0072 | 26/32 | 71 |
| DR5TAA-0066 | 23/30 | 71 |
| DR5TAA-0075 | 23/29 | 68 |

Humanized variants of DR5TAA-0011 reveal a high thermal stability with aggregation temperatures of 68° C. and higher.

Chemical Stability

Generation of Stressed DR5 Antibody Samples:

To test the chemical stability of DR5 antibodies, stressed samples were generated and functionally characterized with regard to DR5 binding. High-pH stress induces—among others—deamidation of reactive Asn hotspots, whereas at pH 6.0 e.g. succinimide formation from reactive Asn and Asp residues may be induced. For high-pH stress, samples were transferred in 20 mM Na-phosphate, pH 8.0 and incubated for 5 days at 40° C. For low-pH stress, samples were transferred into in 20 mM His/HisCl, 140 mM NaCl, pH 6.0 and incubated for 3 weeks at 40° C. A control sample was kept at −80° C.

Analysis of Stressed DR5 Antibody Samples:

A BIAcore 3000 instrument (GE Healthcare) was used with a CM5 sensor mounted into the system. The sensor was preconditioned by a 1 min injection at 100 µl/min of 0.1% SDS, 50 mM NaOH, 10 mM HCl and 100 mM H3PO4. System buffer was 10 mM HEPES pH 7.4, 150 mM NaCl, 0.05% TWEEN 20. The sample buffer was the system buffer supplemented with 1 mg/mL carboxymethyldextran (Sigma). An anti-human antibody capture system was established on the biosensor surface. 8000 relative response units of a goat anti-human Fcγ fragment-specific polyclonal antibody (Jackson Laboratories) were immobilized according to the manufacturer's instructions using EDC/NHS chemistry. The sensor was deactivated using 1M ethanolamine.

20 nM of the respective antibody sample were captured for 1 min at a flow rate of 10 µl/min. As a reference, 20 nM polyclonal human normal IgG (Roche, Ident. 11717570) were captured on the reference flow cell 1 and subtractive signals were monitored.

In another embodiment, the analyte was injected at 100 µl/min for 2 min association time at 0 nM and 500 nM. The complex dissociation was monitored for 5 min.

TABLE 27

Relative active concentrations of humanized variants
of DR5TAA-0011 before and after stress test

| Construct | SEQ ID No VH/VL | Initial (defined) | pH 6.0 2 weeks 40° C. Relative active concentration as compared to the initial state | pH 7.4 2 we 40° C. Relative active concentration as compared to the initial state |
|---|---|---|---|---|
| DR5TAA-0071 | 26/24 | 100% | 103% | 98% |
| DR5TAA-0067 | 23/24 | 100% | 107% | 107% |
| DR5TAA-0074 | 23/31 | 100% | 103% | 100% |
| DR5TAA-0073 | 26/30 | 100% | 104% | 101% |
| DR5TAA-0068 | 26/31 | 100% | 103% | 101% |
| DR5TAA-0072 | 26/32 | 100% | 105% | 101% |
| DR5TAA-0066 | 23/30 | 100% | 102% | 100% |
| DR5TAA-0075 | 23/29 | 100% | 102% | 99% |

The system was regenerated at 30 µl/min by a 1 min injection of 10 mM glycine buffer pH 1.5 followed by a two consecutive 1 min injections of 10 mM glycine buffer pH 1.7. Kinetic parameters were evaluated using the Biacore Evaluation Software according to the manufacturer's instructions.

The antibody/antigen complex half-life was calculated in minutes according to the formula ln(2)/(60*kd). The Molar Ratio was calculated: MW (antibody)/MW (antigen)*BL (antigen)/CL (antibody).

Data report points were recorded shortly before the end of the antibody injection (antibody capture level, CL) as well as shortly before the analyte (Binding Late, BL) injection. Capture Level (CL) and Binding Late (BL) response signal heights were used to characterize the antibody binding performance. The relative binding quotient was calculated BL/CL. A quotient was formed from the relative binding quotient of an antibody sample versus a non-stress impacted antibody sample (relative active binding).

Results are shown in Table 27. Humanized variants of DR5TAA-0011 were subjected to stress test. None of the humanized variants showed impaired binding to human DR5 as compared to the non-stressed initial material.

Example 35: Materials and Methods

Unless otherwise mentioned the following materials and methods have been used in the experiments outlined above.

Recombinant DNA Technologies

All antibody and antigen expression vectors were generated using standard recombinant DNA technology as described in Sambrook, J. et al., Molecular cloning: A laboratory manual; Cold Spring Harbor Laboratory Press, Cold Spring Harbor, N.Y., 1989. Molecular biological reagents were used according the manufacturer's recommendations. Genes or gene fragments were either amplified by polymerase chain reaction (PCR) or generated from synthetic oligonucleotides at Geneart AG (Regensburg, Germany) by automated gene synthesis. PCR-amplified or subcloned DNA fragments were confirmed by DNA sequencing (Synergene GmbH, Switzerland). Plasmid DNA was transformed into and amplified in suitable *E. coli* host strains for preparation of transfection-grade plasmid DNA using standard Maxiprep kits (Qiagen). For production of the bispecific molecules HEK293 EBNA cells were transfected with plasmids encoding the respective genes using a standard polyethlenimine (PEI) based method. The used plasmid ratio of the three expression vectors was 1:1:1. Transfected cells were cultivated for 7 days before supernatants were harvested for purification.

Transfection HEK293 EBNA Cells

All (bispecific) antibodies and antigens (if not obtained from a commercial source) used herein were transiently produced in HEK 293 EBNA cells using a PEI mediated transfection procedure for the required vectors as described below.

HEK293-EBNA cells are cultivated in suspension serum free in CD CHO culture medium. For the production in 500 ml shake flask 400 million HEK293-EBNA cells are seeded 24 hours before transfection. For transfection cells are centrifuged for 5 min by 210×g, supernatant is replaced by pre-warmed 20 ml CD CHO medium. Expression vectors are mixed in 20 ml CD CHO medium to a final amount of 200 m DNA. After addition of 540 µl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 µm filter) and sodium azide in a final concentration of 0.01% w/v is added, and kept at 4° C. After production the supernatants were harvested and the antibody containing supernatants were filtered through 0.22 µm sterile filters and stored at 4° C. until purification.

Purification: Standard+ProtA Beads

The proteins were produced by transient expression in HEK293 EBNA cells. All bispecific molecules described here were purified in two steps using standard procedures, such as proteinA affinity chromatography (Äkta Explorer) and size exclusion chromatography (Superdex 200).

The supernatant was adjusted to pH 8.0 (using 2 M TRIS pH 8.0) and applied to Mabselect Sure resin (GE Healthcare) packed in a Tricorn™ 5/50 column (GE Healthcare, column volume (cv)=1 ml) equilibrated with buffer A (50 mM sodiumphosphate, pH 7.0, 250 mM NaCl). Unbound protein was removed by washing with at least 5 column volumes (CV) of buffer A. The protein of interest was eluted in a linear pH-gradient from 0-100% buffer B (50 mM sodium-phosphate, pH 7.0, 1 M NaCl) over 12 CV. Finally, an additional step was included with 10 CV of buffer B followed by an equilibration step of 5 CV buffer A. Fractions containing the protein of interest were pooled and the pH was gradually adjusted to pH 6.0 (using 2 M TRIS pH 8.0). Samples were concentrated to 0.5-2 ml using ultra-concentrators (Vivaspin 15R 30.000 MWCO HY, Sartorius) and subsequently applied to a HiLoad™ 16/60 Superdex™ 200 preparative grade column (GE Healthcare) equilibrated with 20 mM Histidine, pH 6.0, 140 mM NaCl, 0.01% Tween-20. The aggregate content of eluted fractions was analyzed using a TSKgel G3000 SW XL analytical size-exclusion column (Tosoh) equilibrated in 25 mM K2HPO4, 125 mM NaCl, 200 mM L-Arginine Monohydrocloride, 0.02% (w/v) NaN3, pH 6.7 at 25° C. Fractions containing less than 2% oligomers were pooled and concentrated to a final concentration of 1-1.5 mg/ml using ultra concentrators (Vivaspin 15R 30.000 MWCO HY, Sartorius). Purified proteins were frozen in liquid N2 and stored at −80° C.

For a fast and high throughput purification, supernatants were neutralized using $\frac{1}{40}^{th}$ column of 2M Tris-HCl pH8 and incubated with ProteinA Sepharose Fast Flow beads (GE Healthcare Cat No. 17-5138-01)) for 19 h at 4° C. end over end. The supernatant/bead mixture was then passed over an empty, equilibrated PD-10 column (GE Healthcare Cat No. 17-0435-01) by gravity flow. The retained beads were washed twice with binding buffer (10 mM Tris, 50 mM glycine, 100 mM NaCl, pH 8.0) and the antibody eluted with a low pH step (10 mM Tris, 50 mM glycine, 100 mM NaCl, pH2.5). Finally the eluted protein was neutralized by addition of $\frac{1}{40}^{th}$ volume of 2M Tris-HCl pH8.0. The protein concentration of purified antibodies was calculated from the measured absorbance at 280 nm and the molar extinction coefficient calculated from the amino acid sequence. The aggregate content of the antibody sample was analysed using a Zorbax GF-250 analytical size exclusion column (Agilent Cat No PSMO 845006) equilibrated in running buffer (200 mM sodium phosphate, 0.02% sodium azide pH 7.0) at 25° C.

FACS Binding Analysis

All used target cell lines were analyzed for relative expression levels of tumor-related antigens and DR5 death receptors before apoptosis assays were performed.

Number and viability of cells was determined. For this, adherently growing cells were detached with cell dissociation buffer (Gibco-Invitrogen #13151-014). Cells were harvested by centrifugation (4 min, 400×g), washed with FACS buffer (PBS/0.1% BSA) and the cell number was adjusted to $1.111 \times 10^6$ cells/ml in FACS buffer. 180 µl of this cell suspension was used per well of a 96 well round bottom plate, resulting in $2 \times 10^5$ cell per well. The cells were incubated for 30 min at 4° C. with the first antibody in appropriate dilution. Then the cells were harvested by centrifugation (4 min, 400×g), supernatant was completely removed and cells were washed once with 150 µl of FACS buffer. The cells were resuspended in 12 µl diluted secondary antibody (in case unlabelled first antibody was used) or FACS buffer for 30 min at 4° C. in the dark. After two washing steps with FACS buffer cells were resuspended in 200 µl of FACS buffer and analyzed in a HTS FACSCanto II (BD, Software FACS Diva). Alternatively the cells could be fixed with of 200 µl of 2% PFA (paraformaldehyde) in FACS buffer for 20 min at 4° C. and analyzed later. All assays were performed in triplicates.

TABLE 28

Antibodies and concentrations for FACS binding analysis

| Antibody | Source | Description | Conc. [mg/ml] | Conc. in test [µg/ml] |
|---|---|---|---|---|
| 1. First antibodies | | | | |
| anti hu DR5 (TRAIL R2) | R&D #MAB631 | mu IgG1, clone 71903 | 0.5 | 5-10 |
| Drozitumab | in house | hu IgG1 | 3.8 | 10 |
| 4G8 | in house | hu IgG1 | 20.5 | 15 |
| mouse anti-human FAP | Calbiochem #OP188 | mu IgG1 | 1 | 10 |
| Drozitumab-scFab-FAP | in house | | 1.34 | 25 |
| Drozitumab-X-FAP_A | | | 1.44 | 25 |
| Drozitumab-X-FAP_B | | | 0.83 | 25 |
| 5E11_28H1_N-term VHVL | | | 2.55 | as indicated |

TABLE 28-continued

Antibodies and concentrations for FACS binding analysis

| Antibody | Source | Description | Conc. [mg/ml] | Conc. in test [µg/ml] |
|---|---|---|---|---|
| 5E11_28H1_N-term CH1CL | | | 1.12 | as indicated |
| 5E11_28H1_C-term CH1CL | | | 4.0 | as indicated |
| 2. Secondary antibodies: | | | | |
| PE-conjugated AffiniPure F(ab')2 Fragment goat anti-human IgG Fcg Fragment Specific | Jackson Immuno Research Lab # 109-116-170 | | | 1:20 dilution |
| FITC-conjugated F(ab')2 goat anti-mouse IgG Specific | Serotec # STAR105F | | | 1:20 dilution |
| FITC-conjugated AffiniPure F(ab')2 Fragment goat anti-human IgG Fcg Fragment Specific | Jackson Immuno Research Lab # 109-096-098 | | | 1:20 dilution |

Biacore Analysis (Surface Plasmon Resonance, SPR)

Binding of the various anti-DR5 binders as IgG or in a bispecific format was assessed by surface plasmon resonance (SPR). All SPR experiments were performed on a Biacore T100 at 25° C. with HBS-EP as running buffer (0.01 M HEPES pH 7.4, 0.15 M NaCl, 3 mM EDTA, 0.005% Surfactant P20, Biacore, Freiburg/Germany).

For the determination of the species cross-reactivity of the DR5 binders, biotinlyated DR5 from mouse, human and cynomolgus were directly coupled to different flow cells of a Streptavidin (SA) sensor chip with an immobilization level of approximately 300 RU each. The various DR5 binders as IgGs were injected at a concentration of 500, 100 and 25 nM for 60 s with a flow rate of 30 ul/min, followed by a dissociation phase of 90 s. Bulk refractive index differences were corrected for by subtracting the response obtained on reference flow cell, where no protein was immobilized.

In a second experiment, the specificity of the DR5 binders was determined by immobilizing huDR4Fc, huDcR1Fc, huDcR2Fc and rhuOPGFc to a CM5 sensor chip by amine coupling. Immobilisation levels were between 100 and 400 RU. Each binder was passed over the different flow cells at a concentration of 500, 100 and 25 nM for 60 s with a flow rate of 30 µl/min and the dissociation phase monitored for 90 s. Bulk refractive index differences were corrected for by subtracting the response obtained on the reference flow cell, where no protein was immobilized.

Further, the avidity of the IgGs as well as the 2+2 formats was measured on a CM5 chip with immobilized human and cynomolgus DR5 ECD (immobilization levels were around 100 RU). Each construct or IgG was passed over the different flow cells at a concentration between 500-0.97 nM in 1:2 dilution steps for 90 s at 30 µl/min. The dissociation was analysed for 120 s. Bulk refractive index differences were corrected for by subtracting the response obtained on the reference flow cell, where no protein was immobilized. Kinetic constants were calculated using the Biacore T100 Evaluation Software (vAA, Biacore AB, Uppsala/Sweden), to fit rate equations for 1:1 Langmuir binding by numerical integration either as kinetic analysis or steady state analysis.

Affinity was assessed using a capture format where either an anti-human Fab or anti-human Fc antibody (Biacore, Freiburg/Germany) was directly coupled on a CM5 chip at pH 5.0 using the standard amine coupling kit (Biacore, Freiburg/Germany). The immobilization level was about 8,000-10000 RU. DR5 binders in an IgG or 2+2 format were captured at a concentration of 50 or 30 nM respectively for 60 s at a flow rate of 30 µl/min. Injection of human or cynomolgus DR5 in a concentration range from 500-0.975 nM (cynomolgus DR5) or 1000-0.975 nM (huDR5) in 1:2 dilution steps for 120 s at 30 µl/min was carried out for the 2+2 format. Affinity of the IgGs was only measured for huDR5 at a concentration from 2000-20 nM in 1:3 dilution steps. Dissociation was evaluated over a period of 120 s. Bulk refractive index differences were corrected for by subtracting the response obtained on reference flow cell, where no protein was immobilized. Kinetic constants were calculated using the Biacore T100 Evaluation Software (vAA, Biacore AB, Uppsala/Sweden), to fit rate equations for 1:1 Langmuir binding by numerical integration either as kinetic analysis or steady state analysis.

Epitope binning was measured in two different formats, either with a classical sandwich assay or with a tandem approach. In the classical sandwich assay, each DR5 binders is directly immobilized by amine coupling to one flow cell on the CM5 chip surface with a target immobilization level of around 500 RU. Subsequently, huDR5 is passed over each flow cell at a concentraion of 500 nM for 60 s (flow rate 30 µl/min) followed by an injection of another DR5 binder at a concentration of 30 nM for 60 s (flow rate 30 µl/min). The dissociation is monitored over a period of 60 s with the same flow rate. Injection of the same DR5 binder than the immobilized one is used as a control as this should not lead to a response increase if all DR5 is bound by the immobilized binder.

In the tandem approach, huDR5ECD was immobilized on a CM5 chip with a final response of 250 RU. The first DR5 binder was then passed over the flow cell at a concentration of 20 nM for 90 s, followed by the injection of a second DR5 binder for 90 s. The dissociation was monitored over a period of 90 s. The flow rate was 30 µl/min for all steps. If the two binders recognize a different epitope, one could observe an increase in the response units. Injection of the same DR5 binder was used as a control to confirm that all DR5 molecules were saturated by the first injection and no additional binding to the same epitope can occur.

To further determine if any of the binders are ligand blocking, rhuTRAIL (Peprotech Cat No. 310-04) was immobilized on a CM5 chip by amine coupling with an immobilization level of 2000 RU. huDR5 Fc or huDR5 ECD were complexed with each DR5 binder to be tested (100 nM DR5 with 500 nM IgG) and the complex passed over the flow cell for 90 s with a flow rate of 50 µl/min. The dissociation was assessed over a period of 120 s. In addition, a classical sandwich assay was used, where huDR5Fc or huDR5 ECD was injected first at 100 nM followed by an injection of each DR5 binder at 500 nM. Contact times were 60 s for DR5 and 90 s for the IgGs with a flow rate of 30 µl/min. The dissociation step was carried out for 90 s. Binders which could bind to TRAIL, in addition to DR5, were considered to be non-ligand blocking whereas binders which did not show any additional bind as ligand blocking.

Simultaneous binding of the various DR5 binders in a 2+2 format was confirmed on a SA chip containing immobilized huDR5Fc biotin (immobilisation level around 1000 RU). In a first step, the 2+2 construct was injected for 90 s followed by an injection of either human or murine FAP at a concentration of 500 or 100 nM for 90 s. The dissociation was monitored for 60 s. The flow rate for all steps was 30 µl/min. Simultaneous binding was considered to be true if an additional increase in response units was observed upon injection of human or murine FAP.

Epitope binning was measured in two different formats either a classical sandwich assay or with a tandem approach. In the classical sandwich assay each DR5 binders gets directly immobilized by amine coupling to one flow cell on the CM5 chip surface with a target immobilization level of around 500 RU. Then, huDR5 is passed over each flow cell at a conc. of 500 nM for 60 s (flow rate 30 ul/min) followed by an injection of another DR5 binder at a concentration of 30 nM for 60 s (flow rate 30 ul/min). The dissociation is monitored over a period of 60 s with the same flow rate. Injection of the same DR5 binder than the immobilized one is used as a control as this should not lead to a response increase if all DR5 is bound by the immobilized binder.

In the tandem approach huDR5ECD was immobilized on a CM5 chip with a final response of 250 RU. The first DR5 binder is then passed over the flow cell at a concentration of 20 nM for 90 s, followed by the injection of a second DR5 binder for 90 s. The dissociation was monitored over a period of 90 s. The flow rate was 30 ul/min for all steps. If the two binders recognize a different epitope, one could observe an increase in the response units. Injection of the same DR5 binder was used as a control to confirm that all DR5 molecules were saturated by the first injection and no additional binding to the same epitope can occur.

To further determine if any of the binders are ligand blocking rhuTRAIL (Peprotech Cat No. 310-04) was immobilized on a CM5 chip by amine coupling with an immobilisation level of 2000 RU. huDR5 Fc or huDR5 ECD were complexed with each DR5 binder to be tested (100 nM DR5 with 500 nM IgG) and the compley was passed over the flow cell for 90 s with a flow rate of 50 ul/min. The dissociation was assessed over a period of 120 s. In addition, a classical sandwich assay was used, where huDR5Fc or huDR5 ECD was injected first at 100 nM followed by an injection of each DR5 binder at 500 nM. Contact times were 60 s for DR5 and 90 s for the IgGs with a flow rate of 30 ul/min. The dissociation step was carried out for 90 s. Binders which could bind in addition of DR5 to TRAIL were considered to be non-ligand blocking whereas binders which did not show any additional bind as ligand blocking.

Simultaneous binding of the various DR5 binders in a 2+2 format was confirmed on a SA chip containing immobilized huDR5Fc biotin (immobilisation level around 1000 RU). In a first step, the 2+2 construct was injected for 90 s followed by an injection of either human or murine FAP at a concentration of 500 or 100 nM for 90 s. The dissociation was monitored for 60 s. The flow rate for all steps was 30 µl/min. Simultaneous binding was considered to be true if an additional increase in response units was observed upon injection of human or murine FAP.

DNA Fragmentation ELISA

For determination of induced apoptosis the Cell Death Detection ELISA$^{PLUS}$ kit from Roche was used. In short, $10^4$ FAP expressing GM05389 cells per well of a 96-well plate (after detaching, and determination of cell number and viability) were seeded in 200 µl appropriate medium and were incubated over night at 37° C. in a 5% $CO_2$ atmosphere. The next day the medium was replaced by 100 µl of fresh medium containing the apoptosis inducing antibodies, control antibodies and other controls in appropriate concentrations:

The bispecific antibodies and IgGs were used in a final concentration of 0.7 and 7 nM or as indicated; cross-linking antibodies were used at the same molarity as the primary antibodies. After addition of the antibodies $10^4$ apoptosis sensitive tumour cells were added per well.

The cells were incubated for 24 hrs at 37° C., 5% CO2 to allow induction of apoptosis. The cells were harvested by centrifugation (10 min, 200×g) and incubated for 1 h at room temperature in 200 µl of lysis buffer (supplied by the kit). Intact DNA and the lysed cells were sedimented by centrifugation (10 min, 200×g) and 20 µl of the supernatant containing the fragmented DNA was analyzed according to the manufacturer's recommendations for induction of apoptosis.

Inhibition of Proliferation (CellTiterGlo)

For Cell Viability assays 4,000 tumor cells/well (in 75 µl volume) were seeded in black, clear bottom 96 well plates (BD Falcon cat #BD353220) and incubated overnight at 37° C. in a humidified, 5% CO2 atmosphere. Then 25 µl 4×DR5 binder plus/minus rabbit-Fc (equal nano molar of DR5 binders and Fc) with 6 concentrations of 2.5×serial dilutions were added. After incubation at 37° C. with 5% CO2 for 48 hours 100 µl CellTiter-Glo reagent was added to each well and mixed well. After incubation for another 10 minutes at room temperature results cell viability was determined with a Spectra Max M5 plate reader under luminescence settings.

Induction of Caspase 8 (Caspase Glo)

For Caspase 8 activation assays 10,000 cancer cells/well in 75 µl were seeded in opaque white 96 well plates (BD Falcon cat #BD353296) and incubated at 37° C. in a humidified incubator with 5% $CO_2$ overnight. Then 25 ul 4×DR5 binders plus/minus anti-Fc were added (equimolar ratios of DR5 binders and anti Fc) with 6 concentrations of 2.5× serial dilutions. After 3 hours incubation at 37° C. with 5% $CO_2$ 100 µl caspase 8 substrate in lysis buffer was added to each well. After additional incubation for 30 minutes at 37° C. the results were red in a Spectra Max M5 plate reader under luminescence settings.

FRET Assays

The binding of bispecfic molecules on cells was determined using a time-resolved fluorescence resonance energy transfer (TR-FRET) assay (called TagLite). Hek EBNA cells were grown to 60-80% confluency and transfected with plasmid DNA encoding for DR5 ECD fused to a SNAP Tag and the MalE™. Briefly, 2 µg DNA was mixed with 4 ml OptiMEM medium and 30 µl Lipofectamine 2000 (Invitrogen Cat No. 11668-019). The mixture was incubated for 20 min at RT. In the meantime, the adherent Hek EBNA cells grown in a T75 flask were washed with 5 ml D-PBS prior to adding the transfection mixture and culture medium (6 ml) (DMEM, 10% FCS, glutamax, Non-essential amino acids). The cells were then incubated overnight in a humidified incubator (5% CO2) at 37° C. Cells were washed with 5 ml D-PBS, followed by the addition of a mixture of 5 ml TagLite buffer (Cisbio Cat No.) containing 100 nM SNAP-Lumi4-Tb (Cisbio Cat No.). This resulted in attachment of the fluorescent dye to the SNAP Tag fused to the DR5. After an incubation time of 1 h at 37° C., the cells were washed with TagLite buffer to remove unbound dye. Subsequently, the labelling efficiency was checked by measuring the fluorescent signal at 620 nm (excitation 343 nm) of 10000 cells in a 384 well format (Reader, Victor, Perkin Elmer). Cells were then frozen in culture medium substituted with 10% DMSO and stored at −80° C.

To carry out a binding assay, pre-labeled cells were thawed, washed and 1000 cells per well mixed with 5 µl construct at a final concentration ranging from 50-0.097 nM (1:2 dilution steps) and 5 µl anti-huFc-d2 labeled (final concentration 150 nM). The fluorescent signal was measured at 620 nm for the fluorescent donor (Terbium) and at 665 nm for the fluorescent acceptor dye after 0 h, 1 h and 3 h incubation at RT. The ratio of 665/620*1000 was calculated, and the reference (cells with 150 nM anti-huFc-d2) was subtracted. For KD determination the results were analysed in Graph Pad Prism with one site fit-specific binding.

Determination of the Thermal Stability by Dynamic Light Scattering (DLS)

Thermal stability of the protein is monitored by Dynamic Light Scattering (DLS). 30 µg of filtered protein sample with a protein concentration of 1 mg/ml is applied in duplicate to a Dynapro plate reader (Wyatt Technology Corporation; USA). The temperature is ramped from 25 to 75° C. at 0.05° C./min, with the radius and total scattering intensity being collected.

TABLE 29

Names and Aliases of DR5 Clones and Bispecific Constructs

| DR5-FAP bispecific construct | DR5 Clone (SEQ ID VH/VL) | FAP Clone (SEQ ID VH/VL) | Format | Complete antibody sequence | Scetch of Format |
|---|---|---|---|---|---|
| DR5TAA-0061 | DR5TAA-0011 (SEQ ID NO.: 88/89) | 4B9 (SEQ ID NO.: 39/40) | 1 + 1 | SEQ ID NOs 280, 281, 282, 283 | See FIG. 25 D |
| DR5TAA-0030 | 5E11 (SEQ ID NO.: 7/8) | 28H1 (SEQID NO.: 15/16) | 2 + 2 | SEQ ID NOs 131, 132, 124 | See FIG. 28 A |
| DR5TAA-0032 | DR5TAA-0005 (SEQ ID NO.: 41/46) | 28H1 (SEQ ID NO.: 15/16) | 2 + 2 | SEQ ID NOs 284, 285, 286 | See FIG. 28 A |
| DR5TAA-0033 | DR5TAA-0011 (SEQ ID NO.: 88/89) | 28H1 (SEQ ID NO.: 15/16) | 2 + 2 | SEQ ID NOs 287, 288, 289 | See FIG. 28 A |
| DR5TAA-0034 | DR5TAA-0013 (SEQ ID NO.: 68/71) | 28H1 (SEQ ID NO.: 15/16) | 2 + 2 | SEQ ID NOs 290, 291, 292 | See FIG. 28 A |
| DR5TAA-0035 | DR5TAA-0016 (SEQ ID NO.: 82/85) | 28H1 (SEQ ID NO.: 15/16) | 2 + 2 | SEQ ID NOs 293, 294, 295 | See FIG. 28 A |
| DR5TAA-0036 | DR5TAA-0019 (SEQ ID NO.: 74/78) | 28H1 (SEQ ID NO.: 15/16) | 2 + 2 | SEQ ID NOs 296, 297, 298 | See FIG. 28 A |
| DR5TAA-0037 | 22E9 (SEQ ID NO.: 100/101) | 28H1 (SEQ ID NO.: 15/16) | 2 + 2 | SEQ ID NOs 124, 125, 126 | See FIG. 28 A |
| DR5TAA-0038 | 21H3 (SEQ ID NO.: 102/103) | 28H1 (SEQ ID NO.: 15/16) | 2 + 2 | SEQ ID NOs 127, 128, 124 | See FIG. 28 A |
| DR5TAA-0039 | 20F2 (SEQ ID NO.: 106/107) | 28H1 (SEQ ID NO.: 15/16) | 2 + 2 | SEQ ID NOs 129, 130, 124 | See FIG. 28 A |
| DR5TAA-0055 | 5E11 (SEQ ID NO.: 7/8) | 28H1 (SEQ ID NO.: 15/16) | 2 + 2 | SEQ ID NOs 133, 132, 124 | See FIG. 28 A |
| DR5TAA-0057 | 5E11 (SEQ ID NO.: 7/8) | 28H1 (SEQ ID NO.: 15/16) | 2 + 2 | SEQ ID NOs 134, 132, 124 | See FIG. 28 A |
| DR5TAA-0058 | 5E11 (SEQ ID NO.: 7/8) | 4B9 (SEQ ID NO.: 39/40) | 2 + 2 | SEQ ID NOs 262, 263, 132 | See FIG. 28 A |
| DR5TAA-0077 | 5E11 (SEQ ID NO.: 7/8) | 28H1 (SEQ ID NO.: 15/16) | 2 + 2 | SEQ ID NOs 135, 136, 137 | See FIG. 28 C |
| DR5TAA-0078 | 5E11 (SEQ ID NO.: 7/8) | 28H1 (SEQ ID NO.: 15/16) | 2 + 2 | SEQ ID NOs 138, 139, 137 | See FIG. 28 D |

TABLE 29-continued

Names and Aliases of DR5 Clones and Bispecific Constructs

| DR5-FAP bispecific construct | DR5 Clone (SEQ ID VH/VL) | FAP Clone (SEQ ID VH/VL) | Format | Complete antibody sequence | Scetch of Format |
|---|---|---|---|---|---|
| DR5TAA-0081 | 5E11 (SEQ ID NO.: 7/8) | 28H1 (SEQ ID NO.: 15/16) | 2 + 2 | SEQ ID NOs 278, 132, 279 | See FIG. 28 F |
| DR5TAA-0117 | DR5TAA-0067 (SEQ ID NO.: 23/24) | 28H1 (SEQ ID NO.: 15/16) | 2 + 2 | SEQ ID NOs 299, 300, 301 | See FIG. 28 A |
| DR5TAA-0118 | DR5TAA-0071 (SEQ ID NO.: 26/24) | 28H1 (SEQ ID NO.: 15/16) | 2 + 2 | SEQ ID NOs 302, 303, 281, 282, 283 | See FIG. 28 A |
| DR5TAA-0119 | DR5TAA-0075 (SEQ ID NO.: 23/29) | 28H1 (SEQ ID NO.: 15/16) | 2 + 2 | SEQ ID NOs 305, 306, 307 | See FIG. 28 A |

| DR5 Antibody Clone Name | DR5 Antibody Clone Alias |
|---|---|
| DR5TAA-0005 | „0005" or „039" |
| DR5TAA-0006 | „0006" or „058" |
| DR5TAA-0010 | „0010" or „481" |
| DR5TAA-0013 | "0013" or "298" |
| DR5TAA-0019 | "0019" or "461" |
| DR5TAA-0016 | "0016" or "422" |
| DR5TAA-0011 | "0011" or "174" |

Example 36: In Vivo Antitumor Efficacy of DR5-FAP Bispecific Antibody Comprising Newly Isolated DR5 Binder 5E11 in Combination with 28H1 FAP CrossFab The in vivo antitumor efficacy of the bispecific antibody DR5-FAP (VH SEQ ID NO.:7, VL SEQ ID NO.: 8) was demonstrated in cell and fragment based patient derived (PDX) models of various tumor origin (e.g. CRC and pancreatic cancer) transplanted on nude mice. As example data are shown for the CRC xenograft model DLD-1 (cell line based, co-injection model) and Co5896 (fragment based).

Test Agents

The bispecific antibody DR5-FAP (DR5 binder: VH SEQ ID NO.:7, VL SEQ ID NO.: 8, FAP binder: VH SEQ ID NO.:15, VL SEQ ID NO.: 16) was provided as stock solution from Roche, Penzberg, Germany. Antibody buffer included histidine. Antibody solution was diluted appropriately in buffer from stock prior injections.

Cell Lines and Culture Conditions

DLD-1 human CRC cells were originally obtained from ATCC. The tumor cell line was routinely cultured in DMEM high glucose medium with 1.0 mM Sodium pyruvate supplemented with 10% fetal bovine serum, 2.0 mM L-glutamine, 10 mM HEPES at 37° C. in a water-saturated atmosphere at 5% $CO_2$. Culture passage was performed with trypsin/EDTA 1× splitting every third day. Additionally murine fibroblasts NIH3T3 were purchased from ATCC and cultured in DMEM high glucose with 1.0 mM Sodium pyruvate, FCS 10% and L-Glutamine 2.0 mM.

Patient-Derived Xenograft Model (PDX)

The CRC tumor xenograft Co5896 was originally obtained from patients and passaged approximately three to five times until establishment of stable growth patterns. For the subsequent in vivo studies Co5896 tumor fragments were obtained from xenografts in serial passage in nude mice. After removal from donor mice, tumors were cut into fragments (4-5 mm diameter) and placed in PBS until subcutaneous implantation. Mice under isofluorane anesthesia received unilateral, subcutaneous tumor implants in the flank.

Animals

Nude mice were purchased from breeder (e.g. Charles River, Sulzfeld, Germany) and maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum.

Monitoring

Animals were controlled daily for clinical symptoms and detection of adverse effects. For monitoring throughout the experiment body weight of animals was documented.

Treatment of Animals

Animal treatment started after animal randomisation after cell or fragment transplantation when median tumor size was about 100-200 mm³. Antibody was administered as single agent at 10 or 30 mg/kg i.v. once or twice weekly for several weeks depending on the model. The corresponding vehicle was administered on the same days.

Antibody Efficacy

DLD-1 CRC Co-Injection Cell Line Based Xenograft Model

DLD-1 CRC xenograft bearing mice were treated with bispecific antibody DR5-FAP (DR5 binder: VH SEQ ID NO.:7, VL SEQ ID NO.: 8, FAP binder: VH SEQ ID NO.:15, VL SEQ ID NO.: 16) from study day 9 to 20 at dosages of 10 and 1.0 mg/kg for 4 times. As a result, treatment with bispecific antibody DR5-FAP (DR5 binder: VH SEQ ID NO.:7, VL SEQ ID NO.: 8, FAP binder: VH SEQ ID NO.:15, VL SEQ ID NO.: 16) showed dose-related significant anti-tumor efficacy with strong anti-tumor efficacy against s.c. DLD-1 xenografts. The Tumor Growth Inhibition (TGI) was calculated at 89% (10 mg/kg) and 79% (1.0 mg/kg), respectively. In contrast, after treatment with DR5 Fc mutant antibody drozitumab PG, LALA (10 mg/kg, once weekly) no anti-tumor efficacy was noticed (see FIG. 48). Similar results were obtained with high FAP content (Co-injection study with DLD-1/NIH3T3 fibroblasts; Ratio 80/20, FIG. 48) and low FAP content (Co-injection study with DLD-1/MRC5 fibroblasts; Ratio 30/70, data not shown).

Co5896 CRC Fragment Based Patient Derived Xenograft Model (PDX)

Co5896 CRC xenograft bearing mice were treated with bispecific antibody DR5-FAP (DR5 binder: VH SEQ ID NO.:7, VL SEQ ID NO.: 8, FAP binder: VH SEQ ID NO.:15, VL SEQ ID NO.: 16) from study day 18 to 34 at dose of 30 mg/kg for 6 times. As a result, treatment with bispecific antibody DR5-FAP (DR5 binder: VH SEQ ID NO.:7, VL SEQ ID NO.: 8, FAP binder: VH SEQ ID NO.:15, VL SEQ ID NO.: 16) showed significant anti-tumor efficacy with strong anti-tumor efficacy against s.c. Co5896 patient-derived xenografts. The Tumor Growth Inhibition (TGI) was calculated at 76% (see FIG. 49). Similar results were obtained in other CRC cell models (data not shown).

Example 36: FAP Prevalence in Human Tumors

The prevalence of FAP in human tumors was evaluated by IHC to get an understanding on possible clinical use of bispecific DR5-FAP antibody.

Rat anti-human Seprase antibody (IgG2a, clone D8) from Vitatex (MABS1001) was used to immunostain 2.5 μm FFPET sections from various tumour indications on the Ventana Benchmark XT. Sections were subjected to standard CC1 treatment followed by antibody incubation for 60' at 37° C. at a concentration of 5 μg/mL in Dako antibody diluent (S3022) and positive staining was detected using the Ultraview DAB detection system (Ventana #760-4456). Matched isotype antibody from Abcam (ab18450) was used as the negative control.

FAP+ stromal infiltrate was present in human tumors of different indications including head and neck squamous cell carcinoma (HNSCC), breast cancer, colorectal cancer (CRC), pancreatic cancer (PAC), gastric cancer, non-small-cell lung carcinoma (NSCLC) and Mesothelioma marking potentially interesting clinical indications for a bispecific DR5-FAP antibody (Table 30).

TABLE 30

FAP prevalence in human tumors

| Tumor Type | % cases with moderate to high grade of FAP$^+$ infiltrate | n of samples investigated |
|---|---|---|
| HNSCC | 90 | 10 |
| Breast Cancer | 77 | 105 |
| triple negative BC | 80 | 7 |
| CRC | 77 | 90 |
| PAC | 74 | 19 |
| Gastric Cancer | 68 | 28 |
| NSCLC | 66 | 90 |
| Mesothelioma | 60 | 10 |

Sequences

1. Amino Acid Sequences of Phage Display Derived DR5 Binders

| Description | Amino acid sequence | SEQ ID NO. |
|---|---|---|
| DR5 (22E9)_VH | EVQLLESGGGLVQPGGSLRLSCAAS GFTFSSYAMSWVRQAPGKGLEWVSA ISGSGGSTYYADSVKGRFTISRDNS KNTLYLQMNSLRAEDTAVYYCAKGV RISFDYWGQGTLVTVSS | 100 |
| DR5 (22E9)_CDRH1 | SYAMS | 1 |
| DR5 (22E9)_CDRH2 | AISGSGGSTYYADSVKG | 2 |
| DR5 (22E9)_CDRH3 | GVRISFDY | 96 |
| DR5 (22E9)_VL | EIVLTQSPGTLSLSPGERATLSCRA SQSVSSSYLAWYQQKPGQAPRLLIY GASSRATGIPDRFSGSGSGTDFTLT ISRLEPEDFAVYYCQQGSNQPVTFG QGTKVEIK | 101 |

-continued

| Description | Amino acid sequence | SEQ ID NO. |
|---|---|---|
| DR5 (22E9)_CDRL1 | RASQSVSSSYLA | 4 |
| DR5 (22E9)_CDRL2 | GASSRAT | 5 |
| DR5 (22E9)_CDRL3 | QQGSNQPVT | 99 |
| DR5 (21H3)_VH | EVQLLESGGGLVQPGGSLRLSCAAS GFTFSSYAMSWVRQAPGKGLEWVSA ISGSGGSTYYADSVKGRFTISRDNS KNTLYLQMNSLRAEDMAVYYCAKGA RVSFDYWGQGTLVTVSS | 102 |
| DR5 (21H3)_CDRH1 | SYAMS | 1 |
| DR5 (21H3)_CDRH2 | AISGSGGSTYYADSVKG | 2 |
| DR5 (21H3)_CDRH3 | GARVSFDY | 104 |
| DR5 (21H3)_VL | EIVLTQSPGTLSLSPGERATLSCRA SQSVSSSYLAWYQQKPGQAPRLLIY GASSRATGIPDRFSGSGSGTDFTLT ISRLEPEDFAVYYCQQGSQPPITFG QGTKVEIK | 103 |
| DR5 (21H3)_CDRL1 | RASQSVSSSYLA | 4 |
| DR5 (21H3)_CDRL2 | GASSRAT | 5 |
| DR5 (21H3)_CDRL3 | QQGSQPPIT | 105 |
| DR5 (20F2)_VH | EVQLLESGGGLVQPGGSLRLSCAAS GFTFSSYAMSWVRQAPGKGLEWVSA ISGSGGSTYYADSVKGRFTISRDNS KNTLYLQMNSLRAEDTAVYYCAKGV RKGFDYWGQGTLVTVSS | 106 |
| DR5 (20F2)_CDRH1 | SYAMS | 1 |
| DR5 (20F2)_CDRH2 | AISGSGGSTYYADSVKG | 2 |
| DR5 (20F2)_CDRH3 | GVRKGFDY | 108 |
| DR5 (20F2)_VL | EIVLTQSPGTLSLSPGERATLSCRA SQSVSSSYLAWYQQKPGQAPRLLIY GASSRATGIPDRFSGSGSGTDFTLT ISRLEPEDFAVYYCQQGESPPPTFG QGTKVEIK | 107 |
| DR5 (20F2)_CDRL1 | RASQSVSSSYLA | 4 |
| DR5 (20F2)_CDRL2 | GASSRAT | 5 |
| DR5 (20F2)_CDRL3 | QQGESPPPT | 109 |
| DR5 (5E11)_VH | EVQLLESGGGLVQPGGSLRLSCAAS GFTFSSYAMSWVRQAPGKGLEWVSA ISGSGGSTYYADSVKGRFTISRDNS KNTLYLQMNSLRAEDTAVYYCAKGV RVSFDYWGQGTLVTVSS | 7 |

-continued

| Description | Amino acid sequence | SEQ ID NO. |
|---|---|---|
| DR5 (5E11)_CDRH1 | SYAMS | 1 |
| DR5 (5E11)_CDRH2 | AISGSGGSTYYADSVKG | 2 |
| DR5 (5E11)_CDRH3 | GVRVSFDY | 3 |
| DR5 (5E11)_VL | EIVLTQSPGTLSLSPGERATLSCRA SQSVSSSYLAWYQQKPGQAPRLLIY GASSRATGIPDRFSGSGSGTDFTLT ISRLEPEDFAVYYCQQGTTHPITFG QGTKVEIK | 8 |
| DR5 (5E11)_CDRL1 | RASQSVSSSYLA | 4 |
| DR5 (5E11)_CDRL2 | GASSRAT | 5 |
| DR5 (5E11)_CDRL3 | QQGTTHPIT | 6 |
| DR5 (18F11)_VH | EVQLLESGGGLVQPGGSLRLSCAAS GFTFSSYAMSWVRQAPGKGLEWVSA ISGSGGSTYYADSVKGRFTISRDNS KNTLYLQMNSLRAEDAAVYYCAKGV RKKFDYWGQGTLVTVSS | 94 |
| DR5 (18F11)_CDRH1 | SYAMS | 1 |
| DR5 (18F11)_CDRH2 | AISGSGGSTYYADSVKG | 2 |
| DR5 (18F11)_CDRH3 | GVRKKFDY | 98 |
| DR5 (18F11)_VL | EIVLTQSPGTLSLSPGERATLSCRA SQSVSSSYLAWYQQKPGQAPRLLIY GASSRATGIPDRFSGSGSGTDFTLT ISRLEPEDFAVYYCQQGQLPPITFG QGTKVEIK | 95 |
| DR5 (18F11)_CDRL1 | RASQSVSSSYLA | 4 |
| DR5 (18F11)_CDRL2 | GASSRAT | 5 |
| DR5 (18F11)_CDRL3 | QQGQLPPIT | 97 |

2. Amino Acid Sequences of Non-Functional Phage Display Derived DR5 Binders (CDRH1=SEQ ID NO.:1, CDRH2=SEQ ID NO.:2, CDRL1=SEQ ID NO.:4 AND CDRL2=SEQ ID NO.:5)

| Name | Amino acid sequence | SEQ ID NO |
|---|---|---|
| DR5 (1B12)_CDR H3 | GFGYWYMDY | 266 |
| DR5 (1B12)_CDR L3 | QQSGRRQT | 267 |
| DR5 (19C12)_CDR H3 | SIFYSTLDY | 268 |
| DR5 (19C12)_CDR L3 | QQQGWFQT | 269 |
| DR5 (19D6)_CDR H3 | VLGYASYDY | 270 |
| DR5 (19D6)_CDR L3 | QQQGWSTT | 271 |

3. Amino Acid Sequences of FAP Binders

| Name | Amino acid sequence | SEQ ID NO |
|---|---|---|
| DR5 (20E3)_CDR H3 | GTRRGFDY | 272 |
| DR5 (20E3)_CDR L3 | QQGELTPVT | 273 |

| Name | Amino acid sequence | SEQ ID NO |
|---|---|---|
| FAP(28H1)_VH | EVQLLESGGGLVQPGGSLRLSCAAS GFTFSSHAMSWVRQAPGKGLEWVSA IWASGEQYYADSVKGRFTISRDNSK NTLYLQMNSLRAEDTAVYYCAKGWL GNFDYWGQGTLVTVSS | 15 |
| FAP(28H1)_VL | EIVLTQSPGTLSLSPGERATLSCRA SQSVSRSYLAWYQQKPGQAPRLLII GASTRATGIPDRFSGSGSGTDFTLT ISRLEPEDFAVYYCQQGVIPPTFG QGTKVEIK | 16 |
| FAP(4B9)_VH | EVQLLESGGGLVQPGGSLRLSCAAS GFTFSSYAMSWVRQAPGKGLEWVSA IIGSGASTYYADSVKGRFTISRDNS KNTLYLQMNSLRAEDTAVYYCAKGW FGGFNYWGQGTLVTVSS | 39 |
| FAP(4B9)_VL | EIVLTQSPGTLSLSPGERATLSCRA SQSVTSSYLAWYQQKPGQAPRLLIN VGSRRATGIPDRFSGSGSGTDFTLT ISRLEPEDFAVYYCQQGIMLPPTFG QGTKVEIK | 40 |

| Name | Amino acid sequence | SEQ ID NO |
|---|---|---|
| FAP (28H1)_CDRH1 | SHAMS | 9 |
| FAP (28H1)_CDRH2 | AIWASGEQYYADSVKG | 10 |
| FAP (28H1)_CDRH3 | GWLGNFDY | 11 |
| FAP (28H1)_CDRL1 | RASQSVSRSYLA | 12 |
| FAP (28H1)_CDRL2 | GASTRAT | 13 |
| FAP (28H1)_CDRL3 | QQGVIPPT | 14 |
| FAP (4B9)_CDRH1 | SYAMS | 33 |
| FAP (4B9)_CDRH2 | AIIGSGASTYYADSVKG | 34 |
| FAP (4B9)_CDRH3 | GWFGGFNY | 35 |
| FAP (4B9)_CDRL1 | RASQSVTSSYLA | 36 |
| FAP (4B9)_CDRL2 | VGSRRAT | 37 |
| FAP (4B9)_CDRL3 | QQGIMLPPT | 38 |

4. Amino acid sequences of bispecific molecules comprising conventional DR5 binders

| Name | Amino acid sequence | SEQ ID NO |
|---|---|---|
| Drozitumab_VH | EVQLVQSGGGVERPGGSLRLSCAASGFTFDDYAMSWVRQA PGKGLEWVSGINWQGGSTGYADSVKGRVTISRDNAKNSLY LQMNSLRAEDTAVYYCAKILGAGRGWYFDYWGKGTTVTV SS | 274 |
| Drozitumab_VL | SELTQDPAVSVALGQTVRITCSGDSLRSYYASWYQQKPGQA PVLVIYGANNRPSGIPDRFSGSSSGNTASLTITGAQAEDEADY YCNSADSSGNHVVFGGGTKLTVL | 110 |
| Drozitumab-3F2 VHVL-scFv (HC) pETR6606 | EVQLVQSGGGVERPGGSLRLSCAASGFTFDDYAMSWVRQA PGKGLEWVSGINWQGGSTGYADSVKGRVTISRDNAKNSLY LQMNSLRAEDTAVYYCAKILGAGRGWYFDYWGKGTTVTV SSASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDKTHTCPPCPAPEAAGGPSV FLFPPKPKDTLMISRTPEVTCVVVDVSHEDPEVKFNWYVDG VEVHNAKTKPREEQYNSTYRVVSVLTVLHQDWLNGKEYKC KVSNKALPAPIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GKSGGGGSGGGGSGGGGSGGGGSEVQLLESGGGLVQPGGS LRLSCAASGFITSSYAMSWVRQAPGKCLEWVSAISGSGGST YYADSVKGRFTISRDNSKNTLYLQMNSLRAEDTAVYYCAK GWFGFNYWGQGTLVTVSSGGGGSGGGGSGGGGSGGGGS EIVLTQSPGTLSLYPGERATLSCRASQSVTSSYLAWYQQKPG QAPRLLINVGSRRATGIPDRFSGSGSGTDFTLTISRLEPEDFA VYYCQQGIMLPPTFGCGTKVEIK | 111 |
| Drozitumab-FAP (4G8) VHVL-scFv (HC) pETR7342 | EVQLVQSGGGVERPGGSLRLSCAASGFTFDDYAMSWVRQA PGKGLEWVSGINWQGGSTGYADSVKGRVTISRDNAKNSLY LQMNSLRAEDTAVYYCAKILGAGRGWYFDYWGKGTTVTV SSASTKGPSVFPLAPSSKSTSGGTAALGCLVKDYFPEPVTVS WNSGALTSGVHTFPAVLQSSGLYSLSSVVTVPSSSLGTQTYI | 112 |

| Name | Amino acid sequence | SEQ ID NO |
|---|---|---|
| | CNVNHKPSNTKVDKKVEPKSCDKTHTCPPCPAPELLGGPSV<br>FLFPPKPKDTLMISRTPEVTCVVVDVSHEDPEVKFNWYVDG<br>VEVHNAKTKPREEQYNSTYRVVSVLTVLHQDWLNGKEYKC<br>KVSNKALPAPIEKTISKAKGQPREPQVYTLPPSRDELTKNQV<br>SLTCLVKGFYPSDIAVEWESNGQPENNYKTTPPVLDSDGSFF<br>LYSKLTVDKSRWQQGNVFSCSVMHEALHNHYTQKSLSLSP<br>GGGSGGGGSGGGGSEVQLLESGGGLVQPGGSLRLSCAASGF<br>TFSSYAMSWVRQAPGKCLEWVSAISGSGGSTYYADSVKGR<br>FTISRDNSKNTLYLQMNSLRAEDTAVYYCAKGWLGNFDYW<br>GQGTLVTVSSGGGGSGGGGSGGGGSGGGGSEIVLIQSPGTL<br>SLSPGERATLSCRASQSVSRSYLAWYQQKPGQAPRLLIIGAS<br>TRATGIPDRFSGSGSGTDFTLTISRLEPEDFAVYYCQQGQVIP<br>PTFGCGTKVEIK | |
| Drozitumab-FAP<br>(4G8)<br>VHVL-scFv (LC)<br>pETR7344 | SELTQDPAVSVALGQTVRITCSGDSLRSYYASWYQQKPGQA<br>PVLVIYGANNRPSGIPDRFSGSSSGNTASLTITGAQAEDEADY<br>YCNSADSSGNHVVFGGGTKLTVLGQPKAAPSVTLFPPSSEEL<br>QANKATLVCLISDFYPGAVTVAWKADSSPVKAGVETTTPSK<br>QSNNKYAASSYLSLTPEQWKSHRSYSCQVTHEGSTVEKTVA<br>PTECSGGGGSGGGGSEVQLLESGGGLVQPGGSLRLSCAASG<br>FTFSSYAMSWVRQAPGKCLEWVSAISGSGGSTYYADSVKG<br>RFTISRDNSKNTLYLQMNSLRAEDTAVYYCAKGWLGNFDY<br>WGQGTLVTVSSGGGGSGGGGSGGGGSGGGGSETVLTQSPGT<br>LSLSPGERATLSCRASQSVSRSYLAWYQQKPGQAPRLLIIGA<br>STRATGIPDRFSGSGSGTDFTLTISRLEPEDFAVYYCQQGQVI<br>PPTFGCGTKVEIK | 113 |
| Drozitumab-3F2<br>VLCL_VHCH1-<br>scFab (HC)<br>pETR7369 | EVQLVQSGGGVERPGGSLRLSCAASGFTFDDYAMSWVRQA<br>PGKGLEWVSGINWQGGSTGYADSVKGRVTISRDNAKNSLY<br>LQMNSLRAEDTAVYYCAKILGAGRGWYFDYWGKGTTVTV<br>SSASTKGPSVFPLAPSSKSTSGGTAALGCLVKDYFPEPVTVS<br>WNSGALTSGVHTFPAVLQSSGLYSLSSVVTVPSSSLGTQTYI<br>CNVNHKPSNTKVDKKVEPKSCDKTHTCPPCPAPELLGGPSV<br>FLFPPKPKDTLMISRTPEVTCVVVDVSHEDPEVKFNWYVDG<br>VEVHNAKTKPREEQYNSTYRVVSVLTVLHQDWLNGKEYKC<br>KVSNKALPAPIEKTISKAKGQPREPQVYTLPPSRDELTKNQV<br>SLTCLVKGFYPSDIAVEWESNGQPENNYKTTPPVLDSDGSFF<br>LYSKLTVDKSRWQQGNVFSCSVMHEALHNHYTQKSLSLSP<br>GKSGGGGSGGGGSGGGGSGGGGSEIVLTQSPGTLSLYPGER<br>ATLSCRASQSVTSSYLAWYQQKPGQAPRLLINVGSRRATGIP<br>DRFSGSGSGTDFTLTISRLEPEDFAVYYCQQGIMLPPTFGQGT<br>KVEIKRTVAAPSVFIFPPSDEQLKSGTASVVCLLNNFYPREA<br>KVQWKVDNALQSGNSQESVTEQDSKDSTYSLSSTLTLSKAD<br>YEKHKVYACEVTHQGLSSPVTKSFNRGECSGGGSGGGSEGG<br>GSEGGGSEGGGSEGGGSGGGSEVQLLESGGGLVQPGGSLR<br>LSCAASGFTFSSYAMSWVRQAPGKGLEWVSAISGSGGSTYY<br>ADSVKGRFTISRDNSKNTLYLQMNSLRAEDTAVYYCAKGW<br>FGGFNYWGQGTLVTVSSASTKGPSVFPLAPSSKSTSGGTAAL<br>GCLVKDYFPEPVTVSWNSGALTSGVHTFPAVLQSSGLYSLSS<br>VVTVPSSSLGTQTYICNVNHKPSNTKVDKKVEPKSCD | 114 |
| Drozitumab-3F2<br>VLCL_VHCH1-<br>scFab (LC)<br>pETR7370 | SELTQDPAVSVALGQTVRITCSGDSLRSYYASWYQQKPGQA<br>PVLVIYGANNRPSGIPDRFSGSSSGNTASLTITGAQAEDEADY<br>YCNSADSSGNHVVFGGGTKLTVLGQPKAAPSVTLFPPSSEEL<br>QANKATLVCLISDFYPGAVTVAWKADSSPVKAGVETTTPSK<br>QSNNKYAASSYLSLTPEQWKSHRSYSCQVTHEGSTVEKTVA<br>PTECSGGGGSGGGGSGGGGSGGGGSEIVLTQSPGTLSLYPGE<br>RATLSCRASQSVTSSYLAWYQQKPGQAPRLLINVGSRRATGI<br>PDRFSGSGSGTDFTLTISRLEPEDFAVYYCQQGIMLPPTFGQG<br>TKVEIKRTVAAPSVFIFPPSDEQLKSGTASVVCLLNNFYPREA<br>KVQWKVDNALQSGNSQESVTEQDSKDSTYSLSSTLTLSKAD<br>YEKHKVYACEVTHQGLSSPVTKSFNRGECSGGGSGGGSEGG<br>GSEGGGSEGGGSEGGGSGGGSEVQLLESGGGLVQPGGSLR<br>LSCAASGFTFSSYAMSWVRQAPGKGLEWVSAISGSGGSTYY<br>ADSVKGRFTISRDNSKNTLYLQMNSLRAEDTAVYYCAKGW<br>EGGENYWGQGTLVTVSSASTKGPSVFPLAPSSKSTSGGTAAL<br>GCLVKDYFPEPVTVSWNSGALTSGVHTFPAVLQSSGLYSLSS<br>VVTVPSSSLGTQTYICNVNHKPSNTKVDKKVEPKSCD | 115 |
| Drozitumab-FAP<br>(4G8)<br>VLCL_VHCH1-<br>scFab (HC)<br>pETR7371 | EVQLVQSGGGVERPGGSLRLSCAASGFTFDDYAMSWVRQA<br>PGKGLEWVSGINWQGGSTGYADSVKGRVTISRDNAKNSLY<br>LQMNSLRAEDTAVYYCAKILGAGRGWYFDYWGKGTTVTV<br>SSASTKGPSVFPLAPSSKSTSGGTAALGCLVKDYFPEPVTVS<br>WNSGALTSGVHTFPAVLQSSGLYSLSSVVTVPSSSLGTQTYI<br>CNVNHKPSNTKVDKKVEPKSCDKTHTCPPCPAPELLGGPSV<br>FLFPPKPKDTLMISRTPEVTCVVVDVSHEDPEVKFNWYVDG | 116 |

| Name | Amino acid sequence | SEQ ID NO |
|---|---|---|
| | VEVHNAKTKPREEQYNSTYRVVSVLTVLHQDWLNGKEYKC<br>KVSNKALPAPIEKTISKAKGQPREPQVYTLPPSRDELTKNQV<br>SLTCLVKGFYPSDIAVEWESNGQPENNYKTTPPVLDSDGSFF<br>LYSKLTVDKSRWQQGNVFSCSVMHEALHNHYTQKSLSLSP<br>GKSGGGGSGGGGSGGGGSGGGGSEIVLTQSPGTLSLSPGER<br>ATLSCRASQSVSRSYLAWYQQKPGQAPRLLIIGASTRATGIP<br>DRFSGSGSGTDFTLTISRLEPEDFAVYYCQQGQVIPPTFGQGT<br>KVEIKRTVAAPSVFIFPPSDEQLKSGTASVVCLLNNFYPREA<br>KVQWKVDNALQSGNSQESVTEQDSKDSTYSLSSTLTLSKAD<br>YEKHKVYACEVTHQGLSSPVTKSFNRGECSGGGSGGGSEGG<br>GSEGGGSEGGGSEGGGSGGGSGEVQLLESGGGLVQPGGSLR<br>LSCAASGFTFSSYAMSWVRQAPGKGLEWVSAISGSGGSTYY<br>ADSVKGRFTISRDNSKNTLYLQMNSLRAEDTAVYYCAKGW<br>LGNFDYWGQGTLVTVSSASTKGPSVFPLAPSSKSTSGGTAA<br>LGCLVKDYFPEPVTVSWNSGALTSGVHTFPAVLQSSGLYSL<br>SSVVTVPSSSLGTQTYICNVNHKPSNTKVDKKVEPKSCD | |
| Drozitumab-FAP<br>(4G8)<br>VLCL_VHCH1-<br>scFab(LC)<br>pETR7380 | SELTQDPAVSVALGQTVRITCSGDSLRSYYASWYQQKPGQA<br>PVLVIYGANNRPSGIPDRFSGSSSGNTASLTITGAQAEDEADY<br>YCNSADSSGNHVVFGGGTKLTVLGQPKAAPSVTLFPPSSEEL<br>QANKATLVCLISDFYPGAVTVAWKADSSPVKAGVETTTPSK<br>QSNNKYAASSYLSLTPEQWKSHRSYSCQVTHEGSTVEKTVA<br>PTECSGGGGSGGGGSGGGGSGGGGSEIVLTQSPGTLSLSPGE<br>RATLSCRASQSVSRSYLAWYQQKPGQAPRLLIIGASTRATGI<br>PDRFSGSGSGTDFTLTISRLEPEDFAVYYCQQGQVIPPTFGQG<br>TKVEIKRTVAAPSVFIFPPSDEQLKSGTASVVCLLNNFYPREA<br>KVQWKVDNALQSGNSQESVTEQDSKDSTYSLSSTLTLSKAD<br>YEKHKVYACEVTHQGLSSPVTKSFNRGECSGGGSGGGSEGG<br>GSEGGGSEGGGSEGGGSGGGSGEVQLLESGGGLVQPGGSLR<br>LSCAASGFTFSSYAMSWVRQAPGKGLEWVSAISGSGGSTYY<br>ADSVKGRFTISRDNSKNTLYLQMNSLRAEDTAVYYCAKGW<br>LGNFDYWGQGTLVTVSSASTKGPSVFPLAPSSKSTSGGTAA<br>LGCLVKDYFPEPVTVSWNSGALTSGVHTFPAVLQSSGLYSL<br>SSVVTVPSSSLGTQTYICNVNHKPSNTKVDKKVEPKSCD | 117 |
| Drozitumab-FAP<br>(4G8)<br>VHCL<br>2+ 2 | EVQLVQSGGGVERPGGSLRLSCAASGFTFDDYAMSWVRQA<br>PGKGLEWVSGINWQGGSTGYADSVKGRVTISRDNAKNSLY<br>LQMNSLRAEDTAVYYCAKILGAGRGWYFDYWGKGTTVTV<br>SSASTKGPSVFPLAPSSKSTSGGTAALGCLVKDYFPEPVTVS<br>WNSGALTSGVHTFPAVLQSSGLYSLSSVVTVPSSSLGTQTYI<br>CNVNHKPSNTKVDKKVEPKSCDKTHTCPPCPAPELLGGPSV<br>FLFPPKPKDTLMISRTPEVTCVVVDVSHEDPEVKFNWYVDG<br>VEVHNAKTKPREEQYNSTYRVVSVLTVLHQDWLNGKEYKC<br>KVSNKALPAPIEKTISKAKGQPREPQVYTLPPSRDELTKNQV<br>SLTCLVKGFYPSDIAVEWESNGQPENNYKTTPPVLDSDGSFF<br>LYSKLTVDKSRWQQGNVFSCSVMHEALHNHYTQKSLSLSP<br>GKSGGGGSGGGGSGGGGSGGGGSEVQLLESGGGLVQPGGS<br>LRLSCAASGFTFSSYAMSWVRQAPGKGLEWVSAISGSGGST<br>YYADSVKGRFTISRDNSKNTLYLQMNSLRAEDTAVYYCAK<br>GWLGNFDYWGQGTLVTVSSASVAAPSVFIFPPSDEQLKSGT<br>ASVVCLLNNFYPREAKVQWKVDNALQSGNSQESVTEQDSK<br>DSTYSLSSTLTLSKADYEKHKVYACEVTHQGLSSPVTKSFNR<br>GEC | 118 |
| Drozitumab LC<br>pETR7303 | SELTQDPAVSVALGQTVRITCSGDSLRSYYASWYQQKPGQA<br>PVLVIYGANNRPSGIPDRFSGSSSGNTASLTITGAQAEDEADY<br>YCNSADSSGNHVVFGGGTKLTVLGQPKAAPSVTLFPPSSEEL<br>QANKATLVCLISDFYPGAVTVAWKADSSPVKAGVETTTPSK<br>QSNNKYAASSYLSLTPEQWKSHRSYSCQVTHEGSTVEKTVA<br>PTECS | 119 |
| FAP (4G8)<br>_VLCH1 | EIVLTQSPGTLSLSPGERATLSCRASQSVSRSYLAWYQQKPG<br>QAPRLLIIGASTRATGIPDRFSGSGSGTDFTLTISRLEPEDFAV<br>YYCQQGQVIPPTFGQGTKVEIKSSASTKGPSVFPLAPSSKSTS<br>GGTAALGCLVKDYFPEPVTVSWNSGALTSGVHTFPAVLQSS<br>GLYSLSSVVTVPSSSLGTQTYICNVNHKPSNTKVDKKVEPKS<br>CD | 120 |
| Drozitumab-FAP<br>(4G8)<br>VLCH1<br>2 + 2 | EVQLVQSGGGVERPGGSLRLSCAASGFTFDDYAMSWVRQA<br>PGKGLEWVSGINWQGGSTGYADSVKGRVTISRDNAKNSLY<br>LQMNSLRAEDTAVYYCAKILGAGRGWYFDYWGKGTTVTV<br>SSASTKGPSVFPLAPSSKSTSGGTAALGCLVKDYFPEPVTVS<br>WNSGALTSGVHTFPAVLQSSGLYSLSSVVTVPSSSLGTQTYI<br>CNVNHKPSNTKVDKKVEPKSCDKTHTCPPCPAPELLGGPSV<br>FLFPPKPKDTLMISRTPEVTCVVVDVSHEDPEVKFNWYVDG<br>VEVHNAKTKPREEQYNSTYRVVSVLTVLHQDWLNGKEYKC | 121 |

-continued

| Name | Amino acid sequence | SEQ ID NO |
|---|---|---|
| | KVSNKALPAPIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GKSGGGGSGGGGSGGGGSGGGGSEIVLTQSPGTLSLSPGER ATLSCRASQSVSRSYLAWYQQKPGQAPRLLIIGASTRATGIP DRFSGSGSGTDFTLTISRLEPEDFAVYYCQQGQVIPPTFGQGT KVEIKASTKGPSVFPLAPSSKSTSGGTAALGCLVKDYFPEPV TVSWNSGALTSGVHTFPAVLQSSGLYSLSSVVTVPSSSLGTQ TYICNVNHKPSNTKVDKKVEPKSCD | |
| FAP (4G8)_VHCL | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGWLGNFDYWGQGTLVTVSSASVA APSVFIFPPSDEQLKSGTASVVCLLNNFYPREAKVQWKVDN ALQSGNSQESVTEQDSKDSTYSLSSTLTLSKADYEKHKVYA CEVTHQGLSSPVTKSFNRGEC | 122 |
| Drozitumab-FAP (28H1) VHCL pETR9551 2 + 2 | EVQLVQSGGGVERPGGSLRLSCAASGFTFDDYAMSWVRQA PGKGLEWVSGINWQGGSTGYADSVKGRVTISRDNAKNSLY LQMNSLRAEDTAVYYCAKILGAGRGWYFDYWGKGTTVTV SSASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDKTHTCPPCPAPELLGGPSV FLFPPKPKDTLMISRTPEVTCVVVDVSHEDPEVKFNWYVDG VEVHNAKTKPREEQYNSTYRVVSVLTVLHQDWLNGKEYKC KVSNKALPAPIEKTISKAKGQPREPQVYTLPPSRDELTKNQV SLTCLVKGFYPSDIAVEWESNGQPENNYKTTPPVLDSDGSFF LYSKLTVDKSRWQQGNVFSCSVMHEALHNHYTQKSLSLSP GKSGGGGSGGGGSGGGGSGGGGSEVQLLESGGGLVQPGGS LRLSCAASGFTFSSHAMSWVRQAPGKGLEWVSAIWASGEQ YYADSVKGRFTISRDNSKNTLYLQMNSLRAEDTAVYYCAK GWLGNFDYWGQGTLVTVSSASVAAPSVFIFPPSDEQLKSGT ASVVCLLNNFYPREAKVQWKVDNALQSGNSQESVTEQDSK DSTYSLSSTLTLSKADYEKHKVYACEVTHQGLSSPVTKSFNR GEC | 123 |

5. Amino acid sequences of bispecific molecules comprising phage display derived DR5 binders

| Name | Amino acid sequence | SEQ ID NO |
|---|---|---|
| FAP (28H1)_VLCH1 pETR9537 | EIVLTQSPGTLSLSPGERATLSCRASQSVSRSYLAWYQQKPG QAPRLLIIGASTRATGIPDRFSGSGSGTDFTLTISRLEPEDFAV YYCQQGQVIPPTFGQGTKVEIKSSASTKGPSVFPLAPSSKSTS GGTAALGCLVKDYFPEPVTVSWNSGALTSGVHTFPAVLQSS GLYSLSSVVTVPSSSLGTQTYICNVNHKPSNTKVDKKVEPKS CD | 124 |
| DR5 (22E9)-FAP (28H1) VHCL pETR9711 2 + 2 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRISFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGKSGGGG SGGGGSGGGGSGGGGSEVQLLESGGGLVQPGGSLRLSCAAS GFTFSSHAMSWVRQAPGKGLEWVSAIWASGEQYYADSVKG RFTISRDNSKNTLYLQMNSLRAEDTAVYYCAKGWLGNFDY WGQGTLVTVSSASVAAPSVFIFPPSDEQLKSGTASVVCLLNN FYPREAKVQWKVDNALQSGNSQESVTEQDSKDSTYSLSSTL TLSKADYEKHKVYACEVTHQGLSSPVTKSFNRGEC | 125 |
| DR5 (22E9) LC pETR9076 | EIVLTQSPGTLSLSPGERATLSCRASQSVSSSYLAWYQQKPG QAPRLLIYGASSRATGIPDRFSGSGSGTDFTLTISRLEPEDFAV YYCQQGSNQPVTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 126 |

-continued

| Name | Amino acid sequence | SEQ ID NO |
|---|---|---|
| DR5 (21H3)-FAP (28H1) VHC L pETR10626 2 + 2 | EVQLLESGGGLVQPGGSLRLSCAASGFTFSSYAMSWVRQAP GKGLEWVSAISGSGGSTYYADSVKGRFTISRDNSKNTLYLQ MNSLRAEDMAVYYCAKGARVSFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGKSGGGG SGGGGSGGGGSGGGGSEVQLLESGGGLVQPGGSLRLSCAAS GFTFSSHAMSWVRQAPGKGLEWVSAIWASGEQYYADSVKG RFTISRDNSKNTLYLQMNSLRAEDTAVYYCAKGWLGNFDY WGQGTLVTVSSASVAAPSVFIFPPSDEQLKSGTASVVCLLNN FYPREAKVQWKVDNALQSGNSQESVTEQDSKDSTYSLSSTL TLSKADYEKHKVYACEVTHQGLSSPVTKSFNRGEC | 127 |
| DR5 (21H3) LC pETR9075 | EIVLTQSPGTLSLSPGERATLSCRASQSVSSSYLAWYQQKPG QAPRLLIYGASSRATGIPDRFSGSGSGTDFTLTISRLEPEDFAV YYCQQGSQPPITFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 128 |
| DR5 (20F2)-FAP (28H1) VHCL pETR10135 2 + 2 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRKGFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGKSGGGG SGGGGSGGGGSGGGGSEVQLLESGGGLVQPGGSLRLSCAAS GFTFSSHAMSWVRQAPGKGLEWVSAIWASGEQYYADSVKG RFTISRDNSKNTLYLQMNSLRAEDTAVYYCAKGWLGNFDY WGQGTLVTVSSASVAAPSVFIFPPSDEQLKSGTASVVCLLNN FYPREAKVQWKVDNALQSGNSQESVTEQDSKDSTYSLSSTL TLSKADYEKHKVYACEVTHQGLSSPVTKSFNRGEC | 129 |
| DR5 (20F2) LC pETR9061 | EIVLTQSPGTLSLSPGERATLSCRASQSVSSSYLAWYQQKPG QAPRLLIYGASSRATGIPDRFSGSGSGTDFTLTISRLEPEDFAV YYCQQGESPPPTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 130 |
| DR5(5E11)-FAP (28H1) VHCL pETR10334 2 + 2 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGKSGGGG SGGGGSGGGGSGGGGSEVQLLESGGGLVQPGGSLRLSCAAS GFTFSSHAMSWVRQAPGKGLEWVSAIWASGEQYYADSVKG RFTISRDNSKNTLYLQMNSLRAEDTAVYYCAKGWLGNFDY WGQGTLVTVSSASVAAPSVFIFPPSDEQLKSGTASVVCLLNN FYPREAKVQWKVDNALQSGNSQESVTEQDSKDSTYSLSSTL TLSKADYEKHKVYACEVTHQGLSSPVTKSFNRGEC | 131 |
| DR5(5E11) LC pETR9044 | EIVLTQSPGTLSLSPGERATLSCRASQSVSSSYLAWYQQKPG QAPRLLIYGASSRATGIPDRFSGSGSGTDFTLTISRLEPEDFAV YYCQQGTTHPITFCiQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 132 |

| Name | Amino acid sequence | SEQ ID NO |
|---|---|---|
| DR5(5E11)-FAP (28H1) VHCL 2 + 2 Removal of C-term. Lysine in Fc pETR11052 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGGGGGSG GGGSGGGGSGGGGSEVQLLESGGGLVQPGGSLRLSCAASGF TFSSHAMSWVRQAPGKGLEWVSAIWASGEQYYADSVKGRF TISRDNSKNTLYLQMNSLRAEDTAVYYCAKGWLGNFDYW GQGTLVTVSSASVAAPSVFIFPPSDEQLKSGTASVVCLLNNF YPREAKVQWKVDNALQSGNSQESVTEQDSKDSTYSLSSTLT LSKADYEKHKVYACEVTHQGLSSPVTKSFNRGEC | 133 |
| DR5(5E11)-FAP (28H1) VHCL 2 + 2 Removal of C-term. Ly sine in Fc P329G/LALA mut. pETR11025 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPEAAGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL GAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGGGGGSG GGGSGGGGSGGGGSEVQLLESGGGLVQPGGSLRLSCAASGF TFSSHAMSWVRQAPGKGLEWVSAIWASGEQYYADSVKGRF TISRDNSKNTLYLQMNSLRAEDTAVYYCAKGWLGNFDYW GQGTLVTVSSASVAAPSVFIFPPSDEQLKSGTASVVCLLNNF YPREAKVQWKVDNALQSGNSQESVTEQDSKDSTYSLSSTLT LSKADYEKHKVYACEVTHQGLSSPVTKSFNRGEC | 134 |
| VHVL DR5(5E11)-FAP (28H1) pETR11827 2 + 2 | EIVLTQSPGTLSLSPGERATLSCRASQSVSSSYLAWYQQKPG QAPRLLIYGASSRATGIPDRFSGSGSGTDFTLTISRLEPEDFAV YYCQQGTTHPITFGQGTKVEIKSSASTKGPSVFPLAPSSKSTS GGTAALGCLVKDYFPEPVTVSWNSGALTSGVHTFPAVLQSS GLYSLSSVVTVPSSSLGTQTYICNVNHKPSNTKVDKKVEPKS CDKTHTCPPCPAPELLGGPSVFLFPPKPKDTLMISRTPEVTCV VVDVSHEDPEVKFNWYVDGVEVHNAKTKPREEQYNSTYR VVSVLTVLHQDWLNGKEYKCKVSNKALPAPIEKTISKAKGQ PREPQVYTLPPSRDELTKNQVSLTCLVKGFYPSDIAVEWESN GQPENNYKTTPPVLDSDGSFFLYSKLTVDKSRWQQGNVFSC SVMHEALHNHYTQKSLSLSPGKSGGGGSGGGGSGGGGSGG GGSEVQLLESGGGLVQPGGSLRLSCAASGFTFSSHAMSWVR QAPGKGLEWVSAIWASGEQYYADSVKGRFTISRDNSKNTLY LQMNSLRAEDTAVYYCAKGWLGNFDYWGQGTLVTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKVEPKSCD | 135 |
| DR5(5E11) VHCL pETR11484 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASVA APSVFIFPPSDEQLKSGTASVVCLLNNFYPREAKVQWKVDN ALQSGNSQESVTEQDSKDSTYSLSSTLTLSKADYEKHKVYA CEVTHQGLSSPVTKSFNRGEC | 136 |
| FAP (28H1) VLCL pETR9366 | EIVLTQSPGTLSLSPGERATLSCRASQSVSRSYLAWYQQKPG QAPRLLIIGASTRATGIPDRFSGSGSGTDFTLTISRLEPEDFAV YYCQQGQVIPPTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 137 |
| CH1CL DR5(5E11)-FAP (28H1) pETR11828 2 + 2 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASVA APSVFIFPPSDEQLKSGTASVVCLLNNFYPREAKVQWKVDN ALQSGNSQESVTEQDSKDSTYSLSSTLTLSKADYEKHKVYA CEVTHQGLSSPVTKSFNRGECDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK | 138 |

-continued

| Name | Amino acid sequence | SEQ ID NO |
|---|---|---|
| | VSNKALPAPIEKTISKAKGQPREPQVYTLPPSRDELTKNQVS LTCLVKGFYPSDIAVEWESNGQPENNYKTTPPVLDSDGSFFL YSKLTVDKSRWQQGNVFSCSVMHEALHNHYTQKSLSLSPG GGGGSGGGGSGGGGSGGGGSEVQLLESGGGLVQPGGSLRL SCAASGFTFSSHAMSWVRQAPGKGLEWVSAIWASGEQYYA DSVKGRFTISRDNSKNTLYLQMNSLRAEDTAVYYCAKGWL GNEDYWGQGTINTVSSASTKGPSVFPLAPSSKSTSGGTAAL GCLVKDYFPEPVTVSWNSGALTSGVHTFPAVLQSSGLYSLSS VVTVPSSSLGTQTYICNVNHKPSNTKVDKKVEPKSCD | |
| DR5(5E11) VLCH1 pETR11480 | EIVLTQSPGTLSLSPGERATLSCRASQSVSSSYLAVVYQQKPG QAPRLLIYGASSRATGIPDRFSGSGSGTDFTLTISRLEPEDFAV YYCQQGTTHPITFGQGTKVEIKSSASTKGPSVFPLAPSSKSTS GGTAALGCLVKDYFPEPVTVSWNSGALTSGVHTFPAVLQSS GLYSLSSVVTVPSSSLGTQTYICNVNHKPSNTKVDKKVEPKS CD | 139 |
| DR5(18F11)-FAP (28H1) VHCL 2 + 2 | EVQLLESGGGLVQPGGSLRLSCAASGFTFSSYAMSWVRQAP GKGLEWVSAISGSGGSTYYADSVKGRFTISRDNSKNTLYLQ MNSLRAEDAAVYYCAKGVRKKFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGKSGGGG SGGGGSGGGGSGGGGSEVQLLESGGGLVQPGGSLRLSCAAS GFTFSSHAMSWVRQAPGKGLEWVSAIWASGEQYYADSVKG RFTISRDNSKNTLYLQMNSLRAEDTAVYYCAKGWLGNEDY WGQGTLVTVSSASVAAPSVFIFPPSDEQLKSGTASVVCLLNN FYPREAKVQWKVDNALQSGNSQESVTEQDSKDSTYSLSSTL TLSKADYEKHKVYACEVTHQGLSSPVTKSFNRGEC | 140 |
| DR5(18F11) LC | EIVLTQSPGTLSLSPGERATLSCRASQSVSSSYLAWYQQKPG QAPRLLIYGASSRATGIPDRFSGSGSGTDFTLTISRLEPEDFAV YYCQQGQLPPITFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 141 |
| DR5(5E11)-FAP (28H1) Fc knob VHC 2 + 1 pETR10427 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG LPSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPCRDELTKNQVSLWCLVK GFYPSDIAVEWESNGQPENNYKTTPPVLDSDGSFFLYSKLTV DKSRWQQGNVFSCSVMHEALHNHYTQKSLSLSPGGGGGSG GGGSGGGGSGGGGSEVQLLESGGGLVQPGGSLRLSCAASGF TFSSHAMSWVRQAPGKGLEWVSAIWASGEQYYADSVKGRF TISRDNSKNTLYLQMNSLRAEDTAVYYCAKGWLGNFDYW GQGTLVTVSSASVAAPSVFIFPPSDEQLKSGTASVVCLLNNF YPREAKVQWKVDNALQSGNSQESVTEQDSKDSTYSLSSTLT LSKADYEKHKVYACEVTHQGLSSPVTKSFNRGEC | 142 |
| DR5(5E11) Fc hole pETR10336 | EVQLLESGGGLVQPGGSLRLSCAASGFITSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVCTLPPSRDELTKNQVSLSCAVK GFYPSDIAVEWESNGQPENNYKTTPPVLDSDGSFFLVSKLTV DKSRWQQGNVFSCSVMHEALHNHYTQKSLSLSPGK | 143 |
| DR5 (5E11)-FAP (28H1) Fc knob VHCL | as above | 143 |

| Name | Amino acid sequence | SEQ ID NO |
|---|---|---|
| 3 + 1 pETR10427 DR5(5E11)- DR5(5E11) Fc hole pETR10429 3 + 1 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVCTLPPSRDELTKNQVSLSCAVK GFYPSDIAVEWESNGQPENNYKTTPPVLDSDGSFFLVSKLTV DKSRWQQGNVFSCSVMHEALHNHYTQKSLSLSPGGGGGSG GGGSGGGGSGGGGSEVQLLESGGGLVQPGGSLRLSCAASGF TFSSYAMSWVRQAPGKGLEWVSAISGSGGSTYYADSVKGR FTISRDNSKNTLYLQMNSLRAEDTAVYYCAKGVRVSFDYW GQGTLVTVSSASTKGPSVFPLAPSSKSTSGGTAALGCLVKDY FPEPVTVSWNSGALTSGVHTFPAVLQSSGLYSLSSVVTVPSS SLGTQTYICNVNHKPSNTKVDKKVEPKSCD | 144 |
| DR5(5E11)_Fc knob Fab-Fab Head-to-tail 2 + 1 pETR10662 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCGGGGSGGGGSEVQLLESGGGLVQPGG SLRLSCAASGFTFSSYAMSWVRQAPGKGLEWVSAISGSGGS TYYADSVKGRFTISRDNSKNTLYLQMNSLRAEDTAVYYCA KGVRVSFDYWGQGTLVTVSSASTKGPSVFPLAPSSKSTSGG TAALGCLVKDYFPEPVTVSWNSGALTSGVHTFPAVLQSSGL YSLSSVVTVPSSSLGTQTYICNVNHKPSNTKVDKKVEPKSCD KTHTCPPCPAPELLGGPSVFLFPPKPKDTLMISRTPEVTCVVV DVSHEDPEVKFNWYVDGVEVHNAKTKPREEQYNSTYRVVS VLTVLHQDWLNGKEYKCKVSNKALPAPIEKTISKAKGQPRE PQVYTLPPCRDELTKNQVSLWCLVKGFYPSDIAVEWESNGQ PENNYKTTPPVLDSDGSFFLYSKLTVDKSRWQQGNVFSCSV MHEALHNHYTQKSLSLSPGK | 145 |
| FAP (28H1)_Fc hole VHCL pETR10130 | EVQLLESGGGLVQPGGSLRLSCAASGFTFSSHAMSWVRQAP GKGLEWVSAIWASGEQYYADSVKGRFTISRDNSKNTLYLQ MNSLRAEDTAVYYCAKGWLGNFDYWGQGTLVTVSSASVA APSVFIFPPSDEQLKSGTASVVCLLNNFYPREAKVQWKVDN ALQSGNSQESVTEQDSKDSTYSLSSTLTLSKADYEKHKVYA CEVTHQGLSSPVTKSFNRGECDKTHTCPPCPAPELLGGPSVF LFPPKPKDTLMISRTPEVTCVVVDVSHEDPEVKFNWYVDGV EVHNAKTKPREEQYNSTYRVVSVLTVLHQDWLNGKEYKCK VSNKALPAPIEKTISKAKGQPREPQVCTLPPSRDELTKNQVSL SCAVKGFYPSDIAVEWESNGQPENNYKTTPPVLDSDGSFFLV SKLTVDKSRWQQGNVFSCSVMHEALHNHYTQKSLSLSPGK | 146 |
| DR5(18F11)-FAP (28H1) Fc knob VHCL 2 + 1 pETR9807 | EVQLLESGGGLVQPGGSLRLSCAASGFTFSSYAMSWVRQAP GKGLEWVSAISGSGGSTYYADSVKGRFTISRDNSKNTLYLQ MNSLRAEDAAVYYCAKGVRKKFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LPAPIEKTISKAKGQPREPQVYTLPPCRDELTKNQVSLWCLV KGFYPSDIAVEWESNGQPENNYKTTPPVLDSDGSFFLYSKLT VDKSRWQQGNVFSCSVMHEALHNHYTQKSLSLSPGKSGGG GSGGGGSGGGGSGGGGSEVQLLESGGGLVQPGGSLRLSCA ASGFTFSSHAMSWVRQAPGKGLEWVSAIWASGEQYYADSV KGRFTISRDNSKNTLYLQMNSLRAEDTAVYYCAKGWLGNF DYWGQGTLVTVSSASVAAPSVFIFPPSDEQLKSGTASVVCLL NNFYPREAKVQWKVDNALQSGNSQESVTEQDSKDSTYSLSS TLTLSKADYEKHKVYACEVTHQGLSSPVTKSFNRGEC | 147 |
| DR5(18F11) Fc hole pETR9808 | EVQLLESGGGLVQPGGSLRLSCAASGFTFSSYAMSWVRQAP GKGLEWVSAISGSGGSTYYADSVKGRFTISRDNSKNTLYLQ MNSLRAEDAAVYYCAKGVRKKFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPELLGGPSVFLFPPKP KDTLMISRTPEVTCVVVDVSHEDPEVKFNWYVDGVEVHNA | 148 |

| Name | Amino acid sequence | SEQ ID NO |
|---|---|---|
| | KTKPREEQYNSTYRVVSVLTVLHQDWLNGKEYKCKVSNKA<br>LPAPIEKTISKAKGQPREPQVCTLPPSRDELTKNQVSLSCAVK<br>GFYPSDIAVEWESNGQPENNYK'TTPPVLDSDGSFELVSKLTV<br>DKSRWQQGNVFSCSVMHEALHNHYTQKSLSLSPGK | |
| DR5 (18F11)-FAP<br>(28H1)<br>VHCL<br>Fc knob<br>3 + 1<br>pETR10333 | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDAAVYYCAKGVRKKFDYWGQGTLVTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKKVEPKSCDKTHTCPPCPAPELLGGPSVFLFPPKP<br>KDTLMISRTPEVTCVVVDVSHEDPEVKFNWYVDGVEVHNA<br>KTKPREEQYNSTYRVVSVLTVLHQDWLNGKEYKCKVSNKA<br>LPAPIEKTISKAKGQPREPQVYTLPPCRDELTKNQVSLWCLV<br>KGFYPSDIAVEWESNGQPENNYKTTPPVLDSDGSFFLYSKLT<br>VDKSRWQQGNVFSCSVMHEALHNHYTQKSLSLSPGGGGGS<br>GGGGSGGGGSGGGGSEVQLLESGGGLVQPGGSLRLSCAAS<br>GFTFSSHAMSWVRQAPGKGLEWVSAIWASGEQYYADSVKG<br>RFTISRDNSKNTLYLQMNSLRAEDTAVYYCAKGWLGNFDY<br>WGQGTLVTVSSASVAAPSVFIFPPSDEQLKSGTASVVCLLNN<br>FYPREAKVQWKVDNALQSGNSQESVTEQDSKDSTYSLSSTL<br>TLSKADYEKHKVYACEVTHQGLSSPVTKSFNRGEC | 149 |
| DR5(18F11)-<br>DR5(18F11)<br>Fc hole<br>pETR10288 | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDAAVYYCAKGVRKKFDYWGQGTLVTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKKVEPKSCDKTHTCPPCPAPELLGGPSVFLFPPKP<br>KDTLMISRTPEVTCVVVDVSHEDPEVKFNWYVDGVEVHNA<br>KTKPREEQYNSTYRVVSVLTVLHQDWLNGKEYKCKVSNKA<br>LPAPIEKTISKAKGQPREPQVCTLPPSRDELTKNQVSLSCAVK<br>GFYPSDIAVEWESNGQPENNYKTTPPVLDSDGSFFLVSKLTV<br>DKSRWQQGNVFSCSVMHEALHNHYTQKSLSLSPGGGGGSG<br>GGGSGGGGSGGGGSEVQLLESGGGLVQPGGSLRLSCAASGF<br>TFSSYAMSWVRQAPGKGLEWVSAISGSGGSTYYADSVKGR<br>FTISRDNSKNTLYLQMNSLRAEDAAVYYCAKGVRKKFDYW<br>GQGTLVTVSSASTKGPSVFPLAPSSKSTSGGTAALGCLVKDY<br>FPEPVTVSWNSGALTSGVHTFPAVLQSSGLYSLSSVVTVPSS<br>SLGTQTYICNVNHKPSNTKVDKKVEPKSCD | 150 |
| FAP (28H1)_Fc<br>hole<br>VHCL<br>pETR10130 | EVQLLESGGGLVQPGGSLRLSCAASGFTFSSHAMSWVRQAP<br>GKGLEWVSAIWASGEQYYADSVKGRFTISRDNSKNTLYLQ<br>MNSLRAEDTAVYYCAXGWLGNFDYWGQGTLVTVSSASVA<br>APSVFIFPPSDEQLKSGTASVVCLLNNFYPREAKVQWKVDN<br>ALQSGNSQESVTEQDSKDSTYSLSSTLTLSKADYEKHKVYA<br>CEVTHQGLSSPVTKSFNRGECDKTHTCPPCPAPELLGGPSVF<br>LFPPKPKDTLMISRTPEVTCVVVDVSHEDPEVKFNWYVDGV<br>EVHNAKTKPREEQYNSTYRVVSVLTVLHQDWLNGKEYKCK<br>VSNKALPAPIEKTISKAKGQPREPQVCTLPPSRDELTKNQVSL<br>SCAVKGFYPSDIAVEWESNGQPENNYKTTPPVLDSDGSFFLV<br>SKLTVDKSRWQQGNVFSCSVMHEALHNHYTQKSLSLSPGK | 159 |
| FAP (28H1)<br>VLCH1<br>pETR9537 | EIVLTQSPGTLSLSPGERATLSCRASQSVSRSYLAWYQQKPG<br>QAPRLLIIGASTRATGIPDRFSGSGSGTDFTLTISRLEPEDFAV<br>YYCQQGVIPPTFGQGTKVEIKSSASTKGPSVFPLAPSSKSTS<br>GGTAALGCLVKDYFPEPVTVSWNSGALTSGVHTFPAVLQSS<br>GLYSLSSVVTVPSSSLGTQTYICNVNHKPSNTKVDKKVEPKS<br>CD | 160 |
| DR5 (5E11)-Fc<br>knob | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDTAVYYCAKGVRVSFDYWGQGTLVTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKP<br>SNTKVDKKVEPKSCDKTHTCPPCPAPELLGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>PAPIEKTISKAKGQPREPQVYTLPPCRDELTKNQVSLWCLVK<br>GFYPSDIAVEWESNGQPENNYKTTPPVLDSDGSFFLYSKLTV<br>DKSRWQQGNVFSCSVMHEALHNHYTQKSLSLSPGK | 161 |
| DR5 (5E11)_LC<br>pETR9044 | EIVLTQSPGTLSLSPGERATLSCRASQSVSSSYLAWYQQKPG<br>QAPRLLIYGASSRATGIPDRFSGSGSGTDFTLTISRLEPEDFAV<br>YYCQQGTTHPITEGQGTKVEIKRTVAAPSVFIFPPSDEQLKSG<br>TASVVCLLNNFYPREAKVQWKVDNALQSGNSQESVTEQDS | 162 |

| Name | Amino acid sequence | SEQ ID NO |
|---|---|---|
| | KDSTYSLSSTLTLSKADYEKHKVYACEVTHQGLSSPVTKSF NRGEC | |
| DR5 (5E11) FAP(4B9) VHCL pETR11060 | EVQLLESGGGLVQPGGSLRLSCAASGFTFSSYAMSWVRQAP GKGLEWVSAISGSGQSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGICEYKCKVSNKAL PAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGGGGGSG GGGSGGGGSGGGGSEVQLLESGGGLVQPGGSLRLSCAASGF TESSYAMSWVRQAPGKGLEWVSAIIGSGASTYYADSVKGRF TISRDNSKNTLYLQMNSLRAEDTAVYYCAKGWFGGFNYWG QGTLVTVSSASVAAPSVFIFPPSDEQLKSGTASVVCLLNNFY PREAKVQWKVDNALQSGNSQESVTEQDSKDSTYSLSSTLTL SKADYEICHKVYACEVTHQGLSSPVTKSENRGEC | 262 |
| FAP(4B9) VLCH1 pETR10020 | EIVLTQSPGTLSLSPGERATLSCRASQSVTSSYLAWYQQKPG QAPRLLINVGSRRATGIPDRFSGSGSGTDFTLTISRLEPEDFA VYYCQQGIMLPPTFGQGTKVEIKSSASTKGPSVFPLAPSSKST SGGTAALGCLVKDYFPEPVTVSWNSGALTSGVHTFPAVLQS SGLYSLSSVVTVPSSSLGTQTYICNVNHKPSNTKVDKKVEPK SCD | 263 |
| 11826 5E11 (VLCL)-Fc-28H1 (VHCH1) | EIVLTQSPGTLSLSPGERATLSCRASQSVSSSYLAWYQQKPG QAPRLLIYGASSRATGIPDRFSGSGSGTDFTLTISRLEPEDFAV YYCQQGTTHPITEGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGECDKTHTCPPCPAPELLGGPSVFLEPPKPKDTLMISRTPE VTCVVVDVSHEDPEVKFNWYVDGVEVHNAKTKPREEQYN STYRVVSVLTVLHQDWLNGKEYKCKVSNKALPAPIEKTISK AKGQPREPQVYTLPPSRDELTKNQVSLTCLVKGFYPSDIAVE WESNGQPENNYKTTPPVLDSDGSFFLYSKLTVDKSRWQQG NVFSCSVMHEALHNHYTQKSLSLSPGGGGGSGGGGSGGGG SGGGGSEVQLLESGGGLVQPGGSLRLSCAASGFTFSSHAMS WVRQAPGKGLEWVSAIWASGEQYYADSVKGRFTISRDNSK NTLYLQMNSLRAEDTAVYYCAKGWLGNEDYWGQGTLVTV SSASTKGPSVFPLAPSSKSTSGGTAALGCLVICDYFPEPVTVS WNSGVHTFPAVLQSSGLYSLSSVVTVPSSSLGTQTYI CNVNHKPSNTKVDKKVEPKSCD | 274 |
| 11478 5E11 VHCH1 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCD | 275 |
| 11829 5E11-28H1 VHCH1 | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPELLGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL PAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGGGGGSG GGGSGGGGSGGGGSEIVLTQSPGTLSLSPGERATLSCRASQS VSRSYLAWYQQKPGQAPRLLIIGASTRATGIPDRFSGSGSGT DFTLTISRLEPEDFAVYYCQQGVIPPTFGQGTKVEIKRTVA APSVFIFPPSDEQLKSGTASVVCLLNNFYPREAKVQWKVDN ALQSGNSQESVTEQDSKDSTYSLSSTLTLSKADYEKHKVYA CEVTHQGLSSPVTKSFNRGEC | 276 |
| 11830 28H1 VHCH1 | EVQLLESGGGLVQPGGSLRLSCAASGFTFSSHAMSWVRQAP GKGLEWVSAIWASGEQYYADSVKGRFTISRDNSKNTLYLQ MNSLRAEDTAVYYCAKGWLGNFDYWGQGTLVTVSSASTK GPSVFPLAPSSKSTSGGTAALGCLVKDYFPEPVTVSWNSGAL | 277 |

| Name | Amino acid sequence | SEQ ID NO |
|---|---|---|
| | TSGVHTFPAVLQSSGLYSLSSVVTVPSSSLGTQTYICNVNHK PSNTKVDKKVEPKSCD | |
| 12207 5E11-28H1 (VLCH1) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGVRVSFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDKTHTCPPCPAPEAAGGPSVFLFPPKPK DTLMISRTPEVTCVVVDVSHEDPEVKFNWYVDGVEVHNAK TKPREEQYNSTYRVVSVLTVLHQDWLNGKEYKCKVSNKAL GAPIEKTISKAKGQPREPQVYTLPPSRDELTKNQVSLTCLVK GFYPSDIAVEWESNGQPENNYKTTPPVLDSDGSFFLYSKLTV DKSRWQQGNVFSCSVMHEALHNHYTQKSLSLSPGGGGGSG GGGSGGGGSGGGGSEIVLTQSPGTLSLSPGERATLSCRASQS VSRSYLAWYQQKPGQAPRLLIIGASTRATGIPDRFSGSGSGT DFTLTISRLEPEDFAVYYCQQGQVIPPTFGQGTKVEIKSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKVEPKSCD | 278 |
| 12152 28H1 (VHCL) | EVQLLESGGGLVQPGGSLRLSCAASGFTFSSHAMSWVRQAP GKGLEWVSAIWASGEQYYADSVKGRFTISRDNSKNTLYLQM NSLRAEDTAVYYCAKGWLGNFDYWGQGTLVTVSSASVAAP SVFIFPPSDEQLKSGTASVVCLLNNFYPREAKVQWKVDNALQ SGNSQESVTEQDSKDSTYSLSSTLTLSKADYEKHKVYACEVT HQGLSSPVTKSFNRGEC | 279 |

6. Amino Acid Sequences of Fc Domain and Constant Light Chains

| Name | Amino acid sequence | SEQ ID NO |
|---|---|---|
| hu Fc_wt | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDKTHTCPPC PAPELLGGPSVFLFPPKPKDTLMISRTP EVTCVVVDVSHEDPEVKFNWYVDGVEVH NAKTKPREEQYNSTYRVVSVLTVLHQDW LNGKEYKCKVSNKALPAPIEKTISKAKG QPREPQVYTLPPSRDELTKNQVSLTCLV KGFYPSDIAVEWESNGQPENNYKTTPPV LDSDGSFFLYSKLTVDKSRWQQGNVFSC SVMHEALHNHYTQKSLSLSPGK | 151 |
| hu Fc_P329G/ LALA | ASTKGPSVFPLAPSSKSTSGGTAALGCL VKDYFPEPVTVSWNSGALTSGVHTFPAV LQSSGLYSLSSVVTVPSSSLGTQTYICN VNHKPSNTKVDKKVEPKSCDKTHTCPPC PAPEAAGGPSVFLFPPKPKDTLMISRTP EVTCVVVDVSHEDPEVKFNWYVDGVEVH NAKTKPREEQYNSTYRVVSVLTVLHQDW LNGKEYKCKVSNKALGAPIEKTISKAKG QPREPQVYTLPPSRDELTKNQVSLTCLV KGFYPSDIAVEWESNGQPENNYKTTPPV LDSDGSFFLYSKLTVDKSRWQQGNVFSC SVMHEALHNHYTQKSLSLSPK | 152 |
| hu kappa light chain | RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC | 153 |
| hu lambda light chain | GQPKAAPSVTLFPPSSEELQANKATLVC LISDFYPGAVTVAWKADSSPVKAGVETT TPSKQSNNKYAASSYLSLTPEQWKSHRS YSCQVTHEGSTVEKTVAPTECS | 154 |

7. Amino Acid Sequences of DR5 Binders Derived from Rabbit Immunization

Clone DR5TAA-0005 (Alias: clone 039)
Heavy chain
VH (SEQ ID NO.: 41)
qsleesggrlvtpgtpltltctasgfslssaymswvrqapgkglewig yiysgsgstwyaswvkgrftisktsttvdlkitspttedtatyfcarg ystmgdlwgpgtlvtvss

CH1-3

(SEQ ID NO.: 42)
gqpkapsvfplapccgdtpsstvtlgclvkgylpepvtvtwnsgtltn gvrtfpsvrqssglyslssvvsvtsssqpvtcnvahpatntkvdktva pstcskptcpppellggpsvfifppkpkdtlmisrtpevtcvvvdvsq ddpevqftwyinneqvrtarpplreqqfnstirvvstlpiahqdwlrg kefkckvhnkalpapiektiskargqplepkvytmgppreelssrsys ltcmingfypsdisvewekngkaednyktttpavldsdgsyflynklsv ptsewqrgdyftcsvmhealhnhytqksisrspgk

CDR1 =

(SEQ ID NO.: 43)
sayms

CDR2 =

(SEQ ID NO.: 44)
yiysgsgstwyaswvkg

CDR3 =

(SEQ ID NO.: 45)
gystmgdl

Light Chain
VL (SEQ ID NO.: 46)
qvltqtpspvsaavggtvtincqasqsvynnrlawyqqkpgqppkll i ylastlasgvpsrfkgsgsgtqftltisdlqcddaatyycaggysgni nafgggtevvvk Ckappa (SEQ ID NO.: 47)

gdpvaptvlifppaadqvatgtvtivcvankyfpdvtvtwevdgttqt tgiensktpqnsadctynlsstltltstqynshkeytckvtqgttsvv qsfnrgdc

CDR1 =

(SEQ ID NO.: 48)

qasqsvynnrla

CDR2 =

(SEQ ID NO.: 49)

lastlas

CDR3 =

(SEQ ID NO.: 50)

aggysgnina

Clone DR5TAA-0006 (Alias: clone 058)
Heavy chain
VH (SEQ ID NO.: 51)

qsleesggrlvtpgtpltltctasgfslssnhmswvrqapgkglewig yiyagsgsayyaswakgrftisrtsttvdlkmtslttedtatyfcagd agssywefnlwgpgtlvtvss

CH1-3

(SEQ ID NO.: 42)

gqpkapsvfplapccgdtpsstvtlgclvkgylpepvtvtwnsgtltn gvrtfpsvrqssglyslssvvsvtsssqpvtcnvahpatntkvdktva pstcskptcpppellggpsvfifppkpkdtlmisrtpevtcvvvdsq ddpevqftwyinneqvrtarpplreqqfnstirvvstlpiahqdwlrg kefkckvhnkalpapiektiskargqplepkvytmgppreelssrsys ltcmingfypsdisvewekngkaednyktttpavldsdgsyflynklsv ptsewqrgdyftcsvmhealhnhytqksisrspgk

CDR1 =

(SEQ ID NO.: 52)

snhms

CDR2 =

(SEQ ID NO.: 53)

yiyagsgsayyaswakg

CDR3 =

(SEQ ID NO.: 54)

dagssywefnl

Light chain
VL (SEQ ID NO.: 55)

lvmtqtpsstsepvggtvtikcqasqsigsslswyqqkpgqppklliy hastlasgvpsrfsgsrsgiqttltisgvqcddaatyyclgvadarrd dgfafgggtevvvk Ckappa (SEQ ID NO.: 56)

gdpvaptvlifppaadqvatgtvtivcvankyfpdvtvtwevdgttqt tgiensktpqnsadctynlsstltltstqynshkeytckvtqgttsvv qsfnrgdc

CDR1 =

(SEQ ID NO.: 57)

qasqsigssls

CDR2 =

(SEQ ID NO.: 58)

hastlas

CDR3 =

(SEQ ID NO.: 59)

lgvadarrddgfa

Clone DR5TAA-0010 (Alias: clone 481)
Heavy chain
VH (SEQ ID NO.: 60)

qsleesggrlvkpdetltltctvsgfslssnaiswvrqapgmglewig iigssgytyyaswakgrftvsktsttvdleiaspttedtatyfcargy sgasdysfnlwgpgtlvtvss

CH1-3

(SEQ ID NO.: 42)

gqpkapsvfplapccgdtpsstvtlgclvkgylpepvtvtwnsgtltn gvrtfpsvrqssglyslssvvsvtsssqpvtcnvahpatntkvdktva pstcskptcpppellggpsvfifppkpkdtlmisrtpevtcvvvdsq ddpevqftwyinneqvrtarpplreqqfnstirvvstlpiahqdwlrg kefkckvhnkalpapiektiskargqplepkvytmgppreelssrsys ltcmingfypsdisvewekngkaednyktttpavldsdgsyflynklsv ptsewqrgdyftcsvmhealhnhytqksisrspgk

CDR1 =

(SEQ ID NO.: 61)

snais

CDR2 =

(SEQ ID NO.: 62)

iigssgytyyaswakg

CDR3 =

(SEQ ID NO.: 63)

gysgasdysfnl

Light chain
VL (SEQ ID NO.: 64)

aydmtqtpdsvevavggtvtikcqasqtigdalawyqqkpgqrpnlli yrtstlasgvpsrfsgsgsgthftltisgvecadaatyycqqgatynn vlntfgggtevvvk Ckappa (SEQ ID NO.: 47)

gdpvaptvlifppaadqvatgtvtivcvankyfpdvtvtwevdgttqt tgiensktpqnsadctynlsstltltstqynshkeytckvtqgttsvv qsfnrgdc

CDR1 =

(SEQ ID NO.: 65)

qasqtigdala

CDR2 =

(SEQ ID NO.: 66)

rtstlas

CDR3 =

(SEQ ID NO.: 67)

qqgatynnvlnt

Clone DR5TAA-0013 (Alias: clone 298)
Heavy chain
VH

-continued (SEQ ID NO.: 68)
Qsleesggrlvtpgtpltltctasgftissyhmswvrqapgkglewig yiyagsastwyaswvkgrftisktsttvdlkmtslttedtatyfcard agssywefnlwgpgtlvtvss CH1-3
(SEQ ID NO.: 42)
gqpkapsvfplapccgdtpsstvtlgclvkgylpepvtvtwnsgtltn gvrtfpsvrqssglyslssvvsvtsssqpvtcnvahpatntkvdktva pstcskptcpppellggpsvfifppkpkdtlmisrtpevtcvvvdvsq ddpevqftwyinneqvrtarpplreqqfnstirvvstlpiahqdwlrg kefkckvhnkalpapiektiskargqplepkvytmgppreelssrsys ltcmingfypsdisveweknqkaednyktt
ltcmingfypsdisveweknqkaednykttpavldsdgsyflynklsv ptsewqrgdyftcsvmhealhnhytqksisrspgk CDR1 =
(SEQ ID NO.: 69)
syhms CDR2 =
(SEQ ID NO.: 70)
yiyagsastwyaswvkg CDR3 =
(SEQ ID NO.: 54)
dagssywefnl Light chain
VL
(SEQ ID NO.: 71)
Lvmtqtpsstsepvggtvtikcqasqsigsslswyqqtpgqppklliy tasslassvpkrfsgsrsgtqftltisgvqcadaatyyclgiddvrrd dgfafgggtevvvk Ckappa
(SEQ ID NO.: 47)
gdpvaptvlifppaadqvatgtvtivcvankyfpdvtvtwevdgttqt tgiensktpqnsadctynlsstltltstqynshkeytckvtqgttsvv qsfnrgdc CDR1 =
(SEQ ID NO.: 57)
qasqsigssls CDR2 =
(SEQ ID NO.: 72)
tasslas CDR3 =
(SEQ ID NO.: 73)
lgiddvrrddgfa Clone DR5TAA-0019 (Alias: clone 461)
Heavy chain
VH
(SEQ ID NO.: 74)
Qsveesggrlvtpgtpltltctvsgfslsnyamswvrqapgkglewig iisssgttyyaswakgrftisktsttvdlkvtspttedtatyfcaret yygysyaaglwgpgtlvtvss CH1-3
(SEQ ID NO.: 42)
gqpkapsvfplapccgdtpsstvtlgclvkgylpepvtvtwnsgtltn gvrtfpsvrqssglyslssvvsvtsssqpvtcnvahpatntkvdktva pstcskptcpppellggpsvfifppkpkdtlmisrtpevtcvvvdvsq ddpevqftwyinneqvrtarpplreqqfnstirvvstlpiahqdwlrg kefkckvhnkalpapiektiskargqplepkvytmgppreelssrsys ltcmingfypsdisveweknqkaednykttpavldsdgsyflynklsv ptsewqrgdyftcsvmhealhnhytqksisrspgk CDR1 =
(SEQ ID NO.: 75)
nyams CDR2 =
(SEQ ID NO.: 76)
iisssgttyyaswakg CDR3 =
(SEQ ID NO.: 77)
etyygysyaagl Light chain
VL
(SEQ ID NO.: 78)
Alvmtqtpssysaavggtvtincqasqniysnlawfqqkpgqppklli yetsklasgvpsrfsgsgsgteftltisdlecddaatyycqsswhsis tdcafgggtevvvk Ckappa
(SEQ ID NO.: 47)
gdpvaptvlifppaadqvatgtvtivcvankyfpdvtvtwevdgttqt tgiensktpqnsadctynlsstltltstqynshkeytckvtqgttsvv qsfnrgdc CDR1 =
(SEQ ID NO.: 79)
qasqniysnla CDR2 =
(SEQ ID NO.: 80)
etsklas CDR3 =
(SEQ ID NO.: 81)
qsswhsistdca Clone DR5TAA-0016 (Alias: clone 422)
Heavy chain
VH
(SEQ ID NO.: 82)
Qsleesggrlvkpdetltltctvsgfslnnyamswvrqapgkglewig minkygtkyyatwtkgratisktsttldleitspttedtatyfcarvr yagddyaewldvwgqgilvtvss CH1-3
(SEQ ID NO.: 42)
gqpkapsvfplapccgdtpsstvtlgclvkgylpepvtvtwnsgtltn gvrtfpsvrqssglyslssvvsvtsssqpvtcnvahpatntkvdktva pstcskptcpppellggpsvfifppkpkdtlmisrtpevtcvvvdvsq ddpevqftwyinneqvrtarpplreqqfnstirvvstlpiahqdwlrg kefkckvhnkalpapiektiskargqplepkvytmgppreelssrsys ltcmingfypsdisveweknqkaednykttpavldsdgsyflynklsv ptsewqrgdyftcsvmhealhnhytqksisrspgk CDR1 =
(SEQ ID NO.: 75)
nyams

CDR2 =

```
                                               (SEQ ID NO.: 83)
minkygtkyyatwtkg CDR3 =
                                               (SEQ ID NO.: 84)
vryagddyaewldv Light chain
VL
                                               (SEQ ID NO.: 85)
Adivmtqtaspvsaavggtvtincqasqsisssyyswyqqkpgqppki
liykastlasgvpsrfsgsgsgtqlsltirgvqcddaatyyclygysd
vssseyvfgggtevvvr Ckappa
                                               (SEQ ID NO.: 47)
gdpvaptvlifppaadqvatgtvtivcvankyfpdvtvtwevdgttqt
tgiensktpqnsadctynlsstltltstqynshkeytckvtqgttsvv
qsfnrgdc CDR1 =
                                               (SEQ ID NO.: 86)
qasqsisssyvs CDR2 =
                                               (SEQ ID NO.: 28)
kastlas CDR3 =
                                               (SEQ ID NO.: 87)
lygysdvssseyv Clone DR5TAA-0011 (Alias: clone 174)
Heavy chain
VH
                                               (SEQ ID NO.: 88)
Qsveesggrlvtpgtpltltctvsgfsisryamiwvrqapgegleyig
fitsdssayyaswakgrftisktsttvdlkmtspttedtatyfcaryt
ysdgtdlwgpgtlvtvss CH1-3
                                               (SEQ ID NO.: 42)
Gqpkapsvfplapccgdtpsstvtlgclvkgylpepvtvtwnsgtltn
gvrtfpsvrqssglyslssvvsvtsssqpvtcnvahpatntkvdktva
pstcskptcpppellggpsvfifppkpkdtlmisrtpevtcvvvdvsq
ddpevqftwyinneqvrtarpplreqqfnstirvvstlpiahqdwlrg
kefkckvhnkalpapiektiskargqplepkvytmgppreelssrsys
ltcmingfypsdisvewekngkaednykttpavldsdgsyflynklsv
ptsewqrgdyftcsvmhealhnhytqksisrspgk CDR1 =
                                               (SEQ ID NO.: 17)
ryami CDR2 =
                                               (SEQ ID NO.: 25)
fitsdssayyaswakg CDR3 =
                                               (SEQ ID NO.: 19)
ytysdgtdl Light Chain
VL
                                               (SEQ ID NO.: 89)
Adivmtqtpasysepvggtvtikcqasqsistylswyqqkpgqppkrl
iykastlasgvpsrfkgsgsgtdftltirdlecadaatyycqpnsgia
tygaafgggtevvvk Ckappa
                                               (SEQ ID NO.: 47)
gdpvaptvlifppaadqvatgtvtivcvankyfpdvtvtwevdgttqt
tgiensktpqnsadctynlsstltltstqynshkeytckvtqgttsvv
qsfnrgdc CDR1 =
                                               (SEQ ID NO.: 27)
qasqsistyls CDR2 =
                                               (SEQ ID NO.: 28)
kastlas CDR3 =
                                               (SEQ ID NO.: 22)
qpnsgiatygaa
```

8. Amino Acid Sequences of Chimerized Variant of Rabbit Mab DR5TAA-0011

```
Clone DR5TAA-0052 (chimeric variant)
Heavy chain
VH
                                               (SEQ ID NO.: 90)
Qsveesggrlvtpgtpltltctvsgfsisryamiwvrqapgegleyig
fitsdssayyaswakgrftisktsttvdlkmtspttedtatyfcaryt
ysdgtdlwgpgtlvtvss CH1-3
                                               (SEQ ID NO.: 91)
Astkgpsvfplapsskstsggtaalgclvkdyfpepvtvswnsgalts
gvhtfpavlqssglyslssvvtvpssslgtqtyicnvnhkpsntkvdk
kvepkscdkthtcppcpapeaaggpsvflfppkpkdtlmisrtpevtc
vvvdvshedpevkfnwyvdgvevhnaktkpreeqynstyrvvsyltvl
hqdwingkeykckvsnkalgapiektiskakgqprepqvytlppsrde
ltknqvsltclvkgfypsdiavewesngqpennykttppvldsdgsff
lysklkvdksrwqqgnvfscsvmhealhnhytqkslslspgk
```

```
CDR1 =
                                               (SEQ ID NO.: 17)
ryami CDR2 =
                                               (SEQ ID NO.: 25)
fitsdssayyaswakg CDR3 =
                                               (SEQ ID NO.: 19)
ytysdgtdl Light chain
VH
                                               (SEQ ID NO.: 92)
Adivmtqtpasysepvggtvtikcqasqsistylswyqqkpgqppkrl
iykastlasgvpsrfkgsgsgtdftltirdlesadaatyycqpnsgia
tygaafgggtevvvk Ckappa
                                               (SEQ ID NO.: 93)
Rtvaapsvfifppsdeqlksgtasvvcllnnfypreakvqwkvdnalq
sgnsqesvteqdskdstyslsstltlskadyekhkvyacevthqglss
pvtksfnrgec
```

```
CDR1 =
                                      (SEQ ID NO.: 27)
qasqsistyls

CDR2 =
                                      (SEQ ID NO.: 28)
kastlas

CDR3 =
                                      (SEQ ID NO.: 22)
qpnsgiatygaa
```

9. Sequences of Humanized Variants of Rabbit Mab DR5TAA-0011

| Variant | | HC variant | LC variant |
|---|---|---|---|
| DR5TAA-0066 | humanized | VH7 | VL3 |
| DR5TAA-0067 | humanized | VH7 | VL15 |
| DR5TAA-0068 | Humanized | VH17 | VL10 |
| DR5TAA-0071 | Humanized | VH17 | VL15 |
| DR5TAA-0072 | Humanized | VH17 | VL2 |
| DR5TAA-0073 | Humanized | VH17 | VL3 |
| DR5TAA-0074 | Humanized | VH7 | VL10 |
| DR5TAA-0075 | Humanized | VH7 | VL11 |

```
Humanized variants Heavy Chain
VH7
VH
                                      (SEQ ID NO.: 23)
Evqlvetgggliqpggslrlscaasgftvsryamiwvrqapgkgleyi
gfitsdgstyyadsakgrftisrdnskntlylqmnslraedtavyyca
rytysdgtdlwgrgtlvtvss CH1-3
                                      (SEQ ID NO.: 91)
astkgpsvfplapssksstsggtaalgclvkdyfpepvtvswnsgalts
gvhtfpavlqssglyslssvvtvpssslgtqtyicnvnhkpsntkvdk
kvepkscdkthtcppcpapeaaggpsvflfppkpkdtlmisrtpevtc
vvvdvshedpevkfnwyvdgvevhnaktkpreeqynstyrvvsyltvl
hqdwingkeykckvsnkalgapiektiskakgqprepqvytlppsrde
ltknqvsltclvkgfypsdiavewesngqpennykttppvldsdgsff
lyskltvdksrwqqgnvfscsvmhealhnhytqkslslspgk
constant chain
CDR1 =
                                      (SEQ ID NO.: 17)
ryami CDR2 =
                                      (SEQ ID NO.: 18)
fitsdgstyyadsakg CDR3 =
                                      (SEQ ID NO.: 19)
ytysdgtdl VH17
VH
                                      (SEQ ID NO.: 26)
qvqlvesggglvqpggslrlscsasgfsisryamiwvrqapgkgleyv
gfitsdssayyaswakgrftisrdnskntlylqmnslraedtavyyca
rytysdgtdlwgqgtlvtvss CH1-3
                                      (SEQ ID NO.: 91)
astkgpsvfplapssksstsggtaalgclvkdyfpepvtvswnsgalts
gvhtfpavlqssglyslssvvtvpssslgtqtyicnvnhkpsntkvdk
kvepkscdkthtcppcpapeaaggpsvflfppkpkdtlmisrtpevtc
vvvdvshedpevkfnwyvdgvevhnaktkpreeqynstyrvvsyltvl
hqdwingkeykckvsnkalgapiektiskakgqprepqvytlppsrde
ltknqvsltclvkgfypsdiavewesngqpennykttppvldsdgsff
lyskltvdksrwqqgnvfscsvmhealhnhytqkslslspgk CDR1 =
                                      (SEQ ID NO.: 17)
ryami CDR2 =
                                      (SEQ ID NO.: 25)
fitsdssayyaswakg CDR3 =
                                      (SEQ ID NO.: 19)
ytysdgtdl Humanized variants Light Chain
VL2
VL
                                      (SEQ ID NO.: 32)
Diqmtqspstlsasvgdrvtitcrasqsistylswyqqkpgkapkrli
ykasslasgvpsrfsgsgsgteftltisslqpddaatyycqpnsgiat
ygaafgggtkveik Ckappa
                                      (SEQ ID NO.: 93)
Rtvaapsvfifppsdeqlksgtasvvcllnnfypreakvqwkvdnalq
sgnsqesvteqdskdstyslsstltlskadyekhkvyacevthqglss
pvtksfnrgec CDR1 =
                                      (SEQ ID NO.: 20)
rasqsistyls CDR2 =
                                      (SEQ ID NO.: 21)
kasslas CDR3 =
                                      (SEQ ID NO.: 22)
qpnsgiatygaa VL3
VL
                                      (SEQ ID NO.: 30)
Diqmtqspsslsasvgdrvtitcrasqsistylswyqqkpgkapkrli
ykastlasgvpsrfsgsgsgtdftltisslqpedaatyycqpnsgiat
ygaafgggtkveik Ckappa
                                      (SEQ ID NO.: 93)
Rtvaapsvfifppsdeqlksgtasvvcllnnfypreakvqwkvdnalq
sgnsqesvteqdskdstyslsstltlskadyekhkvyacevthqglss
pvtksfnrgec
```

CDR1 =
(SEQ ID NO.: 20)
rasqsistyls

CDR2 =
(SEQ ID NO.: 28)
kastlas

CDR3 =
(SEQ ID NO.: 22)
qpnsgiatygaa

VL10
VL
(SEQ ID NO.: 31)
diqmtqspsslsasvgdrvtitcrasqsistylswyqqkpgqppkrli
ykastlasgvpsrfsgsgsgtdftltisslqpedfatyycqpnsgiat
ygaafgggtkveik Ckappa
(SEQ ID NO.: 93)
rtvaapsvfifppsdeqlksgtasvvcllnnfypreakvqwkvdnalq
sgnsqesvteqdskdstyslsstltlskadyekhkvyacevthqglss
pvtksfnrgec CDR1 =
(SEQ ID NO.: 20)
rasqsistyls CDR2 =
(SEQ ID NO.: 28)
kastlas CDR3 =
(SEQ ID NO.: 22)
qpnsgiatygaa VL11
VL
(SEQ ID NO.: 29)
diqmtqspsslsasvgdrvtitcqasqsistylswyqqkpgqppkrli
ykastlasgvpsrfsgsgsgtdftltisslqpedfatyycqpnsgiat
ygaafgggtkveik Ckappa
(SEQ ID NO.: 93)
rtvaapsvfifppsdeqlksgtasvvcllnnfypreakvqwkvdnalq
sgnsqesvteqdskdstyslsstltlskadyekhkvyacevthqglss
pvtksfnrgec CDR1 =
(SEQ ID NO.: 27)
qasqsistyls CDR2 =
(SEQ ID NO.: 28)
kastlas CDR3 =
(SEQ ID NO.: 22)
qpnsgiatygaa VL15
VL
(SEQ ID NO.: 24)
Adiqmtqspstlsasvgdrvtitcrasqsistylswyqqkpgkapkrl
iykasslasgvpsrfsgsgsgteftltisslqpddaatyycqpnsgia
tygaafgggtkveik Ckappa
(SEQ ID NO.: 93)
Rtvaapsvfifppsdeqlksgtasvvcllnnfypreakvqwkvdnalq
sgnsqesvteqdskdstyslsstltlskadyekhkvyacevthqglss
pvtksfnrgec CDR1 =
(SEQ ID NO.: 20)
rasqsistyls CDR2 =
(SEQ ID NO.: 21)
kasslas CDR3 =
(SEQ ID NO.: 22)
qpnsgiatygaa 10. Amino Acid Sequences of Chimeric Bispecific Constructs Containing Rabbit-Derived DR5-Binder Construct DR5TAA-0061 (1 + 1 chimeric Crossmab containing 4B9 and DR5TAA-0011)
LC (DR5)
(SEQ ID NO.: 280)
adivmtqtpasysepvggtvtikcqasqsistylswyqqkpgqppk
rliykastlasgvpsrfkgsgsgtdftltirdlecadaatyycqpn
sgiatygaafgggtevvvkrtvaapsvfifppsdeqlksgtasvvc
llnnfypreakvqwkvdnalqsgnsqesvteqdskdstyslsstlt
lskadyekhkvyacevthqglsspvtksfnrgec Crossed LC (FAP)
(SEQ ID NO.: 281)
eivltqspgtlslspgeratlscrasqsvtssylawyqqkpgqapr
llinvgsrratgipdrfsgsgsgtdftltisrlepedfavyycqqg
imlpptfgqgtkveikssastkgpsvfplapsskstsggtaalgcl
vkdyfpepvtvswnsgaltsgvhtfpavlqssglyslssvvtvpss
slgtqtyicnvnhkpsntkvdkkvepkscd HC (DR5)
(SEQ ID NO.: 282)
qsveesgggrlvtpgtpltltctvsgfsisryamiwvrqapgegley
igfitsdssayyaswakgrftisktsttvdlkmtspttedtatyfc
arytysdgtdlwgpgtivtvssastkgpsvfplapsskstsggtaa
lgclvkdyfpepvtvswnsgaltsgvhtfpavlqssglyslssvvt
vpssslgtqtyicnvnhkpsntkvdkkvepkscdkthtcppcpape
aaggpsvflfppkpkdtlmisrtpevtcvvvdvshedpevkfnwyv
dgvevhnaktkpreeqynstyrvvsvltvlhqdwlngkeykckvsn
kalgapiektiskakgqprepqvctlppsrdeltknqvslscavkg
fypsdiavewesngqpennykttppvldsdgsfflvskltvdksrw
qqgnvfscsvmhealhnhytqkslslspgk Crossed HC (FAP)
(SEQ ID NO.: 283)
evqllesgggglvqpggslrlscaasgftfssyamswvrqapgkgle
wvsaiigsgastyyadsvkgrftisrdnskntlylqmnslraedta
vyycakgwfggfnywgqgtivtvssasvaapsvfifppsdeqlksg
tasvvcllnnfypreakvqwkvdnalqsgnsqesvteqdskdstys

```
lsstltlskadyekhkvyacevthqglsspvtksfnrgecdkthtc
ppcpapeaaggpsvflfppkpkdtlmisrtpevtcvvvdvshedpe
vkfnwyvdgvevhnaktkpreeqynstyrvvsvltvlhqdwlngke
ykckvsnkalgapiektiskakgqprepqvytlppcrdeltknqvs
lwclvkgfypsdiavewesngqpennyktttppvldsdgsfflyskl
tvdksrwqqgnvfscsvmhealhnhytqkslslspgk
```

Construct DR5TAA-0032 (2 + 2 chimeric CrossMab containing 28H1 and DR5TAA-0005)
LC (DR5)
(SEQ ID NO.: 284)
```
aqvltqtpspvsaavggtvtincqasqsvynnrlawyqqkpgqppk
lliylastlasgvpsrfkgsgsgtqftltisdlqcddaatyycagg
ysgninafgggtevvvkrtvaapsvfifppsdeqlksgtasvvcll
nnfypreakvqwkvdnalqsgnsqesvteqdskdstyslsstltls
kadyekhkvyacevthqglsspvtksfnrgec
```

Crossed LC (FAP)
(SEQ ID NO.: 285)
```
eivltqspgtlslspgeratlscrasqsysrsylawyqqkpgqapr
lliigastratgipdrfsgsgsgtdftltisrlepedfavyycqqg
qvipptfgqgtkveikssastkgpsvfplapssksstsggtaalgcl
vkdyfpepvtvswnsgaltsgvhtfpavlqssglyslssvvtvpss
slgtqtyicnvnhkpsntkvdkkvepkscd
```

HC (DR5-crossed FAP)
(SEQ ID NO.: 286)
```
qsleesggrlvtpgtpitlictasgfslssaymswvrqapgkglew
igyiysgsgstwyaswvkgrftisktsttvdikitspttedtatyf
cargystmgdlwgpgtivtvssastkgpsvfplapssksstsggtaa
lgclvkdyfpepvtvswnsgaltsgvhtfpavlqssglyslssvvt
vpssslgtqtyicnvnhkpsntkvdkkvepkscdkthtcppcpape
llggpsvflfppkpkdtlmisrtpevtcvvvdvshedpevkfnwyv
dgvevhnaktkpreeqynstyrvvsvitvlhqdwingkeykckvsn
kalpapiektiskakgqprepqvytippsrdeltknqvsliclvkg
fypsdiavewesngqpennyktttppvldsdgsfflyskitvdksrw
qqgnvfscsvmhealhnhytqkslslspgksggggsggggsggggs
ggggsevqllesgglvqpggslrlscaasgftfsshamswvrqap
gkglewvsaiwasgeqyyadsvkgrftisrdnskntlylqmnslra
edtavyycakgwlgnfdywgqgtivtvssasvaapsvfifppsdeq
lksgtasvvcllnnfypreakvqwkvdnalqsgnsqesvteqdskd
styslsstititskadyekhkvyacevthqglsspvtksfnrgec
```

Construct DR5TAA-0033 (2 + 2 chimeric CrossMab containing 28H1 and DR5TAA-0011)
LC (DR5)
(SEQ ID NO.: 287)
```
adivmtqtpasysepvggtvtikcqasqsistylswyqqkpgqppk
rliykastlasgvpsrfkgsgsgtdftltirdlecadaatyycqpn
sgiatygaafgggtevvvkrtvaapsvfifppsdeqlksgtasvvc
llnnfypreakvqwkvdnalqsgnsqesvteqdskdstyslsstlt
lskadyekhkvyacevthqglsspvtksfnrgec
```

Crossed LC (FAP)
(SEQ ID NO.: 288)
```
eivltqspgtlslspgeratlscrasqsysrsylawyqqkpgqapr
lliigastratgipdrfsgsgsgtdftltisrlepedfavyycqqg
qvipptfgqgtkveikssastkgpsvfplapssksstsggtaalgcl
vkdyfpepvtvswnsgaltsgvhtfpavlqssglyslssvvtvpss
slgtqtyicnvnhkpsntkvdkkvepkscd
```

HC (DR5-crossed FAP)
(SEQ ID NO.: 289)
```
qsveesggrlvtpgtpltltctvsgfsisryamiwvrqapgegley
igfitsdssayyaswakgrftisktsttvdlkmtspttedtatyfc
arytysdgtdlwgpgtivtvssastkgpsvfplapssksstsggtaa
lgclvkdyfpepvtvswnsgaltsgvhtfpavlqssglyslssvvt
vpssslgtqtyicnvnhkpsntkvdkkvepkscdkthtcppcpape
llggpsvflfppkpkdtlmisrtpevtavvvdvshedpevkfnwyv
dgvevhnaktkpreeqynstyrvvsvltvlhqdwlngkeykckvsn
kalpapiektiskakgqprepqvytlppsrdeltknqvsltclvkg
fypsdiavewesngqpennyktttppvldsdgsfflyskltvdksrw
qqgnvfscsvmhealhnhytqkslslspgksggggsggggsggggs
ggggsevqllesgglvqpggslrlscaasgftfsshamswvrqap
gkglewvsaiwasgeqyyadsvkgrftisrdnskntlylqmnslra
edtavyycakgwlgnfdywgqgtivtvssasvaapsvfifppsdeq
lksgtasvvcllnnfypreakvqwkvdnalqsgnsqesvteqdskd
styslsstltlskadyekhkvyacevthqglsspvtksfnrgec
```

Construct DR5TAA-0034 (2 + 2 chimeric CrossMab containing 28H1 and DR5TAA-0013)
LC (DR5)
(SEQ ID NO.: 290)
```
alvmtqtpsstsepvggtvtikcqasqsigsslswyqqtpgqppkl
liytasslassvpkrfsgsrsgtqftltisgvqcadaatyyclgid
dvrrddgfafgggtevvvkrtvaapsvfifppsdeqlksgtasvvc
llnnfypreakvqwkvdnalqsgnsqesvteqdskdstyslsstlt
lskadyekhkvyacevthqglsspvtksfnrgec
```

Crossed LC (FAP)
(SEQ ID NO.: 291)
```
eivltqspgtlslspgeratlscrasqsysrsylawyqqkpgqapr
lliigastratgipdrfsgsgsgtdftltisrlepedfavyycqqg
qvipptfgqgtkveikssastkgpsvfplapssksstsggtaalgcl
vkdyfpepvtvswnsgaltsgvhtfpavlqssglyslssvvtvpss
slgtqtyicnvnhkpsntkvdkkvepkscd
```

HC (DR5-crossed FAP)
(SEQ ID NO.: 292)
```
qsleesggrlvtpgtpltltctasgftissyhmswvrqapgkglew
igyiyagsastwyaswvkgrftisktsttvdlkmtslttedtatyf
cardagssywefnlwgpgtivtvssastkgpsvfplapssksstsgg
```

```
taalgclvkdyfpepvtvswnsgaltsgvhtfpavlqssglyslss vvtvpssslgtqtyicnvnhkpsntkvdkkvepkscdkthtcppcp apellggpsvflfppkpkdtlmisrtpevtavvvdvshedpevkfn wyvdgvevhnaktkpreeqynstyrvvsvltvlhqdwlngkeykck vsnkalpapiektiskakgqprepqvytlppsrdeltknqvsltcl vkgfypsdiavewesngqpennykttppvldsdgsfflyskltvdk srwqqgnvfscsvmhealhnhytqkslslspgksggggsggggsgg ggsggggsevqllesgggvqpggslrlscaasgftfsshamswvr qapgkglewvsaiwasgeqyyadsvkgrftisrdnskntlylqmns lraedtavyycakgwlgnfdywgqgtivtvssasvaapsvfifpps deqlksgtasvvcllnnfypreakvqwkvdnalqsgnsqesvteqd skdstyslsstltlskadyekhkvyacevthqglsspvtksfnrge c
```

Construct DR5TAA-0035 (2 + 2 chimeric CrossMab containing 28H1 and DR5TAA-0016)
LC (DR5)
(SEQ ID NO.: 293)

```
adivmtqtaspvsaavggtvtincqasqsisssyvswyqqkpgqpp klliykastlasgvpsrfsgsgsgtqlsltirgvqcddaatyycly gysdvssseyvfggtevvvrrtvaapsvfifppsdeqlksgtasv vcllnnfypreakvqwkvdnalqsgnsqesvteqdskdstyslsst ltlskadyekhkvyacevthqglsspvtksfnrgec
```

Crossed LC (FAP)
(SEQ ID NO.: 294)

```
eivltqspgtlslspgeratlscrasqsysrsylawyqqkpgqapr lliigastratgipdrfsgsgsgtdftltisrlepedfavyycqqg qvipptfgqgtkveikssastkgpsvfplapsskstsggtaalgcl vkdyfpepvtvswnsgaltsgvhtfpavlqssglyslssvvtvpss slgtqtyicnvnhkpsntkvdkkvepkscd
```

HC (DR5-crossed FAP)
(SEQ ID NO.: 295)

```
qsleesggrlvkpdetltltctvsgfslnnyamswvrqapgkglew igminkygtkyyatwtkgratisktsttldleitspttedtatyfc arvryagddyaewldvwgqgilvtvssastkgpsvfplapsskstss ggtaalgclvkdyfpepvtvswnsgaltsgvhtfpavlqssglysl ssvvtvpssslgtqtyicnvnhkpsntkvdkkvepkscdkthtcpp cpapellggpsvflfppkpkdtlmisrtpevtcvvvdvshedpevk fnwyvdgvevhnaktkpreeqynstyrvvsvltvlhqdwlngkeyk ckvsnkalpapiektiskakgqprepqvytlppsrdeltknqvslt clvkgfypsdiavewesngqpennykttppvldsdgsfflyskltv dksrwqqgnvfscsvmhealhnhytqkslslspgksggggsgggs ggggsggggsevqllesgggvqpggslrlscaasgftfsshamsw vrqapgkglewvsaiwasgeqyyadsvkgrftisrdnskntlylqm nslraedtavyycakgwlgnfdywgqgtivtvssasvaapsvfifp psdeqlksgtasvvcllnnfypreakvqwkvdnalqsgnsqesvte qdskdstyslsstltlskadyekhkvyacevthqglsspvtksfnr gec
```

Construct DR5TAA-0036 (2 + 2 chimeric CrossMab containing 28H1 and DR5TAA-0019)
LC (DR5)
(SEQ ID NO.: 296)

```
alvmtqtpssysaavggtvtincqasqniysnlawfqqkpgqppkl liyetsklasgvpsrfsgsgsgteftltisdlecddaatyycqssw hsistdcafgggtevvvkrtvaapsvfifppsdeqlksgtasvvcl lnnfypreakvqwkvdnalqsgnsqesvteqdskdstyslsstltl skadyekhkvyacevthqglsspvtksfnrgec
```

Crossed LC (FAP)
(SEQ ID NO.: 297)

```
eivltqspgtlslspgeratlscrasqsysrsylawyqqkpgqapr lliigastratgipdrfsgsgsgtdftltisrlepedfavyycqqg qvipptfgqgtkveikssastkgpsvfplapsskstsggtaalgcl vkdyfpepvtvswnsgaltsgvhtfpavlqssglyslssvvtvpss slgtqtyicnvnhkpsntkvdkkvepkscd
```

HC (DR5-crossed FAP)
(SEQ ID NO.: 298)

```
qsveesggrlvtpgtpltltctvsgfslsnyamswvrqapgkglew igiisssgttyyaswakgrftisktsttvdlkvtspttedtatyfc aretyygysyaaglwgpgtivtvssastkgpsvfplapsskstsgg taalgclvkdyfpepvtvswnsgaltsgvhtfpavlqssglyslss vvtvpssslgtqtyicnvnhkpsntkvdkkvepkscdkthtcppcp apellggpsvflfppkpkdtlmisrtpevtcvvvdvshedpevkfn wyvdgvevhnaktkpreeqynstyrvvsvltvlhqdwlngkeykck vsnkalpapiektiskakgqprepqvytlppsrdeltknqvsltcl vkgfypsdiavewesngqpennykttppvldsdgsfflyskltvdk srwqqgnvfscsvmhealhnhytqkslslspgksggggsggggsgg ggsggggsevqllesgggvqpggslrlscaasgftfsshamswvr qapgkglewvsaiwasgeqyyadsvkgrftisrdnskntlylqmns lraedtavyycakgwlgnfdywgqgtivtvssasvaapsvfifpps deqlksgtasvvcllnnfypreakvqwkvdnalqsgnsqesvteqd skdstyslsstltlskadyekhkvyacevthqglsspvtksfnrge c
```

11. Amino Acid Sequences of Bispecific Constructs Containing Humanized Rabbit-Derived DR5-Binder Construct DR5TAA-0117 (2 + 2 humanized CrossMab containing 28H1 and DR5TAA-0067)
LC (DR5)
(SEQ ID NO.: 299)

```
adiqmtqspstlsasvgdrvtitcrasqsistylswyqqkpgkapk rliykasslasgvpsrfsgsgsgteftltisslqpddaatyycqpn sgiatygaafgggtkveikrtvaapsvfifppsdeqlksgtasvvc
```

```
llnnfypreakvqwkvdnalqsgnsqesvteqdskdstyslsstlt
lskadyekhkvyacevthqglsspvtksfnrgec Crossed LC (FAP)
                                (SEQ ID NO.: 300)
eivltqspgtlslspgeratlscrasqsysrsylawyqqkpgqapr lliigastratgipdrfsgsgsgtdftltisrlepedfavyycqqg qvipptfgqgtkveikssastkgpsvfplapssksstsggtaalgcl vkdyfpepvtvswnsgaltsgvhtfpavlqssglyslssvvtvpss slgtqtyicnvnhkpsntkvdkkvepkscd HC (DR5-crossed FAP)
                                (SEQ ID NO.: 301)
evqlvetgggliqpggslrlscaasgftvsryamiwvrqapgkgle yigfitsdgstyyadsakgrftisrdnskntlylqmnslraedtav yycarytysdgtdlwgrgtivtvssastkgpsvfplapssksttsgg taalgclvkdyfpepvtvswnsgaltsgvhtfpavlqssglyslss vvtvpssslgtqtyicnvnhkpsntkvdkkvepkscdkthtcppcp apeaaggpsvflfppkpkdtlmisrtpevtcvvvdvshedpevkfn wyvdgvevhnaktkpreeqynstyrvvsvltvlhqdwlngkeykck vsnkalgapiektiskakgqprepqvytlppsrdeltknqvsltcl vkgfypsdiavewesngqpennykttppvldsdgsfflyskltvdk srwqqgnvfscsvmhealhnhytqkslslspggggsgggsgggg sggggsevqllesgggqlvqpggslrlscaasgftfsshamswvrqa pgkglewvsaiwasgeqyyadsvkgrftisrdnskntlylqmnslr aedtavyycakgwlgnfdywgqgtivtvssasvaapsvfifppsde qlksgtasvvcllnnfypreakvqwkvdnalqsgnsqesvteqdsk dstyslsstltlskadyekhkvyacevthqglsspvtksfnrgec Construct DR5TAA-0118 (2 + 2 humanized CrossMab
containing 28H1 and DR5TAA-0071)
LC (DR5)
                                (SEQ ID NO.: 302)
adiqmtqspstlsasvgdrvtitcrasqsistylswyqqkpgkapk rliykasslasgvpsrfsgsgsgteftltisslqpddaatyycqpn sgiatygaafgggtkveikrtvaapsvfifppsdeqlksgtasvvc llnnfypreakvqwkvdnalqsgnsqesvteqdskdstyslsstlt lskadyekhkvyacevthqglsspvtksfnrgec Crossed LC (FAP)
                                (SEQ ID NO.: 303)
eivltqspgtlslspgeratlscrasqsysrsylawyqqkpgqapr lliigastratgipdrfsgsgsgtdftltisrlepedfavyycqqg qvipptfgqgtkveikssastkgpsvfplapssksstsggtaalgcl vkdyfpepvtvswnsgaltsgvhtfpavlqssglyslssvvtvpss slgtqtyicnvnhkpsntkvdkkvepkscd HC (DR5-crossed FAP)
                                (SEQ ID NO.: 304)
qvqlvesgggglvqpggslrlscsasgfsisryamiwvrqapgkgle yvgfitsdssayyaswakgrftisrdnskntlylqmnslraedtav yycarytysdgtdlwgqgtivtvssastkgpsvfplapssksttsgg taalgclvkdyfpepvtvswnsgaltsgvhtfpavlqssglyslss vvtvpssslgtqtyicnvnhkpsntkvdkkvepkscdkthtcppcp apeaaggpsvflfppkpkdtlmisrtpevtcvvvdvshedpevkfn wyvdgvevhnaktkpreeqynstyrvvsvltvlhqdwlngkeykck vsnkalgapiektiskakgqprepqvytlppsrdeltknqvsltcl vkgfypsdiavewesngqpennykttppvldsdgsfflyskltvdk srwqqgnvfscsvmhealhnhytqkslslspggggsgggsgggg sggggsevqllesgggqlvqpggslrlscaasgftfsshamswvrqa pgkglewvsaiwasgeqyyadsvkgrftisrdnskntlylqmnslr aedtavyycakgwlgnfdywgqgtivtvssasvaapsvfifppsde qlksgtasvvcllnnfypreakvqwkvdnalqsgnsqesvteqdsk dstyslsstltlskadyekhkvyacevthqglsspvtksfnrgec Construct DR5TAA-0119 (2 + 2 humanized CrossMab
containing 28H1 and DR5TAA-0075)
LC (DR5)
                                (SEQ ID NO.: 305)
diqmtqspsslsasvgdrvtitcqasqsistylswyqqkpgqppkr liykastlasgvpsrfsgsgsgtdftltisslqpedfatyycqpns giatygaafgggtkveikrtvaapsvfifppsdeqlksgtasvvcl lnnfypreakvqwkvdnalqsgnsqesvteqdskdstyslsstltl skadyekhkvyacevthqglsspvtksfnrgec Crossed LC (FAP)
                                (SEQ ID NO.: 306)
eivltqspgtlslspgeratlscrasqsysrsylawyqqkpgqapr lliigastratgipdrfsgsgsgtdftltisrlepedfavyycqqg qvipptfgqgtkveikssastkgpsvfplapssksstsggtaalgcl vkdyfpepvtvswnsgaltsgvhtfpavlqssglyslssvvtvpss slgtqtyicnvnhkpsntkvdkkvepkscd HC (DR5-crossed FAP)
                                (SEQ ID NO.: 307)
evqlvetgggliqpggslrlscaasgftvsryamiwvrqapgkgle yigfitsdgstyyadsakgrftisrdnskntlylqmnslraedtav yycarytysdgtdlwgrgtivtvssastkgpsvfplapssksttsgg taalgclvkdyfpepvtvswnsgaltsgvhtfpavlqssglyslss vvtvpssslgtqtyicnvnhkpsntkvdkkvepkscdkthtcppcp apeaaggpsvflfppkpkdtlmisrtpevtcvvvdvshedpevkfn wyvdgvevhnaktkpreeqynstyrvvsvltvlhqdwlngkeykck vsnkalgapiektiskakgqprepqvytlppsrdeltknqvsltcl vkgfypsdiavewesngqpennykttppvldsdgsfflyskltvdk srwqqgnvfscsvmhealhnhytqkslslspggggsgggsgggg sggggsevqllesgggqlvqpggslrlscaasgftfsshamswvrqa pgkglewvsaiwasgeqyyadsvkgrftisrdnskntlylqmnslr aedtavyycakgwlgnfdywgqgtivtvssasvaapsvfifppsde qlksgtasvvcllnnfypreakvqwkvdnalqsgnsqesvteqdsk
```

-continued dstyslsstltlskadyekhkvyacevthqglsspvtksfnrgec

12. Amino Acid Sequences of C-Terminal Fusions of Humanized Rabbit-Derived DR5-Binder

| Description | Amino acid sequences | SEQ ID NO |
|---|---|---|
| huFc-hVH007 | DKTHTCPPCPAPELLGGPSVFLFP PKPKDTLMISRTPEVTCVVVDVSH EDPEVKFNWYVDGVEVHNAKTKPR EEQYNSTYRVVSVLTVLHQDWLNG KEYKCKVSNKALPAPIEKTISKAK GQPREPQVYTLPPSRDELTKNQVS LTCLVKGFYPSDIAVEWESNGQPE NNYKTTPPVLDSDGSFFLYSKLTV DKSRWQQGNVFSCSVMHEALHNHY TQKSLSLSPGGGGSGGGGSGGGG SGGGGSEVQLVETGGGLIQPGGSL RLSCAASGFTVSRYAMIWVRQAPG KGLEYIGFITSDGSTYYADSAKGR FTISRDNSKNTLYLQMNSLRAEDT AVYYCARYTYSDGTDLWGRGTLVT VSSASTKGPSVFPLAPSSKSTSGG TAALGCLVKDYFPEPVTVSWNSGA LTSGVHTFPAVLQSSGLYSLSSVV TVPSSSLGTQTYICNVNHKPSNTK VDKKVEPKSCD | 308 |
| hVL015 | DIQMTQSPSTLSASVGDRVTITCR ASQSISTYLSWYQQKPGKAPKRLI YKASSLASGVPSRFSGSGSGTEFT LTISSLQPDDAATYYCQPNSGIAT YGAAFGGGTKVEIKRTVAAPSVFI FPPSDEQLKSGTASVVCLLNNFYP REAKVQWKVDNALQSGNSQESVTE QDSKDSTYSLSSTLTLSKADYEKH KVYACEVTHQGLSSPVTKSFNRGE C | 309 |
| huFc-hVH017 | DKTHTCPPCPAPELLGGPSVFLFP PKPKDTLMISRTPEVTCVVVDVSH EDPEVKFNWYVDGVEVHNAKTKPR EEQYNSTYRVVSVLTVLHQDWLNG KEYKCKVSNKALPAPIEKTISKAK GQPREPQVYTLPPSRDELTKNQVS LTCLVKGFYPSDIAVEWESNGQPE NNYKTTPPVLDSDGSFFLYSKLTV DKSRWQQGNVFSCSVMHEALHNHY TQKSLSLSPGGGGSGGGGSGGGG SGGGGSQVQLVESGGGLVQPGGSL RLSCSASGFSISRYAMIWVRQAPG KGLEYVGFITSDSSAYYASWAKGR FTISRDNSKNTLYLQMNSLRAEDT AVYYCARYTYSDGTDLWGQGTLVT VSSASTKGPSVFPLAPSSKSTSGG TAALGCLVKDYFPEPVTVSWNSGA LTSGVHTFPAVLQSSGLYSLSSVV TVPSSSLGTQTYICNVNHKPSNTK VDKKVEPKSCD | 310 |
| hVL011 | DIQMTQSPSSLSASVGDRVTITCQ ASQSISTYLSWYQQKPGQPPKRLI YKASTLASGVPSRFSGSGSGTDFT LTISSLQPEDFATYYCQPNSGIAT YGAAFGGGTKVEIKRTVAAPSVFI FPPSDEQLKSGTASVVCLLNNFYP REAKVQWKVDNALQSGNSQESVTE QDSKDSTYSLSSTLTLSKADYEKH KVYACEVTHQGLSSPVTKSFNRGE C | 311 |

13. Nucleic Acid Sequences of DR5 Binders and Bispecific Molecules Comprising them

| Description | Nucleotide sequences | SEQ ID NO |
|---|---|---|
| DR5 (22E9)_VH | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC TGCAGATGAACAGCCTGAGAGCCGAGGACACGGCCGTATATTACTGTG CGAAAGGTGTGCGGATTTCGTTTGACTACTGGGGCCAAGGAACCCTGG TCACCGTCTCGAGT | 167 |
| DR5 (22E9)_CDRH1 | AGTTATGCCATGAGC | 168 |
| DR5 (22E9)_CDRH2 | GCTATTAGTGGTAGTGGTGGTAGCACATACTACGCAGACTCCGTGAAG GGC | 169 |
| DR5 (22E9)_CDRH3 | GGTGTGCGGATTTCGTTTGACTAC | 170 |
| DR5 (22E9)_VL | GAAATCGTGTTAACGCAGTCTCCAGGCACCCTGTCTTTGTCTCCAGGGG AAAGAGCCACCCTCTCTTGCAGGGCCAGTCAGAGTGTTAGCAGCAGCT ACTTAGCCTGGTACCAGCAGAAACCTGGCCAGGCTCCCAGGCTCCTCA TCTATGGAGCATCCAGCAGGGCCACTGGCATCCCAGACAGGTTCAGTG GCAGTGGATCCGGGACAGACTTCACTCTCACCATCAGCAGACTGGAGC CTGAAGATTTTGCAGTGTATTACTGTCAGCAGGGTTCTAATCAGCCCGT TACGTTCGGCCAGGGGACCAAAGTGGAAATCAAA | 171 |
| DR5 (22E9)_CDRL1 | AGGGCCAGTCAGAGTGTTAGCAGCAGCTACTTAGCC | 172 |
| DR5 (22E9)_CDRL2 | GGAGCATCCAGCAGGGCCACT | 173 |
| DR5 (22E9)_CDRL3 | CAGCAGGGTTCTAATCAGCCCGTTACG | 174 |

-continued

| Description | Nucleotide sequences | SEQ ID NO |
|---|---|---|
| DR5 (21H3)_VH | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC TGCAGATGAACAGCCTGAGAGCCGAGGACATGGCCGTATATTACTGTG CGAAAGGTGCTCGTGTTTCTTTTGACTACTGGGGCCAAGGAACCCTGG TCACCGTCTCGAGT | 175 |
| DR5 (21H3)_CDRH1 | AGTTATGCCATGAGC | 176 |
| DR5 (21H3)_CDRH2 | GCTATTAGTGGTAGTGGTGGTAGCACATACTACGCAGACTCCGTGAAG GGC | 177 |
| DR5 (21H3)_CDRH3 | GGTGCTCGTGTTTCTTTTGACTAC | 178 |
| DR5 (21H3)_VL | GAAATCGTGTTAACGCAGTCTCCAGGCACCCTGTCTTTGTCTCCAGGGG AAAGAGCCACCCTCTCTTGCAGGGCCAGTCAGAGTGTTAGCAGCAGCT ACTTAGCCTGGTACCAGCAGAAACCTGGCCAGGCTCCCAGGCTCCTCA TCTATGGAGCATCCAGCAGGGCCACTGGCATCCCAGACAGGTTCAGTG GCAGTGGATCCGGGACAGACTTCACTCTCACCATCAGCAGACTGGAGC CTGAAGATTTTGCGGTGTATTACTGTCAGCAGGGTTCTCAGCCGCCCAT TACGTTCGGCCAGGGGACCAAAGTGGAAATCAAA | 179 |
| DR5 (21H3)_CDRL1 | AGGGCCAGTCAGAGTGTTAGCAGCAGCTACTTAGCC | 180 |
| DR5 (21H3)_CDRL2 | GGAGCATCCAGCAGGGCCACT | 181 |
| DR5 (21H3)_CDRL3 | CAGCAGGGTTCTCAGCCGCCCATTACG | 182 |
| DR5 (20F2)_VH | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC TGCAGATGAACAGCCTGAGAGCCGAGGACACGGCCGTATATTACTGTG CGAAAGGTGTGAGGAAGGGGTTTGACTACTGGGGCCAAGGAACCCTG GTCACCGTCTCGAGT | 183 |
| DR5 (20F2)_CDRH1 | AGTTATGCCATGAGC | 184 |
| DR5 (20F2)_CDRH2 | GCTATTAGTGGTAGTGGTGGTAGCACATACTACGCAGACTCCGTGAAG GGC | 185 |
| DR5 (20F2)_CDRH3 | GGTGTGAGGAAGGGGTTTGACTAC | 186 |
| DR5 (20F2)_VL | GAAATCGTGTTAACGCAGTCTCCAGGCACCCTGTCTTTGTCTCCAGGGG AAAGAGCCACCCTCTCTTGCAGGGCCAGTCAGAGTGTTAGCAGCAGCT ACTTAGCCTGGTACCAGCAGAAACCTGGCCAGGCTCCCAGGCTCCTCA TCTATGGAGCATCCAGCAGGGCCACTGGCATCCCAGACAGGTTCAGTG GCAGTGGATCCGGGACAGACTTCACTCTCACCATCAGCAGACTGGAGC CTGAAGATTTTGCAGTGTATTACTGTCAGCAGGGTGAGTCGCCTCCCCC GACGTTCGGCCAGGGGACCAAAGTGGAAATCAAA | 187 |
| DR5 (20F2)_CDRL1 | AGGGCCAGTCAGAGTGTTAGCAGCAGCTACTTAGCC | 188 |
| DR5 (20F2)_CDRL2 | GGAGCATCCAGCAGGGCCACT | 189 |
| DR5 (20F2)_CDRL3 | CAGCAGGGTGAGTCGCCTCCCCCGACG | 190 |
| DR5 (5E11)_VH | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC | 191 |

-continued

| Description | Nucleotide sequences | SEQ ID NO |
|---|---|---|
| | TGCAGATGAACAGCCTGAGAGCCGAGGACACGGCCGTATATTACTGTG CGAAAGGGGTGAGGGTGTCTTTTGACTACTGGGGCCAAGGAACCCTGG TCACCGTCTCGAGT | |
| DR5 (5E11)_CDRH1 | AGTTATGCCATGAGC | 192 |
| DR5 (5E11)_CDRH2 | GCTATTAGTGGTAGTGGTGGTAGCACATACTACGCAGACTCCGTGAAG GGC | 193 |
| DR5 (5E11)_CDRH3 | GGGGTGAGGGTGTCTTTTGACTAC | 194 |
| DR5 (5E11)_VL | GAAATCGTGTTAACGCAGTCTCCAGGCACCCTGTCTTTGTCTCCAGGGG AAAGAGCCACCCTCTCTTGCAGGGCCAGTCAGAGTGTTAGCAGCAGCT ACTTAGCCTGGTACCAGCAGAAACCTGGCCAGGCTCCCAGGCTCCTCA TCTATGGAGCATCCAGCAGGGCCACTGGCATCCCAGACAGGTTCAGTG GCAGTGGATCCGGGACAGACTTCACTCTCACCATCAGCAGACTGGAGC CTGAAGATTTTGCAGTGTATTACTGTCAGCAGGGTACTACTCATCCCAT TACGTTCGGCCAGGGGACCAAAGTGGAAATCAAA | 195 |
| DR5 (5E11)_CDRL1 | AGGGCCAGTCAGAGTGTTAGCAGCAGCTACTTAGCC | 196 |
| DR5 (5E11)_CDRL2 | GGAGCATCCAGCAGGGCCACT | 197 |
| DR5 (5E11)_CDRL3 | CAGCAGGGTACTACTCATCCCATTACG | 198 |
| DR5 (18F11)_VH | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC TGCAGATGAACAGCCTGAGAGCCGAGGACGCGGCCGTATATTACTGTG CGAAAGGGGTGCGTAAGAAGTTTGACTACTGGGGCCAAGGAACCCTG GTCACCGTCTCGAGT | 199 |
| DR5 (18F11)_CDRH1 | AGTTATGCCATGAGC | 200 |
| DR5 (18F11)_CDRH2 | GCTATTAGTGGTAGTGGTGGTAGCACATACTACGCAGACTCCGTGAAG GGC | 201 |
| DR5 (18F11)_CDRH3 | GGGGTGCGTAAGAAGTTTGACTAC | 202 |
| DR5 (18F11)_VL | GAAATCGTGTTAACGCAGTCTCCAGGCACCCTGTCTTTGTCTCCAGGGG AAAGAGCCACCCTCTCTTGCAGGGCCAGTCAGAGTGTTAGCAGCAGCT ACTTAGCCTGGTACCAGCAGAAACCTGGCCAGGCTCCCAGGCTCCTCA TCTATGGAGCATCCAGCAGGGCCACTGGCATCCCAGACAGGTTCAGTG GCAGTGGATCCGGGACAGACTTCACTCTCACCATCAGCAGACTGGAGC CTGAAGATTTTGCAGTGTATTACTGTCAGCAGGGTCAGTTGCCTCCCAT TACGTTCGGCCAGGGGACCAAAGTGGAAATCAAA | 203 |
| DR5 (18F11)_CDRL1 | AGGGCCAGTCAGAGTGTTAGCAGCAGCTACTTAGCC | 204 |
| DR5 (18F11)_CDRL2 | GGAGCATCCAGCAGGGCCACT | 205 |
| DR5 (18F11)_CDRL3 | CAGCAGGGTCAGTTGCCTCCCATTACG | 206 |
| FAP (28H1)_VH | GAAGTGCAGCTGCTGGAATCCGGCGGAGGCCTGGTGCAGCCTGGCGG ATCTCTGAGACTGTCCTGCGCCGCCTCCGGCTTCACCTTCTCCTCCCAC GCCATGTCCTGGGTCCGACAGGCTCCTGGCAAAGGCCTGGAATGGGTG TCCGCCATCTGGGCCTCCGGCGAGCAGTACTACGCCGACTCTGTGAAG GGCCGGTTCACCATCTCCCGGGACAACTCCAAGAACACCCTGTACCTG CAGATGAACAGCCTGCGGGCCGAGGACACCGCCGTGTACTACTGTGCC AAGGGCTGGCTGGGCAACTTCGACTACTGGGGACAGGGCACCCTGGTC ACCGTGTCCAGC | 207 |
| FAP (28H1)_VL | GAGATCGTGCTGACCCAGTCCCCCGGCACCCTGTCTCTGAGCCCTGGC GAGAGAGCCACCCTGTCCTGCAGAGCCTCCCAGTCCGTGTCCCGGTCC | 208 |

-continued

| Description | Nucleotide sequences | SEQ ID NO |
|---|---|---|
| | TACCTCGCCTGGTATCAGCAGAAGCCCGGCCAGGCCCCTCGGCTGCTG ATCATCGGCGCCTCTACCAGAGCCACCGGCATCCCTGACCGGTTCTCC GGCTCTGGCTCCGGCACCGACTTCACCCTGACCATCTCCCGGCTGGAA CCCGAGGACTTCGCCGTGTACTACTGCCAGCAGGGCCAGGTCATCCCT CCCACCTTTGGCCAGGGCACCAAGGTGGAAATCAAG | |
| FAP (4B9)_VH | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CTATGAGCTGGGTCCGCCAGGCTCCAGGGAAGGGGCTGGAGTGGGTCT CAGCTATTATTGGTAGTGGTGCTAGCACATACTACGCAGACTCCGTGA AGGGCCGGTTCACCATCTCCAGAGACAATTCCAAGAACACGCTGTATC TGCAGATGAACAGCCTGAGAGCCGAGGACACGGCCGTATATTACTGTG CGAAAGGGTGGTTTGGTGGTTTTAACTACTGGGGCCAAGGAACCCTGG TCACCGTCTCGAGT | 209 |
| FAP (4B9)_VL | GAGATCGTGCTGACCCAGTCCCCCGGCACCCTGTCTCTGAGCCCTGGC GAGAGAGCCACCCTGTCCTGCAGAGCCTCCCAGTCCGTGACCTCCTCC TACCTCGCCTGGTATCAGCAGAAGCCCGGCCAGGCCCCTCGGCTGCTG ATCAACGTGGGCAGTCGGAGAGCCACCGGCATCCCTGACCGGTTCTCT GGCTCTGGCTCCGGCACCGACTTCACCCTGACCATCTCCCGGCTGGAA CCCGAGGACTTCGCCGTGTACTACTGCCAGCAGGGCATCATGCTGCCC CCCACCTTTGGCCAGGGCACCAAGGTGGAAATCAAG | 210 |
| Drozitumab_VH | GAAGTGCAGCTGGTGCAGTCTGGCGGCGGAGTGGAAAGACCTGGCGG CAGCCTGAGACTGAGCTGCGCCGCCAGCGGCTTCACCTTCGACGACTA CGCCATGTCTTGGGTCCGCCAGGCCCCTGGAAAGGGCCTGGAATGGGT GTCCGGCATCAACTGGCAGGGCGGCAGCACCGGCTACGCCGACAGCG TGAAGGGCAGAGTGACCATCAGCCGGGACAACGCCAAGAACAGCCTG TACCTGCAGATGAACAGCCTGAGAGCCGAGGACACCGCCGTGTACTAC TGCGCCAAGATCCTGGGAGCCGGCAGAGGCTGGTACTTCGACTACTGG GGCAAGGGCACCACCGTGACTGTGTCTAGC | 211 |
| Drozitumab_VL | AGCGAGCTGACCCAGGATCCTGCCGTGTCTGTGGCTCTGGGCCAGACC GTGCGGATCACCTGTAGCGGCGACAGCCTGCGGAGCTACTACGCCAGC TGGTATCAGCAGAAGCCCGGCCAGGCTCCCGTGCTGGTGATCTACGGC GCCAACAACAGACCCAGCGGCATCCCCGACAGATTCAGCGGCAGCAG CAGCGGCAATACCGCCAGCCTGACCATCACAGGCGCCCAGGCCGAGG ACGAGGCCGACTACTACTGCAACAGCGCCGACAGCTCCGGCAACCAC GTGGTGTTCGGCGGAGGCACCAAGCTGACCGTCCTAGGT | 212 |
| Drozitumab-3F2 scFv(HC) pETR6606 | GAGGTGCAGCTGGTGCAGAGCGGCGGAGGGGTGGAGAGGCCTGGCGG CAGCCTGAGACTGAGCTGCGCCGCCAGCGGCTTCACCTTCGACGACTA CGCCATGAGCTGGGTGCGCCAGGCCCCTGGCAAGGGCCTGGAATGGGT GTCCGGCATCAACTGGCAGGGAGGCAGCACCGGCTACGCCGACAGCG TGAAGGGCAGAGTGACCATCAGCCGGGACAACGCCAAGAACAGCCTG TACCTGCAGATGAACAGCCTGCGGGCCGAGGACACAGCCGTGTACTAC TGCGCCAAGATCCTGGGAGCCGGCAGGGGCTGGTACTTCGACTACTGG GGCAAGGGCACCACCGTGACCGTGTCCAGCGCTAGCACCAAGGGCCC ATCGGTCTTCCCCCTGGCACCCTCCTCCAAGAGCACCTCTGGGGGCAC AGCGGCCCTGGGCTGCCTGGTCAAGGACTACTTCCCCGAACCGGTGAC GGTGTCGTGGAACTCAGGCGCCCTGACCAGCGGCGTGCACACCTTCCC GGCTGTCCTACAGTCCTCAGGACTCTACTCCCTCAGCAGCGTGGTGAC CGTGCCCTCCAGCAGCTTGGGCACCCAGACCTACATCTGCAACGTGAA TCACAAGCCCAGCAACACCAAGGTGGACAAGAAAGTTGAGCCCAAAT CTTGTGACAAAACTCACACATGCCCACCGTGCCCAGCACCTGAAGCTG CAGGGGGGACCGTCAGTCTTCCTCTTCCCCCCAAAACCCAAGGACACCC TCATGATCTCCCGGACCCCTGAGGTCACATGCGTGGTGGTGGACGTGA GCCACGAAGACCCTGAGGTCAAGTTCAACTGGTACGTGGACGGCGTGG AGGTGCATAATGCCAAGACAAAGCCGCGGGAGGAGCAGTACAACAGC ACGTACCGTGTGGTCAGCGTCCTCACCGTCCTGCACCAGGACTGGCTG AATGGCAAGGAGTACAAGTGCAAGGTCTCCAACAAAGCCCTCCCAGC CCCCATCGAGAAAACCATCTCCAAAGCCAAAGGGCAGCCCCGAGAAC CACAGGTGTACACCCTGCCCCCATCCCGGGATGAGCTGACCAAGAACC AGGTCAGCCTGACCTGCCTGGTCAAAGGCTTCTATCCCAGCGACATCG CCGTGGAGTGGGAGAGCAATGGGCAGCCGGAGAACAACTACAAGACC ACGCCTCCCGTGCTGGACTCCGACGGCTCCTTCTTCCTCTACAGCAAGC TCACCGTGGACAAGAGCAGGTGGCAGCAGGGGAACGTCTTCTCATGCT CCGTGATGCATGAGGCTCTGCACAACCACTACACGCAGAAGAGCCTCT CCCTGTCTCCGGGTAAATCCGGAGGCGGAGGAAGTGGAGGGGGAGGA TCCGGAGGGGGCGGATCTGGCGGCGGAGGCGCGAGGTGCAATTGCT GGAAAGCGGAGGCGGACTCGTGCAGCCTGGCGGCAGCCTGAGACTGA GCTGCGCCGCCAGCGGCTTCACCTTCAGCAGCTACGCCATGTCTTGGG TCCGGCAGGCCCCTGGAAAGTGCCTGGAATGGGTGTCCGCCATCAGCG GCAGCGGCGGCAGCACCTACTACGCCGACAGCGTGAAGGGCCGGTTC ACCATCAGCCGGGACAACAGCAAGAACACCCTGTACCTCCAGATGAA CAGCCTGAGAGCCGAGGACACCGCCGTGTACTACTGCGCCAAGGGAT | 213 |

| Description | Nucleotide sequences | SEQ ID NO |
|---|---|---|
| | GGTTCGGCGGCTTCAACTACTGGGGCCAGGGCACCCTGGTCACAGTCT<br>CGAGTGGCGGAGGGGGATCTGGGGGAGGCGGATCAGGAGGAGGAGG<br>AAGCGGGGGAGGGGGCAGCGAGATCGTGTTAACGCAGAGCCCCGGCA<br>CCCTGAGCCTGTATCCCGGCGAGAGAGCCACCCTGAGCTGCAGAGCCA<br>GCCAGAGCGTGACCAGCAGCTACCTGGCCTGGTATCAGCAGAAGCCCG<br>GCCAGGCCCCCAGACTGCTGATCAACGTGGGCAGCAGAAGGGCCACC<br>GGCATCCCCGACAGATTCAGCGGCTCCGGCAGCGGCACCGACTTCACC<br>CTGACCATCAGCAGACTGGAACCCGAGGATTTCGCCGTGTATTATTGC<br>CAGCAGGGCATCATGCTGCCCCCTACCTTCGGATGCGGCACCAAGGTG<br>GAGATCAAG | |
| Drozitumab-<br>FAP(4G8)<br>scFv(HC)<br>pETR7342 | GAGGTGCAGCTGGTGCAGAGCGGCGGAGGGGTGGAGAGGCCTGGCGG<br>CAGCCTGAGACTGAGCTGCGCCGCCAGCGGCTTCACCTTCGACGACTA<br>CGCCATGAGCTGGGTGCGCCAGGCCCCTGGCAAGGGCCTGGAATGGGT<br>GTCCGGCATCAACTGGCAGGGAGGCAGCACCGGCTACGCCGACGCG<br>TGAAGGGCAGAGTGACCATCAGCCGGGACAACGCCAAGAACAGCCTG<br>TACCTGCAGATGAACAGCCTGCGGGCCGAGGACACAGCCGTGTACTAC<br>TGCGCCAAGATCCTGGGAGCCGGCAGGGGCTGGTACTTCGACTACTGG<br>GGCAAGGGCACCACCGTGACCGTGTCCAGCGCTAGCACCAAGGGCCC<br>ATCGGTCTTCCCCCTGGCACCCTCCTCCAAGAGCACCTCTGGGGGCAC<br>AGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCC<br>GGCTGTCCTACAGTCCTCAGGACTCTACTCCCTCAGCAGCGTGGTGAC<br>CGTGCCCTCCAGCAGCTTGGGCACCCAGACCTACATCTGCAACGTGAA<br>TCACAAGCCCAGCAACACCAAGGTGGACAAGAAAGTTGAGCCCAAAT<br>CTTGTGACAAAACTCACACATGCCCACCGTGCCCAGCACCTGAACTCC<br>TGGGGGGACCGTCAGTCTTCCTCTTCCCCCCAAAACCCAAGGACACCC<br>TCATGATCTCCCGGACCCCTGAGGTCACATGCGTGGTGGTGGACGTGA<br>GCCACGAAGACCCTGAGGTCAAGTTCAACTGGTACGTGGACGGCGTGG<br>AGGTGCATAATGCCAAGACAAAGCCGCGGGAGGAGCAGTACAACAGC<br>ACGTACCGTGTGGTCAGCGTCCTCACCGTCCTGCACCAGGACTGGCTG<br>AATGGCAAGGAGTACAAGTGCAAGGTCTCCAACAAAGCCCTCCCAGC<br>CCCCATCGAGAAAACCATCTCCAAAGCCAAAGGGCAGCCCCGAGAAC<br>CACAGGTGTACACCCTGCCCCCATCCCGGGATGAGCTGACCAAGAACC<br>AGGTCAGCCTGACCTGCCTGGTCAAAGGCTTCTATCCCAGCGACATCG<br>CCGTGGAGTGGGAGAGCAATGGGCAGCCGGAGAACAACTACAAGACC<br>ACGCCTCCCGTGCTGGACTCCGACGGCTCCTTCTTCCTCTACAGCAAGC<br>TCACCGTGGACAAGAGCAGGTGGCAGCAGGGGAACGTCTTCTCATGCT<br>CCGTGATGCATGAGGCTCTGCACAACCACTACACGCAGAAGAGCCTCT<br>CCCTGTCTCCGGGTGGCGGGTCCGGAGGCGGAGGAAGTGGCGGCGGA<br>GGCAGCGAAGTGCAGCTGCTGGAAAGCGGCGGAGGACTGGTGCAGCC<br>TGGCGGCAGCCTGAGACTGAGCTGCGCCGCCAGCGGCTTCACCTTCAG<br>CAGCTACGCCATGTCTTGGGTCCGCCAGGCCCCTGGAAAGTGCCTGGA<br>ATGGGTGTCCGCCATCAGCGGCAGCGGCGGCAGCACCTACTACGCCGA<br>CAGCGTGAAGGGCCGGTTCACCATCAGCCGGGACAACAGCAAGAACA<br>CCCTGTACCTGCAGATGAACAGCCTGAGAGCCGAGGACACCGCCGTGT<br>ACTACTGCGCCAAGGGCTGGCTGGGCAACTTCGACTACTGGGGCCAGG<br>GCACTCTGGTCACAGTGTCTAGCGGAGGCGGCGGATCTGGCGGAGGTG<br>GAAGCGGAGGGGGAGGATCAGGGGCGGAGGCTCCGAGATCGTGCTG<br>ACCCAGAGCCCTGGCACACTGTCTCTGAGCCCTGGCGAGAGAGCCACC<br>CTGAGCTGCAGAGCCAGCCAGAGCGTGTCCAGAAGCTACCTGGCTTGG<br>TATCAGCAGAAGCCGGCCAGGCCCCCAGACTGCTGATCATCGGCGCT<br>AGCACCAGAGCCACCGGCATTCCCGACAGATTCAGCGGCTCCGGCAGC<br>GGCACCGACTTCACCCTGACCATCAGCAGACTGGAACCCGAGGATTTC<br>GCCGTCTATTATTGCCAGCAGGGCCAAGTCATCCCTCCTACCTTCGGAT<br>GCGGCACTAAGGTGGAGATCAAG | 214 |
| Drozitumab-<br>FAP(4G8)<br>scFv(LC)<br>pETR7344 | AGCGAGCTGACCCAGGACCCCGCCGTGAGCGTGGCCCTGGGACAGAC<br>CGTGCGGATCACCTGCAGCGGCGACAGCCTGCGCAGCTACTACGCCAG<br>CTGGTATCAGCAGAAGCCCGGCCAGGCCCCCGTGCTGGTGATCTACGG<br>CGCCAACAACCGGCCCAGCGGCATCCCCGACCGGTTCAGCGGCAGCA<br>GCAGCGGCAACACCGCCAGCCTGACCATCACAGGCGCCCAGGCCGAG<br>GACGAGGCCGACTACTACTGCAACAGCGCCGACAGCTCCGGCAACCA<br>CGTGGTGTTTGGCGGCGGAACAAAGCTGACCGTCCTAGGTCAACCCAA<br>GGCTGCCCCCAGCGTGACCCTGTTCCCCCCCAGCAGCGAGGAACTGCA<br>GGCCAACAAGGCCACCCTGGTCTGCCTGATCAGCGACTTCTACCCAGG<br>CGCCGTGACCGTGGCCTGGAAGGCCGACAGCAGCCCCGTGAAGGCCG<br>GCGTGGAGACCACCACCCCCAGCAAGCAGAGCAACAACAAGTACGCC<br>GCCAGCAGCTACCTGAGCCTGACCCCCGAGCAGTGGAAGAGCCACAG<br>GTCCTACAGCTGCCAGGTGACCCACGAGGGCAGCACCGTGGAGAAAA<br>CCGTGGCCCCCACCGAGTGCTCCGGAGGCGGAGGAAGTGGCGGCGGA<br>GGCAGCGAAGTGCAGCTGCTGGAAAGCGGCGGAGGACTGGTGCAGCC<br>TGGCGGCAGCCTGAGACTGAGCTGCGCCGCCAGCGGCTTCACCTTCAG<br>CAGCTACGCCATGTCTTGGGTCCGCCAGGCCCCTGGAAAGTGCCTGGA<br>ATGGGTGTCCGCCATCAGCGGCAGCGGCGGCAGCACCTACTACGCCGA<br>CAGCGTGAAGGGCCGGTTCACCATCAGCCGGGACAACAGCAAGAACA | 215 |

| Description | Nucleotide sequences | SEQ ID NO |
|---|---|---|
| | CCCTGTACCTGCAGATGAACAGCCTGAGAGCCGAGGACACCGCCGTGT ACTACTGCGCCAAGGGCTGGCTGGGCAACTTCGACTACTGGGGCCAGG GCACTCTGGTCACAGTGTCTAGCGGAGGCGGCGGATCTGGCGGAGGTG GAAGCGGAGGGGGAGGATCAGGGGGCGGAGGCTCCGAGATCGTGCTG ACCCAGAGCCCTGGCACACTGTCTCTGAGCCCTGGCGAGAGAGCCACC CTGAGCTGCAGAGCCAGCCAGAGCGTGTCCAGAAGCTACCTGGCTTGG TATCAGCAGAAGCCCGGCCAGGCCCCCAGACTGCTGATCATCGGCGCT AGCACCAGAGCCACCGGCATTCCCGACAGATTCAGCGGCTCCGGCAGC GGCACCGACTTCACCCTGACCATCAGCAGACTGGAACCCGAGGATTTC GCCGTCTATTATTGCCAGCAGGGCCAAGTCATCCCTCCTACCTTCGGAT GCGGCACTAAGGTGGAGATCAAG | |
| Drozitumab-3F2 scFab(HC) pETR7369 | GAGGTGCAGCTGGTGCAGAGCGGCGGAGGGGTGGAGAGGCCTGGCGG CAGCCTGAGACTGAGCTGCGCCGCCAGCGGCTTCACCTTCGACGACTA CGCCATGAGCTGGGTGCGCCAGGCCCCTGGCAAGGGCCTGGAATGGGT GTCCGGCATCAACTGGCAGGGAGGCAGCACCGGCTACGCCGACAGCG TGAAGGGCAGAGTGACCATCAGCCGGGACAACGCCAAGAACAGCCTG TACCTGCAGATGAACAGCCTGCGGGCCGAGGACACAGCCGTGTACTAC TGCGCCAAGATCCTGGGAGCCGGCAGGGCTGGTACTTCGACTACTGG GGCAAGGGCACCACCGTGACCGTGTCCAGCGCTAGCACCAAGGGCCC ATCGGTCTTCCCCCTGGCACCCTCCTCCAAGAGCACCTCTGGGGGCAC AGCGGCCCTGGGCTGCCTGGTCAAGGACTACTTCCCCGAACCGGTGAC GGTGTCGTGGAACTCAGGCGCCCTGACCAGCGGCGTGCACACCTTCCC GGCTGTCCTACAGTCCTCAGGACTCTACTCCCTCAGCAGCGTGGTGAC CGTGCCCTCCAGCAGCTTGGGCACCCAGACCTACATCTGCAACGTGAA TCACAAGCCCAGCAACACCAAGGTGGACAAGAAAGTTGAGCCCAAAT CTTGTGACAAAACTCACACATGCCCACCGTGCCCAGCACCTGAACTC CTGGGGGGACCGTCAGTCTTCCTCTTCCCCCCAAAACCCAAGGACACCC TCATGATCTCCCGGACCCCTGAGGTCACATGCGTGGTGGTGGACGTGA GCCACGAAGACCCTGAGGTCAAGTTCAACTGGTACGTGGACGGCGTGG AGGTGCATAATGCCAAGACAAAGCCGCGGGAGGAGCAGTACAACAGC ACGTACCGTGTGGTCAGCGTCCTCACCGTCCTGCACCAGGACTGGCTG AATGGCAAGGAGTACAAGTGCAAGGTCTCCAACAAAGCCCTCCCAGC CCCCATCGAGAAAACCATCTCCAAAGCCAAAGGGCAGCCCCGAGAAC CACAGGTGTACACCCTGCCCCCATCCCGGGATGAGCTGACCAAGAACC AGGTCAGCCTGACCTGCCTGGTCAAAGGCTTCTATCCCAGCGACATCG CCGTGGAGTGGGAGAGCAATGGGCAGCCGGAGAACAACTACAAGACC ACGCCTCCCGTGCTGGACTCCGACGGCTCCTTCTTCCTCTACAGCAAGC TCACCGTGGACAAGAGCAGGTGGCAGCAGGGGAACGTCTTCTCATGCT CCGTGATGCATGAGGCTCTGCACAACCACTACACGCAGAAGAGCCTCT CCCTGTCTCCGGGTAAATCCGGAGGCGGAGGTTCCGGTGGAGGCGGAT CCGGAGGAGGTGGCAGCGGAGGTGGTGGCTCCGAAATCGTGTTAACG CAGTCTCCAGGCACCCTGTCTTTGTATCCAGGGGAAAGAGCCACCCTC TCTTTGCAGGGCCAGTCAGAGTGTTACCAGTAGCTACTTAGCCTGGTAC CAGCAGAAACCTGGCCAGGCTCCCAGGCTCCTCATCAATGTGGGCTCC CGTAGGGCCACTGGCATCCCAGACAGGTTCAGTGGCAGTGGATCCGGG ACAGACTTCACTCTCACCATCAGCAGACTGGAGCCTGAAGATTTTGCA GTGTATTACTGTCAGCAGGGTATTATGCTTCCCCCGACGTTCGGCCAGG GGACCAAAGTGGAAATCAAACGTACGGTGGCCGCTCCCAGCGTGTTCA TCTTCCCCCCCAGCGACGAGCAGCTGAAGTCCGGCACCGCCAGCGTGG TGTGCCTGCTGAACAACTTCTACCCCCGGGAGGCCAAGGTGCAGTGGA AGGTGGACAACGCCCTGCAGAGCGGCAACAGCCAGGAAAGCGTCACC GAGCAGGACAGCAAGGACTCCACCTACAGCCTGTCCAGCACCCTGACC CTGAGCAAGGCCGACTACGAGAAGCACAAGGTGTACGCCTGCGAAGT GACCCACCAGGGCCTGAGCAGCCCCGTGACCAAGAGCTTCAACCGGG GCGAGTGCTCCGGCGGAGGATCTGGGGGAGGAAGCGAAGGAGGCGGA TCTGAGGGCGGTGGCTCTGAAGGCGGTGGAAGTGAGGGAGGCGGTAG CGGAGGTGGATCCGGCGAGGTGCAATTGTTGGAGTCTGGGGGAGGCTT GGTACAGCCTGGGGGGTCCCTGAGACTCTCCTGTGCAGCCTCCGGATT CACCTTTAGCAGTTATGCCATGAGCTGGGTCCGCCAGGCTCCAGGGAA GGGGCTGGAGTGGGTCTCAGCTATTAGTGGTAGTGGTGGTAGCACATA CTACGCAGACTCCGTGAAGGGCCGGTTCACCATCTCCAGAGACAATTC CAAGAACACGCTGTATCTGCAGATGAACAGCCTGAGAGCCGAGGACA CGGCCGTATATTACTGTGCGAAAGGGTGGTTTGGTGGTTTTAACTACTG GGGCCAAGGAACCCTGGTCACCGTCTCGAGTGCTAGCACAAAGGGCCC CAGCGTGTTCCCTCTGGCCCCCAGCAGCAAGAGCACAAGCGGCGGAAC AGCCGCCCTGGGCTGCCTGGTCAAGGACTACTTCCCCGAGCCCGTGAC TGTGTCCTGGAACAGCGGTGCTCTCACATCTGGGGTCCACACCTTTCCA GCCGTGCTCCAGTCCTCAGGGCTCTACAGCCTGAGCAGCGTCGTCACA GTCCCATCTAGCAGCCTGGGCACCCAGACCTACATCTGCAACGTGAAC CACAAGCCCAGCAACACCAAGGTGGACAAGAAGGTGGAGCCCAAGAG CTGTGAC | 216 |
| Drozitumab-3F2 scFab(LC) | AGCGAGCTGACCCAGGACCCCGCCGTGAGCGTGGCCCTGGGACAGAC CGTGCGGATCACCTGCAGCGGCGACAGCCTGCGCAGCTACTACGCCAG CTGGTATCAGCAGAAGCCCGGCCAGGCCCCCGTGCTGGTGATCTACGG | 217 |

-continued

| Description | Nucleotide sequences | SEQ ID NO |
|---|---|---|
| pETR7370 | CGCCAACAACCGGCCCAGCGGCATCCCCGACCGGTTCAGCGGCAGCA<br>GCAGCGGCAACACCGCCAGCCTGACCATCACAGGCGCCCAGGCCGAG<br>GACGAGGCCGACTACTACTGCAACAGCGCCGACAGCTCCGGCAACCA<br>CGTGGTGTTTGGCGGCGGAACAAAGCTGACCGTCCTAGGTCAACCCAA<br>GGCTGCCCCCAGCGTGACCCTGTTCCCCCCCAGCAGCGAGGAACTGCA<br>GGCCAACAAGGCCACCCTGGTCTGCCTGATCAGCGACTTCTACCCAGG<br>CGCCGTGACCGTGGCCTGGAAGGCCGACAGCAGCCCCGTGAAGGCCG<br>GCGTGGAGACCACCACCCCCAGCAAGCAGAGCAACAACAAGTACGCC<br>GCCAGCAGCTACCTGAGCCTGACCCCCGAGCAGTGGAAGAGCCACAG<br>GTCCTACAGCTGCCAGGTGACCCACGAGGGCAGCACCGTGGAGAAAA<br>CCGTGGCCCCCACCGAGTGCTCCGGAGGCGGAGGTTCCGGTGGAGGCG<br>GATCCGGAGGAGGTGGCAGCGGAGGTGGTGGCTCCGAAATCGTGTTA<br>ACGCAGTCTCCAGGCACCCTGTCTTTGTATCCAGGGGAAAGAGCCACC<br>CTCTCTTGCAGGGCCAGTCAGAGTGTTACCAGTAGCTACTTAGCCTGGT<br>ACCAGCAGAAACCTGGCCAGGCTCCCAGGCTCCTCATCAATGTGGGCT<br>CCCGTAGGGCCACTGGCATCCCAGACAGGTTCAGTGGCAGTGGATCCG<br>GGACAGACTTCACTCTCACCATCAGCAGACTGGAGCCTGAAGATTTTG<br>CAGTGTATTACTGTCAGCAGGGTATTATGCTTCCCCCGACGTTCGGCCA<br>GGGGACCAAAGTGGAAATCAAACGTACGGTGGCCGCTCCCAGCGTGTT<br>CATCTTCCCCCCCAGCGACGAGCAGCTGAAGTCCGGCACCGCCAGCGT<br>GGTGTGCCTGCTGAACAACTTCTACCCCGGGAGGCCAAGGTGCAGTG<br>GAAGGTGGACAACGCCCTGCAGAGCGGCAACAGCCAGGAAAGCGTCA<br>CCGAGCAGGACAGCAAGGACTCCACCTACAGCCTGTCCAGCACCCTGA<br>CCCTGAGCAAGGCCGACTACGAGAAGCACAAGGTGTACGCCTGCGAA<br>GTGACCCACCAGGGCCTGAGCAGCCCCGTGACCAAGAGCTTCAACCGG<br>GGCGAGTGCTCCGGCGGAGGATCTGGGGGAGGAAGCGAAGGAGGCGG<br>ATCTGAGGGCGGTGGCTCTGAAGGCGGTGGAAGTGAGGGAGGCGGTA<br>GCGGAGGTGGATCCGGCGAGGTGCAATTGTTGGAGTCTGGGGGAGGCT<br>TGGTACAGCCTGGGGGGTCCCTGAGACTCTCCTGTGCAGCCTCCGGAT<br>TCACCTTTAGCAGTTATGCCATGAGCTGGGTCCGCCAGGCTCCAGGGA<br>AGGGGCTGGAGTGGGTCTCAGCTATTAGTGGTAGTGGTGGTAGCACAT<br>ACTACGCAGACTCCGTGAAGGGCCGGTTCACCATCTCCAGAGACAATT<br>CCAAGAACACGCTGTATCTGCAGATGAACAGCCTGAGAGCCGAGGAC<br>ACGGCCGTATATTACTGTGCGAAAGGGTGGTTTGGTGGTTTTAACTACT<br>GGGGCCAAGGAACCCTGGTCACCGTCTCGAGTGCTAGCACAAAGGGC<br>CCCAGCGTGTTCCCTCTGGCCCCCAGCAGCAAGAGCACAAGCGGCGGA<br>ACAGCCGCCCTGGGCTGCCTGGTCAAGGACTACTTCCCCGAGCCCGTG<br>ACTGTGTCCTGGAACAGCGGTGCTCTCACATCTGGGGTCCACACCTTTC<br>CAGCCGTGCTCCAGTCCTCAGGGCTCTACAGCCTGAGCAGCGTCGTCA<br>CAGTCCCATCTAGCAGCCTGGGCACCCAGACCTACATCTGCAACGTGA<br>ACCACAAGCCCAGCAACACCAAGGTGGACAAGAAGGTGGAGCCCAAG<br>AGCTGTGAC | |
| Drozitumab-<br>FAP(4G8)<br>scFab(HC)<br>pETR7371 | GAGGTGCAGCTGGTGCAGAGCGGCGGAGGGGTGGAGAGGCCTGGCGG<br>CAGCCTGAGACTGAGCTGCGCCGCCAGCGGCTTCACCTTCGACGACTA<br>CGCCATGAGCTGGGTGCGCCAGGCCCCTGGCAAGGGCCTGGAATGGGT<br>GTCCGGCATCAACTGGCAGGGAGGCAGCACCGGCTACGCCGACAGCG<br>TGAAGGGCAGAGTGACCATCAGCCGGGACAACGCCAAGAACAGCCTG<br>TACCTGCAGATGAACAGCCTGCGGGCCGAGGACACAGCCGTGTACTAC<br>TGCGCCAAGATCCTGGGAGCCGGCAGGGGCTGGTACTTCGACTACTGG<br>GGCAAGGGCACCACCGTGACCGTGTCCAGCGCTAGCACCAAGGGCCC<br>ATCGGTCTTCCCCCTGGCACCCTCCTCCAAGAGCACCTCTGGGGGCAC<br>AGCGGCCCTGGGCTGCCTGGTCAAGGACTACTTCCCCGAACCGGTGAC<br>GGTGTCGTGGAACTCAGGCGCCCTGACCAGCGGCGTGCACACCTTCCC<br>GGCTGTCCTACAGTCCTCAGGACTCTACTCCCTCAGCAGCGTGGTGAC<br>CGTGCCCTCCAGCAGCTTGGGCACCCAGACCTACATCTGCAACGTGAA<br>TCACAAGCCCAGCAACACCAAGGTGGACAAGAAAGTTGAGCCCAAAT<br>CTTGTGACAAAACTCACACATGCCCACCGTGCCCAGCACCTGAACTCC<br>TGGGGGGACCGTCAGTCTTCCTCTTCCCCCCAAAACCCAAGGACACCC<br>TCATGATCTCCCGGACCCCTGAGGTCACATGCGTGGTGGTGGACGTGA<br>GCCACGAAGACCCTGAGGTCAAGTTCAACTGGTACGTGGACGGCGTGG<br>AGGTGCATAATGCCAAGACAAAGCCGCGGGAGGAGCAGTACAACAGC<br>ACGTACCGTGTGGTCAGCGTCCTCACCGTCCTGCACCAGGACTGGCTG<br>AATGGCAAGGAGTACAAGTGCAAGGTCTCCAACAAAGCCCTCCCAGC<br>CCCCATCGAGAAAACCATCTCCAAAGCCAAAGGGCAGCCCCGAGAAC<br>CACAGGTGTACACCCTGCCCCCATCCCGGGATGAGCTGACCAAGAACC<br>AGGTCAGCCTGACCTGCCTGGTCAAAGGCTTCTATCCCAGCGACATCG<br>CCGTGGAGTGGGAGAGCAATGGGCAGCCGGAGAACAACTACAAGACC<br>ACGCCTCCCGTGCTGGACTCCGACGGCTCCTTCTTCCTCTACAGCAAGC<br>TCACCGTGGACAAGAGCAGGTGGCAGCAGGGGAACGTCTTCTCATGCT<br>CCGTGATGCATGAGGCTCTGCACAACCACTACACGCAGAAGAGCCTCT<br>CCCTGTCTCCGGGTAAATCCGGAGGCGGAGGAAGCGGAGGGGGAGGA<br>TCAGGCGGCGGTGGATCAGGCGGTGGAGGATCCGAGATCGTGCTGACC<br>CAGTCCCCTGGCACCCTGTCTCTGAGCCCAGGCGAGAGAGCCACCCTG<br>AGCTGCAGAGCCAGCCAGAGCGTGTCCAGAAGCTATCTGGCTTGGTAT<br>CAGCAGAAGCCCGGCCAGGCCCCCAGACTGCTGATCATCGGCGCCAGC | 218 |

| Description | Nucleotide sequences | SEQ ID NO |
|---|---|---|
| | ACCAGAGCCACCGGCATCCCCGACAGATTCAGCGGCAGCGGCTCCGGC<br>ACCGACTTCACCCTGACCATCTCCCGGCTGGAACCCGAGGACTTCGCC<br>GTGTACTACTGCCAGCAGGGCCAGGTCATCCCTCCTACCTTCGGCCAG<br>GGCACCAAGGTGGAGATCAAGCGTACGGTGGCCGCTCCCAGCGTGTTC<br>ATCTTCCCACCCAGCGACGAGCAGCTGAAGTCCGGCACAGCCAGCGTG<br>GTCTGCCTGCTGAACAACTTCTACCCCCGGGAGGCCAAGGTGCAGTGG<br>AAGGTGGACAACGCCCTGCAGAGCGGCAACAGCCAGGAAAGCGTCAC<br>CGAGCAGGACAGCAAGGACTCCACCTACAGCCTGAGCAGCACACTGA<br>CCCTGAGCAAGGCCGACTACGAGAAGCACAAGGTGTACGCCTGCGAA<br>GTGACCCACCAGGGCCTGTCCAGCCCCGTGACCAAGAGCTTCAACCGG<br>GGCGAGTGTTCTGGTGGCGGATCTGGCGGAGGCAGTGAAGGCGGCGG<br>AAGTGAGGGTGGAGGCAGCGAGGGGGGAGGCTCTGAAGGGGGAGGA<br>AGTGGAGGCGGTTCAGGGGAAGTGCAATTGTTGGAGTCTGGGGGAGG<br>CTTGGTACAGCCTGGGGGGTCCCTGAGACTCTCCTGTGCAGCCTCCGG<br>ATTCACCTTTAGCAGTTATGCCATGAGCTGGGTCCGCCAGGCTCCAGG<br>GAAGGGGCTGGAGTGGGTCTCAGCTATTAGTGGTAGTGGTGGTAGCAC<br>ATACTACGCAGACTCCGTGAAGGGCCGGTTCACCATCTCCAGAGACAA<br>TTCCAAGAACACGCTGTATCTGCAGATGAACAGCCTGAGAGCCGAGGA<br>CACGGCCGTATATTACTGTGCGAAAGGGTGGCTGGGTAATTTTGACTA<br>CTGGGGCCAAGGAACCCTGGTCACCGTCTCGAGTGCTAGCACAAAGGG<br>CCCCAGCGTGTTCCCTCTGGCCCCCAGCAGCAAGAGCACAAGCGGCGG<br>AACAGCCGCCCTGGGCTGCCTGGTCAAGGACTACTTCCCCGAGCCCGT<br>GACTGTGTCCTGGAACAGCGGTGCTCTCACATCTGGGGTCCACACCTTT<br>CCAGCCGTGCTCCAGTCCTCAGGGCTCTACAGCCTGAGCAGCGTCGTC<br>ACAGTCCCATCTAGCAGCCTGGGCACCCAGACCTACATCTGCAACGTG<br>AACCACAAGCCCAGCAACACCAAGGTGGACAAGAAGGTGGAGCCCAA<br>GAGCTGTGAC | |
| Drozitumab-<br>FAP(4G8)<br>scFab(LC)<br>pETR7380 | AGCGAGCTGACCCAGGACCCCGCCGTGAGCGTGGCCCTGGGACAGAC<br>CGTGCGGATCACCTGCAGCGGCGACAGCCTGCGCAGCTACTACGCCAG<br>CTGGTATCAGCAGAAGCCCGGACAGGCCCCCGTGCTGGTGATCTACGG<br>CGCCAACAACCGGCCCAGCGGCATCCCCGACCGGTTCAGCGGCAGCA<br>GCAGCGGCAACACCGCCAGCCTGACCATCACAGGCGCCCAGGCCGAG<br>GACGAGGCCGACTACTACTGCAACAGCGCCGACAGCTCCGGCAACCA<br>CGTGGTGTTTGGCGGCGGAACAAAGCTGACCGTCCTAGGTCAACCCAA<br>GGCTGCCCCCAGCGTGACCCTGTTCCCCCCCAGCAGCGAGGAACTGCA<br>GGCCAACAAGGCCACCCTGGTCTGCCTGATCAGCGACTTCTACCCAGG<br>CGCCGTGACCGTGGCCTGGAAGGCCGACAGCAGCCCCGTGAAGGCCG<br>GCGTGGAGACCACCACCCCCAGCAAGCAGAGCAACAACAAGTACGCC<br>GCCAGCAGCTACCTGAGCCTGACCCCCGAGCAGTGGAAGAGCCACAG<br>GTCCTACAGCTGCCAGGTGACCCACGAGGGCAGCACCGTGGAGAAAA<br>CCGTGGCCCCCACCGAGTGCTCCGGAGGCGGAGGAAGCGGAGGGGGA<br>GGATCAGGCGGCGGTGGATCAGGCGGTGGAGGATCCGAGATCGTGCT<br>GACCCAGTCCCCTGGCACCCTGTCTCTGAGCCCAGGCGAGAGAGCCAC<br>CCTGAGCTGCAGAGCCAGCCAGAGCGTGTCCAGAAGCTATCTGGCTTG<br>GTATCAGCAGAAGCCCGGCCAGGCCCCCAGACTGCTGATCATCGGCGC<br>CAGCACCAGAGCCACCGGCATCCCCGACAGATTCAGCGGCAGCGGCTC<br>CGGCACCGACTTCACCCTGACCATCTCCCGGCTGGAACCCGAGGACTT<br>CGCCGTGTACTACTGCCAGCAGGGCCAGGTCATCCCTCCTACCTTCGG<br>CCAGGGCACCAAGGTGGAGATCAAGCGTACGGTGGCCGCTCCCAGCG<br>TGTTCATCTTCCCACCCAGCGACGAGCAGCTGAAGTCCGGCACAGCCA<br>GCGTGGTCTGCCTGCTGAACAACTTCTACCCCCGGGAGGCCAAGGTGC<br>AGTGGAAGGTGGACAACGCCCTGCAGAGCGGCAACAGCCAGGAAAGC<br>GTCACCGAGCAGGACAGCAAGGACTCCACCTACAGCCTGAGCAGCAC<br>ACTGACCCTGAGCAAGGCCGACTACGAGAAGCACAAGGTGTACGCCT<br>GCGAAGTGACCCACCAGGGCCTGTCCAGCCCCGTGACCAAGAGCTTCA<br>ACCGGGGCGAGTGTTCTGGTGGCGGATCTGGCGGAGGCAGTGAAGGC<br>GGCGGAAGTGAGGGTGGAGGCAGCGAGGGGGGAGGCTCTGAAGGGG<br>GAGGAAGTGGAGGCGGTTCAGGGGAAGTGCAATTGTTGGAGTCTGGG<br>GGAGGCTTGGTACAGCCTGGGGGGTCCCTGAGACTCTCCTGTGCAGCC<br>TCCGGATTCACCTTTAGCAGTTATGCCATGAGCTGGGTCCGCCAGGCTC<br>CAGGGAAGGGGCTGGAGTGGGTCTCAGCTATTAGTGGTAGTGGTGGTA<br>GCACATACTACGCAGACTCCGTGAAGGGCCGGTTCACCATCTCCAGAG<br>ACAATTCCAAGAACACGCTGTATCTGCAGATGAACAGCCTGAGAGCCG<br>AGGACACGGCCGTATATTACTGTGCGAAAGGGTGGCTGGGTAATTTTG<br>ACTACTGGGGCCAAGGAACCCTGGTCACCGTCTCGAGTGCTAGCACAA<br>AGGGCCCCAGCGTGTTCCCTCTGGCCCCCAGCAGCAAGAGCACAAGCG<br>GCGGAACAGCCGCCCTGGGCTGCCTGGTCAAGGACTACTTCCCCGAGC<br>CCGTGACTGTGTCCTGGAACAGCGGTGCTCTCACATCTGGGGTCCACA<br>CCTTTCCAGCCGTGCTCCAGTCCTCAGGGCTCTACAGCCTGAGCAGCGT<br>CGTCACAGTCCCATCTAGCAGCCTGGGCACCCAGACCTACATCTGCAA<br>CGTGAACCACAAGCCCAGCAACACCAAGGTGGACAAGAAGGTGGAGC<br>CCAAGAGCTGTGAC | 219 |
| Drozitumab-<br>FAP(4G8) | GAAGTGCAGCTGGTGCAGTCTGGCGGCGGAGTGGAAAGACCTGGCGG<br>CAGCCTGAGACTGAGCTGCGCCGCCAGCGGCTTCACCTTCGACGACTA | 220 |

-continued

| Description | Nucleotide sequences | SEQ ID NO |
|---|---|---|
| VHCL 2 + 2 | CGCCATGTCTTGGGTCCGCCAGGCCCCTGGAAAGGGCCTGGAATGGGT<br>GTCCGGCATCAACTGGCAGGGCGGCAGCACCGGCTACGCCGACAGCG<br>TGAAGGGCAGAGTGACCATCAGCCGGGACAACGCCAAGAACAGCCTG<br>TACCTGCAGATGAACAGCCTGAGAGCCGAGGACACCGCCGTGTACTAC<br>TGCGCCAAGATCCTGGGAGCCGGCAGAGGCTGGTACTTCGACTACTGG<br>GGCAAGGGCACCACCGTGACTGTGTCTAGCGCTAGCACCAAGGGCCCA<br>AGCGTGTTCCCTCTGGCCCCCAGCAGCAAGAGCACAAGCGGCGGAAC<br>AGCCGCCCTGGGCTGCCTGGTCAAGGACTACTTCCCCGAGCCCGTGAC<br>AGTGTCCTGGAACAGCGGAGCCCTGACCAGCGGCGTGCACACCTTTCC<br>AGCCGTGCTGCAGAGCAGCGGCCTGTACAGCCTGAGCAGCGTGGTCAC<br>AGTGCCTAGCAGCAGCCTGGGCACCCAGACCTACATCTGCAACGTGAA<br>CCACAAGCCCAGCAACACCAAGGTGGACAAGAAGGTGGAGCCCAAGA<br>GCTGCGACAAGACCCACACCTGTCCCCCTTGTCCTGCCCCTGAGCTGCT<br>GGGCGGACCCAGCGTGTTCCTGTTCCCCCCAAAGCCCAAGGACACCCT<br>GATGATCAGCCGGACCCCCGAAGTGACCTGCGTGGTGGTGGACGTGTC<br>CCACGAGGACCCTGAAGTGAAGTTCAATTGGTACGTGGACGGCGTGGA<br>GGTGCACAATGCCAAGACCAAGCCCCGGGAGGAACAGTACAACAGCA<br>CCTACCGGGTGGTGTCCGTGCTGACCGTGCTGCACCAGGACTGGCTGA<br>ACGGCAAAGAGTACAAGTGCAAGGTCTCCAACAAGGGCCCTGCCTGCC<br>CCATCGAGAAAACCATCAGCAAGGCCAAGGGCCAGCCCAGAGAACCC<br>CAGGTGTACACCCTGCCCCCAGCAGATGAGCTGACCAAGAACCA<br>GGTGTCCCTGACCTGTCTGGTCAAGGGCTTCTACCCCAGCGATATCGCC<br>GTGGAGTGGGAGAGCAACGGCCAGCCTGAGAACAACTACAAGACCAC<br>CCCCCCTGTGCTGGACAGCGACGGCAGCTTCTTCCTGTACTCCAAACTG<br>ACCGTGGACAAGAGCCGGTGGCAGCAGGGCAACGTGTTCAGCTGCAG<br>CGTGATGCACGAGGCCCTGCACAACCACTACACCCAGAAGTCCCTGAG<br>CCTGAGCCCCGGCAAGTCCGGAGGCGGCGGAAGCGGAGGAGGAGGAT<br>CCGGAGGAGGGGGAAGTGGCGGCGGAGGATCTGAGGTGCAGCTGCTG<br>GAATCTGGAGGCGGCCTGGTGCAGCCTGGCGGCAGCCTGAGACTGTCT<br>TGCGCCGCCAGCGGCTTCACCTTCAGCAGCTACGCCATGAGCTGGGTC<br>CGACAGGCTCCTGGCAAGGGACTGGAATGGGTGTCCGCCATCTCCGGC<br>AGCGGAGGCAGCACCTACTACGCCGACAGCGTGAAGGGCCGGTTCAC<br>CATCAGCAGAGACAACAGCAAGAACACCCTGTACCTGCAGATGAACA<br>GCCTGCGGGCCGAGGATACCGCCGTGTATTATTGCGCCAAGGGATGGC<br>TGGGCAACTTCGACTACTGGGGCCAGGGAACCCTGGTGACAGTGTCCA<br>GCGCTAGCGTGGCCGCTCCCAGCGTGTTCATCTTCCCACCCAGCGACG<br>AGCAGCTGAAGTCCGGCACAGCCAGCGTGGTGTGCCTGCTGAACAACT<br>TCTACCCCCGCGAGGCCAAGGTGCAGTGGAAGGTGGACAACGCCCTGC<br>AGAGCGGCAACAGCCAGGAATCCGTGACCGAGCAGGACAGCAAGGAC<br>TCCACCTACAGCCTGAGCAGCACCCTGACCCTGAGCAAGGCCGACTAC<br>GAGAAGCACAAGGTGTACGCCTGCGAAGTGACCCACCAGGGCCTGTC<br>CAGCCCCGTGACCAAGAGCTTCAACCGGGGCGAGTGC | |
| Drozitumab LC pETR7303 | AGCGAGCTGACCCAGGATCCTGCCGTGTCTGTGGCTCTGGGCCAGACC<br>GTGCGGATCACCTGTAGCGGCGACAGCCTGCGGAGCTACTACGCCAGC<br>TGGTATCAGCAGAAGCCCGGCCAGGCTCCCGTGCTGGTGATCTACGGC<br>GCCAACAACAGACCCAGCGGCATCCCCGACAGATTCAGCGGCAGCAG<br>CAGCGGCAATACCGCCAGCCTGACCATCACAGGCGCCCAGGCCGAGG<br>ACGAGGCCGACTACTACTGCAACAGCGCCGACAGCTCCGGCAACCAC<br>GTGGTGTTCGGCGGAGGCACCAAGCTGACCGTCCTAGGTCAGCCCAAA<br>GCCGCCCCTAGCGTGACCCTGTTCCCCCCAAGCAGCGAGGAACTGCAG<br>GCCAACAAGGCCACCCTGGTGTGCCTGATCAGCGACTTCTACCCTGGC<br>GCCGTGACAGTGGCCTGGAAGGCCGACTCTAGCCCTGTGAAGGCCGGC<br>GTGGAGACAACCACCCCCAGCAAGCAGAGCAACAACAAGTACGCCGC<br>CAGCAGCTACCTGAGCCTGACCCCCGAGCAGTGGAAGTCCCACCGGTC<br>CTACAGCTGCCAGGTGACACACGAGGGCAGCACCGTGGAGAAAACCG<br>TGGCCCCCACCGAGTGCAGC | 221 |
| FAP(4G8)_VLCH1 | GAGATCGTGCTGACCCAGTCTCCCGGCACCCTGAGCCTGAGCCCTGGC<br>GAGAGAGCCACCCTGAGCTGCAGAGCCAGCCAGAGCGTGAGCCGGAG<br>CTACCTGGCCTGGTATCAGCAGAAGCCCGGCCAGGCCCCCAGACTGCT<br>GATCATCGGCGCCAGCACCCGGGCCACCGGCATCCCCGATAGATTCAG<br>CGGCAGCGGCTCCGGCACCGACTTCACCCTGACCATCAGCCGGCTGGA<br>ACCCGAGGACTTCGCCGTGTACTACTGCCAGCAGGGCCAGGTGATCCC<br>CCCCACCTTCGGCCAGGGCACCAAGGTGGAAATCAAGAGCTCCGCTAG<br>CACCAAGGGCCCCTCCGTGTTTCCTCTGGCCCCCAGCAGCAAGAGCAC<br>CTCTGGCGGAACAGCCGCCCTGGGCTGCCTGGTAAAGACTACTTCCC<br>CGAGCCCGTGACCGTGTCCTGGAACTCTGGCGCCCTGACCAGCGGCGT<br>GCACACCTTTCCAGCCGTGCTGCAGAGCAGCGGCCTGTACTCCCTGAG<br>CAGCGTGGTGACAGTGCCCTCCAGCAGCCTGGGCACCCAGACCTACAT<br>CTGCAACGTGAACCACAAGCCCAGCAACACCAAGGTGGACAAGAAGG<br>TGGAACCCAAGAGCTGCGAC | 222 |
| Drozitumab-FAP(4G8) VLCH1 | GAAGTGCAGCTGGTGCAGTCTGGCGGCGGAGTGGAAAGACCTGGCGG<br>CAGCCTGAGACTGAGCTGCGCCGCCAGCGGCTTCACCTTCGACGACTA<br>CGCCATGTCTTGGGTCCGCCAGGCCCCTGGAAAGGGCCTGGAATGGGT | 223 |

| Description | Nucleotide sequences | SEQ ID NO |
|---|---|---|
| 2 + 2 | GTCCGGCATCAACTGGCAGGGCGGCAGCACCGGCTACGCCGACAGCG<br>TGAAGGGCAGAGTGACCATCAGCCGGGACAACGCCAAGAACAGCCTG<br>TACCTGCAGATGAACAGCCTGAGAGCCGAGGACACCGCCGTGTACTAC<br>TGCGCCAAGATCCTGGGAGCCGGCAGAGGCTGGTACTTCGACTACTGG<br>GGCAAGGGCACCACCGTGACTGTGTCTAGCGCTAGCACCAAGGGCCCA<br>AGCGTGTTCCCTCTGGCCCCCAGCAGCAAGAGCACAAGCGGCGGAAC<br>AGCCGCCCTGGGCTGCCTGGTCAAGGACTACTTCCCCGAGCCCGTGAC<br>AGTGTCCTGGAACAGCGGAGCCCTGACCAGCGGCGTGCACACCTTTCC<br>AGCCGTGCTGCAGAGCAGCGGCCTGTACAGCCTGAGCAGCGTGGTCAC<br>AGTGCCTAGCAGCAGCCTGGGCACCCAGACCTACATCTGCAACGTGAA<br>CCACAAGCCCAGCAACACCAAGGTGGACAAGAAGGTGGAGCCCAAGA<br>GCTGCGACAAGACCCACACCTGTCCCCCTTGTCCTGCCCCTGAGCTGCT<br>GGGCGGACCCAGCGTGTTCCTGTTCCCCCCAAAGCCCAAGGACACCCT<br>GATGATCAGCCGGACCCCCGAAGTGACCTGCGTGGTGGTGGACGTGTC<br>CCACGAGGACCCTGAAGTGAAGTTCAATTGGTACGTGGACGGCGTGGA<br>GGTGCACAATGCCAAGACCAAGCCCCGGGAGGAACAGTACAACAGCA<br>CCTACCGGGTGGTGTCCGTGCTGACCGTGCTGCACCAGGACTGGCTGA<br>ACGGCAAAGAGTACAAGTGCAAGGTCTCCAACAAGGGCCCTGCCTGCCC<br>CCATCGAGAAAACCATCAGCAAGGCCAAGGGCCAGCCCAGAGAACCC<br>CAGGTGTACACCCTGCCCCCCAGCAGAGATGAGCTGACCAAGAACCA<br>GGTGTCCCTGACCTGTCTGGTCAAGGGCTTCTACCCCAGCGATATCGCC<br>GTGGAGTGGGAGAGCAACGGCCAGCCTGAGAACAACTACAAGACCAC<br>CCCCCCTGTGCTGGACAGCGACGGCAGCTTCTTCCTGTACTCCAAACTG<br>ACCGTGGACAAGAGCCGGTGGCAGCAGGGCAACGTGTTCAGCTGCAG<br>CGTGATGCACGAGGCCCTGCACAACCACTACACCCAGAAGTCCCTGAG<br>CCTGAGCCCCGGCAAGTCCGGAGGCGGCGGAAGCGGAGGAGGAGGAT<br>CCGGAGGAGGGGGAAGTGGCGGCGGAGGATCTGAGATCGTGCTGACC<br>CAGTCTCCCGGCACCCTGAGCCTGAGCCCTGGCGAGAGAGCCACCCTG<br>AGCTGCAGAGCCAGCCAGAGCGTGAGCCGGAGCTACCTGGCCTGGTAT<br>CAGCAGAAGCCCGGCCAGGCCCCCAGACTGCTGATCATCGGCGCCAGC<br>ACCCGGGCCACCGGCATCCCCGATAGATTCAGCGGCAGCGGCTCCGGC<br>ACCGACTTCACCCTGACCATCAGCCGGCTGGAACCCGAGGACTTCGCC<br>GTGTACTACTGCAGCAGGGCCAGGTGATCCCCCCCACCTTCGGCCAG<br>GGCACCAAGGTGGAAATCAAGGCTAGCACCAAGGGCCCCTCCGTGTTT<br>CCTCTGGCCCCCAGCAGCAAGAGCACCTCTGGCGGAACAGCCGCCCTG<br>GGCTGCCTGGTGAAAGACTACTTCCCCGAGCCCGTGACCGTGTCCTGG<br>AACTCTGGCGCCCTGACCAGCGGCGTGCACACCTTTCCAGCCGTGCTG<br>CAGAGCAGCGGCCTGTACTCCCTGAGCAGCGTGGTGACAGTGCCCTCC<br>AGCAGCCTGGGCACCCAGACCTACATCTGCAACGTGAACCACAAGCCC<br>AGCAACACCAAAGTGGACAAGAAGGTGGAACCCAAGAGCTGCGAC | |
| FAP(4G8)_VHCL | GAGGTGCAGCTGCTGGAATCTGGAGGCGGCCTGGTGCAGCCTGGCGGC<br>AGCCTGAGACTGTCTTGCGCCGCCAGCGGCTTCACCTTCAGCAGCTAC<br>GCCATGAGCTGGGTCCGACAGGCTCCTGGCAAGGGACTGGAATGGGTG<br>TCCGCCATCTCCGGCAGCGGAGGCAGCACCTACTACGCCGACAGCGTG<br>AAGGGCCGGTTCACCATCAGCAGAGACAACAGCAAGAACACCCTGTA<br>CCTGCAGATGAACAGCCTGCGGGCCGAGGATACCGCCGTGTATTATTG<br>CGCCAAGGGATGGCTGGGCAACTTCGACTACTGGGGCCAGGGAACCCT<br>GGTGACAGTGTCCAGCGCTAGCGTGGCCGCTCCCAGCGTGTTCATCTTC<br>CCACCCAGCGACGAGCAGCTGAAGTCCGGCACAGCCAGCGTGGTGTG<br>CCTGCTGAACAACTTCTACCCCCGCGAGGCCAAGGTGCAGTGGAAGGT<br>GGACAACGCCCTGCAGAGCGGCAACAGCCAGGAATCCGTGACCGAGC<br>AGGACAGCAAGGACTCCACCTACAGCCTGAGCAGCACCCTGACCCTGA<br>GCAAGGCCGACTACGAGAAGCACAAGGTGTACGCCTGCGAAGTGACC<br>CACCAGGGCCTGTCCAGCCCCGTGACCAAGAGCTTCAACCGGGGCGAG<br>TGC | 224 |
| Drozitumab-<br>FAP(28H1)<br>VHCL<br>pETR9551<br>2 + 2 | GAAGTGCAGCTGGTGCAGTCTGGCGGCGGAGTGGAAAGACCTGGCGG<br>CAGCCTGAGACTGAGCTGCGCCGCCAGCGGCTTCACCTTCGACGACTA<br>CGCCATGTCTTGGGTCCGCCAGGCCCCTGGAAAGGGCCTGGAATGGGT<br>GTCCGGCATCAACTGGCAGGGCGGCAGCACCGGCTACGCCGACAGCG<br>TGAAGGGCAGAGTGACCATCAGCCGGGACAACGCCAAGAACAGCCTG<br>TACCTGCAGATGAACAGCCTGAGAGCCGAGGACACCGCCGTGTACTAC<br>TGCGCCAAGATCCTGGGAGCCGGCAGAGGCTGGTACTTCGACTACTGG<br>GGCAAGGGCACCACCGTGACTGTGTCTAGCGCTAGCACCAAGGGCCCA<br>AGCGTGTTCCCTCTGGCCCCCAGCAGCAAGAGCACAAGCGGCGGAAC<br>AGCCGCCCTGGGCTGCCTGGTCAAGGACTACTTCCCCGAGCCCGTGAC<br>AGTGTCCTGGAACAGCGGAGCCCTGACCAGCGGCGTGCACACCTTTCC<br>AGCCGTGCTGCAGAGCAGCGGCCTGTACAGCCTGAGCAGCGTGGTCAC<br>AGTGCCTAGCAGCAGCCTGGGCACCCAGACCTACATCTGCAACGTGAA<br>CCACAAGCCCAGCAACACCAAGGTGGACAAGAAGGTGGAGCCCAAGA<br>GCTGCGACAAGACCCACACCTGTCCCCCTTGTCCTGCCCCTGAGCTGCT<br>GGGCGGACCCAGCGTGTTCCTGTTCCCCCCAAAGCCCAAGGACACCCT<br>GATGATCAGCCGGACCCCCGAAGTGACCTGCGTGGTGGTGGACGTGTC<br>CCACGAGGACCCTGAAGTGAAGTTCAATTGGTACGTGGACGGCGTGGA<br>GGTGCACAATGCCAAGACCAAGCCCCGGGAGGAACAGTACAACAGCA | 225 |

| Description | Nucleotide sequences | SEQ ID NO |
|---|---|---|
| | CCTACCGGGTGGTGTCCGTGCTGACCGTGCTGCACCAGGACTGGCTGA<br>ACGGCAAAGAGTACAAGTGCAAGGTCTCCAACAAGGCCCTGCCTGCCC<br>CCATCGAGAAAACCATCAGCAAGGCCAAGGGCCAGCCCAGAGAACCC<br>CAGGTGTACACCCTGCCCCCAGCAGAGATGAGCTGACCAAGAACCA<br>GGTGTCCCTGACCTGTCTGGTCAAGGGCTTCTACCCCAGCGATATCGCC<br>GTGGAGTGGGAGAGCAACGGCCAGCCTGAGAACAACTACAAGACCAC<br>CCCCCCTGTGCTGGACAGCGACGGCAGCTTCTTCCTGTACTCCAAACTG<br>ACCGTGGACAAGAGCCGGTGGCAGCAGGGCAACGTGTTCAGCTGCAG<br>CGTGATGCACGAGGCCCTGCACAACCACTACACCCAGAAGTCCCTGAG<br>CCTGAGCCCCGGCAAGTCCGGAGGCGGCGGAAGCGGAGGAGGAGGAT<br>CCGGAGGAGGGGGAAGTGGCGGCGGAGGATCTGAGGTGCAGCTGCTG<br>GAATCCGGCGGAGGCCTGGTGCAGCCTGGCGGATCTCTGAGACTGTCC<br>TGCGCCGCCTCCGGCTTCACCTTCTCCTCCCACGCCATGTCCTGGGTCC<br>GACAGGCTCCTGGCAAAGGCCTGGAATGGGTGTCCGCCATCTGGGCCT<br>CCGGCGAGCAGTACTACGCCGACTCTGTGAAGGGCCGGTTCACCATCT<br>CCCGGGACAACTCCAAGAACACCCTGTACCTGCAGATGAACTCCCTGC<br>GGGCCGAGGACACCGCCGTGTACTACTGTGCCAAGGGCTGGCTGGGCA<br>ACTTCGACTACTGGGGCCAGGGCACCCTGGTCACCGTGTCCAGCGCTA<br>GCGTGGCCGCTCCCAGCGTGTTCATCTTCCCACCCAGCGACGAGCAGC<br>TGAAGTCCGGCACAGCCAGCGTGGTGTGCCTGCTGAACAACTTCTACC<br>CCCGCGAGGCCAAGGTGCAGTGGAAGGTGGACAACGCCCTGCAGAGC<br>GGCAACAGCCAGGAATCCGTGACCGAGCAGGACAGCAAGGACTCCAC<br>CTACAGCCTGAGCAGCACCCTGACCCTGAGCAAGGCCGACTACGAGA<br>AGCACAAGGTGTACGCCTGCGAAGTGACCCACCAGGGCCTGTCCAGCC<br>CCGTGACCAAGAGCTTCAACCGGGGCGAGTGC | |
| FAP(28H1)_VLCH1<br>pETR9537 | GAGATCGTGCTGACCCAGTCTCCCGGCACCCTGAGCCTGAGCCCTGGC<br>GAGAGAGCCACCCTGAGCTGCAGAGCCAGCCAGAGCGTGAGCCGGAG<br>CTACCTGGCCTGGTATCAGCAGAAGCCCGGCCAGGCCCCCAGACTGCT<br>GATCATCGGCGCCAGCACCCGGGCCACCGGCATCCCCGATAGATTCAG<br>CGGCAGCGGCTCCGGCACCGACTTCACCCTGACCATCAGCCGGCTGGA<br>ACCCGAGGACTTCGCCGTGTACTACTGCCAGCAGGGCCAGGTGATCCC<br>CCCCACCTTCGGCCAGGGCACCAAGGTGGAAATCAAGAGCTCCGCTAG<br>CACCAAGGGCCCCTCCGTGTTTCCTCTGGCCCCCAGCAGCAAGAGCAC<br>CTCTGGCGGAACAGCCGCCTGGGCTGCCTGGTGAAAGACTACTTCCC<br>CGAGCCCGTGACCGTGTCCTGGAACTCTGGCGCCCTGACCAGCGGCGT<br>GCACACCTTTCCAGCCGTGCTGCAGAGCAGCGGCCTGTACTCCCTGAG<br>CAGCGTGGTGACAGTGCCCTCCAGCAGCCTGGGCACCCAGACCTACAT<br>CTGCAACGTGAACCACAAGCCCAGCAACACCAAAGTGGACAAGAAGG<br>TGGAACCCAAGAGCTGCGAC | 226 |
| DR5(22E9)-<br>FAP(28H1)<br>VHCL<br>pETR9711<br>2 + 2 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGTGTGCGGATTTCGTTTGACTACTGGGGCCAAGGAACCCTGG<br>TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAGGTGCACAATGCCAAG<br>ACCAAGCCCCGGGAGGAACAGTACAACAGCACCTACCGGGTGGTGTC<br>CGTGCTGACCGTGCTGCACCAGGACTGGCTGAACGGCAAAGAGTACAA<br>GTGCAAGGTCTCCAACAAGGCCCTGCCTGCCCCCATCGAGAAAACCAT<br>CAGCAAGGCCAAGGGCCAGCCCAGAGAACCCCAGGTGTACACCCTGC<br>CCCCCAGCAGAGATGAGCTGACCAAGAACCAGGTGTCCCTGACCTGTC<br>TGGTCAAGGGCTTCTACCCCAGCGATATCGCCGTGGAGTGGGAGAGCA<br>ACGGCCAGCCTGAGAACAACTACAAGACCACCCCCCCTGTGCTGGACA<br>GCGACGGCAGCTTCTTCCTGTACTCCAAACTGACCGTGGACAAGAGCC<br>GGTGGCAGCAGGGCAACGTGTTCAGCTGCAGCGTGATGCACGAGGCCC<br>TGCACAACCACTACACCCAGAAGTCCCTGAGCCTGAGCCCCGGCAAGT<br>CCGGAGGCGGCGGAAGCGGAGGAGGAGGATCGGAGGAGGGGGAAG<br>TGGCGGCGGAGGATCTGAGGTGCAGCTGCTGGAATCCGGCGGAGGCCT<br>GGTGCAGCCTGGCGGATCTCTGAGACTGTCCTGCGCCGCCTCCGGCTT<br>CACCTTCTCCTCCCACGCCATGTCCTGGGTCCGACAGGCTCCTGGCAAA<br>GGCCTGGAATGGGTGTCCGCCATCTGGGCCTCCGGCGAGCAGTACTAC<br>GCCGACTCTGTGAAGGGCCGGTTCACCATCTCCCGGGACAACTCCAAG<br>AACACCCTGTACCTGCAGATGAACTCCCTGCGGGCCGAGGACACCGCC | 227 |

| Description | Nucleotide sequences | SEQ ID NO |
|---|---|---|
| | GTGTACTACTGTGCCAAGGGCTGGCTGGGCAACTTCGACTACTGGGGC<br>CAGGGCACCCTGGTCACCGTGTCCAGCGCTAGCGTGGCCGCTCCCAGC<br>GTGTTCATCTTCCCACCCAGCGACGAGCAGCTGAAGTCCGGCACAGCC<br>AGCGTGGTGTGCCTGCTGAACAACTTCTACCCCCGCGAGGCCAAGGTG<br>CAGTGGAAGGTGGACAACGCCCTGCAGAGCGGCAACAGCCAGGAATC<br>CGTGACCGAGCAGGACAGCAAGGACTCCACCTACAGCCTGAGCAGCA<br>CCCTGACCCTGAGCAAGGCCGACTACGAGAAGCACAAGGTGTACGCCT<br>GCGAAGTGACCCACCAGGGCCTGTCCAGCCCCGTGACCAAGAGCTTCA<br>ACCGGGGCGAGTGC | |
| DR5(22E9)<br>LC<br>pETR9076 | GAAATCGTGTTAACGCAGTCTCCAGGCACCCTGTCTTTGTCTCCAGGGG<br>AAAGAGCCACCCTCTCTTGCAGGGCCAGTCAGAGTGTTAGCAGCAGCT<br>ACTTAGCCTGGTACCAGCAGAAACCTGGCCAGGCTCCCAGGCTCCTCA<br>TCTATGGAGCATCCAGCAGGGCCACTGGCATCCCAGACAGGTTCAGTG<br>GCAGTGGATCCGGGACAGACTTCACTCTCACCATCAGCAGACTGGAGC<br>CTGAAGATTTTGCAGTGTATTACTGTCAGCAGGGTTCTAATCAGCCCGT<br>TACGTTCGGCCAGGGGACCAAAGTGGAAATCAAACGTACGGTGGCTGC<br>ACCATCTGTCTTCATCTTCCCGCCATCTGATGAGCAGTTGAAATCTGGA<br>ACTGCCTCTGTTGTGTGCCTGCTGAATAACTTCTATCCCAGAGAGGCCA<br>AAGTACAGTGGAAGGTGGATAACGCCCTCCAATCGGGTAACTCCCAGG<br>AGAGTGTCACAGAGCAGGACAGCAAGGACAGCACCTACAGCCTCAGC<br>AGCACCCTGACGCTGAGCAAAGCAGACTACGAGAAACACAAAGTCTA<br>CGCCTGCGAAGTCACCCATCAGGGCCTGAGCTCGCCCGTCACAAAGAG<br>CTTCAACAGGGGAGAGTGT | 228 |
| DR5(21H3)-<br>FAP(28H1)<br>VHCL<br>pETR10626<br>2 + 2 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACATGGCCGTATATTACTGTG<br>CGAAAGGTGCTCGTGTTTCTTTTGACTACTGGGGCCAAGGAACCCTGG<br>TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAGGTGCACAATGCCAAG<br>ACCAAGCCCCGGGAGGAACAGTACAACAGCACCTACCGGGTGGTGTC<br>CGTGCTGACCGTGCTGCACCAGGACTGGCTGAACGGCAAAGAGTACAA<br>GTGCAAGGTCTCCAACAAGGCCCTGCCTGCCCCCATCGAGAAAACCAT<br>CAGCAAGGCCAAGGGCCAGCCCAGAGAACCCCAGGTGTACACCCTGC<br>CCCCCAGCAGAGATGAGCTGACCAAGAACCAGGTGTCCCTGACCTGTC<br>TGGTCAAGGGCTTCTACCCCAGCGATATCGCCGTGGAGTGGGAGAGCA<br>ACGGCCAGCCTGAGAACAACTACAAGACCACCCCCCCTGTGCTGGACA<br>GCGACGGCAGCTTCTTCCTGTACTCCAAACTGACCGTGGACAAGAGCC<br>GGTGGCAGCAGGGCAACGTGTTCAGCTGCAGCGTGATGCACGAGGCCC<br>TGCACAACCACTACACCCAGAAGTCCCTGAGCCTGAGCCCCGGCAAGT<br>CCGGAGGCGGCGGAAGCGGAGGAGGAGGATCCGGAGGAGGGGGAAG<br>TGGCGGCGGAGGATCTGAGGTGCAGCTGCTGGAATCCGGCGGAGGCCT<br>GGTGCAGCCTGGCGGATCTCTGAGACTGTCCTGCGCCGCCTCCGGCTT<br>CACCTTCTCCTCCCACGCCATGTCCTGGGTCCGACAGGCTCCTGGCAAA<br>GGCCTGGAATGGGTGTCCGCCATCTGGGCCTCCGGCGAGCAGTACTAC<br>GCCGACTCTGTGAAGGGCCGGTTCACCATCTCCCGGGACAACTCCAAG<br>AACACCCTGTACCTGCAGATGAACTCCCTGCGGGCCGAGGACACCGCC<br>GTGTACTACTGTGCCAAGGGCTGGCTGGGCAACTTCGACTACTGGGGC<br>CAGGGCACCCTGGTCACCGTGTCCAGCGCTAGCGTGGCCGCTCCCAGC<br>GTGTTCATCTTCCCACCCAGCGACGAGCAGCTGAAGTCCGGCACAGCC<br>AGCGTGGTGTGCCTGCTGAACAACTTCTACCCCCGCGAGGCCAAGGTG<br>CAGTGGAAGGTGGACAACGCCCTGCAGAGCGGCAACAGCCAGGAATC<br>CGTGACCGAGCAGGACAGCAAGGACTCCACCTACAGCCTGAGCAGCA<br>CCCTGACCCTGAGCAAGGCCGACTACGAGAAGCACAAGGTGTACGCCT<br>GCGAAGTGACCCACCAGGGCCTGTCCAGCCCCGTGACCAAGAGCTTCA<br>ACCGGGGCGAGTGC | 229 |
| DR5(21H3)<br>LC<br>pETR9075 | GAAATCGTGTTAACGCAGTCTCCAGGCACCCTGTCTTTGTCTCCAGGGG<br>AAAGAGCCACCCTCTCTTGCAGGGCCAGTCAGAGTGTTAGCAGCAGCT<br>ACTTAGCCTGGTACCAGCAGAAACCTGGCCAGGCTCCCAGGCTCCTCA<br>TCTATGGAGCATCCAGCAGGGCCACTGGCATCCCAGACAGGTTCAGTG<br>GCAGTGGATCCGGGACAGACTTCACTCTCACCATCAGCAGACTGGAGC<br>CTGAAGATTTTGCAGTGTATTACTGTCAGCAGGGTTCTCAGCCGCCCAT | 230 |

| Description | Nucleotide sequences | SEQ ID NO |
|---|---|---|
| | TACGTTCGGCCAGGGGACCAAAGTGGAAATCAAACGTACGGTGGCTGC<br>ACCATCTGTCTTCATCTTCCCGCCATCTGATGAGCAGTTGAAATCTGGA<br>ACTGCCTCTGTTGTGTGCCTGCTGAATAACTTCTATCCCAGAGAGGCCA<br>AAGTACAGTGGAAGGTGGATAACGCCCTCCAATCGGGTAACTCCCAGG<br>AGAGTGTCACAGAGCAGGACAGCAAGGACAGCACCTACAGCCTCAGC<br>AGCACCCTGACGCTGAGCAAAGCAGACTACGAGAAACACAAAGTCTA<br>CGCCTGCGAAGTCACCCATCAGGGCCTGAGCTCGCCCGTCACAAAGAG<br>CTTCAACAGGGGAGAGTGT | |
| DR5(20F2)-<br>FAP(28H1)<br>VHCL<br>pETR10135<br>2 + 2 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGTGTGAGGAAGGGGTTTGACTACTGGGGCCAAGGAACCCTG<br>GTCACCGTCTCGAGTGCTAGCACCAAGGGCCCAAGCGTGTTCCCTCTG<br>GCCCCCAGCAGCAAGAGCACAAGCGGCGGAACAGCCGCCCTGGGCTG<br>CCTGGTCAAGGACTACTTCCCCGAGCCCGTGACAGTGTCCTGGAACAG<br>CGGAGCCCTGACCAGCGGCGTGCACACCTTTCCAGCCGTGCTGCAGAG<br>CAGCGGCCTGTACAGCCTGAGCAGCGTGGTCACAGTGCCTAGCAGCAG<br>CCTGGGCACCCAGACCTACATCTGCAACGTGAACCACAAGCCCAGCAA<br>CACCAAGGTGGACAAGAAGGTGGAGCCCAAGAGCTGCGACAAGACCC<br>ACACCTGTCCCCCTTGTCCTGCCCCTGAGCTGCTGGGCGGACCCAGCGT<br>GTTCCTGTTCCCCCCAAAGCCCAAGGACACCCTGATGATCAGCCGGAC<br>CCCCGAAGTGACCTGCGTGGTGGTGGACGTGTCCCACGAGGACCCTGA<br>AGTGAAGTTCAATTGGTACGTGGACGGCGTGGAGGTGCACAATGCCAA<br>GACCAAGCCCCGGGAGGAACAGTACAACAGCACCTACCGGGTGGTGT<br>CCGTGCTGACCGTGCTGCACCAGGACTGGCTGAACGGCAAAGAGTACA<br>AGTGCAAGGTCTCCAACAAGGCCCTGCCTGCCCCCATCGAGAAAACCA<br>TCAGCAAGGCCAAGGGCCAGCCCAGAGAACCCCAGGTGTACACCCTG<br>CCCCCCAGCAGAGATGAGCTGACCAAGAACCAGGTGTCCCTGACCTGT<br>CTGGTCAAGGGCTTCTACCCCAGCGATATCGCCGTGGAGTGGGAGAGC<br>AACGGCCAGCCTGAGAACAACTACAAGACCACCCCCCCTGTGCTGGAC<br>AGCGACGGCAGCTTCTTCCTGTACTCCAAACTGACCGTGGACAAGAGC<br>CGGTGGCAGCAGGGCAACGTGTTCAGCTGCAGCGTGATGCACGAGGCC<br>CTGCACAACCACTACACCCAGAAGTCCCTGAGCCTGAGCCCCGGCAAG<br>TCCGGAGGCGGCGGAAGCGGAGGAGGAGGATCCGGAGGAGGGGGAA<br>GTGGCGGCGGAGGATCTGAGGTGCAGCTGCTGGAATCCGGCGGAGGC<br>CTGGTGCAGCCTGGCGGATCTCTGAGACTGTCCTGCGCCGCCTCCGGC<br>TTCACCTTCTCCTCCCACGCCATGTCCTGGGTCCGACAGGCTCCTGGCA<br>AAGGCCTGGAATGGGTGTCCGCCATCTGGGCCTCCGGCGAGCAGTACT<br>ACGCCGACTCTGTGAAGGGCCGGTTCACCATCTCCCGGGACAACTCCA<br>AGAACACCCTGTACCTGCAGATGAACTCCCTGCGGGCCGAGGACACCG<br>CCGTGTACTACTGTGCCAAGGGCTGGCTGGGCAACTTCGACTACTGGG<br>GCCAGGGCACCCTGGTCACCGTGTCCAGCGCTAGCGTGGCCGCTCCCA<br>GCGTGTTCATCTTCCCACCCAGCGACGAGCAGCTGAAGTCCGGCACAG<br>CCAGCGTGGTGTGCCTGCTGAACAACTTCTACCCCCGCGAGGCCAAGG<br>TGCAGTGGAAGGTGGACAACGCCCTGCAGAGCGGCAACAGCCAGGAA<br>TCCGTGACCGAGCAGGACAGCAAGGACTCCACCTACAGCCTGAGCAG<br>CACCCTGACCCTGAGCAAGGCCGACTACGAGAAGCACAAGGTGTACG<br>CCTGCGAAGTGACCCACCAGGGCCTGTCCAGCCCCGTGACCAAGAGCT<br>TCAACCGGGGCGAGTGC | 231 |
| DR5(20F2)<br>LC<br>pETR9061 | GAAATCGTGTTAACGCAGTCTCCAGGCACCCTGTCTTTGTCTCCAGGGG<br>AAAGAGCCACCCTCTCTTGCAGGGCCAGTCAGAGTGTTAGCAGCAGCT<br>ACTTAGCCTGGTACCAGCAGAAACCTGGCCAGGCTCCCAGGCTCCTCA<br>TCTATGGAGCATCCAGCAGGGCCACTGGCATCCCAGACAGGTTCAGTG<br>GCAGTGGATCCGGGACAGACTTCACTCTCACCATCAGCAGACTGGAGC<br>CTGAAGATTTTGCAGTGTATTACTGTCAGCAGGGTGAGTCGCCTCCCC<br>GACGTTCGGCCAGGGGACCAAAGTGGAAATCAAACGTACGGTGGCTG<br>CACCATCTGTCTTCATCTTCCCGCCATCTGATGAGCAGTTGAAATCTGG<br>AACTGCCTCTGTTGTGTGCCTGCTGAATAACTTCTATCCCAGAGAGGCC<br>AAAGTACAGTGGAAGGTGGATAACGCCCTCCAATCGGGTAACTCCCAG<br>GAGAGTGTCACAGAGCAGGACAGCAAGGACAGCACCTACAGCCTCAG<br>CAGCACCCTGACGCTGAGCAAAGCAGACTACGAGAAACACAAAGTCT<br>ACGCCTGCGAAGTCACCCATCAGGGCCTGAGCTCGCCCGTCACAAAGA<br>GCTTCAACAGGGGAGAGTGT | 232 |
| DR5(5E11)-<br>FAP(28H1)<br>VHCL<br>pETR10334<br>2 + 2 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGG | 233 |

| Description | Nucleotide sequences | SEQ ID NO |
|---|---|---|
| | TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAGGTGCACAATGCCAAG<br>ACCAAGCCCCGGGAGGAACAGTACAACAGCACCTACCGGGTGGTGTC<br>CGTGCTGACCGTGCTGCACCAGGACTGGCTGAACGGCAAAGAGTACAA<br>GTGCAAGGTCTCCAACAAGGCCCTGCCTGCCCCCATCGAGAAACCAT<br>CAGCAAGGCCAAGGGCCAGCCCAGAGAACCCCAGGTGTACACCCTGC<br>CCCCCAGCAGAGATGAGCTGACCAAGAACCAGGTGTCCCTGACCTGTC<br>TGGTCAAGGGCTTCTACCCCAGCGATATCGCCGTGGAGTGGGAGAGCA<br>ACGGCCAGCCTGAGAACAACTACAAGACCACCCCCCCTGTGCTGGACA<br>GCGACGGCAGCTTCTTCCTGTACTCCAAACTGACCGTGGACAAGAGCC<br>GGTGGCAGCAGGGCAACGTGTTCAGCTGCAGCGTGATGCACGAGGCCC<br>TGCACAACCACTACACCCAGAAGTCCCTGAGCCTGAGCCCCGGCAAGT<br>CCGGAGGCGGCGGAAGCGGAGGAGGAGGATCCGGAGGAGGGGGAAG<br>TGGCGGCGGAGGATCTGAGGTGCAGCTGCTGGAATCCGGCGGAGGCCT<br>GGTGCAGCCTGGCGGATCTCTGAGACTGTCCTGCGCCGCCTCCGGCTT<br>CACCTTCTCCTCCCACGCCATGTCCTGGGTCCGACAGGCTCCTGGCAAA<br>GGCCTGGAATGGGTGTCCGCCATCTGGGCCTCCGGCGAGCAGTACTAC<br>GCCGACTCTGTGAAGGGCCGGTTCACCATCTCCCGGGACAACTCCAAG<br>AACACCCTGTACCTGCAGATGAACTCCCTGCGGGCCGAGGACACCGCC<br>GTGTACTACTGTGCCAAGGGCTGGTGGGCAACTTCGACTACTGGGGC<br>CAGGGCACCCTGGTCACCGTGTCCAGCGCTAGCGTGGCCGCTCCCAGC<br>GTGTTCATCTTCCCACCCAGCGACGAGCAGCTGAAGTCCGGCACAGCC<br>AGCGTGGTGTGCCTGCTGAACAACTTCTACCCCGCGAGGCCAAGGTG<br>CAGTGGAAGGTGGACAACGCCCTGCAGAGCGGCAACAGCCAGGAATC<br>CGTGACCGAGCAGGACAGCAAGGACTCCACCTACAGCCTGAGCAGCA<br>CCCTGACCCTGAGCAAGGCCGACTACGAGAAGCACAAGGTGTACGCCT<br>GCGAAGTGACCCACCAGGGCCTGTCCAGCCCCGTGACCAAGAGCTTCA<br>ACCGGGGCGAGTGC | |
| DR5(5E11)<br>LC<br>pETR9044 | GAAATCGTGTTAACGCAGTCTCCAGGCACCCTGTCTTTGTCTCCAGGGG<br>AAAGAGCCACCCTCTCTTGCAGGGCCAGTCAGAGTGTTAGCAGCAGCT<br>ACTTAGCCTGGTACCAGCAGAAACCTGGCCAGGCTCCCAGGCTCCTCA<br>TCTATGGAGCATCCAGCAGGGCCACTGGCATCCCAGACAGGTTCAGTG<br>GCAGTGGATCCGGGACAGACTTCACTCTCACCATCAGCAGACTGGAGC<br>CTGAAGATTTTGCAGTGTATTACTGTCAGCAGGGTACTACTCATCCCAT<br>TACGTTCGGCCAGGGGACCAAAGTGGAAATCAAACGTACGGTGGCTGC<br>ACCATCTGTCTTCATCTTCCCGCCATCTGATGAGCAGTTGAAATCTGGA<br>ACTGCCTCTGTTGTGTGCCTGCTGAATAACTTCTATCCCAGAGAGGCCA<br>AAGTACAGTGGAAGGTGGATAACGCCCTCCAATCGGGTAACTCCCAGG<br>AGAGTGTCACAGAGCAGGACAGCAAGGACAGCACCTACAGCCTCAGC<br>AGCACCCTGACGCTGAGCAAAGCAGACTACGAGAAACACAAAGTCTA<br>CGCCTGCGAAGTCACCCATCAGGGCCTGAGCTCGCCCGTCACAAAGAG<br>CTTCAACAGGGGAGAGTGT | 234 |
| DR5(5E11)-<br>FAP(28H1)<br>VHCL<br>2 + 2<br>Removal of<br>C-term.<br>Lysine in<br>Fc<br>pETR11052 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGA<br>TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAGGTGCACAATGCCAAG<br>ACCAAGCCCCGGGAGGAACAGTACAACAGCACCTACCGGGTGGTGTC<br>CGTGCTGACCGTGCTGCACCAGGACTGGCTGAACGGCAAAGAGTACAA<br>GTGCAAGGTCTCCAACAAGGCCCTGCCTGCCCCCATCGAGAAACCAT<br>CAGCAAGGCCAAGGGCCAGCCCAGAGAACCCCAGGTGTACACCCTGC<br>CCCCTAGCAGAGATGAGCTGACCAAGAACCAGGTGTCCCTGACCTGTC | 235 |

| Description | Nucleotide sequences | SEQ ID NO |
|---|---|---|
| | TCGTGAAAGGCTTCTACCCCTCCGATATCGCCGTGGAATGGGAGAGCA<br>ACGGCCAGCCCGAGAACAACTACAAGACCACCCCCCCTGTGCTGGACT<br>CCGACGGCTCATTCTTCCTGTACTCTAAGCTGACAGTGGACAAGTCCCG<br>GTGGCAGCAGGGCAACGTGTTCTCCTGCTCCGTGATGCACGAGGCCCT<br>GCACAACCACTACACCCAGAAGTCCCTGTCCCTGTCTCCCGGGGGAGG<br>CGGAGGATCTGGCGGAGGCGGATCCGGTGGTGGCGGATCTGGGGGCG<br>GTGGATCTGAGGTGCAGCTGCTGGAATCTGGGGGAGGACTGGTGCAGC<br>CAGGCGGATCTCTGAGGCTGTCCTGCGCTGCTTCCGGCTTTACCTTCTC<br>CAGCCACGCCATGAGTTGGGTGCGCCAGGCACCCGGAAAAGGACTGG<br>AATGGGTGTCAGCCATCTGGGCCTCCGGCGAGCAGTACTACGCCGATA<br>GCGTGAAGGGCCGGTTCACCATCTCTCGGGATAACAGCAAGAATACTC<br>TGTACCTGCAGATGAACTCCCTGCGCGCTGAAGATACCGCTGTGTATT<br>ACTGCGCCAAGGGCTGGCTGGGCAACTTCGATTACTGGGGCCAGGGAA<br>CCCTCGTGACTGTCTCGAGCGCTTCTGTGGCCGCTCCCTCCGTGTTCAT<br>CTTCCCACCTTCCGACGAGCAGCTGAAGTCCGGCACTGCCTCTGTCGTG<br>TGCCTGCTGAACAACTTCTACCCTCGGGAAGCCAAGGTGCAGTGGAAA<br>GTGGATAACGCCCTGCAGTCCGGCAACTCCCAGGAATCCGTGACCGAG<br>CAGGACTCCAAGGACAGCACCTACTCCCTGAGCAGCACCCTGACCCTG<br>TCCAAGGCCGACTACGAGAAGCACAAGGTGTACGCCTGTGAAGTGACC<br>CACCAGGGCCTGTCCAGCCCCGTGACCAAGTCCTTCAACCGGGGCGAG<br>TGC | |
| DR5(5E11)-<br>FAP(28H1)<br>VHCL<br>2 + 2<br>Removal of<br>C-term.<br>Lysine in<br>Fc<br>P329G/LALA<br>mut.<br>pETR11025 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGG<br>TCACCGTCTCGAGTGCTAGCACCAAGGGCCCATCCGTGTTCCCTCTGGC<br>CCCTTCCAGCAAGTCTACCTCTGGCGGCACAGCCGCTCTGGGCTGCCTC<br>GTGAAGGACTACTTCCCCGAGCCTGTGACAGTGTCCTGGAACTCTGGC<br>GCCCTGACATCCGGCGTGCACACCTTTCCAGCTGTGCTGCAGTCCTCCG<br>GCCTGTACTCCCTGTCCTCCGTCGTGACAGTGCCCTCCAGCTCTCTGGG<br>CACCCAGACCTACATCTGCAACGTGAACCACAAGCCCTCCAACACCAA<br>GGTGGACAAGAAGGTGGAACCCAAGTCCTGCGACAAGACCCACACCT<br>GTCCCCCTTGTCCTGCCCCTGAAGCTGCTGGCGGCCCCAGCGTGTTCCT<br>GTTCCCCCCAAAGCCCAAGGACACCCTGATGATCTCCCGGACCCCCGA<br>AGTGACCTGCGTGGTGGTGGATGTGTCCCACGAGGACCCTGAAGTGAA<br>GTTCAATTGGTACGTGGACGGCGTGGAAGTGCACAATGCCAAGACCAA<br>GCCTAGAGAGGAACAGTACAACTCCACCTACCGGGTGGTGTCCGTGCT<br>GACCGTGCTGCACCAGGATTGGCTGAACGGCAAGGAGTACAAGTGCA<br>AGGTGTCCAACAAGGCCCTGGGAGCCCCCATCGAAAAGACCATCTCCA<br>AGGCCAAGGGCCAGCCTCGCGAGCCTCAGGTGTACACCCTGCCCCCTA<br>GCAGAGATGAGCTGACCAAGAACCAGGTGTCCCTGACCTGTCTCGTGA<br>AAGGCTTCTACCCCTCCGATATCGCCGTGGAATGGGAGAGCAACGGCC<br>AGCCCGAGAACAACTACAAGACCACCCCCCCTGTGCTGGACTCCGACG<br>GCTCATTCTTCCTGTACTCTAAGCTGACAGTGGACAAGTCCCGGTGGCA<br>GCAGGGCAACGTGTTCTCCTGCTCCGTGATGCACGAGGCCCTGCACAA<br>CCACTACACCCAGAAGTCCCTGTCCCTGTCTCCCGGGGGAGGCGGAGG<br>ATCTGGCGGAGGCGGATCCGGTGGTGGCGGATCTGGGGGCGGTGGATC<br>TGAGGTGCAGCTGCTGGAATCTGGGGGAGGACTGGTGCAGCCAGGCG<br>GATCTCTGAGGCTGTCCTGCGCTGCTTCCGGCTTTACCTTCTCCAGCCA<br>CGCCATGAGTTGGGTGCGCCAGGCACCCGGAAAAGGACTGGAATGGG<br>TGTCAGCCATCTGGGCCTCCGGCGAGCAGTACTACGCCGATAGCGTGA<br>AGGGCCGGTTCACCATCTCTCGGGATAACAGCAAGAATACTCTGTACC<br>TGCAGATGAACTCCCTGCGCGCTGAAGATACCGCTGTGTATTACTGCG<br>CCAAGGGCTGGCTGGGCAACTTCGATTACTGGGGCCAGGGAACCCTCG<br>TGACTGTCTCGAGCGCTTCTGTGGCCGCTCCCTCCGTGTTCATCTTCCC<br>ACCTTCCGACGAGCAGCTGAAGTCCGGCACTGCCTCTGTCGTGTGCCT<br>GCTGAACAACTTCTACCCTCGGGAAGCCAAGGTGCAGTGGAAAGTGGA<br>TAACGCCCTGCAGTCCGGCAACTCCCAGGAATCCGTGACCGAGCAGGA<br>CTCCAAGGACAGCACCTACTCCCTGAGCAGCACCCTGACCCTGTCCAA<br>GGCCGACTACGAGAAGCACAAGGTGTACGCCTGTGAAGTGACCCACC<br>AGGGCCTGTCCAGCCCCGTGACCAAGTCCTTCAACCGGGGCGAGTGC | 236 |
| VHVL<br>Cross<br>DR5(5E11)-<br>FAP(28H1)<br>pETR11827<br>2 + 2 | GAAATCGTGTTAACGCAGTCTCCAGGCACCCTGTCTTTGTCTCCAGGGG<br>AAAGAGCCACCCTCTCTTGCAGGGCCAGTCAGAGTGTTAGCAGCAGCT<br>ACTTAGCCTGGTACCAGCAGAAACCTGGCCAGGCTCCCAGGCTCCTCA<br>TCTATGGAGCATCCAGCAGGGCCACTGGCATCCCAGACAGGTTCAGTG<br>GCAGTGGATCCGGGACAGACTTCACTCTCACCATCAGCAGACTGGAGC<br>CTGAAGATTTTGCAGTGTATTACTGTCAGCAGGGTACTACTCATCCCAT<br>TACGTTCGGCCAGGGGACCAAAGTGGAAATCAAAAGCTCCGCTAGCAC<br>CAAGGGCCCAAGCGTGTTCCCTCTGGCCCCCAGCAGCAAGAGCACAAG<br>CGGCGGAACAGCCGCCCTGGGCTGCCTGGTCAAGGACTACTTCCCCGA<br>GCCCGTGACAGTGTCCTGGAACAGCGGAGCCCTGACCAGCGGCGTGCA | 237 |

| Description | Nucleotide sequences | SEQ ID NO |
|---|---|---|
| | CACCTTTCCAGCCGTGCTGCAGAGCAGCGGCCTGTACAGCCTGAGCAG<br>CGTGGTCACAGTGCCTAGCAGCAGCCTGGGCACCCAGACCTACATCTG<br>CAACGTGAACCACAAGCCCAGCAACACCAAGGTGGACAAGAAGGTGG<br>AGCCCAAGAGCTGCGACAAGACCCACACCTGTCCCCCTTGTCCTGCCC<br>CTGAGCTGCTGGGCGGACCCAGCGTGTTCCTGTTCCCCCCAAAGCCCA<br>AGGACACCCTGATGATCAGCCGGACCCCCGAAGTGACCTGCGTGGTGG<br>TGGACGTGTCCCACGAGGACCCTGAAGTGAAGTTCAATTGGTACGTGG<br>ACGGCGTGGAGGTGCACAATGCCAAGACCAAGCCCCGGGAGGAACAG<br>TACAACAGCACCTACCGGGTGGTGTCCGTGCTGACCGTGCTGCACCAG<br>GACTGGCTGAACGGCAAAGAGTACAAGTGCAAGGTCTCCAACAAGGC<br>CCTGCCTGCCCCCATCGAGAAAACCATCAGCAAGGCCAAGGGCCAGCC<br>CAGAGAACCCCAGGTGTACACCCTGCCCCCCAGCAGAGATGAGCTGAC<br>CAAGAACCAGGTGTCCCTGACCTGTCTGGTCAAGGGCTTCTACCCCAG<br>CGATATCGCCGTGGAGTGGGAGAGCAACGGCCAGCCTGAGAACAACT<br>ACAAGACCACCCCCCCTGTGCTGGACAGCGACGGCAGCTTCTTCCTGT<br>ACTCCAAACTGACCGTGGACAAGAGCCGGTGGCAGCAGGGCAACGTG<br>TTCAGCTGCAGCGTGATGCACGAGGCCCTGCACAACCACTACACCCAG<br>AAGTCCCTGAGCCTGAGCCCCGGCAAGTCCGGAGGCGGCGGAAGCGG<br>AGGAGGAGGATCCGGAGGAGGGGGAAGTGGCGGCGGAGGATCTGAG<br>GTGCAGCTGCTGGAATCCGGCGGAGGCCTGGTGCAGCCTGGCGGATCT<br>CTGAGACTGTCCTGCGCCGCCTCCGGCTTCACCTTCTCCTCCCACGCCA<br>TGTCCTGGGTCCGACAGGCTCCTGGCAAAGGCCTGGAATGGGTGTCCG<br>CCATCTGGGCCTCCGGCGAGCAGTACTACGCCGACTCTGTGAAGGGCC<br>GGTTCACCATCTCCCGGGACAACTCCAAGAACACCCTGTACCTGCAGA<br>TGAACTCCCTGCGGGCCGAGGACACCGCCGTGTACTACTGTGCCAAGG<br>GCTGGCTGGGCAACTTCGACTACTGGGGCCAGGGCACCCTGGTCACCG<br>TGTCCAGCGCTAGCACCAAGGGCCCCTCCGTGTTTCCTCTGGCCCCTAG<br>CTCTAAGAGCACCAGCGGAGGAACAGCCGCCCTGGGCTGCCTCGTGAA<br>AGACTACTTCCCCGAGCCCGTGACAGTGTCTTGGAACTCTGGCGCCCT<br>GACCAGCGGCGTGCACACATTTCCAGCTGTGCTGCAGTCCAGCGGCCT<br>GTACTCTCTGAGCAGCGTCGTGACTGTGCCCAGCTCTAGCCTGGGAAC<br>CCAGACCTACATCTGCAACGTGAACCACAAGCCCAGCAACACCAAAGT<br>GGATAAGAAGGTGGAACCCAAGAGCTGCGAC | |
| DR5 (5E11)<br>VHCL<br>pETR11484 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGG<br>TCACCGTCTCGAGTGCTAGCGTGGCTGCACCATCTGTCTTCATCTTCCC<br>GCCATCTGATGAGCAGTTGAAATCTGGAACTGCCTCTGTTGTGTGCCTG<br>CTGAATAACTTCTATCCCAGAGAGGCCAAAGTACAGTGGAAGGTGGAT<br>AACGCCCTCCAATCGGGTAACTCCCAGGAGAGTGTCACAGAGCAGGA<br>CAGCAAGGACAGCACCTACAGCCTCAGCAGCACCCTGACGCTGAGCA<br>AAGCAGACTACGAGAAACACAAAGTCTACGCCTGCGAAGTCACCCAT<br>CAGGGCCTGAGCTCGCCCGTCACAAAGAGCTTCAACAGGGGAGAGTGT | 238 |
| FAP (28H1)<br>VLCL<br>pETR9366 | GAGATCGTGCTGACCCAGTCCCCCGGCACCCTGTCTCTGAGCCCTGGC<br>GAGAGAGCCACCCTGTCCTGCAGAGCCTCCCAGTCCGTGTCCCGGTCC<br>TACCTCGCCTGGTATCAGCAGAAGCCCGGCCAGGCCCCTCGGCTGCTG<br>ATCATCGGCGCCTCTACCAGAGCCACCGGCATCCCTGACCGGTTCTCC<br>GGCTCTGGCTCCGGCACCGACTTCACCCTGACCATCTCCCGGCTGGAA<br>CCCGAGGACTTCGCCGTGTACTACTGCCAGCAGGGCAGGTCATCCCT<br>CCCACCTTTGGCCAGGGCACCAAGGTGGAAATCAAGCGTACGGTGGCT<br>GCACCATCTGTCTTCATCTTCCCGCCATCTGATGAGCAGTTGAAATCTG<br>GAACTGCCTCTGTTGTGTGCCTGCTGAATAACTTCTATCCCAGAGAGGC<br>CAAAGTACAGTGGAAGGTGGATAACGCCCTCCAATCGGGTAACTCCCA<br>GGAGAGTGTCACAGAGCAGGACAGCAAGGACAGCACCTACAGCCTCA<br>GCAGCACCCTGACGCTGAGCAAAGCAGACTACGAGAAACACAAAGTC<br>TACGCCTGCGAAGTCACCCATCAGGGCCTGAGCTCGCCCGTCACAAAG<br>AGCTTCAACAGGGGAGAGTGT | 239 |
| CH1CL<br>Cross<br>DR5 (5E11)-<br>FAP (28H1)<br>pETR11828<br>2 + 2 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGG<br>TCACCGTCTCGAGTGCTAGCGTGGCCGCTCCCAGCGTGTTCATCTTCCC<br>ACCTAGCGACGAGCAGCTGAAGTCCGGACACGCCTCTGTCGTGTGCCT<br>GCTGAACAACTTCTACCCCCGCGAGGCCAAGGTGCAGTGGAAGGTGGA<br>CAATGCCCTGCAGAGCGGCAACAGCCAGGAAAGCGTGACCGAGCAGG<br>ACAGCAAGGACTCCACCTACAGCCTGAGCAGCACACTGACCCTGAGCA | 240 |

| Description | Nucleotide sequences | SEQ ID NO |
|---|---|---|
| | AGGCCGACTACGAGAAGCACAAGGTGTACGCCTGCGAAGTGACCCAC<br>CAGGGCCTGTCTAGCCCCGTGACCAAGAGCTTCAACCGGGGCGAGTGC<br>GACAAGACCCACACCTGCCCCCCTTGTCCTGCCCCTGAACTGCTGGGA<br>GGCCCTAGCGTGTTCCTGTTCCCCCCAAAGCCCAAGGACACCCTGATG<br>ATCAGCCGGACCCCTGAAGTGACCTGCGTGGTGGTGGATGTGTCCCAC<br>GAGGACCCAGAAGTGAAGTTCAATTGGTACGTGGACGGCGTGGAGGT<br>GCACAATGCCAAGACCAAGCCCCGGGAGGAACAGTACAACAGCACCT<br>ACCGGGTGGTGTCCGTGCTGACCGTGCTGCACCAGGACTGGCTGAACG<br>GCAAAGAGTACAAGTGCAAGGTCTCCAACAAGGCCCTGCCTGCCCCCA<br>TCGAGAAAACCATCAGCAAGGCCAAGGGCCAGCCCAGAGAACCCCAG<br>GTGTACACCCTGCCCCCTAGCAGAGATGAGCTGACCAAGAACCAGGTG<br>TCCCTGACCTGTCTCGTGAAAGGCTTCTACCCCTCCGATATCGCCGTGG<br>AATGGGAGAGCAACGGCCAGCCCGAGAACAACTACAAGACCACCCCC<br>CCTGTGCTGGACTCCGACGGCTCATTCTTCCTGTACTCTAAGCTGACAG<br>TGGACAAGTCCCGGTGGCAGCAGGGCAACGTGTTCTCCTGCTCCGTGA<br>TGCACGAGGCCCTGCACAACCACTACACCCAGAAGTCCCTGTCCCTGT<br>CTCCCGGGGGAGGCGGAGGATCTGGCGGAGGCGGATCCGGAGGAGGG<br>GGAAGTGGCGGCGGAGGATCTGAGGTGCAGCTGCTGGAATCCGGCGG<br>AGGCCTGGTGCAGCCTGGCGGATCTCTGAGACTGTCCTGCGCCGCCTC<br>CGGCTTCACCTTCTCCTCCCACGCCATGTCCTGGGTCCGACAGGCTCCT<br>GGCAAAGGCCTGGAATGGGTGTCCGCCATCTGGGCCTCCGGCAGCAG<br>TACTACGCCGACTCTGTGAAGGGCCGGTTCACCATCTCCCGGGACAAC<br>TCCAAGAACACCCTGTACCTGCAGATGAACTCCCTGCGGGCCGAGGAC<br>ACCGCCGTGTACTACTGTGCCAAGGGCTGGCTGGGCAACTTCGACTAC<br>TGGGGCCAGGGCACCCTGGTCACCGTGTCCAGCGCTAGCACCAAGGGC<br>CCCTCCGTGTTTCCTCTGGCCCCTAGCTCTAAGAGCACCAGCGGAGGA<br>ACAGCCGCCCTGGGCTGCCTCGTGAAAGACTACTTCCCCGAGCCCGTG<br>ACAGTGTCTTGGAACTCTGGCGCCCTGACCAGCGGCGTGCACACATTT<br>CCAGCTGTGCTGCAGTCCAGCGGCCTGTACTCTCTGAGCAGCGTCGTG<br>ACTGTGCCCAGCTCTAGCCTGGGAACCCAGACCTACATCTGCAACGTG<br>AACCACAAGCCCAGCAACACCAAAGTGGATAAGAAGGTGGAACCCAA<br>GAGCTGCGAC | |
| DR5(5E11)<br>VLCH1<br>pETR11480 | GAAATCGTGTTAACGCAGTCTCCAGGCACCCTGTCTTTGTCTCCAGGGG<br>AAAGAGCCACCCTCTCTTGCAGGGCCAGTCAGAGTGTTAGCAGCAGCT<br>ACTTAGCCTGGTACCAGCAGAAACCTGGCCAGGCTCCCAGGCTCCTCA<br>TCTATGGAGCATCCAGCAGGGCCACTGGCATCCCAGACAGGTTCAGTG<br>GCAGTGGATCCGGGACAGACTTCACTCTCACCATCAGCAGACTGGAGC<br>CTGAAGATTTTGCAGTGTATTACTGTCAGCAGGGTACTACTCATCCCAT<br>TACGTTCGGCCAGGGGACCAAAGTGGAAATCAAAGCTCCGCTAGCAC<br>CAAGGGCCCCTCCGTGTTTCCTCTGGCCCCCAGCAGCAAGAGCACCTC<br>TGGCGGAACAGCCGCCCTGGGCTGCCTGGTGAAAGACTACTTCCCCGA<br>GCCCGTGACCGTGTCCTGGAACTCTGGCGCCCTGACCAGCGGCGTGCA<br>CACCTTTCCAGCCGTGCTGCAGAGCAGCGGCCTGTACTCCCTGAGCAG<br>CGTGGTGACAGTGCCCTCCAGCAGCCTGGGCACCCAGACCTACATCTG<br>CAACGTGAACCACAAGCCCAGCAACACCAAAGTGGACAAGAAGGTGG<br>AACCCAAGAGCTGCGAC | 241 |
| DR5(18F11)-<br>FAP(28H1)<br>VHCL<br>2 + 2<br>pETR9801 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACGCGGCCGTATATTACTGTG<br>CGAAAGGGGTGCGTAAGAAGTTTGACTACTGGGGCCAAGGAACCCTG<br>GTCACCGTCTCGAGTGCTAGCACCAAGGGCCCAAGCGTGTTCCCTCTG<br>GCCCCCAGCAGCAAGAGCACAAGCGGCGGAACAGCCGCCCTGGGCTG<br>CCTGGTCAAGGACTACTTCCCCGAGCCCGTGACAGTGTCCTGGAACAG<br>CGGAGCCCTGACCAGCGGCGTGCACACCTTTCCAGCCGTGCTGCAGAG<br>CAGCGGCCTGTACAGCCTGAGCAGCGTGGTCACAGTGCCTAGCAGCAG<br>CCTGGGCACCCAGACCTACATCTGCAACGTGAACCACAAGCCCAGCAA<br>CACCAAGGTGGACAAGAAGGTGGAGCCCAAGAGCTGCGACAAGACCC<br>ACACCTGTCCCCCTTGTCCTGCCCCTGAGCTGCTGGGCGGACCCAGCGT<br>GTTCCTGTTCCCCCCAAAGCCCAAGGACACCCTGATGATCAGCCGGAC<br>CCCCGAAGTGACCTGCGTGGTGGTGGACGTGTCCCACGAGGACCCTGA<br>AGTGAAGTTCAATTGGTACGTGGACGGCGTGGAGGTGCACAATGCCAA<br>GACCAAGCCCCGGGAGGAACAGTACAACAGCACCTACCGGGTGGTGT<br>CCGTGCTGACCGTGCTGCACCAGGACTGGCTGAACGGCAAAGAGTACA<br>AGTGCAAGGTCTCCAACAAGGCCCTGCCTGCCCCCATCGAGAAAACCA<br>TCAGCAAGGCCAAGGGCCAGCCCAGAGAACCCCAGGTGTACACCCTG<br>CCCCCCAGCAGAGATGAGCTGACCAAGAACCAGGTGTCCCTGACCTGT<br>CTGGTCAAGGGCTTCTACCCCAGCGATATCGCCGTGGAGTGGGAGAGC<br>AACGGCCAGCCTGAGAACAACTACAAGACCACCCCCCCTGTGCTGGAC<br>AGCGACGGCAGCTTCTTCCTGTACTCCAAACTGACCGTGGACAAGAGC<br>CGGTGGCAGCAGGGCAACGTGTTCAGCTGCAGCGTGATGCACGAGGCC<br>CTGCACAACCACTACACCCAGAAGTCCCTGAGCCTGAGCCCCGGCAAG | 242 |

-continued

| Description | Nucleotide sequences | SEQ ID NO |
|---|---|---|
| | TCCGGAGGCGGCGGAAGCGGAGGAGGAGGATCCGGAGGAGGGGGAA GTGGCGGCGGAGGATCTGAGGTGCAGCTGCTGGAATCCGGCGGAGGC CTGGTGCAGCCTGGCGGATCTCTGAGACTGTCCTGCGCCGCCTCCGGC TTCACCTTCTCCTCCCACGCCATGTCCTGGGTCCGACAGGCTCCTGGCA AAGGGCCTGGAATGGGTGTCCGCCATCTGGGCCTCCGGCGAGCAGTACT ACGCCGACTCTGTGAAGGGCCGGTTCACCATCTCCCGGGACAACTCCA AGAACACCCTGTACCTGCAGATGAACTCCCTGCGGGCCGAGGACACCG CCGTGTACTACTGTGCCAAGGGCTGGCTGGGCAACTTCGACTACTGGG GCCAGGGCACCCTGGTCACCGTGTCCAGCGCTAGCGTGGCCGCTCCCA GCGTGTTCATCTTCCCACCCAGCGACGAGCAGCTGAAGTCCGGCACAG CCAGCGTGGTGTGCCTGCTGAACAACTTCTACCCCCGCGAGGCCAAGG TGCAGTGGAAGGTGGACAACGCCCTGCAGAGCGGCAACAGCCAGGAA TCCGTGACCGAGCAGGACAGCAAGGACTCCACCTACAGCCTGAGCAG CACCCTGACCCTGAGCAAGGCCGACTACGAGAAGCACAAGGTGTACG CCTGCGAAGTGACCCACCAGGGCCTGTCCAGCCCCGTGACCAAGAGCT TCAACCGGGGCGAGTGC | |
| DR5(18F11) LC pETR9070 | GAAATCGTGTTAACGCAGTCTCCAGGCACCCTGTCTTTGTCTCCAGGGG AAAGAGCCACCCTCTCTTGCAGGGCCAGTCAGAGTGTTAGCAGCAGCT ACTTAGCCTGGTACCAGCAGAAACCTGGCCAGGCTCCCAGGCTCCTCA TCTATGGAGCATCCAGCAGGGCCACTGGCATCCCAGACAGGTTCAGTG GCAGTGGATCCGGGACAGACTTCACTCTCACCATCAGCAGACTGGAGC CTGAAGATTTTGCAGTGTATTACTGTCAGCAGGGTCAGTTGCCTCCCAT TACGTTCGGCCAGGGGACCAAAGTGGAAATCAAACGTACGGTGGCTGC ACCATCTGTCTTCATCTTCCCGCCATCTGATGAGCAGTTGAAATCTGGA ACTGCCTCTGTTGTGTGCCTGCTGAATAACTTCTATCCCAGAGAGGCCA AAGTACAGTGGAAGGTGGATAACGCCCTCCAATCGGGTAACTCCCAGG AGAGTGTCACAGAGCAGGACAGCAAGGACAGCACCTACAGCCTCAGC AGCACCCTGACGCTGAGCAAAGCAGACTACGAGAAACACAAAGTCTA CGCCTGCGAAGTCACCCATCAGGGCCTGAGCTCGCCCGTCACAAAGAG CTTCAACAGGGGAGAGTGT | 243 |
| DR5(5E11)- FAP(28H1) Fc knob VHCL 2 + 1 pETR10427 | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC TGCAGATGAACAGCCTGAGAGCCGAGGACACGGCCGTATATTACTGTG CGAAAGGGGTGAGGGTGTCTTTTGACTACTGGGGCCAAGGAACCCTGG TCACCGTCTCGAGTGCTAGCACCAAGGGCCCAAGCGTGTTCCCTCTGG CCCCCAGCAGCAAGAGCACAAGCGGCGGAACAGCCGCCCTGGGCTGC CTGGTCAAGGACTACTTCCCCGAGCCCGTGACAGTGTCCTGGAACAGC GGAGCCCTGACCAGCGGCGTGCACACCTTTCCAGCCGTGCTGCAGAGC AGCGGCCTGTACAGCCTGAGCAGCGTGGTCACAGTGCCTAGCAGCAG CTGGGCACCCAGACCTACATCTGCAACGTGAACCACAAGCCCAGCAAC ACCAAGGTGGACAAGAAGGTGGAGCCCAAGAGCTGCGACAAGACCCA CACCTGTCCCCCTTGTCCTGCCCCTGAGCTGCTGGGCGGACCCAGCGTG TTCCTGTTCCCCCCAAAGCCCAAGGACACCCTGATGATCAGCCGGACC CCCGAAGTGACCTGCGTGGTGGTGGACGTGTCCCACGAGGACCCTGAA GTGAAGTTCAATTGGTACGTGGACGGCGTGGAGGTGCACAATGCCAAG ACCAAGCCCCGGGAGGAACAGTACAACAGCACCTACCGGGTGGTGTC CGTGCTGACCGTGCTGCACCAGGACTGGCTGAACGGCAAAGAGTACAA GTGCAAGGTCTCCAACAAGGCCCTGCCTGCCCCCATCGAGAAAACCAT CAGCAAGGCCAAGGGCCAGCCCAGAGAACCCCAGGTGTACACCCTGC CCCCCTGCAGAGATGAGCTGACCAAGAACCAGGTGTCCCTGTGGTGTC TGGTCAAGGGCTTCTACCCCAGCGATATCGCCGTGGAGTGGGAGAGCA ACGGCCAGCCTGAGAACAACTACAAGACCACCCCCCCTGTGCTGGACA GCGACGGCAGCTTCTTCCTGTACTCCAAACTGACCGTGGACAAGAGCC GGTGGCAGCAGGGCAACGTGTTCAGCTGCAGCGTGATGCACGAGGCCC TGCACAACCACTACACCCAGAAGTCCCTGAGCCTGAGCCCCGGCGGAG GCGGCGAAGCGGAGGAGGAGGATCCGGAGGAGGGGGAAGTGGCGG CGGAGGATCTGAGGTGCAGCTGCTGGAATCCGGCGGAGGCCTGGTGCA GCCTGGCGGATCTCTGAGACTGTCCTGCGCCGCCTCCGGCTTCACCTTC TCCTCCCACGCCATGTCCTGGGTCCGACAGGCTCCTGGCAAAGGCCTG GAATGGGTGTCCGCCATCTGGGCCTCCGGCGAGCAGTACTACGCCGAC TCTGTGAAGGGCCGGTTCACCATCTCCCGGGACAACTCCAAGAACACC CTGTACCTGCAGATGAACTCCCTGCGGGCCGAGGACACCGCCGTGTAC TACTGTGCCAAGGGCTGGCTGGGCAACTTCGACTACTGGGGCCAGGGC ACCCTGGTCACCGTGTCCAGCGCTAGCGTGGCCGCTCCCAGCGTGTTC ATCTTCCCACCCAGCGACGAGCAGCTGAAGTCCGGCACAGCCAGCGTG GTGTGCCTGCTGAACAACTTCTACCCCCGCGAGGCCAAGGTGCAGTGG AAGGTGGACAACGCCCTGCAGAGCGGCAACAGCCAGGAATCCGTGAC CGAGCAGGACAGCAAGGACTCCACCTACAGCCTGAGCAGCACCCTGA CCCTGAGCAAGGCCGACTACGAGAAGCACAAGGTGTACGCCTGCGAA GTGACCCACCAGGGCCTGTCCAGCCCCGTGACCAAGAGCTTCAACCGG GGCGAGTGC | 244 |

-continued

| Description | Nucleotide sequences | SEQ ID NO |
|---|---|---|
| DR5(5E11) Fc hole pETR10336 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGG<br>TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAGGTGCACAATGCCAAG<br>ACCAAGCCCCGGGAGGAACAGTACAACAGCACCTACCGGGTGGTGTC<br>CGTGCTGACCGTGCTGCACCAGGACTGGCTGAACGGCAAGAGTACAA<br>GTGCAAGGTCTCCAACAAGGCCCTGCCTGCCCCCATCGAGAAAACCAT<br>CAGCAAGGCCAAGGGCCAGCCCAGAGAACCCCAGGTGTGCACCCTGC<br>CCCCCAGCAGAGATGAGCTGACCAAGAACCAGGTGTCCCTGAGCTGTG<br>CCGTCAAGGGCTTCTACCCCAGCGATATCGCCGTGGAGTGGGAGAGCA<br>ACGGCCAGCCTGAGAACAACTACAAGACCACCCCCCCTGTGCTGGACA<br>GCGACGGCAGCTTCTTCCTGGTGTCCAAACTGACCGTGGACAAGAGCC<br>GGTGGCAGCAGGGCAACGTGTTCAGCTGCAGCGTGATGCACGAGGCCC<br>TGCACAACCACTACACCCAGAAGTCCCTGAGCCTGAGCCCCGGCAAG | 245 |
| DR5(5E11)-<br>FAP(28H1)<br>Fc knob<br>VHCL<br>3 + 1<br>pETR10427 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGG<br>TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAGGTGCACAATGCCAAG<br>ACCAAGCCCCGGGAGGAACAGTACAACAGCACCTACCGGGTGGTGTC<br>CGTGCTGACCGTGCTGCACCAGGACTGGCTGAACGGCAAGAGTACAA<br>GTGCAAGGTCTCCAACAAGGCCCTGCCTGCCCCCATCGAGAAAACCAT<br>CAGCAAGGCCAAGGGCCAGCCCAGAGAACCCCAGGTGTACACCCTGC<br>CCCCCTGCAGAGATGAGCTGACCAAGAACCAGGTGTCCTGTGGTGTC<br>TGGTCAAGGGCTTCTACCCCAGCGATATCGCCGTGGAGTGGGAGAGCA<br>ACGGCCAGCCTGAGAACAACTACAAGACCACCCCCCCTGTGCTGGACA<br>GCGACGGCAGCTTCTTCCTGTACTCCAAACTGACCGTGGACAAGAGCC<br>GGTGGCAGCAGGGCAACGTGTTCAGCTGCAGCGTGATGCACGAGGCCC<br>TGCACAACCACTACACCCAGAAGTCCCTGAGCCTGAGCCCCGGCGGAG<br>GCGGCGGAAGCGGAGGAGGAGGATCCGGAGGAGGGGAAGTGGCGG<br>CGGAGGATCTGAGGTGCAGCTGCTGGAATCCGGCGGAGGCCTGGTGCA<br>GCCTGGCGGATCTCTGAGACTGTCCTGCGCCGCCTCCGGCTTCACCTTC<br>TCCTCCCACGCCATGTCCTGGGTCCGACAGGCTCCTGGCAAAGGCCTG<br>GAATGGGTGTCCGCCATCTGGGCCTCCGGCGAGCAGTACTACGCCGAC<br>TCTGTGAAGGGCCGGTTCACCATCTCCCGGGACAACTCCAAGAACACC<br>CTGTACCTGCAGATGAACTCCCTGCGGGCCGAGGACACCGCCGTGTAC<br>TACTGTGCCAAGGGCTGGCTGGGCAACTTCGACTACTGGGGCCAGGGC<br>ACCCTGGTCACCGTGTCCAGCGCTAGCGTGGCCGCTCCCAGCGTGTTC<br>ATCTTCCCACCCAGCGACGAGCAGCTGAAGTCCGGACAGGCCGTG<br>GTGTGCCTGCTGAACAACTTCTACCCCCGCGAGGCCAAGGTGCAGTGG<br>AAGGTGGACAACGCCCTGCAGAGCGGCAACAGCCAGGAATCCGTGAC<br>CGAGCAGGACAGCAAGGACTCCACCTACAGCCTGAGCAGCACCCTGA<br>CCCTGAGCAAGGCCGACTACGAGAAGCACAAGGTGTACGCCTGCGAA<br>GTGACCCACCAGGGCCTGTCCAGCCCCGTGACCAAGAGCTTCAACCGG<br>GGCGAGTGC | 246 |

| Description | Nucleotide sequences | SEQ ID NO |
|---|---|---|
| DR5(5E11)-DR5(5E11) Fc hole pETR10429 | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC TGCAGATGAACAGCCTGAGAGCCGAGGACACGGCCGTATATTACTGTG CGAAAGGGGTGAGGGTGTCTTTTGACTACTGGGGCCAAGGAACCCTGG TCACCGTCTCGAGTGCTAGCACCAAGGGCCCAAGCGTGTTCCCTCTGG CCCCCAGCAGCAAGAGCACAAGCGGCGGAACAGCCGCCCTGGGCTGC CTGGTCAAGGACTACTTCCCCGAGCCCGTGACAGTGTCCTGGAACAGC GGGAGCCCTGACCAGCGGCGTGCACACCTTTCCAGCCGTGCTGCAGAGC AGCGGCCTGTACAGCCTGAGCAGCGTGGTCACAGTGCCTAGCAGCAGC CTGGGCACCCAGACCTACATCTGCAACGTGAACCACAAGCCCAGCAAC ACCAAGGTGGACAAGAAGGTGGAGCCCAAGAGCTGCGACAAGACCCA CACCTGTCCCCCTTGTCCTGCCCCTGAGCTGCTGGGCGGACCCAGCGTG TTCCTGTTCCCCCCAAAGCCCAAGGACACCCTGATGATCAGCCGGACC CCCGAAGTGACCTGCGTGGTGGTGGACGTGTCCCACGAGGACCCTGAA GTGAAGTTCAATTGGTACGTGGACGGCGTGGAGGTGCACAATGCCAAG ACCAAGCCCCGGGAGGAACAGTACAACAGCACCTACCGGGTGGTGTC CGTGCTGACCGTGCTGCACCAGGACTGGCTGAACGGCAAGGAGTACAA GTGCAAGGTCTCCAACAAGGCCCTGCCTGCCCCCATCGAGAAAACCAT CAGCAAGGCCAAGGGCCAGCCCAGAGAACCCCAGGTGTGCACCCTGC CCCCCAGCAGAGATGAGCTGACCAAGAACCAGGTGTCCCTGAGCTGTG CCGTCAAGGGCTTCTACCCCAGCGATATCGCCGTGGAGTGGGAGAGCA ACGGCCAGCCTGAGAACAACTACAAGACCACCCCCCCTGTGCTGGACA GCGACGGCAGCTTCTTCCTGGTGTCCAAACTGACCGTGGACAAGAGCC GGTGGCAGCAGGGCAACGTGTTCAGCTGCAGCGTGATGCACGAGGCCC TGCACAACCACTACACCCAGAAGTCCCTGAGCCTGAGCCCCGGCGGAG GCGGCGGAAGCGGAGGAGGAGGATCCGGAGGGGGAGGATCTGGCGG AGGCGGCAGCGAGGTGCAATTGTTGGAGTCTGGGGGAGGCTTGGTACA GCCTGGGGGGTCCCTGAGACTCTCCTGTGCAGCCTCCGGATTCACCTTT AGCAGTTATGCCATGAGCTGGGTCCGCCAGGCTCCAGGGAAGGGGCTG GAGTGGGTCTCAGCTATTAGTGGTAGTGGTGGTAGCACATACTACGCA GACTCCGTGAAGGGCCGGTTCACCATCTCCAGAGACAATTCCAAGAAC ACGCTGTATCTGCAGATGAACAGCCTGAGAGCCGAGGACACGGCCGTA TATTACTGTGCGAAAGGGGTGAGGGTGTCTTTTGACTACTGGGGCCAA GGAACCCTGGTCACCGTCTCGAGTGCTAGCACCAAGGGCCCCTCCGTG TTTCCTCTGGCCCCCAGCAGCAAGAGCACCTCTGGCGGAACAGCCGCC CTGGGCTGCCTGGTGAAAGACTACTTCCCCGAGCCCGTGACCGTGTCC TGGAACTCTGGCGCCCTGACCAGCGGCGTGCACACCTTTCCAGCCGTG CTGCAGAGCAGCGGCCTGTACTCCCTGAGCAGCGTGGTGACAGTGCCC TCCAGCAGCCTGGGCACCCAGACCTACATCTGCAACGTGAACCACAAG CCCAGCAACACCAAAGTGGACAAGAAGGTGGAACCCAAGAGCTGCGA C | 247 |
| DR5(5E11)_Fc knob Fab-Fab Head-to-tail 2 + 1 pETR10662 | GAGGTGCAATTGTTGGAGTCTGGGGGAGGCTTGGTACAGCCTGGGGGG TCCCTGAGACTCTCCTGTGCAGCCTCCGGATTCACCTTTAGCAGTTATG CCATGAGCTGGGTCCGCCAGGCTCCAGGGAAGGGGCTGGAGTGGGTCT CAGCTATTAGTGGTAGTGGTGGTAGCACATACTACGCAGACTCCGTGA AGGGCCGGTTCACCATCTCCAGAGACAATTCCAAGAACACGCTGTATC TGCAGATGAACAGCCTGAGAGCCGAGGACACGGCCGTATATTACTGTG CGAAAGGGGTGAGGGTGTCTTTTGACTACTGGGGCCAAGGAACCCTGG TCACCGTCTCGAGTGCTAGCACCAAGGGCCCATCGGTCTTCCCCCTGG CACCCTCCTCCAAGAGCACCTCTGGGGGCACAGCGGCCCTGGGCTGCC TGGTCAAGGACTACTTCCCCGAACCGGTGACGGTGTCGTGGAACTCAG GCGCCCTGACCAGCGGCGTGCACACCTTCCCGGCTGTCCTACAGTCCT CAGGACTCTACTCCCTCAGCAGCGTGGTGACCGTGCCCTCCAGCAGCT TGGGCACCCAGACCTACATCTGCAACGTGAATCACAAGCCCAGCAACA CCAAGGTGGACAAGAAAGTTGAGCCCAAATCTTGTGGAGGCGGAGGA TCCGGCGGAGGCGGATCTGAGGTGCAATTGTTGGAGTCTGGGGGAGGC TTGGTACAGCCTGGGGGGTCCCTGAGACTCTCCTGTGCAGCCTCCGGA TTCACCTTTAGCAGTTATGCCATGAGCTGGGTCCGCCAGGCTCCAGGG AAGGGGCTGGAGTGGGTCTCAGCTATTAGTGGTAGTGGTGGTAGCACA TACTACGCAGACTCCGTGAAGGGCCGGTTCACCATCTCCAGAGACAAT TCCAAGAACACGCTGTATCTGCAGATGAACAGCCTGAGAGCCGAGGAC ACGGCCGTATATTACTGTGCGAAAGGGGTGAGGGTGTCTTTTGACTAC TGGGGCCAAGGAACCCTGGTCACCGTCTCGAGTGCTAGCACCAAGGGC CCAAGCGTGTTCCCTCTGGCCCCCAGCAGCAAGAGCACAAGCGGCGGA ACAGCCGCCCTGGGCTGCCTGGTCAAGGACTACTTCCCCGAGCCCGTG ACAGTGTCCTGGAACAGCGGGAGCCCTGACCAGCGGCGTGCACACCTTT CCAGCCGTGCTGCAGAGCAGCGGCCTGTACAGCCTGAGCAGCGTGGTC ACAGTGCCTAGCAGCAGCCTGGGCACCCAGACCTACATCTGCAACGTG AACCACAAGCCCAGCAACACCAAGGTGGACAAGAAGGTGGAGCCCAA GAGCTGCGACAAGACCCACACCTGTCCCCCTTGTCCTGCCCCTGAGCT GCTGGGCGGACCCAGCGTGTTCCTGTTCCCCCCAAAGCCCAAGGACAC | 248 |

| Description | Nucleotide sequences | SEQ ID NO |
|---|---|---|
| | CCTGATGATCAGCCGGACCCCCGAAGTGACCTGCGTGGTGGTGGACGT<br>GTCCCACGAGGACCCTGAAGTGAAGTTCAATTGGTACGTGGACGGCGT<br>GGAAGTGCACAATGCCAAGACCAAGCCGCGGGAGGAGCAGTACAACA<br>GCACGTACCGTGTGGTCAGCGTCCTCACCGTCCTGCACCAGGACTGGC<br>TGAATGGCAAGGAGTACAAGTGCAAGGTCTCCAACAAAGCCCTCCCAG<br>CCCCCATCGAGAAAACCATCTCCAAAGCCAAAGGGCAGCCCCGAGAA<br>CCACAGGTGTACACCCTGCCCCCATGCCGGGATGAGCTGACCAAGAAC<br>CAGGTCAGCCTGTGGTGCCTGGTCAAAGGCTTCTATCCCAGCGACATC<br>GCCGTGGAGTGGGAGAGCAATGGGCAGCCGGAGAACAACTACAAGAC<br>CACGCCTCCCGTGCTGGACTCCGACGGCTCCTTCTTCCTCTACAGCAAG<br>CTCACCGTGGACAAGAGCAGGTGGCAGCAGGGGAACGTCTTCTCATGC<br>TCCGTGATGCATGAGGCTCTGCACAACCACTACACGCAGAAGAGCCTC<br>TCCCTGTCTCCGGGTAAA | |
| FAP<br>(28H1)_Fc<br>hole<br>VHCL<br>Cross<br>pETR10130 | GAAGTGCAGCTGCTGGAATCCGGCGGAGGCCTGGTGCAGCCTGGCGG<br>ATCTCTGAGACTGTCCTGCGCCGCCTCCGGCTTCACCTTCTCCTCCCAC<br>GCCATGTCCTGGGTCCGACAGGCTCCTGGCAAAGGCCTGGAATGGGTG<br>TCCGCCATCTGGGCCTCCGGCGAGCAGTACTACGCCGACTCTGTGAAG<br>GGCCGGTTCACCATCTCCCGGGACAACTCCAAGAACACCCTGTACCTG<br>CAGATGAACTCCCTGCGGGCCGAGGACACCGCCGTGTACTACTGTGCC<br>AAGGGCTGGTGGCAACTTCGACTACTGGGGACAGGGCACCCTGGTC<br>ACCGTGTCCAGCGCTAGCGTGGCCGCTCCCAGCGTGTTCATCTTCCCAC<br>CCAGCGACGAGCAGCTGAAGTCCGGCACAGCCAGCGTGGTGTGCCTGC<br>TGAACAACTTCTACCCCCGCGAGGCCAAGGTGCAGTGGAAGGTGGACA<br>ACGCCCTGCAGAGCGGCAACAGCCAGGAATCCGTGACCGAGCAGGAC<br>AGCAAGGACTCCACCTACAGCCTGAGCAGCACCCTGACCCTGAGCAAG<br>GCCGACTACGAGAAGCACAAGGTGTACGCCTGCGAAGTGACCCACCA<br>GGGCCTGTCCAGCCCCGTGACCAAGAGCTTCAACCGGGGCGAGTGCGA<br>CAAGACCCACACCTGTCCCCCTTGCCCTGCCCCTGAACTGCTGGGTGG<br>CCCCTTCCGTGTTCCTGTTCCCCCCAAAGCCCAAGGACACCCTGATGATC<br>AGCCGGACCCCCGAAGTGACCTGCGTGGTGGTGGACGTGTCCCACGAG<br>GACCCTGAAGTGAAGTTCAATTGGTACGTGGACGGCGTGGAGGTGCAC<br>AATGCCAAGACCAAGCCCCGGGAGGAACAGTACAACAGCACCTACCG<br>GGTGGTGTCCGTGCTGACCGTGCTGCACCAGGACTGGCTGAACGGCAA<br>AGAGTACAAGTGCAAGGTCTCCAACAAGGCCCTGCCTGCCCCCATCGA<br>GAAAACCATCAGCAAGGCCAAGGGCCAGCCCAGAGAACCCCAGGTGT<br>GCACCCTGCCCCCCAGCAGAGATGAGCTGACCAAGAACCAGGTGTCCC<br>TGAGCTGTGCCGTCAAGGGCTTCTACCCCAGCGATATCGCCGTGGAGT<br>GGGAGAGCAACGGCCAGCCTGAGAACAACTACAAGACCACCCCCCCT<br>GTGCTGGACAGCGACGGCAGCTTCTTCCTGGTGTCCAAACTGACCGTG<br>GACAAGAGCCGGTGGCAGCAGGGCAACGTGTTCAGCTGCAGCGTGAT<br>GCACGAGGCCCTGCACAACCACTACACCCAGAAGTCCCTGAGCCTGAG<br>CCCCGGCAAG | 249 |
| DR5(18F11)-<br>FAP(28H1)<br>Fc knob<br>VHCL<br>2 + 1<br>pETR9807 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACGCGGCCGTATATTACTGTG<br>CGAAAGGGGTGCGTAAGAAGTTTGACTACTGGGGCCAAGGAACCCTG<br>GTCACCGTCTCGAGTGCTAGCACCAAGGGCCCATCGGTCTTCCCTCTG<br>GCCCCCAGCAGCAAGAGCACAAGCGGCGGAACAGCCGCCCTGGGCTG<br>CCTGGTCAAGGACTACTTCCCCGAGCCCGTGACAGTGTCCTGGAACAG<br>CGGAGCCCTGACCAGCGGCGTGCACACCTTTCCAGCCGTGCTGCAGAG<br>CAGCGGCCTGTACAGCCTGAGCAGCGTGGTCACAGTGCCTAGCAGCAG<br>CCTGGGCACCCAGACCTACATCTGCAACGTGAACCACAAGCCCAGCAA<br>CACCAAGGTGGACAAGAAGGTGGAGCCCAAGAGCTGCGACAAGACCC<br>ACACCTGTCCCCCTTGTCCTGCCCCTGAGCTGCTGGGCGGACCCAGCGT<br>GTTCCTGTTCCCCCCAAAGCCCAAGGACACCCTGATGATCAGCCGGAC<br>CCCCGAAGTGACCTGCGTGGTGGTGGACGTGTCCCACGAGGACCCTGA<br>AGTGAAGTTCAATTGGTACGTGGACGGCGTGGAGGTGCACAATGCCAA<br>GACCAAGCCCCGGGAGGAACAGTACAACAGCACCTACCGGGTGGTGT<br>CCGTGCTGACCGTGCTGCACCAGGACTGGCTGAACGGCAAAGAGTACA<br>AGTGCAAGGTCTCCAACAAGGCCCTGCCTGCCCCCATCGAGAAAACCA<br>TCAGCAAGGCCAAGGGCCAGCCCAGAGAACCCCAGGTGTACACCCTG<br>CCCCCCTGCAGAGATGAGCTGACCAAGAACCAGGTGTCCCTGTGGTGT<br>CTGGTCAAGGGCTTCTACCCCAGCGATATCGCCGTGGAGTGGGAGAGC<br>AACGGCCAGCCTGAGAACAACTACAAGACCACCCCCCCTGTGCTGGAC<br>AGCGACGGCAGCTTCTTCCTGTACTCCAAACTGACCGTGGACAAGAGC<br>CGGTGGCAGCAGGGCAACGTGTTCAGCTGCAGCGTGATGCACGAGGCC<br>CTGCACAACCACTACACCCAGAAGTCCCTGAGCCTGAGCCCCGGCAAG<br>TCCGAGGCGGCGGAAGCGAGGAGGAGGATCCGAGGAGGGGGAA<br>GTGGCGGCGGAGGATCTGAGGTGCAGCTGCTGGAATCCGGCGGAGGC<br>CTGGTGCAGCCTGGCGGATCTCTGAGACTGTCCTGCGCCGCCTCCGGC<br>TTCACCTTCTCCTCCCACGCCATGTCCTGGGTCCGACAGGCTCCTGGCA | 250 |

| Description | Nucleotide sequences | SEQ ID NO |
|---|---|---|
| | AAGGCCTGGAATGGGTGTCCGCCATCTGGGCCTCCGGCGAGCAGTACT<br>ACGCCGACTCTGTGAAGGGCCGGTTCACCATCTCCCGGGACAACTCCA<br>AGAACACCCTGTACCTGCAGATGAACTCCCTGCGGGCCGAGGACACCG<br>CCGTGTACTACTGTGCCAAGGGCTGGCTGGGCAACTTCGACTACTGGG<br>GCCAGGGCACCCTGGTCACCGTGTCCAGCGCTAGCGTGGCCGCTCCCA<br>GCGTGTTCATCTTCCCACCCAGCGACGAGCAGCTGAAGTCCGGCACAG<br>CCAGCGTGGTGTGCCTGCTGAACAACTTCTACCCCCGCGAGGCCAAGG<br>TGCAGTGGAAGGTGGACAACGCCCTGCAGAGCGGCAACAGCCAGGAA<br>TCCGTGACCGAGCAGGACAGCAAGGACTCCACCTACAGCCTGAGCAG<br>CACCCTGACCCTGAGCAAGGCCGACTACGAGAAGCACAAGGTGTACG<br>CCTGCGAAGTGACCCACCAGGGCCTGTCCAGCCCCGTGACCAAGAGCT<br>TCAACCGGGGCGAGTGC | |
| DR5(18F11) Fc hole pETR9808 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACGCGGCCGTATATTACTGTG<br>CGAAAGGGGTGCGTAAGAAGTTTGACTACTGGGGCCAAGGAACCCTG<br>GTCACCGTCTCGAGTGCTAGCACCAAGGGCCCAAGCGTGTTCCCTCTG<br>GCCCCCAGCAGCAAGAGCACAAGCGGCGGAACAGCCGCCCTGGGCTG<br>CCTGGTCAAGGACTACTTCCCCGAGCCCGTGACAGTGTCCTGGAACAG<br>CGGAGCCCTGACCAGCGGCGTGCACACCTTTCCAGCCGTGCTGCAGAG<br>CAGCGGCCTGTACAGCCTGAGCAGCGTGGTCACAGTGCCTAGCAGCAG<br>CCTGGGCACCCAGACCTACATCTGCAACGTGAACCACAAGCCCAGCAA<br>CACCAAGGTGGACAAGAAGGTGGAGCCCAAGAGCTGCGACAAGACCC<br>ACACCTGTCCCCCTTGTCCTGCCCCTGAGCTGCTGGGCGGACCCAGCGT<br>GTTCCTGTTCCCCCCAAAGCCCAAGGACACCCTGATGATCAGCCGGAC<br>CCCCGAAGTGACCTGCGTGGTGGTGGACGTGTCCCACGAGGACCCTGA<br>AGTGAAGTTCAATTGGTACGTGGACGGCGTGGAGGTGCACAATGCCAA<br>GACCAAGCCCCGGGAGGAACAGTACAACAGCACCTACCGGGTGGTGT<br>CCGTGCTGACCGTGCTGCACCAGGACTGGCTGAACGGCAAAGAGTACA<br>AGTGCAAGGTCTCCAACAAGGCCCTGCCTGCCCCCATCGAGAAAACCA<br>TCAGCAAGGCCAAGGGCCAGCCCAGAGAACCCCAGGTGTGCACCCTG<br>CCCCCCAGCAGAGATGAGCTGACCAAGAACCAGGTGTCCCTGAGCTGT<br>GCCGTCAAGGGCTTCTACCCCAGCGATATCGCCGTGGAGTGGGAGAGC<br>AACGGCCAGCCTGAGAACAACTACAAGACCACCCCCCCTGTGCTGGAC<br>AGCGACGGCAGCTTCTTCCTGGTGTCCAAACTGACCGTGGACAAGAGC<br>CGGTGGCAGCAGGGCAACGTGTTCAGCTGCAGCGTGATGCACGAGGCC<br>CTGCACAACCACTACACCCAGAAGTCCCTGAGCCTGAGCCCCGGCAAG | 251 |
| DR5(18F11)-<br>FAP(28H1)<br>VHCL<br>Fc knob<br>3 + 1<br>pETR10333 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACGCGGCCGTATATTACTGTG<br>CGAAAGGGGTGCGTAAGAAGTTTGACTACTGGGGCCAAGGAACCCTG<br>GTCACCGTCTCGAGTGCTAGCACCAAGGGCCCAAGCGTGTTCCCTCTG<br>GCCCCCAGCAGCAAGAGCACAAGCGGCGGAACAGCCGCCCTGGGCTG<br>CCTGGTCAAGGACTACTTCCCCGAGCCCGTGACAGTGTCCTGGAACAG<br>CGGAGCCCTGACCAGCGGCGTGCACACCTTTCCAGCCGTGCTGCAGAG<br>CAGCGGCCTGTACAGCCTGAGCAGCGTGGTCACAGTGCCTAGCAGCAG<br>CCTGGGCACCCAGACCTACATCTGCAACGTGAACCACAAGCCCAGCAA<br>CACCAAGGTGGACAAGAAGGTGGAGCCCAAGAGCTGCGACAAGACCC<br>ACACCTGTCCCCCTTGTCCTGCCCCTGAGCTGCTGGGCGGACCCAGCGT<br>GTTCCTGTTCCCCCCAAAGCCCAAGGACACCCTGATGATCAGCCGGAC<br>CCCCGAAGTGACCTGCGTGGTGGTGGACGTGTCCCACGAGGACCCTGA<br>AGTGAAGTTCAATTGGTACGTGGACGGCGTGGAGGTGCACAATGCCAA<br>GACCAAGCCCCGGGAGGAACAGTACAACAGCACCTACCGGGTGGTGT<br>CCGTGCTGACCGTGCTGCACCAGGACTGGCTGAACGGCAAAGAGTACA<br>AGTGCAAGGTCTCCAACAAGGCCCTGCCTGCCCCCATCGAGAAAACCA<br>TCAGCAAGGCCAAGGGCCAGCCCAGAGAACCCCAGGTGTACACCCTG<br>CCCCCCTGCAGAGATGAGCTGACCAAGAACCAGGTGTCCCTGTGGTGT<br>CTGGTCAAGGGCTTCTACCCCAGCGATATCGCCGTGGAGTGGGAGAGC<br>AACGGCCAGCCTGAGAACAACTACAAGACCACCCCCCCTGTGCTGGAC<br>AGCGACGGCAGCTTCTTCCTGTACTCCAAACTGACCGTGGACAAGAGC<br>CGGTGGCAGCAGGGCAACGTGTTCAGCTGCAGCGTGATGCACGAGGCC<br>CTGCACAACCACTACACCCAGAAGTCCCTGAGCCTGAGCCCCGGCGGA<br>GGCGGCGGAAGCGGAGGAGGAGGATCCGGAGGAGGGGAAGTGGCG<br>GCGGAGGATCTGAGGTGCAGCTGCTGGAATCCGGCGGAGGCCTGGTGC<br>AGCCTGGCGGATCTCTGAGACTGTCCTGCGCCGCCTCCGGCTTCACCTT<br>CTCCTCCCACGCCATGTCCTGGGTCCGACAGGCTCCTGGCAAAGGCCT<br>GGAATGGGTGTCCGCCATCTGGGCCTCCGGCGAGCAGTACTACGCCGA<br>CTCTGTGAAGGGCCGGTTCACCATCTCCCGGGACAACTCCAAGAACAC | 252 |

| Description | Nucleotide sequences | SEQ ID NO |
|---|---|---|
| | CCTGTACCTGCAGATGAACTCCCTGCGGGCCGAGGACACCGCCGTGTA<br>CTACTGTGCCAAGGGCTGGCTGGGCAACTTCGACTACTGGGGCCAGGG<br>CACCCTGGTCACCGTGTCCAGCGCTAGCGTGGCCGCTCCCAGCGTGTT<br>CATCTTCCCACCCAGCGACGAGCAGCTGAAGTCCGGCACAGCCAGCGT<br>GGTGTGCCTGCTGAACAACTTCTACCCCCGCGAGGCCAAGGTGCAGTG<br>GAAGGTGGACAACGCCCTGCAGAGCGGCAACAGCCAGGAATCCGTGA<br>CCGAGCAGGACAGCAAGGACTCCACCTACAGCCTGAGCAGCACCCTG<br>ACCCTGAGCAAGGCCGACTACGAGAAGCACAAGGTGTACGCCTGCGA<br>AGTGACCCACCAGGGCCTGTCCAGCCCCGTGACCAAGAGCTTCAACCG<br>GGGCGAGTGC | |
| DR5(18F11)-<br>DR5(18F11)<br>Fc hole<br>pETR10288 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACGCGGCCGTATATTACTGTG<br>CGAAAGGGGTGCGTAAGAAGTTTGACTACTGGGGCCAAGGAACCCTG<br>GTCACCGTCTCGAGTGCTAGCACCAAGGGCCCAAGCGTGTTCCCTCTG<br>GCCCCCAGCAGCAAGAGCACAAGCGGCGGAACAGCCGCCCTGGGCTG<br>CCTGGTCAAGGACTACTTCCCCGAGCCCGTGACAGTGTCCTGGAACAG<br>CGGAGCCCTGACCAGCGGCGTGCACACCTTTCCAGCCGTGCTGCAGAG<br>CAGCGGCCTGTACAGCCTGAGCAGCGTGGTCACAGTGCCTAGCAGCAG<br>CCTGGGCACCCAGACCTACATCTGCAACGTGAACCACAAGCCCAGCAA<br>CACCAAGGTGGACAAGAAGGTGGAGCCCAAGAGCTGCGACAAGACCC<br>ACACCTGTCCCCCTTGTCCTGCCCCTGAGCTGCTGGGCGGACCCAGCGT<br>GTTCCTGTTCCCCCCAAAGCCCAAGGACACCCTGATGATCAGCCGGAC<br>CCCCGAAGTGACCTGCGTGGTGGTGGACGTGTCCCACGAGGACCCTGA<br>AGTGAAGTTCAATTGGTACGTGGACGGCGTGGAGGTGCACAATGCCAA<br>GACCAAGCCCCGGGAGGAACAGTACAACAGCACCTACCGGGTGGTGT<br>CCGTGCTGACCGTGCTGCACCAGGACTGGCTGAACGGCAAAGAGTACA<br>AGTGCAAGGTCTCCAACAAGGCCCTGCCTGCCCCCATCGAGAAAACCA<br>TCAGCAAGGCCAAGGGCCAGCCCAGAGAACCCCAGGTGTGCACCCTG<br>CCCCCCAGCAGAGATGAGCTGACCAAGAACCAGGTGTCCCTGAGCTGT<br>GCCGTCAAGGGCTTCTACCCCAGCGATATCGCCGTGGAGTGGGAGAGC<br>AACGGCCAGCCTGAGAACAACTACAAGACCACCCCCCCTGTGCTGGAC<br>AGCGACGGCAGCTTCTTCCTGGTGTCCAAACTGACCGTGGACAAGAGC<br>CGGTGGCAGCAGGGCAACGTGTTCAGCTGCAGCGTGATGCACGAGGCC<br>CTGCACAACCACTACACCCAGAAGTCCCTGAGCCTGAGCCCCGGCGGA<br>GGCGGCGGAAGCGGAGGAGGAGGATCCGGAGGGGGAGGATCTGGCG<br>GAGGCGGCAGCGAGGTGCAATTGTTGGAGTCTGGGGGAGGCTTGGTAC<br>AGCCTGGGGGGTCCCTGAGACTCTCCTGTGCAGCCTCCGGATTCACCTT<br>TAGCAGTTATGCCATGAGCTGGGTCCGCCAGGCTCCAGGGAAGGGGCT<br>GGAGTGGGTCTCAGCTATTAGTGGTAGTGGTGGTAGCACATACTACGC<br>AGACTCCGTGAAGGGCCGGTTCACCATCTCCAGAGACAATTCCAAGAA<br>CACGCTGTATCTGCAGATGAACAGCCTGAGAGCCGAGGACGCGGCCGT<br>ATATTACTGTGCGAAAGGGGTGCGTAAGAAGTTTGACTACTGGGGCCA<br>AGGAACCCTGGTCACCGTCTCGAGTGCTAGCACCAAGGGCCCCTCCGT<br>GTTTCCTCTGGCCCCCAGCAGCAAGAGCACCTCTGGCGGAACAGCCGC<br>CCTGGGCTGCCTGGTGAAAGACTACTTCCCCGAGCCCGTGACCGTGTC<br>CTGGAACTCTGGCGCCCTGACCAGCGGCGTGCACACCTTTCCAGCCGT<br>GCTGCAGAGCAGCGGCCTGTACTCCCTGAGCAGCGTGGTGACAGTGCC<br>CTCCAGCAGCCTGGGCACCCAGACCTACATCTGCAACGTGAACCACAA<br>GCCCAGCAACACCAAAGTGGACAAGAAGGTGGAACCCAAGAGCTGCG<br>AC | 253 |
| hu Fc_wt | GCTAGCACCAAGGGCCCATCGGTCTTCCCCCTGGCACCCTCCTCCAAG<br>AGCACCTCTGGGGGCACAGCGGCCCTGGGCTGCCTGGTCAAGGACTAC<br>TTCCCCGAACCGGTGACGGTGTCGTGGAACTCAGGCGCCCTGACCAGC<br>GGCGTGCACACCTTCCCGGCTGTCCTACAGTCCTCAGGACTCTACTCCC<br>TCAGCAGCGTGGTGACCGTGCCCTCCAGCAGCTTGGGCACCCAGACCT<br>ACATCTGCAACGTGAATCACAAGCCCAGCAACACCAAGGTGGACAAG<br>AAAGTTGAGCCCAAATCTTGTGACAAAACTCACACATGCCCACCGTGC<br>CCAGCACCTGAACTCCTGGGGGGACCGTCAGTCTTCCTCTTCCCCCCAA<br>AACCCAAGGACACCCTCATGATCTCCCGGACCCCTGAGGTCACATGCG<br>TGGTGGTGGACGTGAGCCACGAAGACCCTGAGGTCAAGTTCAACTGGT<br>ACGTGGACGGCGTGGAGGTGCATAATGCCAAGACAAAGCCGCGGGAG<br>GAGCAGTACAACAGCACGTACCGTGTGGTCAGCGTCCTCACCGTCCTG<br>CACCAGGACTGGCTGAATGGCAAGGAGTACAAGTGCAAGGTCTCCAA<br>CAAAGCCCTCCCAGCCCCCATCGAGAAAACCATCTCCAAAGCCAAAGG<br>GCAGCCCCGAGAACCACAGGTGTACACCCTGCCCCCATCCCGGGATGA<br>GCTGACCAAGAACCAGGTCAGCCTGACCTGCCTGGTCAAAGGCTTCTA<br>TCCCAGCGACATCGCCGTGGAGTGGGAGAGCAATGGGCAGCCGGAGA<br>ACAACTACAAGACCACGCCTCCCGTGCTGGACTCCGACGGCTCCTTCT<br>TCCTCTACAGCAAGCTCACCGTGGACAAGAGCAGGTGGCAGCAGGGG | 254 |

US 11,214,622 B2

229                                                                                    230
-continued

| Description | Nucleotide sequences | SEQ ID NO |
|---|---|---|
| | AACGTCTTCTCATGCTCCGTGATGCATGAGGCTCTGCACAACCACTACA<br>CGCAGAAGAGCCTCTCCCTGTCTCCGGGTAAA | |
| hu<br>Fc_P329G/<br>LALA | GCTAGCACCAAGGGCCCATCCGTGTTCCCTCTGGCCCCTTCCAGCAAG<br>TCTACCTCTGGCGGCACAGCCGCTCTGGGCTGCCTCGTGAAGGACTAC<br>TTCCCCGAGCCTGTGACAGTGTCCTGGAACTCTGGCGCCCTGACATCC<br>GGCGTGCACACCTTTCCAGCTGTGCTGCAGTCCTCCGGCCTGTACTCC<br>CTGTCCTCCGTCGTGACAGTGCCCTCCAGCTCTCTGGGCACCCAGACCTA<br>CATCTGCAACGTGAACCACAAGCCCTCCAACACCAAGGTGGACAAGA<br>AGGTGGAACCCAAGTCCTGCGACAAGACCCACACCTGTCCCCCTTGTC<br>CTGCCCCTGAAGCTGCTGGCGGCCCTAGCGTGTTCCTGTTCCCCCCAAA<br>GCCCAAGGACACCCTGATGATCTCCCGGACCCCCGAAGTGACCTGCGT<br>GGTGGTGGATGTGTCCCACGAGGACCCTGAAGTGAAGTTCAATTGGTA<br>CGTGGACGGCGTGGAAGTGCACAATGCCAAGACCAAGCCTAGAGAGG<br>AACAGTACAACTCCACCTACCGGGTGGTGTCCGTGCTGACCGTGCTGC<br>ACCAGGATTGGCTGAACGGCAAAGAGTACAAGTGCAAGGTGTCCAAC<br>AAGGCCCTGGGAGCCCCCATCGAAAAGACCATCTCCAAGGCCAAGGG<br>CCAGCCTCGCGAGCCTCAGGTGTACACCCTGCCCCCTAGCAGAGATGA<br>GCTGACCAAGAACCAGGTGTCCCTGACCTGTCTCGTGAAAGGCTTCTA<br>CCCCTCCGATATCGCCGTGGAATGGGAGAGCAACGGCCAGCCCGAGA<br>CAACTACAAGACCACCCCCCCTGTGCTGGACTCCGACGGCTCATTCT<br>TCCTGTACTCTAAGCTGACAGTGGACAAGTCCCGGTGGCAGCAGGGCA<br>ACGTGTTCTCCTGCTCCGTGATGCACGAGGCCCTGCACAACCACTACA<br>CCCAGAAGTCCCTGTCCCTGTCTCCCGGGAAA | 255 |
| hu kappa<br>light chain | CGTACGGTGGCTGCACCATCTGTCTTCATCTTCCCGCCATCTGATGAGC<br>AGTTGAAATCTGGAACTGCCTCTGTTGTGTGCCTGCTGAATAACTTCTA<br>TCCCAGAGAGGCCAAAGTACAGTGGAAGGTGGATAACGCCCTCCAATC<br>GGGTAACTCCCAGGAGAGTGTCACAGAGCAGGACAGCAAGGACAGCA<br>CCTACAGCCTCAGCAGCACCCTGACGCTGAGCAAAGCAGACTACGAG<br>AAACACAAAGTCTACGCCTGCGAAGTCACCCATCAGGGCCTGAGCTCG<br>CCCGTCACAAAGAGCTTCAACAGGGGAGAGTGT | 256 |
| hu lambda<br>light chain | GGTCAGCCCAAAGCCGCCCCTAGCGTGACCCTGTTCCCCCCAAGCAGC<br>GAGGAACTGCAGGCCAACAAGGCCACCCTGGTGTGCCTGATCAGCGA<br>CTTCTACCCTGGCGCCGTGACAGTGGCCTGGAAGGCCGACTCTAGCCC<br>TGTGAAGGCCGGCGTGGAGACAACCACCCCCAGCAAGCAGAGCAACA<br>ACAAGTACGCCGCCAGCAGCTACCTGAGCCTGACCCCCGAGCAGTGGA<br>AGTCCCACCGGTCCTACAGCTGCCAGGTGACACACGAGGGCAGCACCG<br>TGGAGAAAACCGTGGCCCCCACCGAGTGCAGC | 257 |
| 28H1_Fc<br>hole<br>VHCL<br>pETR10130 | GAAGTGCAGCTGCTGGAATCCGGCGGAGGCCTGGTGCAGCCTGGCGG<br>ATCTCTGAGACTGTCCTGCGCCGCCTCCGGCTTCACCTTCTCCTCCCAC<br>GCCATGTCCTGGGTCCGACAGGCTCCTGGCAAAGGCCTGGAATGGGTG<br>TCCGCCATCTGGGCCTCCGGCGAGCAGTACTACGCCGACTCTGTGAAG<br>GGCCGGTTCACCATCTCCCGGGACAACTCCAAGAACACCCTGTACCTG<br>CAGATGAACTCCCTGCGGGCCGAGGACACCGCCGTGTACTACTGTGCC<br>AAGGGCTGGCTGGGCAACTTCGACTACTGGGGACAGGGCACCCTGGTC<br>ACCGTGTCCAGCGCTAGCGTGGCCGCTCCCAGCGTGTTCATCTTCCCAC<br>CCAGCGACGAGCAGCTGAAGTCCGGCACAGCCAGCGTGGTGTGCCTGC<br>TGAACAACTTCTACCCCCGCGAGGCCAAGGTGCAGTGGAAGGTGGACA<br>ACGCCCTGCAGAGCGGCAACAGCCAGGAATCCGTGACCGAGCAGGAC<br>AGCAAGGACTCCACCTACAGCCTGAGCAGCACCCTGACCCTGAGCAAG<br>GCCGACTACGAGAAGCACAAGGTGTACGCCTGCGAAGTGACCCACCA<br>GGGCCTGTCCAGCCCCGTGACCAAGAGCTTCAACCGGGGCGAGTGCGA<br>CAAGACCCACACCTGTCCCCCTTGCCCTGCCCCTGAACTGCTGGGTGG<br>CCCTTCCGTGTTCCTGTTCCCCCCAAAGCCCAAGGACACCCTGATGATC<br>AGCCGGACCCCCGAAGTGACCTGCGTGGTGGTCGATGTGTCCCACGAG<br>GACCCTGAAGTGAAGTTCAATTGGTACGTGGACGGCGTGGAGGTGCAC<br>AATGCCAAGACCAAGCCCCGGGAGGAACAGTACAACAGCACCTACCG<br>GGTGGTGTCCGTGCTGACCGTGCTGCACCAGGACTGGCTGAACGGCAA<br>AGAGTACAAGTGCAAGGTCTCCAACAAGGCCCTGCCTGCCCCCATCGA<br>GAAAACCATCAGCAAGGCCAAGGGCCAGCCCAGAGAACCCCCAGGTGT<br>GCACCCTGCCCCCAGCAGAGATGAGCTGACCAAGAACCAGGTGTCCC<br>TGAGCTGTGCCGTCAAGGGCTTCTACCCCAGCGATATCGCCGTGGAGT<br>GGGAGAGCAACGGCCAGCCTGAGAACAACTACAAGACCACCCCCCCT<br>GTGCTGGACAGCGACGGCAGCTTCTTCCTGGTGTCCAAACTGACCGTG<br>GACAAGAGCCGGTGGCAGCAGGGCAACGTGTTCAGCTGCAGCGTGAT<br>GCACGAGGCCCTGCACAACCACTACACCCAGAAGTCCCTGAGCCTGAG<br>CCCCGGCAAG | 258 |
| 28H1<br>VLCH1<br>pETR9537 | GAGATCGTGCTGACCCAGTCTCCCGGCACCCTGAGCCTGAGCCCTGGC<br>GAGAGAGCCACCCTGAGCTGCAGAGCCAGCCAGAGCGTGAGCCGGAG<br>CTACCTGGCCTGGTATCAGCAGAAGCCCGGCCAGGCCCCCAGACTGCT<br>GATCATCGGCGCCAGCACCCGGGCCACCGGCATCCCCGATAGATTCAG<br>CGGCAGCGGCTCCGGCACCGACTTCACCCTGACCATCAGCCGGCTGGA | 259 |

| Description | Nucleotide sequences | SEQ ID NO |
|---|---|---|
| | ACCCGAGGACTTCGCCGTGTACTACTGCCAGCAGGGCCAGGTGATCCC<br>CCCCACCTTCGGCCAGGGCACCAAGGTGGAAATCAAGAGCTCCGCTAG<br>CACCAAGGGCCCCTCCGTGTTTCCTCTGGCCCCCAGCAGCAAGAGCAC<br>CTCTGGCGGAACAGCCGCCCTGGGCTGCCTGGTGAAAGACTACTTCCC<br>CGAGCCCGTGACCGTGTCCTGGAACTCTGGCGCCCTGACCAGCGGCGT<br>GCACACCTTTCCAGCCGTGCTGCAGAGCAGCGGCCTGTACTCCCTGAG<br>CAGCGTGGTGACAGTGCCCTCCAGCAGCCTGGGCACCCAGACCTACAT<br>CTGCAACGTGAACCACAAGCCCAGCAACACCAAAGTGGACAAGAAGG<br>TGGAACCCAAGAGCTGCGAC | |
| 5E11_4B9<br>VHCL<br>pETR11060 | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG<br>CGAAAGGGGTGAGGGTGTCTTTTGACTACTGGGGCCAAGGAACCCTGG<br>TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAGGTGCACAATGCCAAG<br>ACCAAGCCCCGGGAGGAACAGTACAACAGCACCTACCGGGTGGTGTC<br>CGTGCTGACCGTGCTGCACCAGGACTGGCTGAACGGCAAAGAGTACAA<br>GTGCAAGGTCTCCAACAAGGCCCTGCCTGCCCCCATCGAGAAAACCAT<br>CAGCAAGGCCAAGGGCCAGCCCAGAGAACCCCAGGTGTACACCCTGC<br>CCCCTAGCAGAGATGAGCTGACCAAGAACCAGGTGTCCCTGACCTGTC<br>TCGTGAAAGGCTTCTACCCCTCCGATATCGCCGTGGAATGGGAGAGCA<br>ACGGCCAGCCCGAGAACAACTACAAGACCACCCCCCCTGTGCTGGACT<br>CCGACGGCTCATTCTTCCTGTACTCTAAGCTGACAGTGGACAAGTCCCG<br>GTGGCAGCAGGGCAACGTGTTCTCCTGCTCCGTGATGCACGAGGCCCT<br>GCACAACCACTACACCCAGAAGTCCCTGTCCCTGTCTCCGGGGGAGG<br>CGGAGGATCTGGCGGAGGCGGATCCGGAGGAGGGGGAAGTGGCGGCG<br>GAGGATCTGAGGTGCAATTGTTGGAGTCTGGGGGAGGCTTGGTACAGC<br>CTGGGGGGTCCCTGAGACTCTCCTGTGCAGCCTCTGGATTCACCTTTAG<br>CAGTTATGCTATGAGCTGGGTCCGCCAGGCTCCAGGGAAGGGGCTGGA<br>GTGGGTCTCAGCTATTATTGGTAGTGGTGCCAGCACATACTACGCAGA<br>CTCCGTGAAGGGCCGGTTCACCATCTCCAGAGACAATTCCAAGAACAC<br>GCTGTATCTGCAGATGAACAGCCTGAGAGCCGAGGACACGGCCGTATA<br>TTACTGTGCGAAAGGGTGGTTTGGTGGTTTTAACTACTGGGGCCAAGG<br>AACCCTGGTCACCGTCTCGAGTGCTAGCGTGGCCGCTCCCAGCGTGTT<br>CATCTTCCCACCCAGCGACGAGCAGCTGAAGTCCGGCACAGCCAGCGT<br>GGTGTGCCTGCTGAACAACTTCTACCCCCGCGAGGCCAAGGTGCAGTG<br>GAAGGTGGACAACGCCCTGCAGAGCGGCAACAGCCAGGAATCCGTGA<br>CCGAGCAGGACAGCAAGGACTCCACCTACAGCCTGAGCAGCACCCTG<br>ACCCTGAGCAAGGCCGACTACGAGAAGCACAAGGTGTACGCCTGCGA<br>AGTGACCCACCAGGGCCTGTCCAGCCCCGTGACCAAGAGCTTCAACCG<br>GGGCGAGTGC | 260 |
| 4B9<br>VLCH1<br>pETR10020 | GAGATCGTGCTGACCCAGTCCCCCGGCACCCTGTCTCTGAGCCCTGGC<br>GAGAGAGCCACCCTGTCCTGCAGAGCCTCCCAGTCCGTGACCTCCTCC<br>TACCTCGCCTGGTATCAGCAGAAGCCCGGCCAGGCCCCTCGGCTGCTG<br>ATCAACGTGGGCAGTCGGAGAGCCACCGGCATCCCTGACCGGTTCTCC<br>GGCTCTGGCTCCGGCACCGACTTCACCCTGACCATCTCCCGGCTGGAA<br>CCCGAGGACTTCGCCGTGTACTACTGCCAGCAGGGCATCATGCTGCCC<br>CCCACCTTTGGCCAGGGCACCAAGGTGGAAATCAAGAGCTCCGCTAGC<br>ACCAAGGGCCCCTCCGTGTTTCCTCTGGCCCCCAGCAGCAAGAGCACC<br>TCTGGCGGAACAGCCGCCCTGGGCTGCCTGGTGAAAGACTACTTCCCC<br>GAGCCCGTGACCGTGTCCTGGAACTCTGGCGCCCTGACCAGCGGCGTG<br>CACACCTTTCCAGCCGTGCTGCAGAGCAGCGGCCTGTACTCCCTGAGC<br>AGCGTGGTGACAGTGCCCTCCAGCAGCCTGGGCACCCAGACCTACATC<br>TGCAACGTGAACCACAAGCCCAGCAACACCAAAGTGGACAAGAAGGT<br>GGAACCCAAGAGCTGCGAC | 261 |
| 5E11-Fc<br>knob | GAGGTGCAATTGTTGGAGTCTGGGGGAGGCTTGGTACAGCCTGGGGGG<br>TCCCTGAGACTCTCCTGTGCAGCCTCCGGATTCACCTTTAGCAGTTATG<br>CCATGAGCTGGGTCCGCCAGGCTCCAGGGAAGGGGCTGGAGTGGGTCT<br>CAGCTATTAGTGGTAGTGGTGGTAGCACATACTACGCAGACTCCGTGA<br>AGGGCCGGTTCACCATCTCCAGAGACAATTCCAAGAACACGCTGTATC<br>TGCAGATGAACAGCCTGAGAGCCGAGGACACGGCCGTATATTACTGTG | 264 |

| Description | Nucleotide sequences | SEQ ID NO |
|---|---|---|
| | CGAAAGGGGTGAGGGTGTCTTTTGACTACTGGGGCCAAGGAACCCTGG<br>TCACCGTCTCGAGTGCTAGCACCAAGGGCCCAAGCGTGTTCCCTCTGG<br>CCCCCAGCAGCAAGAGCACAAGCGGCGGAACAGCCGCCCTGGGCTGC<br>CTGGTCAAGGACTACTTCCCCGAGCCCGTGACAGTGTCCTGGAACAGC<br>GGAGCCCTGACCAGCGGCGTGCACACCTTTCCAGCCGTGCTGCAGAGC<br>AGCGGCCTGTACAGCCTGAGCAGCGTGGTCACAGTGCCTAGCAGCAGC<br>CTGGGCACCCAGACCTACATCTGCAACGTGAACCACAAGCCCAGCAAC<br>ACCAAGGTGGACAAGAAGGTGGAGCCCAAGAGCTGCGACAAGACCCA<br>CACCTGTCCCCCTTGTCCTGCCCCTGAGCTGCTGGGCGGACCCAGCGTG<br>TTCCTGTTCCCCCCAAAGCCCAAGGACACCCTGATGATCAGCCGGACC<br>CCCGAAGTGACCTGCGTGGTGGTGGACGTGTCCCACGAGGACCCTGAA<br>GTGAAGTTCAATTGGTACGTGGACGGCGTGGAAGTGCACAATGCCAAG<br>ACCAAGCCGCGGGAGGAGCAGTACAACAGCACGTACCGTGTGGTCAG<br>CGTCCTCACCGTCCTGCACCAGGACTGGCTGAATGGCAAGGAGTACAA<br>GTGCAAGGTCTCCAACAAAGCCCTCCCAGCCCCCATCGAGAAAACCAT<br>CTCCAAAGCCAAAGGGCAGCCCCGAGAACCACAGGTGTACACCCTGC<br>CCCCATGCCGGGATGAGCTGACCAAGAACCAGGTCAGCCTGTGGTGCC<br>TGGTCAAAGGCTTCTATCCCAGCGACATCGCCGTGGAGTGGGAGAGCA<br>ATGGGCAGCCGGAGAACAACTACAAGACCACGCCTCCCGTGCTGGACT<br>CCGACGGCTCCTTCTTCCTCTACAGCAAGCTCACCGTGGACAAGAGCA<br>GGTGGCAGCAGGGGAACGTCTTCTCATGCTCCGTGATGCATGAGGCTC<br>TGCACAACCACTACACGCAGAAGAGCCTCTCCCTGTCTCCGGGTAAA | |
| 5E11_LC pETR9044 | GAAATCGTGTTAACGCAGTCTCCAGGCACCCTGTCTTTGTCTCCAGGGG<br>AAAGAGCCACCCTCTCTTGCAGGGCCAGTCAGAGTGTTAGCAGCAGCT<br>ACTTAGCCTGGTACCAGCAGAAACCTGGCCAGGCTCCCAGGCTCCTCA<br>TCTATATGGAGCATCCAGCAGGGCCACTGGCATCCCAGACAGGTTCAGTG<br>GCAGTGGATCCGGGACAGACTTCACTCTCACCATCAGCAGACTGGAGC<br>CTGAAGATTTTGCAGTGTATTACTGTCAGCAGGGTACTACTCATCCCAT<br>TACGTTCGGCCAGGGGACCAAAGTGGAAATCAAACGTACGGTGGCTGC<br>ACCATCTGTCTTCATCTTCCCGCCATCTGATGAGCAGTTGAAATCTGGA<br>ACTGCCTCTGTTGTGTGCCTGCTGAATAACTTCTATCCCAGAGAGGCCA<br>AAGTACAGTGGAAGGTGGATAACGCCCTCCAATCGGGTAACTCCCAGG<br>AGAGTGTCACAGAGCAGGACAGCAAGGACAGCACCTACAGCCTCAGC<br>AGCACCCTGACGCTGAGCAAAGCAGACTACGAGAAACACAAAGTCTA<br>CGCCTGCGAAGTCACCCATCAGGGCCTGAGCTCGCCCGTCACAAAGAG<br>CTTCAACAGGGGAGAGTGT | 265 |
| huFc-hVH007 | GACAAGACCCACACCTGTCCCCCTTGTCCTGCCCCTGAGCTGCTGGGC<br>GGACCCAGCGTGTTCCTGTTCCCCCCAAAGCCCAAGGACACCCTGATG<br>ATCAGCCGGACCCCCGAAGTGACCTGCGTGGTGGTGGACGTGTCCCAC<br>GAGGACCCTGAAGTGAAGTTCAATTGGTACGTGGACGGCGTGGAGGTG<br>CACAATGCCAAGACCAAGCCCCGGGAGGAACAGTACAACAGCACCTA<br>CCGGGTGGTGTCCGTGCTGACCGTGCTGCACCAGGACTGGCTGAACGG<br>CAAAGAGTACAAGTGCAAGGTCTCCAACAAGGCCCTGCCTGCCCCCAT<br>CGAGAAAACCATCAGCAAGGCCAAGGGCCAGCCCAGAGAACCCCAGG<br>TGTACACCCTGCCCCCAGCAGAGATGAGCTGACCAAGAACCAGGTGT<br>CCCTGACCTGTCTGGTCAAGGGCTTCTACCCCAGCGATATCGCCGTGG<br>AGTGGGAGAGCAACGGCCAGCCTGAGAACAACTACAAGACCACCCCC<br>CCTGTGCTGGACAGCGACGGCAGCTTCTTCCTGTACTCCAAACTGACC<br>GTGGACAAGAGCCGGTGGCAGCAGGGCAACGTGTTCAGCTGCAGCGT<br>GATGCACGAGGCCCTGCACAACCACTACACCCAGAAGTCCCTGAGCCT<br>GAGCCCCGGCGAGGAGGCGGAAGTGGAGGCGGAGGATCCGGAGGG<br>GGAGGATCTGGCGGAGGCGGCAGCGAAGTGCAGCTTGTCGAAACCGG<br>CGGGGGACTCATCCAGCCCGGCGGTAGCCTGAGGCTTTCCTGCGCCGC<br>TTCTGGGTTCACAGTGTCAAGATACGCCATGATTTGGGTCGCCAGGC<br>CCCTGGCAAGGGACTGGAGTATATCGGTTTTATTACCAGCGACGGCTC<br>CACTTACTATGCTGATTCTGCAAAAGGGCGGTTCACAATCAGTAGGGA<br>CAACAGCAAGAATACCCTCTACCTCCAGATGAACTCCTTGAGAGCCGA<br>GGATACTGCTGTGTACTATTGTGCACGCTACACCTATTCTGACGGAACA<br>GACCTGTGGGGCCGGGAACCCTCGTCACTGTCTCCTCAGCTAGCACC<br>AAGGGCCCCTCCGTGTTTCCTCTGGCCCCCAGCAGCAAGAGCACCTCT<br>GGCGGAACAGCCGCCCTGGGCTGCCTGGTGAAAGACTACTTCCCCGAG<br>CCCGTGACCGTGTCCTGGAACTCTGGCGCCCTGACCAGCGGCGTGCAC<br>ACCTTTCCAGCCGTGCTGCAGAGCAGCGGCCTGTACTCCCTGAGCAGC<br>GTGGTGACAGTGCCCTCCAGCAGCCTGGGCACCCAGACCTACATCTGC<br>AACGTGAACCACAAGCCCAGCAACACCAAAGTGGACAAGAAGGTGGA<br>ACCCAAGAGCTGCGAC | 312 |
| hVL015 | GACATCCAGATGACCCAGAGCCCCTCCACACTGTCTGCTTCAGTGGGC<br>GATAGGGTCACCATTACTTGCAGAGCAAGCCAGTCCATCTCTACATAC<br>CTCAGTTGGTATCAGCAAAAGCCTGGGAAAGCCCAAAGCGCCTGATT<br>TACAAGGCCAGCTCCCTTGCATCTGGAGTGCCCTCACGGTTCAGCGGC<br>TCCGGTTCTGGGACCGAGTTTACTCTGACCATCAGTAGCCTCCAGCCTG<br>ACGATGCCGCTACATATTACTGTCAGCCAAACTCCGGCATAGCAACCT<br>ACGGAGCCGCTTTCGGTGGCGGGACAAAAGTCGAAATCAAACGTACG | 313 |

| Description | Nucleotide sequences | SEQ ID NO |
|---|---|---|
| | GTGGCTGCACCATCTGTCTTCATCTTCCCGCCATCTGATGAGCAGTTGA AATCTGGAACTGCCTCTGTTGTGTGCCTGCTGAATAACTTCTATCCCAG AGAGGCCAAAGTACAGTGGAAGGTGGATAACGCCCTCCAATCGGGTA ACTCCCAGGAGAGTGTCACAGAGCAGGACAGCAAGGACAGCACCTAC AGCCTCAGCAGCACCCTGACGCTGAGCAAAGCAGACTACGAGAAACA CAAAGTCTACGCCTGCGAAGTCACCCATCAGGGCCTGAGCTCGCCCGT CACAAAGAGCTTCAACAGGGGAGAGTGT | |
| huFc-hVH017 | GACAAGACCCACACCTGTCCCCCTTGTCCTGCCCCTGAGCTGCTGGGC GGACCCCAGCGTGTTCCTGTTCCCCCCAAAGCCCAAGGACACCCTGATG ATCAGCCGGACCCCCGAAGTGACCTGCGTGGTGGTGGACGTGTCCCAC GAGGACCCTGAAGTGAAGTTCAATTGGTACGTGGACGGCGTGGAGGTG CACAATGCCAAGACCAAGCCCCGGGAGGAACAGTACAACAGCACCTA CCGGGTGGTGTCCGTGCTGACCGTGCTGCACCAGGACTGGCTGAACGG CAAAGAGTACAAGTGCAAGGTCTCCAACAAGGCCCTGCCTGCCCCCAT CGAGAAAACCATCAGCAAGGCCAAGGGCCAGCCCAGAGAACCCCAGG TGTACACCCTGCCCCCCAGCAGAGATGAGCTGACCAAGAACCAGGTGT CCCTGACCTGTCTGGTCAAGGGCTTCTACCCCAGCGATATCGCCGTGG AGTGGGAGAGCAACGGCCAGCCTGAGAACAACTACAAGACCACCCCC CCTGTGCTGGACAGCGACGGCAGCTTCTTCCTGTACTCCAAACTGACC GTGGACAAGAGCCGGTGGCAGCAGGGCAACGTGTTCAGCTGCAGCGT GATGCACGAGGCCCTGCACAACCACTACACCCAGAAGTCCCTGAGCCT GAGCCCCGGCGGAGGAGGCGGAAGTGGAGGCGGAGGATCCGGAGGG GGAGGATCTGGCGGAGGCGGCAGCCAAGTGCAGCTCGTCGAGAGCGG CGGGGGACTCGTGCAGCCCGGCGGTTCCTGAGGCTTTCTTGCTCAGC CAGCGGGTTCTCCATCTCCAGATACGCTATGATTTGGGTCCGCCAGGC ACCTGGCAAGGGACTGGAATATGTGGGTTTTATCACCAGTGACAGCTC CGCCTACTATGCTTCTTGGGCAAAAGGCCGGTTCACAATTTCAAGGGA TAACAGCAAGAATACCCTCTACCTTCAAATGAACTCCTTGAGAGCCGA GGACACTGCTGTTTACTATTGTGCACGCTACACATATTCTGATGGGACC GACCTGTGGGGACAGGGCACTCTCGTCACTGTCTCCTCAGCTAGCACC AAGGGCCCCTCCGTGTTTCCTCTGGCCCCCAGCAGCAAGAGCACCTCT GGCGGAACAGCCGCCCTGGGCTGCCTGGTGAAAGACTACTTCCCCGAG CCCGTGACCGTGTCCTGGAACTCTGGCGCCCTGACCAGCGGCGTGCAC ACCTTTCCAGCCGTGCTGCAGAGCAGCGGCCTGTACTCCCTGAGCAGC GTGGTGACAGTGCCCTCCAGCAGCCTGGGCACCCAGACCTACATCTGC AACGTGAACCACAAGCCCAGCAACACCAAAGTGGACAAGAAGGTGGA ACCCAAGAGCTGCGAC | 314 |
| hVL011 | GACATCCAGATGACCCAGAGCCCCTCCTCTCTGTCAGCCAGCGTGGGC GATAGGGTCACAATTACCTGTCAGGCTTCCCAATCTATCAGTACTTACC TGAGCTGGTATCAACAGAAGCCTGGGCAGCCACCCAAAAGACTGATTT ACAAGGCATCCACACTTGCCTCTGGAGTGCCTTCACGCTTCAGCGGCT CCGGTTCTGGGACCGACTTTACTCTGACCATCAGTAGCCTCCAGCCAG AGGATTTCGCTACATATTACTGTCAACCCAACTCCGGCATAGCAACCT ACGGAGCCGCTTTTGGTGGCGGGACAAAGGTCGAAATCAAACGTACG GTGGCTGCACCATCTGTCTTCATCTTCCCGCCATCTGATGAGCAGTTGA AATCTGGAACTGCCTCTGTTGTGTGCCTGCTGAATAACTTCTATCCCAG AGAGGCCAAAGTACAGTGGAAGGTGGATAACGCCCTCCAATCGGGTA ACTCCCAGGAGAGTGTCACAGAGCAGGACAGCAAGGACAGCACCTAC AGCCTCAGCAGCACCCTGACGCTGAGCAAAGCAGACTACGAGAAACA CAAAGTCTACGCCTGCGAAGTCACCCATCAGGGCCTGAGCTCGCCCGT CACAAAGAGCTTCAACAGGGGAGAGTGT | 315 |

14. DR5 Sequences

| Name | Sequence | Seq ID No |
|---|---|---|
| Human DR5 swissprot O14763 | MEQRGQNAPA ASGARKRHGP GPREARGARP GPRVPKTLVL VVAAVLLLVS AESALITQQD LAPQQRAAPQ QKRSSPSEGL CPPGHHISED GRDCISCKYG DYSTHWNDL LFCLRCTRCD SGEVELSPCT TTRNTVCQCE EGTFREEDSP EMCRKCRTGC PRGMVKVGDC TPWSDIECVH KESGTKHSGE APAVEETVTS SPGTPASPCS LSGIIIGVTV AAVVLIVAVF VCKSLLWKKV LPYLKGICSG GGDPERVDR SSQRPGAEDN VLNEIVSILQ PTQVPEQEME VQEPAEPTGV NMLSPGESEH LLEPAEAERS QRRRLLVPAN EGDPTETLRQ CFDDFADLVP FDSWEPLMRK LGLMDNEIKV AKAEAAGHRD TLYTMLIKWV NKTGRDASVH TLLDALETLG ERLAKQKIED HLLSSGKFMY LEGNADSAMS | 155 |
| Hu DR5 (ECD)- AcTev-Fc-Avi | ITQQDLAPQQRAAPQQKRSSPSEGLC PPGHHISEDGRDCISCKYGQDYSTHW NDLLFCLRCTRCDSGEVELSPCTTTR NTVCQCEEGTFREEDSPEMCRKCRTG CPRGMVKVGDCTPWSDIECVHKESGT KHSGEAPAVEETVTSSPGTPASVDEQ | 316 |

| Name | Sequence | Seq ID No |
|---|---|---|
| | LYFQGGSPKSADKTHTCPPCPAPELL GGPSVFLFPPKPKDTLMISRTPEVTC VVVDVSHEDPEVKFNWYVDGVEVHNA KTKPREEQYNSTYRVVSVLTVLHQDW LNGKEYKCKVSNKALPAPIEKTISKA KGQPREPQVYTLPPSRDELTKNQVSL TCLVKGFYPSDIAVEWESNGQPENNY KTTPPVLDSDGSFFLYSKLTVDKSRW QQGNVFSCSVMHEALHNHYTQKSLSL SPGGGSGGLNDIFEAQKIEWHE | |
| Cynom. DR5 (ECD)-AcTev-Fc-Avi | ITRQSLDPQRRAAPQQKRSSPTEGLC PPGHHISEDSRECISCKYGQDYSTHW NDFLFCLRCTKCDSGEVEVNSCTTTR NTVCQCEEGTFREEDSPEICRKCRTG CPRGMVKVKDCTPWSDIECVHKESVD EQLYFQGGSPKSADKTHTCPPCPAPE LLGGPSVFLFPPKPKDTLMISRTPEV TCVVVDVSHEDPEVKFNWYVDGVEVH NAKTKPREEQYNSTYRVVSVLTVLHQ DWLNGKEYKCKVSNKALPAPIEKTIS KAKGQPREPQVYTLPPSRDELTKNQV SLTCLVKGFYPSDIAVEWESNGQPEN NYKTTPPVLDSDGSFFLYSKLTVDKS RWQQGNVFSCSVMHEALHNHYTQKSL SLSPGGGSGGLNDIFEAQKIEWHE | 317 |

15. FAP Sequences

| Construct | POLYPEPTIDE SEQUENCE | SEQ ID NO |
|---|---|---|
| Human FAP ectodomain + poly-lys-tag + his₆-tag | RPSRVHNSEENTMRALTLKDILNGTFSY KTFFPNWISGQEYLHQSADNNIVLYNIE TGQSYTILSNRTMKSVNASNYGLSPDRQ FVYLESDYSKLWRYSYTATYYIYDLSNG EFVRGNELPRPIQYLCWSPVGSKLAYVY QNNIYLKQRPGDPPFQITFNGRENKIFN GIPDWVYEEEMLATKYALWWSPNGKFLA YAEFNDTDIPVIAYSYYGDEQYPRTINI PYPKAGAKNPVRIFIIDTTYPAYVGPQ EVPVPAMIASSDYYFSWLTWVTDERVCL QWLKRVQNVSVLSICDFREDWQTWDCPK TQEHIEESRTGWAGGFFVSTPVFSYDAI SYYKIFSDKDGYKHIHYIKDTVENAIQI TSGKWEAINIFRVTQDSLFYSSNEFEEY PGRRNIYRISIGSYPPSKKCVTCHLRKE RCQYYTASFSDYAKYYALVCYGPGIPIS TLHDGRTDQEIKILEENKELENALKNIQ LPKEEIKKLEVDEITLWYKMILPPQFDR SKKYPLLIQVYGGPCSQSVRSVFAVNWI SYLASKEGMVIALVDGRGTAFQGDKLLY AVYRKLGVYEVEDQITAVRKFIEMGFID EKRIAIWGWSYGGYVSSLALASGTGLFK CGIAVAPVSSWEYYASVYTERFMGLPTK DDNLEHYKNSTVMARAEYFRNVDYLLIH GTADDNVHFQNSAQIAKALVNAQVDFQA MWYSDQNHGLSGLSTNHLYTHMTHFLKQ CFSLSDGKKKKKKGHHHHHH | 156 |
| Murine FAP ectodomain + poly-lys-tag + his₆-tag | RPSRVYKPEGNTKRALTLKDILNGTFSY KTYFPNWISEQEYLHQSEDDNIVFYNIE TRESYIILSNSTMKSVNATDYGLSPDRQ FVYLESDYSKLWRYSYTATYYIYDLQNG EFVRGYELPRPIQYLCWSPVGSKLAYVY QNNIYLKQRPGDPPFQITYTGRENRIFN GIPDWVYEEEMLATKYALWWSPDGKFLA YVEFNDSDIPIIAYSYYGDGQYPRTINI PYPKAGAKNPVVRVFIVDTTYPHHVGPM EVPVPEMIASSDYYFSWLTWVSSERVCL QWLKRVQNVSVLSICDFREDWHAWECPK NQEHVEESRTGWAGGFFVSTPAFSQDAT SYYKIFSDKDGYKHIHYIKDTVENAIQI TSGKWEAIYIFRVTQDSLFYSSNEFEGY PGRRNIYRISIGNSPPSKKCVTCHLRKE RCQYYTASFSYKAKYYALVCYGPGLPIS TLHDGRTDQEIQVLEENKELENSLRNIQ LPKVEIKKLKDGGLTFWYKMILPPQFDR SKKYPLLIQVYGGPCSQSVKSVFAVNWI TYLASKEGIVIALVDGRGTAFQGDKFLH AVYRKLGVYEVEDQLTAVRKFIEMGFID EERIAIWGWSYGGYVSSLALASGTGLFK CGIAVAPVSSWEYYASIYSERFMGLPTK DDNLEHYKNSTVMARAEYFRNVDYLLIH GTADDNVHFQNSAQIAKALVNAQVDFQA MWYSDQNHGILSGRSQNHLYTHMTHFLK QCFSLSDGKKKKKKGHHHHHH | 157 |
| Cynomolgus FAP ectodomain + poly-lys-tag + his₆-tag | RPPRVHNSEENTMRALTLKDILNGTFSY KTFFPNWISGQEYLHQSADNNIVLYNIE TGQSYTILSNRTMKSVNASNYGLSPDRQ FVYLESDYSKLWRYSYTATYYIYDLSNG EFVRGNELPRPIQYLCWSPVGSKLAYVY QNNIYLKQRPGDPPFQITFNGRENKIFN GIPDWVYEEEMLATKYALWWSPNGKFLA YAEFNDTDIPVIAYSYYGDEQYPRTINI PYPKAGAKNPFVRIFIIDTTYPAYVGPQ EVPVPAMIASSDYYFSWLTWVTDERVCL QWLKRVQNVSVLSICDFREDWQTWDCPK TQEHIEESRTGWAGGFFVSTPVFSYDAI SYYKIFSDKDGYKHIHYIKDTVENAIQI TSGKWEAINIFRVTQDSLFYSSNEFEDY PGRRNIYRISIGSYPPSKKCVTCHLRKE RCQYYTASFSDYAKYYALVCYGPGIPIS TLHDGRTDQEIKILEENKELENALKNIQ LPKEEIKKLEVDEITLWYKMILPPQFDR SKKYPLLIQVYGGPCSQSVRSVFAVNWI SYLASKEGMVIALVDGRGTAFQGDKLLY AVYRKLGVYEVEDQITAVRKFIEMGFID EKRIAIWGWSYGGYVSSLALASGTGLFK CGIAVAPVSSWEYYASVYTERFMGLPTK DDNLEHYKNSTVMARAEYFRNVDYLLIH GTADDNVHFQNSAQIAKALVNAQVDFQA MWYSDQNHGLSGLSTNHLYTHMTHFLKQ CFSLSDGKKKKKKGHHHHHH | 158 |

While there are shown and described presently preferred embodiments of the invention, it is to be distinctly understood that the invention is not limited thereto but may be otherwise variously embodied and practiced within the scope of the following claims. The disclosures of all patent and scientific literature cited herein are expressly incorporated in their entirety by reference.

We claim:

1. A method of treating cancer in an individual, the method comprising administering to the individual an effective amount of an antibody that specifically binds to DR5, wherein the antibody comprises at least one antigen binding site specific for DR5, and wherein the antigen binding site specific for DR5 comprises:
   (a) a heavy chain complementarity determining region 1 (CDR1) comprising an amino acid sequence of SEQ ID NO.:1;
   (b) a heavy chain complementarity determining region 2 (CDR2) comprising an amino acid sequence of SEQ ID NO.:2;
   (c) a heavy chain complementarity determining region 3 (CDR3) comprising an amino acid sequence of SEQ ID NO.:3;
   (d) a light chain CDR1 comprising an amino acid sequence of SEQ ID NO.:4;
   (e) a light chain CDR2 comprising an amino acid sequence of SEQ ID NO.:5; and
   (f) a light chain CDR3 comprising an amino acid sequence of SEQ ID NO.:6.

2. The method of claim 1, wherein the cancer is pancreatic cancer or colorectal carcinoma.

3. The method of claim 1, wherein the antigen binding site specific for DR5 comprises a variable heavy chain comprising an amino acid sequence of SEQ ID NO.:7 and a variable light chain comprising an amino acid sequence of SEQ ID NO.:8.

4. The method of claim 1, wherein the antibody is human.

5. The method of claim 1, wherein the antibody is monovalent for DR5.

6. The method of claim 1, wherein the antibody is bivalent for DR5.

7. The method of claim 1, wherein the antibody is trivalent for DR5.

8. The method of claim 1, wherein the antibody comprises an Fc domain and at least one Fab fragment comprising the antigen binding site specific for DR5.

9. The method of claim 8, wherein at least one of the Fab fragments is connected to the Fc domain via a peptide linker.

10. The method of claim 8, wherein the Fc domain comprises one or more amino acid substitutions that reduce binding to an Fc receptor and/or that reduce effector function.

11. The method of claim 10, wherein the one or more amino acid substitutions are at one or more residues selected from the group consisting of L234, L235, and P329 according to EU numbering.

12. The method of claim 10, wherein the one or more amino acid substitutions are L234A, L235A, and P329G.

13. The method of claim 1, wherein the antibody is administered to the individual in a pharmaceutical composition comprising the antibody and a pharmaceutically acceptable carrier.

* * * * *